US009440963B2

(12) United States Patent
Peters et al.

(10) Patent No.: US 9,440,963 B2
(45) Date of Patent: *Sep. 13, 2016

(54) COMPOSITIONS, FORMULATIONS AND METHODS FOR TREATING OCULAR DISEASES

(71) Applicant: Aerpio Therapeutics Inc., Cincinnati, OH (US)

(72) Inventors: Kevin Peters, Cincinnati, OH (US); Robert Shalwitz, Bexley, OH (US); John Janusz, West Chester, OH (US); Alexander Smith, Apex, NC (US)

(73) Assignee: AERPIO THERAPEUTICS, INC., Cincinnati, OH (US)

( * ) Notice: Subject to any disclaimer, the term of this patent is extended or adjusted under 35 U.S.C. 154(b) by 65 days.

This patent is subject to a terminal disclaimer.

(21) Appl. No.: 13/999,670

(22) Filed: Mar. 14, 2014

(65) Prior Publication Data

US 2014/0275103 A1    Sep. 18, 2014

Related U.S. Application Data

(60) Provisional application No. 61/792,868, filed on Mar. 15, 2013, provisional application No. 61/792,679, filed on Mar. 15, 2013, provisional application No. 61/882,056, filed on Sep. 25, 2013, provisional application No. 61/882,048, filed on Sep. 25, 2013, provisional application No. 61/934,570, filed on Jan. 31, 2014.

(51) Int. Cl.
| *A61K 31/497* | (2006.01) |
| *A61K 31/4965* | (2006.01) |
| *A61K 31/505* | (2006.01) |
| *A61K 31/44* | (2006.01) |
| *A61K 31/41* | (2006.01) |
| *C07D 417/12* | (2006.01) |
| *C07D 277/30* | (2006.01) |
| *C07D 277/60* | (2006.01) |
| *C07D 417/04* | (2006.01) |
| *C07D 277/56* | (2006.01) |
| *C07D 277/64* | (2006.01) |

(52) U.S. Cl.
CPC .......... *C07D 417/12* (2013.01); *C07D 277/30* (2013.01); *C07D 277/56* (2013.01); *C07D 277/60* (2013.01); *C07D 277/64* (2013.01); *C07D 417/04* (2013.01)

(58) Field of Classification Search
None
See application file for complete search history.

(56) References Cited

U.S. PATENT DOCUMENTS

| 5,078,486 A | 1/1992 | Evans |
| 5,736,536 A | 4/1998 | Siegall et al. |
| 7,226,755 B1 | 6/2007 | Peters et al. |
| 7,507,568 B2 | 3/2009 | Evdokimov et al. |
| 7,589,212 B2 | 9/2009 | Gray et al. |
| 7,622,593 B2 | 11/2009 | Gray et al. |
| 7,632,862 B2 | 12/2009 | Peters et al. |
| 7,691,963 B2 | 4/2010 | Prickett et al. |
| 7,769,575 B2 | 8/2010 | Evdokimov et al. |
| 7,795,444 B2 | 9/2010 | Gray et al. |
| 7,973,142 B2 | 7/2011 | Rotello et al. |
| 8,029,808 B2 | 10/2011 | Srivastava |
| 8,106,078 B2 | 1/2012 | Gray et al. |
| 8,178,570 B2 | 5/2012 | Chen et al. |
| 8,188,125 B2 | 5/2012 | Gray et al. |
| 8,258,311 B2 | 9/2012 | Gray et al. |
| 8,329,916 B2 | 12/2012 | Gray et al. |
| 8,338,615 B2 | 12/2012 | Gray et al. |
| 8,524,235 B2 | 9/2013 | Rotello et al. |
| 8,569,348 B2 | 10/2013 | Shalwitz et al. |
| 8,591,890 B2 | 11/2013 | Srivastava et al. |
| 8,846,685 B2 | 9/2014 | Gray et al. |
| 8,883,774 B2 | 11/2014 | Shalwitz et al. |
| 8,883,832 B2 | 11/2014 | Shalwitz et al. |
| 8,895,563 B2 | 11/2014 | Gray et al. |
| 8,946,232 B2 | 2/2015 | Gray et al. |
| 8,999,325 B2 | 4/2015 | Peters et al. |
| 9,096,555 B2 | 8/2015 | Shalwitz et al. |
| 9,126,958 B2 | 9/2015 | Gray et al. |
| 9,174,950 B2 | 11/2015 | Shalwitz et al. |
| 2003/0158199 A1 | 8/2003 | Stieber et al. |
| 2004/0077065 A1 | 4/2004 | Evdokimov et al. |
| 2007/0299116 A1 | 12/2007 | Gray et al. |
| 2008/0004267 A1 | 1/2008 | Gray et al. |

(Continued)

FOREIGN PATENT DOCUMENTS

| WO | WO 96/31598 A1 | 10/1996 |
| WO | WO 2004/043927 A1 | 5/2004 |

(Continued)

OTHER PUBLICATIONS

Cascone, Targeting the Angiopoietin/Tie-2 Pathway: Cutting Tumor Vessels With a Double-Edged Sword?, Journal of Clinical Oncology, 30, (4), 441-444, 2012.*
Cho et al., COMP-Ang1: A designed angiopoietin-1 variant with nonleaky angiogenic activity, PNAS, 101(15):5547-5552, 2004.*
U.S. Appl. No. 14/214,413, filed Mar. 14, 2014, Peters et al.

(Continued)

*Primary Examiner* — Jeffrey S Lundgren
*Assistant Examiner* — Michael Schmitt
(74) *Attorney, Agent, or Firm* — Wilson Sonsini Goodrich & Rosati

(57) ABSTRACT

Disclosed herein are compounds effective for activation of Tie-2 and inhibition of HPTP-beta. The compounds can provide effective therapy for conditions associated with angiogenesis, for example, ocular conditions. Formulations for increased solubility are disclosed. Combination therapy with antibodies and PK/PD data are also disclosed.

60 Claims, 9 Drawing Sheets

(56) References Cited

U.S. PATENT DOCUMENTS

| | | |
|---|---|---|
| 2008/0076764 A1 | 3/2008 | Peters et al. |
| 2008/0108631 A1 | 5/2008 | Gray et al. |
| 2009/0022715 A1 | 1/2009 | Rotello et al. |
| 2009/0227639 A1 | 9/2009 | Gray et al. |
| 2010/0016336 A1 | 1/2010 | Gray et al. |
| 2010/0030487 A1 | 2/2010 | Evdokimov et al. |
| 2010/0056610 A1 | 3/2010 | Peters et al. |
| 2010/0069448 A1 | 3/2010 | Gray et al. |
| 2011/0212951 A1 | 9/2011 | Gray et al. |
| 2011/0268694 A1 | 11/2011 | Shalwitz et al. |
| 2011/0274699 A1 | 11/2011 | Rotello et al. |
| 2011/0319455 A1 | 12/2011 | Klein et al. |
| 2012/0077853 A1 | 3/2012 | Gray et al. |
| 2012/0077975 A1 | 3/2012 | Gray et al. |
| 2012/0128625 A1 | 5/2012 | Shalwitz et al. |
| 2012/0129847 A1 | 5/2012 | Peters et al. |
| 2012/0207682 A1 | 8/2012 | Ashton |
| 2013/0023542 A1 | 1/2013 | Gray et al. |
| 2013/0023543 A1 | 1/2013 | Gray et al. |
| 2013/0095065 A1 | 4/2013 | Peters et al. |
| 2013/0095105 A1 | 4/2013 | Peters et al. |
| 2013/0096140 A1 | 4/2013 | Gray et al. |
| 2013/0324558 A1 | 12/2013 | Gray et al. |
| 2013/0331386 A1 | 12/2013 | Shalwitz et al. |
| 2014/0044707 A1 | 2/2014 | Rotello et al. |
| 2014/0066458 A1 | 3/2014 | Shalwitz et al. |
| 2014/0107391 A1 | 4/2014 | Srivastava et al. |
| 2014/0179693 A1 | 6/2014 | Shalwitz et al. |
| 2014/0221666 A1 | 8/2014 | Gray et al. |
| 2014/0242026 A1 | 8/2014 | Shalwitz et al. |
| 2014/0249100 A1 | 9/2014 | Shalwitz et al. |
| 2014/0288134 A1 | 9/2014 | Peters et al. |
| 2015/0050277 A1 | 2/2015 | Peters et al. |
| 2015/0210656 A1 | 7/2015 | Gray et al. |
| 2015/0232425 A1 | 8/2015 | Alberico |
| 2015/0232575 A1 | 8/2015 | Peters et al. |
| 2015/0259335 A1 | 9/2015 | Janusz et al. |

FOREIGN PATENT DOCUMENTS

| | | | |
|---|---|---|---|
| WO | WO 2004/043928 A2 | 5/2004 | |
| WO | WO 2007/116360 A2 | 10/2007 | |
| WO | WO 2008/002569 A2 | 1/2008 | |
| WO | WO 2008/002570 A2 | 1/2008 | |
| WO | WO 2008/002571 A2 | 1/2008 | |
| WO | WO 2010/081172 A1 | 7/2010 | |
| WO | WO 2011/005330 A1 | 1/2011 | |
| WO | WO 2011/057112 A1 | 5/2011 | |
| WO | WO 2011/057115 A1 | 5/2011 | |
| WO | WO 2011/057121 A1 | 5/2011 | |
| WO | WO 2011/134056 A1 * | 11/2011 | ............ A61K 38/17 |
| WO | WO 2012/047966 A2 | 4/2012 | |
| WO | WO 2013/056233 A1 | 4/2013 | |
| WO | WO 2013/056240 A1 | 4/2013 | |
| WO | WO 2014/145068 A1 | 9/2014 | |
| WO | WO 2015/126860 A1 | 8/2015 | |
| WO | WO 2015/138882 A1 | 9/2015 | |

OTHER PUBLICATIONS

Amarasinge, et al. Design and synthesis of potent, non-peptidic inhibitors of HPTPbeta. Bioorg Med Chem Lett. Aug. 15, 2006;16(16):4252-6. Epub Jun. 12, 2006.

Brewster, et al. Comparative interaction of 2-hydroxypropyl-beta-cyclodextrin and sulfobutylether-beta-cyclodextrin with itraconazole: phase-solubility behavior and stabilization of supersaturated drug solutions. Eur J Pharm Sci. Jul. 3, 2008;34(2-3):94-103. doi: 10.1016/j.ejps.2008.02.007. Epub Feb. 26, 2008.

Davis, et al. Isolation of angiopoietin-1, a ligand for the TIE2 receptor, by secretion-trap expression cloning Cell. Dec. 27, 1996;87(7):1161-9.

Derevjanik, et al. Quantitative assessment of the integrity of the blood-retinal barrier in mice. Invest Ophthalmol Vis Sci. Jul. 2002;43(7):2462-7.

Dumont, et al. Dominant-negative and targeted null mutations in the endothelial receptor tyrosine kinase, tek, reveal a critical role in vasculogenesis of the embryo. Genes Dev. Aug. 15, 1994;8(16):1897-909.

Fachinger, et al. Functional interaction of vascular endothelial-protein-tyrosine phosphatase with the angiopoietin receptor Tie-2. Oncogene. Oct. 21, 1999;18(43):5948-53.

Hackett, et al. Angiopoietin 2 expression in the retina: upregulation during physiologic and pathologic neovascularization. J Cell Physiol. Sep. 2000;184(3):275-84.

Hackett, et al. Angiopoietin-2 plays an important role in retinal angiogenesis J Cell Physiol. Aug. 2002;192(2):182-7.

Heiderstadt, et al. Increased juvenile and adult body weights in BALB/cByJ mice reared in a communal nest. J Am Assoc Lab Anim Sci. Jul. 2011;50(4):484-7.

International search report and written opinion dated Aug. 20, 2014 for PCT/US2014/029723.

Klein, et al. The Wisconsin epidemiologic study of diabetic retinopathy. II. Prevalence and risk of diabetic retinopathy when age at diagnosis is less than 30 years. Arch Ophthalmol. Apr. 1984;102(4):520-6.

Klopfenstein, et al. 1,2,3,4-Tetrahydroisoquinolinyl sulfamic acids as phosphatase PTP1B inhibitors. Bioorg Med Chem Lett. Mar. 15, 2006;16(6):1574-8. Epub Jan. 4, 2006.

Krueger, et al. Structural diversity and evolution of human receptor-like protein tyrosine phosphatases. EMBO J. Oct. 1990;9(10):3241-52.

Nambu, et al. Angiopoietin 1 inhibits ocular neovascularization and breakdown of the blood-retinal barrier. Gene Ther. May 2004;11(10):865-73.

Nguyen, et al. Primary End Point (Six Months) Results of the Ranibizumab for Edema of the mAcula in diabetes (READ-2) study. Ophthalmology. Nov. 2009;116(11):2175-81.e1. doi: 10.1016/j.ophtha.2009.04.023. Epub Aug. 22, 2009 .

Nguyen, et al. Supplemental oxygen improves diabetic macular edema: a pilot study. Invest Ophthalmol Vis Sci. Feb. 2004;45(2):617-24.

Nguyen, et al. Vascular endothelial growth factor is a critical stimulus for diabetic macular edema. Am J Ophthalmol. Dec. 2006;142(6):961-9. Epub Aug. 2, 2006.

Oshima, et al. Angiopoietin-2 enhances retinal vessel sensitivity to vascular endothelial growth factor. J Cell Physiol. Jun. 2004;199(3):412-7.

Ozaki, et al. Intravitreal sustained release of VEGF causes retinal neovascularization in rabbits and breakdown of the blood-retinal barrier in rabbits and primates. Exp Eye Res. Apr. 1997;64(4):505-17.

Tobe, et al. Targeted disruption of the FGF2 gene does not prevent choroidal neovascularization in a murine model. Am J Pathol. Nov. 1998;153(5):1641-6.

Yacyshyn, et al. Tyrosine phosphatase beta regulates angiopoietin-Tie2 signaling in human endothelial cells. Angiogenesis. 2009;12(1):25-33. doi: 10.1007/s10456-008-9126-0. Epub Jan. 1, 2009.

U.S. Appl. No. 14/819,871, filed Aug. 6, 2015, Peters.
U.S. Appl. No. 14/862,948, filed Sep. 23, 2015, Peters.
U.S. Appl. No. 14/864,462, filed Sep. 24, 2015, Shalwitz et al.

Do, et al. One-year outcomes of the Da Vinci study of VEGF trap-eye in eyes of diabetic macular edema. J. Ophthalmology. Aug. 2012; 119(8): 1658-1665.

International search report and written opinion dated Jul. 30, 2015 for PCT/US2015/020425.

Office action dated Jul. 17, 2015 for U.S. Appl. No. 14/214,413.

Pubchem. Compound Summary for: CID 52799544. Create Date: May 20, 2011. Retrieved on Apr. 27, 2015. https://pubchem.ncbi.nlm.nih.gov/compound/52799544.

U.S. Appl. No. 14/569,106, filed Dec. 12, 2014, Gray et al.
U.S. Appl. No. 14/627,463, filed Feb. 20, 2015, Peters et al.
U.S. Appl. No. 14/657,276, filed Mar. 13, 2015, Janusz et al.

* cited by examiner

COMPOSITIONS, FORMULATIONS AND METHODS FOR TREATING OCULAR DISEASES

CROSS REFERENCE

This application claims the benefit of U.S. Provisional Application No. 61/792,868, filed Mar. 15, 2013, U.S. Provisional Application No. 61/792,679, filed Mar. 15, 2013, U.S. Provisional Application No. 61/882,056, filed Sep. 25, 2013, U.S. Provisional Application No. 61/882,048, filed Sep. 25, 2013 and U.S. Provisional Application No. 61/934,570, filed Jan. 31, 2014, each of which is incorporated herein by reference in its entirety.

SEQUENCE LISTING

This disclosure includes a sequence listing submitted as a text file pursuant to 37 C.F.R. §1.52(e)(v) named 45725-712.201_SL.txt, created on May 28, 2014, with a size of 4.65 kilobytes, which is incorporated herein by reference.

FIELD

Disclosed herein are compositions, formulations, and methods for treating ocular diseases, inter alia, diabetic macular edema, age-related macular degeneration (wet form), choroidal neovascularization, diabetic retinopathy, retinal vein occlusion (central or branch), ocular trauma, surgery induced edema, surgery induced neovascularization, cystoid macular edema, ocular ischemia, uveitis, and the like. These diseases or conditions are characterized by changes in the ocular vasculature whether progressive or non-progressive, whether a result of an acute disease or condition, or a chronic disease or condition.

INCORPORATION BY REFERENCE

Each patent, publication, and non-patent literature cited in the application is hereby incorporated by reference in its entirety as if each was incorporated by reference individually.

BACKGROUND

The eye comprises several structurally and functionally distinct vascular beds, which supply ocular components critical to the maintenance of vision. These include the retinal and choroidal vasculatures, which supply the inner and outer portions of the retina, respectively, and the limbal vasculature located at the periphery of the cornea. Injuries and diseases that impair the normal structure or function of these vascular beds are among the leading causes of visual impairment and blindness. For example, diabetic retinopathy is the most common disease affecting the retinal vasculature, and is the leading cause of vision loss among the working age population in the United States. Vascularization of the cornea secondary to injury or disease is yet another category of ocular vascular disease that can lead to severe impairment of vision.

SUMMARY OF THE INVENTION

Figure 1:
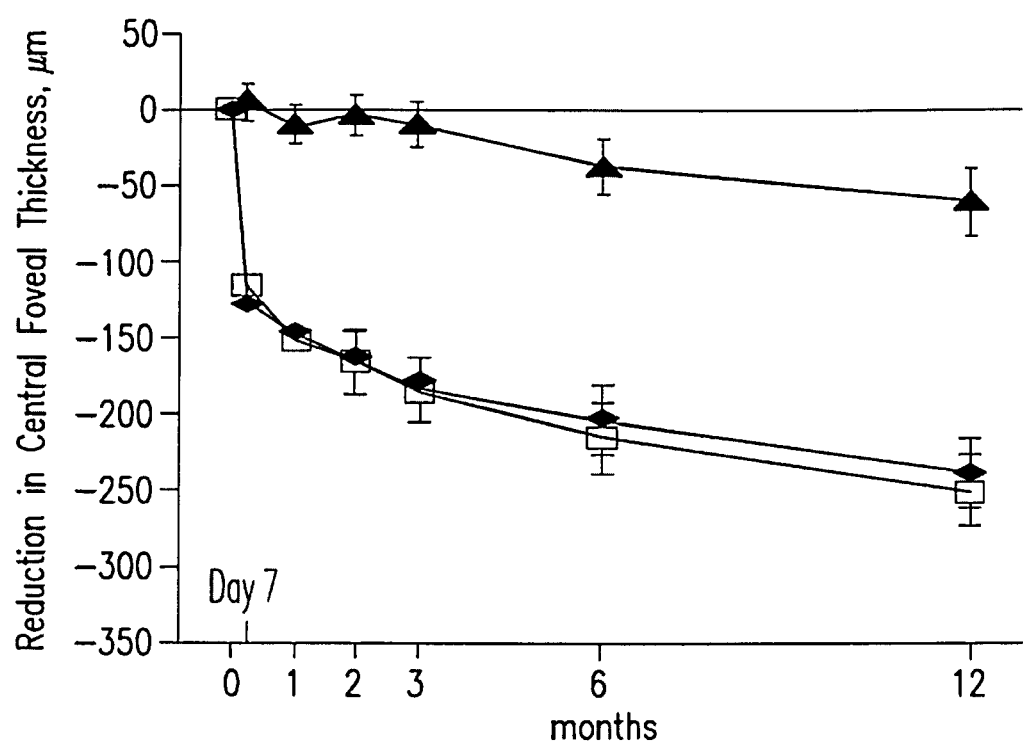
FIG. 1 depicts the results of two phase three studies to determine the effect of intravitreal injections of ranibizumab in patients with diabetic macular edema.

In some embodiments, the invention provides a method of treating a condition in a subject in need thereof, the method comprising administering to the subject a therapeutically-effective amount of a compound that activates Tie-2, or a pharmaceutically-acceptable salt thereof, and an agent that increases solubility of the compound that activates Tie-2, or the pharmaceutically-acceptable salt thereof as compared to solubility in absence of the agent.

In some embodiments, the invention provides a method of treating a condition in a subject in need thereof, the method comprising administering to the subject a therapeutically-effective amount of a compound that activates Tie-2, or a pharmaceutically-acceptable salt thereof, wherein the administration provides a plasma concentration in the subject of the compound that activates Tie-2 or the pharmaceutically-acceptable salt thereof of about 25 ng/mL to about 500 ng/ml.

In some embodiments, the invention provides a pharmaceutical composition comprising: a) a compound that activates Tie-2, or a pharmaceutically-acceptable salt thereof; and b) an agent that improves the aqueous solubility of the compound that activates Tie-2, or the pharmaceutically-acceptable salt thereof.

In some embodiments, the invention provides a pharmaceutical composition comprising: a) a Tie-2 activator or a pharmaceutically-acceptable salt thereof; and b) an antibody.

In some embodiments, the invention provides a kit comprising: a) a Tie-2 activator or a pharmaceutically-acceptable salt thereof; b) an antibody; and c) written instructions on use of the kit in treatment of a condition.

In some embodiments, the invention provides a method of treating a condition, the method comprising administering to a subject in need thereof: a) a therapeutically-effective amount of a Tie-2 activator or a pharmaceutically-acceptable salt thereof; and b) a therapeutically-effective amount of an antibody.

In some embodiments, the invention provides a complex comprising: a) a Tie-2 activator, or a pharmaceutically-acceptable salt thereof; and b) a molecule comprising a channel, wherein the compound that activates Tie-2, or the pharmaceutically-acceptable salt thereof is held in the channel of the molecule by non-covalent interactions.

In some embodiments, the invention provides a method of treating a condition, the method comprising administering to a subject in need thereof a therapeutically-effective amount of complex comprising: a) a Tie-2 activator, or a pharmaceutically-acceptable salt thereof; and b) a molecule comprising a channel, wherein the compound that activates Tie-2, or the pharmaceutically-acceptable salt thereof is held in the channel of the molecule by non-covalent interactions.

DETAILED DESCRIPTION

Provided herein are compounds and methods of treating ocular disorders that are characterized by vascular instability, vascular leakage, and neovascularization. HPTP-β is a member of the receptor-like family of the protein tyrosine phosphatases (PTPases). HPTP-β is a transmembrane protein found primarily in endothelial cells that displays structural and functional similarity to cell adhesion molecules (CAMs). HPTP-β is unique among receptor-like PTPases in that it contains a single catalytic domain. One of the main functions of HPTP-β is to regulate Tie-2 negatively.

Tie-2 is a receptor tyrosine kinase found almost exclusively in endothelial cells. The principle regulators of Tie-2 phosphorylation are Angiopoietin-1 (Ang-1) and Angiopoietin-2 (Ang-2). Upon Angiopoietin-1 binding to Tie-2, the level of Tie-2 receptor phosphorylation increases. The duration of Tie-2 receptor phosphorylation is regulated by HPTP-β, which cleaves off the phosphate. Tie-2 receptor phosphorylation helps maintain endothelial cell proximity; therefore, the duration of Tie-2 receptor phosphorylation is an important determinant of endothelial cell proximity. For example, when severe inflammation occurs, the capillary endothelial cells separate, allowing proteins, to enter the interstitial space. Separation of the capillary endothelial cells, and subsequent leak of proteins in the interstitial space, is known as vascular leak and can lead to dangerous hypotension (low blood pressure), edema, hemoconcentration, and hypoalbuminemia. Inhibition of HPTP-β leads to increased levels and Tie-2 receptor phosphorylation, a process that can maintain or restore capillary endothelial cell proximity.

The present disclosure relates to compositions and methods for treating conditions, such as ocular diseases, for example, those wherein neovascularization and vascular leakage are present. These diseases are sometimes characterized as diseases wherein there is an elevated angiogenic response in the vessels associated with the eye. The present disclosure provides a Human Protein Tyrosine Phosphatase-beta (HPTP-β) inhibitor that provides vascular stabilization. Human Protein Tyrosine Phosphatase-Beta (HPTP-β) Inhibitors.

Compounds disclosed herein can be effective as Tie-2 activators. The compounds can effect that activity, for example, by binding or inhibiting HPTP-β Such compounds can bind, for example, by mimicking the binding mechanism of a native substrate, such as a phosphorylated compound. A compound can be a phosphate mimetic or bioisostere, for example, a sulfamic acid. The compound could also be derived from an amino acid building block or comprise an amino acid backbone for efficiency and economy of synthesis.

In some embodiments, a compound of the invention is a compound of formula:

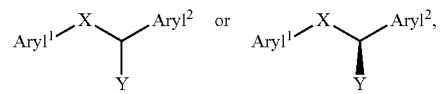

wherein:
Aryl$^1$ is an aryl group which is substituted or unsubstituted;
Aryl$^2$ is an aryl group which is substituted or unsubstituted;
X is alkylene, alkenylene, alkynylene, an ether linkage, an amine linkage, an amide linkage, an ester linkage, a thioether linkage, a carbamate linkage, a carbonate linkage, a urethane linkage, a sulfone linkage, any of which is substituted or unsubstituted, or a chemical bond; and Y is H, aryl, heteroaryl, NH(aryl), NH(heteroaryl), NHSO$_2$R$^g$, or NHCOR$^g$, any of which is substituted or unsubstituted, or

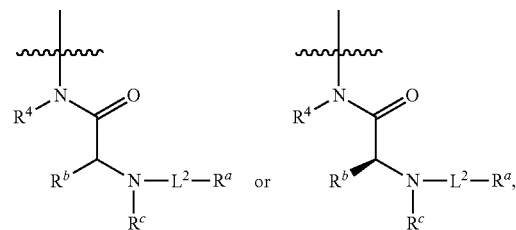

wherein
L$^2$ is alkylene, alkenylene, or alkynylene, any of which is substituted or unsubstituted, or together with the nitrogen atom to which L is bound forms an amide linkage, a carbamate linkage, a urethane linkage, or a sulfonamide linkage, or a chemical bond, or together with any of R$^a$, R$^b$, R$^c$, and R$^d$ forms a ring that is substituted or unsubstituted. R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^b$, R$^c$, and R$^d$ forms a ring that is substituted or unsubstituted. R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^a$, R$^c$, and R$^d$ forms a ring that is substituted or unsubstituted. R$^c$ is H or alkyl which is substituted or unsubstituted, or together with any of L$^2$, R$^a$, R$^b$, and R$^d$ forms a ring that is substituted or unsubstituted.

$R^d$ is H or alkyl which is substituted or unsubstituted, or together with any of $L^2$, $R^a$, $R^b$, and $R^c$ forms a ring that is substituted or unsubstituted, and $R^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

In some embodiments, aryl$^1$ is substituted or unsubstituted phenyl, aryl$^2$ is substituted or unsubstituted heteroaryl, and X is alkylene. In some embodiments, aryl$^1$ is substituted phenyl, aryl$^2$ is substituted heteroaryl, and X is methylene.

In some embodiments, a compound is of the formula:

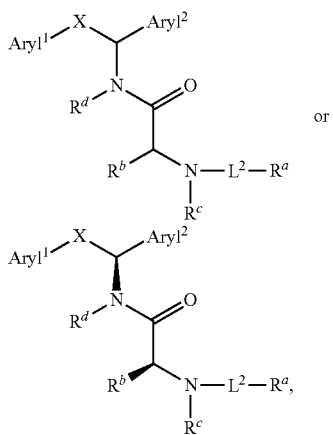

wherein
wherein aryl$^1$ is para-substituted phenyl, aryl$^2$ is substituted heteroaryl, X is methylene. $L^2$ is alkylene, alkenylene, or alkynylene, any of which is substituted or unsubstituted, or together with the nitrogen atom to which L is bound forms an amide linkage, a carbamate linkage, a urethane linkage, or a sulfonamide linkage, or a chemical bond. $R^a$ is H, alkyl, alkenyl, alkynyl, aryl, arylalkyl, heterocyclyl, heterocyclylalkyl, heteroaryl, or heteroarylalkyl, any of which is substituted or unsubstituted. $R^b$ is H, alkyl, alkenyl, alkynyl, aryl, arylalkyl, heterocyclyl, heterocyclylalkyl, heteroaryl, or heteroarylalkyl, any of which is substituted or unsubstituted. $R^c$ is H or alkyl which is substituted or unsubstituted, and $R^d$ is H or alkyl which is substituted or unsubstituted.

In some embodiments, aryl$^1$ is para-substituted phenyl, aryl$^2$ is a substituted thiazole moiety. X is methylene, $L^2$ together with the nitrogen atom to which L is bound forms a carbamate linkage, $R^a$ is alkyl, which is substituted or unsubstituted, $R^b$ is arylalkyl, which is substituted or unsubstituted, $R^c$ is H, and $R^d$ is H.

In some embodiments, Aryl$^2$ is:

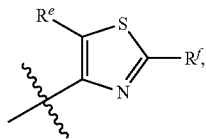

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a urethane group, a thioether group, a thioester group, a thioacid group, aryl, arylalkyl, heterocyclyl, heterocyclylalkyl, heteroaryl, or heteroarylalkyl, any of which is substituted or unsubstituted, and $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a urethane group, a thioether group, a thioester group, a thioacid group, aryl, arylalkyl, heterocyclyl, heterocyclylalkyl, heteroaryl, or heteroarylalkyl, any of which is substituted or unsubstituted.

In some embodiments, $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted, and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, or an alkoxy group, any of which is substituted or unsubstituted and $R^f$ is alkyl, aryl, heterocyclyl, or heteroaryl, any of which is substituted or unsubstituted. In some embodiments, aryl$^1$ is 4-phenylsulfamic acid, $R^a$ is alkyl, which is substituted or unsubstituted, $R^b$ is arylalkyl, which is substituted or unsubstituted, $R^e$ is H; and $R^f$ is heteroaryl. In some embodiments, aryl$^1$ is 4-phenylsulfamic acid, $R^a$ is alkyl, which is substituted or unsubstituted, $R^b$ is arylalkyl, which is substituted or unsubstituted, $R^e$ is H; and $R^f$ is alkyl In some embodiments, Aryl$^2$ is:

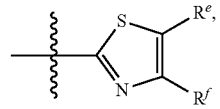

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a urethane group, a thioether group, a thioester group, a thioacid group, aryl, arylalkyl, heterocyclyl, heterocyclylalkyl, heteroaryl, or heteroarylalkyl, any of which is substituted or unsubstituted, $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a urethane group, a thioether group, a thioester group, a thioacid group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, or an alkoxy group, any of which is substituted or unsubstituted and $R^f$ is alkyl, aryl, heterocyclyl, or heteroaryl, any of which is substituted or unsubstituted. In some embodiments, aryl$^1$ is 4-phenylsulfamic acid, $R^a$ is alkyl, which is substituted or unsubstituted, $R^b$ is arylalkyl, which is substituted or unsubstituted, $R^e$ is H; and $R^f$ is heteroaryl.

In some embodiments, a substituted phenyl group is:

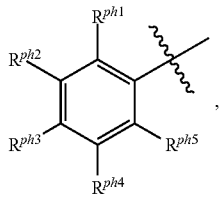

wherein:
each of $R^{ph1}$, $R^{ph2}$, $R^{ph3}$, $R^{ph4}$, and $R^{ph5}$ is independently H, OH, F, Cl, Br, I, CN, sulamic acid, tosylate, mesylate, triflate, besylate, alkyl, alkenyl, alkynyl, an alkoxy group, a sulfhydryl group, a nitro group, a nitroso group, an azido group, a sulfoxide group, a sulfone group, a sulfonamide group, an ether group, a carboxylic acid group, a carboxaldehyde group, an ester group, an amine group, an amide group, a carbonate group, a carbamate group, a urethane group, a thioether group, a thioester group, a thioacid group, aryl, arylalkyl, heterocyclyl, heterocyclylalkyl, heteroaryl, or heteroarylalkyl Optional Substituents for Chemical Groups.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, and ester groups.

The following are non-limiting examples of units which can substitute for hydrogen atoms:
i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings;
v) substituted or unsubstituted $C_1$-$C_9$ heteroaryl rings;
vi) $-(CR^{102a}R^{102b})_aOR^{101}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;
vii) $-(CR^{102a}R^{102b})_aC(O)R^{101}$; for example, —COCH$_3$, —CH$_2$COCH$_3$, —COCH$_2$CH$_3$, —CH$_2$COCH$_2$CH$_3$, —COCH$_2$CH$_2$CH$_3$, and —CH$_2$COCH$_2$CH$_2$CH$_3$;
viii) $-(CR^{102a}R^{102b})_aC(O)OR^{101}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;
ix) $-(CR^{102a}R^{102b})_aC(O)N(R^{101})_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;
x) $-(CR^{102a}R^{102b})_aN(R^{101})_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;
xi) halogen; —F, —Cl, —Br, and —I;
xii) $-(CR^{102a}R^{102b})_aCN$;
xiii) $-(CR^{102a}R^{102b})_aNO_2$;
xiv) $-CH_jX_k$; wherein X is halogen, the index j is an integer from 0 to 2, j+k=3; for example, —CH$_2$F, —CHF$_2$, —CF$_3$, —CCl$_3$, or —CBr$_3$;
xv) $-(CR^{102a}R^{102b})_aSR^{101}$; —SH, —CH$_2$SH, —SCH$_3$, —CH$_2$SCH$_3$, —SC$_6$H$_5$, and —CH$_2$SC$_6$H$_5$;
xvi) $-(CR^{102a}R^{102b})_aSO_2R^{101}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and
xvii) $-(CR^{102a}R^{102b})_aSO_3R^{101}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each $R^{101}$ is independently hydrogen, substituted or unsubstituted $C_1$-$C_6$ linear, branched, or cyclic alkyl, phenyl, benzyl, heterocyclic, or heteroaryl; or two $R^{101}$ units can be taken together to form a ring comprising 3-7 atoms; $R^{102a}$ and $R^{102b}$ are each independently hydrogen or $C_1$-$C_4$ linear or branched alkyl; the index "a" is from 0 to 4.

Non-limiting examples of alkyl and alkylene groups include straight, branched, and cyclic alkyl and alkylene groups. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of substituted and unsubstituted acyclic hydrocarbyl include:

1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), and 3-carboxypropyl ($C_3$).

2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), and 7-hydroxy-7-methyloct-3,5-dien-2-yl ($C_9$).

3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), and 5-hydroxy-5-ethylhept-3-ml ($C_9$).

Non-limiting examples of substituted and unsubstituted cyclic hydrocarbyl include: rings comprising from 3 to 20 carbon atoms, wherein the atoms which comprise said rings are limited to carbon atoms, and further each ring can be independently substituted with one or more moieties capable of replacing one or more hydrogen atoms. The following are non-limiting examples of substituted and unsubstituted carbocyclic rings:

i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).

ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$).

iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Also included are $C_1$-$C_6$ tethered cyclic hydrocarbyl units (whether carbocyclic units, $C_6$ or $C_{10}$ aryl units, heterocyclic units, or heteroaryl units) can be connected to another moiety, unit, or core of the molecule by way of a $C_1$-$C_6$ alkylene unit. Non-limiting examples of tethered cyclic hydrocarbyl units include benzyl $C_1$-($C_6$) having the formula:

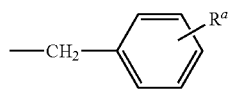

wherein $R^a$ is optionally one or more independently chosen substitutions for hydrogen. Further examples include other aryl units, inter alia, (2-hydroxyphenyl)hexyl $C_6$—($C_6$); naphthalen-2-ylmethyl $C_1$-($C_{10}$), 4-fluorobenzyl $C_1$-($C_6$), 2-(3-hydroxyphenyl)ethyl $C_2$—($C_6$), as well as substituted and unsubstituted $C_3$-$C_{10}$ alkylenecarbocyclic units, for example, cyclopropylmethyl $C_1$-($C_3$), cyclopentylethyl $C_2$—($C_5$), cyclohexylmethyl $C_1$-($C_6$); Included within this category are substituted and unsubstituted $C_1$-$C_{10}$ alkyleneheteroaryl units, for example a 2-picolyl $C_1$-($C_6$) unit having the formula:

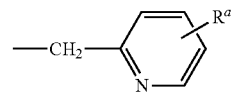

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

A halo group can be any halogen atom, for example, fluorine, chlorine, bromine, or iodine.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluoyl, naphthyl, pyrrolyl, pyridyl, imidazolyl, thiophenyl, and furyl.

Non-limiting examples of aryl groups can include: i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$); and ii) $C_6$ or $C_{10}$ aryl rings fused with 1 or 2 saturated rings to afford $C_8$-$C_{20}$ ring systems, non-limiting examples of which include, bicyclo[4.2.0]octa-1,3,5-trienyl ($C_8$), and indanyl ($C_9$).

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), thiazolidinyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydroquinoline ($C_9$); and ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).

Non-limiting examples of heteroaryl include: i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), isoxazolyl ($C_3$), isothiazolyl ($C_3$), furanyl ($C_4$), thiophenyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$); and ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-c]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

Non-limiting examples of heteroaryl include 1,2,3,4-tetrahydroquinoline having the formula:

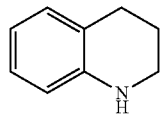

6,7-Dihydro-5H-cyclopentapyrimidine having the formula:

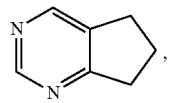

and
1,2,3,4-tetrahydro-[1,8]naphthpyridine having the formula:

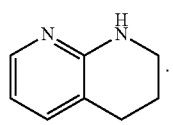

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

Compounds of the Invention.

In some embodiments, a compound of the disclosure has Formula (I):

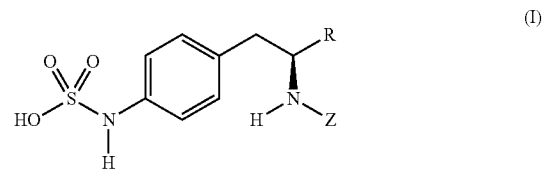

wherein the carbon atom having the amino unit has the stereochemistry indicated in the following formula:

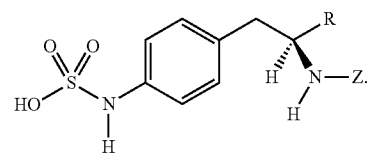

The units which comprise R and Z can comprise units having any configuration, and, as such, a compound of the disclosure can be a single enantiomer, a diastereomer, or pairs or combinations thereof. In addition, the compounds can be isolated as salts or hydrates. In the case of salts, the compounds can comprise more than one cation or anion. In the case of hydrates, any number of water molecules, or fractional part thereof (for example, less than 1 water molecule present for each molecule of analogue) can be present.

R Units

R is a substituted or unsubstituted thiazolyl unit having the formula:

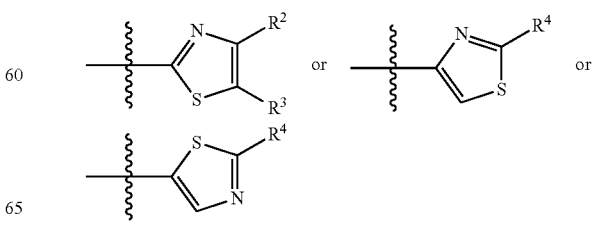

$R^2$, $R^3$, and $R^4$ are substituent groups that can be independently chosen from a wide variety of non-carbon atom containing units (for example, hydrogen, hydroxyl, amino, halogen, and nitro) or organic substituent units, such as substituted and unsubstituted acyclic hydrocarbyl and cyclic hydrocarbyl units as described herein. The carbon comprising units can comprise, for example, from 1 to 12 carbon atoms, or 1 to 10 carbon atoms, or 1 to 6 carbon atoms.

An example of compounds of Formula (I) include compounds wherein R units are thiazol-2-yl units having the formula:

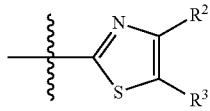

wherein $R^2$ and $R^3$ are each independently chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted $C_2$-$C_6$ linear, $C_3$-$C_6$ branched, or $C_3$-$C_6$ cyclic alkenyl;
iv) substituted or unsubstituted $C_2$-$C_6$ linear or $C_3$-$C_6$ branched alkynyl;
v) substituted or unsubstituted $C_6$ or $C_{10}$ aryl;
vi) substituted or unsubstituted $C_1$-$C_9$ heteroaryl;
vii) substituted or unsubstituted $C_1$-$C_9$ heterocyclic; or
viii) $R^2$ and $R^3$ can be taken together to form a saturated or unsaturated ring having from 5 to 7 atoms; wherein from 1 to 3 atoms can optionally be heteroatoms chosen from oxygen, nitrogen, and sulfur.

The following are non-limiting examples of units that can substitute for one or more hydrogen atoms on the $R^2$ and $R^3$ units. The following substituents, as well as others not herein described, are each independently chosen from:
i) $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein;
v) substituted or unsubstituted $C_1$-$C_9$ heteroaryl rings; as described herein;
vi) —$(CR^{21a}R^{21b})_pOR^{20}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{21a}R^{21b})_pC(O)R^{20}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
viii) —$(CR^{21a}R^{21b})_pC(O)OR^{20}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

ix) —$(CR^{21a}R^{21b})_pC(O)N(R^{20})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
x) —$(CR^{21a}R^{21b})_pN(R^{20})_2$; for example, —$NH_2$, —$CH_2NH_2$, —$NHCH_3$, —$CH_2NHCH_3$, —$N(CH_3)_2$, and —$CH_2N(CH_3)_2$;
xi) halogen; —F, —Cl, —Br, and —I;
xii) —$(CR^{21a}R^{21b})_pCN$;
xiii) —$(CR^{21a}R^{21b})_pNO_2$;
xiv) —$(CH_jX_k)_hCH_{j'}X_{k'}$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;
xv) —$(CR^{21a}R^{21b})_pSR^{20}$; —SH, —$CH_2SH$, —$SCH_3$, —$CH_2SCH_3$, —$SC_6H_5$, and —$CH_2SC_6H_5$;
xvi) —$(CR^{21a}R^{21b})_pSO_2R^{20}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and
xvii) —$(CR^{21a}R^{21b})_pSO_3R^{20}$; for example, —$SO_3H$, —$CH_2SO_3H$, —$SO_3CH_3$, —$CH_2SO_3CH_3$, —$SO_3C_6H_5$, and —$CH_2SO_3C_6H_5$;
wherein each $R^{20}$ is independently hydrogen, substituted or unsubstituted $C_1$-$C_4$ linear, $C_3$-$C_4$ branched, or $C_3$-$C_4$ cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or $C_3$-$C_4$ branched alkyl; the index p is from 0 to 4.

An example of compounds of Formula (I) includes R units having the formula:

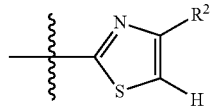

wherein $R^3$ is hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), 1-methylbutyl ($C_5$), 2-methylbutyl ($C_5$), 3-methylbutyl ($C_5$), cyclopropyl ($C_3$), n-hexyl ($C_6$), 4-methylpentyl ($C_6$), and cyclohexyl ($C_6$).

An example of compounds of Formula (I) include R units having the formula:

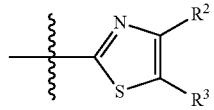

wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl ($C_1$) or ethyl ($C_2$). Non-limiting examples of this aspect of R includes 4,5-dimethylthiazol-2-yl, 4-ethyl-5-methylthiazol-2-yl, 4-methyl-5-ethylthiazol-2-yl, and 4,5-diethylthiazol-2-yl.

An example of compounds of Formula (I) includes R units wherein $R^3$ is hydrogen and $R^2$ is a substituted alkyl unit, said substitutions chosen from:
i) halogen: —F, —Cl, —Br, and —I;
ii) —$N(R^{11})_2$; and
iii) —$OR^{11}$;

wherein each $R^{11}$ is independently hydrogen or $C_1$-$C_4$ linear or $C_3$-$C_4$ branched alkyl. Non-limiting examples of units that can be a substitute for a $R^2$ or $R^3$ hydrogen atom on R units include —$CH_2F$, —$CHF_2$, —$CF_3$, —$CH_2CF_3$, —$CH_2CH_2CF_3$, —$CH_2Cl$, —$CH_2OH$, —$CH_2OCH_3$, —$CH_2CH_2OH$, —$CH_2CH_2OCH_3$, —$CH_2NH_2$, —$CH_2NHCH_3$, —$CH_2N(CH_3)_2$, and —$CH_2NH(CH_2CH_3)$.

Further non-limiting examples of units that can be a substitute for a $R^2$ or $R^3$ hydrogen atom on R units include 2,2-difluorocyclopropyl, 2-methoxycyclohexyl, and 4-chlorocyclohexyl.

An example of compounds of Formula (I), R units include units wherein $R^3$ is hydrogen and $R^2$ is phenyl or substituted phenyl, wherein non-limiting examples of $R^2$ units include phenyl, 3,4-dimethylphenyl, 4-tert-butylphenyl, 4-cyclopropylphenyl, 4-diethylaminophenyl, 4-(trifluoromethyl)phenyl, 4-methoxyphenyl, 4-(difluoromethoxy)-phenyl, 4-(trifluoromethoxy)phenyl, 3-chlropheny, 4-chlorophenyl, and 3,4-dichlorophenyl, which when incorporated into the definition of R affords the following R units 4-phenylthiazol-2-yl, 3,4-dimethylphenylthiazol-2-yl, 4-tert-butylphenylthiazol-2-yl, 4-cyclopropylphenylthiazol-2-yl, 4-diethylaminophenylthiazol-2-yl, 4-(trifluoromethyl)-phenylthiazol-2-yl, 4-methoxyphenylthiazol-2-yl, 4-(difluoromethoxy)phenylthiazol-2-yl, 4-(trifluoromethoxy)phenylthiazol-2-yl, 3-chlorophenylthiazol-2-yl, 4-chlorophenylthiazol-2-yl, and 3,4-dichlorophenylthiazol-2-yl.

An example of compounds of Formula (I) includes R units wherein $R^2$ is chosen from hydrogen, methyl, ethyl, n-propyl, and iso-propyl and $R^3$ is phenyl or substituted phenyl. A non-limiting example of a R unit according to the fifth aspect of the first category of R units includes 4-methyl-5-phenylthiazol-2-yl and 4-ethyl-5-phenylthiazol-2-yl.

An example of compounds of Formula (I) includes R units wherein $R^3$ is hydrogen and $R^2$ is a substituted or unsubstituted heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Further non-limiting example of compounds of Formula (I) includes R units wherein $R^2$ is substituted or unsubstituted thiophen-2-yl, for example thiophen-2-yl, 5-chlorothiophen-2-yl, and 5-methylthiophen-2-yl.

An example of compounds of Formula (I) includes R units wherein $R^2$ is substituted or unsubstituted thiophen-3-yl, for example thiophen-3-yl, 5-chlorothiophen-3-yl, and 5-methylthiophen-3-yl.

An example of compounds of Formula (I) includes R units wherein $R^2$ and $R^3$ are taken together to form a saturated or unsaturated ring having from 5 to 7 atoms. Non-limiting examples of the sixth aspect of the first category of R units include 5,6-dihydro-4H-cyclopenta[d]thiazol-2-yl and 4,5,6,7-tetrahydrobenzo[d]thiazol-2-yl.

Further examples of compounds of Formula (I) include R units that are thiazol-4-yl or thiazol-5-yl units having the formula:

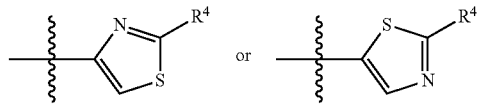

wherein $R^4$ is a unit chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted $C_2$-$C_6$ linear, $C_3$-$C_6$ branched, or $C_3$-$C_6$ cyclic alkenyl;
iv) substituted or unsubstituted $C_2$-$C_6$ linear or branched alkynyl;
v) substituted or unsubstituted $C_6$ or $C_{10}$ aryl;
vi) substituted or unsubstituted $C_1$-$C_9$ heteroaryl; or
vii) substituted or unsubstituted $C_1$-$C_9$ heterocyclic.

The following are non-limiting examples of units that can substitute for one or more hydrogen atoms on the $R^4$ units. The following substituents, as well as others not herein, described, are each independently chosen:

i) $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings;
v) substituted or unsubstituted $C_1$-$C_9$ heteroaryl rings;
vi) —$(CR^{21a}R^{21b})_pC(O)R^{20}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{21a}R^{21b})_pC(O)R^{20}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
viii) —$(CR^{21a}R^{21b})_pC(O)OR^{20}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
ix) —$(CR^{21a}R^{21b})_pC(O)N(R^{20})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
x) —$(CR^{21a}R^{21b})_pN(R^{20})_2$; for example, —$NH_2$, —$CH_2NH_2$, —$NHCH_3$, —$CH_2NHCH_3$, —$N(CH_3)_2$, and —$CH_2N(CH_3)_2$;
xi) halogen; —F, —Cl, —Br, and —I;
xii) —$(CR^{21a}R^{21b})_pCN$;
xiii) —$(CR^{21a}R^{21b})_pNO_2$;
xiv) —$(CH_jX_k)_hCH_jX_k$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;
xv) —$(CR^{21a}R^{21b})_pSR^{20}$; —SH, —$CH_2SH$, —$SCH_3$, —$CH_2SCH_3$, —$SC_6H_5$, and —$CH_2SC_6H_5$;

xvi) —$(CR^{21a}R^{21b})_pSO_2R^{20}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and xvii) —$(CR^{21a}R^{21b})_pSO_3R^{20}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{20}$ is independently hydrogen, substituted or unsubstituted $C_1$-$C_4$ linear, $C_3$-$C_4$ branched, or $C_3$-$C_4$ cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or $C_3$-$C_4$ branched alkyl; the index p is from 0 to 4.

An example of compounds of Formula (I) includes R units wherein $R^4$ is hydrogen.

An example of compounds of Formula (I) includes R units wherein $R^4$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$). Non-limiting examples of this aspect of R includes 2-methylthiazol-4-yl, 2-(n-propyl)thiazol-4-yl, and 2-(iso-propyl)thiazol-4-yl.

An example of compounds of Formula (I) includes R units wherein $R^4$ is substituted or unsubstituted phenyl, non-limiting examples of which include phenyl, 2-fluorophenyl, 2-chlorophenyl, 2-methylphenyl, 2-methoxyphenyl, 3-fluorophenyl, 3-chlorophenyl, 3-methylphenyl, 3-methoxyphenyl, 4-fluorophenyl, 4-chlorophenyl, 4-methylphenyl, and 4-methoxyphenyl.

An example of compounds of Formula (I) includes R units wherein $R^4$ is substituted or unsubstituted heteroaryl, non-limiting examples of which include thiophen-2-yl, thiophen-3-yl, thiazol-2-yl, thiazol-4-yl, thiazol-5-yl, 2,5-dimethylthiazol-4-yl, 2,4-dimethylthiazol-5-yl, 4-ethylthiazol-2-yl, oxazol-2-yl, oxazol-4-yl, oxazol-5-yl, and 3-methyl-1,2,4-oxadiazol-5-yl.

Another example of 5-member ring R units includes substituted or unsubstituted imidazolyl units having the formula:

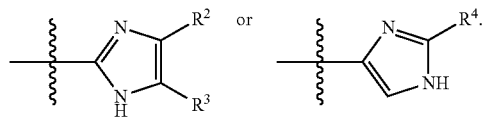

One example of imidazolyl R units includes imidazol-2-yl units having the formula:

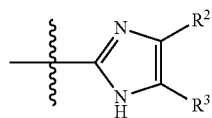

wherein $R^2$ and $R^3$ are each independently chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted $C_2$-$C_6$ linear, $C_3$-$C_6$ branched, or $C_3$-$C_6$ cyclic alkenyl;
iv) substituted or unsubstituted $C_2$-$C_6$ linear or branched alkynyl;
v) substituted or unsubstituted $C_6$ or $C_{10}$ aryl;
vi) substituted or unsubstituted $C_1$-$C_9$ heteroaryl;
vii) substituted or unsubstituted $C_1$-$C_9$ heterocyclic; or
viii) $R^2$ and $R^3$ can be taken together to form a saturated or unsaturated ring having from 5 to 7 atoms; wherein from 1 to 3 atoms can optionally be heteroatoms chosen from oxygen, nitrogen, and sulfur.

The following are non-limiting examples of units that can substitute for one or more hydrogen atoms on the $R^2$ and $R^3$ units. The following substituents, as well as others not herein described, are each independently chosen:
i) $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein;
v) substituted or unsubstituted $C_1$-$C_9$ heteroaryl rings; as described herein;
vi) —$(CR^{21a}R^{21b})_zOR^{20}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{21a}R^{21b})_zC(O)OR^{20}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
viii) —$(CR^{21a}R^{21b})_zC(O)OR^{20}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
ix) —$(CR^{21a}R^{21b})_zC(O)N(R^{20})_2$; for example, —$CONH_2$, —$CH_2CONH_2$; —$CONHCH_3$, —$CH_2CONHCH_3$, —$CON(CH_3)_2$, and —$CH_2CON(CH_3)_2$;
x) —$(CR^{21a}R^{21b})_zN(R^{20})_2$; for example, —$NH_2$, —$CH_2NH_2$, —$NHCH_3$, —$CH_2NHCH_3$, —$N(CH_3)_2$, and —$CH_2N(CH_3)_2$;
xi) halogen; —F, —Cl, —Br, and —I;
xii) —$(CR^{21a}R^{21b})_zCN$;
xiii) —$(CR^{21a}R^{21b})_zNO_2$;
xiv) —$(CH_jX_k)_hCH_jX_k$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;
xv) —$(CR^{21a}R^{21b})_zSR^{20}$; —SH, —$CH_2SH$, —$SCH_3$, —$CH_2SCH_3$, —$SC_6H_5$, and —$CH_2SC_6H_5$;
xvi) —$(CR^{21a}R^{21b})_zSO_2R^{20}$, for example, —$SO_2H$, —$CH_2SO_2H$, —$SO_2CH_3$, —$CH_2SO_2CH_3$, —$SO_2C_6H_5$, and —$CH_2SO_2C_6H_5$; and
xvii) —$(CR^{21a}R^{21b})_zSO_3R^{20}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{20}$ is independently hydrogen, substituted or unsubstituted $C_1$-$C_4$ linear, $C_3$-$C_4$ branched, or $C_3$-$C_4$ cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or $C_3$-$C_4$ branched alkyl; the index p is from 0 to 4.

One example of R units includes compounds wherein R units have the formula:

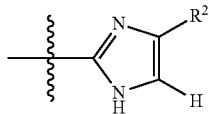

wherein $R^3$ is hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$).

Another example of R units includes compounds wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl ($C_1$) or ethyl ($C_2$). Non-limiting examples of this aspect of R includes 4,5-dimethylimidazol-2-yl, 4-ethyl-5-methylimidazol-2-yl, 4-methyl-5-ethylimidazol-2-yl, and 4,5-diethylimidazol-2-yl.

An example of R units includes compounds wherein $R^3$ is hydrogen and $R^2$ is a substituted alkyl unit chosen, said substitutions chosen from:
i) halogen: —F, —Cl, —Br, and —I;
ii) —N($R^{11}$)$_2$; and
iii) —O$R^{11}$;
wherein each $R^{11}$ is independently hydrogen or $C_1$-$C_4$ linear or $C_3$-$C_4$ branched alkyl.

Non-limiting examples of units comprising this embodiment of R includes: —CH$_2$F, —CHF$_2$, —CF$_3$, —CH$_2$CF$_3$, —CH$_2$Cl, —CH$_2$OH, —CH$_2$OCH$_3$, —CH$_2$CH$_2$OH, —CH$_2$CH$_2$OCH$_3$, —CH$_2$NH$_2$, —CH$_2$NHCH$_3$, —CH$_2$N(CH$_3$)$_2$, and —CH$_2$NH(CH$_2$CH$_3$).

An example of R units includes units wherein $R^3$ is hydrogen and $R^2$ is phenyl.

An example of R units includes units wherein $R^3$ is hydrogen and $R^2$ is a heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Z Units

Z is a unit having the formula:

$R^1$ is chosen from:
i) hydrogen;
ii) hydroxyl;
iii) amino;
iv) substituted or unsubstituted $C_1$-$C_6$ linear, $C_3$-$C_6$ branched or $C_3$-$C_6$ cyclic alkyl;
v) substituted or unsubstituted $C_1$-$C_6$ linear, $C_3$-$C_6$ branched or $C_3$-$C_6$ cyclic alkoxy;
vi) substituted or unsubstituted $C_6$ or $C_{10}$ aryl;
vii) substituted or unsubstituted $C_1$-$C_9$ heterocyclic rings; or
viii) substituted or unsubstituted $C_1$-$C_9$ heteroaryl rings.

The following are non-limiting examples of units that can substitute for one or more hydrogen atoms on the $R^1$ units. The following substituents, as well as others not herein described, are each independently chosen:

i) $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein;
v) substituted or unsubstituted $C_1$-$C_9$ heteroaryl rings; as described herein;
vi) —(C$R^{31a}R^{31b}$)$_q$O$R^{30}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;
vii) —(C$R^{31a}R^{31b}$)$_q$C(O)$R^{30}$; for example, —COCH$_3$, —CH$_2$COCH$_3$, —COCH$_2$CH$_3$, —CH$_2$COCH$_2$CH$_3$, —COCH$_2$CH$_2$CH$_3$, and —CH$_2$COCH$_2$CH$_2$CH$_3$;
viii) —(C$R^{31a}R^{31b}$)$_q$C(O)O$R^{30}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;
ix) —(C$R^{31a}R^{31b}$)$_q$C(O)N($R^{30}$)$_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;
x) —(C$R^{31a}R^{31b}$)$_q$N($R^{30}$)$_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;
xi) halogen; —F, —Cl, —Br, and —I;
xii) —(C$R^{31a}R^{31b}$)$_q$CN;
xiii) —(C$R^{31a}R^{31b}$)$_q$NO$_2$;
xiv) —(CH$_j$X$_k$)$_h$CH$_{j'}$X$_{k'}$; wherein X is halogen, the index j is an integer from 0 to 2, j+k=3, the index j' is an integer from 0 to 2, j'+k'=2, the index h is from 0 to 6; for example, —CH$_2$F, —CHF$_2$, —CF$_3$, —CH$_2$CF$_3$, —CHFCF$_3$, —CCl$_3$, or —CBr$_3$;
xv) —(C$R^{31a}R^{31b}$)$_q$S$R^{30}$; —SH, —CH$_2$SH, —SCH$_3$, —CH$_2$SCH$_3$, —SC$_6$H$_5$, and —CH$_2$SC$_6$H$_5$;
xvi) —(C$R^{31a}R^{31b}$)$_q$SO$_2$$R^{30}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and
xvii) —(C$R^{31a}R^{31b}$)$_q$SO$_3$$R^{30}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;
wherein each $R^{30}$ is independently hydrogen, substituted or unsubstituted $C_1$-$C_6$ linear, $C_3$-$C_6$ branched, or $C_3$-$C_6$ cyclic alkyl, phenyl, benzyl, heterocyclic, or heteroaryl; or two $R^{30}$ units can be taken together to form a ring comprising 3-7 atoms; $R^{31a}$ and $R^{31b}$ are each independently hydrogen or $C_1$-$C_4$ linear or $C_3$-$C_4$ branched alkyl; the index q is from 0 to 4.

One example of $R^1$ units includes substituted or unsubstituted phenyl ($C_6$ aryl) units, wherein each substitution is independently chosen from: halogen, $C_1$-$C_4$ linear, branched alkyl, or cyclic alkyl, —O$R^{11}$, —CN, —N($R^{11}$)$_2$, —CO$_2$$R^{11}$, —C(O)N($R^{11}$)$_2$, —N$R^{11}$C(O)$R^{11}$, —NO$_2$, and —SO$_2$$R^{11}$; each $R^{11}$ is independently hydrogen; substituted or unsubstituted $C_1$-$C_4$ linear, $C_3$-$C_4$ branched, $C_3$-$C_4$ cyclic alkyl, alkenyl, or alkynyl; substituted or unsubstituted phenyl or benzyl; or two $R^{11}$ units can be taken together to form a ring comprising from 3-7 atoms.

An example of $R^1$ units includes substituted $C_6$ aryl units chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl.

An example of $R^1$ units includes substituted or unsubstituted $C_6$ aryl units chosen from 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, and 2,4,6-trichlorophenyl.

An example of $R^1$ units includes substituted $C_6$ aryl units chosen from 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

An example of $R^1$ units includes substituted $C_6$ aryl units chosen from 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

$R^1$ can comprise heteroaryl units. Non-limiting examples of $C_1$-$C_9$ heteroaryl units include:

i)

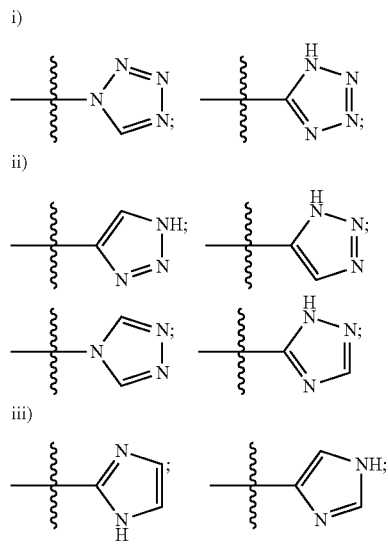

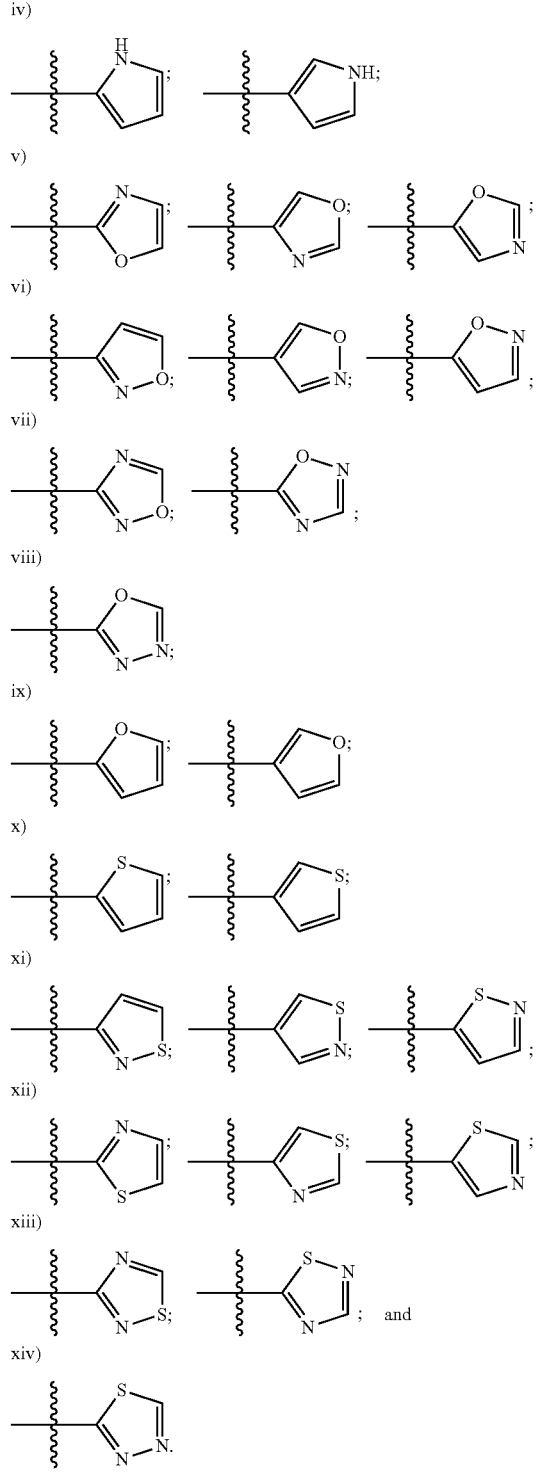

$R^1$ heteroaryl units can be substituted or unsubstituted. Non-limiting examples of units that can substitute for hydrogen include units chosen from:
i) $C_1$-$C_6$ linear, $C_3$-$C_6$ branched, and $C_3$-$C_6$ cyclic alkyl;
ii) substituted or unsubstituted phenyl and benzyl;
iii) substituted of unsubstituted $C_1$-$C_9$ heteroaryl;
iv) —C(O)$R^9$; and
v) —NHC(O)$R^9$;

wherein $R^9$ is $C_1$-$C_6$ linear and branched alkyl; $C_1$-$C_6$ linear and $C_3$-$C_6$ branched alkoxy; or —NHCH$_2$C(O)R$^{10}$; R$^{10}$ is chosen from hydrogen, methyl, ethyl, and tert-butyl.

An example of $R^1$ relates to units substituted by an alkyl unit chosen from methyl, ethyl, n-propyl, iso-propyl, n-butyl, iso-butyl, sec-butyl, and tert-butyl.

An example of $R^1$ includes units that are substituted by substituted or unsubstituted phenyl and benzyl, wherein the phenyl and benzyl substitutions are chosen from one or more:
 i) halogen;
 ii) $C_1$-$C_3$ alkyl;
 iii) $C_1$-$C_3$ alkoxy;
 iv) —CO$_2$R$^{11}$; and
 v) —NHCOR$^{16}$;
wherein $R^{11}$ and $R^{16}$ are each independently hydrogen, methyl, or ethyl.

An example of $R^1$ relates to phenyl and benzyl units substituted by a carboxy unit having the formula —C(O)R$^9$; $R^9$ is chosen from methyl, methoxy, ethyl, and ethoxy.

An example of $R^1$ includes phenyl and benzyl units substituted by an amide unit having the formula —NHC(O)R$^9$; $R^9$ is chosen from methyl, methoxy, ethyl, ethoxy, tert-butyl, and tert-butoxy.

An example of $R^1$ includes phenyl and benzyl units substituted by one or more fluoro or chloro units.

L Units

L is a linking unit which is present when the index n is equal to 1, but is absent when the index n is equal to 0. L units have the formula:

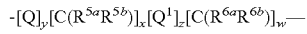
-[Q]$_y$-[C(R$^{5a}$R$^{5b}$)]$_x$[Q$^1$]$_z$[C(R$^{6a}$R$^{6b}$)]$_w$— wherein Q and Q$^1$ are each independently:
 i) —C(O)—;
 ii) —NH—;
 iii) —C(O)NH—;
 iv) —NHC(O)—;
 v) —NHC(O)NH—;
 vi) —NHC(O)O—;
 vii) —C(O)O—;
 viii) —C(O)NHC(O)—;
 ix) —O—;
 x) —S—;
 xi) —SO$_2$—;
 xii) —C(=NH)—;
 xiii) —C(=NH)NH—;
 xiv) —NHC(=NH)—; or
 xv) —NHC(=NH)NH—.

When the index y is equal to 1, Q is present. When the index y is equal to 0, Q is absent.

When the index z is equal to 1, Q$^1$ is present. When the index z is equal to 0, Q$^1$ is absent.

$R^{5a}$ and $R^{5b}$ are each independently:
 i) hydrogen;
 ii) hydroxy;
 iii) halogen;
 iv) substituted or unsubstituted $C_1$-$C_6$ linear or $C_3$-$C_6$ branched alkyl; or
 v) a unit having the formula:

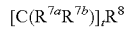
[C(R$^{7a}$R$^{7b}$)]$_t$R$^8$ wherein $R^{7a}$ and $R^{7b}$ are each independently:
 i) hydrogen; or
 ii) substituted or unsubstituted $C_1$-$C_6$ linear, $C_3$-$C_6$ branched, or $C_3$-$C_6$ cyclic alkyl.

$R^8$ is:
 i) hydrogen;
 ii) substituted or unsubstituted $C_1$-$C_6$ linear, $C_3$-$C_6$ branched, or $C_3$-$C_6$ cyclic alkyl;
 iii) substituted or unsubstituted $C_6$ or $C_{10}$ aryl;
 iv) substituted or unsubstituted $C_1$-$C_9$ heteroaryl; or
 v) substituted or unsubstituted $C_1$-$C_9$ heterocyclic.

$R^{6a}$ and $R^{6b}$ are each independently:
 i) hydrogen; or
 ii) $C_1$-$C_4$ linear or $C_3$-$C_4$ branched alkyl.

The indices t, w and x are each independently from 0 to 4.

The following are non-limiting examples of units that can substitute for one or more hydrogen atoms on $R^{5a}$, $R^{5b}$, $R^{7a}$, $R^{7b}$, and $R^8$ units. The following substituents, as well as others not herein described, are each independently chosen:
 i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
 ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
 iii) substituted or unsubstituted $C_6$ or $C_{10}$ alkylenearyl; for example, benzyl, 2-phenylethyl, naphthylen-2-ylmethyl;
 iv) substituted or unsubstituted $C_1$-$C_9$ heterocyclic rings; as described herein below;
 v) substituted or unsubstituted $C_1$-$C_9$ heteroaryl rings; as described herein below;
 vi) —(CR$^{41a}$R$^{41b}$)$_r$OR$^{40}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;
 vii) —(CR$^{41a}$R$^{41b}$)$_r$C(O)R$^{40}$; for example, —COCH$_3$, —CH$_2$COCH$_3$, —COCH$_2$CH$_3$, —CH$_2$COCH$_2$CH$_3$, —COCH$_2$CH$_2$CH$_3$, and —CH$_2$COCH$_2$CH$_2$CH$_3$;
 viii) —(CR$^{41a}$R$^{41b}$)$_r$C(O)OR$^{40}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;
 ix) —(CR$^{41a}$R$^{41b}$)$_r$C(O)N(R$^{40}$)$_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;
 x) —(CR$^{41a}$R$^{41b}$)$_r$N(R$^{40}$)$_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;
 xi) halogen; —F, —Cl, —Br, and —I;
 xii) —(CR$^{41a}$R$^{41b}$)$_r$CN;
 xiii) —(CR$^{41a}$R$^{41b}$)$_r$NO$_2$;
 xiv) —(CH$_j$X$_k$)$_h$CH$_{j'}$X$_{k'}$; wherein X is halogen, the index j is an integer from 0 to 2, j+k=3, the index j' is an integer from 0 to 2, j'+k'=2, the index h is from 0 to 6; for example, —CH$_2$F, —CHF$_2$, —CF$_3$, —CH$_2$CF$_3$, —CHFCF$_3$, —CCl$_3$, or —CBr$_3$;
 xv) —(CR$^{41a}$R$^{41b}$)$_r$SR$^{40}$; —SH, —CH$_2$SH, —SCH$_3$, —CH$_2$SCH$_3$, —SC$_6$H$_5$, and —CH$_2$SC$_6$H$_5$;
 xvi) —(CR$^{41a}$R$^{41b}$)$_r$SO$_2$R$^{40}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and)
 xvii) —(CR$^{41a}$R$^{41b}$)$_r$SO$_3$R$^{40}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;
wherein each $R^{40}$ is independently hydrogen, substituted or unsubstituted $C_1$-$C_6$ linear, $C_3$-$C_6$ branched, or $C_3$-$C_6$ cyclic alkyl, phenyl, benzyl, heterocyclic, or heteroaryl; or two $R^{40}$ units can be taken together to form a ring comprising 3-7 atoms; $R^{41a}$ and $R^{41b}$ are each independently hydrogen or $C_1$-$C_4$ linear or $C_3$-$C_4$ branched alkyl; the index r is from 0 to 4.

One aspect of L units relates to units having the formula:

—C(O)[C($R^{5a}R^{5b}$)]$_x$NHC(O)— wherein $R^{5a}$ is hydrogen, substituted or unsubstituted $C_1$-$C_4$ alkyl, substituted or unsubstituted phenyl, and substituted or unsubstituted heteroaryl; and the index x is 1 or 2. Some embodiments relate to linking units having the formula:

i) —C(O)[C($R^{5a}$H)]NHC(O)O—;
ii) —C(O)[C($R^{5a}$H)][CH$_2$]NHC(O)O—;
iii) —C(O)[CH$_2$][C($R^{5a}$H)]NHC(O)O—;
iv) —C(O)[C($R^{5a}$H)]NHC(O)—;
v) —C(O)[C($R^{5a}$H)][CH$_2$]NHC(O)—; or
vi) —C(O)[CH$_2$][C($R^{5a}$H)]NHC(O)—;

wherein $R^{5a}$ is:
i) hydrogen;
ii) methyl;
iii) ethyl;
iv) isopropyl;
v) phenyl;
vi) benzyl;
vii) 4-hydroxybenzyl;
viii) hydroxymethyl; or
ix) 1-hydroxyethyl.

When the index x is equal to 1, this embodiment provides the following non-limiting examples of L units:

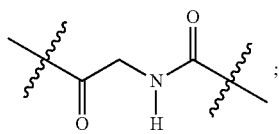

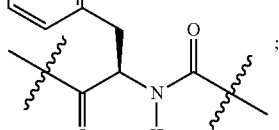

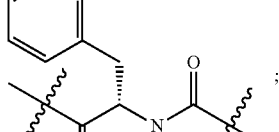

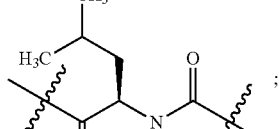

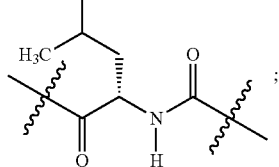

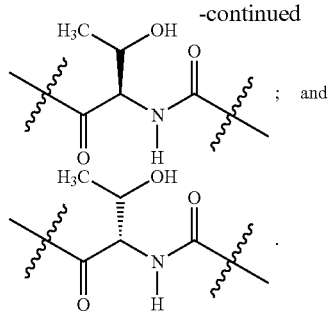

When the index x is equal to 2, this embodiment provides the following non-limiting examples of L units:

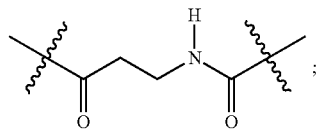

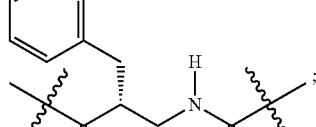

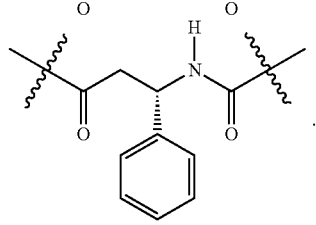

Another embodiment of L units includes units wherein Q is —C(O)—, the indices x and z are equal to 0, w is equal to 1 or 2, a first $R^{6a}$ unit chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl; a second $R^{6a}$ unit is hydrogen and $R^{6b}$ units are hydrogen. For example a linking unit having the formula:

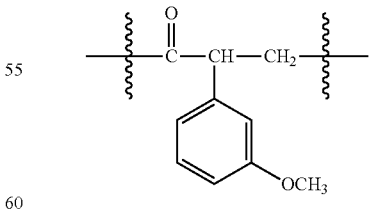

An example of this embodiment of L includes a first $R^{6a}$ unit as depicted herein above that is a substituted or unsubstituted heteroaryl unit as described herein above.

An example of this embodiment of L includes units having the formula:

—C(O)[C($R^{6a}R^{6b}$)]$_w$—;

wherein $R^{6a}$ and $R^{6b}$ are hydrogen and the index w is equal to 1 or 2; said units chosen from:
  i) —C(O)CH$_2$—; and
  ii) —C(O)CH$_2$CH$_2$—.

Another embodiment of L units includes units having the formula:

wherein $R^{5a}$ and $R^{5b}$ are hydrogen and the index x is equal to 1 or 2; said units chosen from:
  i) —C(O)CH$_2$C(O)—; and
  ii) —C(O)CH$_2$CH$_2$C(O)—.

Another embodiment of L units includes units having the formula:

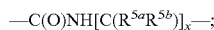

wherein $R^{5a}$ and $R^{5b}$ are hydrogen and the index w is equal to 0, 1 or 2; said units chosen from:
  ii) —C(O)NH—;
  ii) —C(O)NHCH$_2$—; and
  iii) —C(O)NHCH$_2$CH$_2$—.

An example of L units includes units having the formula:

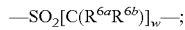

wherein $R^8$ and $R^{8b}$ are hydrogen or methyl and the index w is equal to 0, 1 or 2; said units chosen from:
  i) —SO$_2$—;
  ii) —SO$_2$CH$_2$—; and
  iii) —SO$_2$CH$_2$CH$_2$—.

Synthetic Schema.

Disclosed herein are categories of compounds useful for the methods described herein, and pharmaceutically acceptable salt forms thereof. For example, a compound having the formula:

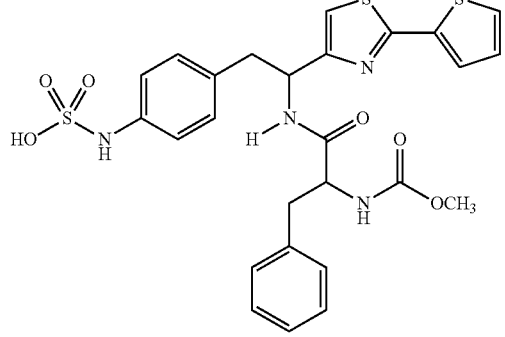

can form salts, for example, a salt of the sulfamic acid:

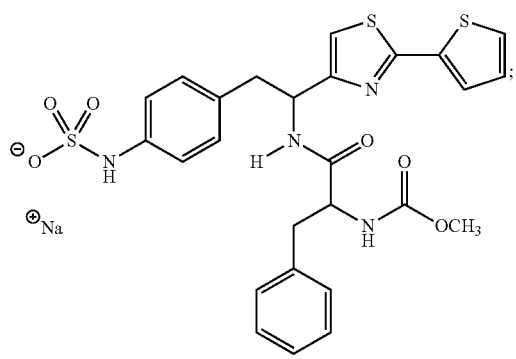

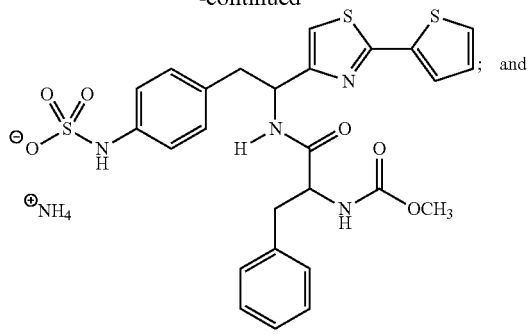

; and

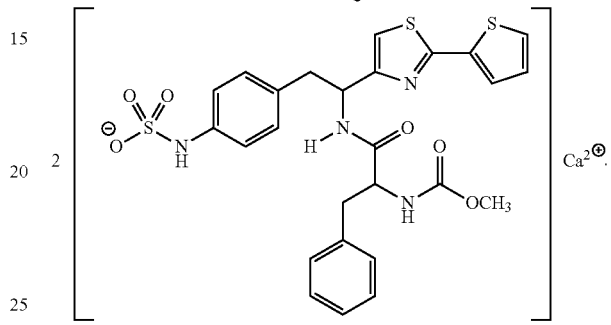

The compounds can also exist in a zwitterionic form, for example:

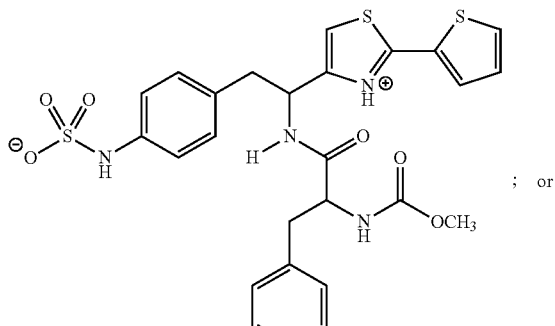

; or

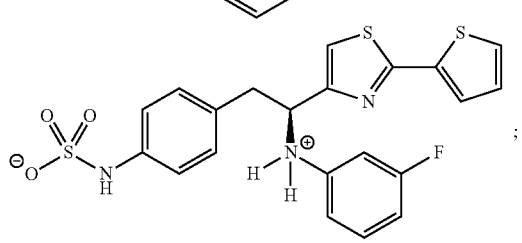

as a salt of a strong acid, for example:

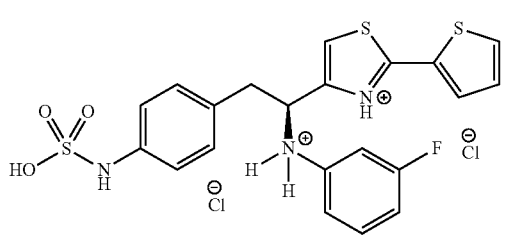

An aspect of Category I of the present disclosure relates to compounds wherein R is a substituted or unsubstituted thiazol-2-yl unit having the formula:

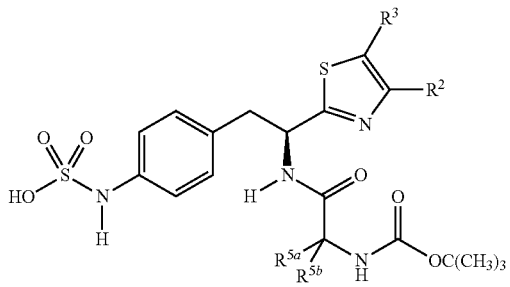

one embodiment of which relates to inhibitors having the formula:

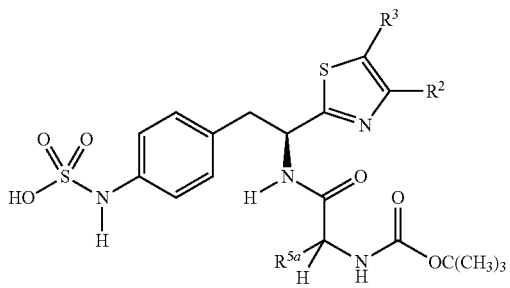

wherein R units are thiazol-2-yl units, that when substituted, are substituted with $R^2$ and $R^3$ units. R and $R^{5a}$ units are further described in Table I.

TABLE I

| No. | R | $R^{5a}$ |
| --- | --- | --- |
| A1 | thiazol-2-yl | (S)-benzyl |
| A2 | 4-methylthiazol-2-yl | (S)-benzyl |
| A3 | 4-ethylthiazol-2-yl | (S)-benzyl |
| A4 | 4-propylthiazol-2-yl | (S)-benzyl |
| A5 | 4-iso-propylthiazol-2-yl | (S)-benzyl |
| A6 | 4-cyclopropylthiazol-2-yl | (S)-benzyl |
| A7 | 4-butylthiazol-2-yl | (S)-benzyl |
| A8 | 4-tert-butylthiazol-2-yl | (S)-benzyl |
| A9 | 4-cyclohexylthiazol-2-yl | (S)-benzyl |
| A10 | 4-(2,2,2-trifluoroethyl)thiazol-2-yl | (S)-benzyl |
| A11 | 4-(3,3,3-trifluoropropyl)thiazol-2-yl | (S)-benzyl |
| A12 | 4-(2,2-difluorocyclopropyl)thiazol-2-yl | (S)-benzyl |
| A13 | 4-(methoxymethyl)thiazol-2-yl | (S)-benzyl |
| A14 | 4-(carboxylic acid ethyl ester)thiazol-2-yl | (S)-benzyl |
| A15 | 4,5-dimethylthiazol-2-yl | (S)-benzyl |
| A16 | 4-methyl-5-ethylthiazol-2-yl | (S)-benzyl |
| A17 | 4-phenylthiazol-2-yl | (S)-benzyl |
| A18 | 4-(4-chlorophenyl)thiazol-2-yl | (S)-benzyl |
| A19 | 4-(3,4-dimethylphenyl)thiazol-2-yl | (S)-benzyl |
| A20 | 4-methyl-5-phenylthiazol-2-yl | (S)-benzyl |
| A21 | 4-(thiophen-2-yl)thiazol-2-yl | (S)-benzyl |
| A22 | 4-(thiophen-3-yl)thiazol-2-yl | (S)-benzyl |
| A23 | 4-(5-chlorothiophen-2-yl)thiazol-2-yl | (S)-benzyl |
| A24 | 5,6-dihydro-4H-cyclopenta[d]thiazol-2-yl | (S)-benzyl |
| A25 | 4,5,6,7-tetrahydrobenzo[d]thiazol-2-yl | (S)-benzyl |

The compounds encompassed within the first aspect of Category I of the present disclosure can be prepared by the procedure outlined in Scheme I and described in Example 1 below.

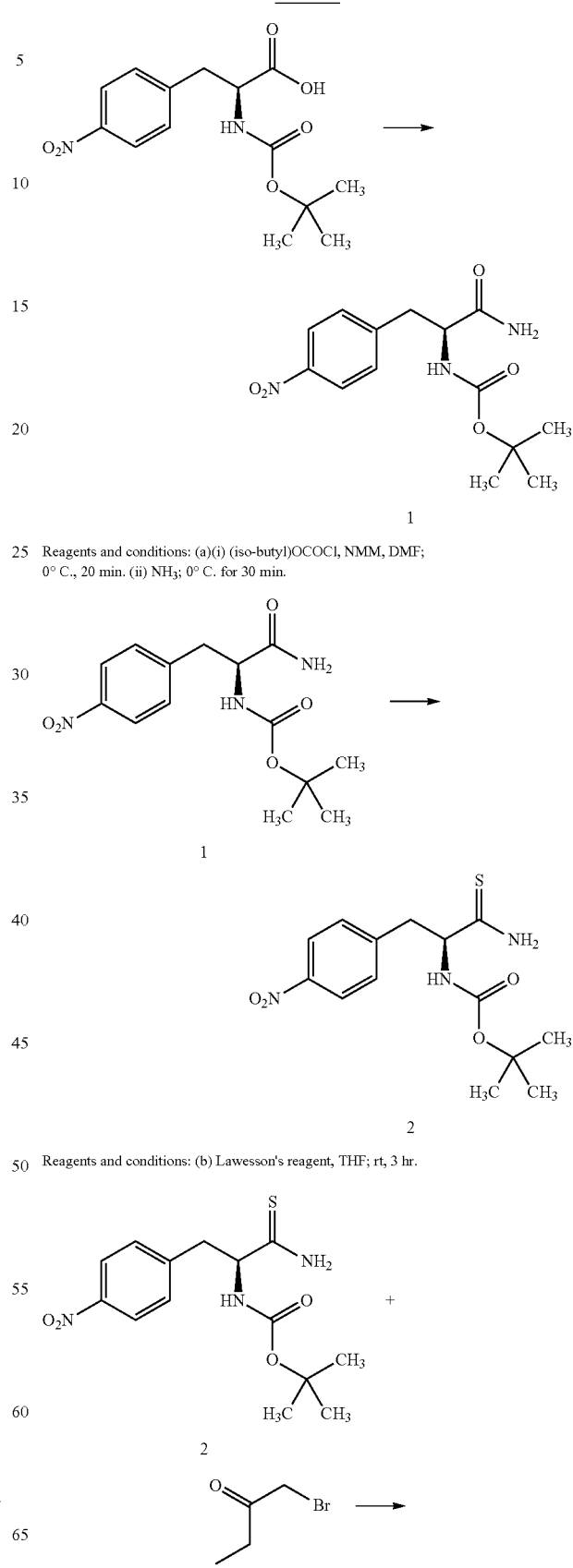

Scheme I

Reagents and conditions: (a)(i) (iso-butyl)OCOCl, NMM, DMF; 0° C., 20 min. (ii) NH₃; 0° C. for 30 min.

Reagents and conditions: (b) Lawesson's reagent, THF; rt, 3 hr.

-continued

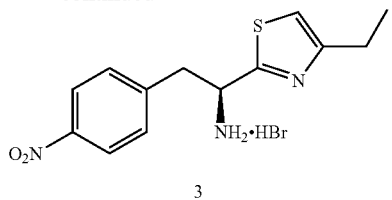

Reagents and conditions: (c) CH₃CN; reflux, 3 hr.

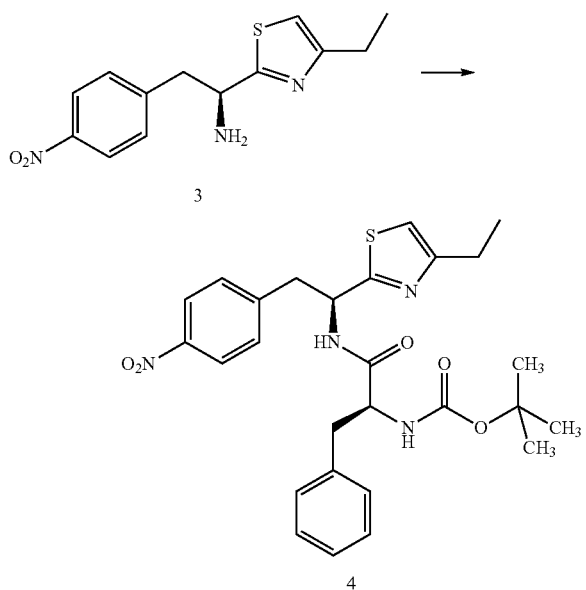

Reagents and conditions: (d) Boc-Phe, EDCI, HOBt, DIPEA, DMF; rt, 18 hr.

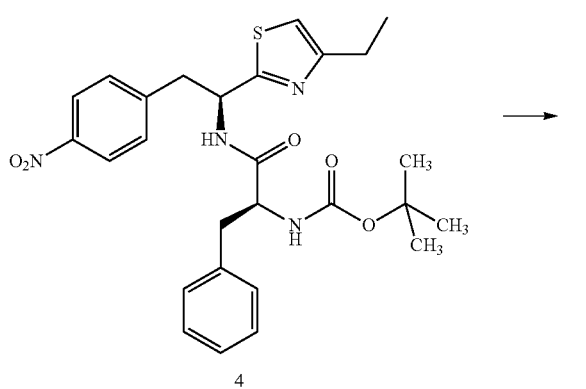

Reagents and conditions: (e) (i) H₂:Pd/C, MeOH; (ii) SO₃-pyridine, NH₄OH; rt, 2 hr.

EXAMPLE 1

4-{(S)-2-[(S)-2-(tert-Butoxycarbonylamino)-3-phenylpropanamido]-2-(4-ethylthiazol-2-yl) ethyl}phenylsulfamic acid (5)

Preparation of [1-(S)-carbamoyl-2-(4-nitrophenyl)ethylcarbamic acid tert-butyl ester (1): To a 0° C. solution of 2-(S)-tert-butoxycarbonylamino-3-(4-nitrophenyl)-propionic acid and N-methylmorpholine (1.1 mL, 9.65 mmol) in DMF (10 mL) is added dropwise iso-butyl chloroformate (1.25 mL, 9.65 mmol). The mixture is stirred at 0° C. for 20 minutes after which NH₃ (g) is passed through the reaction mixture for 30 minutes at 0° C. The reaction mixture is concentrated and the residue dissolved in EtOAc, washed successively with 5% citric acid, water, 5% NaHCO₃, water and brine, dried (Na₂SO₄), filtered and concentrated in vacuo to a residue that is triturated with a mixture of EtOAc/petroleum ether to provide 2.2 g (74%) of the desired product as a white solid.

Preparation of [2-(4-nitrophenyl)-1-(S)-thiocarbamoylethyl]carbamic acid tert-butyl ester (2): To a solution of [1-(S)-carbamoyl-2-(4-nitrophenyl)ethyl-carbamic acid tert-butyl ester, 1, (0.400 g, 1.29 mmol) in THF (10 mL) is added Lawesson's reagent (0.262 g. 0.65 mmol). The reaction mixture is stirred for 3 hours and concentrated to a residue which is purified over silica to provide 0.350 g (83%) of the desired product. ¹H NMR (300 MHz, CDCl₃) δ 8.29 (s, 1H), 8.10 (d. J=8.4 Hz, 2H), 8.01 (s, 1H), 7.42 (d, J=8.4 Hz, 2H), 5.70 (d, J=7.2 Hz, 1H), 4.85 (d, J=7.2 Hz, 1H), 3.11-3.30 (m, 1H), 1.21 (s, 9H).

Preparation of 1-(S)-(4-ethylthiazol-2-yl)-2-(4-nitrophenyl)ethyl amine (3): A mixture of [2-(4-nitrophenyl)-1-(S)-thiocarbamoylethyl]-carbamic acid tert-butyl ester, 2, (0.245 g, 0.753 mmol), 1-bromo-2-butanone (0.125 g, 0.828 mmol) in CH₃CN (5 mL) is refluxed 3 hours. The reaction mixture is cooled to room temperature and diethyl ether is added to the solution and the precipitate which forms is removed by filtration. The solid is dried under vacuum to afford 0.242 g (90% yield) of the desired product. ESI+ MS 278 (M+1).

Preparation of {1-[1-(4-ethylthiazol-2-yl)-2-(4-nitrophenyl)ethylcarbamoyl]-2-phenylethyl}carbamic acid tert-butyl ester (4): To a solution of 1-(S)-(4-ethylthiazol-2-yl)-2-(4-nitrophenyl)ethyl amine hydrobromide, 3, (0.393 g, 1.1 mmol), (S)-(2-tert-butoxycarbonylamino)-3-phenylpropionic acid (0.220 g, 0.828 mmol) and 1-hydroxybenzotriazole (HOBt) (0.127 g, 0.828 mmol) in DMF (10 mL) at 0° C., is added 1-(3-dimethylaminopropyl)-3-ethylcarbodiimide (EDCI) (0.159 g, 0.828 mmol) followed by diisopropylamine (0.204 g, 1.58 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.345 g of the desired product which is used without further purification. LC/MS ESI+ 525 (M+1).

Preparation of 4-{(S)-2-[(S)-2-(tert-butoxycarbonylamino)-3-phenylpropanamido]-2-(4-ethylthiazol-2-yl) ethyl}phenylsulfamic acid ammonium salt (5): {1-[1-(4-ethylthiazol-2-yl)-2-(4-nitrophenyl)ethylcarbamoyl]-2-phenylethyl}carbamic acid tert-butyl ester, 4, (0.345 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (12 mL) and treated with SO₃-pyridine (0.314 g). The reaction is stirred at room temperature for 5 minutes after which a 7% solution of NH₄OH (50 mL) is added. The mixture is then concentrated and the resulting residue is purified by reverse phase chromatography to afford 0.222 g of the desired product as the ammonium salt. ¹H NMR (CD₃OD δ 7.50-6.72 (m, 10H), 5.44-5.42 (d, 1H, J=6.0 Hz), 4.34 (s, 1H), 3.34-2.79 (m, 4H), 2.83-2.76 (q, 2H, J=7.2 Hz), 1.40 (s, 9H), 1.31 (t, 3H, J=7.5 Hz).

The disclosed inhibitors can also be isolated as the free acid. A non-limiting example of this procedure is described herein below in Example 4.

The following is a non-limiting example of compounds encompassed within this embodiment of the first aspect of Category I of the present disclosure.

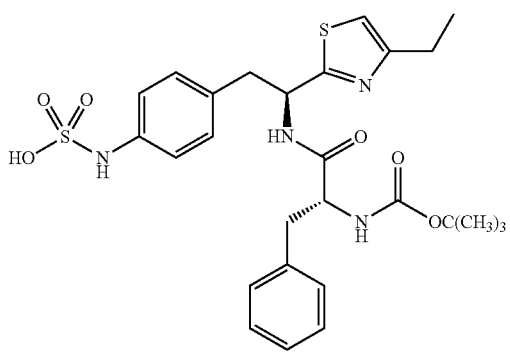

4-{(S)-2-[(R)-2-(tert-butoxycarbonylamino)-3-phenyl-propanamido]-2-(4-ethylthiazol-2-yl)ethyl}phenylsulfamic acid: ¹H NMR (CD₃OD δ 7.22-7.02 (m, 10H), 5.39 (s, 1H), 4.34 (s, 1H), 3.24-2.68 (m, 6H), 1.37 (s, 9H), 1.30 (t, 3H, J=7.5 Hz).

Another embodiment of this aspect of Category I relates to inhibitors having the formula:

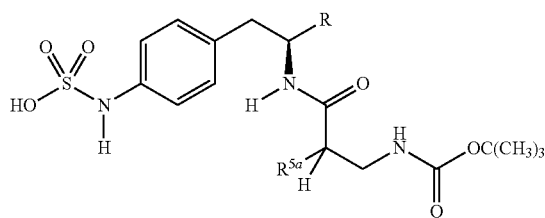

wherein R units and $R^{5a}$ units further described in Table II.

TABLE II

| No. | R | $R^{5a}$ |
|---|---|---|
| B26 | thiazol-2-yl | (S)-benzyl |
| B27 | 4-methylthiazol-2-yl | (S)-benzyl |
| B28 | 4-ethylthiazol-2-yl | (S)-benzyl |
| B29 | 4-propylthiazol-2-yl | (S)-benzyl |
| B30 | 4-iso-propylthiazol-2-yl | (S)-benzyl |
| B31 | 4-cyclopropylthiazol-2-yl | (S)-benzyl |
| B32 | 4-butylthiazol-2-yl | (S)-benzyl |
| B33 | 4-tert-butylthiazol-2-yl | (S)-benzyl |
| B34 | 4-cyclohexylthiazol-2-yl | (S)-benzyl |
| B35 | 4-(2,2,2-trifluoroethyl)thiazol-2-yl | (S)-benzyl |
| B36 | 4-(3,3,3-trifluoropropyl)thiazol-2-yl | (S)-benzyl |
| B37 | 4-(2,2-difluorocyclopropyl)thiazol-2-yl | (S)-benzyl |
| B38 | 4-(methoxymethyl)thiazol-2-yl | (S)-benzyl |

TABLE II-continued

| No. | R | $R^{5a}$ |
|---|---|---|
| B39 | 4-(carboxylic acid ethyl ester)thiazol-2-yl | (S)-benzyl |
| B40 | 4,5-dimethylthiazol-2-yl | (S)-benzyl |
| B41 | 4-methyl-5-ethylthiazol-2-yl | (S)-benzyl |
| B42 | 4-phenylthiazol-2-yl | (S)-benzyl |
| B43 | 4-(4-chlorophenyl)thiazol-2-yl | (S)-benzyl |
| B44 | 4-(3,4-dimethylphenyl)thiazol-2-yl | (S)-benzyl |
| B45 | 4-methyl-5-phenylthiazol-2-yl | (S)-benzyl |
| B46 | 4-(thiophen-2-yl)thiazol-2-yl | (S)-benzyl |
| B47 | 4-(thiophen-3-yl)thiazol-2-yl | (S)-benzyl |
| B48 | 4-(5-chlorothiophen-2-yl)thiazol-2-yl | (S)-benzyl |
| B49 | 5,6-dihydro-4H-cyclopenta[d]thiazol-2-yl | (S)-benzyl |
| B50 | 4,5,6,7-tetrahydrobenzo[d]thiazol-2-yl | (S)-benzyl |

The compounds of this embodiment can be prepared according to the procedure outlined above in Scheme I and described in Example 1 by substituting the appropriate Boc-β-amino acid for (S)-(2-tert-butoxycarbonylamino)-3-phenylpropionic acid in step (d).

The following are non-limiting examples of compounds according to this embodiment.

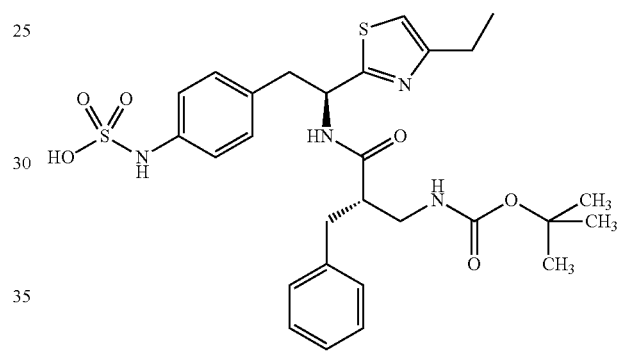

{1-[1-(4-Ethylthiazol-2-yl)-(S)-2-(4-sulfoaminophenyl) ethylcarbamoyl]-(S)-2-phenylethyl}methyl carbamic acid tert-butyl ester: ¹H NMR (300 MHz, MeOH-d₄) δ 8.36 (d, J=8.1 Hz, 1H), 7.04-7.22 (m, 9H), 5.45 (s, 1H), 3.01-3.26 (m, 2H), 2.60-2.88 (m, 4H), 2.33 (s, 3H), 1.30 (s, 9H).

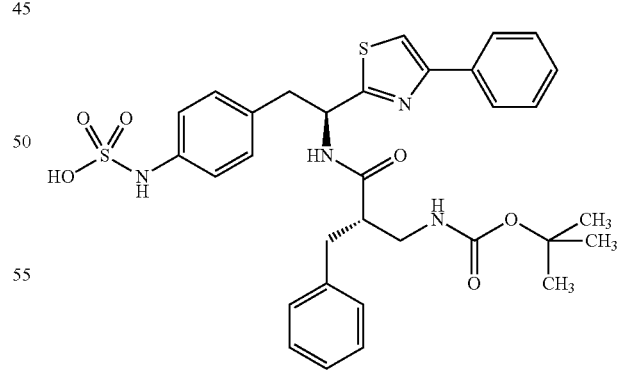

{1-[1-(4-Phenylthiazol-2-yl)-(S)-2-(4-sulfoaminophenyl) ethylcarbamoyl]-(S)-2-phenylethyl}methyl carbamic acid tert-butyl ester: ¹H NMR (300 MHz, MeOH-d₄) δ 8.20 (d, J=8.1 Hz, 1H), 7.96-7.99 (m, 2H), 7.48-7.52 (m, 3H), 7.00-7.23 (m, 7H), 6.89 (s, 1H), 5.28 (q, J=7.5 Hz, 1H), 4.33 (t, J=6.6 Hz, 1H), 3.09-3.26 (m, 2H), 3.34 (dd, J=13.2 and 8.4 Hz, 1H), 2.82 (dd, J=13.2 and 8.4 Hz, 1H), 1.38 (s, 9H).

The second aspect of Category I of the present disclosure relates to compounds wherein R is a substituted or unsubstituted thiazol-4-yl having the formula:

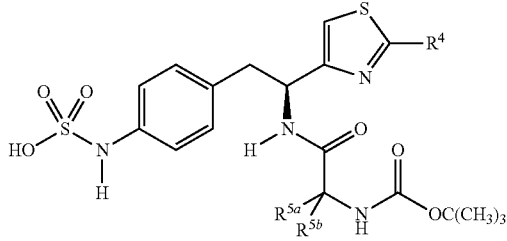

one embodiment of which relates to inhibitors having the formula:

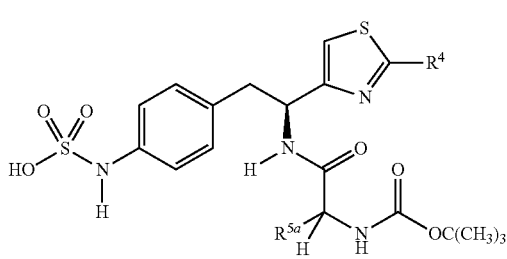

wherein R units and $R^{5a}$ units further described in Table III.

TABLE III

| No. | R | $R^{5a}$ |
|---|---|---|
| C51 | thiazol-4-yl | (S)-benzyl |
| C52 | 2-methylthiazol-4-yl | (S)-benzyl |
| C53 | 2-ethylthiazol-4-yl | (S)-benzyl |
| C54 | 2-propylthiazol-4-yl | (S)-benzyl |
| C55 | 2-iso-propylthiazol-4-yl | (S)-benzyl |
| C56 | 2-cyclopropylthiazol-4-yl | (S)-benzyl |
| C57 | 2-butylthiazol-4-yl | (S)-benzyl |
| C58 | 2-tert-butylthiazol-4-yl | (S)-benzyl |
| C59 | 2-cyclohexylthiazol-4-yl | (S)-benzyl |
| C60 | 2-(2,2,2-trifluoroethyl)thiazol-4-yl | (S)-benzyl |
| C61 | 2-(3,3,3-trifluoropropyl)thiazol-4-yl | (S)-benzyl |
| C62 | 2-(2,2-difluorocyclopropyl)thiazol-4-yl | (S)-benzyl |
| C63 | 2-phenylthiazol-4-yl | (S)-benzyl |
| C64 | 2-(4-chlorophenyl)thiazol-4-yl | (S)-benzyl |
| C65 | 2-(3,4-dimethylphenyl)thiazol-4-yl | (S)-benzyl |
| C66 | 2-(thiophen-2-yl)thiazol-4-yl | (S)-benzyl |
| C67 | 2-(thiophen-3-yl)thiazol-4-yl | (S)-benzyl |
| C68 | 2-(3-chlorothiophen-2-yl)thiazol-4-yl | (S)-benzyl |
| C69 | 2-(3-methylthiophen-2-yl)thiazol-4-yl | (S)-benzyl |
| C70 | 2-(2-methylthiazol-4-yl)thiazol-4-yl | (S)-benzyl |
| C71 | 2-(furan-2-yl)thiazol-4-yl | (S)-benzyl |
| C72 | 2-(pyrazin-2-yl)thiazol-4-yl | (S)-benzyl |
| C73 | 2-[(2-methyl)pyridin-5-yl]thiazol-4-yl | (S)-benzyl |
| C74 | 2-(4-chlorobenzenesulfonylmethyl)thiazol-4-yl | (S)-benzyl |
| C75 | 2-(tert-butylsulfonylmethyl)thiazol-4-yl | (S)-benzyl |

The compounds encompassed within the second aspect of Category I of the present disclosure can be prepared by the procedure outlined in Scheme II and described in Example 2 herein below.

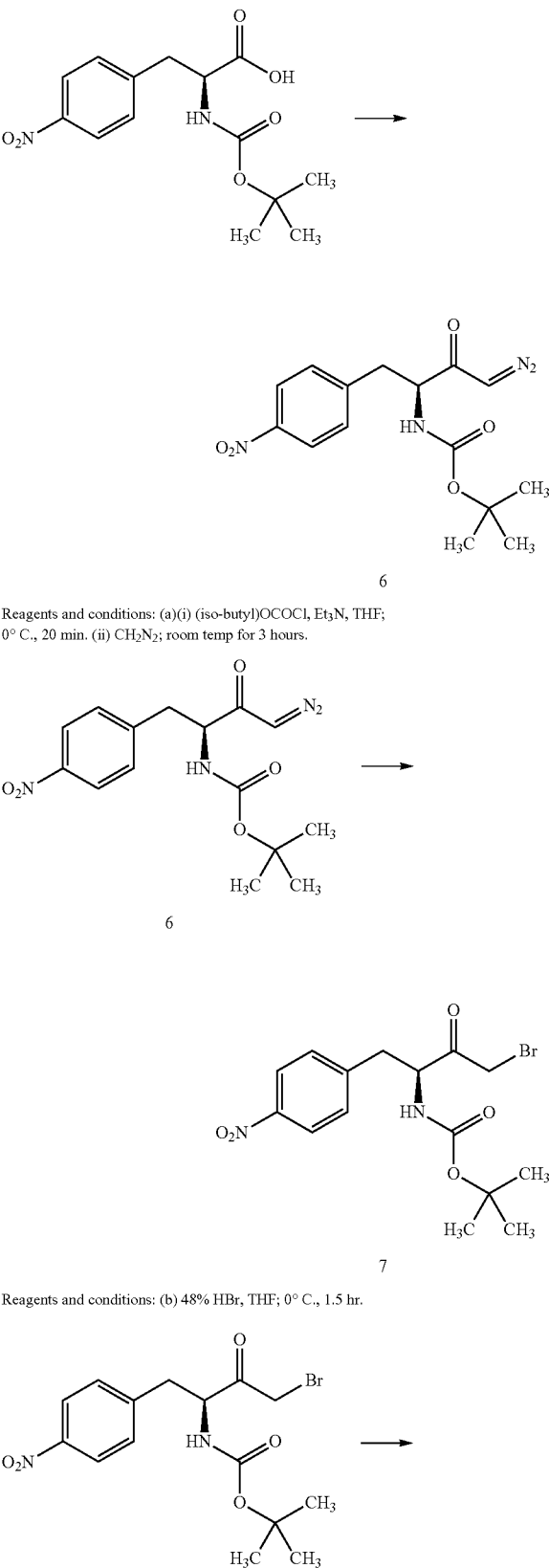

Scheme II

Reagents and conditions: (a)(i) (iso-butyl)OCOCl, Et₃N, THF; 0° C., 20 min. (ii) CH₂N₂; room temp for 3 hours.

Reagents and conditions: (b) 48% HBr, THF; 0° C., 1.5 hr.

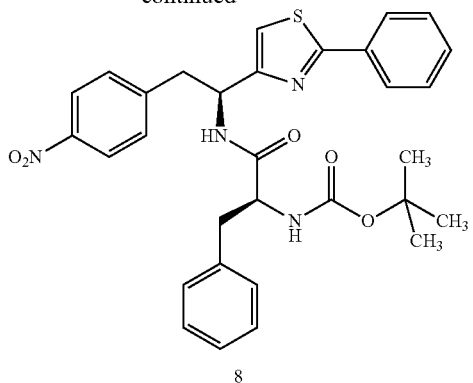

8

Reagents and conditions: (c)(i) thiobenzamide, CH₃CN; reflux, 2 hr. (ii) Boc-Phe, HOBt, DIPEA, DMF; rt, 18 hr.

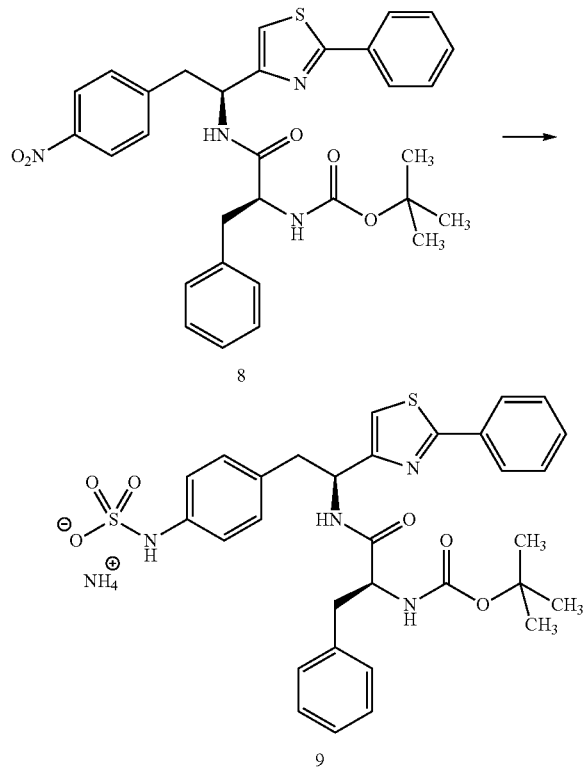

Reagents and conditions: (d) (i) H₂:Pd/C, MeOH; (ii) SO₃-pyridine, NH₄OH; rt, 12 hr.

EXAMPLE 2

4-{(S)-2-(S)-2-(tert-Butoxycarbonylamino)-3-phenylpropanamido-2-(2-phenylthiazol-4-yl)}phenylsulfamic acid (9)

Preparation of (S)[3-diazo-1-(4-nitrobenzyl)-2-oxo-propyl]-carbamic acid tert-butyl ester (6): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by iso-butyl chloroformate (0.57 mL, 4.4 mmol). The reaction mixture is stirred at 0° C. for 20 minutes and filtered. The filtrate is treated with an ether solution of diazomethane (~16 mmol) at 0° C. The reaction mixture is stirred at room temperature for 3 hours then concentrated in vacuo. The resulting residue is dissolved in EtOAc and washed successively with water and brine, dried (Na₂SO₄), filtered and concentrated. The residue is purified over silica (hexane/EtOAc 2:1) to afford 1.1 g (82% yield) of the desired product as a slightly yellow solid. ¹H NMR (300 MHz, CDCl₃) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of (S)-tert-butyl 4-bromo-1-(4-nitrophenyl)-3-oxobutan-2-ylcarbamate (7): To a 0° C. solution of (S)-[3-diazo-1-(4-nitrobenzyl)-2-oxo-propyl]-carbamic acid tert-butyl ester, 6, (0.350 g, 1.04 mmol) in THF (5 mL) is added dropwise 48% aq. HBr (0.14 mL, 1.25 mmol). The reaction mixture is stirred at 0° C. for 1.5 hours then the reaction is quenched at 0° C. with sat. Na₂CO₃. The mixture is extracted with EtOAc (3×25 mL) and the combined organic extracts are washed with brine, dried (Na₂SO₄), filtered and concentrated to obtain 0.400 g of the product which is used in the next step without further purification. ¹H NMR (300 MHz, CDCl₃) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of tert-butyl (S)-1-(S)-2-(4-nitrophenyl)-1-(2-phenylthiazole-4-yl)ethylamino-1-oxo-3-phenylpropan-2-ylcarbamate (8): A mixture of thiobenzamide (0.117 g, 0.85 mmol) and (S)-tert-butyl 4-bromo-1-(4-nitrophenyl)-3-oxobutan-2-ylcarbamate, 7, (0.300 g, 0.77 mmol) in CH₃CN (4 mL) is refluxed 2 hours. The reaction mixture is cooled to room temperature and diethyl ether is added to precipitate the intermediate 2-(nitrophenyl)-(S)-1-(4-phenylthiazol-2-yl)ethylamine which is isolated by filtration as the hydrobromide salt. The hydrobromide salt is dissolved in DMF (3 mL) together with diisoproylethylamine (0.42 mL, 2.31 mmol), 1-hydroxybenzotriazole (0.118 g, 0.79 mmol) and (S)-(2-tert-butoxycarbonyl-amino)-3-phenylpropionic acid (0.212 g, 0.80 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.395 g (90% yield) of the desired product which is used without further purification. LC/MS ESI+ 573 (M+1).

Preparation of 4-{(S)-2-(S)-2-(tert-butoxycarbonyl)-3-phenylpropaneamido-2-(2-phenylthiazole-4-yl)}phenylsulfamic acid (9): tert-butyl (S)-1-(S)-2-(4-nitrophenyl)-1-(2-phenylthiazole-4-yl)ethylamino-1-oxo-3-phenylpropan-2-ylcarbamate, 8, (0.360 g) is dissolved in MeOH (4 mL). A catalytic amount of Pd/C (10% w/w) is added and the mixture is stirred under a hydrogen atmosphere 12 hours. The reaction mixture is filtered through a bed of CELITE™ and the solvent is removed under reduced pressure. The crude product is dissolved in pyridine (12 mL) and treated with SO₃-pyridine (0.296 g). The reaction is stirred at room temperature for 5 minutes after which a 7% solution of NH₄OH (10 mL) is added. The mixture is then concentrated and the resulting residue is purified by reverse phase chromatography to afford 0.050 g of the desired product as the ammonium salt. ¹H NMR (300 MHz, MeOH-d₄) δ 8.20 (d, J=8.1 Hz, 1H), 7.96-7.99 (m, 2H), 7.48-7.52 (m, 3H), 7.00-7.23 (m, 7H), 6.89 (s, 1H), 5.28 (q, J=7.5 Hz, 1H), 4.33 (t, J=6.6 Hz, 1H), 3.09-3.26 (m, 2H), 3.34 (dd, J=13.2 and 8.4 Hz, 1H), 2.82 (dd, J=13.2 and 8.4 Hz, 1H), 1.38 (s, 9H).

An aspect of Category II of the present disclosure relates to compounds wherein R is a substituted or unsubstituted thiazol-4-yl unit having the formula:

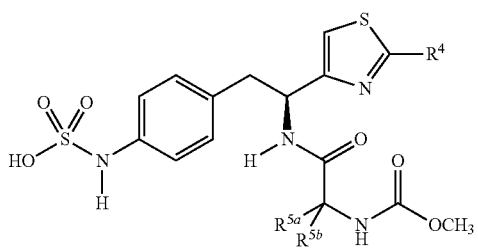

one embodiment of which relates to inhibitors having the formula:

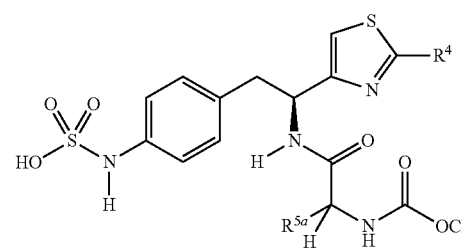

wherein R units are thiazol-4-yl units, that when substituted, are substituted with $R^4$ units. R and $R^{5a}$ units are further described in Table IV.

TABLE IV

| No. | R | $R^{5a}$ |
| --- | --- | --- |
| D76 | thiazol-4-yl | (S)-benzyl |
| D77 | 2-methylthiazol-4-yl | (S)-benzyl |
| D78 | 2-ethylthiazol-4-yl | (S)-benzyl |
| D79 | 2-propylthiazol-4-yl | (S)-benzyl |
| D80 | 2-iso-propylthiazol-4-yl | (S)-benzyl |
| D81 | 2-cyclopropylthiazol-4-yl | (S)-benzyl |
| D82 | 2-butylthiazol-4-yl | (S)-benzyl |
| D83 | 2-tert-butylthiazol-4-yl | (S)-benzyl |
| D84 | 2-cyclohexylthiazol-4-yl | (S)-benzyl |
| D85 | 2-(2,2,2-trifluoroethyl)thiazol-4-yl | (S)-benzyl |
| D86 | 2-(3,3,3-trifluoropropyl)thiazol-4-yl | (S)-benzyl |
| D87 | 2-(2,2-difluorocyclopropyl)thiazol-4-yl | (S)-benzyl |
| D88 | 2-phenylthiazol-4-yl | (S)-benzyl |
| D89 | 2-(4-chlorophenyl)thiazol-4-yl | (S)-benzyl |
| D90 | 2-(3,4-dimethylphenyl)thiazol-4-yl | (S)-benzyl |
| D91 | 2-(thiophen-2-yl)thiazol-4-yl | (S)-benzyl |
| D92 | 2-(thiophen-3-yl)thiazol-4-yl | (S)-benzyl |
| D93 | 2-(3-chlorothiophen-2-yl)thiazol-4-yl | (S)-benzyl |
| D94 | 2-(3-methylthiophen-2-yl)thiazol-4-yl | (S)-benzyl |
| D95 | 2-(2-methylthiazol-4-yl)thiazol-4-yl | (S)-benzyl |
| D96 | 2-(furan-2-yl)thiazol-4-yl | (S)-benzyl |
| D97 | 2-(pyrazin-2-yl)thiazol-4-yl | (S)-benzyl |
| D98 | 2-[(2-methyl)pyridin-5-yl]thiazol-4-yl | (S)-benzyl |
| D99 | 2-(4-chlorobenzenesulfonylmethyl)thiazol-4-yl | (S)-benzyl |
| D100 | 2-(tert-butylsulfonylmethyl)thiazol-4-yl | (S)-benzyl |

The compounds encompassed within the second aspect of Category II of the present disclosure can be prepared by the procedure outlined in Scheme III and described in Example 3 herein below.

Scheme III

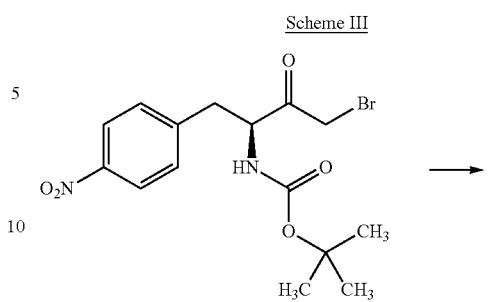

7

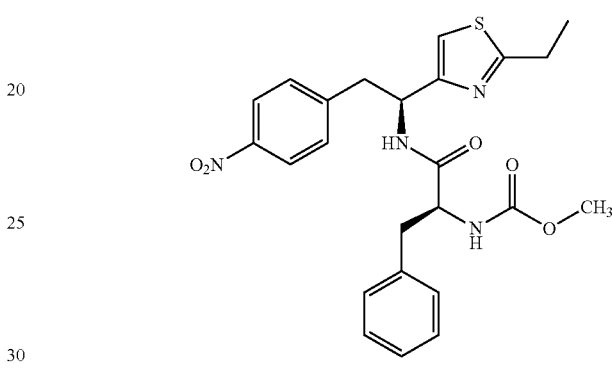

12

Reagents and conditions: (a)(i) propanethioamide, $CH_3CN$; reflux, 2 hr. (ii) Boc-Phe, HOBt, DIPEA, DMF; rt, 18 hr.

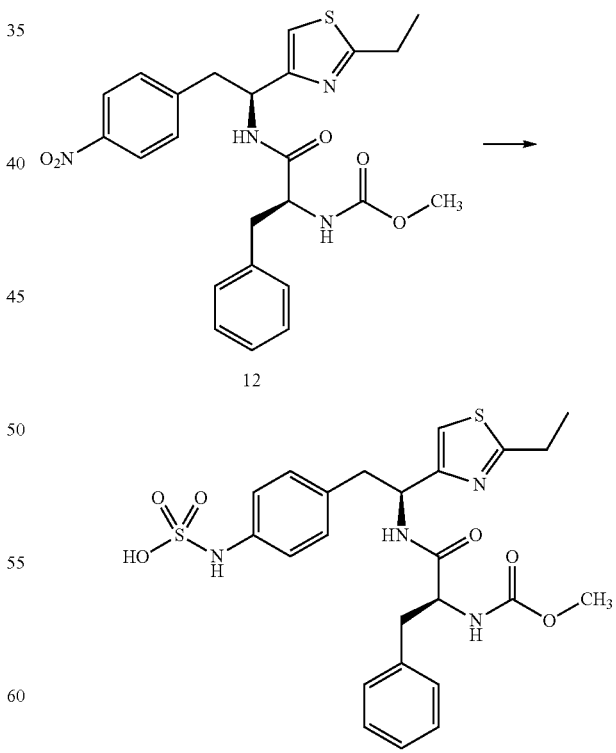

12

13

Reagents and conditions: (b) (i) $H_2$:Pd/C, MeOH; (ii) $SO_3$-pyridine, $NH_4OH$; rt, 18 hr.

EXAMPLE 3

4-{(S)-2-[(S)-2-(Methoxycarbonylamino)-3-phenyl-propanamido]-2-(2-ethylthiazol-4-yl)ethyl}phenylsulfamic acid (13)

Preparation of methyl (S)-1-[(S)-1-(2-ethylthiazole-4-yl)-2-(4-nitrophenyl)-ethyl]amino-1-oxo-3-phenylpropane-2-ylcarbamate (12): A mixture of propanethioamide (69 mg, 0.78 mmol) and (S)-tert-butyl 4-bromo-1-(4-nitrophenyl)-3-oxobutan-2-ylcarbamate, 7, (0.300 g, 0.77 mmol) in CH₃CN (4 mL) is refluxed for 2 hours. The reaction mixture is cooled to room temperature and diethyl ether is added to precipitate the intermediate 2-(nitrophenyl)-(S)-1-(4-ethyl-thiazol-2-yl)ethylamine which is isolated by filtration as the hydrobromide salt. The hydrobromide salt is dissolved in DMF (8 mL) together with diisoproylethylamine (0.38 mL, 2.13 mmol), 1-hydroxybenzotriazole (107 mg, 0.71 mmol) and (S)-(2-methoxycarbonyl-amino)-3-phenylpropionic acid (175 mg, 0.78 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.300 g (81% yield) of the desired product which is used without further purification. LC/MS ESI+MS 483 (M+1).

Preparation of 4-((S)-2-((S)-2-(methoxycarbonylamino)-3-phenylpropanamido)-2-(2-ethylthiazol-4-yl)ethyl)phenyl-sulfamic acid ammonium salt (13): tert-Butyl (S)-1-(S)-2-(4-nitrophenyl)-1-(2-ethylthiazole-4-yl)ethylamino-1-oxo-3-phenylpropan-2-ylcarbamate, 12, (0.300 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (223 mg, 1.40 mmol). The reaction is stirred at room temperature for 5 minutes after which a 7% solution of NH₄OH (12 mL) is added. The mixture is then concentrated and the resulting residue is purified by reverse phase chromatography to afford 25 mg of the desired product as the ammonium salt. ¹H NMR (300 MHz, MeOH-d₄) δ 7.14-7.24 (m, 6H), 6.97-7.0 (m, 4H), 6.62 (s, 1H), 5.10-5.30 (μ, 1H), 4.36 (t, J=7.2 Hz, 1H), 3.63 (s, 3H), 3.14 (dd, J=13.5 and 6.3 Hz, 1H), 2.93-3.07 (m, 5H), 2.81 (dd, J=13.5 and 6.3 HZ, 1H), 1.39 (t, J=7.8 Hz, 3H).

In another iteration of the process of the present disclosure, compound 13, as well as the other analogues which comprise the present disclosure, can be isolated as the free acid by adapting the procedure described herein below.

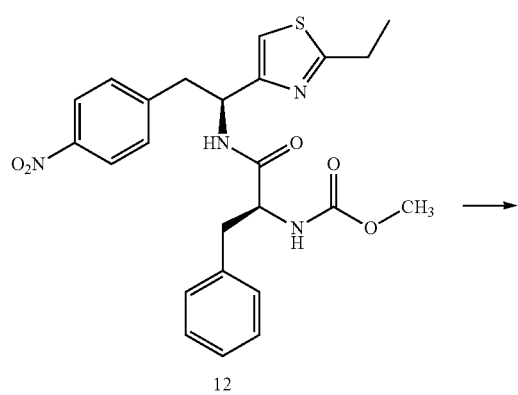

12

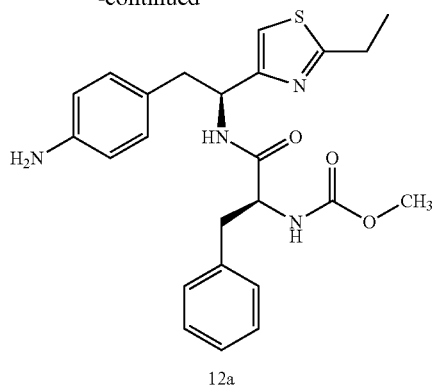

12a

Reagents and conditions: (a) H₂:Pd/C, MeOH; rt, 40 hr.

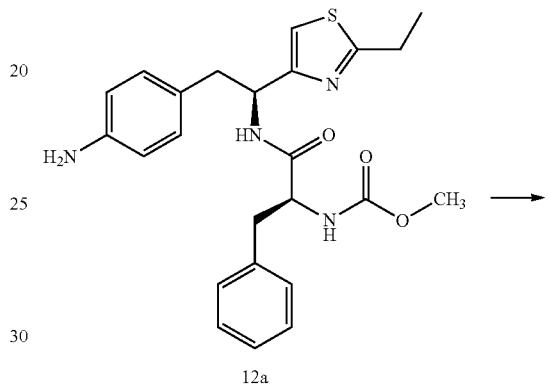

12a

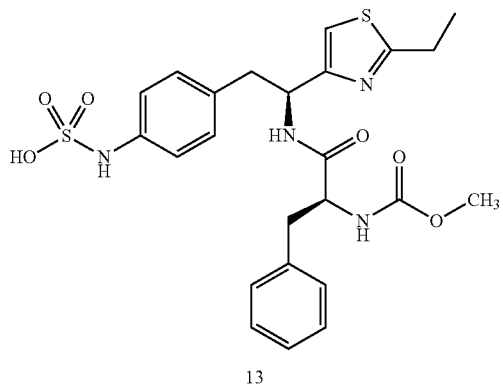

13

Reagents and conditions: (b) (i) SO₃-pyridine, CH₃CN; heat, 45 min; (ii) Conc. H₃PO₄

EXAMPLE 4

4-((S)-2-(S)-2-(Methoxycarbonylamino)-3-phenyl-propanamido)-2-(2-ethylthiazol-4-yl)ethyl)phenyl-sulfamic acid [Free Acid Form] (13)

Preparation of {1-[2-(S)-(4-(S)-aminophenyl)-1-(2-ethyl-thiazol-4-yl)ethyl-carbamoyl]-2-phenylethyl}-carbamic acid methyl ester (12a): A Parr hydrogenation vessel is charged with tert-butyl (S)-1-(S)-2-(4-nitrophenyl)-1-(2-ethylthiazole-4-yl)ethylamino-1-oxo-3-phenylpropan-2-yl-carbamate, 12, (18.05 g, 37.4 mmol, 1.0 eq) and Pd/C (10% Pd on C, 50% wet, Degussa-type E101 NE/W, 2.68 g, 15 wt %) as solids. MeOH (270 mL, 15 mL/g) is added to provide a suspension. The vessel is put on a Parr hydrogenation apparatus. The vessel is submitted to a fill/vacuum evacuate process with N₂ (3×20 psi) to inert, followed by the same procedure with H₂ (3×40 psi). The vessel is filled with H₂ and the vessel is shaken under 40 psi H₂ for ~40 hr. The vessel is evacuated and the atmosphere is purged with N₂ (5×20 psi). An aliquot is filtered and analyzed by HPLC to insure complete conversion. The suspension is filtered through a pad of celite to remove the catalyst, and the homogeneous yellow filtrate is concentrated by rotary evaporation to afford 16.06 g (95% yield) of the desired product as a tan solid, which is used without further purification.

Preparation of 4-((S)-2-((S)-2-(methoxycarbonyl)-3-phenylpropanamido)-2-(2-ethylthiazol-4-yl)ethyl)phenylsulfamic acid (13): A 100 mL RBF is charged with {1-[2-(S)-(4-(S)-aminophenyl)-1-(2-ethylthiazol-4-yl)ethyl-carbamoyl]-2-phenylethyl}-carbamic acid methyl ester, 12a, (10.36 g, 22.9 mmol, 1.0 eq.) prepared in the step described herein above. Acetonitrile (50 mL, 5 mL/g) is added and the yellow suspension is stirred at room temperature. A second 3-necked 500 mL RBF is charged with SO₃.pyr (5.13 g, 32.2 mmol, 1.4 eq.) and acetonitrile (50 mL 5 mL/g) and the white suspension is stirred at room temperature. Both suspensions are gently heated until the reaction solution containing {1-[2-(S)-(4-(S)-aminophenyl)-1-(2-ethylthiazol-4-yl)ethyl-carbamoyl]-2-phenylethyl}-carbamic acid methyl ester becomes red-orange in color (typically for this example about 44° C.). This substrate containing solution is poured in one portion into the stirring suspension of SO₃.pyr at 35° C. The resulting opaque mixture (39° C.) is stirred vigorously while allowed to slowly cool to room temperature. After stirring for 45 min, the reaction is determined to be complete by HPLC. H₂O (200 mL, 20 mL/g) is added to the orange suspension to provide a yellow-orange homogeneous solution having a pH of approximately 2.4. Concentrated H₃PO₄ is added slowly over 12 minutes to lower the pH to approximately 1.4. During this pH adjustment, an off-white precipitate is formed and the solution is stirred at room temperature for 1 hr. The suspension is filtered and the filter cake is washed with the filtrate. The filter cake is air-dried on the filter overnight to afford 10.89 g (89% yield) of the desired product as a tan solid.

The following are further non-limiting examples of the second aspect of Category II of the present disclosure.

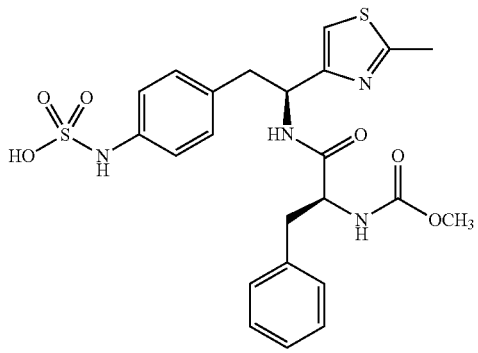 [SMILES: COC(=O)N[C@@H](Cc1ccccc1)C(=O)N[C@@H](Cc1ccc(NS(=O)(=O)O)cc1)c1csc(C)n1]

4-{(S)-2-[(S)-2-(Methoxycarbonylamino)-3-phenylpropanamido]-2-(2-methylthiazol-4-yl)ethyl}phenylsulfamic acid: ¹H NMR (300 MHz, MeOH-d₄) δ 8.15 (d, J=8.4 Hz, 1H), 7.16-7.25 (m, 5H), 6.97-7.10 (m, 4H), 6.61 (s, 1H), 5.00-5.24 (m, 1H), 4.36 (t, J=7.2 Hz, 1H), 3.64 (s, 3H), 3.11-3.19 (s, 1H), 2.92-3.04 (s, 2H), 2.81 (dd, J=13.5 and 8.1 Hz, 1H), 2.75 (s, 3H).

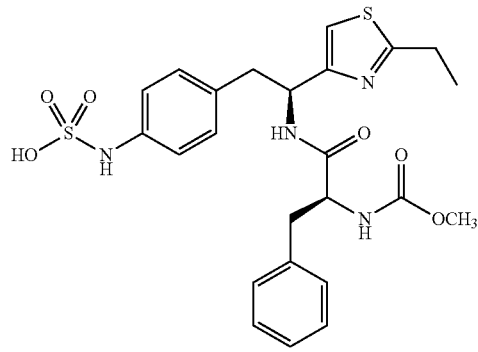 [SMILES: CCc1nc([C@H](Cc2ccc(NS(=O)(=O)O)cc2)NC(=O)[C@H](Cc2ccccc2)NC(=O)OC)cs1]

4-{(S)-2-(2-Ethylthiazole-4-yl)-2-[(S)-2-(methoxycarbonylamino)-3-phenylpropan-amido]ethyl}phenylsulfamic acid: ¹H NMR (300 MHz, MeOH-d₄) δ 7.16-7.29 (m, 5H), 7.02-7.12 (m, 4H), 6.83 (s, 1H), 5.10-5.35 (m, 1H), 3.52-3.67 (m, 3H), 3.18-3.25 (m, 2H), 3.05 (q, J=7.5 Hz, 2H), 2.82-2.95 (m, 2H), 2.65 (s, 3H), 1.39 (t, J=7.5 Hz, 3H).

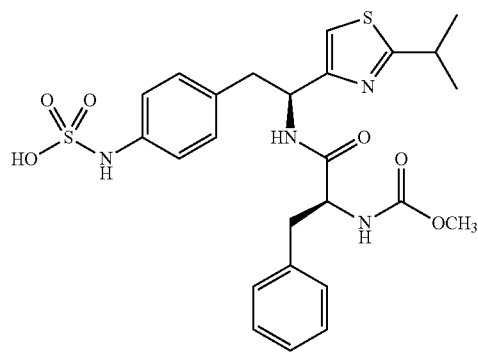 [SMILES: COC(=O)N[C@@H](Cc1ccccc1)C(=O)N[C@@H](Cc1ccc(NS(=O)(=O)O)cc1)c1csc(C(C)C)n1]

4-{(S)-2-(2-Isopropylthiazol-4-yl)-2-[(S)-2-(methoxycarbonylamino)-3-phenylpropan-amido]ethyl}phenylsulfamic acid: ¹H NMR (CD₃OD) δ 8.16 (d, 1H, J=8.7 Hz), 7.22-7.13 (m, 3H), 7.07 (d, 1H, J=8.4 Hz), 6.96 (d, 1H, J=8.1 Hz), 6.62 (s, 1H), 5.19 (t, 1H, J=7.2 Hz), 4.36 (t, 1H, J=7.8 Hz), 3.63 (s, 3H), 3.08 (1H, A of ABX, J=3.6, 14.5 Hz), 2.99 (1H, B of ABX, J=7.2, 13.8 Hz), 2.85-2.78 (m, 1H), 1.41 (d, 6H, J=6.9 Hz).

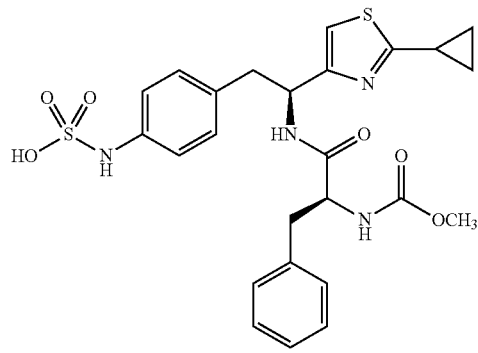 [SMILES: COC(=O)N[C@@H](Cc1ccccc1)C(=O)N[C@@H](Cc1ccc(NS(=O)(=O)O)cc1)c1csc(C2CC2)n1]

4-{(S)-2-(2-Cyclopropylthiazol-4-yl)-2-[(S)-2-(methoxycarbonylamino)-3-phenylpropanamido]ethyl}phenylsulfamic acid: ¹H NMR (CD₃OD): δ 7.15-7.02 (m, 5H), 6.96-6.93 (d, 2H, J=8.4 Hz), 6.86-6.83 (d, 2H, J=8.3 Hz), 6.39 (s, 1H), 5.01 (t, 1H, J=5.0 Hz), 4.22 (t, 1H, J=7.4 Hz), 3.51 (s, 3H), 2.98-2.69 (m, 2H), 2.22-2.21 (m, 1H), 1.06-1.02 (m, 2H), 0.92-0.88 (m, 2H).

ethyl}phenylsulfamic acid: ¹H NMR (CD₃OD): δ 7.78-7.76 (d, 1H, J=5.4 Hz), 7.36-7.14 (m, 10H), 7.03 (s, 1H), 5.39 (t, 1H, J=6.9 Hz), 4.54 (t, 1H, J=7.3 Hz), 3.80 (s, 3H), 3.39-2.98 (m, 4H).

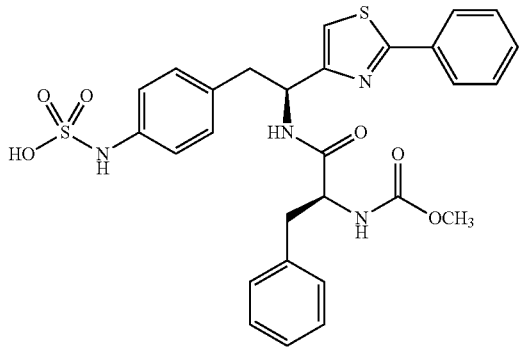 [SMILES: COC(=O)N[C@@H](Cc1ccccc1)C(=O)N[C@@H](Cc1ccc(NS(=O)(=O)O)cc1)c1csc(-c2ccccc2)n1]

4-{(S)-2-[(S)-2-(Methoxycarbonylamino)-3-phenylpropionamido]-2-(2-phenylthiazole-4-yl)ethyl}phenylsulfamic acid: ¹H NMP (300 MHz, DMSO-d₆) δ 7.96-7.99 (m, 2H), 7.51-7.56 (m, 3H), 7.13-7.38 (m, 6H), 6.92-6.95 (m, 4H), 5.11-5.16 (m, 1H), 4.32-4.35 (m, 1H), 3.51 (s, 3H), 3.39-3.40 (m, 2H), 3.09-3.19 (m, 1H), 2.92-3.02 (m, 2H), 2.75 (dd, J=10.5 Hz and 9.9 Hz, 1H).

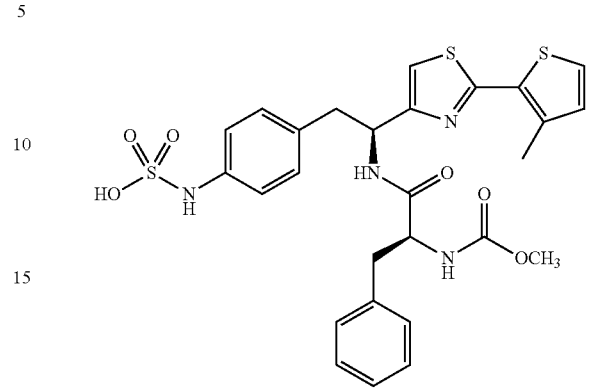

4-{(S)-2-[(S)-2-(Methoxycarbonylamino)-3-phenylpropanamido]-2-[2-(3-methylthiophen-2-yl)thiazol-4-yl]ethyl}phenylsulfamic acid: ¹H NMR (CD₃OD): δ 7.38 (d, 1H, J=5.1 Hz), 7.15-6.93 (m, 10H), 6.73 (s, 1H), 5.17 (t, 1H, J=6.9 Hz), 4.31 (t, 1H, J=7.3 Hz), 3.57 (s, 3H), 3.18-3.11 (m, 1H), 3.02-2.94 (m, 2H), 2.80-2.73 (m, 1H), 2.46 (s, 3H).

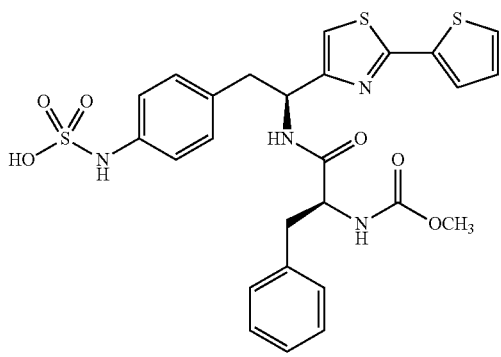 [SMILES: COC(=O)N[C@@H](Cc1ccccc1)C(=O)N[C@@H](Cc1ccc(NS(=O)(=O)O)cc1)c1csc(-c2cccs2)n1]

4-{(S)-2-[(S)-2-(Methoxycarbonylamino)-3-phenylpropanamido]-2-[2-(thiophen-2-yl)thiazol-4-yl]ethyl}phenylsulfamic acid: ¹H NMR (CD₃OD): δ 7.61-7.56 (m, 2H), 7.25-7.01 (m, 10H), 6.75 (s, 1H), 5.24-5.21 (q, 1H, J=7.2 Hz), 4.38 (t, 1H, J=7.2 Hz), 3.60 (s, 3H), 3.23-3.14 (m, 1H), 3.08-3.00 (m, 2H), 2.87-2.80 (m, 1H).

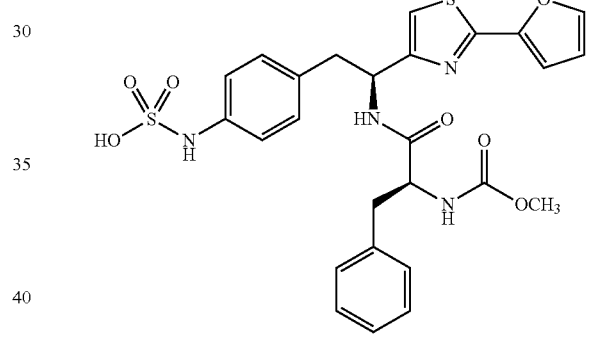

4-{[(S)-2-(2-(Furan-2-yl)thiazol-4-yl]-2-[(S)-2-(methoxycarbonylamino)-3-phenylpropanamido]ethyl}phenylsulfamic acid: ¹H NMR (CD₃OD): δ 7.54-7.46 (m, 1H), 7.02-6.79 (m, 10H), 6.55-6.51 (m, 1H), 6.44-6.41 (m, 1H), 5.02-5.00 (q, 1H, J=6.4 Hz), 4.16-4.14 (q, 1H, J=7.1 Hz), 3.43 (s, 3H), 2.96-2.58 (m, 4H).

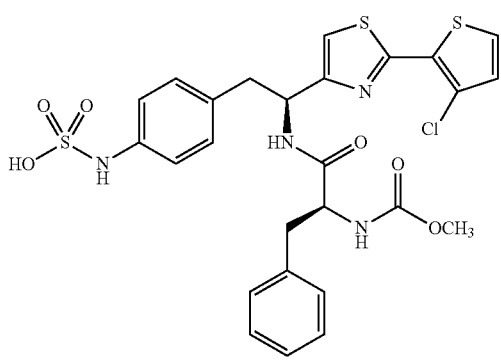 [SMILES: COC(=O)N[C@@H](Cc1ccccc1)C(=O)N[C@@H](Cc1ccc(NS(=O)(=O)O)cc1)c1csc(-c2sccc2Cl)n1]

4-{(S)-2-[2-(3-Chlorothiophen-2-yl)thiazol-4-yl]-2-[(S)-2-(methoxycarbonylamino)-3-phenylpropanamido]

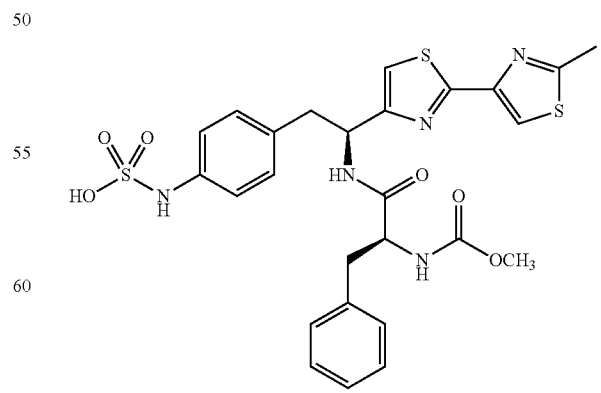

4-{(S)-2-[(S)-2-(Methoxycarbonylamino)-3-phenylpropanamido]-2-[2-(2-methylthiazole-4-yl)thiazole-4yl]

ethyl}phenylsulfamic acid: $^1$H NMR (300 MHz, MeOH-d$_4$) δ 8.27 (d, J=5.4 Hz, 1H), 7.97 (s, 1H), 6.99-7.21 (m, 8H), 5.18-5.30 (m, 1H), 4.30-4.39 (m, 1H), 3.64 (s, 3H), 3.20 (dd, J=14.1 and 6.6 Hz, 1H), 2.98-3.08 (m, 2H), 2.84 (dd, J=14.1 and 6.6 Hz, 1H), 2.78 (s, 3H).

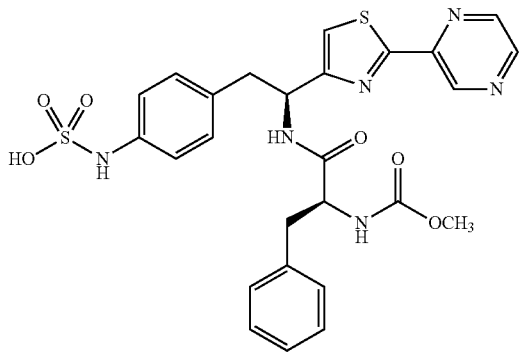 [SMILES: COC(=O)N[C@@H](Cc1ccccc1)C(=O)N[C@@H](Cc1ccc(NS(=O)(=O)O)cc1)c1csc(-c2cnccn2)n1]

4-{(S)-2-[(S)-2-(Methoxycarbonylamino)-3-phenylpropanamido]-2-[(2-pyrazin-2-yl)thiazole-4-yl]ethyl}phenylsulfamic acid: $^1$H NMR (300 MHz, MeOH-d$_4$) δ 9.34 (s, 1H), 8.65 (s, 2H), 8.34 (d, J=8.1 Hz, 1H), 7.00-5.16 (m. 9H), 5.30 (q, J=7.2 Hz, 1H), 4.41 (t, J=7.2 Hz, 1H), 3.65 (s, 3H), 3.23 (dd, J=13.8 and 6.9 Hz, 1H), 2.98-3.13 (m, 2H), 2.85 (dd, J=13.8 and 6.9 Hz, 1H).

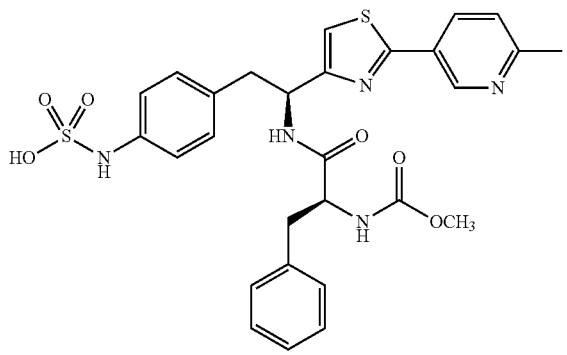 [SMILES: COC(=O)N[C@@H](Cc1ccccc1)C(=O)N[C@@H](Cc1ccc(NS(=O)(=O)O)cc1)c1csc(-c2ccc(C)nc2)n1]

4-{(S)-2-[(S)-2-(Methoxycarbonylamino)-3-phenylpropanamido]-2-[2-(6-methylpyridin-3-yl)thiazol-4-yl]ethyl}phenylsulfamic acid: $^1$H NMR (CD$_3$OD): δ 8.90 (s, 1H), 8.19-8.13 (m, 1H), 7.39-7.36 (d, 1H, J=8.2 Hz), 7.07-6.88 (m, 9H), 6.79 (s, 1H), 5.17 (t, 1H, J=7.0 Hz), 4.29 (t, 1H, J=7.4 Hz), 3.54 (s, 3H), 3.10-2.73 (m, 4H), 2.53 (s, 3H).

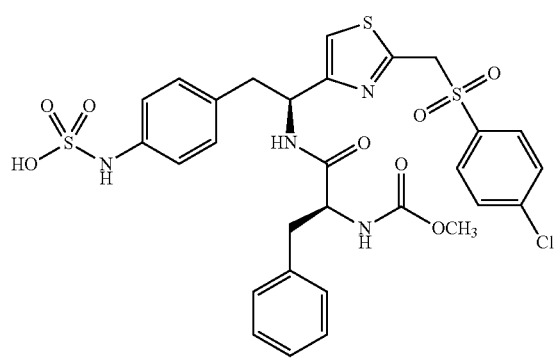 [SMILES: COC(=O)N[C@@H](Cc1ccccc1)C(=O)N[C@@H](Cc1ccc(NS(=O)(=O)O)cc1)c1csc(CS(=O)(=O)c2ccc(Cl)cc2)n1]

4-{(S)-2-{2-[(4-Chlorophenylsulfonyl)methyl]thiazol-4-yl}-2-[(S)-2-(methoxy-carbonylamino)-3-phenylpropanamido]ethyl}phenylsulfamic acid: $^1$H NMR (CD$_3$OD): δ 7.96-7.93 (d, 2H, J=8.6 Hz), 7.83-7.80 (d, 2H, J=8.6 Hz), 7.44-7.34 (m, 5H), 7.29-7.27 (d, 2H, J=8.4 Hz), 7.14-7.11 (d, 2H, J=8.4 Hz), 6.97 (s, 1H), 5.31 (t, 1H, J=6.8 Hz), 5.22-5.15 (m, 2H), 4.55 (t, 1H, J=7.3 Hz), 3.84 (s, 3H), 3.20-2.96 (m, 4H).

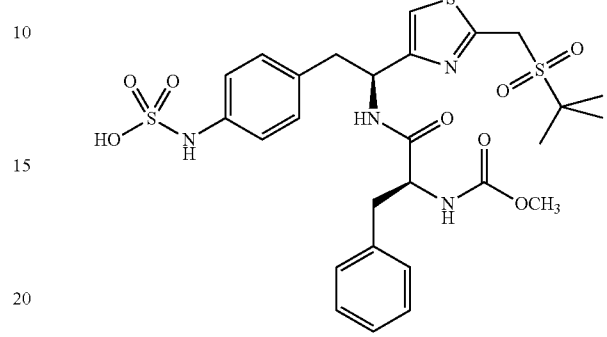

4-{(S)-2-[2-(tert-Butylsulfonylmethyl)thiazol-4-yl]-2-[(S)-2-(methoxycarbonyl-amino)-3-phenylpropanamido]ethyl}phenylsulfamic acid: $^1$H NMR (CD$_3$OD): δ 7.40-7.30 (m, 5H), 7.21-7.10 (m, 4H), 7.02 (s, 1H), 5.37 (t, 1H, J=6.9 Hz), 5.01-4.98 (m, 2H), 4.51 (t, 1H, J=7.1 Hz), 3.77 (s, 3H), 3.34-2.91 (m, 4H), 1.58 (s, 9H).

Category III of the present disclosure relates to compounds wherein R is a substituted or unsubstituted thiazol-2-yl unit having the formula:

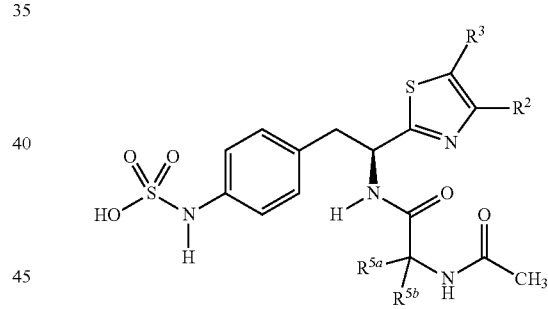

one embodiment of which relates to inhibitors having the formula:

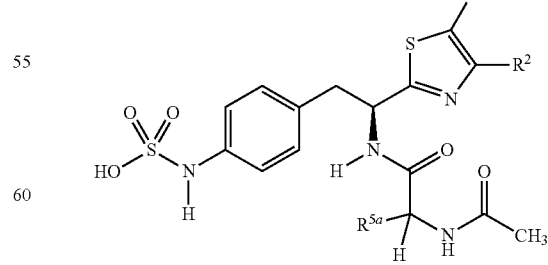

wherein R units are thiazol-2-yl units, that when substituted, are substituted with $R^2$ and $R^3$ units. R and $R^{5a}$ units are further described in Table V.

TABLE V

| No. | R | R$^{5a}$ |
| --- | --- | --- |
| E101 | thiazol-2-yl | (S)-benzyl |
| E102 | 4-methylthiazol-2-yl | (S)-benzyl |
| E103 | 4-ethylthiazol-2-yl | (S)-benzyl |
| E104 | 4-propylthiazol-2-yl | (S)-benzyl |
| E105 | 4-iso-propylthiazol-2-yl | (S)-benzyl |
| E106 | 4-cyclopropylthiazol-2-yl | (S)-benzyl |
| E107 | 4-butylthiazol-2-yl | (S)-benzyl |
| E108 | 4-tert-butylthiazol-2-yl | (S)-benzyl |
| E109 | 4-cyclohexylthiazol-2-yl | (S)-benzyl |
| E110 | 4-(2,2,2-trifluoroethyl)thiazol-2-yl | (S)-benzyl |
| E111 | 4-(3,3,3-trifluoropropyl)thiazol-2-yl | (S)-benzyl |
| E112 | 4-(2,2-difluorocyclopropyl)thiazol-2-yl | (S)-benzyl |
| E113 | 4-(methoxymethyl)thiazol-2-yl | (S)-benzyl |
| E114 | 4-(carboxylic acid ethyl ester)thiazol-2-yl | (S)-benzyl |
| E115 | 4,5-dimethylthiazol-2-yl | (S)-benzyl |
| E116 | 4-methyl-5-ethylthiazol-2-yl | (S)-benzyl |
| E117 | 4-phenylthiazol-2-yl | (S)-benzyl |
| E118 | 4-(4-chlorophenyl)thiazol-2-yl | (S)-benzyl |
| E119 | 4-(3,4-dimethylphenyl)thiazol-2-yl | (S)-benzyl |
| E120 | 4-methyl-5-phenylthiazol-2-yl | (S)-benzyl |
| E121 | 4-(thiophen-2-yl)thiazol-2-yl | (S)-benzyl |
| E122 | 4-(thiophen-3-yl)thiazol-2-yl | (S)-benzyl |
| E123 | 4-(5-chlorothiophen-2-yl)thiazol-2-yl | (S)-benzyl |
| E124 | 5,6-dihydro-4H-cyclopenta[d]thiazol-2-yl | (S)-benzyl |
| E125 | 4,5,6,7-tetrahydrobenzo[d]thiazol-2-yl | (S)-benzyl |

The compounds encompassed within Category III of the present disclosure can be prepared by the procedure outlined in Scheme IV and described in Example 5 herein below.

Scheme IV

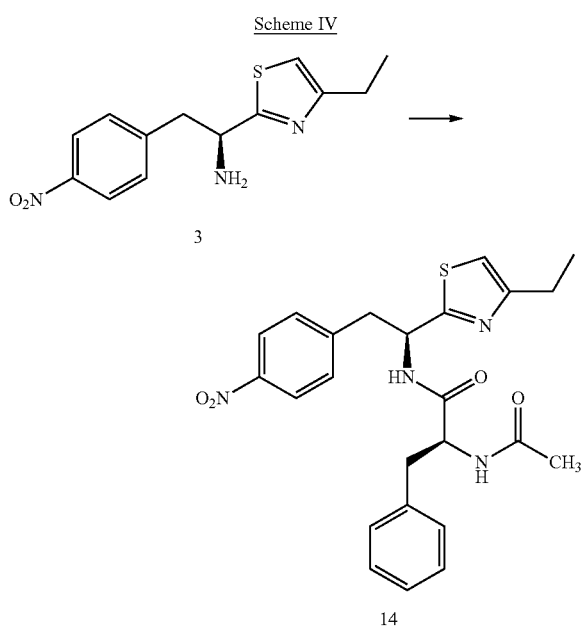

Reagents and conditions: (a) Ac-Phe, EDCI, HOBt, DIPEA, DMF; rt, 18 hr.

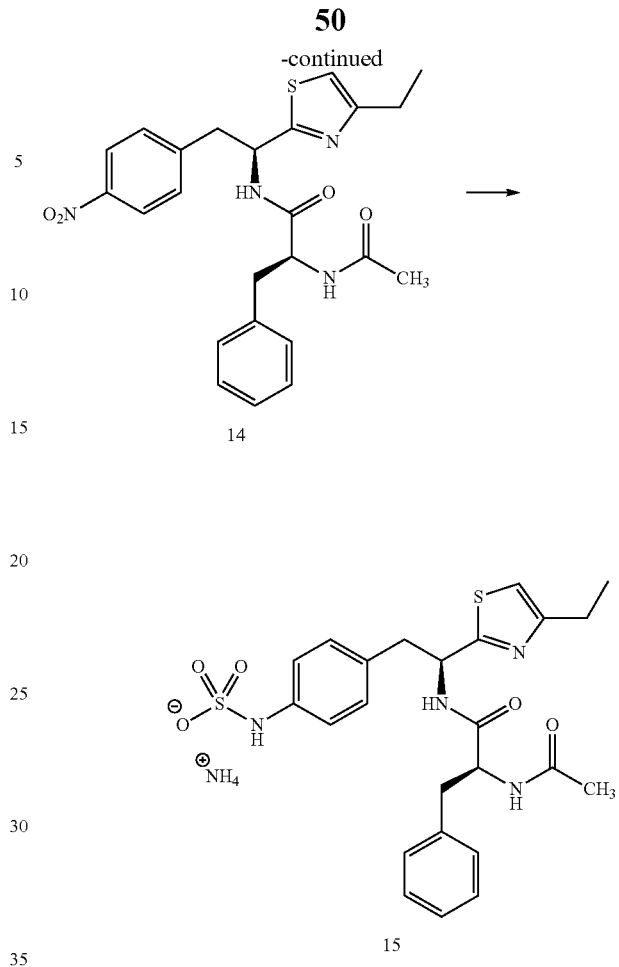

Reagents and conditions: (b) (i) H$_2$:Pd/C, MeOH; (ii) SO$_3$-pyridine, NH$_4$OH.

EXAMPLE 5

4-[(S)-2-(S)-2-Acetamido-3-phenylpropanamido)-2-(4-ethylthiazol-2-yl)ethyl]phenylsulfamic acid (15)

Preparation of (S)-2-acetamido-N—[(S)-1-(4-ethylthiazol-2-yl)-2-(4-nitrophenyl)-ethyl]-3-phenylpropanamide (14): To a solution of 1-(S)-(4-ethylthiazol-2-yl)-2-(4-nitrophenyl)ethyl amine hydrobromide, 3, (0.343 g, 0.957 mmol), N-acetyl-L-phenylalanine (0.218 g), 1-hydroxybenzotriazole (HOBt) (0.161 g), diisopropyl-ethylamine (0.26 g), in DMF (10 mL) at 0°, is added 1-(3-dimethylaminopropyl)-3-ethylcarbodiimide (EDCI) (0.201 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO$_3$, water and brine, and dried over Na$_2$SO$_4$. The solvent is removed in vacuo to afford 0.313 g (70% yield) of the desired product which is used without further purification. LC/MS ESI+ 467 (M+1).

Preparation of 4-((S)-2-((S)-2-acetamido-3-phenylpropanamido)-2-(4-ethylthiazol-2-yl)ethyl)phenylsulfamic acid (15): (S)-2-Acetamido-N—[(S)-1-(4-ethylthiazol-2-yl)-2-(4-nitrophenyl)ethyl]-3-phenylpropanamide, 14, (0.313 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (12 mL) and treated with SO$_3$-pyridine (0.320 g). The reaction is stirred at room temperature for 5 minutes after which a 7% solution of NH$_4$OH (30 mL) is added. The mixture is then concentrated and the resulting residue is purified by reverse phase chromatography to afford 0.215 g of the desired product as the ammonium salt. $^1$H NMR (CD$_3$OD) δ 7.23-6.98 (m, 10H), 5.37 (t, 1H), 4.64 (t, 1H, J=6.3 Hz), 3.26-2.74 (m, 6H), 1.91 (s, 3H), 1.29 (t, 3H, J=7.5 Hz).

The following are further non-limiting examples of compounds encompassed within Category III of the present disclosure.

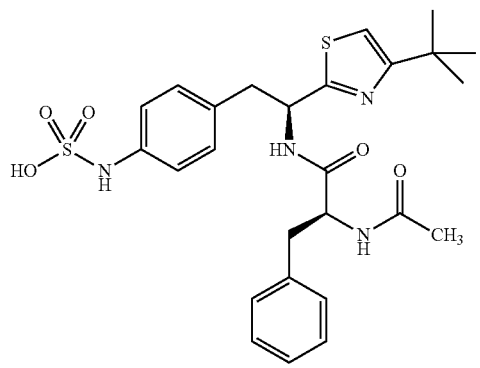 [SMILES: CC(=O)N[C@@H](Cc1ccccc1)C(=O)N[C@@H](Cc1ccc(NS(=O)(=O)O)cc1)c1nc(C(C)(C)C)cs1]

4-[(S)-2-(S)-2-Acetamido-3-phenylpropanamido)-2-(4-tert-butylthiazol-2-yl)ethyl]phenylsulfamic acid: $^1$H NMR (300 MHz, CD$_3$OD): δ 7.22-7.17 (m, 5H), 7.06 (dd, J=14.1, 8.4 Hz, 4H), 6.97 (d, J=0.9 Hz, 1H), 5.39 (dd, J=8.4, 6.0 Hz, 1H), 4.65 (t, J=7.2 Hz, 1H), 3.33-3.26 (m, 1H), 3.13-3.00 (m, 2H), 2.80 (dd, J=13.5, 8.7 Hz, 1H), 1.91 (s, 3H), 1.36 (s, 9H).

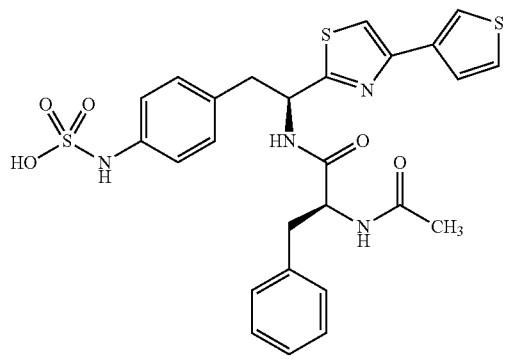 [SMILES: CC(=O)N[C@@H](Cc1ccccc1)C(=O)N[C@@H](Cc1ccc(NS(=O)(=O)O)cc1)c1nc(-c2ccsc2)cs1]

4-{(S)-2-(S)-2-Acetamido-3-phenylpropanamido)-2-[4-(thiophen-3-yl)thiazol-2-yl]ethyl}phenylsulfamic acid: $^1$H NMR (300 MHz, CD$_3$OD): δ 8.58 (d, J=8.1 Hz, 1H), 7.83-7.82 (m, 1H), 7.57-7.46 (m, 3H), 7.28-6.93 (m, 11H), 5.54-5.43 (m, 1H), 4.69-4.55 (m, 2H), 3.41-3.33 (m, 1H), 3.14-3.06 (3H), 2.86-2.79 (m, 1H), 1.93 (s, 3H).

The first aspect of Category IV of the present disclosure relates to compounds wherein R is a substituted or unsubstituted thiazol-2-yl unit having the formula:

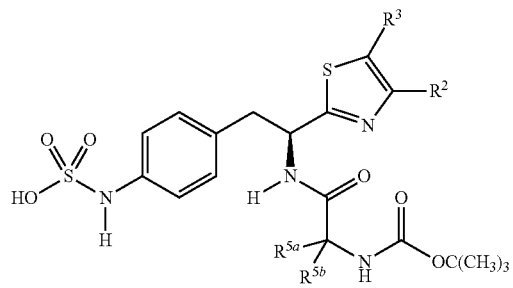

one embodiment of which relates to inhibitors having the formula:

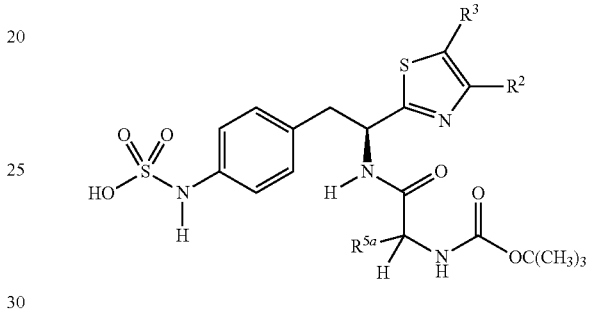

wherein R units and $R^{5a}$ units further described in Table VI.

TABLE VI

| No. | R | $R^{5a}$ |
|---|---|---|
| F126 | thiazol-2-yl | hydrogen |
| F127 | 4-methylthiazol-2-yl | hydrogen |
| F128 | 4-ethylthiazol-2-yl | hydrogen |
| F129 | 4-propylthiazol-2-yl | hydrogen |
| F130 | 4-iso-propylthiazol-2-yl | hydrogen |
| F131 | 4-cyclopropylthiazol-2-yl | hydrogen |
| F132 | 4-butylthiazol-2-yl | hydrogen |
| F133 | 4-tert-butylthiazol-2-yl | hydrogen |
| F134 | 4-cyclohexylthiazol-2-yl | hydrogen |
| F135 | 4,5-dimethylthiazol-2-yl | hydrogen |
| F136 | 4-methyl-5-ethylthiazol-2-yl | hydrogen |
| F137 | 4-phenylthiazol-2-yl | hydrogen |
| F138 | thiazol-2-yl | (S)-iso-propyl |
| F139 | 4-methylthiazol-2-yl | (S)-iso-propyl |
| F140 | 4-ethylthiazol-2-yl | (S)-iso-propyl |
| F141 | 4-propylthiazol-2-yl | (S)-iso-propyl |
| F142 | 4-iso-propylthiazol-2-yl | (S)-iso-propyl |
| F143 | 4-cyclopropylthiazol-2-yl | (S)-iso-propyl |
| F144 | 4-butylthiazol-2-yl | (S)-iso-propyl |
| F145 | 4-tert-butylthiazol-2-yl | (S)-iso-propyl |
| F146 | 4-cyclohexylthiazol-2-yl | (S)-iso-propyl |
| F147 | 4,5-dimethylthiazol-2-yl | (S)-iso-propyl |
| F148 | 4-methyl-5-ethylthiazol-2-yl | (S)-iso-propyl |
| F149 | 4-phenylthiazol-2-yl | (S)-iso-propyl |
| F150 | 4-(thiophen-2-yl)thiazol-2-yl | (S)-iso-propyl |

The compounds encompassed within Category IV of the present disclosure can be prepared by the procedure outlined in Scheme V and described in Example 6 herein below.

Scheme V

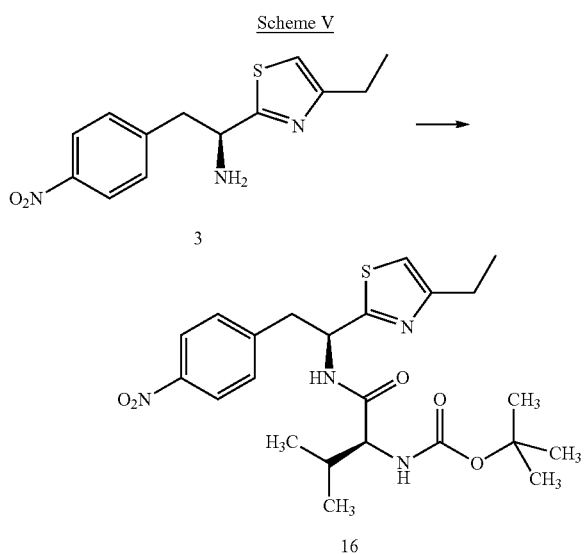

Reagents and conditions: (a) Boc-Val; EDCI, HOBt, DIPEA, DMF; rt, 18 hr.

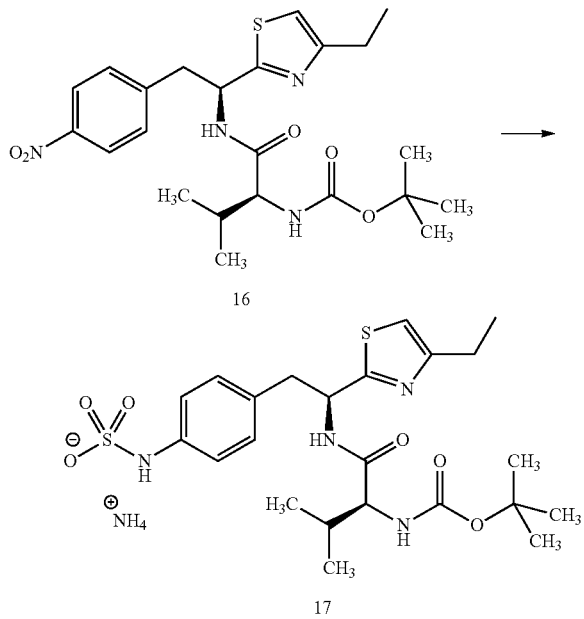

Reagents and conditions: (b) (i) H₂:Pd/C, MeOH; (ii) SO₃-pyridine, NH₄OH, rt, 2 hr.

EXAMPLE 6

4-{(S)-2-[(S)-2-(tert-Butoxycarbonylamino)-3-methylbutanamido]-2-(4-ethylthiazol-2-yl)ethyl}phenylsulfamic acid (17)

Preparation of tert-butyl (S)-1-[(S)-(4-ethylthiazol-2-yl)-2-(4-nitrophenyl)ethylamino]-3-methyl-1-oxobutan-2-yl-carbamate (16): To a solution of 1-(S)-(4-ethylthiazol-2-yl)-2-(4-nitrophenyl)ethyl amine hydrobromide, 3, (0.200 g, 0.558 mmol), (S)-(2-tert-butoxycarbonylamino)-3-methyl-butyric acid (0.133 g) and 1-hydroxybenzotriazole (HOBt) (0.094 g) in DMF (5 mL) at 0°, is added 1-(3-dimethylaminopropyl)-3-ethylcarbodiimide (EDCI) (0.118 g) followed by diisopropylamine (0.151 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.219 g (82% yield) of the desired product which is used without further purification. LC/MS ESI+ 477 (M+1).

Preparation of 4-{(S)-2-[(S)-2-(tert-butoxycarbonylamino)-3-methylbutanamido]-2-(4-ethylthiazol-2-yl)ethyl}phenylsulfamic acid (17): tert-Butyl (S)-(4-ethylthiazol-2-yl)-2-(4-nitrophenyl)ethylamino]-3-methyl-1-oxobutan-2-ylcarbamate, 16, (0.219 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (5 mL) and treated with SO₃-pyridine (0.146 g). The reaction is stirred at room temperature for 5 minutes after which a 7% solution of NH₄OH (30 mL) is added. The mixture is then concentrated and the resulting residue is purified by reverse phase chromatography to afford 0.148 g of the desired product as the ammonium salt. $^1$H NMR (CD₃OD) δ 7.08 (s, 4H), 7.02 (s, 1H), 5.43 (s, 1H), 3.85 (s, 1H), 3.28-2.77 (m, 4H), 1.94 (hep, 1H), 1.46 (s, 9H), 1.29 (s, 3H, J=7.3 Hz), 0.83 (d, 6H).

The following are further non-limiting examples of the second aspect of Category IV of the present disclosure.

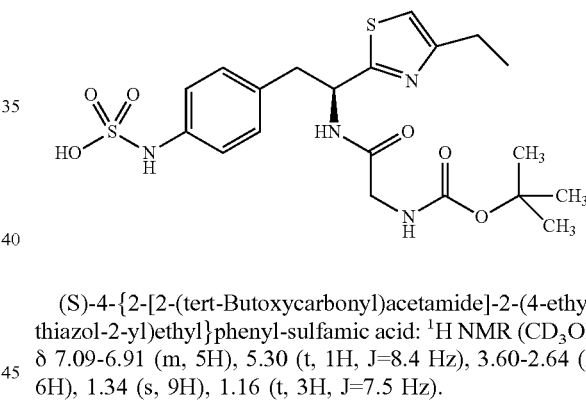

(S)-4-{2-[2-(tert-Butoxycarbonyl)acetamide]-2-(4-ethyl-thiazol-2-yl)ethyl}phenyl-sulfamic acid: $^1$H NMR (CD₃OD) δ 7.09-6.91 (m, 5H), 5.30 (t, 1H, J=8.4 Hz), 3.60-2.64 (m, 6H), 1.34 (s, 9H), 1.16 (t, 3H, J=7.5 Hz).

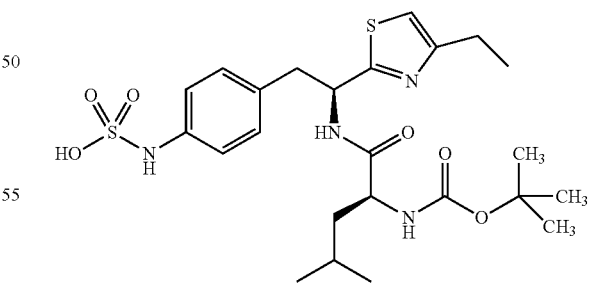

4-{(S)-2-[(S)-2-(tert-Butoxycarbonylamino)-4-methyl-pentanamido]-2-(4-ethylthiazol-2-yl)ethyl}phenylsulfamic acid: $^1$H NMR (CD₃OD) δ 7.19-7.00 (m, 5H), 5.50-5.40 (m, 1H), 4.13-4.06 (m, 1H), 3.32 (1H, A of ABX, J=7.5, 18 Hz), 3.12 (1H, B of ABX, J=8.1, 13.8 Hz), 2.79 (q, 2H, J=7.8, 14.7 Hz), 1.70-1.55 (m, 1H), 1.46 (s, 9H), 1.33 (t, 3H, J=2.7 Hz), 0.92 (q, 6H, J=6, 10.8 Hz).

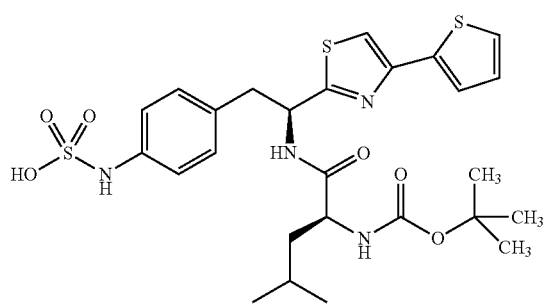 [SMILES: CC(C)C[C@H](NC(=O)OC(C)(C)C)C(=O)N[C@@H](Cc1ccc(NS(=O)(=O)O)cc1)c1nc(-c2cccs2)cs1]

4-{(S)-2-[(S)-2-(tert-Butoxycarbonylamino)-4-methyl-pentanamido]-2-[2-(thiophen-2-yl)thiazol-4-yl]ethyl}phenylsulfamic acid: $^1$H NMR (CD$_3$OD) δ 8.06 (d, 1H, J=8.4 Hz), 7.61-7.58 (m, 1H), 7.57 (s, 1H), 7.15 (t, 1H, J=0.6 Hz), 7.09-6.98 (m, 6H), 5.30-5.20 (m, 1H), 4.10-4.00 (m, 1H), 3.19-3.13 (m, 2H), 1.63-1.55 (m, 2H), 1.48-1.33 (m, 10H), 0.95-0.89 (m, 6H).

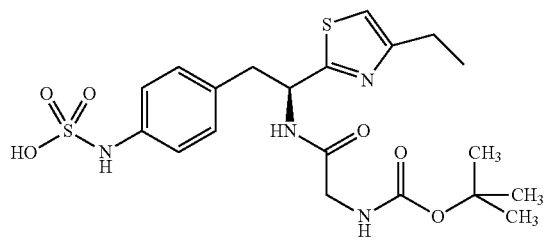 [SMILES: CCc1csc([C@H](Cc2ccc(NS(=O)(=O)O)cc2)NC(=O)CNC(=O)OC(C)(C)C)n1]

(S)-4-{2-[2-(tert-Butoxycarbonyl)acetamide]-2-(4-ethyl-thiazol-2-yl)ethyl}-phenylsulfamic acid: $^1$H NMR (CD$_3$OD) δ 7.09-6.91 (m, 5H), 5.30 (t, 1H, J=8.4 Hz), 3.60-2.64 (m, 6H), 1.34 (s, 9H), 1.16 (t, 3H, J=7.5 Hz).

A further embodiment of Category IV relates to inhibitors having the formula:

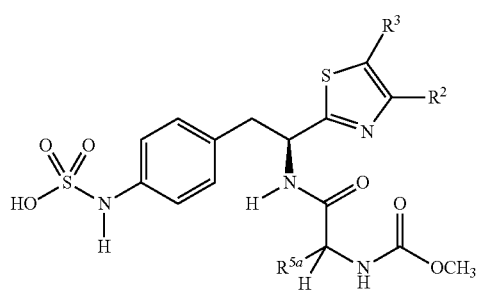

wherein R units and R$^{5a}$ units further described in Table VII.

TABLE VII

| No. | R | R$^{5a}$ |
| --- | --- | --- |
| G151 | thiazol-2-yl | hydrogen |
| G152 | 4-methylthiazol-2-yl | hydrogen |
| G153 | 4-ethylthiazol-2-yl | hydrogen |
| G154 | 4-propylthiazol-2-yl | hydrogen |
| G155 | 4-iso-propylthiazol-2-yl | hydrogen |
| G156 | 4-cyclopropylthiazol-2-yl | hydrogen |
| G157 | 4-butylthiazol-2-yl | hydrogen |
| G158 | 4-tert-butylthiazol-2-yl | hydrogen |
| G159 | 4-cyclohexylthiazol-2-yl | hydrogen |

TABLE VII-continued

| No. | R | R$^{5a}$ |
| --- | --- | --- |
| G160 | 4,5-dimethylthiazol-2-yl | hydrogen |
| G161 | 4-methyl-5-ethylthiazol-2-yl | hydrogen |
| G162 | 4-phenylthiazol-2-yl | hydrogen |
| G163 | thiazol-2-yl | (S)-iso-propyl |
| G164 | 4-methylthiazol-2-yl | (S)-iso-propyl |
| G165 | 4-ethylthiazol-2-yl | (S)-iso-propyl |
| G166 | 4-propylthiazol-2-yl | (S)-iso-propyl |
| G167 | 4-iso-propylthiazol-2-yl | (S)-iso-propyl |
| G168 | 4-cyclopropylthiazol-2-yl | (S)-iso-propyl |
| G169 | 4-butylthiazol-2-yl | (S)-iso-propyl |
| G170 | 4-tert-butylthiazol-2-yl | (S)-iso-propyl |
| G171 | 4-cyclohexylthiazol-2-yl | (S)-iso-propyl |
| G172 | 4,5-dimethylthiazol-2-yl | (S)-iso-propyl |
| G173 | 4-methyl-5-ethylthiazol-2-yl | (S)-iso-propyl |
| G174 | 4-phenylthiazol-2-yl | (S)-iso-propyl |
| G175 | 4-(thiophen-2-yl)thiazol-2-yl | (S)-iso-propyl |

The compounds encompassed within this embodiment of Category IV can be made according to the procedure outlined in Scheme V and described in Example 6 by substituting the corresponding methylcarbamate for the Boc-protected reagent. The following are non-limiting examples of this embodiment.

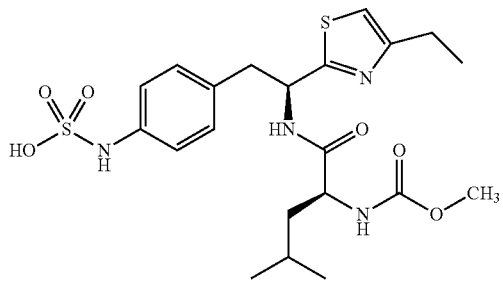 [SMILES: CCc1csc([C@H](Cc2ccc(NS(=O)(=O)O)cc2)NC(=O)[C@H](CC(C)C)NC(=O)OC)n1]

4-{(S)-2-(4-Ethylthiazol-2-yl)-2-[(S)-2-(methoxycarbonyl)-4-methylpentanamido]ethyl}phenylsulfamic acid: $^1$H NMR (CD$_3$OD) δ 7.12-7.03 (m, 5H), 6.84 (d, 1H, J=8.4 Hz), 5.40 (t, 1H, J=5.7 Hz), 4.16 (t, 1H, J=6.3 Hz), 3.69 (s, 3H), 3.61-3.55 (m, 1H), 3.29-3.27 (m, 1H), 3.14-3.07 (m, 1H), 2.81 (q, 2H, J=3.9, 11.2 Hz), 1.66-1.59 (m, 1H), 1.48-1.43 (m, 2H), 1.31 (t, 3H, J=4.5 Hz), 0.96-0.90 (m, 6H).

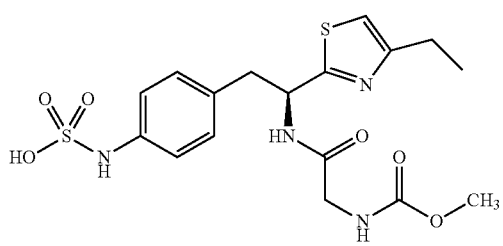 [SMILES: CCc1csc([C@H](Cc2ccc(NS(=O)(=O)O)cc2)NC(=O)CNC(=O)OC)n1]

(S)-4-{2-(4-Ethylthiazol-2-yl)-2-[2-(methoxycarbonyl)acetamido]ethyl}-phenylsulfamic acid: $^1$H NMR (CD$_3$OD) δ 7.12-7.07 (m, 4H), 7.03 (s, 1H), 5.42 (t, 1H, J=5.7 Hz), 3.83-3.68 (q, 2H, J=11.4 Hz), 3.68 (s, 3H), 3.34-3.04 (m, 2H), 2.83-2.76 (q, 2H, J=7.8 Hz), 1.31 (t, 3H, J=7.5 Hz).

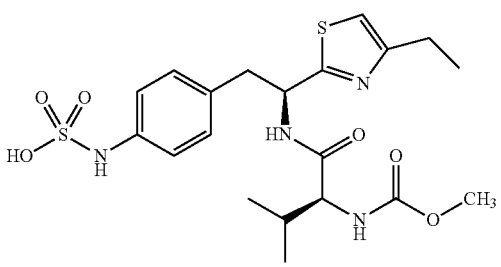 [SMILES: CCc1csc([C@H](Cc2ccc(NS(=O)(=O)O)cc2)NC(=O)[C@@H](NC(=O)OC)C(C)C)n1]

4-{(S)-2-(4-Ethylthiazol-2-yl)-2-[(S)-2-(methoxycarbonyl)-3-methylbutanamido]-ethyl}phenylsulfamic acid: $^1$H NMR (CD$_3$OD) δ 8.56 (d, 1H, J=7.8 Hz), 7.09 (s, 4H), 7.03 (s, 1H), 5.26-5.20 (m, 1H), 3.90 (d, 1H, J=7.8 Hz), 3.70 (s, 3H), 3.30 (1H, A of ABX, obscured by solvent), 3.08 (1H, B of ABX, J=9.9, 9 Hz), 2.79 (q, 2H, J=11.1, 7.2 Hz), 2.05-1.97 (m, 1H), 1.31 (t, 3H, J=7.5 Hz), 0.88 (s, 3H), 0.85 (s, 3H), 0.79-0.75 (m, 1H).

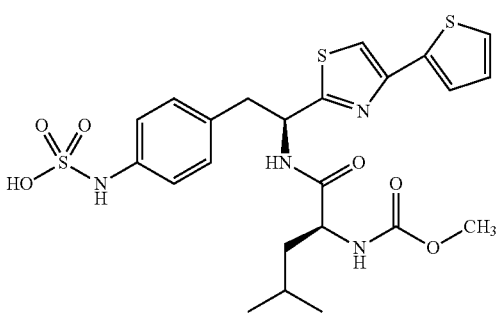 [SMILES: COC(=O)N[C@@H](CC(C)C)C(=O)N[C@@H](Cc1ccc(NS(=O)(=O)O)cc1)c1nc(-c2cccs2)cs1]

4-{(S)-2-[(S)-2-(Methoxycarbonyl)-4-methylpentanamido]-2-[2-(thiophen-2-yl)thiazol-4-yl]ethyl}phenylsulfamic acid: $^1$H NMR (CD$_3$OD) δ 8.22 (d, 1H, J=9 Hz), 7.62-7.57 (m, H), 7.15 (t, 1H, J=0.6 Hz), 7.10-6.97 (m, 4H), 5.30-5.20 (m, 1H), 4.16-4.11 (m, 1H), 3.67 (s, 2H), 3.22 (1H, A of ABX, J=6.9, 13.5 Hz), 3.11 (1H, B of ABX, J=7.8, 13.6 Hz), 1.65-1.58 (m, 1H), 1.50-1.45 (m, 2H), 0.95-0.88 (m, 6H).

Category IV of the present disclosure relates to compounds having the formula:

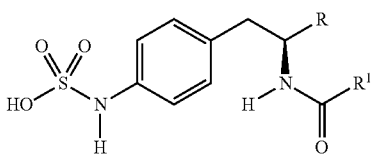

wherein R is a substituted or unsubstituted thiophen-2-yl or thiophen-4-yl unit and non-limiting examples of R⁰ are further described in Table VIII.

TABLE VIII

| No. | R | R$^1$ |
| --- | --- | --- |
| H176 | thiazol-2-yl | —OC(CH$_3$)$_3$ |
| H177 | 4-methylthiazol-2-yl | —OC(CH$_3$)$_3$ |
| H178 | 4-ethylthiazol-2-yl | —OC(CH$_3$)$_3$ |
| H179 | 4-cyclopropylthiazol-2-yl | —OC(CH$_3$)$_3$ |
| H180 | 4-tert-butylthiazol-2-yl | —OC(CH$_3$)$_3$ |
| H181 | 4-cyclohexylthiazol-2-yl | —OC(CH$_3$)$_3$ |
| H182 | 4-(2,2,2-trifluoroethyl)thiazol-2-yl | —OC(CH$_3$)$_3$ |
| H183 | 4-(3,3,3-trifluoropropyl)thiazol-2-yl | —OC(CH$_3$)$_3$ |
| H184 | 4-(2,2-difluorocyclopropyl)thiazol-2-yl | —OC(CH$_3$)$_3$ |
| H185 | 4,5-dimethylthiazol-2-yl | —OC(CH$_3$)$_3$ |
| H186 | 4-methyl-5-ethylthiazol-2-yl | —OC(CH$_3$)$_3$ |
| H187 | 4-phenylthiazol-2-yl | —OC(CH$_3$)$_3$ |
| H188 | 4-(4-chlorophenyl)thiazol-2-yl | —OC(CH$_3$)$_3$ |
| H189 | 4-(3,4-dimethylphenyl)thiazol-2-yl | —OC(CH$_3$)$_3$ |
| H190 | 4-methyl-5-phenylthiazol-2-yl | —OC(CH$_3$)$_3$ |
| H191 | 4-(thiophen-2-yl)thiazol-2-yl | —OC(CH$_3$)$_3$ |
| H192 | thiazol-4-yl | —OC(CH$_3$)$_3$ |
| H193 | 4-methylthiazol-4-yl | —OC(CH$_3$)$_3$ |
| H194 | 4-ethylthiazol-4-yl | —OC(CH$_3$)$_3$ |
| H195 | 4-cyclopropylthiazol-4-yl | —OC(CH$_3$)$_3$ |
| H196 | 4-tert-butylthiazol-4-yl | —OC(CH$_3$)$_3$ |
| H197 | 4-cyclohexylthiazol-4-yl | —OC(CH$_3$)$_3$ |
| H198 | 4-(2,2,2-trifluoroethyl)thiazol-4-yl | —OC(CH$_3$)$_3$ |
| H199 | 4-(3,3,3-trifluoropropyl)thiazol-4-yl | —OC(CH$_3$)$_3$ |
| H200 | 4-(2,2-difluorocyclopropyl)thiazol-4-yl | —OC(CH$_3$)$_3$ |
| H201 | 4,5-dimethylthiazol-4-yl | —OC(CH$_3$)$_3$ |
| H202 | 4-methyl-5-ethylthiazol-4-yl | —OC(CH$_3$)$_3$ |
| H203 | 4-phenylthiazol-4-yl | —OC(CH$_3$)$_3$ |
| H204 | 4-(4-chlorophenyl)thiazol-4-yl | —OC(CH$_3$)$_3$ |
| H205 | 4-(3,4-dimethylphenyl)thiazol-4-yl | —OC(CH$_3$)$_3$ |
| H206 | 4-methyl-5-phenylthiazol-4-yl | —OC(CH$_3$)$_3$ |
| H207 | 4-(thiophen-2-yl)thiazol-4-yl | —OC(CH$_3$)$_3$ |
| H208 | thiazol-2-yl | —OCH$_3$ |
| H209 | 4-methylthiazol-2-yl | —OCH$_3$ |
| H210 | 4-ethylthiazol-2-yl | —OCH$_3$ |
| H211 | 4-cyclopropylthiazol-2-yl | —OCH$_3$ |
| H212 | 4-tert-butylthiazol-2-yl | —OCH$_3$ |
| H213 | 4-cyclohexylthiazol-2-yl | —OCH$_3$ |
| H214 | 4-(2,2,2-trifluoroethyl)thiazol-2-yl | —OCH$_3$ |
| H215 | 4-(3,3,3-trifluoropropyl)thiazol-2-yl | —OCH$_3$ |
| H216 | 4-(2,2-difluorocyclopropyl)thiazol-2-yl | —OCH$_3$ |
| H217 | 4,5-dimethylthiazol-2-yl | —OCH$_3$ |
| H218 | 4-methyl-5-ethylthiazol-2-yl | —OCH$_3$ |
| H219 | 4-phenylthiazol-2-yl | —OCH$_3$ |
| H220 | 4-(4-chlorophenyl)thiazol-2-yl | —OCH$_3$ |
| H221 | 4-(3,4-dimethylphenyl)thiazol-2-yl | —OCH$_3$ |
| H222 | 4-methyl-5-phenylthiazol-2-yl | —OCH$_3$ |
| H223 | 4-(thiophen-2-yl)thiazol-2-yl | —OCH$_3$ |
| H224 | thiazol-4-yl | —OCH$_3$ |
| H225 | 4-methylthiazol-4-yl | —OCH$_3$ |
| H226 | 4-ethylthiazol-4-yl | —OCH$_3$ |
| H227 | 4-cyclopropylthiazol-4-yl | —OCH$_3$ |
| H228 | 4-tert-butylthiazol-4-yl | —OCH$_3$ |
| H229 | 4-cyclohexylthiazol-4-yl | —OCH$_3$ |
| H230 | 4-(2,2,2-trifluoroethyl)thiazol-4-yl | —OCH$_3$ |
| H231 | 4-(3,3,3-trifluoropropyl)thiazol-4-yl | —OCH$_3$ |
| H232 | 4-(2,2-difluorocyclopropyl)thiazol-4-yl | —OCH$_3$ |
| H233 | 4,5-dimethylthiazol-4-yl | —OCH$_3$ |
| H234 | 4-methyl-5-ethylthiazol-4-yl | —OCH$_3$ |
| H235 | 4-phenylthiazol-4-yl | —OCH$_3$ |
| H236 | 4-(4-chlorophenyl)thiazol-4-yl | —OCH$_3$ |
| H237 | 4-(3,4-dimethylphenyl)thiazol-4-yl | —OCH$_3$ |
| H238 | 4-methyl-5-phenylthiazol-4-yl | —OCH$_3$ |
| H239 | 4-(thiophen-2-yl)thiazol-4-yl | —OCH$_3$ |
| H240 | thiazol-2-yl | —CH$_3$ |
| H241 | 4-methylthiazol-2-yl | —CH$_3$ |
| H242 | 4-ethylthiazol-2-yl | —CH$_3$ |
| H243 | 4-cyclopropylthiazol-2-yl | —CH$_3$ |
| H244 | 4-tert-butylthiazol-2-yl | —CH$_3$ |
| H245 | 4-cyclohexylthiazol-2-yl | —CH$_3$ |
| H246 | 4-(2,2,2-trifluoroethyl)thiazol-2-yl | —CH$_3$ |
| H247 | 4-(3,3,3-trifluoropropyl)thiazol-2-yl | —CH$_3$ |
| H248 | 4-(2,2-difluorocyclopropyl)thiazol-2-yl | —CH$_3$ |
| H249 | 4,5-dimethylthiazol-2-yl | —CH$_3$ |
| H250 | 4-methyl-5-ethylthiazol-2-yl | —CH$_3$ |
| H251 | 4-phenylthiazol-2-yl | —CH$_3$ |
| H252 | 4-(4-chlorophenyl)thiazol-2-yl | —CH$_3$ |
| H253 | 4-(3,4-dimethylphenyl)thiazol-2-yl | —CH$_3$ |
| H254 | 4-methyl-5-phenylthiazol-2-yl | —CH$_3$ |
| H255 | 4-(thiophen-2-yl)thiazol-2-yl | —CH$_3$ |
| H256 | thiazol-4-yl | —CH$_3$ |
| H257 | 4-methylthiazol-4-yl | —CH$_3$ |
| H258 | 4-ethylthiazol-4-yl | —CH$_3$ |

TABLE VIII-continued

| No. | R | R[1] |
|---|---|---|
| H259 | 4-cyclopropylthiazol-4-yl | —CH$_3$ |
| H260 | 4-tert-butylthiazol-4-yl | —CH$_3$ |
| H261 | 4-cyclohexylthiazol-4-yl | —CH$_3$ |
| H262 | 4-(2,2,2-trifluoroethyl)thiazol-4-yl | —CH$_3$ |
| H263 | 4-(3,3,3-trifluoropropyl)thiazol-4-yl | —CH$_3$ |
| H264 | 4-(2,2-difluorocyclopropyl)thiazol-4-yl | —CH$_3$ |
| H265 | 4,5-dimethylthiazol-4-yl | —CH$_3$ |
| H266 | 4-methyl-5-ethylthiazol-4-yl | —CH$_3$ |
| H267 | 4-phenylthiazol-4-yl | —CH$_3$ |
| H268 | 4-(4-chlorophenyl)thiazol-4-yl | —CH$_3$ |
| H269 | 4-(3,4-dimethylphenyl)thiazol-4-yl | —CH$_3$ |
| H270 | 4-methyl-5-phenylthiazol-4-yl | —CH$_3$ |
| H271 | 4-(thiophen-2-yl)thiazol-4-yl | —CH$_3$ |

The compounds encompassed within Category IV of the present disclosure can be prepared by the procedure outlined in Scheme VI and described in Example 7 herein below.

Scheme VI

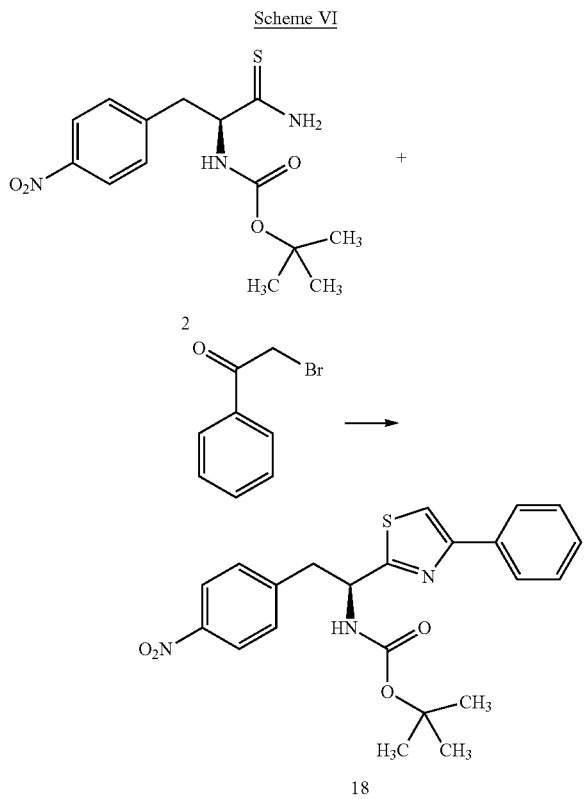

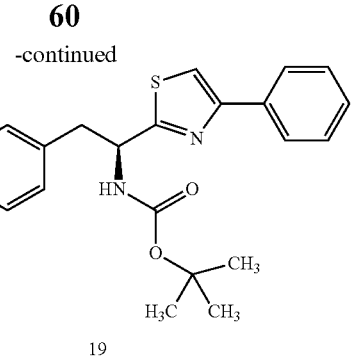

Reagents and conditions: (a)(i) CH$_3$CN; reflux, 1.5 hr. (ii) Boc$_2$O, pyridine, CH$_2$Cl$_2$; rt, 2 hr.

Reagents and conditions: (b) (i) H$_2$:Pd/C, MeOH; reflux (ii) SO$_3$-pyridine, NH$_4$OH; rt, 12 hr.

EXAMPLE 7

[1-(S)-(Phenylthiazol-2-yl)-2-(4-sulfoaminophenyl) ethyl]-carbamic acid tert-butyl ester (19)

Preparation of [2-(4-nitrophenyl)-1-(S)-(4-phenylthiazol-2-yl)ethyl]-carbamic acid tert-butyl ester (18): A mixture of [2-(4-nitrophenyl)-1-(S)-thiocarbamoylethyl]-carbamic acid tert-butyl ester, 2, (0.343 g, 1.05 mmol), 2-bromoacetophenone (0.231 g, 1.15 mmol), in CH$_3$CN (5 mL) is refluxed 1.5 hour. The solvent is removed under reduced pressure and the residue re-dissolved in CH$_2$Cl$_2$ then pyridine (0.24 mL, 3.0 mmol) and Boc$_2$O (0.24 mL, 1.1 mmol) are added. The reaction is stirred for 2 hours and diethyl ether is added to the solution and the precipitate which forms is removed by filtration. The organic layer is dried (Na$_2$SO$_4$), filtered, and concentrated to a residue which is purified over silica to afford 0.176 g (39%) of the desired product ESI+ MS 426 (M+1).

Preparation of [1-(S)-(phenylthiazol-2-yl)-2-(4-sulfoaminophenyl)ethyl]-carbamic acid tert-butyl ester (19): [2-(4-nitrophenyl)-1-(S)-(4-phenylthiazol-2-yl)ethyl]-carbamic acid tert-butyl ester, 18, (0.176 g, 0.41 mmol) is dissolved in MeOH (4 mL). A catalytic amount of Pd/C (10% w/w) is added and the mixture is stirred under a hydrogen atmosphere 12 hours. The reaction mixture is filtered through a bed of CELITE™ and the solvent is removed under reduced pressure. The crude product is dissolved in pyridine (12 mL) and treated with SO$_3$-pyridine (0.195 g, 1.23 mmol). The reaction is stirred at room temperature for 5 minutes after which a 7% solution of NH$_4$OH (10 mL) is added. The mixture is then concentrated and the resulting residue is purified by reverse phase chromatography to afford 0.080 g of the desired product as the ammonium salt. $^1$H NMR (300 MHz, MeOH-d$_4$) δ 7.93 (d, J=6.0 Hz, 2H), 7.68 (s, 1H), 7.46-7.42 (m, 3H), 7.37-7.32 (m, 1H), 7.14-7.18 (m, 3H), 5.13-5.18 (m, 1H), 3.40 (dd, J=4.5 and 15.0 Hz, 1H), 3.04 (dd, J=9.6 and 14.1 Hz, 1H), 1.43 (s, 9H).

The following are further non-limiting examples of Category IV of the present disclosure.

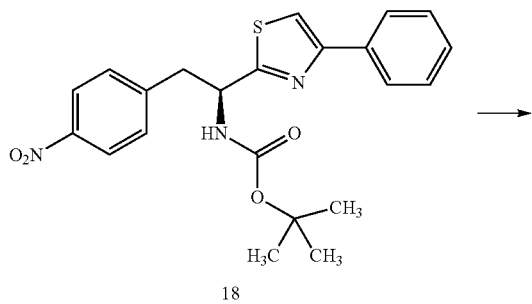

(S)-4-(2-(4-Methylthiazol-2-yl)-2-pivalamidoethyl)phenylsulfamic acid: $^1$H NMR (CD$_3$OD) δ 7.31 (s, 4H), 7.20 (s, 1H), 5.61-5.56 (m, 1H), 3.57-3.22 (m, 2H), 2.62 (s, 3H), 1.31 (s, 3H).

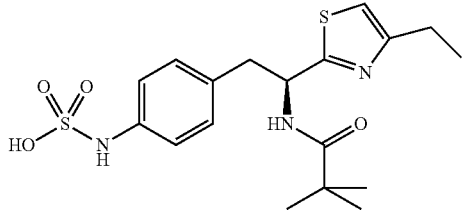 [SMILES: CCc1csc([C@H](Cc2ccc(NS(=O)(=O)O)cc2)NC(=O)C(C)(C)C)n1]

(S)-4-(2-(4-Ethylthiazol-2-yl)-2-pivalamidoethyl)phenylsulfamic acid: $^1$H NMR (300 MHz, MeOH-d$_4$) δ 7.92 (d, J=8.1 Hz, 1H), 7.12-7.14 (m, 4H), 7.03 (s, 1H), 5.38-5.46 (m, 1H), 3.3-3.4 (m, 1H), 3.08 (dd, J=10.2 and 13.8 Hz, 1H), 2.79 (q, J=7.2 Hz, 2H), 1.30 (t, J=7.2 Hz, 3H), 1.13 (s, 9H).

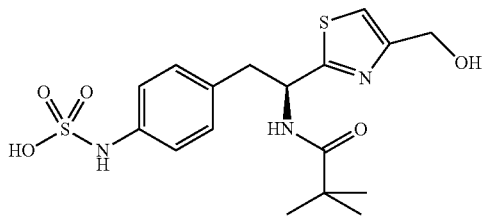 [SMILES: CC(C)(C)C(=O)N[C@@H](Cc1ccc(NS(=O)(=O)O)cc1)c1nc(CO)cs1]

(S)-4-(2-(4-(Hydroxymethyl)thiazol-2-yl)-2-pivalamidoethyl)phenylsulfamic acid: $^1$H NMR (300 MHz, MeOH-d$_4$) δ 7.92 (d, J=8.1 Hz, 1H), 7.24 (s, 1H), 7.08 (d, J=8.7 Hz, 2H), 7.00 (d, J=8.7 Hz, 2H), 5.29-5.37 (m, 1H), 4.55 (s, 2H), 3.30 (dd, J=4.8 and 13.5 Hz, 1H), 2.99 (dd, J=10.5 and 13.5 Hz, 1H), 0.93 (s, 9H).

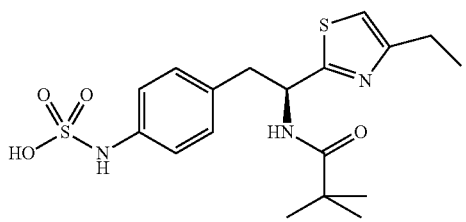 [SMILES: CCc1csc([C@H](Cc2ccc(NS(=O)(=O)O)cc2)NC(=O)C(C)(C)C)n1]

(S)-4-(2-(4-(Ethoxycarbonyl)thiazol-2-yl)-2-pivalamidoethyl)phenylsulfamic acid: $^1$H NMR (300 MHz, MeOH-d$_4$) δ 8.30 (s, 1H), 8.04 (d, J=8.1 Hz, 1H), 7.13 (s, 4H), 5.41-5.49 (m, 1H), 4.41 (q, J=7.2 Hz, 2H), 3.43 (dd, J=5.1 and 13.8 Hz, 1H), 3.14 (dd, J=5.7 and 9.9 Hz, 1H), 1.42 (t, J=7.2 Hz, 3H), 1.14 (s, 9H).

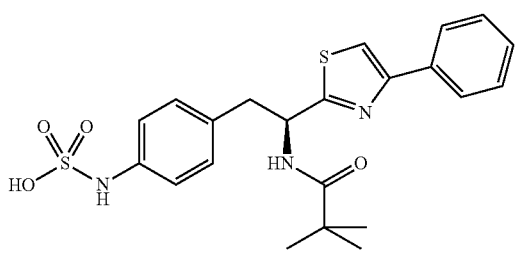 [SMILES: CC(C)(C)C(=O)N[C@@H](Cc1ccc(NS(=O)(=O)O)cc1)c1nc(-c2ccccc2)cs1]

(S)-4-(2-(4-Phenylthiazol-2-yl)-2-pivalamidoethyl)phenylsulfamic acid: $^1$H NMR (300 MHz, MeOH-d$_4$) δ 7.94-8.01 (m, 3H), 7.70 (s, 1H), 7.42-7.47 (m, 2H), 7.32-7.47 (m, 1H), 7.13-7.20 (m, 3H), 5.48-5.55 (m, 1H), 3.50 (dd, J=5.1 and 14.1 Hz, 1H), 3.18 (dd, J=10.2 and 14.1 Hz, 1H), 1.17 (s, 9H).

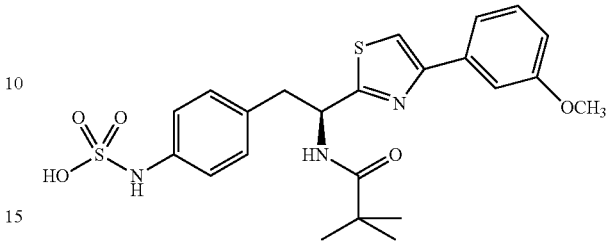

4-((S)-2-(4-(3-Methoxyphenyl)thiazol-2-yl)-2-pivalamidoethyl)phenylsulfamic acid: $^1$H NMR (CD$_3$OD) δ 7.96-7.93 (d, 1H, J=8.1 Hz), 7.69 (s, 1H), 7.51-7.49 (d, 2H, J=7.9 Hz), 7.33 (t, 1H, J=8.0 Hz), 7.14 (s, 4H), 6.92-6.90 (d, 1H, J=7.8 Hz), 5.50 (t, 1H, J=5.1 Hz), 3.87 (s, 3H), 3.50-3.13 (m, 2H), 1.15 (s, 9H).

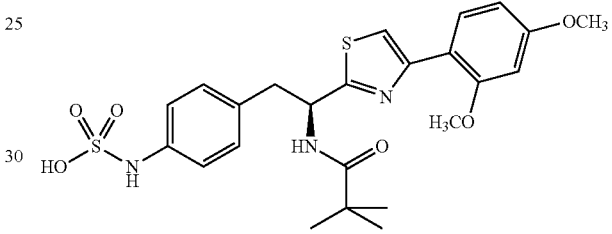

4-((S)-2-(4-(2,4-Dimethoxyphenyl)thiazol-2-yl)-2-pivalamidoethyl)phenylsulfamic acid: $^1$H NMR (CD$_3$OD) δ 8.11-8.09 (d, 1H, J=7.8 Hz), 7.96-7.93 (d, 1H, J=8.4 Hz), 7.74 (s, 1H), 7.18-7.16 (m, 4H), 6.67-6.64 (d, 2H, J=9.0 Hz), 5.55-5.47 (m, 1H), 3.95 (s, 3H), 3.87 (s, 3H), 3.52-3.13 (m, 2H), 1.17 (s, 9H).

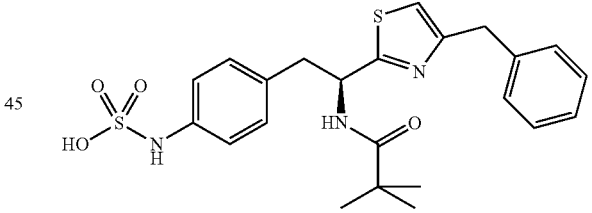

(S)-4-(2-(4-Benzylthiazol-2-yl)-2-pivalamidoethyl)phenylsulfamic acid: $^1$H NMR (CD$_3$OD) δ 7.85 (d, 1H, J=8.4 Hz), 7.38-7.20 (m, 4H), 7.11-7.02 (m, 1H), 7.00 (s, 1H), 5.42-5.37 (m, 1H), 4.13 (s, 2H), 3.13-3.08 (m, 2H), 1.13 (s, 9H).

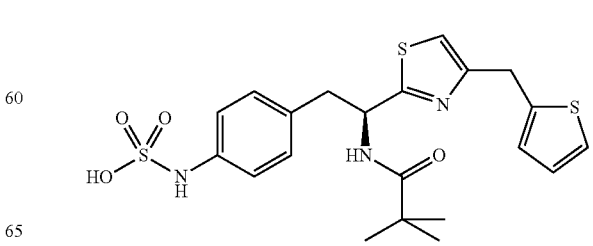

(S)-4-(2-Pivalamido-2-(4-(thiophen-2-ylmethyl)thiazol-2-yl)ethyl)phenylsulfamic acid: ¹H NMR (CD₃OD) δ 7.88-7.85 (d, 1H), 7.38-7.35 (m, 1H), 7.10-7.01 (m, 4H), 7.02 (s, 1H), 5.45-5.38 (m, 1H), 4.13 (s, 2H), 3.13-3.05 (m, 2H), 1.13 (2, 9H).

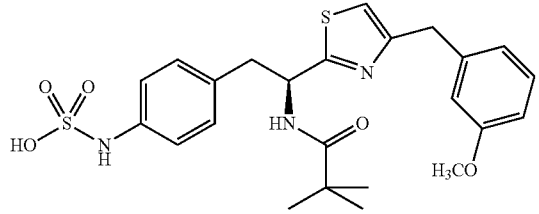 [SMILES: COc1cccc(Cc2csc([C@H](Cc3ccc(NS(=O)(=O)O)cc3)NC(=O)C(C)(C)C)n2)c1]

(S)-4-(2-(4-(3-Methoxybenzyl)thiazol-2-yl)-2-pivalamidoethyl)phenylsulfamic acid: ¹H NMR (CD₃OD) δ 7.85 (d, 1H, J=8.4 Hz), 7.25-7.20 (m, 1H), 7.11-7.02 (m, 4H), 7.01 (s, 1H), 6.90-6.79 (m, 2H), 5.45-5.40 (m, 1H), 4.09 (s, 2H), 3.79 (s, 3H), 3.12-3.08 (m, 2H), 1.10 (s, 9H).

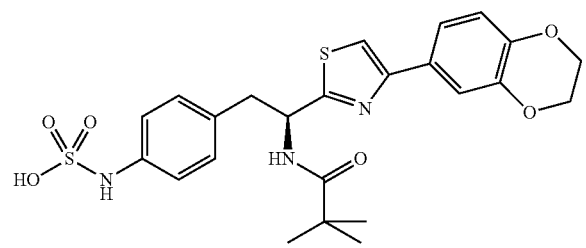 [SMILES: CC(C)(C)C(=O)N[C@@H](Cc1ccc(NS(=O)(=O)O)cc1)c1nc(-c2ccc3c(c2)OCCO3)cs1]

4-((S)-2-(4-(2,3-Dihydrobenzo[b][1,4]dioxin-6-yl)thiazol-2-yl)-2-pivalamidoethyl)-phenylsulfamic acid: ¹H NMR (CD₃OD) δ 7.53 (s, 1H), 7.45 (s, 1H), 7.42-7.40 (d, 1H, J=8.4 Hz), 7.19-7.15 (m, 4H), 6.91-6.88 (d, 2H, J=8.4 Hz), 5.51-5.46 (m, 1H), 4.30 (s, 4H), 3.51-3.12 (m, 2H), 1.16 (s, 9H).

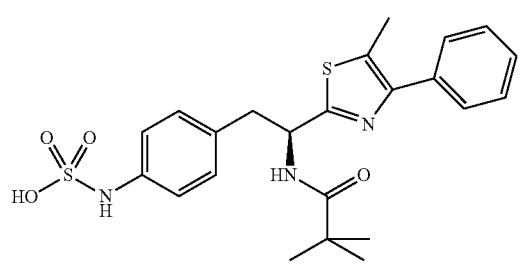 [SMILES: Cc1sc([C@H](Cc2ccc(NS(=O)(=O)O)cc2)NC(=O)C(C)(C)C)nc1-c1ccccc1]

(S)-4-(2-(5-Methyl-4-phenylthiazol-2-yl)-2-pivalamidoethyl)phenylsulfamic acid: ¹H NMR (CD₃OD) δ 7.63-7.60 (d, 2H, J=7.1 Hz), 7.49-7.35 (m, 3H), 7.14 (s, 4H), 5.43-5.38 (m, 1H), 3.42-3.09 (m, 2H), 2.49 (s, 3H), 1.14 (s, 9H).

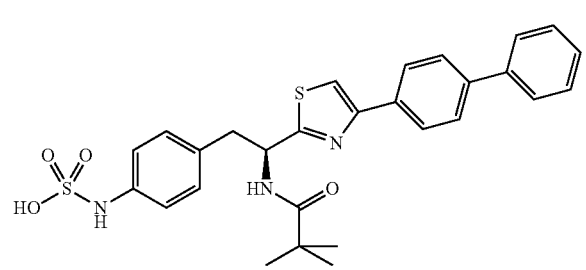 [SMILES: CC(C)(C)C(=O)N[C@@H](Cc1ccc(NS(=O)(=O)O)cc1)c1nc(-c2ccc(-c3ccccc3)cc2)cs1]

(S)-4-(2-(4-(Biphen-4-yl)thiazol-2-yl)-2-pivalamido-ethyl)phenylsulfamic acid: ¹H NMR (CD₃OD) δ 8.04-8.01 (m, 2H), 7.72-7.66 (m, 5H), 7.48-7.35 (m, 3H), 7.15 (s, 4H), 5.50 (t, 1H, J=5.0 Hz), 3.57-3.15 (d, 2H), 1.16 (s, 9H).

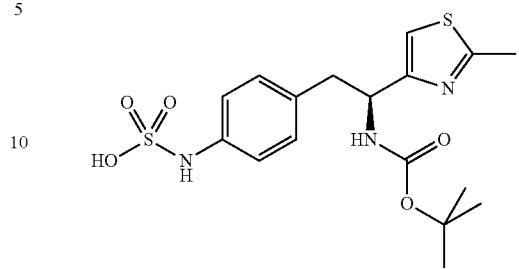

(S)-4-(2-tert-Butoxycarbonyl-2-(2-methylthiazol-4-yl)-phenylsulfamic acid ¹H NMR (300 MHz, D₂O) δ 6.99-7.002 (m, 4H), 6.82 (s, 1H), 2.26 (dd, J=13.8 and 7.2 Hz, 1H), 2.76 (dd, J=13.8 and 7.2 Hz, 1H), 2.48 (s, 3H), 1.17 (s, 9H).

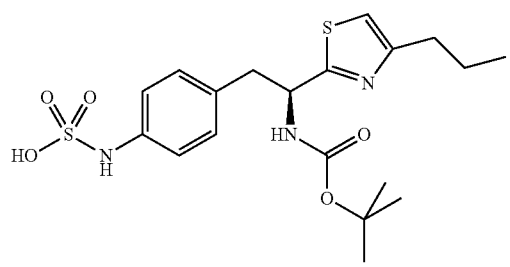 [SMILES: CCCc1csc([C@H](Cc2ccc(NS(=O)(=O)O)cc2)NC(=O)OC(C)(C)C)n1]

(S)-4-(2-(tert-Butoxycarbonyl)-2-(4-propylthiazol-2-yl)ethyl)-phenyl sulfamic acid: ¹H NMR (300 MHz, CD₃OD): δ 7.18-7.02 (m, 5H), 5.06-5.03 (m, 1H), 3.26 (dd, J=13.8, 4.8 Hz, 1H), 2.95 (dd, J=13.8, 9.3 Hz, 1H), 2.74 (dd, J=15.0, 7.2 Hz, 2H), 1.81-1.71 (m, 2H), 1.40 (s, 7H), 1.33 (bs, 2H), 0.988 (t, J=7.5 Hz 3H).

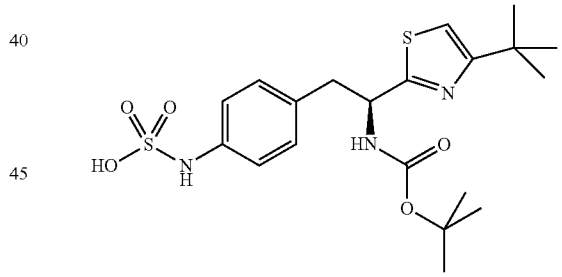

(S)-4-(2-(tert-Butoxycarbonyl)-2-(4-tert-butylthiazol-2-yl)ethyl)-phenyl sulfamic acid: ¹H NMR (300 MHz, CD₃OD): δ 7.12 (s, 4H), 7.01 (s, 1H), 5.11-5.06 (m, 1H), 3.32-3.25 (m, 1H), 2.96 (m, 1H), 1.42 (s, 8H), 1.38 (s, 9H), 1.32 (s, 1H).

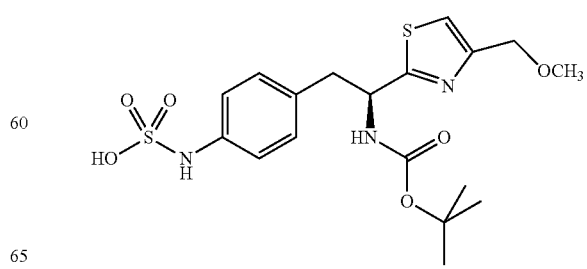

(S)-4-(2-(tert-Butoxycarbonylamino)-2-(4-(methoxymethyl)thiazol-2-yl)ethyl)-phenyl sulfamic acid: $^1$H NMR (300 MHz, CD$_3$OD): δ 7.36 (s, 1H), 7.14-7.05 (m, 4H), 5.06 (dd, J=9.0, 5.1 Hz, 1H), 4.55 (s, 2H), 3.42 (s, 3H), 3.31-3.24 (m, 1H), 2.97 (dd, J=13.8, 9.9 Hz, 1H), 1.47-1.31 (m, 9H).

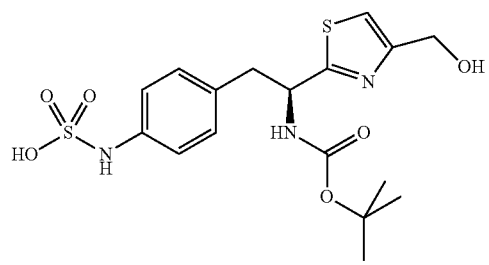 [SMILES: CC(C)(C)OC(=O)N[C@@H](Cc1ccc(NS(=O)(=O)O)cc1)c1nc(CO)cs1]

(S)-4-(2-tert-Butoxycarbonylamino)-2-(4-(2-hydroxymethyl)thiazol-2-yl)ethyl)phenylsulfamic acid: $^1$H NMR (300 MHz, MeOH-d$_4$) δ 7.22-7.25 (m, 1H), 7.09-7.15 (m, 4H), 5.00-5.09 (m, 1H), 4.32-4.35 (m, 1H), 3.87 (t, J=6.6 Hz, 2H), 3.23-3.29 (m, 1H), 3.09-3.18 (m, 1H), 2.98 (t, J=6.6 Hz, 2H), 1.41 (s, 9H).

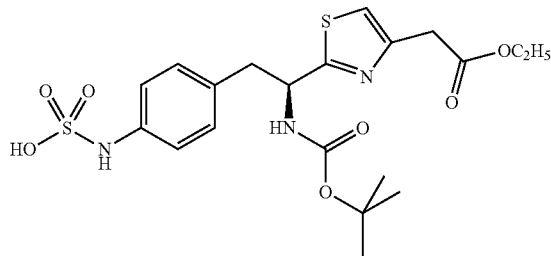 [SMILES: CCOC(=O)Cc1csc([C@H](Cc2ccc(NS(=O)(=O)O)cc2)NC(=O)OC(C)(C)C)n1]

(S)-4-(2-tert-Butoxycarbonylamino)-2-(4-(2-ethoxy-2-oxoethyl)-thiazole-2-yl)-ethyl)phenylsulfamic acid: $^1$H NMR (300 MHz, MeOH-d$_4$) δ 7.29 (s, 1H), 7.09-7.16 (m, 4H), 5.04-5.09 (m, 1H), 4.20 (q, J=6.9 Hz, 2H), 3.84 (s, 2H), 3.30 (dd, J=4.8 and 14.1 HZ, 1H), 2.97 (dd, J=9.6 Hz and 13.8 Hz, 1H), 1.41 (s, 9H), 1.29 (t, J=7.2 Hz, 3H).

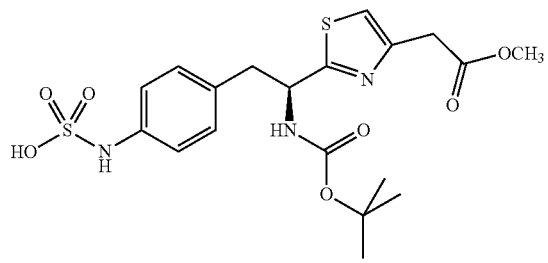 [SMILES: COC(=O)Cc1csc([C@H](Cc2ccc(NS(=O)(=O)O)cc2)NC(=O)OC(C)(C)C)n1]

(S)-4-(2-(tert-Butoxycarbonylamino)-2-(4-(2-methoxy-2-oxoethyl)thiazol-2-yl)ethyl)phenylsulfamic acid: $^1$H NMR (300 MHz, MeOH-d$_4$) δ 7.31 (s, 1H), 7.01-7.16 (m, 4H), 5.04-5.09 (m, 1H), 4.01 (s, 2H), 3.78 (s, 2H), 3.74 (s, 3H), 3.29 (dd, J=5.1 and 13.8 Hz, 1H), 2.99 (dd, J=9.3 and 13.8 Hz, 1H), 1.41 (s, 9H).

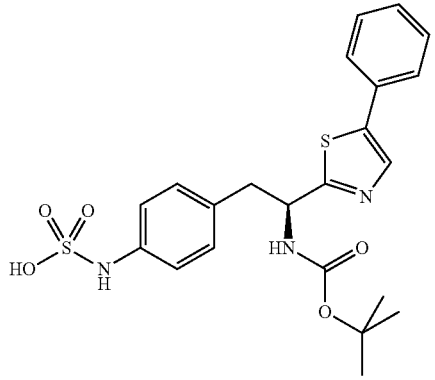 [SMILES: CC(C)(C)OC(=O)N[C@@H](Cc1ccc(NS(=O)(=O)O)cc1)c1ncc(-c2ccccc2)s1]

(S)-4-(2-(tert-Butoxycarbonylamino)-2-(5-phenylthiazol-2-yl)ethyl)-phenyl sulfamic acid: $^1$H NMR (300 MHz, CD$_3$OD): δ 7.98 (s, 1H), 7.62 (d, J=7.2 Hz, 2H), 7.46-7.35 (m, 4H), 7.14 (s, 4H), 5.09 (bs, 1H), 3.07-2.99 (m, 2H), 1.43 (s, 9H).

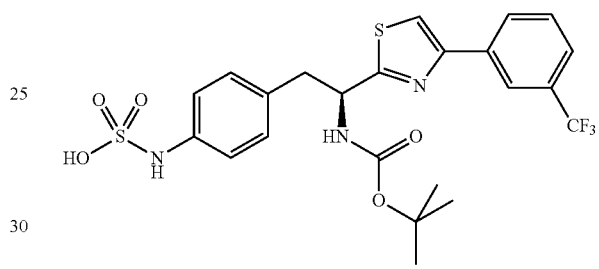

4-((S)-2-(tert-Butoxycarbonylamino)-2-(4-(3-(trifluoromethyl)phenyl)thiazol-2-yl)ethyl)phenyl sulfamic acid: $^1$H NMR (300 MHz, CD$_3$OD): δ 8.28 (s, 1H), 8.22-8.19 (m, 1H), 7.89 (s, 1H), 7.65 (d, J=5.1 Hz, 2H), 7.45 (d, J=8.1 Hz, 1H), 7.15 (s, 4H), 5.17-5.14 (m, 1H), 3.43-3.32 (m, 1H), 3.05 (dd, J=14.1, 9.6 Hz, 1H), 1.42 (s, 9H).

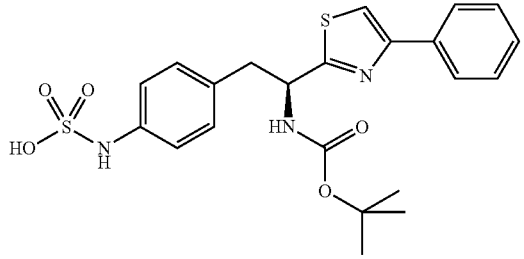 [SMILES: CC(C)(C)OC(=O)N[C@@H](Cc1ccc(NS(=O)(=O)O)cc1)c1nc(-c2ccccc2)cs1]

(S)-4-(2-(tert-Butoxycarbonylamino)-2-(4-phenylthiazol-2-yl)ethyl)-phenyl sulfamic acid: $^1$H NMR (300 MHz, CD$_3$OD): δ 7.98 (s, 1H), 7.94 (d, J=7.2 Hz, 2H), 7.46-7.35 (m, 4H), 7.14 (s, 4H), 5.09 (bs, 1H), 3.07-2.99 (m, 2H), 1.43 (s, 9H).

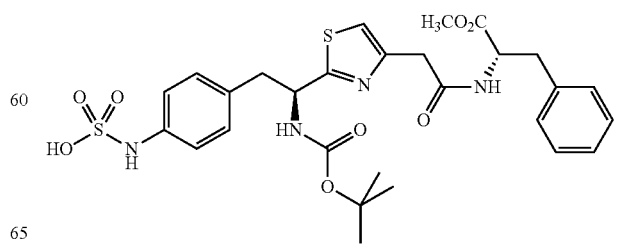

(S,S)-2-(2-{2-[2-tert-Butoxycarbonylamino-2-(4-sulfoaminophenyl)ethyl]thiazol-4-yl}acetylamido)-3-phenyl-propionic acid methyl ester: $^1$H NMR (300 MHz, MeOH-d$_4$) δ 6.85-6.94 (m, 9H), 6.64 (s, 1H), 4.83 (s, 1H), 4.54-4.58 (m, 1H), 3.49 (s, 3H), 3.39 (s, 2H), 2.80-2.97 (m, 1H), 2.64-2.78 (m, 1H), 1.12 (s, 9H).

(S)-[1-{1-Oxo-4-[2-(1-phenyl-1H-tetrazol-5-sulfonyl)ethyl]-1H-1λ$^4$-thiazol-2-yl}-2-(4-sulfamino-phenyl)-ethyl]-carbamic acid tert-butyl ester: $^1$H NMR (300 MHz, MeOH-d$_4$) δ 7.22-7.75 (m, 2H), 7.62-7.69 (m, 2H), 7.55 (s, 1H), 7.10-7.20 (m, 5H), 5.25 (m, 1H), 4.27-4.36 (m, 1H), 4.11-4.21 (m, 1H), 3.33-3.44 (m, 4H), 2.84-2.90 (m, 1H), 1.33 (s, 9H).

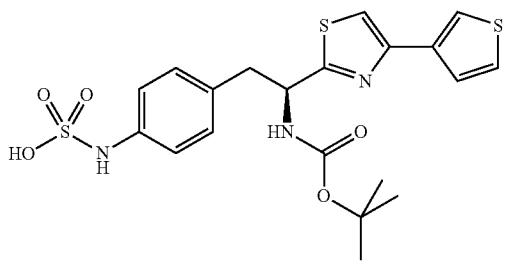 [SMILES: CC(C)(C)OC(=O)N[C@@H](Cc1ccc(NS(=O)(=O)O)cc1)c1nc(-c2ccsc2)cs1]

4-((S)-2-(tert-Butoxycarbonylamino)-2-(4-(thiophen-3-yl)thiazol-2-yl)ethyl)phenyl sulfamic acid: $^1$H NMR (300 MHz, CD$_3$OD): δ 7.84 (dd, J=3.0, 1.5 Hz, 1H), 7.57-7.55 (m, 2H), 7.47 (dd, J=4.8, 3.0 Hz, 1H), 7.15 (s, 4H), 5.15-5.10 (m, 1H), 3.39-3.34 (m, 1H), 3.01 (dd, J=14.1, 9.6 Hz, 1H), 1.42 (s, 8H), 1.32 (s, 1H).

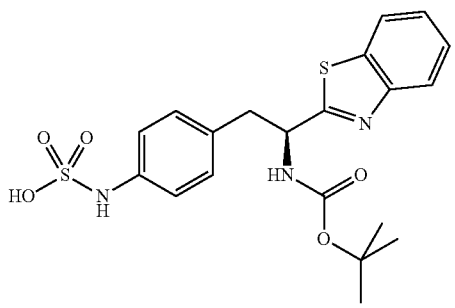 [SMILES: CC(C)(C)OC(=O)N[C@@H](Cc1ccc(NS(=O)(=O)O)cc1)c1nc2ccccc2s1]

(S)-4-(2-(Benzo[d]thiazol-2-ylamino)-2-(tert-butoxycarbonyl)ethyl)phenylsulfamic acid: $^1$H NMR (CD$_3$OD) δ 7.86-7.82 (m, 2H), 7.42 (t, 2H, J=7.1 Hz), 7.33 (t, 1H, J=8.2 Hz), 7.02 (s, 4H), 5.10-5.05 (m, 1H), 2.99-2.91 (m, 2H), 1.29 (s, 9H).

(S)-4-(2-tert-Butoxycarbonylamino-2-methylthiazol-4-yl)-phenylsulfamic acid $^1$H NMR (300 MHz, D$_2$O) δ 6.99-7.002 (m, 4H), 6.82 (s, 1H), 2.26 (dd, J=13.8 and 7.2 Hz, 1H), 2.76 (dd, J=13.8 and 7.2 Hz, 1H), 2.48 (s, 3H), 1.17 (s, 9H).

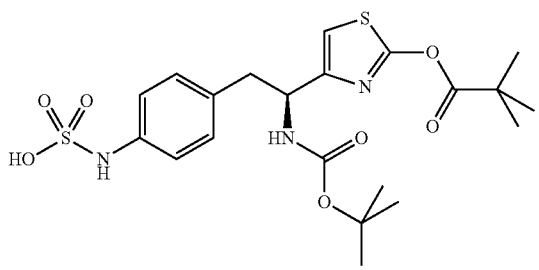 [SMILES: CC(C)(C)OC(=O)N[C@@H](Cc1ccc(NS(=O)(=O)O)cc1)c1csc(OC(=O)C(C)(C)C)n1]

(S)-4-(2-(tert-Butoxycarbonylamino)-2-(2-(pivaloyloxy)thiazol-4-yl)ethyl)-phenylsulfamic acid: $^1$H NMR (300 MHz, D$_2$O) δ 6.95 (s, 4H), 6.63 (s, 1H), 2.94 (dd, J=13.5 and 4.8 Hz, 1H), 2.75 (dd, J=13.5 and 4.8 Hz, 1H), 1.16 (s, 9H), 1.13 (s, 9H).

The first aspect of Category V of the present disclosure relates to 2-(thiazol-2-yl) compounds having the formula:

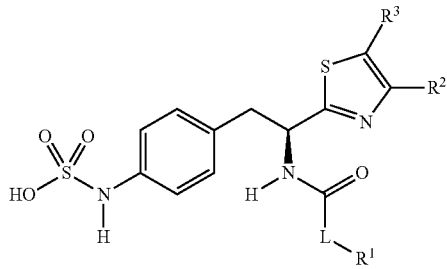

wherein $R^1$, $R^2$, $R^3$, and L are further defined herein in Table IX below.

TABLE IX

| No. | L | $R^1$ | $R^2$ | $R^3$ |
|---|---|---|---|---|
| I272 | —CH$_2$— | phenyl | —CH$_3$ | —H |
| I273 | —CH$_2$— | 2-fluorophenyl | —CH$_3$ | —H |
| I274 | —CH$_2$— | 3-fluorophenyl | —CH$_3$ | —H |
| I275 | —CH$_2$— | 4-fluorophenyl | —CH$_3$ | —H |
| I276 | —CH$_2$— | 2,3-difluorophenyl | —CH$_3$ | —H |
| I277 | —CH$_2$— | 3,4-difluorophenyl | —CH$_3$ | —H |
| I278 | —CH$_2$— | 3,5-difluorophenyl | —CH$_3$ | —H |
| I279 | —CH$_2$— | 2-chlorophenyl | —CH$_3$ | —H |
| I280 | —CH$_2$— | 3-chlorophenyl | —CH$_3$ | —H |
| I281 | —CH$_2$— | 4-chlorophenyl | —CH$_3$ | —H |
| I282 | —CH$_2$— | 2,3-dichlorophenyl | —CH$_3$ | —H |
| I283 | —CH$_2$— | 3,4-dichlorophenyl | —CH$_3$ | —H |
| I284 | —CH$_2$— | 3,5-dichlorophenyl | —CH$_3$ | —H |
| I285 | —CH$_2$— | 2-hydroxyphenyl | —CH$_3$ | —H |
| I286 | —CH$_2$— | 3-hydroxyphenyl | —CH$_3$ | —H |
| I287 | —CH$_2$— | 4-hydroxyphenyl | —CH$_3$ | —H |
| I288 | —CH$_2$— | 2-methoxyphenyl | —CH$_3$ | —H |
| I289 | —CH$_2$— | 3-methoxyphenyl | —CH$_3$ | —H |
| I290 | —CH$_2$— | 4-methoxyphenyl | —CH$_3$ | —H |
| I291 | —CH$_2$— | 2,3-dimethoxyphenyl | —CH$_3$ | —H |
| I292 | —CH$_2$— | 3,4-dimethoxyphenyl | —CH$_3$ | —H |
| I293 | —CH$_2$— | 3,5-dimethoxyphenyl | —CH$_3$ | —H |
| I294 | —CH$_2$— | phenyl | —CH$_2$CH$_3$ | —H |
| I295 | —CH$_2$— | 2-fluorophenyl | —CH$_2$CH$_3$ | —H |
| I296 | —CH$_2$— | 3-fluorophenyl | —CH$_2$CH$_3$ | —H |
| I297 | —CH$_2$— | 4-fluorophenyl | —CH$_2$CH$_3$ | —H |
| I298 | —CH$_2$— | 2,3-difluorophenyl | —CH$_2$CH$_3$ | —H |
| I299 | —CH$_2$— | 3,4-difluorophenyl | —CH$_2$CH$_3$ | —H |
| I300 | —CH$_2$— | 3,5-difluorophenyl | —CH$_2$CH$_3$ | —H |
| I301 | —CH$_2$— | 2-chlorophenyl | —CH$_2$CH$_3$ | —H |
| I302 | —CH$_2$— | 3-chlorophenyl | —CH$_2$CH$_3$ | —H |
| I303 | —CH$_2$— | 4-chlorophenyl | —CH$_2$CH$_3$ | —H |
| I304 | —CH$_2$— | 2,3-dichlorophenyl | —CH$_2$CH$_3$ | —H |
| I305 | —CH$_2$— | 3,4-dichlorophenyl | —CH$_2$CH$_3$ | —H |
| I306 | —CH$_2$— | 3,5-dichlorophenyl | —CH$_2$CH$_3$ | —H |
| I307 | —CH$_2$— | 2-hydroxyphenyl | —CH$_2$CH$_3$ | —H |
| I308 | —CH$_2$— | 3-hydroxyphenyl | —CH$_2$CH$_3$ | —H |
| I309 | —CH$_2$— | 4-hydroxyphenyl | —CH$_2$CH$_3$ | —H |
| I310 | —CH$_2$— | 2-methoxyphenyl | —CH$_2$CH$_3$ | —H |
| I311 | —CH$_2$— | 3-methoxyphenyl | —CH$_2$CH$_3$ | —H |
| I312 | —CH$_2$— | 4-methoxyphenyl | —CH$_2$CH$_3$ | —H |
| I313 | —CH$_2$— | 2,3-dimethoxyphenyl | —CH$_2$CH$_3$ | —H |
| I314 | —CH$_2$— | 3,4-dimethoxyphenyl | —CH$_2$CH$_3$ | —H |
| I315 | —CH$_2$— | 3,5-dimethoxyphenyl | —CH$_2$CH$_3$ | —H |
| I316 | —CH$_2$CH$_2$— | phenyl | —CH$_3$ | —H |
| I317 | —CH$_2$CH$_2$— | 2-fluorophenyl | —CH$_3$ | —H |
| I318 | —CH$_2$CH$_2$— | 3-fluorophenyl | —CH$_3$ | —H |
| I319 | —CH$_2$CH$_2$— | 4-fluorophenyl | —CH$_3$ | —H |
| I320 | —CH$_2$CH$_2$— | 2,3-difluorophenyl | —CH$_3$ | —H |

TABLE IX-continued

| No. | L | R¹ | R² | R³ |
|---|---|---|---|---|
| I321 | —CH₂CH₂— | 3,4-difluorophenyl | —CH₃ | —H |
| I322 | —CH₂CH₂— | 3,5-difluorophenyl | —CH₃ | —H |
| I323 | —CH₂CH₂— | 2-chlorophenyl | —CH₃ | —H |
| I324 | —CH₂CH₂— | 3-chlorophenyl | —CH₃ | —H |
| I325 | —CH₂CH₂— | 4-chlorophenyl | —CH₃ | —H |
| I326 | —CH₂CH₂— | 2,3-dichlorophenyl | —CH₃ | —H |
| I327 | —CH₂CH₂— | 3,4-dichlorophenyl | —CH₃ | —H |
| I328 | —CH₂CH₂— | 3,5-dichlorophenyl | —CH₃ | —H |
| I329 | —CH₂CH₂— | 2-hydroxyphenyl | —CH₃ | —H |
| I330 | —CH₂CH₂— | 3-hydroxyphenyl | —CH₃ | —H |
| I331 | —CH₂CH₂— | 4-hydroxyphenyl | —CH₃ | —H |
| I332 | —CH₂CH₂— | 2-methoxyphenyl | —CH₃ | —H |
| I333 | —CH₂CH₂— | 3-methoxyphenyl | —CH₃ | —H |
| I334 | —CH₂CH₂— | 4-methoxyphenyl | —CH₃ | —H |
| I335 | —CH₂CH₂— | 2,3-dimethoxyphenyl | —CH₃ | —H |
| I336 | —CH₂CH₂— | 3,4-dimethoxyphenyl | —CH₃ | —H |
| I337 | —CH₂CH₂— | 3,5-dimethoxyphenyl | —CH₃ | —H |
| I338 | —CH₂CH₂— | phenyl | —CH₂CH₃ | —H |
| I339 | —CH₂CH₂— | 2-fluorophenyl | —CH₂CH₃ | —H |
| I340 | —CH₂CH₂— | 3-fluorophenyl | —CH₂CH₃ | —H |
| I341 | —CH₂CH₂— | 4-fluorophenyl | —CH₂CH₃ | —H |
| I342 | —CH₂CH₂— | 2,3-difluorophenyl | —CH₂CH₃ | —H |
| I343 | —CH₂CH₂— | 3,4-difluorophenyl | —CH₂CH₃ | —H |
| I344 | —CH₂CH₂— | 3,5-difluorophenyl | —CH₂CH₃ | —H |
| I345 | —CH₂CH₂— | 2-chlorophenyl | —CH₂CH₃ | —H |
| I346 | —CH₂CH₂— | 3-chlorophenyl | —CH₂CH₃ | —H |
| I347 | —CH₂CH₂— | 4-chlorophenyl | —CH₂CH₃ | —H |
| I348 | —CH₂CH₂— | 2,3-dichlorophenyl | —CH₂CH₃ | —H |
| I349 | —CH₂CH₂— | 3,4-dichlorophenyl | —CH₂CH₃ | —H |
| I350 | —CH₂CH₂— | 3,5-dichlorophenyl | —CH₂CH₃ | —H |
| I351 | —CH₂CH₂— | 2-hydroxyphenyl | —CH₂CH₃ | —H |
| I352 | —CH₂CH₂— | 3-hydroxyphenyl | —CH₂CH₃ | —H |
| I353 | —CH₂CH₂— | 4-hydroxyphenyl | —CH₂CH₃ | —H |
| I354 | —CH₂CH₂— | 2-methoxyphenyl | —CH₂CH₃ | —H |
| I355 | —CH₂CH₂— | 3-methoxyphenyl | —CH₂CH₃ | —H |
| I356 | —CH₂CH₂— | 4-methoxyphenyl | —CH₂CH₃ | —H |
| I357 | —CH₂CH₂— | 2,3-dimethoxyphenyl | —CH₂CH₃ | —H |
| I358 | —CH₂CH₂— | 3,4-dimethoxyphenyl | —CH₂CH₃ | —H |
| I359 | —CH₂CH₂— | 3,5-dimethoxyphenyl | —CH₂CH₃ | —H |

The compounds encompassed within the first aspect of Category V of the present disclosure can be prepared by the procedure outlined in Scheme VII and described in Example 8 herein below.

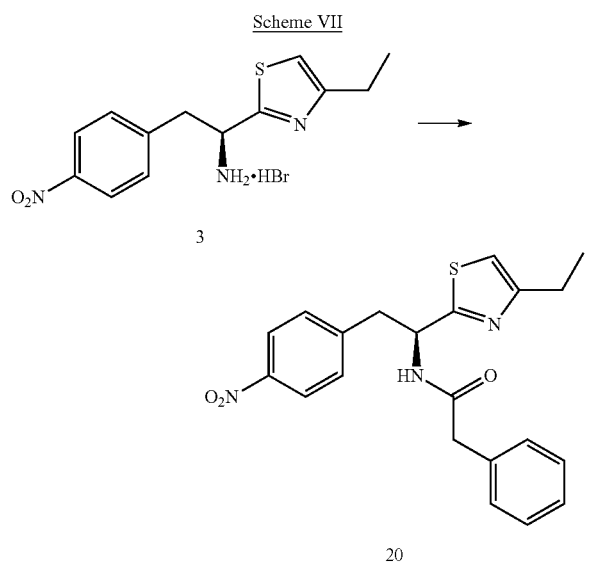

Scheme VII

Reagents and conditions: (a) C₆H₅CH₂CO₂H, EDCI, HOBt, DIPEA, DMF; rt, 18 hr.

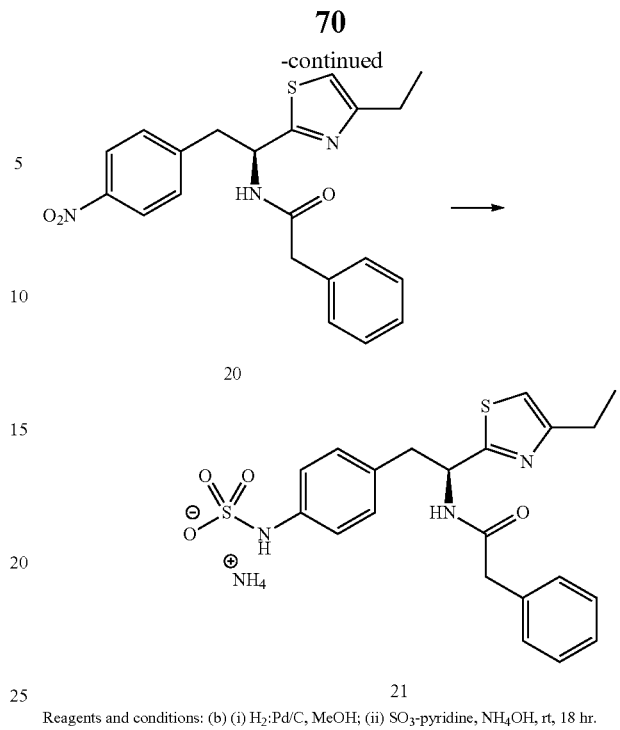

Reagents and conditions: (b) (i) H₂:Pd/C, MeOH; (ii) SO₃-pyridine, NH₄OH, rt, 18 hr.

EXAMPLE 8

{4-[2-(S)-(4-Ethylthiazol-2-yl)-2-(2-phenylacetylamido)ethyl]phenyl}sulfamic acid (21)

Preparation of N-[1-(4-ethylthiazol-2-yl)-2-(4-nitrophenyl)ethyl]-2-phenyl-acetamide (20): To a solution of 1-(S)-(4-ethylthiazol-2-yl)-2-(4-nitrophenyl)ethyl amine hydrobromide, 3, (0.393 g, 1.1 mmol), phenylacetic acid (0.190 g, 1.4 mmol) and 1-hydroxybenzotriazole (HOBt) (0.094 g, 0.70 mmol) in DMF (10 mL) at 0°, is added 1-(3-dimethylaminopropyl)-3-ethylcarbodiimide (EDCI) (0.268 g, 1.4 mmol) followed by triethylamine (0.60 mL, 4.2 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.260 g (60% yield) of the desired product which is used without further purification. ESI+ MS 396 (M+1).

Preparation of {4-[2-(S)-(4-ethylthiazol-2-yl)-2-(2-phenylacetylamido)ethyl]-phenyl}sulfamic acid (21): N-[1-(4-ethylthiazol-2-yl)-2-(4-nitrophenyl)ethyl]-2-phenyl-acetamide, 20, (0.260 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.177 g, 1.23). The reaction is stirred at room temperature for 5 minutes after which a 7% solution of NH₄OH (10 mL) is added. The mixture is then concentrated and the resulting residue is purified by reverse phase chromatography to afford 0.136 g of the desired product as the ammonium salt. ¹H NMR (CD₃OD) δ 8.60 (d, 1H, J=8.1 Hz), 7.33-7.23 (m, 3H), 7.16-7.00 (m, 6H), 5.44-5.41 (m, 1H), 3.28 (1H, A of ABX, obscured by solvent), 3.03 (1H, B of ABX, J=14.1, 9.6 Hz), 2.80 (q, 2H, J=10.5, 7.8 Hz) 1.31 (t, 3H, J=4.6 Hz).

The following are non-limiting examples of the first aspect of Category V of the present disclosure.

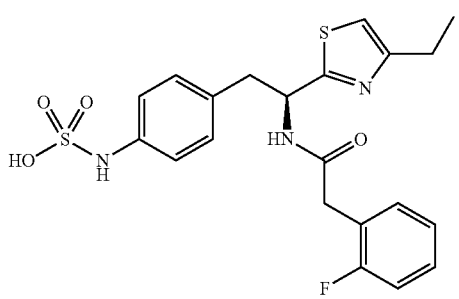

(S)-4-(2-(4-Ethylthiazol-2-yl)-2-(2-(2-fluorophenyl)acetamido)ethyl)phenylsulfamic acid: $^1$H NMR (CD$_3$OD) δ 8.65 (d, 1H, J=8.4 Hz), 7.29-7.15 (m, 1H), 7.13-7.03 (m, 7H), 5.46-5.42 (m, 1H), 3.64-3.51 (m, 2H), 3.29 (1H), 3.04 (1H, B of ABX, J=13.8, 9.6 Hz), 2.81 (q, 2H, J=15.6, 3.9 Hz), 1.31 (t, 3H, J=7.8 Hz). $^{19}$F NMR (CD$_3$OD) δ 43.64.

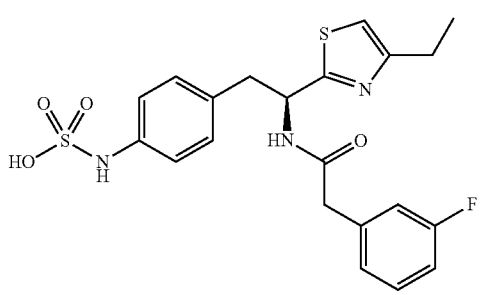 [SMILES: CCc1csc([C@H](Cc2ccc(NS(=O)(=O)O)cc2)NC(=O)Cc2cccc(F)c2)n1]

(S)-4-(2-(4-Ethylthiazol-2-yl)-2-(2-(3-fluorophenyl)acetamido)ethyl)phenylsulfamic acid: $^1$H NMR (CD$_3$OD) δ 8.74 (d, 1H, J=8.4 Hz), 7.32 (q, 1H, J=6.6, 14.2 Hz), 7.10-6.91 (m, 8H), 5.47-5.40 (m, 1H), 3.53 (s, 2H), 3.30 (1H), 3.11 (1H, B of ABX, J=9.6, 14.1 Hz), 2.80 (q, 2H, J=6.6, 15.1 Hz), 1.31 (t, 3H, J=7.8 Hz). 19F NMR δ 47.42.

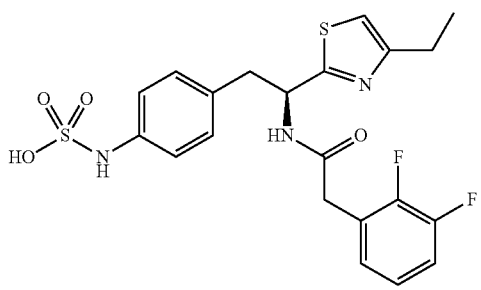 [SMILES: CCc1csc([C@H](Cc2ccc(NS(=O)(=O)O)cc2)NC(=O)Cc2cccc(F)c2F)n1]

(S)-4-(2-(2-(2,3-Difluorophenyl)acetamido)-2-(4-ethylthiazol-2-yl)ethyl)-phenylsulfamic acid: $^1$H NMR (CD$_3$OD) δ 7.16-7.05 (m, 5H), 6.85-6.80 (m, 1H), 5.48-5.43 (m, 1H), 3.63 (s, 2H), 3.38 (1H, A of ABX, obscured by solvent), 3.03 (1H), 2.80 (q, H, J=15.1, 7.8 Hz), 1.31 (t, 3H, J=7.5 Hz).

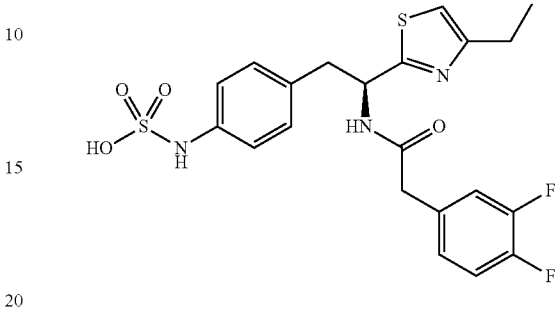

(S)-4-(2-(2-(3,4-Difluorophenyl)acetamido)-2-(4-ethylthiazol-2-yl)ethyl)-phenylsulfamic acid: $^1$H NMR (CD$_3$OD) δ 8.75 (d, 1H, J=7.8 Hz), 7.23-7.04 (m, 6H), 6.88-6.84 (m, 1H), 5.44-5.40 (m, 1H), 3.49 (s, 2H), 3.34 (1H), 3.02 (1H, B of ABX, J=14.1, 9.9 Hz), 2.80 (q, 2H, J=15.1, 7.8 Hz), 1.31 (t, 1H, J=7.5 Hz). 19F NMR (CD$_3$OD) δ 22.18, 19.45.

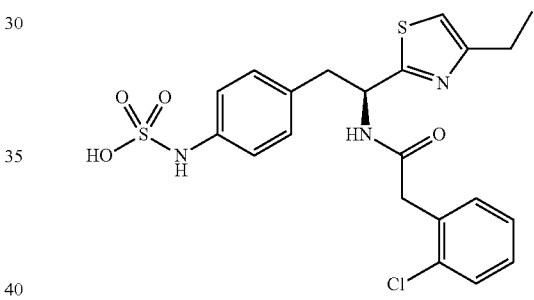

(S)-4-(2-(2-(2-Chlorophenyl)acetamido)-2-(4-ethylthiazol-2-yl)ethyl)phenylsulfamic acid: $^1$H NMR (CD$_3$OD) δ 7.39-7.36 (m, 1H), 7.27-7.21 (m, 2H), 7.15-6.98 (m, 5H), 5.49-5.44 (m, 1H), 3.69 (d, 2H, J=11.7 Hz), 3.32 (1H), 3.04 (1H, B of ABX, J=9.3, 13.9 Hz), 2.80 (q, 2H, J=7.8, 15.3 Hz), 1.31 (t, 3H, J=7.5 Hz).

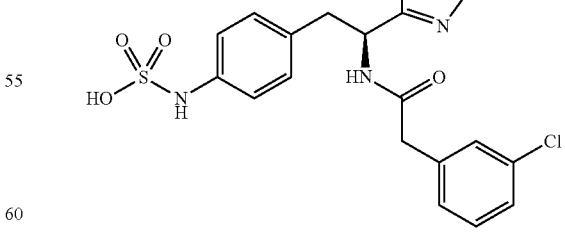

(S)-4-(2-(2-(3-Chlorophenyl)acetamido)-2-(4-ethylthiazol-2-yl)ethyl)phenylsulfamic acid: $^1$H NMR (CD$_3$OD) δ 7.33-7.23 (m, 3H), 7.13-7.03 (m, 5H), 5.43 (q, 1H, J=5.1, 9.6 Hz), 3.51 (s, 2H), 3.29 (1H), 3.03 (1H, B of ABX, J=9.9, 14.1 Hz), 2.80 (q, 2H, J=7.5, 15 Hz), 1.31 (t, 3H, J=7.8 Hz).

1H), 3.79 (s, 3H), 3.50 (s, 2H), 3.29 (1H, A of ABX, obscured by solvent), 3.08 (1H, B of ABX, J=11.8, 5.1 Hz), 2.80 (q, 2H, J=15, 7.5 Hz), 1.31 (t, 3H, J=6.6 Hz).

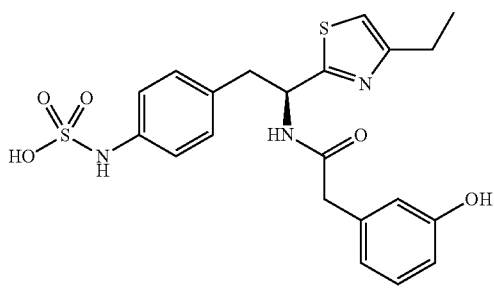 [SMILES: CCc1csc([C@H](Cc2ccc(NS(=O)(=O)O)cc2)NC(=O)Cc2cccc(O)c2)n1]

(S)-4-(2-(4-Ethylthiazol-2-yl)-2-(2-(3-hydroxyphenyl)acetamido)ethyl)-phenylsulfamic acid: $^1$H NMR (CD$_3$OD) δ 7.16-7.08 (m, 3H), 7.03-7.00 (m, 3H), 6.70-6.63 (m, 2H), 5.42-5.40 (m, 1H), 3.44 (s, 2H), 3.28 (1H, A of ABX, obscured by solvent), 3.04 (B of ABX, J=14.1, 9.6 Hz), 2.89 (q, 2H, J=15, 7.5 Hz), 1.31 (t, 3H, J=7.5 Hz).

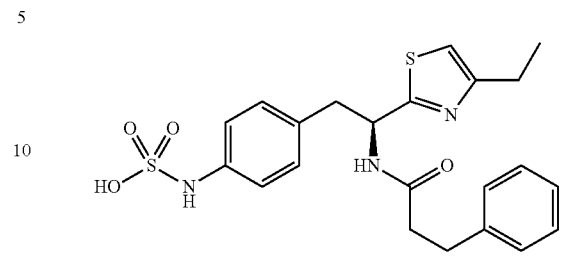

(S)-4-(2-(4-Ethylthiazol-2-yl)-2-(3-phenylpropanamido)ethyl)phenylsulfamic acid: $^1$H NMR (CD$_3$OD) δ 8.56 (d, 1H, J=8.4 Hz), 7.25-6.98 (m, 9H), 5.43-5.38 (m, 1H), 3.26, (1H, A of ABX, J=14.1, 9.6 Hz), 2.97 (1H, B of ABX, J=10.9, 3 Hz), 2.58-2.76 (m, 3H), 2.98 (q, 2H, J=13.8, 7.2 Hz), 1.29 (t, 3H, J=8.7 Hz).

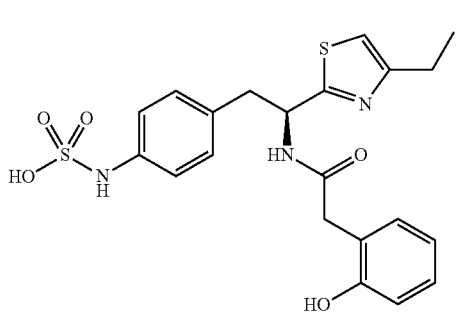

(S)-4-(2-(4-Ethylthiazol-2-yl)-2-(2-(2-methoxyphenyl)acetamido)ethyl)-phenylsulfamic acid: $^1$H NMR (CD$_3$OD) δ 8.00 (d, 1H, J=7.8 Hz), 7.26 (t, 1H, J=13.2 Hz), 7.09-7.05 (m, 4H), 7.01 (s, 1H), 6.91-6.89 (m, 4H), 5.44-5.39 (m, 1H), 3.71 (s, 3H), 3.52 (s, 2H), 3.26 (1H, A of ABX, J=14.1, 5.1 Hz), 3.06 (1H B of ABX, J=13.8, 8.4 Hz), 2.80 (q, 2H, J=8.1, 15.6 Hz), 1.31 (t, 3H, J=1.2 Hz).

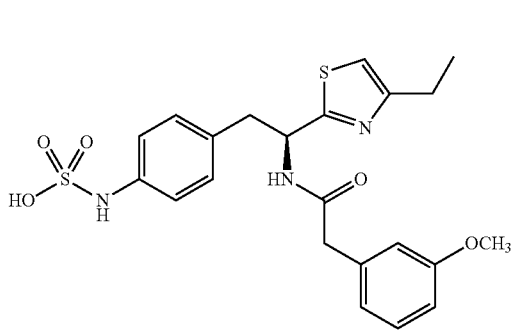 [SMILES: CCc1csc([C@H](Cc2ccc(NS(=O)(=O)O)cc2)NC(=O)Cc2cccc(OC)c2)n1]

(S)-4-{2-(4-Ethylthiazol-2-yl)-2-[2-(3-methoxyphenyl)acetamido]ethyl}-phenylsulfamic acid: $^1$H NMR (CD$_3$OD) δ 8.58 (d, 1H, J=8.1 Hz), 7.21 (t, 1H, J=7.8 Hz), 7.12-7.02 (m, 4H), 6.81 (s, 2H), 6.72 (d, 1H, J=7.5 Hz), 5.45-5.40 (m,

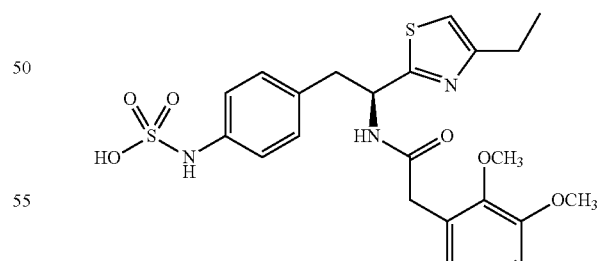

(S)-4-(2-(2-(3,4-Dimethoxyphenyl)acetamido)-2-(4-ethylthiazol-2-yl)ethyl)-phenylsulfamic acid: $^1$H NMR (CD$_3$OD) δ 7.12-7.03 (m, 3H), 6.91 (d, 1H, J=8.4 Hz), 6.82 (s, 1H), 6.66 (d, 1H, J=2.1 Hz), 6.63 (d, 1H, J=2.1 Hz), 5.43 (m, 1H), 3.84 (s, 3H), 3.80 (s, 3H), 3.45 (s, 2H), 3.30 (1H), 3.03 (1H, B of ABX, J=14.1, 9.6 Hz), 2.79 (q, 2H, J=15.1, 7.2 Hz), 1.30 (t, 3H, J=7.2 Hz).

(S)-4-(2-(2-(2,3-Dimethoxyphenyl)acetamido)-2-(4-ethylthiazol-2-yl)ethyl)-phenylsulfamic acid: $^1$H NMR (CD$_3$OD) δ 8.31 (d, 1H, J=7.8 Hz), 7.11-6.93 (m, 6H), 6.68 (d, 1H, J=7.5 Hz), 5.49-5.40 (m, 1H), 3.87 (s, 3H), 3.70 (s, 3H), 3.55 (s, 2H), 3.26 (1H, A of ABX, obscured by solvent), 3.06 (1H, B of ABX, J=13.9, 9 Hz), 2.80 (q, 2H, J=14.8, 7.5 Hz), 1.31 (t, 3H, J=7.5 Hz).

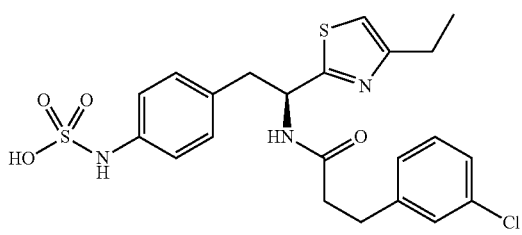 [SMILES: CCc1csc([C@H](Cc2ccc(NS(=O)(=O)O)cc2)NC(=O)CCc2cccc(Cl)c2)n1]

(S)-4-(2-(3-(3-Chlorophenyl)propanamido)-2-(4-ethyl-thiazol-2-yl)ethyl)phenyl-sulfamic acid: $^1$H NMR (CD$_3$OD) δ 7.27-7.18 (m, 3H), 7.13-7.08 (m, 5H), 7.01 (s, 1H), 5.39 (q, 1H, J=5.1, 9.4 Hz), 3.28 (1H, A of ABX, J=5.1, 14.1 Hz), 2.97 (1H, B of ABX, J=9.3, 13.9 Hz), 2.88-2.76 (m, 4H), 2.50 (t, 2H, J=8.1 Hz), 1.31 (t, 3H, J=7.8 Hz).

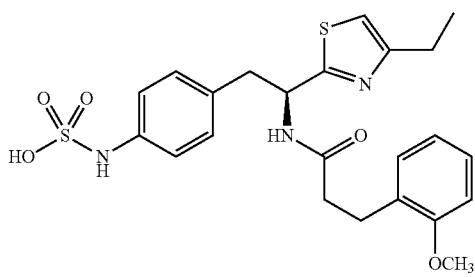 [SMILES: CCc1csc([C@H](Cc2ccc(NS(=O)(=O)O)cc2)NC(=O)CCc2ccccc2OC)n1]

(S)-4-(2-(4-Ethylthiazol-2-yl)-2-(3-(2-methoxyphenyl)propanamido)ethyl)-phenylsulfamic acid: $^1$H NMR (CD$_3$OD) δ 7.18-7.08 (m, 6H), 6.92 (d, 1H, J=8.1 Hz), 6.82 (t, 1H, J=7.5 Hz), 5.40-5.35 (m, 1H), 3.25 (1H, A of ABX, J=15, 5.4 Hz), 3.00 (1H, B of ABX, J=10.5, 7.5 Hz), 2.88-2.76 (m, 4H), 2.47 (q, 2H, J=9.1, 6 Hz), 1.31 (t, 3H, J=7.8 Hz).

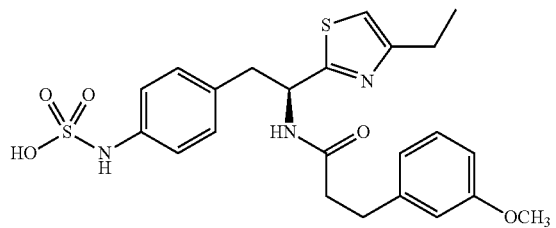 [SMILES: CCc1csc([C@H](Cc2ccc(NS(=O)(=O)O)cc2)NC(=O)CCc2cccc(OC)c2)n1]

(S)-4-(2-(4-Ethylthiazol-2-yl)-2-(3-(3-methoxyphenyl)propanamido)ethyl)-phenyl sulfamic acid: $^1$H NMR (CD$_3$OD) δ 7.19-7.00 (m, 5H), 6.75 (s, 1H), 6.73 (s, 1H), 5.42-5.37 (m, 1H), 3.76 (s, 3H), 3.25 (1H, A of ABX, J=13.9, 5.4 Hz), 2.98 (1H, B of ABX, J=14.1, 9.6 Hz), 2.86-2.75 (m, 4H), 2.48 (q, 2H, J=11.7, 1.2 Hz), 1.31 (t, 3H, J=7.5 Hz).

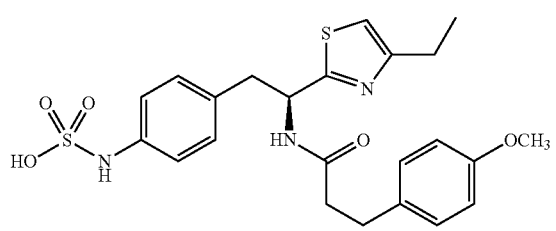 [SMILES: CCc1csc([C@H](Cc2ccc(NS(=O)(=O)O)cc2)NC(=O)CCc2ccc(OC)cc2)n1]

(S)-4-(2-(4-Ethylthiazol-2-yl)-2-(3-(4-methoxyphenyl)propanamido)ethyl)-phenylsulfamic acid: $^1$H NMR (CD$_3$OD) δ 7.13-6.99 (m, 7H), 6.82-6.78 (m, 2H), 5.42-5.37 (m, 1H), 3.33 (s, 3H), 3.23 (1H), 2.97 (1H, B of ABX, J=13.3, 11.4 Hz), 2.83-2.75 (m, 4H), 2.49 (q, 2H, J=6.4, 3.3 Hz), 1.31 (t, 3H, J=7.5 Hz).

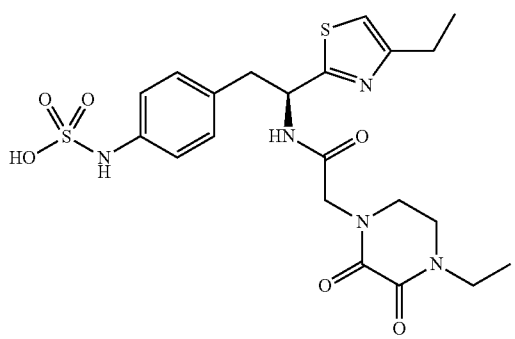 [SMILES: CCc1csc([C@H](Cc2ccc(NS(=O)(=O)O)cc2)NC(=O)CN2CCN(CC)C(=O)C2=O)n1]

(S)-4-{2-[2-(4-Ethyl-2,3-dioxopiperazin-1-yl)acetamido]-2-(4-ethylthiazol-2-yl)ethyl}phenylsulfamic acid: $^1$H NMR (CD$_3$OD) δ 7.14 (s, 4H), 7.08 (s, 1H), 5.56-5.51 (m, 1H), 4.34 (d, 2H, J=16.2 Hz), 3.88 (d, 2H, J=17.6 Hz), 3.59-3.40 (m, 3H), 3.26-3.14 (m, 3H), 2.98 (1H, B of ABX, J=10.8, 13.9 Hz), 2.82 (q, 2H, J=6.9, 15 Hz), 1.32 (t, 3H, J=7.5 Hz), 1.21 (t, 3H, J=7.2 Hz).

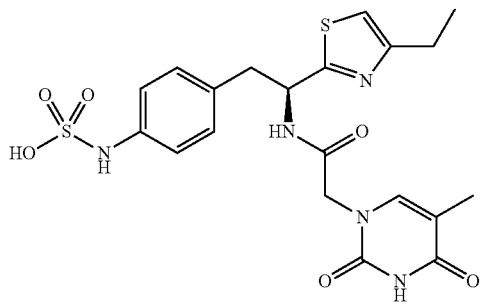 [SMILES: CCc1csc([C@H](Cc2ccc(NS(=O)(=O)O)cc2)NC(=O)Cn2cc(C)c(=O)[nH]c2=O)n1]

(S)-4-{2-(4-Ethylthiazol-2-yl)-2-[2-(5-methyl-2,4-dioxo-3,4-dihydropyrimidin-1(2H)-yl)acetamido]ethyl}phenylsulfamic acid: $^1$H NMR (CD$_3$OD) δ 7.13 (s, 1H), 7.06-7.02 (m, 4H), 6.95 (s, 1H), 5.42-5.31 (m, 1H), 4.43-4.18 (dd, 2H, J=16.5 Hz), 3.24-2.93 (m, 2H), 2.74-2.69 (q, 2H, J=7.3 Hz), 1.79 (s, 3H), 1.22 (t, 3H, J=7.5 Hz).

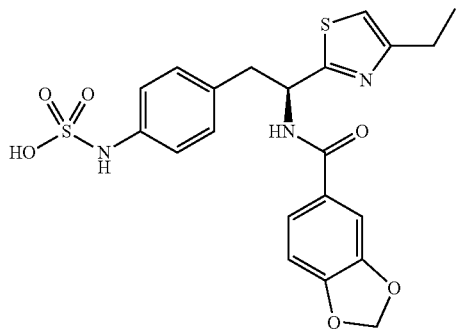 [SMILES: CCc1csc([C@H](Cc2ccc(NS(=O)(=O)O)cc2)NC(=O)c2ccc3c(c2)OCO3)n1]

(S)-4-[2-(benzo[d][1,3]dioxole-5-carboxamido)-2-(4-ethylthiazol-2-yl)ethyl]-phenylsulfamic acid: $^1$H NMR (CD₃OD) δ 7.25 (d, 1H, J=6.5 Hz), 7.13 (s, 1H), 7.06 (d, 2H, J=8.5 Hz), 7.00 (d, 2H, J=8.5 Hz), 6.91 (s, 1H), 6.76 (d, 1H, J=8.1 Hz), 5.90 (s, 2H), 5.48 (q, 1H, J=5.0 Hz), 3.32=3.24 (m, 2H), 3.07-2.99 (m, 2H), 2.72 (q, 2H, J=7.5 Hz), 1.21 (t, 3H, J=7.5 Hz).

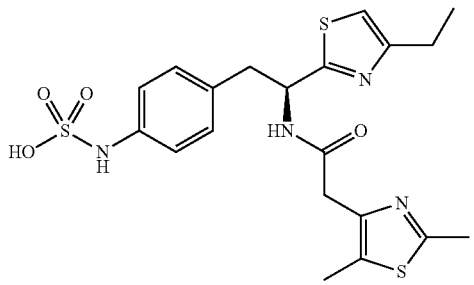 [SMILES: CCc1csc([C@H](Cc2ccc(NS(=O)(=O)O)cc2)NC(=O)Cc2nc(C)sc2C)n1]

(S)-4-{2-[2-(2,5-Dimethylthiazol-4-yl)acetamido]-2-(4-ethylthiazol-2-yl)ethyl}-phenylsulfamic acid: ¹H NMR (CD₃OD) δ 7.10-7.01 (m, 5H), 5.41 (t, 1H, J=6.9 Hz), 3.58 (s, 2H), 3.33-3.01 (m, 2H), 2.82-2.75 (q, 2H, J=7.5 Hz), 2.59 (s, 3H), 2.23 (s, 3H), 1.30 (t, 3H, J=7.5 Hz).

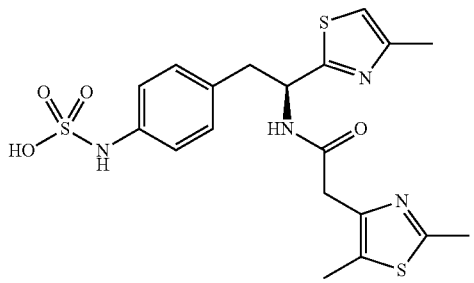 [SMILES: Cc1csc([C@H](Cc2ccc(NS(=O)(=O)O)cc2)NC(=O)Cc2nc(C)sc2C)n1]

(S)-4-{2-[2-(2,4-Dimethylthiazol-5-yl)acetamido]-2-(4-methylthiazol-2-yl)ethyl}-phenylsulfamic acid: ¹H NMR (CD₃OD): δ 8.71-8.68 (d, 1H, J=8.4 Hz), 7.10-7.03 (m, 4H), 7.01 (s, 1H), 5.41 (m, 1H), 3.59 (s, 1H), 3.34-2.96 (m, 2H), 2.59 (s, 3H), 2.40 (s, 3H), 2.23 (s, 3H).

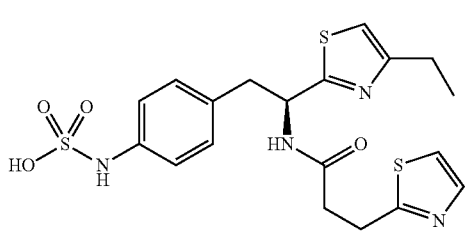 [SMILES: CCc1csc([C@H](Cc2ccc(NS(=O)(=O)O)cc2)NC(=O)CCc2nccs2)n1]

(S)-4-{2-(4-Ethylthiazol-2-yl)-2-[3-(thiazol-2-yl)propanamido]ethyl}phenylsulfamic acid: ¹H NMR (CD₃OD): (S)-4-{2-[2-(2,5-Dimethylthiazol-4-yl)acetamido]-2-(4-ethylthiazol-2-yl)ethyl}-phenylsulfamic acid: ¹H NMR (CD₃OD) δ 7.10-7.01 (m, 5H), 5.41 (t, 1H, J=6.9 Hz), 3.58 (s, 2H), 3.33-3.01 (m, 2H), 2.82-2.75 (q, 2H, J=7.5 Hz), 2.59 (s, 3H), 2.23 (s, 3H), 1.30 (t, 3H, J=7.5 Hz).

7.67-7.65 (m, 1H), 7.49-7.47 (m, 1H), 7.14-7.08 (m, 4H), 7.04 (s, 1H), 5.46-5.41 (q, 1H, J=5.1 Hz), 3.58 (s, 2H), 3.30-3.25 (m, 3H), 3.02-2.67 (m, 5H), 1.31 (t, 3H, J=7.5 Hz).

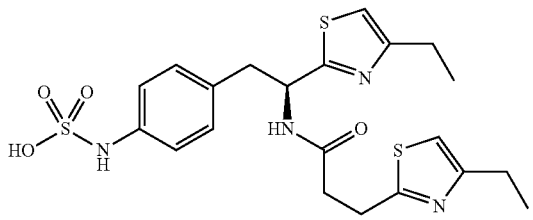 [SMILES: CCc1csc(CCC(=O)N[C@@H](Cc2ccc(NS(=O)(=O)O)cc2)c2nc(CC)cs2)n1]

(S)-4-{2-(4-Ethylthiazol-2-yl)-2-[2-(4-ethylthiazol-2-yl)acetamido]ethyl}-phenylsulfamic acid: ¹H NMR (CD₃OD) δ 7.04-6.91 (m, 6H), 5.32 (t, 1H, J=5.4 Hz), 3.25-2.90 (m, 2H), 2.71-2.61 (m, 4H) 1.93 (s, 2H) 1.22-1.14 (m, 6H).

The second aspect of Category V of the present disclosure relates to 2-(thiazol-4-yl) compounds having the formula:

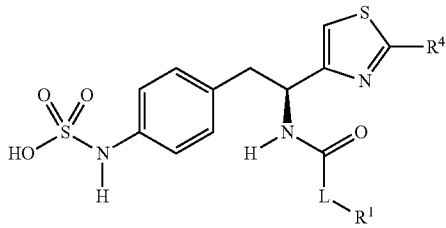

wherein R¹, R⁴, and L are further defined herein in Table X below.

TABLE X

| No. | L | R¹ | R⁴ |
|---|---|---|---|
| J360 | —CH₂— | phenyl | methyl |
| J361 | —CH₂— | phenyl | ethyl |
| J362 | —CH₂— | phenyl | phenyl |
| J363 | —CH₂— | phenyl | thiophen-2-yl |
| J364 | —CH₂— | phenyl | thiazol-2-yl |
| J365 | —CH₂— | phenyl | oxazol-2-yl |
| J366 | —CH₂— | phenyl | isoxazol-3-yl |
| J367 | —CH₂— | 3-chlorophenyl | methyl |
| J368 | —CH₂— | 3-chlorophenyl | ethyl |
| J369 | —CH₂— | 3-chlorophenyl | phenyl |
| J370 | —CH₂— | 3-chlorophenyl | thiophen-2-yl |
| J371 | —CH₂— | 3-chlorophenyl | thiazol-2-yl |
| J372 | —CH₂— | 3-chlorophenyl | oxazol-2-yl |
| J373 | —CH₂— | 3-chlorophenyl | isoxazol-3-yl |
| J374 | —CH₂— | 3-methoxyphenyl | methyl |
| J375 | —CH₂— | 3-methoxyphenyl | ethyl |
| J376 | —CH₂— | 3-methoxyphenyl | phenyl |
| J377 | —CH₂— | 3-methoxyphenyl | thiophen-2-yl |
| J378 | —CH₂— | 3-methoxyphenyl | thiazol-2-yl |
| J379 | —CH₂— | 3-methoxyphenyl | oxazol-2-yl |
| J380 | —CH₂— | 3-methoxyphenyl | isoxazol-3-yl |
| J381 | —CH₂— | 3-fluorophenyl | methyl |
| J382 | —CH₂— | 3-fluorophenyl | ethyl |
| J383 | —CH₂— | 3-fluorophenyl | phenyl |
| J384 | —CH₂— | 3-fluorophenyl | thiophen-2-yl |
| J385 | —CH₂— | 3-fluorophenyl | thiazol-2-yl |
| J386 | —CH₂— | 3-fluorophenyl | oxazol-2-yl |
| J387 | —CH₂— | 3-fluorophenyl | isoxazol-3-yl |
| J388 | —CH₂— | 2,5-dimethylthiazol-4-yl | methyl |
| J389 | —CH₂— | 2,5-dimethylthiazol-4-yl | ethyl |
| J390 | —CH₂— | 2,5-dimethylthiazol-4-yl | phenyl |
| J391 | —CH₂— | 2,5-dimethylthiazol-4-yl | thiophen-2-yl |
| J392 | —CH₂— | 2,5-dimethylthiazol-4-yl | thiazol-2-yl |
| J393 | —CH₂— | 2,5-dimethylthiazol-4-yl | oxazol-2-yl |
| J394 | —CH₂— | 2,5-dimethylthiazol-4-yl | isoxazol-3-yl |
| J395 | —CH₂— | 2,4-dimethylthiazol-5-yl | methyl |
| J396 | —CH₂— | 2,4-dimethylthiazol-5-yl | ethyl |
| J397 | —CH₂— | 2,4-dimethylthiazol-5-yl | phenyl |
| J398 | —CH₂— | 2,4-dimethylthiazol-5-yl | thiophen-2-yl |

TABLE X-continued

| No. | L | R¹ | R⁴ |
|---|---|---|---|
| J399 | —CH₂— | 2,4-dimethylthiazol-5-yl | thiazol-2-yl |
| J400 | —CH₂— | 2,4-dimethylthiazol-5-yl | oxazol-2-yl |
| J401 | —CH₂— | 2,4-dimethylthiazol-5-yl | isoxazol-3-yl |
| J402 | —CH₂— | 4-ethylthiazol-2-yl | methyl |
| J403 | —CH₂— | 4-ethylthiazol-2-yl | ethyl |
| J404 | —CH₂— | 4-ethylthiazol-2-yl | phenyl |
| J405 | —CH₂— | 4-ethylthiazol-2-yl | thiophen-2-yl |
| J406 | —CH₂— | 4-ethylthiazol-2-yl | thiazol-2-yl |
| J407 | —CH₂— | 4-ethylthiazol-2-yl | oxazol-2-yl |
| J408 | —CH₂— | 4-ethylthiazol-2-yl | isoxazol-3-yl |
| J409 | —CH₂— | 3-methyl-1,2,4-oxadiazol-5-yl | methyl |
| J410 | —CH₂— | 3-methyl-1,2,4-oxadiazol-5-yl | ethyl |
| J411 | —CH₂— | 3-methyl-1,2,4-oxadiazol-5-yl | phenyl |
| J412 | —CH₂— | 3-methyl-1,2,4-oxadiazol-5-yl | thiophen-2-yl |
| J413 | —CH₂— | 3-methyl-1,2,4-oxadiazol-5-yl | thiazol-2-yl |
| J414 | —CH₂— | 3-methyl-1,2,4-oxadiazol-5-yl | oxazol-2-yl |
| J415 | —CH₂— | 3-methyl-1,2,4-oxadiazol-5-yl | isoxazol-3-yl |
| J416 | —CH₂CH₂— | phenyl | methyl |
| J417 | —CH₂CH₂— | phenyl | ethyl |
| J418 | —CH₂CH₂— | phenyl | phenyl |
| J419 | —CH₂CH₂— | phenyl | thiophen-2-yl |
| J420 | —CH₂CH₂— | phenyl | thiazol-2-yl |
| J421 | —CH₂CH₂— | phenyl | oxazol-2-yl |
| J422 | —CH₂CH₂— | phenyl | isoxazol-3-yl |
| J423 | —CH₂CH₂— | 3-chlorophenyl | methyl |
| J424 | —CH₂CH₂— | 3-chlorophenyl | ethyl |
| J425 | —CH₂CH₂— | 3-chlorophenyl | phenyl |
| J426 | —CH₂CH₂— | 3-chlorophenyl | thiophen-2-yl |
| J427 | —CH₂CH₂— | 3-chlorophenyl | thiazol-2-yl |
| J428 | —CH₂CH₂— | 3-chlorophenyl | oxazol-2-yl |
| J429 | —CH₂CH₂— | 3-chlorophenyl | isoxazol-3-yl |
| J430 | —CH₂CH₂— | 3-methoxyphenyl | methyl |
| J431 | —CH₂CH₂— | 3-methoxyphenyl | ethyl |
| J432 | —CH₂CH₂— | 3-methoxyphenyl | phenyl |
| J433 | —CH₂CH₂— | 3-methoxyphenyl | thiophen-2-yl |
| J434 | —CH₂CH₂— | 3-methoxyphenyl | thiazol-2-yl |
| J435 | —CH₂CH₂— | 3-methoxyphenyl | oxazol-2-yl |
| J436 | —CH₂CH₂— | 3-methoxyphenyl | isoxazol-3-yl |
| J437 | —CH₂CH₂— | 3-fluorophenyl | methyl |
| J438 | —CH₂CH₂— | 3-fluorophenyl | ethyl |
| J439 | —CH₂CH₂— | 3-fluorophenyl | phenyl |
| J440 | —CH₂CH₂— | 3-fluorophenyl | thiophen-2-yl |
| J441 | —CH₂CH₂— | 3-fluorophenyl | thiazol-2-yl |
| J442 | —CH₂CH₂— | 3-fluorophenyl | oxazol-2-yl |
| J443 | —CH₂CH₂— | 3-fluorophenyl | isoxazol-3-yl |
| J444 | —CH₂CH₂— | 2,5-dimethylthiazol-4-yl | methyl |
| J445 | —CH₂CH₂— | 2,5-dimethylthiazol-4-yl | ethyl |
| J446 | —CH₂CH₂— | 2,5-dimethylthiazol-4-yl | phenyl |
| J447 | —CH₂CH₂— | 2,5-dimethylthiazol-4-yl | thiophen-2-yl |
| J448 | —CH₂CH₂— | 2,5-dimethylthiazol-4-yl | thiazol-2-yl |
| J449 | —CH₂CH₂— | 2,5-dimethylthiazol-4-yl | oxazol-2-yl |
| J450 | —CH₂CH₂— | 2,5-dimethylthiazol-4-yl | isoxazol-3-yl |
| J451 | —CH₂CH₂— | 2,4-dimethylthiazol-5-yl | methyl |
| J452 | —CH₂CH₂— | 2,4-dimethylthiazol-5-yl | ethyl |
| J453 | —CH₂CH₂— | 2,4-dimethylthiazol-5-yl | phenyl |
| J454 | —CH₂CH₂— | 2,4-dimethylthiazol-5-yl | thiophen-2-yl |
| J455 | —CH₂CH₂— | 2,4-dimethylthiazol-5-yl | thiazol-2-yl |
| J456 | —CH₂CH₂— | 2,4-dimethylthiazol-5-yl | oxazol-2-yl |
| J457 | —CH₂CH₂— | 2,4-dimethylthiazol-5-yl | isoxazol-3-yl |
| J458 | —CH₂CH₂— | 4-ethylthiazol-2-yl | methyl |
| J459 | —CH₂CH₂— | 4-ethylthiazol-2-yl | ethyl |
| J460 | —CH₂CH₂— | 4-ethylthiazol-2-yl | phenyl |
| J461 | —CH₂CH₂— | 4-ethylthiazol-2-yl | thiophen-2-yl |
| J462 | —CH₂CH₂— | 4-ethylthiazol-2-yl | thiazol-2-yl |
| J463 | —CH₂CH₂— | 4-ethylthiazol-2-yl | oxazol-2-yl |
| J464 | —CH₂CH₂— | 4-ethylthiazol-2-yl | isoxazol-3-yl |
| J465 | —CH₂CH₂— | 3-methyl-1,2,4-oxadiazol-5-yl | methyl |
| J466 | —CH₂CH₂— | 3-methyl-1,2,4-oxadiazol-5-yl | ethyl |
| J467 | —CH₂CH₂— | 3-methyl-1,2,4-oxadiazol-5-yl | phenyl |
| J468 | —CH₂CH₂— | 3-methyl-1,2,4-oxadiazol-5-yl | thiophen-2-yl |
| J469 | —CH₂CH₂— | 3-methyl-1,2,4-oxadiazol-5-yl | thiazol-2-yl |
| J470 | —CH₂CH₂— | 3-methyl-1,2,4-oxadiazol-5-yl | oxazol-2-yl |
| J471 | —CH₂CH₂— | 3-methyl-1,2,4-oxadiazol-5-yl | isoxazol-3-yl |

The compounds encompassed within the second aspect of Category I of the present disclosure can be prepared by the procedure outlined in Scheme VIII and described in Example 9 below.

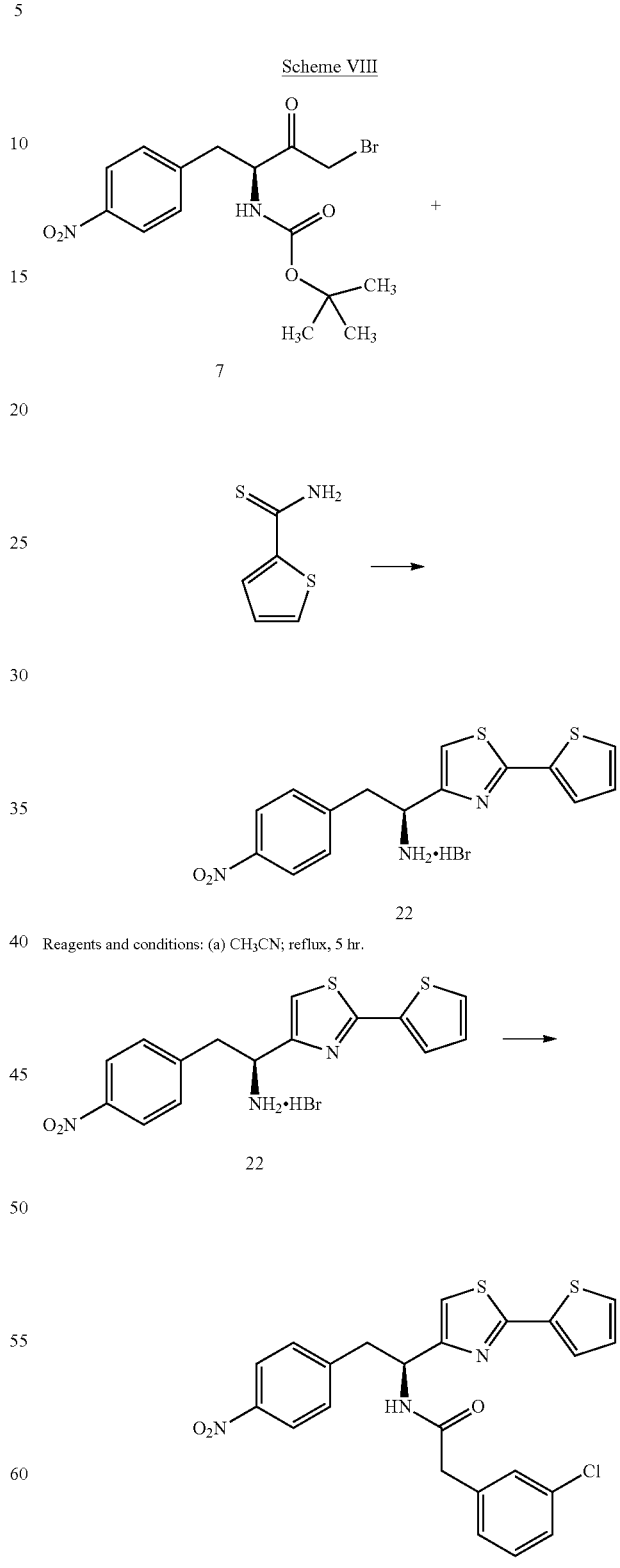

Scheme VIII

Reagents and conditions: (a) CH₃CN; reflux, 5 hr.

Reagents and conditions: (b)(3-Cl)C₆H₄CH₂CO₂H, EDCI, HOBt, DIPEA, DMF; rt, 18 hr.

-continued

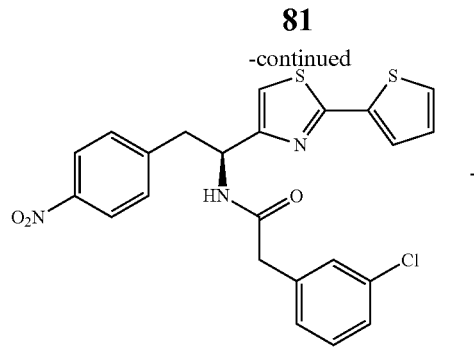

23

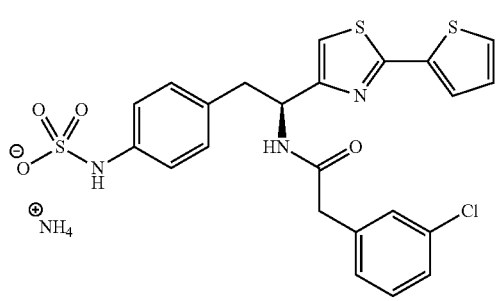

24

Reagents and conditions: (c) (i) H₂:Pd/C, MeOH; (ii) SO₃-pyridine, NH₄OH, rt, 18 hr.

EXAMPLE 9

4-((S)-2-(2-(3-chlorophenyl)acetamido)-2-(2-(thiophen-2-yl)thiazol-4-yl)ethyl)phenylsulfamic acid (24)

Preparation of (S)-2-(4-nitrophenyl)-1-[(thiophen-2-yl)thiazol-4-yl]ethanamine hydrobromide salt (22): A mixture of (S)-tert-butyl 4-bromo-1-(4-nitrophenyl)-3-oxobutan-2-ylcarbamate, 7, (7.74 g, 20 mmol), and thiophen-2-carbothioic acid amide (3.14 g, 22 mmol) in CH₃CN (200 mL) is refluxed for 5 hours. The reaction mixture is cooled to room temperature and diethyl ether (50 mL) is added to the solution. The precipitate which forms is collected by filtration. The solid is dried under vacuum to afford 7.14 g (87% yield) of the desired product. ESI+ MS 332 (M+1).

Preparation of 2-(3-chlorophenyl)-N—{(S)-2-(4-nitrophenyl)-1-[2-(thiophen-2-yl)thiazol-4-yl]ethyl}acetamide (23): To a solution of 2-(4-nitrophenyl)-1-(2-thiophene2-ylthiazol-4-yl)ethylamine, 22, (0.41 g, 1 mmol) 3-chlorophenylacetic acid (0.170 g, 1 mmol) and 1-hydroxybenzotriazole (HOBt) (0.070 g, 0.50 mmol) in DMF (5 mL) at 0° C., is added 1-(3-dimethylaminopropyl)-3-ethylcarbodiimide (EDCI) (0.190 g, 1 mmol) followed by triethylamine (0.42 mL, 3 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.290 g (60% yield) of the desired product which is used without further purification. ESI– MS 482 (M–1).

Preparation of {4-[2-(3-chlorophenyl)acetylamino]-2-(2-thiophen-2-ylthiazol-4-yl)ethyl]phenyl}sulfamic acid (24): 2-(3-chlorophenyl)-N—{(S)-2-(4-nitrophenyl)-1-[2-(thiophene2-yl)thiazol-4-yl]ethyl}acetamide, 23, (0.290 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.157 g). The reaction is stirred at room temperature for 5 minutes after which a 7% solution of NH₄OH is added. The mixture is then concentrated and the resulting residue is purified by reverse phase chromatography to afford 0.078 g of the desired product as the ammonium salt. ¹H NMR (CD₃OD) δ 7.61 (d, 1H, J=3.6 Hz), 7.58 (d, 1H, J=5.1 Hz), 7.41-7.35 (m, 1H), 7.28-7.22 (m, 2H), 7.18-6.98 (m, 6H), 5.33 (t, 1H, J=6.6 Hz), 3.70 (d, 2H, J=3.9 Hz), 3.23 (1H, A of ABX, J=6.6, 13.8 Hz), 3.07 (1H, B of ABX, J=8.1, 13.5 Hz).

The following are non-limiting examples of compounds encompassed within the second aspect of Category V of the present disclosure.

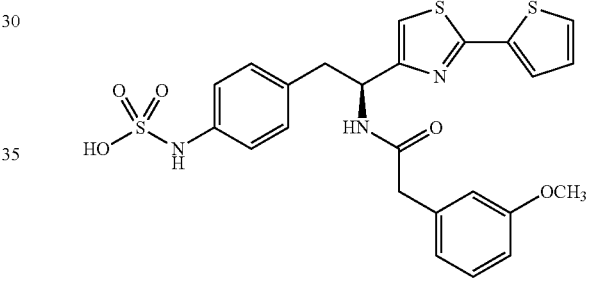

4-((S)-2-(2-(3-Methoxyphenyl)acetamido)-2-(2-(thiophene2-yl)thiazol-4-yl)ethyl)-phenylsulfamic acid: ¹H NMR (CD₃OD) δ 8.35 (d, 1H, J=8.7 Hz), 7.61-7.57 (m, 2H), 7.25-7.20 (m, 2H), 7.25-7.20 (m, 2H), 7.09 (s, 1H), 7.05 (d, 2H, J=4.2 Hz), 6.99 (d, 1H, J=8.7 Hz), 6.81 (d, 1H, J=7.8 Hz), 6.77 (s, 1H), 5.30-5.28 (m, 1H), 3.76 (s, 3H), 3.51 (s, 2H), 3.20 (1H, A of ABX, J=6.3, 13.6 Hz), 3.06 (1H, B of ABX, J=8.1, 13.8 Hz).

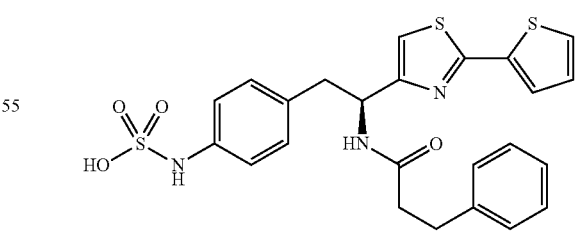

4-{(S)-2-(3-Phenylpropanamido)-2-[2-(thiophene2-yl)thiazol-4-yl]ethyl}-phenylsulfamic acid: ¹H NMR (CD₃OD) δ 8.30 (d, 1H, J=9 Hz), 7.61-7.56 (m, 2H), 7.26-7.14 (m, 7H), 7.12 (d, 1H, J=1.5 Hz), 7.09 (d, 1H, J=2.1 Hz), 6.89 (s, 1H), 5.28-5.26 (m, 1H), 3.18 (1H, A of ABX, J=6.2, 13.8 Hz), 2.96 (1H, B of ABX, J=8.4, 13.6 Hz).

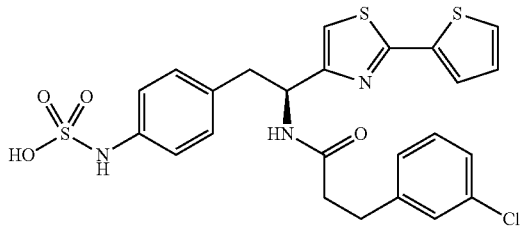 [SMILES: O=C(CCc1cccc(Cl)c1)N[C@@H](Cc1ccc(NS(=O)(=O)O)cc1)c1csc(-c2cccs2)n1]

4-{(S)-2-(3-(3-Chlorophenyl)propanamido)-2-[2-(thiophene2-yl)thiazol-4-yl]ethyl}phenylsulfamic acid: ¹H NMR (CD₃OD) δ 7.61-7.56 (m, 3H), 7.22-7.14 (m, 6H), 7.08 (d, 1H), 7.00 (d, 1H, J=77.5 Hz), 6.870 (s, 1H), 5.25 (t, 1H, J=7.8 Hz), 3.18 (1H, A of ABX, J=6.6, 13.8 Hz), 2.97 (1H, B of ABX, J=7.8, 13.8 Hz), 2.87 (t, 2H, J=7.5 Hz), 2.51 (t, 2H, J=7.2 Hz).

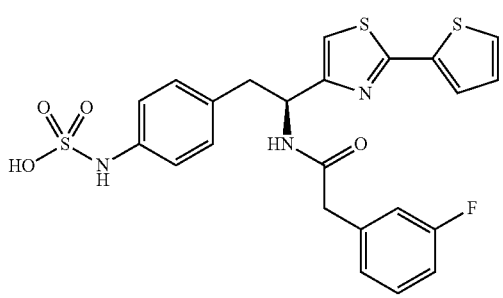 [SMILES: O=C(Cc1cccc(F)c1)N[C@@H](Cc1ccc(NS(=O)(=O)O)cc1)c1csc(-c2cccs2)n1]

4-{(S)-2-[2-(3-Fluorophenyl)acetamido]-2-[2-(thiophen-2-yl)thiazol-4-yl]ethyl}phenylsulfamic acid: ¹H NMR (CD₃OD) δ 7.61-7.57 (m, 2H), 7.32-7.28 (m, 1H), 7.19-7.16 (m, 2H), 7.08 (t, 1H, J=4.5 Hz), 7.02-6.95 (m, 6H), 5.29 (t, 1H, J=8.1 Hz), 3.53 (s, 2H), 3.22 (1H, A of ABX, J=6.6, 13.9 Hz), 3.06 (1H, B of ABX, J=8.4, 13.6 Hz).

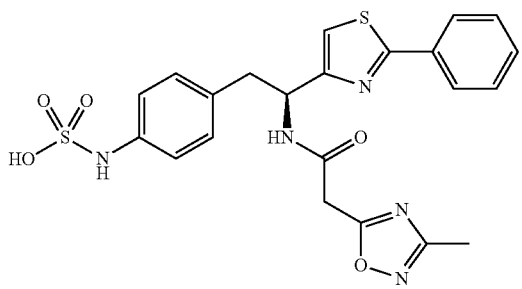 [SMILES: Cc1noc(CC(=O)N[C@@H](Cc2ccc(NS(=O)(=O)O)cc2)c2csc(-c3ccccc3)n2)n1]

(S)-4-{2-[2-(3-Methyl-1,2,4-oxadiazol-5-yl)acetamido]-2-(2-phenylthiazol-4-yl)ethyl}phenylsulfamic acid: ¹H NMR (CD₃OD): δ 7.98-7.95 (m, 2H), 7.48-7.46 (m, 3H), 7.23 (s, 1H), 7.09-7.05 (m, 4H), 5.33 (t, 1H, J=7.2 Hz), 3.33-3.06 (m, 2H), 2.35 (s, 3H).

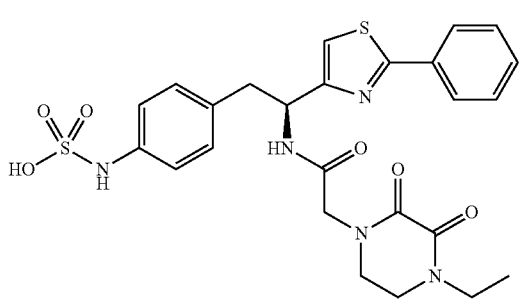 [SMILES: CCN1CCN(CC(=O)N[C@@H](Cc2ccc(NS(=O)(=O)O)cc2)c2csc(-c3ccccc3)n2)C(=O)C1=O]

4-{(S)-2-[2-(4-ethyl-2,3-dioxopiperazin-1-yl)acetamido]-2-[2-(thiophen-2-yl)thiazol-4-yl]ethyl}phenylsulfamic acid: ¹H NMR (CD₃OD) δ 7.62 (d, 1H, J=3 Hz), 7.58 (d, 1H, J=15.6 Hz), 7.27 (s, 1H), 7.16 (t, 1H, J=1.5 Hz), 5.42-5.32 (m, 1H), 4.31 (d, 1H, J=15.6 Hz), 3.91 (d, 1H, J=15.9 Hz), 3.60-3.50 (m, 4H), 3.30-3.23 (m, 2H), 2.98 (1H, B of ABX, J=9.9, 13.8 Hz), 1.21 (t, 3H, J=6.9 Hz).

The third aspect of Category V of the present disclosure relates to compounds having the formula:

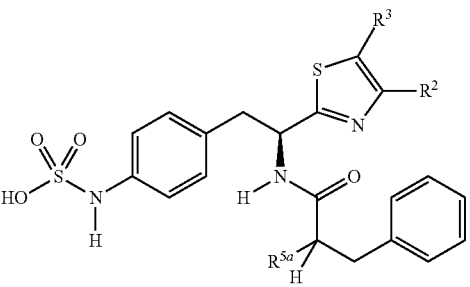

wherein the linking unit L comprises a phenyl unit, said linking group having the formula:

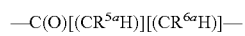

—C(O)[(CR⁵ᵃH)][(CR⁶ᵃH)]—

$R^1$ is hydrogen, $R^{6a}$ is phenyl, $R^{5a}$ is phenyl or substituted phenyl and non-limiting examples of the units $R^2$, $R^3$, and $R^{5a}$ are further exemplified below in Table XI.

TABLE XI

| No. | $R^2$ | $R^3$ | $R^{5a}$ |
|---|---|---|---|
| K472 | methyl | hydrogen | phenyl |
| K473 | methyl | hydrogen | 2-fluorophenyl |
| K474 | methyl | hydrogen | 3-fluorophenyl |
| K475 | methyl | hydrogen | 4-fluorophenyl |
| K476 | methyl | hydrogen | 3,4-difluorophenyl |
| K477 | methyl | hydrogen | 2-chlorophenyl |
| K478 | methyl | hydrogen | 3-chlorophenyl |
| K479 | methyl | hydrogen | 4-chlorophenyl |
| K480 | methyl | hydrogen | 3,4-dichlorophenyl |
| K481 | methyl | hydrogen | 2-methoxyphenyl |
| K482 | methyl | hydrogen | 3-methoxyphenyl |
| K483 | methyl | hydrogen | 4-methoxyphenyl |
| K484 | ethyl | hydrogen | phenyl |
| K485 | ethyl | hydrogen | 2-fluorophenyl |
| K486 | ethyl | hydrogen | 3-fluorophenyl |
| K487 | ethyl | hydrogen | 4-fluorophenyl |
| K488 | ethyl | hydrogen | 3,4-difluorophenyl |
| K489 | ethyl | hydrogen | 2-chlorophenyl |
| K490 | ethyl | hydrogen | 3-chlorophenyl |
| K491 | ethyl | hydrogen | 4-chlorophenyl |
| K492 | ethyl | hydrogen | 3,4-dichlorophenyl |
| K493 | ethyl | hydrogen | 2-methoxyphenyl |
| K494 | ethyl | hydrogen | 3-methoxyphenyl |
| K495 | ethyl | hydrogen | 4-methoxyphenyl |

The compounds encompassed within the third aspect of Category V of the present disclosure can be prepared by the procedure outlined in Scheme IX and described in Example 10 herein below.

Scheme IX

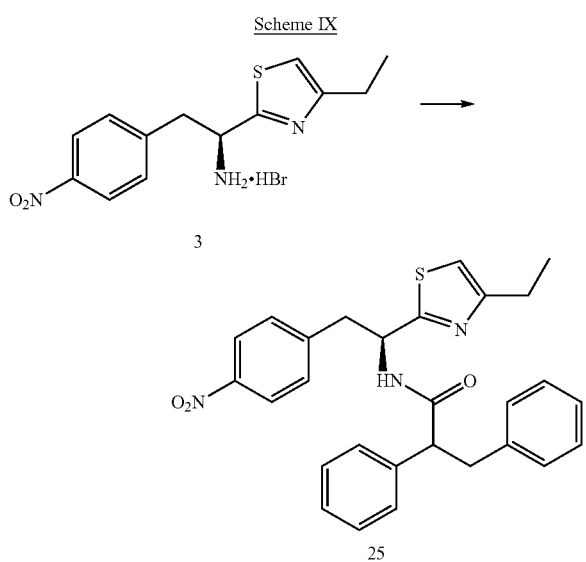

Reagents and conditions: (a) diphenylpropionic acid, EDCI, HOBt, TEA, DMF; 0° C. to rt, 18 hr.

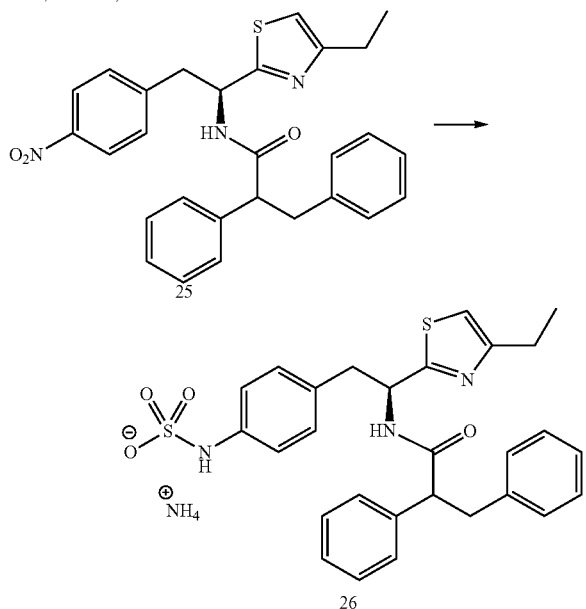

Reagents and conditions: (b) (i) H$_2$:Pd/C, MeOH; (ii) SO$_3$-pyridine, NH$_4$OH; rt, 18 hr.

EXAMPLE 10

(S)-4-(2-(2,3-Diphenylpropanamido)-2-(4-ethylthiazol-2-yl)ethyl)-phenylsulfamic acid (26)

Preparation of (S)—N-[1-(4-ethylthiazol-2-yl)-2-(4-nitrophenyl)ethyl]-2,3-diphenyl-propanamide (25): To a solution of 1-(S)-(4-ethylthiazol-2-yl)-2-(4-nitrophenyl)ethyl amine hydrobromide, 3, (0.95 g, 2.65 mmol), diphenylpropionic acid (0.60 g, 2.65 mmol) and 1-hydroxybenzotriazole (HOBt) (0.180 g, 1.33 mmol) in DMF (10 mL) at 0°, is added 1-(3-dimethylaminopropyl)-3-ethylcarbodiimide (EDCI) (0.502 g, 2.62 mmol) followed by triethylamine (1.1 mL, 7.95 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO$_3$, water and brine, and dried over Na$_2$SO$_4$. The solvent is removed in vacuo to afford 0.903 g (70% yield) of the desired product which is used without further purification.

Preparation of (S)-4-(2-(2,3-diphenylpropanamido)-2-(4-ethylthiazol-2-yl)ethyl)phenylsulfamic acid (26) (S)—N-[1-(4-ethylthiazol-2-yl)-2-(4-nitrophenyl)ethyl]-2,3-diphenyl-propanamide, 25, (0.903 g) is dissolved in MeOH (10 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (30 mL) and treated with SO$_3$-pyridine (0.621 g). The reaction is stirred at room temperature for 5 minutes after which a 7% solution of NH$_4$OH is added. The mixture is then concentrated and the resulting residue is purified by reverse phase chromatography to afford 0.415 g of the desired product as the ammonium salt. $^1$H NMR (CD$_3$OD) δ 8.59-8.52 (m, 1H), 7.37-7.04 (m, 9H), 6.97-6.93 (m, 1H), 6.89-6.85 (m, 2H), 5.36-5.32 (m, 1H), 3.91-3.83 (m, 1H), 3.29 (1H, A of ABX, obscured by solvent), 3.15 (1H, B of ABX, J=5.4, 33.8 Hz), 2.99-2.88 (m, 2H), 2.81-2.69 (m, 2H), 1.32-1.25 (m, 3H).

The following procedure illustrates an example of the procedure which can be used to provide different R$^{5a}$ units according to the present disclosure. Using the procedure outlined in Scheme X and described in Example 11, one can achieve the R$^{5a}$ units encompassed by the present disclosure.

Scheme X

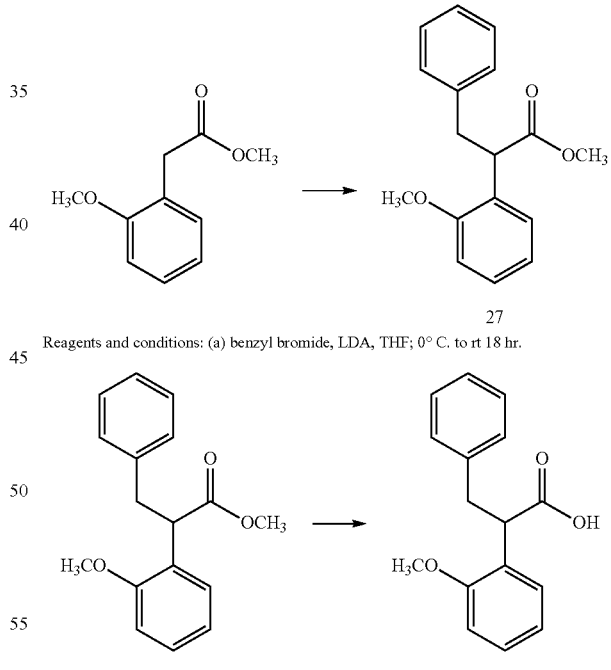

Reagents and conditions: (a) benzyl bromide, LDA, THF; 0° C. to rt 18 hr.

Reagents and conditions: (b) NaOH, THF/MeOH; rt, 18 hr.

EXAMPLE 11

2-(2-Methoxyphenyl)-3-phenylpropanoic acid (28)

Preparation of methyl 2-(2-methoxyphenyl)-3-phenylpropanoate (27): A 500 mL round-bottom flask is charged with methyl 2-(2-methoxyphenyl)acetate (8.496 g, 47 mmol, 1 eq) and THF (200 mL). The homogeneous mixture is cooled to 0° C. in an ice bath. Lithium diisopropyl amide (23.5 mL of a 2.0M solution in heptane/THF) is added, maintaining a temperature less than 3° C. The reaction is stirred 45 minutes at this reduced temperature. Benzyl bromide (5.6 mL, 47 mmol, 1 eq) is added dropwise. The reaction is allowed to gradually warm to room temperature and is stirred for 18 hours. The reaction is quenched with 1N HCl and extracted 3 times with equal portions of EtOAc. The combined extracts are washed with H$_2$O and brine, dried over Na$_2$SO$_4$, filtered, and concentrated. The residue is purified over silica to afford 4.433 g (35%) of the desired compound. ESI+ MS 293 (M+Na).

Preparation of 2-(2-methoxyphenyl)-3-phenylpropanoic acid (28): Methyl 2-(2-methoxyphenyl)-3-phenylpropanoate (4.433 g, 16 mmol, 1 eq) is dissolved in 100 mL of a 1:1 (v:v) mixture of THF and methanol. Sodium hydroxide (3.28 g, 82 mmol, 5 eq) is added and the reaction mixture is stirred 18 hours at room temperature. The reaction is then poured into H$_2$O and the pH is adjusted to 2 via addition of 1N HCl. A white precipitate forms which is removed by filtration. The resulting solution is extracted with 3 portion of diethyl ether. The extracts are pooled, washed with H$_2$O and brine, dried over Na$_2$SO$_4$, filtered, and concentrated in vacuo. The resulting residue is purified over silica to afford 2.107 g (51%) of the desired compound. ESI– MS 255 (M–1), 211 (M–CO$_2$H).

Intermediate 28 can be carried forward according to the procedure outlined in Scheme IX and described in Example 10 to produce the following compound according to the third aspect of Category V.

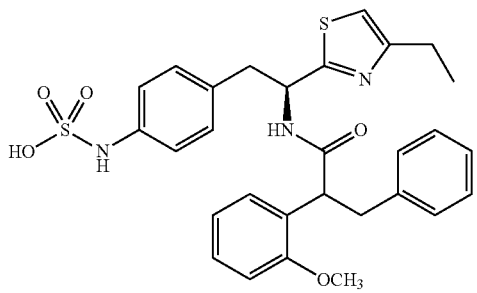 [SMILES: CCc1csc([C@H](Cc2ccc(NS(=O)(=O)O)cc2)NC(=O)C(Cc2ccccc2)c2ccccc2OC)n1]

(S)-4-{2-(4-Ethylthiazol-2-yl)-2-[2-(2-methoxyphenyl)-3-phenylpropanamido]-ethyl}phenylsulfamic acid: $^1$H NMR (CD$_3$OD) δ 7.32-7.12 (m, 7H), 7.05-7.02 (m, 1H), 6.99-6.83 (m, 4H), 6.80-6.75 (m, 2H), 5.35-5.31 (m, 1H), 4.31-4.26 (m, 1H), 3.75 (s, 3H), 3.20-2.90 (m, 4H), 2.79-2.74 (m, 2H), 1.32-1.25 (m, 3H).

The following are further non-limiting examples of compounds according to the third aspect of Category I of the present disclosure.

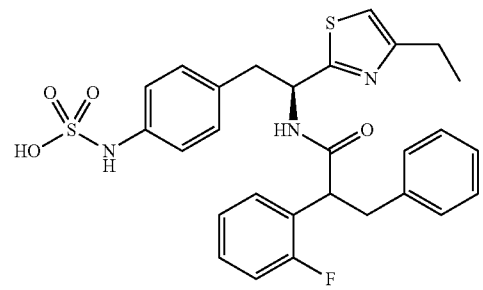 [SMILES: CCc1csc([C@H](Cc2ccc(NS(=O)(=O)O)cc2)NC(=O)C(Cc2ccccc2)c2ccccc2F)n1]

(S)-4-{2-(4-Ethylthiazol-2-yl)-2-[2-(3-fluorophenyl)-3-phenylpropanamido]-ethyl}phenylsulfamic acid: $^1$H NMR (CD$_3$OD) δ 7.33-6.87 (m, 14H), 5.39-5.25 (m, 1H), 3.95-3.83 (m, 1H), 3.31-3.10 (m, 1H), 3.05-2.88 (m, 2H), 2.80-2.70 (m, 2H), 1.32-1.23 (m, 3H). $^{19}$F NMR ☐ 47.59.

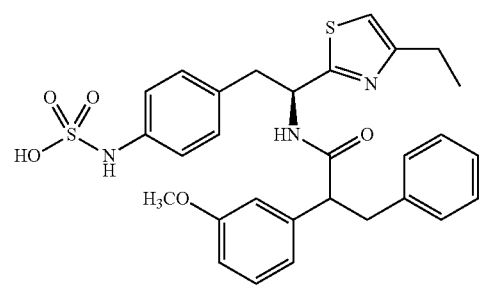 [SMILES: CCc1csc([C@H](Cc2ccc(NS(=O)(=O)O)cc2)NC(=O)C(Cc2ccccc2)c2cccc(OC)c2)n1]

(S)-4-{2-(4-Ethylthiazol-2-yl)-2-[2-(3-methoxyphenyl)-3-phenylpropanamido]-ethyl}phenylsulfamic acid: $^1$H NMR (CD$_3$OD) δ 7.85 (d, 1H, J=8.4 Hz), 7.25-7.20 (m, 1H), 7.11-7.02 (m, 4H), 7.01 (s, 1H), 6.90-6.79 (m, 2H), 5.45-5.40 (m, 1H), 4.09 (s, 2H), 3.79 (s, 3H), 3.12-3.08 (m, 2H), 1.10 (s, 9H).

The fourth aspect of Category V of the present disclosure relates to compounds having the formula:

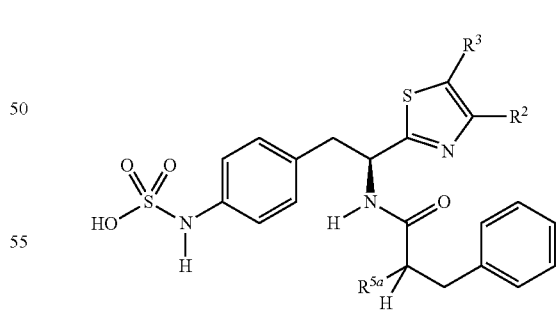

wherein the linking unit L comprises a phenyl unit, said linking group having the formula:

—C(O)[(CR$^{5a}$H)][(CR$^{6a}$H]—

R$^1$ is hydrogen, R$^{6a}$ is phenyl, R$^{5a}$ is substituted or unsubstituted heteroaryl and the units R$^2$, R$^3$, and R$^{5a}$ are further exemplified herein below in Table XII.

TABLE XII

| No. | R² | R³ | R⁵ᵃ |
|---|---|---|---|
| L496 | methyl | hydrogen | 3-methyl-1,2,4-oxadiazol-5-yl |
| L497 | methyl | hydrogen | thiophen-2-yl |
| L498 | methyl | hydrogen | thiazol-2-yl |
| L499 | methyl | hydrogen | oxazol-2-yl |
| L500 | methyl | hydrogen | isoxazol-3-yl |
| L501 | ethyl | hydrogen | 3-methyl-1,2,4-oxadiazol-5-yl |
| L502 | ethyl | hydrogen | thiophen-2-yl |
| L503 | ethyl | hydrogen | thiazol-2-yl |
| L504 | ethyl | hydrogen | oxazol-2-yl |
| L505 | ethyl | hydrogen | isoxazol-3-yl |
| L506 | ethyl | methyl | 3-methyl-1,2,4-oxadiazol-5-yl |
| L507 | ethyl | methyl | thiophen-2-yl |
| L508 | ethyl | methyl | thiazol-2-yl |
| L509 | ethyl | methyl | oxazol-2-yl |
| L510 | ethyl | methyl | isoxazol-3-yl |
| L511 | thiophen-2-yl | hydrogen | 3-methyl-1,2,4-oxadiazol-5-yl |
| L512 | thiophen-2-yl | hydrogen | thiophen-2-yl |
| L513 | thiophen-2-yl | hydrogen | thiazol-2-yl |
| L514 | thiophen-2-yl | hydrogen | oxazol-2-yl |
| L515 | thiophen-2-yl | hydrogen | isoxazol-3-yl |
| L516 | isoxazol-3-yl | hydrogen | 3-methyl-1,2,4-oxadiazol-5-yl |
| L517 | isoxazol-3-yl | hydrogen | thiophen-2-yl |
| L518 | isoxazol-3-yl | hydrogen | thiazol-2-yl |
| L519 | isoxazol-3-yl | hydrogen | oxazol-2-yl |
| L520 | isoxazol-3-yl | hydrogen | isoxazol-3-yl |

The compounds encompassed within the fourth aspect of Category V of the present disclosure can be prepared by the procedure outlined in Scheme XI and described in Example 5 herein below.

Scheme XI

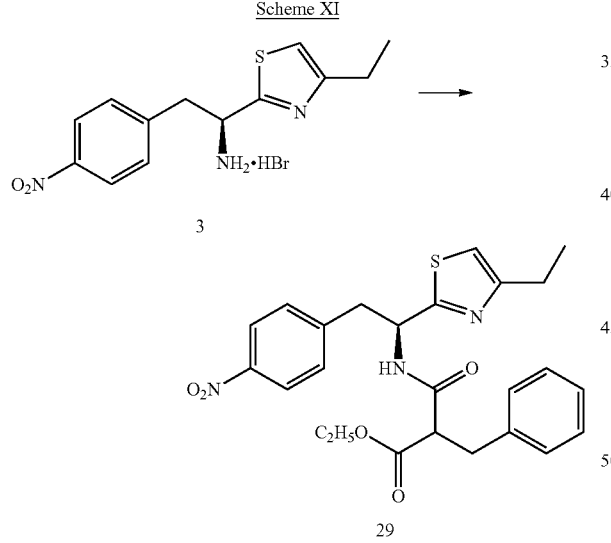

Reagents and conditions: (a) 2-benzyl-3-ethoxy-3-oxopropanoic acid, EDCI, HOBt, DIPEA, DMF; rt, 18 hr.

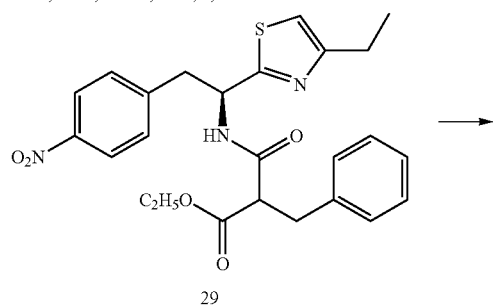

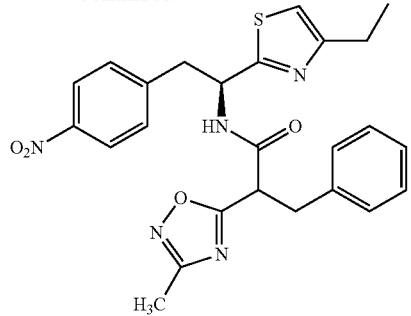

Reagents and conditions: (b) CH₃C(=NOH)NH₂, K₂CO₃, toluene; reflux, 18 hr

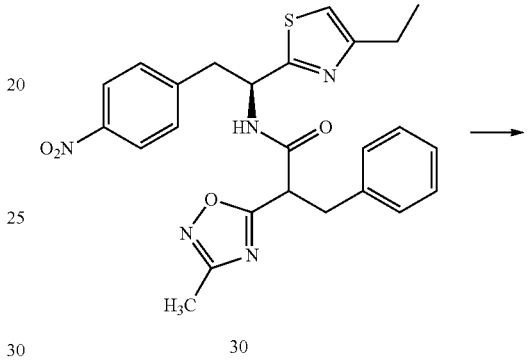

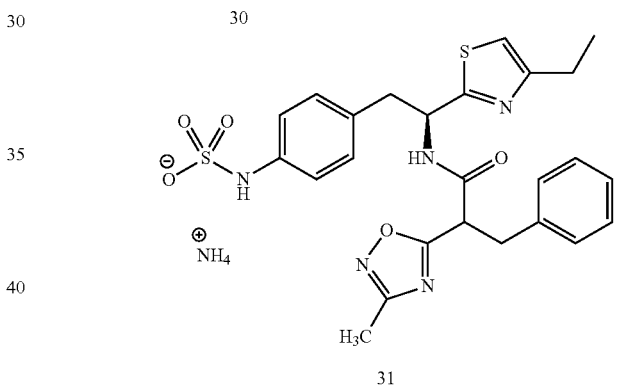

Reagents and conditions: (c) (i) tin (II) chloride, EtOH; (ii) SO₃-pyridine, NH₄OH; rt, 18 hr.

EXAMPLE 12

4-{(S)-2-(4-Ethylthiazol-2-yl)-2-[2-(3-methyl-1,2,4-oxadiazol-5-yl)-3-phenylpropanamido]ethyl}phenylsulfamic acid (31)

Preparation of ethyl-2-benzyl-3-[(S)-1-(4-ethylthiazol-2-yl)-2-(4-nitrophenyl)-ethylamino]-3-oxopropanoate (29): To a solution of 1-(S)-(4-ethylthiazol-2-yl)-2-(4-nitrophenyl)ethyl amine hydrobromide, 3, (0.406 g, 1.13 mmol), 2-benzyl-3-ethoxy-3-oxopropanoic acid (0.277 g) and 1-hydroxybenzotriazole (HOBt) (0.191 g, 1.41 mmol) in DMF (10 mL) at 0°, is added 1-(3-dimethylaminopropyl)-3-ethylcarbodiimide (EDCI) (0.240 g, 1.25 mmol) followed by diisopropylethylamine (DIPEA) (0.306 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na$_2$SO$_4$. The solvent is removed in vacuo to afford 0.169 g (31% yield) of the desired product which is used without further purification.

Preparation of N—[(S)-1-(4-ethylthiazol-2-yl)-2-(4-nitrophenyl)ethyl]-2-(3-methyl-1,2,4-oxadiazol-5-yl)-3-phenylpropanamide (30): Ethyl 2-benzyl-3-((S)-1-(4-ethylthiazol-2-yl)-2-(4-nitrophenyl)ethylamino)-3-oxopropanoate is dissolved in toluene (5 mL) and heated to reflux. Potassium carbonate (80 mg) and acetamide oxime (43 mg) are added. and treated with 80 mg potassium carbonate and 43 mg acetamide oxime at reflux. The reaction mixture is cooled to room temperature, filtered and concentrated. The residue is chromatographed over silica to afford 0.221 g (94%) of the desired product as a yellow oil.

Preparation of 4-{(S)-2-(4-ethylthiazol-2-yl)-2-[(2-(3-methyl-1,2,4-oxadiazol-5-yl)-3-phenylpropanamido]ethyl}phenylsulfamic acid (31): N—[(S)-1-(4-ethylthiazol-2-yl)-2-(4 nitrophenyl)ethyl]-2-(3-methyl-1,2,4-oxadiazol-5-yl)-3-phenylpropanamide, 30, (0.221 g) and tin (II) chloride (507 mg, 2.2 mmol) are dissolved in EtOH (25 mL) and the solution is brought to reflux 4 hours. The solvent is removed in vacuo and the resulting residue is dissolved in EtOAc. A saturated solution of NaHCO$_3$ (50 mL) is added and the solution is stirred 1 hour. The organic layer is separated and the aqueous layer extracted twice with EtOAc. The combined organic layers are dried (Na$_2$SO$_4$), filtered and concentrated to a residue which is dissolved in pyridine (0.143 g) and treated with SO$_3$-pyridine (0.143 g). The reaction is stirred at room temperature for 5 minutes after which a 7% solution of NH$_4$OH is added. The mixture is then concentrated and the resulting residue is purified by reverse phase chromatography to afford 0.071 g of the desired product as the ammonium salt. $^1$H NMR (CD$_3$OD): δ 7.29-6.87 (m, 10H), 5.38-5.30 (m, 1H), 4.37-4.30 (m, 1H), 3.42-2.74 (m, 6H), 2.38-2.33 (m, 3H), 1.34-1.28 (m, 3H).

Category VI of the present disclosure relates to 2-(thiazol-2-yl) compounds having the formula:

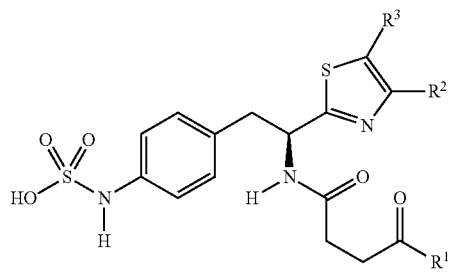

wherein R$^1$, R$^2$, and R$^3$ are further defined herein in Table XIII herein.

TABLE XIII

| No. | R$^2$ | R$^3$ | R$^1$ |
|---|---|---|---|
| M521 | ethyl | hydrogen | thiophen-2-yl |
| M522 | ethyl | hydrogen | thiazol-2-yl |
| M523 | ethyl | hydrogen | oxazol-2-yl |
| M524 | ethyl | hydrogen | isoxazol-3-yl |
| M525 | ethyl | hydrogen | imidazol-2-yl |
| M526 | ethyl | hydrogen | isoxazol-3-yl |
| M527 | ethyl | hydrogen | oxazol-4-yl |
| M528 | ethyl | hydrogen | isoxazol-4-yl |
| M529 | ethyl | hydrogen | thiophen-4-yl |
| M530 | ethyl | hydrogen | thiazol-4-yl |
| M531 | ethyl | methyl | methyl |

TABLE XIII-continued

| No. | R$^2$ | R$^3$ | R$^1$ |
|---|---|---|---|
| M532 | ethyl | methyl | ethyl |
| M533 | ethyl | methyl | propyl |
| M534 | ethyl | methyl | iso-propyl |
| M535 | ethyl | methyl | butyl |
| M536 | ethyl | methyl | phenyl |
| M537 | ethyl | methyl | benzyl |
| M538 | ethyl | methyl | 2-fluorophenyl |
| M539 | ethyl | methyl | 3-fluorophenyl |
| M540 | ethyl | methyl | 4-fluorophenyl |
| M541 | phenyl | hydrogen | methyl |
| M542 | phenyl | hydrogen | ethyl |
| M543 | phenyl | hydrogen | propyl |
| M544 | phenyl | hydrogen | iso-propyl |
| M545 | phenyl | hydrogen | butyl |
| M546 | phenyl | hydrogen | phenyl |
| M547 | phenyl | hydrogen | benzyl |
| M548 | phenyl | hydrogen | 2-fluorophenyl |
| M549 | phenyl | hydrogen | 3-fluorophenyl |
| M550 | phenyl | hydrogen | 4-fluorophenyl |
| M551 | thiophen-2-yl | hydrogen | methyl |
| M552 | thiophen-2-yl | hydrogen | ethyl |
| M553 | thiophen-2-yl | hydrogen | propyl |
| M554 | thiophen-2-yl | hydrogen | iso-propyl |
| M555 | thiophen-2-yl | hydrogen | butyl |
| M556 | thiophen-2-yl | hydrogen | phenyl |
| M557 | thiophen-2-yl | hydrogen | benzyl |
| M558 | thiophen-2-yl | hydrogen | 2-fluorophenyl |
| M559 | thiophen-2-yl | hydrogen | 3-fluorophenyl |
| M560 | thiophen-2-yl | hydrogen | 4-fluorophenyl |

The compounds encompassed within Category VI of the present disclosure can be prepared by the procedure outlined in Scheme XII and described in Example 13 below.

Scheme XII

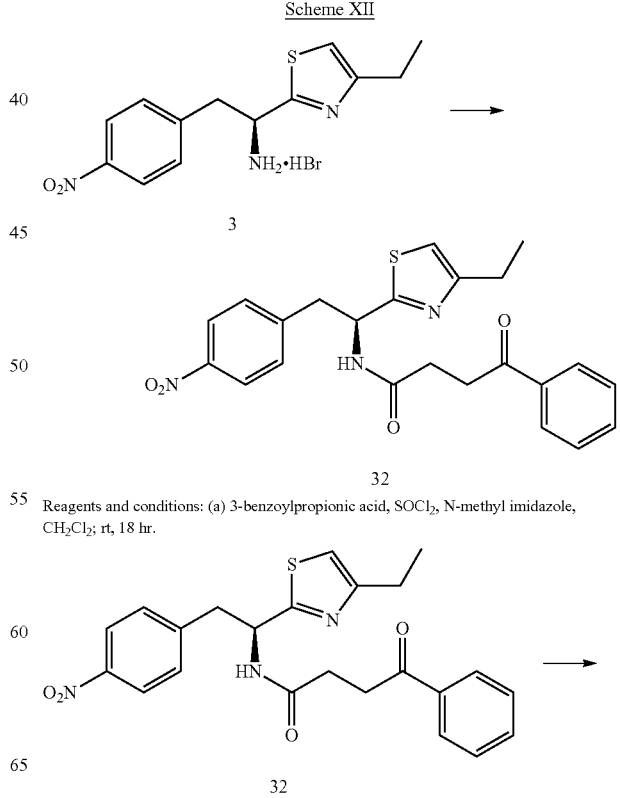

Reagents and conditions: (a) 3-benzoylpropionic acid, SOCl$_2$, N-methyl imidazole, CH$_2$Cl$_2$; rt, 18 hr.

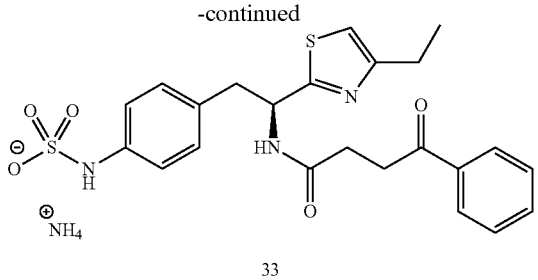

33

Reagents and conditions: (b) (i) H₂:Pd/C, MeOH; (ii) SO₃-pyridine, NH₄OH.

EXAMPLE 13

(S)-4-[2-(4-Ethylthiazol-2-yl)-2-(4-oxo-4-phenylbutanamido)ethyl]-phenylsulfamic acid (33)

Preparation of (S)—N-[1-(4-ethylthiazol-2-yl)-2-(4-nitrophenyl)ethyl]-4-oxo-4-phenylbutanamide (32): 3-Benzoylpropionic acid (0.250 g) is dissolved in $CH_2Cl_2$ (5 mL), N-methyl imidazole (0.333 mL) is added and the resulting solution is cooled to 0° C. after which a solution of thionyl chloride (0.320 g) in $CH_2Cl_2$ (2 mL) is added dropwise. After 0.5 hours (S)-1-(4-ethylthiazol-2-yl)-2-(4-nitrophenyl)ethanamine, 3, (0.388 g) is added. The reaction is stirred for 18 hours at room temperature and then concentrated in vacuo. The resulting residue is dissolved in EtOAc and washed with 1N HCl and brine. The solution is dried over $Na_2SO_4$, filtered, and concentrated and the crude material purified over silica to afford 0.415 g of the desired product.

Preparation of (S)-4-[2-(4-ethylthiazol-2-yl)-2-(4-oxo-4-phenylbutanamido)-ethyl]phenylsulfamic acid (33): (S)—N-[1-(4-ethylthiazol-2-yl)-2-(4-nitrophenyl)ethyl]-2,3-diphenyl-propanamide, 32, (0.2 g) is dissolved in MeOH (15 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (5 mL) and treated with SO₃-pyridine (0.153 g). The reaction is stirred at room temperature for 5 minutes after which a 7% solution of NH₄OH is added. The mixture is then concentrated and the resulting residue is purified by reverse phase chromatography to afford 0.090 g of the desired product as the ammonium salt. ¹H NMR (CD₃OD) δ 8.68 (d, 1H, J=8.2 Hz), 8.00 (d, 2H, J=7.2 Hz), 7.80-7.50 (m, 3H), 7.12 (s, 4H), 7.03 (s, 1H), 5.46-5.38 (m, 1H), 3.29-3.14 (m, 2H), 3.06-2.99 (m, 2H), 2.83 (q, 2H, J=7.5 Hz), 2.69-2.54 (m, 2H), 1.33 (t, 3H, J=7.5 Hz).

The following are non-limiting examples of compounds encompassed within Category II of the present disclosure. The intermediate nitro compounds of the following can be prepared by coupling the appropriate 4-oxo-carboxylic acid with intermediate 3 under the conditions described herein above for the formation of intermediate 4 of scheme I.

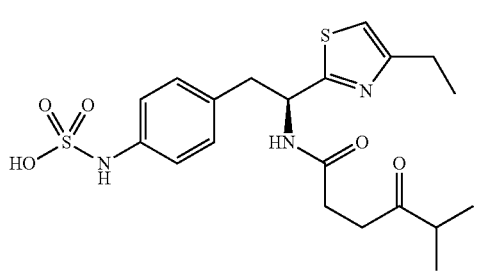 [SMILES: CCc1csc([C@H](Cc2ccc(NS(=O)(=O)O)cc2)NC(=O)CCC(=O)C(C)C)n1]

(S)-4-(2-(4-Ethylthiazol-2-yl)-2-(5-methyl-4-oxohexanamido)ethyl)phenylsulfamic acid: ¹H NMR (CD₃OD) δ 8.59 (d, 1H, J=8.1 Hz), 7.14 (s, 4H), 7.08 (t, 1H, J=13.0 Hz), 5.40-5.35 (m, 1H), 3.37-3.27 (m, 2H), 3.04-2.97 (m, 1H), 2.83-2.61 (m, 4H), 2.54-2.36 (m, 3H), 1.33 (t, 2H, J=7.3 Hz), 1.09 (dd, 6H, J=7.0, 2.2 Hz).

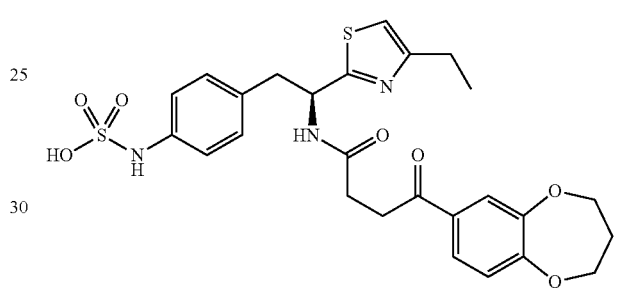

(S)-4-{2-[4-(3,4-Dihydro-2H-benzo[b][1,4]dioxepin-7-yl)-4-oxobutanamido]-2-(4-ethylthiazol-2-yl)ethyl}phenylsulfamic acid: ¹H NMR (CD₃OD) δ 8.64 (d, 1H, J=8.4 Hz), ☐7.60☐☐d, 2H, J=10.6 Hz), 7.11 (s, 3H), 7.04 (d, 2H, J=5.5 Hz), 5.42-5.40 (m, 1H), 4.30-4.22 (m, 4H), 3.20-2.98 (m, 4H), 2.82 (q, 2H, J=7.3 Hz), 2.67-2.48 (m, 2H), 2.23 (t, 2H, J=5.5 Hz), 1.32 (t, 3H, J=7.3 Hz).

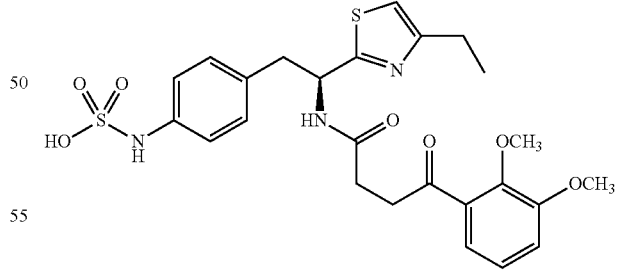

(S)-4-{2-[4-(2,3-Dimethoxyphenyl)-4-oxobutanamido]-2-(4-ethylthiazol-2-yl)ethyl}phenylsulfamic acid: ¹H NMR (CD₃OD), δ 8.64 (d, 1H, J=8.1 Hz), 7.21-7.11 (m, 7H), 7.02 (s, 1H), 5.42 (q, 1H, J=5.9 Hz), 3.90 (d, 3H, J=3.3 Hz), 3.88 (d, 3H, J=2.9 Hz), 3.22-3.18 (m, 2H), 3.07-2.99 (m, 2H), 2.83 (q, 2H, J=7.3 Hz), 2.63-2.54 (m, 2H), 1.34 (t, 3H, J=7.69 Hz).

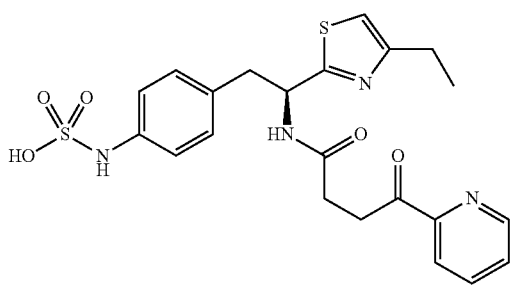 [SMILES: CCc1csc([C@H](Cc2ccc(NS(=O)(=O)O)cc2)NC(=O)CCC(=O)c2ccccn2)n1]

(S)-4-{2-(4-Ethylthiazol-2-yl)-2-[4-oxo-4-(pyridin-2-yl)butanamido]ethyl}-phenylsulfamic acid: $^1$H NMR (CD$_3$OD) δ 8.60 (d, 1H, J=12.8 Hz), 7.91-7.81 (m, 2H), 7.48-7.44 (m, 1H), 7.22-7.21 (m, 1H), 6.99 (s, 3H), 6.91 (s, 1H), 5.30 (q, 1H, J=5.4 Hz), 3.36 (q, 2H, J=7.0 Hz), 3.21-3.15 (m, 1H), 2.91-2.85 (m, 1H), 2.74 (q, 2H, J=10.4 Hz), 2.57-2.50 (m, 2H), 1.20 (t, 3H, J=7.5 Hz).

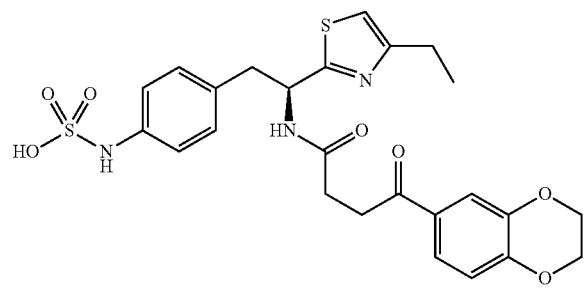 [SMILES: CCc1csc([C@H](Cc2ccc(NS(=O)(=O)O)cc2)NC(=O)CCC(=O)c2ccc3c(c2)OCCO3)n1]

(S)-4-{2-[4-(2,3-dihydrobenzo[b][1,4]dioxin-6-yl)-4-oxobutanamido]-2-(4-ethylthiazol-2-yl)ethyl}phenylsulfamic acid: $^1$H NMR (CD$_3$OD) δ 7.52-7.47 (m, 2H), 7.11 (s, 4H), 7.03 (s, 1H), 6.95 (d, 1H, J=8.4 Hz), 5.41 (q, 1H, J=3.7 Hz), 4.31 (d, 4H, J=5.5 Hz), 3.24-3.12 (m, 2H), 3.06-2.98 (m, 2H), 2.83 (q, 2H, J=7.3 Hz), 2.62-2.53 (m, 2H), 1.33 (t, 3H, J=7.3 Hz).

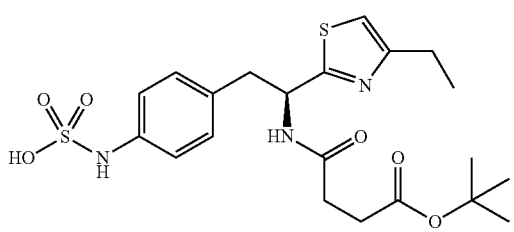 [SMILES: CCc1csc([C@H](Cc2ccc(NS(=O)(=O)O)cc2)NC(=O)CCC(=O)OC(C)(C)C)n1]

(S)-4-[2-(4-tert-butoxy-4-oxobutanamido)-2-(4-ethylthiazol-2-yl)ethyl]phenylsulfamic acid: $^1$H NMR (CD$_3$OD), δ 7.10 (s 4H), 7.02 (s, 1H), 5.41 (q, 1H, J=3.7 Hz), 3.30-3.25 (m, 1H), 3.06-2.99 (m, 1H), 2.83 (q, 2H, J=7.3 Hz), 2.52-2.40 (m, 4H), 1.42 (s, 9H), 1.33 (t, 3H, J=7.3 Hz).

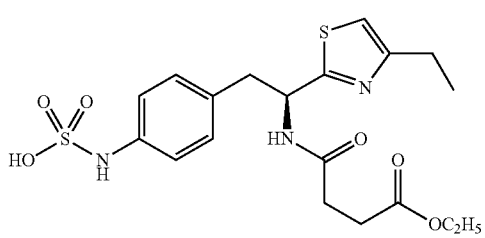 [SMILES: CCOC(=O)CCC(=O)N[C@@H](Cc1ccc(NS(=O)(=O)O)cc1)c1nc(CC)cs1]

(S)-4-[2-(4-ethoxy-4-oxobutanamido)-2-(4-ethylthiazol-2-yl)ethyl]phenylsulfamic acid: $^1$H NMR (CD$_3$OD) δ 8.62 (d, 1H, J=8.4 Hz), 7.10 (s, 4H), 7.02 (s, 1H), 5.40 (q, 1H, 3.7 Hz), 4.15 (q, 2H, J=7.3 Hz), 3.28-3.25 (m, 1H), 3.05-3.02 (m, 1H), 2.82 (q, 2H, J=4.4 Hz), 2.54-2.48 (m, 2H), 1.33 (t, 3H, J=7.3 Hz), 1.24 (t, 3H, J=7.0 Hz).

The first aspect of Category VII of the present disclosure relates to 2-(thiazol-2-yl) compounds having the formula:

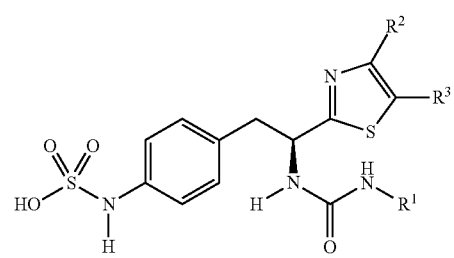

wherein non-limiting examples of R$^1$, R$^2$, and R$^3$ are further described below in Table XIV.

TABLE XIV

| No. | R$^2$ | R$^3$ | R$^1$ |
| --- | --- | --- | --- |
| N561 | methyl | hydrogen | phenyl |
| N562 | methyl | hydrogen | benzyl |
| N563 | methyl | hydrogen | 2-fluorophenyl |
| N564 | methyl | hydrogen | 3-fluorophenyl |
| N565 | methyl | hydrogen | 4-fluorophenyl |
| N566 | methyl | hydrogen | 2-chlorophenyl |
| N567 | methyl | hydrogen | 3-chlorophenyl |
| N568 | methyl | hydrogen | 4-chlorophenyl |
| N569 | ethyl | hydrogen | phenyl |
| N570 | ethyl | hydrogen | benzyl |
| N571 | ethyl | hydrogen | 2-fluorophenyl |
| N572 | ethyl | hydrogen | 3-fluorophenyl |
| N573 | ethyl | hydrogen | 4-fluorophenyl |
| N574 | ethyl | hydrogen | 2-chlorophenyl |
| N575 | ethyl | hydrogen | 3-chlorophenyl |
| N576 | ethyl | hydrogen | 4-chlorophenyl |
| N577 | thiene-2-yl | hydrogen | phenyl |
| N578 | thiene-2-yl | hydrogen | benzyl |
| N579 | thiene-2-yl | hydrogen | 2-fluorophenyl |
| N580 | thiene-2-yl | hydrogen | 3-fluorophenyl |
| N581 | thiene-2-yl | hydrogen | 4-fluorophenyl |
| N582 | thiene-2-yl | hydrogen | 2-chlorophenyl |
| N583 | thiene-2-yl | hydrogen | 3-chlorophenyl |
| N584 | thiene-2-yl | hydrogen | 4-chlorophenyl |

The compounds encompassed within Category VII of the present disclosure can be prepared by the procedure outlined in Scheme XIII and described in Example 14 herein below.

Scheme XIII

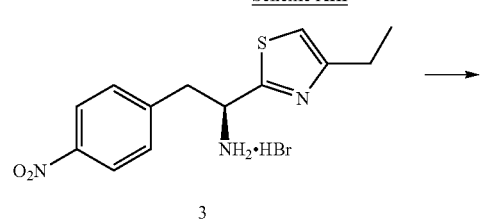

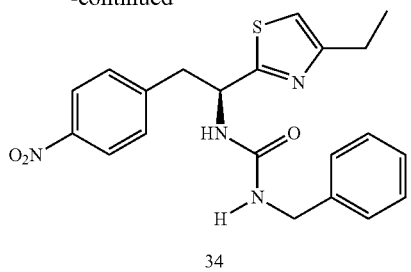

34

Reagents and conditions: (a) benzyl isocyanate, TEA, CH$_2$Cl$_2$; rt, 18 hr.

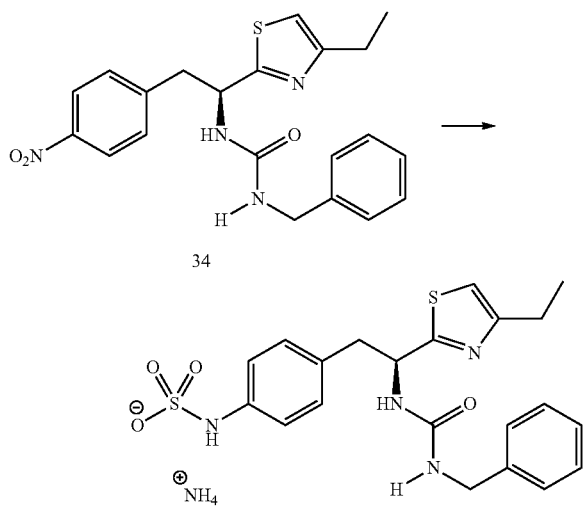

Reagents and conditions: (b) (i) H$_2$:Pd/C, MeOH; (ii) SO$_3$-pyridine, NH$_4$OH.

EXAMPLE 14

(S)-4-(2-(3-Benzylureido)-2-(4-ethylthiazol-2-yl)ethyl)phenylsulfamic acid (35)

Preparation of (S)-1-benzyl-3-[1-(4-ethylthiazol-2-yl)-2-(4-nitrophenyl)ethyl]urea (34): To a solution of 1-(S)-(4-ethylthiazol-2-yl)-2-(4-nitrophenyl)ethyl amine hydrobromide, 3, (0.360 g, 1 mmol) and Et$_3$N (0.42 mL, 3 mmol) in 10 mL CH$_2$Cl$_2$ is added benzyl isocyanate (0.12 mL, 1 mmol). The mixture is stirred at room temperature for 18 hours. The product is isolated by filtration to afford 0.425 g (96% yield) of the desired product which is used without further purification.

Preparation of (S)-4-(2-(3-benzylureido)-2-(4-ethylthiazol-2-yl)ethyl)phenylsulfamic acid (35): (S)-1-benzyl-3-[1-(4-ethylthiazol-2-yl)-2-(4-nitrophenyl)ethyl]urea, 34, (0.425 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO$_3$-pyridine (0.220 g). The reaction is stirred at room temperature for 5 minutes after which a 7% solution of NH$_4$OH is added. The mixture is then concentrated and the resulting residue is purified by reverse phase chromatography to afford 0.143 g of the desired product as the ammonium salt. $^1$H NMR (CD$_3$OD) δ 7.32-7.30 (m, 2H), 7.29-7.22 (m, 3H), 7.12-7.00 (m, 4H), 6.84 (d, 1H, J=8.1 Hz), 5.35-5.30 (m, 1H), 4.29 (s, 2H), 3.27-3.22 (m, 3H), 3.11-3.04 (m, 3H), 2.81 (q, 2H, J=10.2, 13.0 Hz), 1.31 (t, 3H, J=4.5 Hz).

The following is a non-limiting examples of compounds encompassed within the first aspect of Category VII of the present disclosure.

4-{[(S)-2-(2-Ethylthiazol-4-yl)-2-(3-(R)-methoxy-1-oxo-3-phenylpropan-2-yl)ureido]ethyl}phenylsulfamic acid: $^1$H NMR (CD$_3$OD) δ 7.36-7.26 (m, 3H), 7.19-7.17 (m, 2H), 7.10-7.06 (m, 2H), 6.90-6.86 (m, 3H), 5.12-5.06 (m, 1H), 4.60-4.55 (m, 1H), 3.69 (s, 3H) 3.12-2.98 (m, 6H), 1.44-1.38 (m, 3H).

The second aspect of Category VII of the present disclosure relates to 2-(thiazol-4-yl) compounds having the formula:

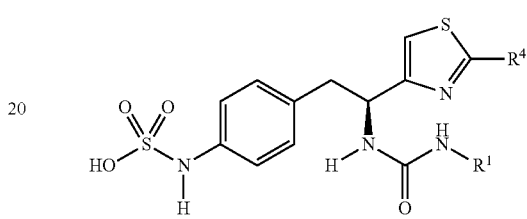

wherein non-limiting examples of R$^1$ and R$^4$ are further described below in Table XV.

TABLE XV

| No. | R$^1$ | R$^4$ |
| --- | --- | --- |
| O585 | Methyl | methyl |
| O586 | Ethyl | methyl |
| O587 | n-propyl | methyl |
| O588 | iso-propyl | methyl |
| O589 | Phenyl | methyl |
| O590 | Benzyl | methyl |
| O591 | 2-fluorophenyl | methyl |
| O592 | 2-chlorophenyl | methyl |
| O593 | thiophen-2-yl | methyl |
| O594 | thiazol-2-yl | methyl |
| O595 | oxazol-2-yl | methyl |
| O596 | isoxazol-3-yl | methyl |
| O597 | Methyl | ethyl |
| O598 | Ethyl | ethyl |
| O599 | n-propyl | ethyl |
| O600 | iso-propyl | ethyl |
| O601 | Phenyl | ethyl |
| O602 | Benzyl | ethyl |
| O603 | 2-fluorophenyl | ethyl |
| O604 | 2-chlorophenyl | ethyl |
| O605 | thiophen-2-yl | ethyl |
| O606 | thiazol-2-yl | ethyl |
| O607 | oxazol-2-yl | ethyl |
| O608 | isoxazol-3-yl | ethyl |
| O609 | Methyl | thiophen-2-yl |
| O610 | Ethyl | thiophen-2-yl |
| O611 | n-propyl | thiophen-2-yl |
| O612 | iso-propyl | thiophen-2-yl |
| O613 | Phenyl | thiophen-2-yl |
| O614 | Benzyl | thiophen-2-yl |
| O615 | 2-fluorophenyl | thiophen-2-yl |
| O616 | 2-chlorophenyl | thiophen-2-yl |
| O617 | thiophen-2-yl | thiophen-2-yl |
| O618 | thiazol-2-yl | thiophen-2-yl |
| O619 | oxazol-2-yl | thiophen-2-yl |
| O620 | isoxazol-3-yl | thiophen-2-yl |
| O621 | Methyl | thiazol-2-yl |
| O622 | Ethyl | thiazol-2-yl |
| O623 | n-propyl | thiazol-2-yl |
| O624 | iso-propyl | thiazol-2-yl |
| O625 | Phenyl | thiazol-2-yl |
| O626 | Benzyl | thiazol-2-yl |
| O627 | 2-fluorophenyl | thiazol-2-yl |

TABLE XV-continued

| No. | R¹ | R⁴ |
|---|---|---|
| O628 | 2-chlorophenyl | thiazol-2-yl |
| O629 | thiophen-2-yl | thiazol-2-yl |
| O630 | thiazol-2-yl | thiazol-2-yl |
| O631 | oxazol-2-yl | thiazol-2-yl |
| O632 | isoxazol-3-yl | thiazol-2-yl |
| O633 | Methyl | oxazol-2-yl |
| O634 | Ethyl | oxazol-2-yl |
| O635 | n-propyl | oxazol-2-yl |
| O636 | iso-propyl | oxazol-2-yl |
| O637 | Phenyl | oxazol-2-yl |
| O638 | Benzyl | oxazol-2-yl |
| O639 | 2-fluorophenyl | oxazol-2-yl |
| O640 | 2-chlorophenyl | oxazol-2-yl |
| O641 | thiophen-2-yl | oxazol-2-yl |
| O642 | thiazol-2-yl | oxazol-2-yl |
| O643 | oxazol-2-yl | oxazol-2-yl |
| O644 | isoxazol-3-yl | oxazol-2-yl |

The compounds encompassed within the second aspect of Category VII of the present disclosure can be prepared by the procedure outlined in Scheme XIV and described in Example 14 below.

Scheme XIV

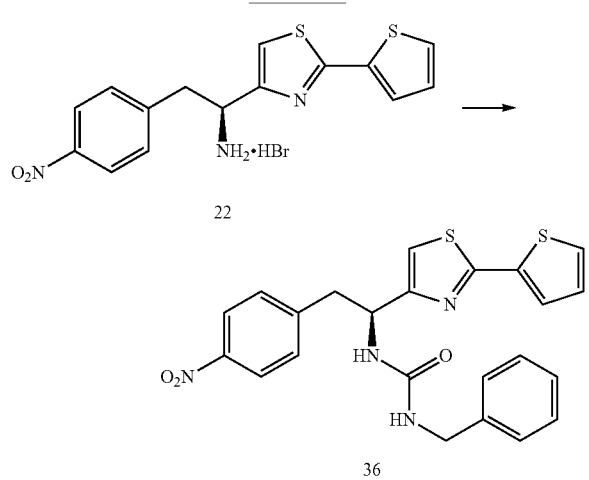

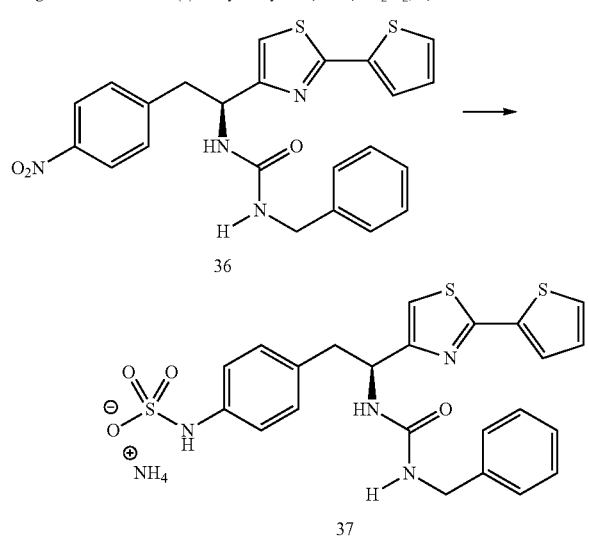

Reagents and conditions: (a) benzyl isocyanate, TEA, CH₂Cl₂; rt, 18 hr.

Reagents and conditions: (b) (i) H₂:Pd/C, MeOH; (ii) SO₃-pyridine, NH₄OH.

EXAMPLE 15

4-{(S)-2-(3-Benzylureido)-2-[2-(thiophen-2-yl)thiazol-4-yl]ethyl}-phenylsulfamic acid (37)

Preparation of 1-benzyl-3-{(S)-2-(4-nitrophenyl)-1-[2-(thiophen-2-yl)thiazol-4-yl]ethyl}urea (36): To a solution of (S)-2-(4-nitrophenyl)-1-[(2-thiophen-2-yl)thiazol-4-yl) ethan-amine hydrobromide salt, 8, and Et₃N (0.42 mL, 3 mmol) in 10 mL DCM is added benzyl isocyanate (0.12 mL, 1 mmol). The mixture is stirred at room temperature for 18 hours. The product is isolated by filtration to afford 0.445 g (96% yield) of the desired product which is used without further purification.

Preparation of 4-{(S)-2-(3-benzylureido)-2-[2-(thiophen-2-yl)thiazol-4-yl]ethyl}phenylsulfamic acid (37): 1-Benzyl-3-{(S)-2-(4-nitrophenyl)-1-[2-(thiophen-2-yl)thiazol-4-yl] ethyl}urea, 36, (0.445 g) is dissolved in MeOH (10 mL) and CH₂Cl₂ (5 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.110 g). The reaction is stirred at room temperature for 5 minutes after which a 7% solution of NH₄OH is added. The mixture is then concentrated and the resulting residue is purified by reverse phase chromatography to afford 0.080 g of the desired product as the ammonium salt. ¹H NMR (CD₃OD) δ 7.61 (d, 1H, J=2.1 Hz), 7.58 (d, 1H, J=6 Hz), 7.33-7.22 (m, 4H), 7.17-7.14 (m, 1H), 7.09-6.94 (m, 6H), 5.16 (t, 1H, J=6.6 Hz), 4.13 (s, 2H), 3.14-3.11 (m, 2H).

Category VIII of the present disclosure relates to 2-(thiazol-4-yl) compounds having the formula:

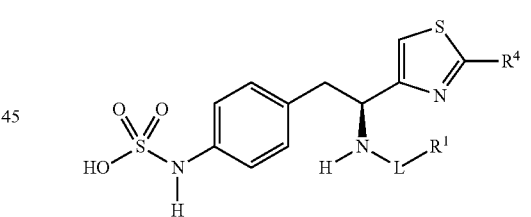

wherein R¹, R⁴, and L are further defined herein in Table XVI herein below.

TABLE XVI

| No. | R⁴ | L | R¹ |
|---|---|---|---|
| P645 | methyl | —SO₂— | methyl |
| P646 | ethyl | —SO₂— | methyl |
| P647 | phenyl | —SO₂— | methyl |
| P648 | thiophen-2-yl | —SO₂— | methyl |
| P649 | methyl | —SO₂— | trifluoromethyl |
| P650 | ethyl | —SO₂— | trifluoromethyl |
| P651 | phenyl | —SO₂— | trifluoromethyl |
| P652 | thiophen-2-yl | —SO₂— | trifluoromethyl |
| P653 | methyl | —SO₂— | ethyl |
| P654 | ethyl | —SO₂— | ethyl |
| P655 | phenyl | —SO₂— | ethyl |
| P656 | thiophen-2-yl | —SO₂— | ethyl |

TABLE XVI-continued

| No. | R⁴ | L | R¹ |
|---|---|---|---|
| P657 | methyl | —SO₂— | 2,2,2-trifluoroethyl |
| P658 | ethyl | —SO₂— | 2,2,2-trifluoroethyl |
| P659 | phenyl | —SO₂— | 2,2,2-trifluoroethyl |
| P660 | thiophen-2-yl | —SO₂— | 2,2,2-trifluoroethyl |
| P661 | methyl | —SO₂— | phenyl |
| P662 | ethyl | —SO₂— | phenyl |
| P663 | phenyl | —SO₂— | phenyl |
| P664 | thiophen-2-yl | —SO₂— | phenyl |
| P665 | methyl | —SO₂— | 4-fluorophenyl |
| P666 | ethyl | —SO₂— | 4-fluorophenyl |
| P667 | phenyl | —SO₂— | 4-fluorophenyl |
| P668 | thiophen-2-yl | —SO₂— | 4-fluorophenyl |
| P669 | methyl | —SO₂— | 3,4-dihydro-2H-benzo[b][1,4]oxazin-7-yl |
| P670 | ethyl | —SO₂— | 3,4-dihydro-2H-benzo[b][1,4]oxazin-7-yl |
| P671 | phenyl | —SO₂— | 3,4-dihydro-2H-benzo[b][1,4]oxazin-7-yl |
| P672 | thiophen-2-yl | —SO₂— | 3,4-dihydro-2H-benzo[b][1,4]oxazin-7-yl |
| P673 | methyl | —SO₂— | 1-methyl-1H-imidazol-4-yl |
| P674 | ethyl | —SO₂— | 1-methyl-1H-imidazol-4-yl |
| P675 | phenyl | —SO₂— | 1-methyl-1H-imidazol-4-yl |
| P676 | thiophen-2-yl | —SO₂— | 1-methyl-1H-imidazol-4-yl |
| P678 | methyl | —SO₂— | 4-acetamidophenyl |
| P679 | ethyl | —SO₂— | 4-acetamidophenyl |
| P680 | phenyl | —SO₂— | 4-acetamidophenyl |
| P681 | thiophen-2-yl | —SO₂— | 4-acetamidophenyl |
| P682 | methyl | —SO₂CH₂— | phenyl |
| P683 | ethyl | —SO₂CH₂— | phenyl |
| P684 | phenyl | —SO₂CH₂— | phenyl |
| P685 | thiophen-2-yl | —SO₂CH₂— | phenyl |
| P686 | methyl | —SO₂CH₂— | (4-methylcarboxyphenyl)methyl |
| P687 | ethyl | —SO₂CH₂— | (4-methylcarboxyphenyl)methyl |
| P688 | phenyl | —SO₂CH₂— | (4-methylcarboxyphenyl)methyl |
| P689 | thiophen-2-yl | —SO₂CH₂— | (4-methylcarboxyphenyl)methyl |
| P690 | methyl | —SO₂CH₂— | (2-methylthiazol-4-yl)methyl |
| P691 | ethyl | —SO₂CH₂— | (2-methylthiazol-4-yl)methyl |
| P692 | phenyl | —SO₂CH₂— | (2-methylthiazol-4-yl)methyl |
| P693 | thiophen-2-yl | —SO₂CH₂— | (2-methylthiazol-4-yl)methyl |
| P694 | methyl | —SO₂CH₂CH₂— | phenyl |
| P695 | ethyl | —SO₂CH₂CH₂— | phenyl |
| P696 | phenyl | —SO₂CH₂CH₂— | phenyl |
| P697 | thiophen-2-yl | —SO₂CH₂CH₂— | phenyl |

The compounds encompassed within Category VIII of the present disclosure can be prepared by the procedure outlined in Scheme XV and described in Example 16 herein below.

Scheme XV

22

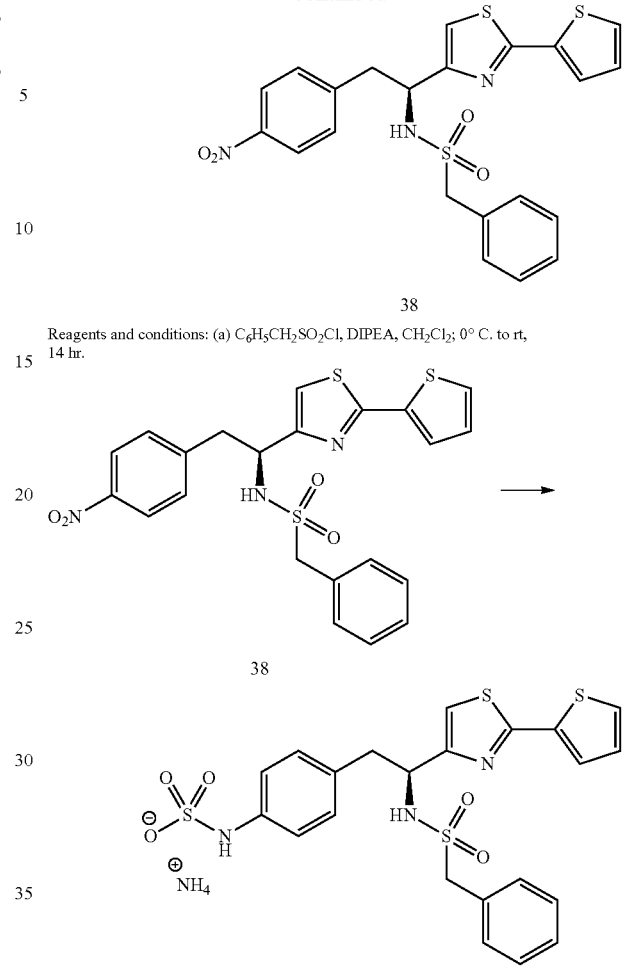

38

Reagents and conditions: (a) C₆H₅CH₂SO₂Cl, DIPEA, CH₂Cl₂; 0° C. to rt, 14 hr.

38

39

Reagents and conditions: (b) (i) H₂:Pd/C, MeOH; (ii) SO₃-pyridine, NH₄OH.

EXAMPLE 16

{4-(S)-[2-Phenylmethanesulfonylamino-2-(2-thiophen-2-ylthiazol-4-yl)ethyl]phenyl}sulfamic acid (39)

Preparation of (S)—N-{2-(4-nitrophenyl)-1-[2-(thiophen-2-yl)thiazol-4-yl]ethyl}-1-phenylmethanesulfonamide (38): To a suspension of 2-(4-nitrophenyl)-1-(2-thiophene2-ylthiazol-4-yl)ethylamine, 8, (330 mg, 0.80 mmol) in CH₂Cl₂ (6 mL) at 0° C. is added diisopropylethylamine (0.30 mL, 1.6 mmol) followed by phenylmethanesulfonyl chloride (167 mg, 0.88 mmol). The reaction mixture is stirred at room temperature for 14 hours. The mixture is diluted with CH₂Cl₂ and washed with sat. NaHCO₃ followed by brine, dried (Na₂SO₄), filtered and concentrated in vacuo. The resulting residue is purified over silica to afford 210 mg of the desired product as a white solid.

Preparation of {4-(S)-[2-phenylmethanesulfonylamino-2-(2-thiophen-2-ylthiazol-4-yl)ethyl]phenyl}sulfamic acid (39): (S)—N-{2-(4-nitrophenyl)-1-[2-(thiophen-2-yl)thiazol-4-yl]ethyl}-1-phenylmethanesulfonamide, 38, (210 mg, 0.41 mmol) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (197 mg, 1.23 mmol). The reaction is stirred at room temperature for 5 minutes after which a 7% solution of NH₄OH is added. The mixture is then concentrated and the resulting residue is purified by reverse phase chromatography to afford 0.060 g of the desired product as the ammonium salt. ¹H NMR (300 MHz, MeOH-d₄) δ 7.52-7.63 (m, 6.70-7.28 (m, 11H), 4.75 (t, J=7.2 Hz, 1H), 3.95-4.09 (m, 2H), 3.20 (dd, J=13.5 and 7.8 Hz, 1H), 3.05 (dd, J=13.5 and 7.8 Hz, 1H). 1013770

Intermediates for use in Step (a) of Scheme XV can be conveniently prepared by the procedure outlined herein below in Scheme XVI and described in Example 17.

Scheme XVI

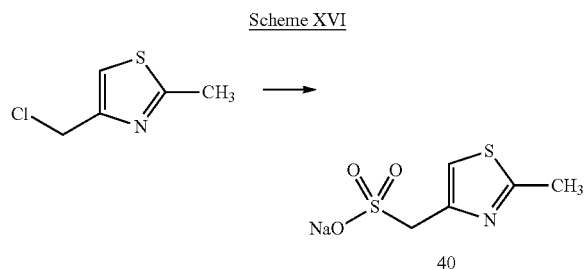

Reagents and conditions: (a) Na₂SO₃, H₂O; microwave @ 200° C., 20 min.

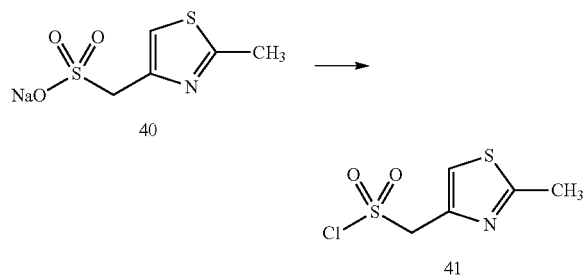

Reagents and conditions: (b) PCl₅, POCl₃; 50° C., 3 hrs.

EXAMPLE 17

(2-Methylthiazol-4-yl)methanesulfonyl chloride (41)

Preparation of sodium (2-methylthiazol-4-yl)methanesulfonate (40): 4-Chloromethyl-2-methylthiazole (250 mg, 1.69 mmol) is dissolved in H₂O (2 mL) and treated with sodium sulfite (224 mg, 1.78 mmol). The reaction mixture is subjected to microwave irradiation for 20 minutes at 200° C. The reaction mixture is diluted with H₂O (30 mL) and washed with EtOAc (2×25 mL). The aqueous layer is concentrated to afford 0.368 g of the desired product as a yellow solid. LC/MS ESI+ 194 (M+1, free acid).

Preparation of (2-methylthiazol-4-yl)methanesulfonyl chloride (41): Sodium (2-methylthiazol-4-yl)methanesulfonate, 40, (357 mg, 1.66 mmol) is dissolved in phosphorous oxychloride (6 mL) and is treated with phosphorous pentachloride (345 mg, 1.66 mmol). The reaction mixture is stirred at 50° C. for 3 hours, then allowed to cool to room temperature. The solvent is removed under reduced pressure and the residue is re-dissolved in CH₂Cl₂ (40 mL) and is washed with sat. NaHCO₃ and brine. The organic layer is dried over MgSO₄, filtered, and the solvent removed in vacuo to afford 0.095 g of the desired product as a brown oil. LC/MS ESI+ 211 (M+1). Intermediates are obtained in sufficient purity to be carried forward according to Scheme IX without the need for further purification.

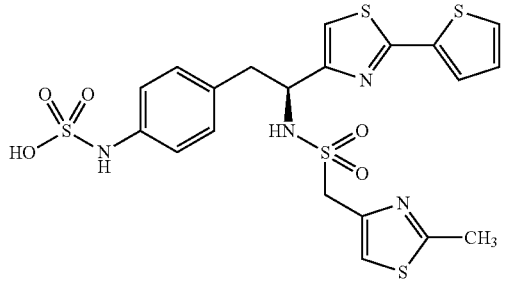 [SMILES: Cc1nc(CS(=O)(=O)N[C@@H](Cc2ccc(NS(=O)(=O)O)cc2)c2csc(-c3cccs3)n2)cs1]

4-{(S)-2-[(2-methylthiazol-4-yl)methylsulfonamido]-2-[2-(thiophen-2-yl)thiazol-4-yl]ethyl}phenylsulfamic acid: ¹H NMR (CD₃OD): δ 7.71-7.66 (m, 2H), 7.27-7.10 (m, 7H), 4.87 (t, 1H, J=7.3 Hz), 4.30-4.16 (q, 2H, J=13.2 Hz), 3.34-3.13 (m, 2H), 2.70 (s, 3H).

The following are non-limiting examples of compounds encompassed within Category VIII of the present disclosure.

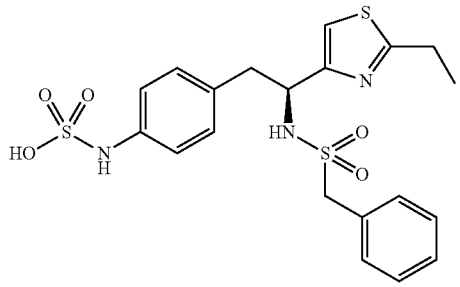 [SMILES: CCc1nc([C@H](Cc2ccc(NS(=O)(=O)O)cc2)NS(=O)(=O)Cc2ccccc2)cs1]

{4-(S)-[2-Phenylmethanesulfonylamino-2-(2-ethylthiazol-4-yl)ethyl]phenyl}-sulfamic acid: ¹H NMR (300 MHz, MeOH-d₄) δ 7.27-7.32 (m, 3H), 7.16-7.20 (m, 3H), 7.05-7.6 (m, 2H), 6.96 (d, J=8.4 Hz, 2H), 4.70 (t, J=9.0 Hz, 1H), 3.91-4.02 (m, 2H), 2.95-3.18 (m, 4H), 1.41 (t, J=7.5 Hz, 3H).

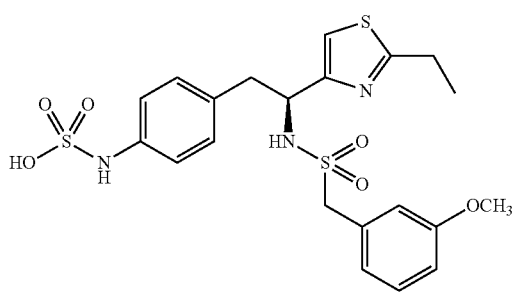 [SMILES: CCc1nc([C@H](Cc2ccc(NS(=O)(=O)O)cc2)NS(=O)(=O)Cc2cccc(OC)c2)cs1]

{4-(S)-[2-(3-Methoxyphenyl)methanesulfonylamino-2-(2-ethylthiazol-4-yl)ethyl]phenyl}sulfamic acid: ¹H NMR (300 MHz, MeOH-d₄) δ 7.20 t, J=8.1 Hz. 1H), 6.94-7.08 (m, 4H), 6.88-6.94 (m, 3H), 6.75-6.80 (m, 1H), 4.67 (t, J=7.2 Hz, 1H), 3.90-4.0 (m, 2H), 3.76 (s, 3H), 2.95-3.16 (m, 4H), 1.40 (t, J=7.5 HZ, 3H).

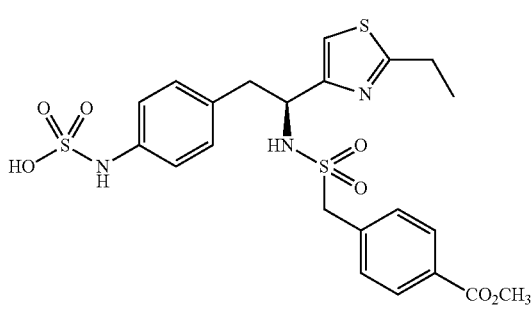 [SMILES: CCc1nc([C@H](Cc2ccc(NS(=O)(=O)O)cc2)NS(=O)(=O)Cc2ccc(C(=O)OC)cc2)cs1]

(S)-4-{[1-(2-Ethylthiazol-4-yl)-2-(4-sulfoaminophenyl) ethylsulfamoyl]methyl}-benzoic acid methyl ester: $^1$H NMR (300 MHz, MeOH-d$_4$) δ 7.90-7.94-(m, 2H), 7.27-7.30 (m, 2H), 7.06-7.11 (m, 3H), 6.97-7.00 (m, 2H), 4.71 (t, J=7.2 Hz, 1H), 3.95-4.08 (4; 2H), 3.92 (s, 3H), 2.80-3.50 (m, 4H), 1.38-1.44 (m, 3H).

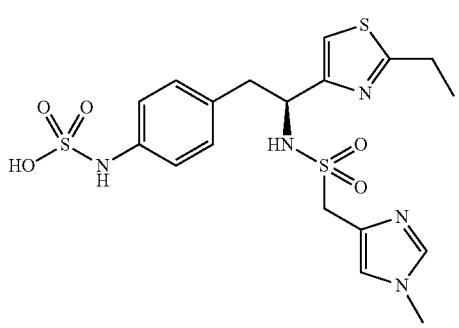 [SMILES: CCc1nc([C@H](Cc2ccc(NS(=O)(=O)O)cc2)NS(=O)(=O)Cc2cn(C)cn2)cs1]

(S)-4-[2-(2-Ethylthiazol-4-yl)-2-(1-methyl-1H-imidazol-4-sulfonamido)ethyl]-phenylsulfamic acid: $^1$H NMR (300 MHz, MeOH-d$_4$) δ 7.54 (s, 1H, 7.20 (s, 1H), 7.09 (s, 1H), 6.92-7.00 (m, 4H), 4.62 (t, J=5.4 Hz, 1H), 3.70 (s, 3H), 2.98-3.14 (m, 3H), 2.79 (dd, J=9.3 and 15.0 Hz, 1H), 1.39 (q, J=7.5 Hz, 3H).

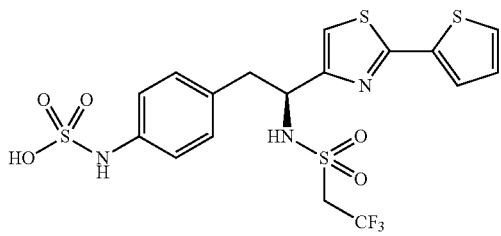 [SMILES: O=S(=O)(O)Nc1ccc(C[C@H](NS(=O)(=O)CC(F)(F)F)c2csc(-c3cccs3)n2)cc1]

4-{(S)-2-[2-(Thiophen-2-yl)thiazol-4-yl]-2-(2,2,2-trifluoroethylsulfonamido)-ethyl}phenylsulfamic acid: $^1$H NMR (CD$_3$OD): δ 7.62-7.56 (m, 2H), 7.22 (s, 1H), 7.16-7.06 (m, 5H), 4.84 (t, 1H, J=7.6 Hz), 3.71-3.62 (m, 2H), 3.32-3.03 (m, 2H).

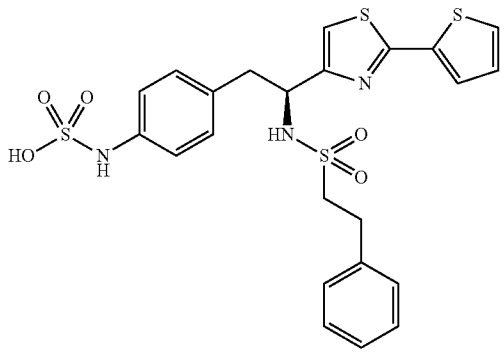 [SMILES: O=S(=O)(O)Nc1ccc(C[C@H](NS(=O)(=O)CCc2ccccc2)c2csc(-c3cccs3)n2)cc1]

{4-(S)-[2-(Phenylethanesulfonylamino)-2-(2thiophen-2-ylthiazol-4-yl)ethyl]-phenyl}sulfamic acid: $^1$H NMR (300 MHz, MeOH-d$_4$) 7.56-7.62 (m, 2H), 7.04-7.19 (m, 9H), 6.94-6.97 (m, 2H), 4.78 (t, J=7.8 Hz, 1H), 3.22-3.30 (m, 2H)), 3.11 (dd, J=13.5 and 7.8 Hz, 1H), 2.78-2.87 (m, 4H).

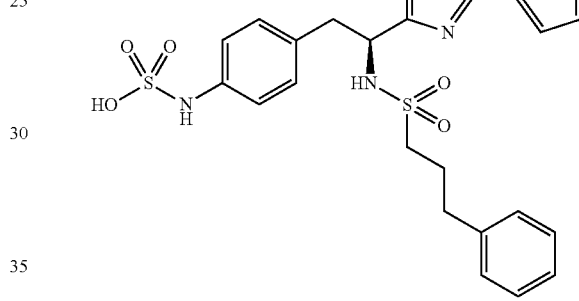

{4-(S)-[3-(Phenylpropanesulfonylamino)-2-(2thiophen-2-ylthiazol-4-yl)ethyl]-phenyl}sulfamic acid: $^1$H NMR (300 MHz, MeOH-d$_4$) δ 7.56-7.62 (m, 2H), 6.99-7.17 (m, 10H), 4.72 (t, J=7.8 Hz, 1H), 3.21 (dd, J=13.5 and 7.2 Hz, 1H), 3.02 (dd, J=13.5 and 7.2 Hz, 1H), 2.39-2.64 (m, 4H), 1.65-1.86 (m, 2H).

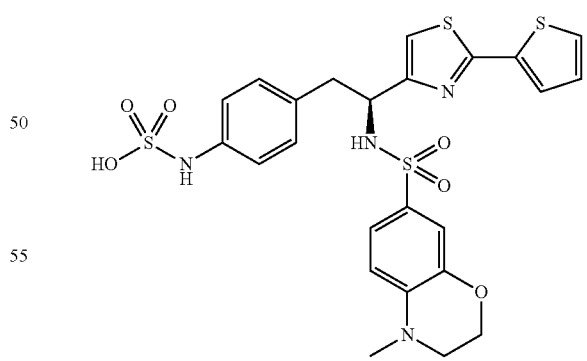

(S)-{4-[2-(4-Methyl-3,4-dihydro-2H-benzo[1,4]oxazine-7-sulfonylamino)-2-(2-thiophen-2-ylthiazol-4-yl)ethyl] phenyl}sulfamic acid: $^1$H NMR (300 MHz, MeOH-d$_4$) S 7.53 (d, J=5.1 Hz, 1H) 7.48 (d, J=5.1 Hz, 1H), 7.13-7.10 (m, 1H), 7.04 (d, J=8.4 Hz, 2H), 6.93-6.88 (m, 3H), 6.75 (d, J=8.1 Hz, 1H), 6.54 (d, J=8.1 Hz, 1H), 4.61 (t, J=7.5 Hz, 1H), 4.20-4.08 (m, 2H), 3.14-3.00 (m, 4H), 2.69 (s, 3H).

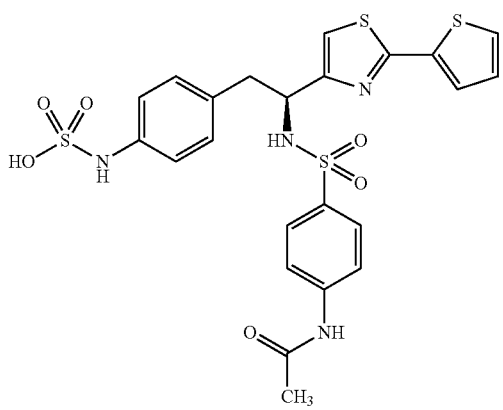 [SMILES: CC(=O)Nc1ccc(S(=O)(=O)N[C@@H](Cc2ccc(NS(=O)(=O)O)cc2)c2csc(-c3cccs3)n2)cc1]

4-{(S)-2-(4-acetamidophenylsulfonamido)-2-[2-(thiophen-2-yl)thiazol-4-yl]ethyl}phenylsulfamic acid: $^1$H NMR (CD$_3$OD): δ 7.67-7.52 (m, 6H), 7.24-7.23 (m, 1H), 7.12-7.09 (m, 3H), 7.02-6.99 (m, 2H), 4.70 (t, 1H, J=7.3 Hz), 3.25-3.00 (m, 2H), 2.24 (s, 3H).

The first aspect of Category IX of the present disclosure relates to compounds having the formula:

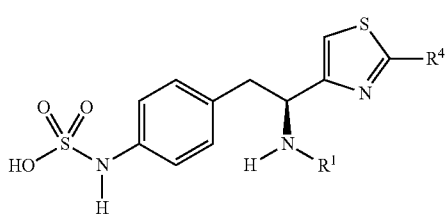

wherein R$^1$ is a substituted or unsubstituted heteroaryl and R$^4$ is C$_1$-C$_6$ linear, branched, or cyclic alkyl as further described herein below in Table XVII.

TABLE XVII

| No. | R$^4$ | R$^1$ |
| --- | --- | --- |
| Q698 | —CH$_3$ | 4-(methoxycarbonyl)thiazol-5-yl |
| Q699 | —CH$_3$ | 4-[(2-methoxy-2-oxoethyl)carbamoyl]thiazol-5-yl |
| Q700 | —CH$_3$ | 5-[1-N-(2-methoxy-2-oxoethyl)-1-H-indol-3-yl]oxazol-2-yl |
| Q701 | —CH$_3$ | 5-(2-methoxyphenyl)oxazol-2-yl |
| Q702 | —CH$_3$ | 5-[(S)-1-(tert-butoxycarbonyl)-2-phenylethyl]oxazol-2-yl |
| Q703 | —CH$_3$ | 5[4-(methylcarboxy)phenyl]oxazol-2-yl |
| Q704 | —CH$_3$ | 5-(3-methoxybenzyl)oxazol-2-yl |
| Q705 | —CH$_3$ | 5-(4-phenyl)oxazol-2-yl |
| Q706 | —CH$_3$ | 5-(2-methoxyphenyl)thiazol-2-yl |
| Q707 | —CH$_3$ | 5-(3-methoxyphenyl)thiazol-2-yl |
| Q708 | —CH$_3$ | 5-(4-fluorophenyl)thiazol-2-yl |
| Q709 | —CH$_3$ | 5-(2,4-difluorophenyl)thiazol-2-yl |
| Q710 | —CH$_3$ | 5-(3-methoxybenzyl)thiazol-2-yl |
| Q711 | —CH$_3$ | 4-(3-methoxyphenyl)thiazol-2-yl |
| Q712 | —CH$_3$ | 4-(4-fluorophenyl)thiazol-2-yl |
| Q713 | —CH$_2$CH$_3$ | 4-(methoxycarbonyl)thiazol-5-yl |
| Q714 | —CH$_2$CH$_3$ | 4-[(2-methoxy-2-oxoethyl)carbamoyl]thiazol-5-yl |
| Q715 | —CH$_2$CH$_3$ | 5-[1-N-(2-methoxy-2-oxoethyl)-1-H-indol-3-yl]oxazol-2-yl |
| Q716 | —CH$_2$CH$_3$ | 5-(2-methoxyphenyl)oxazol-2-yl |
| Q717 | —CH$_2$CH$_3$ | 5-[(S)-1-(tert-butoxycarbonyl)-2-phenylethyl]oxazol-2-yl |
| Q718 | —CH$_2$CH$_3$ | 5[4-(methylcarboxy)phenyl]oxazol-2-yl |
| Q719 | —CH$_2$CH$_3$ | 5-(3-methoxybenzyl)oxazol-2-yl |
| Q720 | —CH$_2$CH$_3$ | 5-(4-phenyl)oxazol-2-yl |
| Q721 | —CH$_2$CH$_3$ | 5-(2-methoxyphenyl)thiazol-2-yl |
| Q722 | —CH$_2$CH$_3$ | 5-(3-methoxyphenyl)thiazol-2-yl |
| Q723 | —CH$_2$CH$_3$ | 5-(4-fluorophenyl)thiazol-2-yl |
| Q724 | —CH$_2$CH$_3$ | 5-(2,4-difluorophenyl)thiazol-2-yl |
| Q725 | —CH$_2$CH$_3$ | 5-(3-methoxybenzyl)thiazol-2-yl |
| Q726 | —CH$_2$CH$_3$ | 4-(3-methoxyphenyl)thiazol-2-yl |
| Q727 | —CH$_2$CH$_3$ | 4-(4-fluorophenyl)thiazol-2-yl |
| Q728 | cyclopropyl | 4-(methoxycarbonyl)thiazol-5-yl |
| Q729 | cyclopropyl | 4-[(2-methoxy-2-oxoethyl)carbamoyl]thiazol-5-yl |
| Q730 | cyclopropyl | 5-[1-N-(2-methoxy-2-oxoethyl)-1-H-indol-3-yl]oxazol-2-yl |
| Q731 | cyclopropyl | 5-(2-methoxyphenyl)oxazol-2-yl |
| Q732 | cyclopropyl | 5-[(S)-1-(tert-butoxycarbonyl)-2-phenylethyl]oxazol-2-yl |
| Q733 | cyclopropyl | 5[4-(methylcarboxy)phenyl]oxazol-2-yl |
| Q734 | cyclopropyl | 5-(3-methoxybenzyl)oxazol-2-yl |
| Q735 | cyclopropyl | 5-(4-phenyl)oxazol-2-yl |
| Q736 | cyclopropyl | 5-(2-methoxyphenyl)thiazol-2-yl |
| Q737 | cyclopropyl | 5-(3-methoxyphenyl)thiazol-2-yl |
| Q738 | cyclopropyl | 5-(4-fluorophenyl)thiazol-2-yl |
| Q739 | cyclopropyl | 5-(2,4-difluorophenyl)thiazol-2-yl |
| Q740 | cyclopropyl | 5-(3-methoxybenzyl)thiazol-2-yl |
| Q741 | cyclopropyl | 4-(3-methoxyphenyl)thiazol-2-yl |
| Q742 | cyclopropyl | 4-(4-fluorophenyl)thiazol-2-yl |

Compounds according to the first aspect of Category IX which comprise a substituted or unsubstituted thiazol-4-yl unit for R$^1$ can be prepared by the procedure outlined in Scheme XVII and described below in Example 18.

Scheme XVII

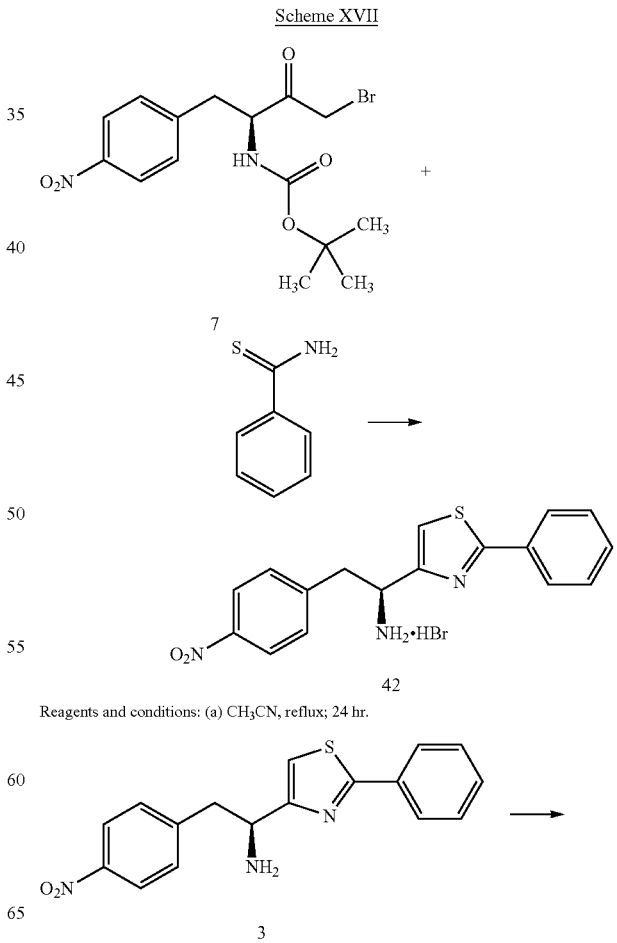

Reagents and conditions: (a) CH$_3$CN, reflux; 24 hr.

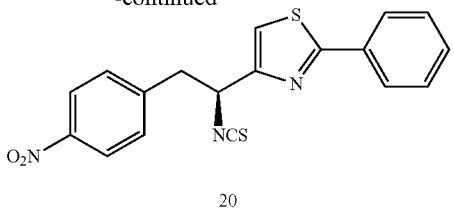

20

Reagents and conditions: (b) thiophosgene, CaCO₃, CCl₄, H₂O; rt, 18 hr.

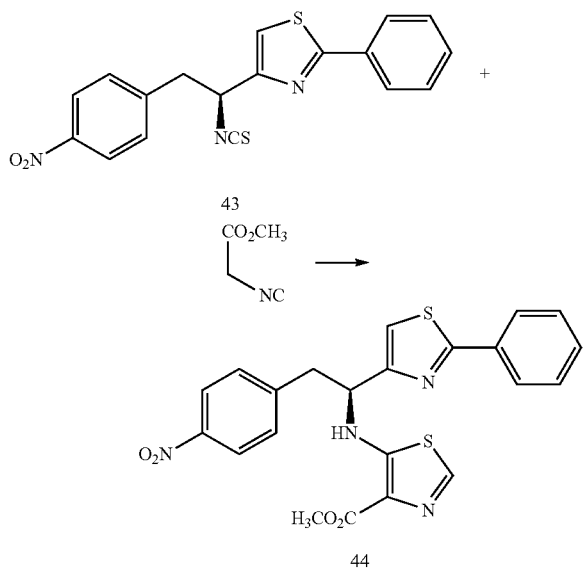

Reagents and conditions: (c) KOtBu, THF; rt, 2 hr.

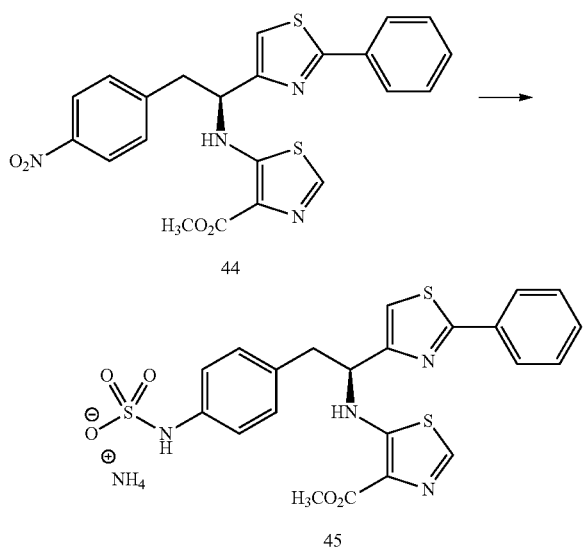

Reagents and conditions: (d) (i) SnCl₂—2H₂O, EtOH; reflux, 4 hours (ii) SO₃-pyridine, NH₄OH.

EXAMPLE 18

(S)-4-(2-(2-Phenylthiazol-4-yl)2-(4-(methoxycarbonyl)thiazole-5-ylamino)ethyl)phenylsulfamic acid (45)

Preparation of (S)-2-(4-nitrophenyl)-1-(2-phenylthiazol-4-yl)ethanamine hydrobromide salt (42): A mixture of (S)-tert-butyl 4-bromo-1-(4-nitrophenyl)-3-oxobutan-2-ylcarbamate, 7, (1.62 g, 4.17 mmol) and thiobenzamide (0.63 g, 4.60 mmol) in CH₃CN (5 mL) is refluxed for 24 hours. The reaction mixture is cooled to room temperature and diethyl ether (50 mL) is added to the solution. The precipitate which forms is collected by filtration. The solid is dried under vacuum to afford 1.2 g (67% yield) of the desired product. LC/MS ESI+ 326 (M+1).

Preparation of (S)-4-(1-isothiocyanato-2-(4-nitrophenyl)ethyl)-2-phenylthiazole (43): To a solution of (S)-2-(4-nitrophenyl)-1-(2-phenylthiazol-4-yl)ethanamine hydrobromide salt, 42, (726 mg, 1.79 mmol) and CaCO₃ (716 mg, 7.16 mmol) in H₂O (2 mL) is added CCl₄ (3 mL) followed by thiophosgene (0.28 mL, 3.58 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue which is purified over silica (CH₂Cl₂) to afford 480 mg (73%) of the desired product as a yellow solid. ¹H NMR (300 MHz, CDCl₃) δ 8.15 (d, J=8.7 Hz, 2H), 7.97-7.99 (m, 2H), 7.43-7.50 (m, 3H), 7.34 (d, J=8.7 Hz, 2H), 7.15 (d, J=0.9 Hz, 1H), 5.40-5.95 (m, 1H), 3.60 (dd, J=13.8 and 6.0 Hz, 1H), 3.46 (dd, J=13.8 and 6.0 Hz).

Preparation of (S)-methyl 5-[1-(2-phenylthiazol-4-yl)-2-(4-nitrophenyl)-ethylamino]thiazole-4-carboxylate (44): To a suspension of potassium tert-butoxide (89 mg, 0.75 mmol) in THF (3 mL) is added methyl isocyanoacetate (65 μL, 0.68 mmol) followed by (S)-2-phenyl-4-(1-isothiocyanato-2-(4-nitrophenyl)ethyl)thiazole, 43, (250 mg, 0.68 mmol). The reaction mixture is stirred at room temperature for 2 hours then poured into sat. NaHCO₃. The mixture is extracted with EtOAc (3×25 mL) and the combined organic layers are washed with brine and dried (Na₂SO₄) and concentrated in vacuo. The crude residue is purified over silica to afford 323 mg (~100% yield) of the desired product as a slightly yellow solid. ¹H NMR (300 MHz, CDCl₃) δ 8.09-8.13 (m, 2H), 7.95-7 98 (m, 3H), 7.84 (d, J=1.2 Hz, 1H), 7.44-7.50 (m, 3H), 7.28-7.31 (m, 2H), 7.96 (d, J=0.6 Hz, 1H), 4.71-4.78 (m, 1H), 3.92 (s, 3H), 3.60 (dd, J=13.8 and 6.0 Hz, 1H), 3.45 (dd, J=13.8 and 6.0 Hz, 1H).

Preparation of (S)-4-(2-(2-phenylthiazol-4-yl)2-(4-(methoxycarbonyl)thiazole-5-ylamino)ethyl)phenylsulfamic acid (45): (S)-methyl 5-[1-(2-phenylthiazol-4-yl)-2-(4-nitrophenyl)-ethylamino]thiazole-4-carboxylate, 44, (323 mg, 0.68 mmol) and tin (II) chloride (612 mg, 2.72 mmol) are dissolved in EtOH and the solution is brought to reflux. The solvent is removed in vacuo and the resulting residue is dissolved in EtOAc. A saturated solution of NaHCO₃ is added and the solution is stirred 1 hour. The organic layer is separated and the aqueous layer extracted twice with EtOAc. The combined organic layers are dried (Na₂SO₄), filtered and concentrated to a residue which is dissolved in pyridine (10 mL) and treated with SO₃-pyridine (130 mg, 0.82 mmol). The reaction is stirred at room temperature for 5 minutes after which a 7% solution of NH₄OH is added. The mixture is then concentrated and the resulting residue is purified by reverse phase chromatography to afford 0.071 g of the desired product as the ammonium salt ¹H NMR (300 MHz, MeOH-d₄) δ 7.97-8.00 (m, 3H), 7.48-7.52 (m, 3H), 7.22 (s, 1H), 7.03-7.13 (m, 4H), 4.74 (t, J=6.6 Hz, 1H), 3.88 (s, 3H), 3.28-3.42 (m, 2H).

Compounds according to the first aspect of Category IX which comprise a substituted or unsubstituted thiazol-2-yl unit for R¹ can be prepared by the procedure outlined in Scheme XVIII and described herein below in Example 19. Intermediate 46 can be prepared according to Scheme II and Example 2 by substituting cyclopropane-carbothioic acid amide for thiophen-2-carbothioic acid amide.

Scheme XVIII

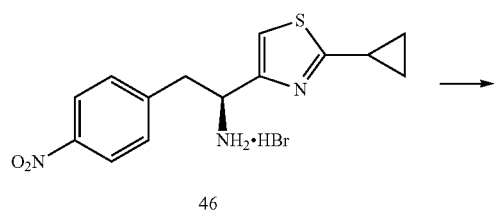

46

Reagents and conditions (a) (i) thiophosgene, CaCO$_3$, CCl$_4$/H$_2$O; rt, 18 hr; (ii) NH$_3$.

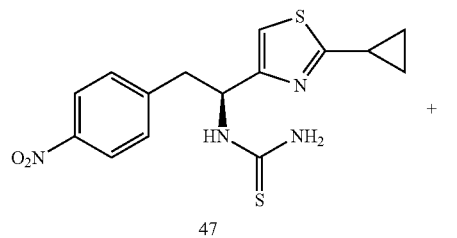

47

+

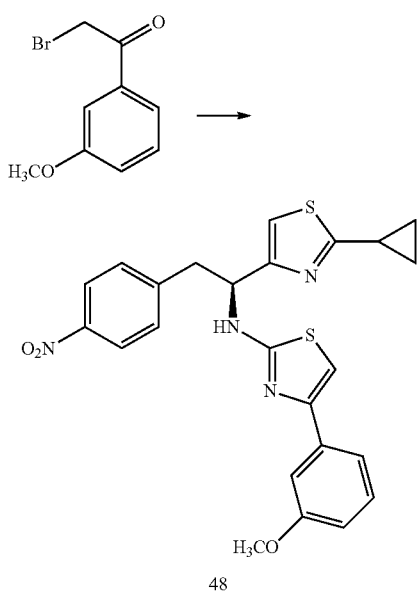

48

Reagents and conditions: (b) CH$_3$CN, reflux, 24 hr.

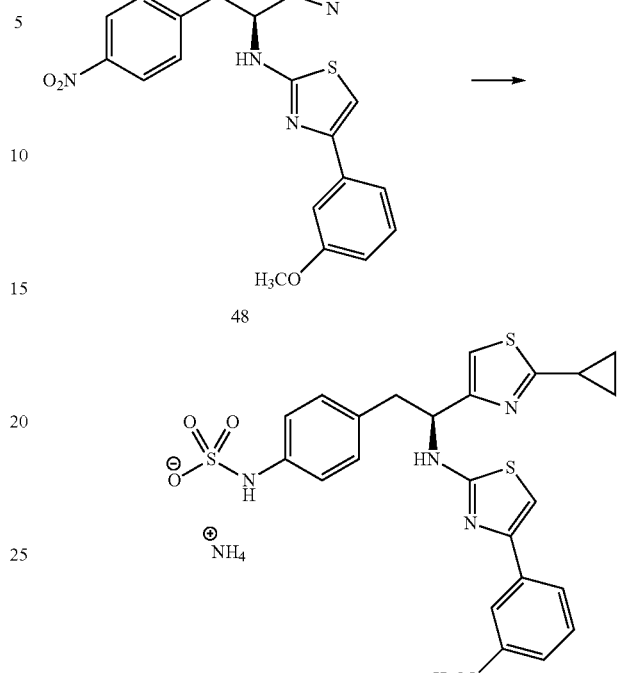

Reagents and conditions: (c) (i) H$_2$:Pd/C, MeOH; (ii) SO$_3$-pyridine, NH$_4$OH.

EXAMPLE 19

4-{(S)-2-(2-Cyclopropylthiazol-4-yl)-2-[4-(3-methoxyphenyl)thiazol-2-ylamino]ethyl}phenylsulfamic acid (50)

Preparation of (S)-1-(1-(2-cyclopropylthiazol-4-yl)-2-(4-nitrophenyl)ethyl)-thiourea (47): To a solution of (S)-1-(2-cyclopropylthiazol-4-yl)-2-(4-nitrophenyl)ethan-amine hydrobromide hydrobromide salt, 32, (4.04 g, 10.9 mmol) and CaCO$_3$ (2.18 g, 21.8 mmol) in CCl$_4$/water (25 mL/20 mL) is added thiophosgene (1.5 g, 13.1 mmol). The reaction is stirred at room temperature for 18 hours then diluted with CH$_2$Cl$_2$ and water. The layers are separated and the aqueous layer extracted with CH$_2$Cl$_2$. The combined organic layers are washed with brine, dried (Na$_2$SO$_4$) and concentrated in vacuo to a residue which is subsequently treated with ammonia (0.5M in 1,4-dioxane, 120 mL) which is purified over silica to afford 2.90 g of the desired product as a red-brown solid. LC/MS ESI-347 (M-1).

Preparation of (S)-4-(3-methoxybenzyl)-N-(1-(2-cyclopropylthiazol-4-yl)-2-(4-nitrophenyl)ethyl)thiazol-2-amine (48): (S)-1-(1-(2-Cyclopropylthiazol-4-yl)-2-(4-nitrophenyl)ethyl)-thiourea, 47, (350 mg, 1.00 mmol) and 2-bromo-3'-methoxyacetophenone (253 mg, 1.10 mmol) are combined in 3 mL CH$_3$CN and heated to reflux for 24 hours. The mixture is concentrated and chromatographed to afford 0.172 g of the product as a yellow solid. LC/MS ESI+ 479 (M+1).

Preparation of 4-{(S)-2-(2-cyclopropylthiazol-4-yl)-2-[4-(3-methoxyphenyl)-thiazol-2-ylamino]

ethyl}phenylsulfamic acid (49): (S)-4-(3-methoxybenzyl)-N-(1-(2-cyclopropylthiazol-4-yl)-2-(4-nitrophenyl)ethyl)thiazol-2-amine, 48, (0.172 g) is dissolved in 10 mL MeOH. A catalytic amount of Pd/C (10% w/w) is added and the mixture is stirred under a hydrogen atmosphere for 18 hours. The reaction mixture is filtered through a bed of CELITE™ and the solvent is removed under reduced pressure. The crude product is dissolved in 5 mL pyridine and treated with SO$_3$-pyridine (114 mg). The reaction is stirred at room temperature for 5 minutes after which 10 mL of a 7% solution of NH$_4$OH is added. The mixture is then concentrated and the resulting residue is purified by reverse-phase chromatography to afford 0.033 g of the desired product as the ammonium salt. $^1$H NMR (CD$_3$OD): δ 7.33-7.22 (m, 3H), 7.10-6.97 (m, 5H), 6.84-6.80 (m, 2H), 5.02 (t, 1H, J=6.9 Hz), 3.82 (s, 1H), 3.18 (q, 2H, J=7.1 Hz), 2.36 (q, 1H, J=4.6 Hz), 1.20-1.13 (m, 2H), 1.04-0.99 (m, 2H).

The following are non-limiting examples of compounds encompassed within the first aspect of Category IX.

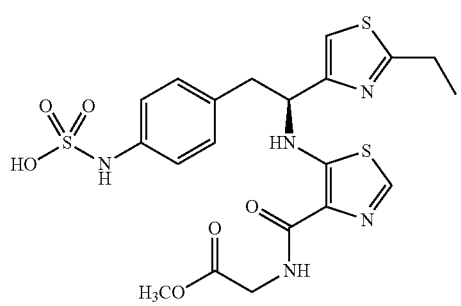 [SMILES: CCc1nc([C@H](Cc2ccc(NS(=O)(=O)O)cc2)Nc2scnc2C(=O)NCC(=O)OC)cs1]

(S)-4-(2-(4-((2-Methoxy-2-oxoethyl)carbamoyl)thiazole-5-ylamino)2-(2-ethylthiazole-4-yl)ethyl)phenylsulfamic acid: $^1$H NMR (300 MHz, MeOH-d$_4$) δ 7.91 (s, 1H), 7.08-7.10 (m, 3H), 6.99 (d, J=8.7 Hz, 2H), 4.58 (t, J=6.9 Hz, 1H), 4.11 (d, J=2.7 Hz, 2H), 3.78 (s, 3H), 3.14-3.28 (m, 2H), 3.06 (q, J=7.5 Hz, 2H), 1.41 (t, J=7.5 Hz, 3H).

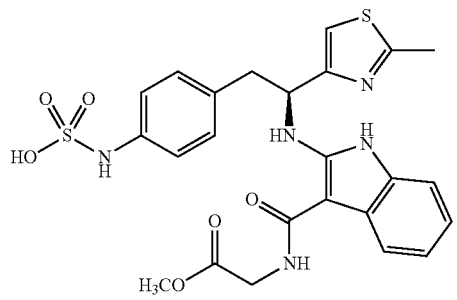 [SMILES: COC(=O)CNC(=O)c1c(N[C@@H](Cc2ccc(NS(=O)(=O)O)cc2)c2csc(C)n2)[nH]c2ccccc12]

(S)-4-(2-{5-[1-N-(2-Methoxy-2-oxoethylcarbamoyl)-1-H-indol-3-yl]oxazol-2-ylamino}-2-(2-methylthiazol-4-yl)ethyl)phenylsulfamic acid: $^1$H NMR (300 MHz, MeOH-d$_4$) δ 7.63 (d, J=7.8 Hz, 1H), 7.37 (s, 1H), 7.18-7.29 (m, 4H), 7.02-7.16 (m, 4H), 6.85 (s, 1H), 5.04-5.09 (m, 1H), 4.85 (s, 3H), 3.27 (dd, J=13.5 and 8.1 Hz, 1H), 3.10 (m, J=13.5 and 8.1 Hz, 1H), 2.69 (s, 3H).

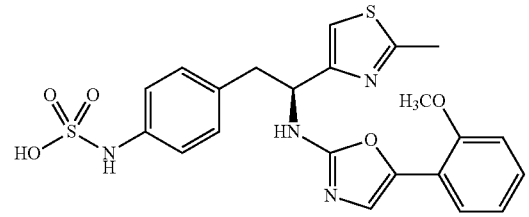 [SMILES: COc1ccccc1-c1cnc(N[C@@H](Cc2ccc(NS(=O)(=O)O)cc2)c2csc(C)n2)o1]

4-((S)-2-(5-(2-Methoxyphenyl)oxazol-2-ylamino)-2-(2-methylthiazol-4-yl)ethyl)phenylsulfamic acid: $^1$H NMR (300 MHz, MeOH-d$_4$) δ 7.52 (dd, J=7.5 and 1.2 Hz, 1H), 6.95-7.24 (m, 10H), 5.04-5.09 (m, 1H), 3.92 (s, 3H), 3.26 (dd, J=13.8 and 8.4 Hz, 1H), 3.10 (dd, J=13.8 and 8.4 Hz, 1H), 2.72 (s, 3H).

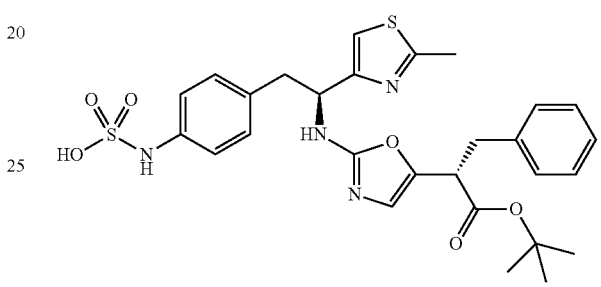

4-((S)-2-(5-((S)-1-(tert-Butoxycarbonyl)-2-phenylethyl)oxazole-2-ylamino)-2-(2-methylthiazole-4-yl)ethyl)phenylsulfamic acid: $^1$H NMR (300 MHz, MeOH-d$_4$) δ 7.03-7.27 (m, 10H), 6.50 (s, 1H), 4.95-5.00 (m, 1H), 4.76 (t, J=6.9 Hz, 1H), 3.22 (dd, J=14.1 and 6.9 Hz, 1H), 3.00-3.10 (m, 2H), 2.90 (dd, J=14.1 and 6.9 Hz, 1H), 2.72 (s, 3H), 1.37 (s, 9H).

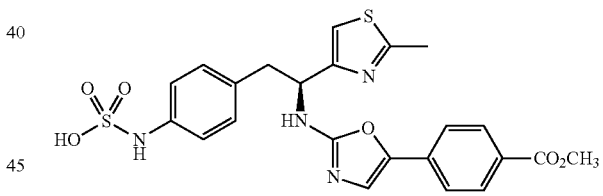

(S)-{4-{2-[5-(4-Methoxycarbonyl)phenyl]oxazol-2-ylamino}-2-(2-methylthiazol-4-yl)ethyl}phenylsulfamic acid: $^1$H NMR (300 MHz, MeOH-d$_4$) δ 7.99 (d, J=7.5 Hz, 2H), 7.56-7.59 (m, 2H), 7.23-7.24 (m, 1H), 7.08-7.14 (m, 4H), 6.83 (d, J=10.2 Hz, 1H), 5.08 (t, J=6.0 Hz, 1H), 3.91 (s, 3H), 3.25-3.35 (m, 1H), 3.09-3.13 (m, 1H), 2.73 (s, 3H).

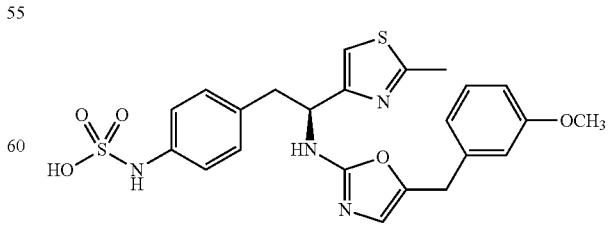

(S)-4-(2-(5-(3-Methoxybenzyl)oxazole-2-ylamino)-2-(2-methylthiazole-4-yl)ethyl)phenylsulfamic acid: $^1$H NMR (300 MHz, MeOH-d$_4$) δ 7.03-7.28 (m, 8H), 6.79-6.83 (m, 1H), 5.70 (s, 1H), 4.99-5.06 (m, 2H), 4.41 (d, J=2.1 Hz, 2H), 3.80 (s, 3H), 3.27-3.37 (m, 1H), 3.03-3.15 (m, 1H), 2.71 (s, 3H).

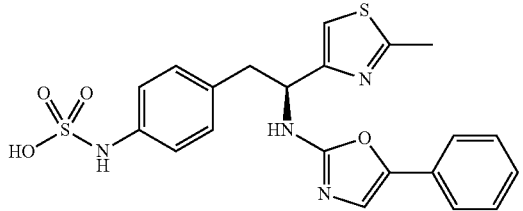 [SMILES: Cc1nc([C@H](Cc2ccc(NS(=O)(=O)O)cc2)Nc2ncc(-c3ccccc3)o2)cs1]

(S)-4-(2-(2-Methylthiazole-4-yl)-2-(5-phenyloxazole-2-ylamino)ethyl)phenyl-sulfamic acid: $^1$H NMR (300 MHz, MeOH-d$_4$) δ 7.45 (d, J=8.7 Hz, 2H), 7.33 (t, J=7.8 Hz, 2H), 7.18-7.22 (m, 1H), 7.10-7.14 (m, 6H), 7.04 (s, 1H), 5.04-5.09 (m, 1H), 3.26 (dd, J=13.8 and 6.3 Hz, 1H), 3.10 (dd, J=13.8 and 6.3 Hz, 1H), 2.70 (s, 3H).

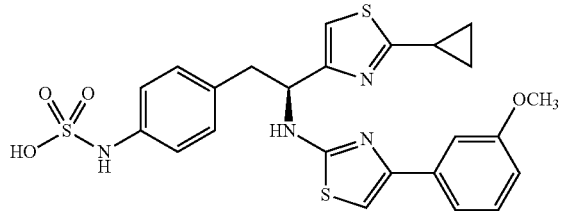 [SMILES: COc1cccc(-c2csc(N[C@@H](Cc3ccc(NS(=O)(=O)O)cc3)c3csc(C4CC4)n3)n2)c1]

4-((S)-2-(2-Cyclopropylthiazol-4-yl)-2-(4-(3-methoxyphenyl)thiazol-2-ylamino)-ethyl)phenylsulfamic acid: $^1$H NMR (CD$_3$OD): δ 7.33-7.22 (m, 3H), 7.10-6.97 (m, 5H), 6.84-6.80 (m, 2H), 5.02 (t, 1H, J=6.9 Hz), 3.82 (s, 1H), 3.18 (q, 2H, J=7.1 Hz), 2.36 (q, 1H, J=4.6 Hz), 1.20-1.13 (m, 2H), 1.04-0.99 (m, 2H).

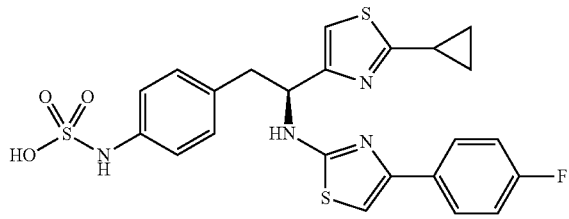 [SMILES: O=S(=O)(O)Nc1ccc(C[C@H](Nc2nc(-c3ccc(F)cc3)cs2)c2csc(C3CC3)n2)cc1]

(S)-4-(2-(2-cyclopropylthiazol-4-yl)-2-(4-(4-fluorophenyl)thiazol-2-ylamino)ethyl)-phenylsulfamic acid: $^1$H NMR (CD$_3$OD): δ 7.79-7.74 (m, 2H), 7.14-7.03 (m, 7H), 7.21 (s, 1H), 6.79 (s, 1H), 5.08 (t, 1H, J=6.6 Hz), 3.29-3.12 (m, 2H), 2.40 (q, 2.40, J=5.1 Hz), 1.23-1.18 (m, 2H), 1.08-1.02 (m, 2H).

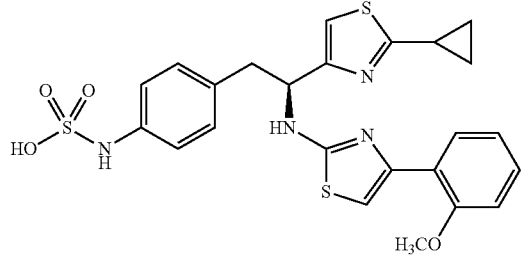 [SMILES: COc1ccccc1-c1csc(N[C@@H](Cc2ccc(NS(=O)(=O)O)cc2)c2csc(C3CC3)n2)n1]

4-((S)-2-(2-cyclopropylthiazol-4-yl)-2-(4-(2-methoxyphenyl)thiazol-2-ylamino)-ethyl)phenylsulfamic acid: $^1$H NMR (CD$_3$OD): δ 7.89-7.87 (d, 1H, J=7.6 Hz), 7.28 (t, 1H, J=7.0 Hz), 7.10-6.96 (m, 8H), 5.03 (t, 1H, J=6.9 Hz), 3.90 (s, 1H), 3.19 (q, 2H, J=6.6 Hz), 2.38 (q, 1H, J=4.8 Hz), 1.21-1.14 (m, 2H), 1.06-1.00 (m, 2H).

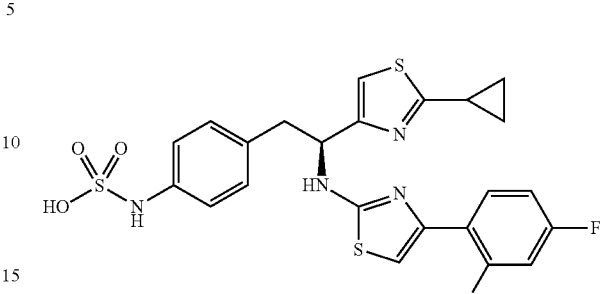

4-((S)-2-(2-cyclopropylthiazol-4-yl)-2-(4-(2,4-difluorophenyl)thiazol-2-ylamino)-ethyl)phenylsulfamic acid: $^1$H NMR (CD$_3$OD): δ 8.06-8.02 (q, 2H, J=6.9 Hz), 7.12-6.95 (m, 7H), 6.88 (s, 1H), 5.11 (t, 1H, J=6.9 Hz), 3.22-3.15 (m, 2H), 2.38 (q, 1H, J=4.8 Hz), 1.22-1.15 (m, 2H), 1.06-1.02 (m, 2H).

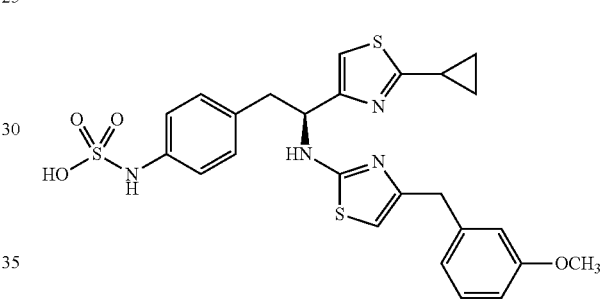

(S)-4-(2-(4-(3-methoxybenzyl)thiazol-2-ylamino)-2-(2-cyclopropylthiazol-4-yl)ethyl)phenylsulfamic acid: $^1$H NMR (CD$_3$OD): δ 7.22-7.17 (m, 3H), 7.09-6.97 (m, 5H), 6.78-6.66 (m, 3H), 3.77 (s, 2H), 3.75 (s, 3H), 3.20-3.07 (m, 2H), 2.35 (q, 1H, J=4.8 Hz), 1.19-1.13 (m, 2H), 1.03-1.00 (m, 2H).

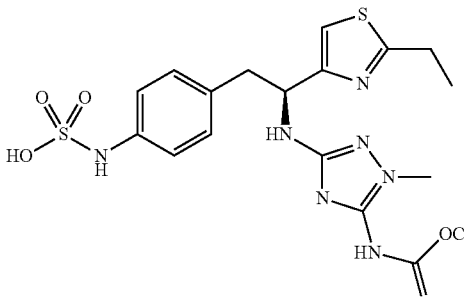

(S)-{5-[1-(2-Ethylthiazol-4-yl)-2-(4-sulfoaminophenyl)ethylamino]-2-methyl-2H-[1,2,4]triazole-3-yl}carbamic acid methyl ester: $^1$H NMR (300 MHz, MeOH-d$_4$) δ 6.97-7.08 (m, 5H), 3.71 (s, 3H), 3.51 (s, 3H), 3.15 (dd, J=13.5 and 6.3 Hz, 1H), 3.02-3.07 (m, 3H), 1.40 (t, J=6.6 Hz, 3H).

The second aspect of Category IX of the present disclosure relates to compounds having the formula:

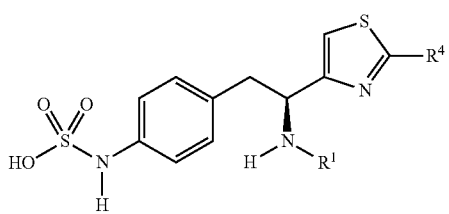

wherein R¹ is a substituted or unsubstituted heteroaryl and R⁴ is substituted or unsubstituted phenyl and substituted or unsubstituted heteroaryl as further described below in Table XVIII.

TABLE XVIII

| No. | R⁴ | R¹ |
|---|---|---|
| R743 | phenyl | 4-(methoxycarbonyl)thiazol-5-yl |
| R744 | phenyl | 4-[(2-methoxy-2-oxoethyl)carbamoyl]thiazol-5-yl |
| R745 | phenyl | 5-[1-N-(2-methoxy-2-oxoethyl)-1-H-indol-3-yl]oxazol-2-yl |
| R746 | phenyl | 5-(2-methoxyphenyl)oxazol-2-yl |
| R747 | phenyl | 5-[(S)-1-(tert-butoxycarbonyl)-2-phenylethyl]oxazol-2-yl |
| R748 | phenyl | 5-[4-(methylcarboxy)phenyl]oxazol-2-yl |
| R749 | phenyl | 5-(3-methoxybenzyl)oxazol-2-yl |
| R750 | phenyl | 5-(4-phenyl)oxazol-2-yl |
| R751 | phenyl | 5-(2-methoxyphenyl)thiazol-2-yl |
| R752 | phenyl | 5-(3-methoxyphenyl)thiazol-2-yl |
| R753 | phenyl | 5-(4-fluorophenyl)thiazol-2-yl |
| R754 | phenyl | 5-(2,4-difluorophenyl)thiazol-2-yl |
| R755 | phenyl | 5-(3-methoxybenzyl)thiazol-2-yl |
| R756 | phenyl | 4-(3-methoxyphenyl)thiazol-2-yl |
| R757 | phenyl | 4-(4-fluorophenyl)thiazol-2-yl |
| R758 | thiophen-2-yl | 4-(methoxycarbonyl)thiazol-5-yl |
| R759 | thiophen-2-yl | 4-[(2-methoxy-2-oxoethyl)carbamoyl]thiazol-5-yl |
| R760 | thiophen-2-yl | 5-[1-N-(2-methoxy-2-oxoethyl)-1-H-indol-3-yl]oxazol-2-yl |
| R761 | thiophen-2-yl | 5-(2-methoxyphenyl)oxazol-2-yl |
| R762 | thiophen-2-yl | 5-[(S)-1-(tert-butoxycarbonyl)-2-phenylethyl]oxazol-2-yl |
| R763 | thiophen-2-yl | 5-[4-(methylcarboxy)phenyl]oxazol-2-yl |
| R764 | thiophen-2-yl | 5-(3-methoxybenzyl)oxazol-2-yl |
| R765 | thiophen-2-yl | 5-(4-phenyl)oxazol-2-yl |
| R766 | thiophen-2-yl | 5-(2-methoxyphenyl)thiazol-2-yl |
| R767 | thiophen-2-yl | 5-(3-methoxyphenyl)thiazol-2-yl |
| R768 | thiophen-2-yl | 5-(4-fluorophenyl)thiazol-2-yl |
| R769 | thiophen-2-yl | 5-(2,4-difluorophenyl)thiazol-2-yl |
| R770 | thiophen-2-yl | 5-(3-methoxybenzyl)thiazol-2-yl |
| R771 | thiophen-2-yl | 4-(3-methoxyphenyl)thiazol-2-yl |
| R772 | thiophen-2-yl | 4-(4-fluorophenyl)thiazol-2-yl |
| R773 | cyclopropyl | 4-(methoxycarbonyl)thiazol-5-yl |
| R774 | cyclopropyl | 4-[(2-methoxy-2-oxoethyl)carbamoyl]thiazol-5-yl |
| R775 | cyclopropyl | 5-[1-N-(2-methoxy-2-oxoethyl)-1-H-indol-3-yl]oxazol-2-yl |
| R776 | cyclopropyl | 5-(2-methoxyphenyl)oxazol-2-yl |
| R777 | cyclopropyl | 5-[(S)-1-(tert-butoxycarbonyl)-2-phenylethyl]oxazol-2-yl |
| R778 | cyclopropyl | 5-[4-(methylcarboxy)phenyl]oxazol-2-yl |
| R779 | cyclopropyl | 5-(3-methoxybenzyl)oxazol-2-yl |
| R780 | cyclopropyl | 5-(4-phenyl)oxazol-2-yl |
| R781 | cyclopropyl | 5-(2-methoxyphenyl)thiazol-2-yl |
| R782 | cyclopropyl | 5-(3-methoxyphenyl)thiazol-2-yl |
| R783 | cyclopropyl | 5-(4-fluorophenyl)thiazol-2-yl |
| R784 | cyclopropyl | 5-(2,4-difluorophenyl)thiazol-2-yl |
| R785 | cyclopropyl | 5-(3-methoxybenzyl)thiazol-2-yl |
| R786 | cyclopropyl | 4-(3-methoxyphenyl)thiazol-2-yl |
| R787 | cyclopropyl | 4-(4-fluorophenyl)thiazol-2-yl |

Compounds according to the second aspect of Category IX which comprise a substituted or unsubstituted thiazol-4-yl unit for R¹ can be prepared by the procedure outlined in Schemes XIX, XX, and XXI, and described below in Examples 20, 21, and 22.

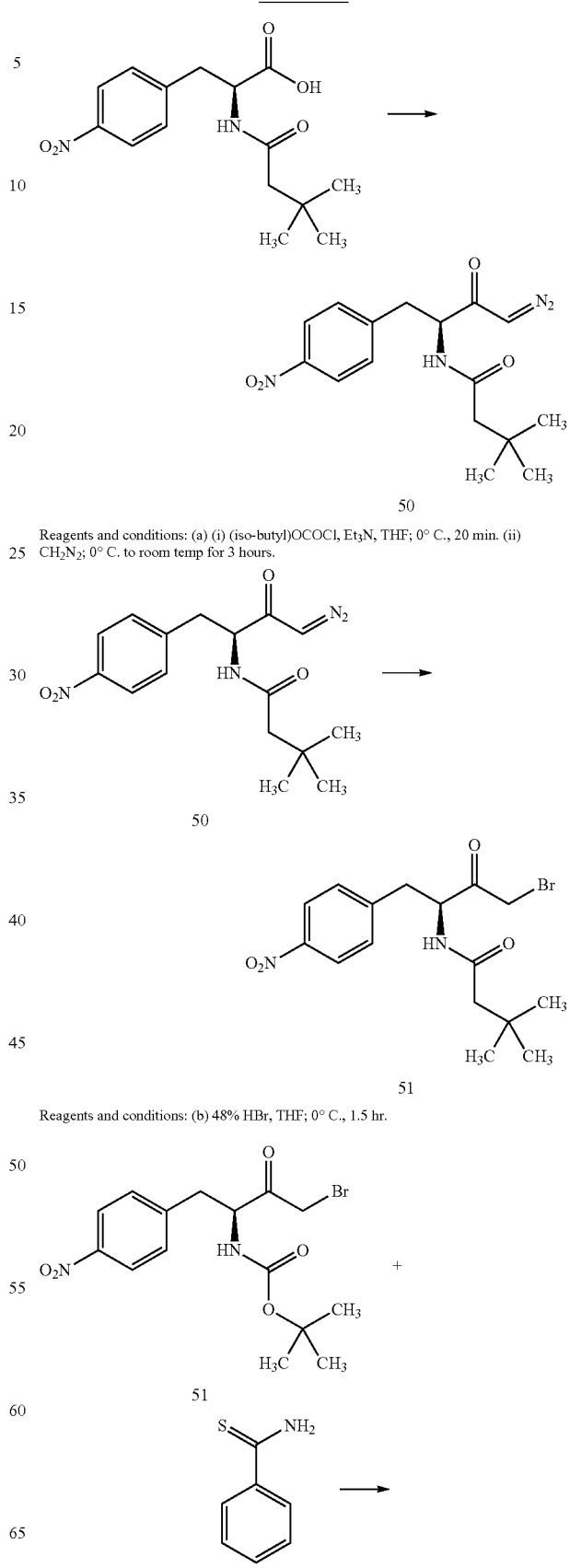

Scheme XIX

Reagents and conditions: (a) (i) (iso-butyl)OCOCl, Et₃N, THF; 0° C., 20 min. (ii) CH₂N₂; 0° C. to room temp for 3 hours.

Reagents and conditions: (b) 48% HBr, THF; 0° C., 1.5 hr.

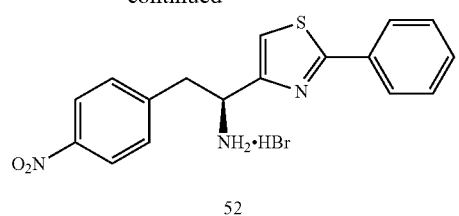

52

Reagents and conditions: (c) CH₃CN; reflux 2 hr.

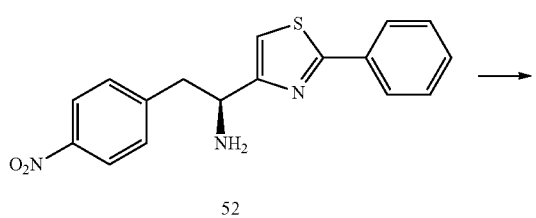

52

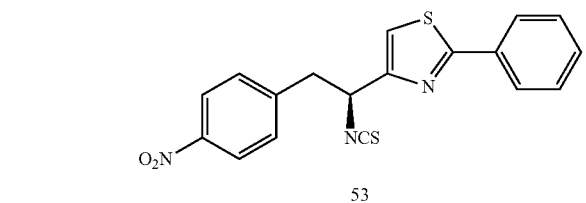

53

Reagents and conditions: (d) thiophosgene, CaCO₃, CCl₄, H₂O; rt, 18 hr.

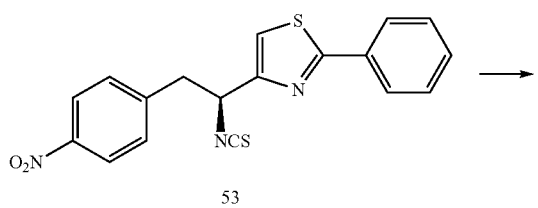

53

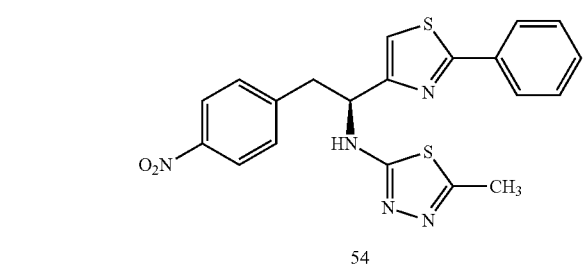

54

Reagents and conditions: (e) (i) CH₃C(O)NHNH₂, EtOH; reflux, 2 hr.
(ii) POCl₃, rt 18 hr; 50° C. 2 hr.

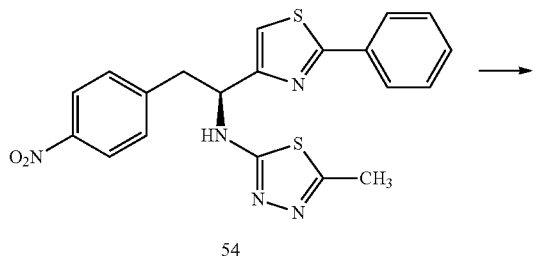

54

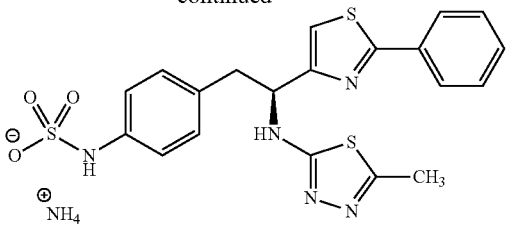

55

Reagents and conditions: (f) (i) H₂:Pd/C, MeOH; (ii) SO₃-pyridine, NH₄OH.

EXAMPLE 20

(S)-4-(2-(5-Methyl-1,3,4-thiadiazol-2-ylamino)-2-(2-phenylthiazol-4-yl)ethyl)phenylsulfamic acid (55)

Preparation of [3-diazo-1-(4-nitrobenzyl)-2-oxo-propyl]-carbamic acid tert-butyl ester (50): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by iso-butyl chloroformate (0.57 mL, 4.4 mmol). The reaction mixture is stirred at 0° C. for 20 minutes then filtered. The filtrate is treated with an ether solution of diazomethane (~16 mmol) at 0° C. The reaction mixture is stirred at room temperature for 3 hours and concentrated. The residue is dissolved in EtOAc and washed successively with water and brine, dried (Na₂SO₄), filtered and concentrated in vacuo. The resulting residue is purified over silica (hexane/EtOAc 2:1) to afford 1.1 g (82% yield) of the desired product as a slightly yellow solid. ¹H NMR (300 MHz, CDCl₃) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of [3-bromo-1-(4-nitro-benzyl)-2-oxo-propyl]-carbamic acid tert-butyl ester (51): To a 0° C. solution of [3-diazo-1-(4-nitrobenzyl)-2-oxo-propyl]carbamic acid tert-butyl ester, 50, (0.350 g, 1.04 mmol) in THF (5 mL) is added dropwise 48% aq. HBr (0.14 mL, 1.25 mmol). The reaction mixture is stirred at 0° C. for 1.5 hours and quenched at 0° C. with saturated aqueous Na₂CO₃. The mixture is extracted with EtOAc (3×25 mL) and the combined organic extracts are washed with brine, dried (Na₂SO₄), filtered and concentrated in vacuo to afford 0.400 g of the desired product that is used in the next step without further purification. ¹H NMR (300 MHz, CDCl₃) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of (S)-2-(4-nitrophenyl)-1-(2-phenylthiazol-4-yl)ethanamine hydrobromide salt (52): A mixture of [3-bromo-1-(4-nitro-benzyl)-2-oxo-propyl]-carbamic acid tert-butyl ester, 51, (1.62 g, 4.17 mmol) and benzothioamide (0.630 g, 4.59 mmol), in CH₃CN (5 mL) is refluxed for 24 hours. The reaction mixture is cooled to room temperature and diethyl ether (50 mL) is added to the solution and the precipitate that forms is collected by filtration. The solid is dried under vacuum to afford 1.059 g (63%) of the desired product. ESI+MS 326 (M+1).

Preparation of (S)-4-[1-isothiocyanato-2-(4-nitrophenyl)-ethyl]-2-phenylthiazole (53): To a solution of (S)-2-(4-nitrophenyl)-1-(2-phenylthiazol-4-yl)ethanamine hydrobromide salt, 52, (2.03 g, 5 mmol) and CaCO₃ (1 g, 10 mmol)

in CCl₄/water (10:7.5 mL) is added thiophosgene (0.46 mL, 6 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue that is purified over silica (CH₂Cl₂) to afford 1.71 g (93% yield) of the desired product. ESI+ MS 368 (M+1).

Preparation of (S)-5-methyl-N-[2-(4-nitrophenyl)-1-(2-phenylthiazol-4-yl)ethyl]-1,3,4-thiadiazol-2-amine (54): A solution of (S)-4-[1-isothiocyanato-2-(4-nitrophenyl)-ethyl]-2-phenylthiazole, 53, (332 mg, 0.876 mmol) and acetic hydrazide (65 mg, 0.876 mmol) in EtOH (5 mL) is refluxed for 2 hours. The solvent is removed under reduced pressure, the residue is dissolved in POCl₃ (3 mL) and the resulting solution is stirred at room temperature for 18 hours after which the solution is heated to 50° C. for 2 hours. The solvent is removed in vacuo and the residue is dissolved in EtOAc (40 mL) and the resulting solution is treated with 1N NaOH until the pH remains approximately 8. The solution is extracted with EtOAc. The combined aqueous layers are washed with EtOAc, the organic layers combined, washed with brine, dried over MgSO₄, filtered, and concentrated in vacuo to afford 0.345 g (93% yield) of the desired product as a yellow solid. ¹H NMR (CDCl₃) 8.09 (d, J=8.4 Hz, 2H), 7.91 (m, 2H), 7.46 (m, 4H), 7.44 (s, 1H), 5.23 (m, 1H), 3.59 (m, 2H), 2.49 (s, 3H). ESI+ MS 424 (M+1).

Preparation of (S)-4-[2-(5-methyl-1,3,4-thiadiazol-2-ylamino)-2-(2-phenylthiazol-4-yl)ethyl]phenylsulfamic acid (55): (S)-5-Methyl-N-[2-(4-nitrophenyl)-1-(2-phenylthiazol-4-yl)ethyl]-1,3,4-thiadiazol-2-amine, 54, (0.404 g, 0.954 mmol) is dissolved in MeOH (5 mL). Pd/C (50 mg, 10% w/w) is added and the mixture is stirred under a hydrogen atmosphere until the reaction is judged to be complete. The reaction mixture is filtered through a bed of CELITE™ and the solvent removed under reduced pressure. The crude product is dissolved in pyridine (4 mL) and treated with SO₃-pyridine (0.304 g, 1.91 mmol). The reaction is stirred at room temperature for 5 minutes after which a 7% solution of NH₄OH (50 mL) is added. The mixture is then concentrated and the resulting residue is purified by reverse phase preparative HPLC to afford 0.052 g (11% yield) of the desired product as the ammonium salt. ¹H NMR (CD₃OD): δ 8.00-7.97 (m, 2H), 7.51-7.47 (m, 3H), 7.23 (s, 1H), 7.11-7.04 (q, 4H, J=9.0 Hz), 5.18 (t, 1H, J=7.2 Hz), 3.34-3.22 (m, 2H), 2.50 (s, 3H). ESI– MS 472 (M–1).

Scheme XX

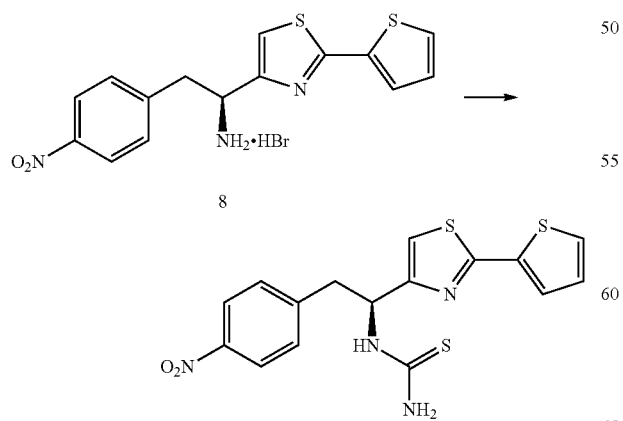

Reagents and conditions: (a) thiophosgene, CaCO₃, CCl₄/H₂O; rt, 18 hr.

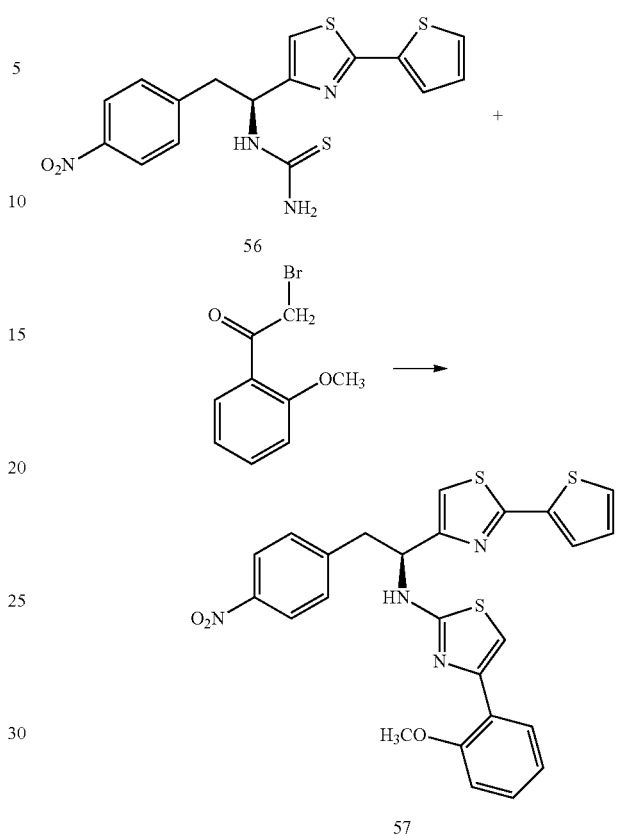

Reagents and conditions: (b) CH₃CN, reflux, 5 hours

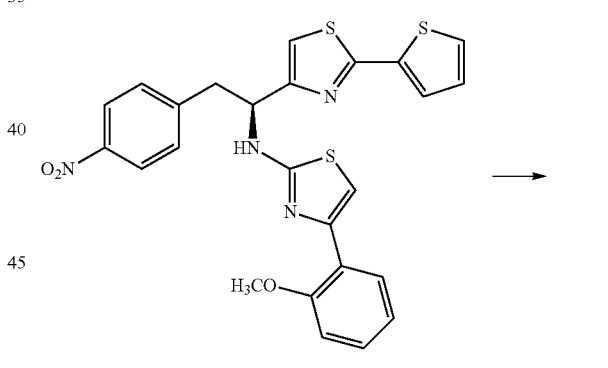

Reagents and conditions: (c) (i) H₂:Pd/C, MeOH; (ii) SO₃-pyridine, NH₄OH; rt, 18 hr.

EXAMPLE 21

4-{(S)-2-[4-(2-Methoxyphenyl)thiazol-2-ylamino)-2-[2-(thiophen-2-yl)thiazol-4-yl]ethyl}phenylsulfamic acid (58)

Preparation of (S)-1-[1-(thiophen-2-ylthiazol-4-yl)-2-(4-nitrophenyl)ethyl]-thiourea (56): To a solution of (S)-2-(4-nitrophenyl)-1-(thiophen-2-ylthiazol-4-yl)ethanamine hydrobromide salt, 8, (1.23 g, 2.98 mmol) and $CaCO_3$ (0.597 g, 5.96 mmol) in $CCl_4$/water (10 mL/5 mL) is added thiophosgene (0.412 g, 3.58 mmol). The reaction is stirred at room temperature for 18 hours then diluted with $CH_2Cl_2$ and water. The layers are separated and the aqueous layer extracted with $CH_2Cl_2$. The combined organic layers are washed with brine, dried ($Na_2SO_4$) and concentrated in vacuo to a residue which is subsequently treated with ammonia (0.5M in 1,4-dioxane, 29.4 mL, 14.7 mmol) which is purified over silica to afford 0.490 g of the desired product as a red-brown solid. ESI+ MS 399 (M+1).

Preparation of 4-(2-methoxyphenyl)-N—{(S)-2-(4-nitrophenyl)-1-[2-(thiophen-2-yl)thiazol-4-yl]ethyl}thiazol-2-amine (57): (S)-1-[1-(thiophen-2-ylthiazol-4-yl)-2-(4-nitrophenyl)ethyl]-thiourea, 56, (265 mg, 0.679 mmol) is treated with bromo-2'-methoxyacetophenone (171 mg, 0.746 mmol) to afford 0.221 g of the product as a yellow solid. ESI+ MS 521 (M+1).

Preparation on 4-{(S)-2-[4-(2-methoxyphenyl)thiazol-2-ylamino)-2-[2-(thiophen-2-yl)thiazol-4-yl]ethyl}phenylsulfamic acid (58): 4-(2-methoxyphenyl)-N—{(S)-2-(4-nitrophenyl)-1-[2-(thiophen-2-yl)thiazol-4-yl]ethyl}thiazol-2-amine, 57, (0.229 g) is dissolved in 12 mL MeOH. A catalytic amount of Pd/C (10% w/w) is added and the mixture is stirred under a hydrogen atmosphere for 18 hours. The reaction mixture is filtered through a bed of CELITE™ and the solvent is removed under reduced pressure. The crude product is dissolved in 6 mL pyridine and treated with $SO_3$-pyridine (140 mg). The reaction is stirred at room temperature for 5 minutes after which 10 mL of a 7% solution of $NH_4OH$ is added. The mixture is then concentrated and the resulting residue is purified by reverse-phase chromatography to afford 0.033 g of the desired product as the ammonium salt. $^1H$ NMR ($CD_3OD$): δ 7.96-7.93 (m, 1H), 7.60-7.55 (m, 2H), 7.29-7.23 (m, 1H), 7.18-6.95 (m, 9H), 5.15 (t, 1H, J=6.9 Hz), 3.90 (s, 3H), 3.35-3.24 (m, 2H).

Compounds according to the second aspect of Category IX which comprise a substituted or unsubstituted oxazol-2-yl unit for $R^1$ can be prepared by the procedure outlined in Scheme XXI and described herein below in Example 22. Intermediate 39 can be prepared according to Scheme XVII and Example 18.

Scheme XXI

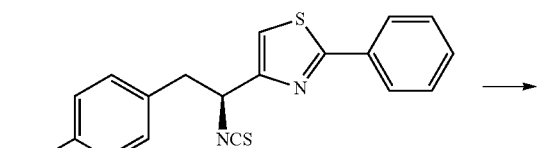

53

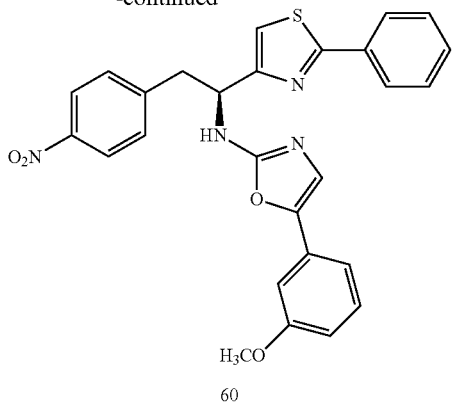

60

Reagents and conditions: (a) 1-azido-1-(3-methoxyphenyl)ethanone, $PPh_3$, dioxane, 90° C. 20 minutes.

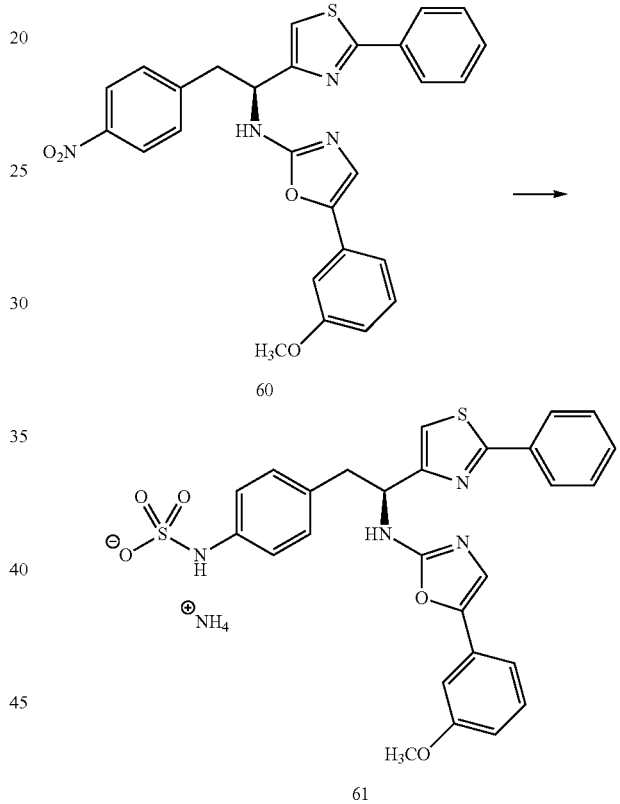

61

Reagents and conditions: (b) (i) $H_2$:Pd/C, MeOH; (ii) $SO_3$-pyridine, $NH_4OH$; rt, 18 hr.

EXAMPLE 22

4-{(S)-2-[5-(3-Methoxyphenyl)oxazole-2-ylamino]-2-(2-phenylthiazole-4-yl)ethyl}phenylsulfamic acid (61)

Preparation of [5-(3-methoxyphenyl)oxazol-2-yl]-[2-(4-nitrophenyl)-1-(2-phenylthiazole-4-yl)ethyl]amine (60): A mixture of (S)-4-(isothiocyanato-2-(4-nitrophenyl)ethyl)-2-phenylthiazole, 53, (300 mg, 0.81 mmol), 1-azido-1-(3-methoxyphenyl)ethanone (382 mg, 2.0 mmol) and $PPh_3$ (0.8 g, polymer bound, ~3 mmol/g) in dioxane (6 mL) is heated at 90° C. for 20 minutes. The reaction solution is cooled to room temperature and the solvent removed in vacuo and the resulting residue is purified over silica to afford 300 mg (74% yield) of the desired product as a yellow solid. $^1$H NMR (300 MHz, MeOH-$d_4$) δ 8.02 (d, J=7.2 Hz, 2H), 7.92-7.99 (m, 2H), 7.42-7.47 (m, 3H), 7.22-7.27 (m, 3H), 6.69-7.03 (m, 4H), 6.75-6.78 (m, 1H), 5.26 (t, J=6.3 Hz, 1H), 3.83 (s, 4H), 3.42-3.45 (m, 2H).

Preparation of 4-{(S)-2-[5-(3-methoxyphenyl)oxazole-2-ylamino]-2-(2-phenylthiazole-4-yl)ethyl}phenylsulfamic acid (61): [5-(3-methoxyphenyl)oxazol-2-yl]-[2-(4-nitrophenyl)-1-(2-phenylthiazole-4-yl)ethyl]amine, 60, (300 mg, 0.60 mmol) is dissolved in MeOH (15 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (10 mL) and treated with $SO_3$-pyridine (190 mg, 1.2 mmol). The reaction is stirred at room temperature for 5 minutes after which a 7% solution of $NH_4OH$ is added. The mixture is then concentrated and the resulting residue is purified by reverse-phase chromatography to afford 0.042 g of the desired product as the ammonium salt. $^1$H NMR (300 MHz, MeOH-$d_4$) δ 7.99 d, J=7.5 Hz, 2H), 7.46-7.50 (m, 3H), 7.23-7.29 (m, 3H), 7.04-7.12 (m, 6H), 6.78 (dd, J=8.4 and 2.4 Hz, 1H), 5.16 (t, J=6.6 Hz, 1H), 3.81 (s, 3H), 3.29-3.39 (m, 1H), 3.17 (dd, J=13.8 and 8.1 Hz, 1H).

The following are non-limiting examples of the second aspect of Category IX of the present disclosure.

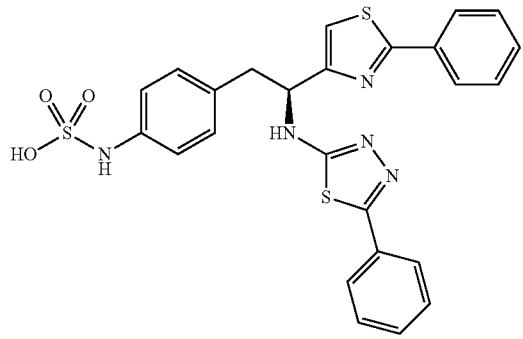 [SMILES: O=S(=O)(O)Nc1ccc(C[C@H](Nc2nnc(-c3ccccc3)s2)c2csc(-c3ccccc3)n2)cc1]

(S)-4-(2-(5-Phenyl-1,3,4-thiadiazol-2-ylamino)-2-(2-phenylthiazol-4-yl)ethyl)-phenylsulfamic acid: $^1$H NMR (CD$_3$OD): δ 7.97-7.94 (m, 2H), 7.73-7.70 (m, 2H), 7.44-7.39 (m, 6H), 7.25 (s, 1H), 7.12 (s, 4H), 5.29 (t, 1H, J=6.9 Hz), 3.35-3.26 (m, 2H).

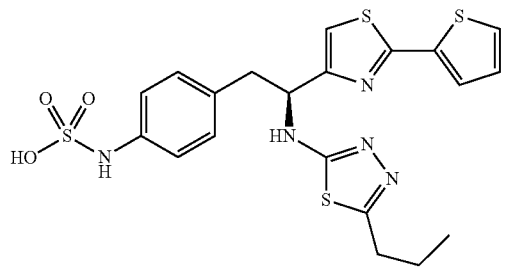 [SMILES: CCCc1nnc(N[C@@H](Cc2ccc(NS(=O)(=O)O)cc2)c2csc(-c3cccs3)n2)s1]

4-((S)-2-(5-Propyl-1,3,4-thiadiazol-2-ylamino)-2-(2-(thiophen-2-yl)thiazol-4-yl)ethyl)phenylsulfamic acid: $^1$H NMR (CD$_3$OD): δ 7.59-7.54 (m, 2H), 7.17-7.03 (m, 6H), 5.13 (t, 1H, J=7.2 Hz), 3.32-3.13 (m, 2H), 2.81 (t, 2H, J=7.4 Hz), 1.76-1.63 (h, 6H, J=7.4 Hz), 0.97 (t, 3H, J=7.3 Hz).

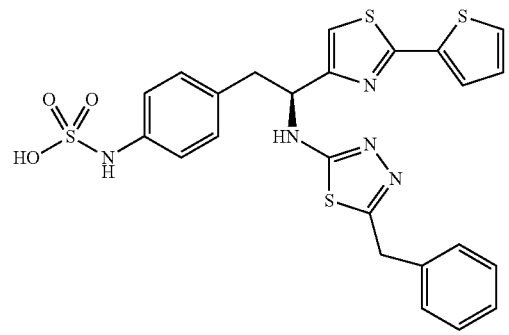 [SMILES: O=S(=O)(O)Nc1ccc(C[C@H](Nc2nnc(Cc3ccccc3)s2)c2csc(-c3cccs3)n2)cc1]

4-((S)-2-(5-Benzyl-1,3,4-thiadiazol-2-ylamino)-2-(2-(thiophen-2-yl)thiazol-4-yl)ethyl)phenylsulfamic acid: $^1$H NMR (CD$_3$OD): δ (m, 2H), 7.49-7.45 (m, 2H), 7.26-7.16 (m, 5H), 7.05-6.94 (m, 6H), 5.04 (t, 1H, J=7.1 Hz), 4.07 (s, 2H), 3.22-3.04 (m, 2H).

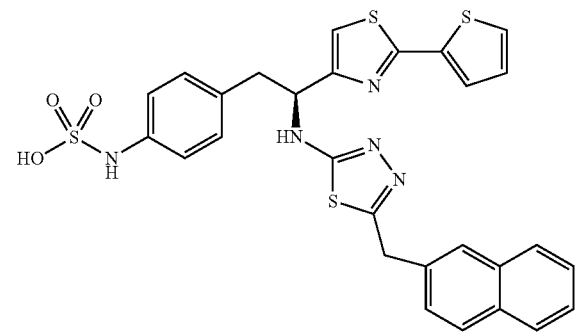 [SMILES: O=S(=O)(O)Nc1ccc(C[C@H](Nc2nnc(Cc3ccc4ccccc4c3)s2)c2csc(-c3cccs3)n2)cc1]

4-((S)-2-(5-(Naphthalen-1-ylmethyl)-1,3,4-thiadiazol-2-ylamino)-2-(2-(thiophen-2-yl)thiazol-4-yl)ethyl)phenylsulfamic acid: $^1$H NMR (CD$_3$OD): δ 8.08-8.05 (m, 1H), 7.89-7.80 (m, 2H), 7.55-7.43 (m, 6H), 7.11-7.00 (m, 6H), 5.08 (t, 1H, J=7.1 Hz), 4.63 (s, 2H), 3.26-3.08 (m, 2H).

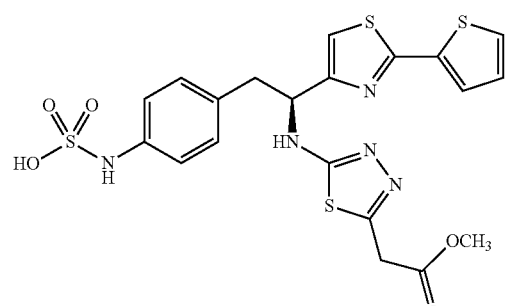

4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid: $^1$H NMR (CD$_3$OD): δ 7.48-7.44 (m, 2H), 7.03-6.92 (m, 6H), 5.02 (t, 1H, J=7.2 Hz), 4.30 (s, 2H), 3.55 (s, 3H), 3.22-3.02 (m, 2H).

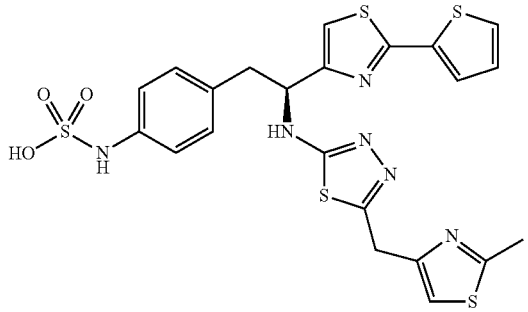 [SMILES: Cc1nc(Cc2nnc(N[C@@H](Cc3ccc(NS(=O)(=O)O)cc3)c3csc(-c4cccs4)n3)s2)cs1]

4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid: ¹H NMR (CD₃OD): δ 7.60-7.56 (m, 2H), 7.19 (s, 1H), 7.15-7.12 (m, 2H), 7.09-7.03 (q, 4H, J=8.7 Hz), 5.14 (t, 1H, J=7.2 Hz), 4.28 (s, 2H), 3.33-3.14 (m, 2H), 2.67 (s, 3H).

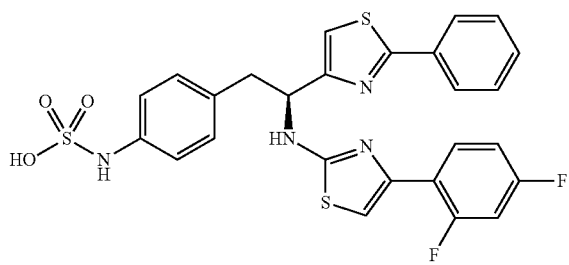 [SMILES: O=S(=O)(O)Nc1ccc(C[C@H](Nc2nc(-c3ccc(F)cc3F)cs2)c2csc(-c3ccccc3)n2)cc1]

4-{(S)-2-[4-(2,4-Difluorophenyl)thiazol-2-ylamino]-2-[2-(thiophen-2-yl)thiazol-4-yl]ethyl}phenylsulfamic acid: ¹H NMR (CD₃OD): δ 8.06-8.02 (q, 1H, J=6.8 Hz), 7.59-7.54 (m, 2H), 7.16-7.08 (m, 6H), 7.01-6.88 (m, 4H), 5.20 (t, 1H, J=7.0 Hz), 3.36-3.17 (m, 2H):

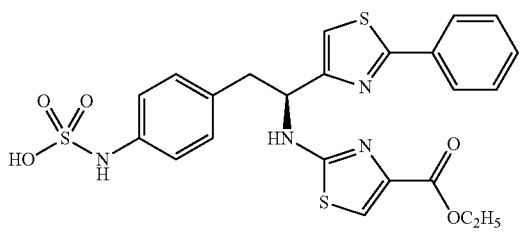 [SMILES: CCOC(=O)c1csc(N[C@@H](Cc2ccc(NS(=O)(=O)O)cc2)c2csc(-c3ccccc3)n2)n1]

(S)-4-{2-[4-(Ethoxycarbonyl)thiazol-2-ylamino]-2-(2-phenylthiazol-4-yl)ethyl}phenylsulfamic acid: ¹H NMR (CD₃OD): δ 8.02-7.99 (m, 2H), 7.54-7.45 (m, 4H), 7.26 (s, 1H), 7.08 (s, 4H), 5.26 (t, 1H, J=6.9 Hz), 4.35-4.28 (q, 2H, J=6.9 Hz), 3.38-3.18 (m, 2H), 1.36 (t, 3H, J=7.2 Hz).

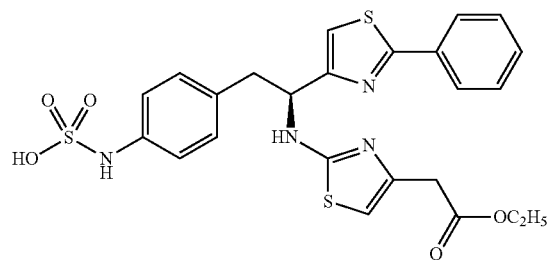 [SMILES: CCOC(=O)Cc1csc(N[C@@H](Cc2ccc(NS(=O)(=O)O)cc2)c2csc(-c3ccccc3)n2)n1]

(S)-4-{2-[4-(2-Ethoxy-2-oxoethyl)thiazol-2-ylamino]-2-(2-phenylthiazol-4-yl)ethyl}phenylsulfamic acid: ¹H NMR (CD₃OD): δ 7.96 (m, 2H), 7.50-7.46 (m, 3H), 7.21 (s, 1H), 7.10-7.04 (m, 4H), 6.37 (s, 1H), 5.09 (t, 1H, J=6.9 Hz), 4.17-4.10 (q, 2H, J=7.1 Hz), 3.54 (s, 2H), 3.35-3.14 (m, 2H), 1.22 (t, 3H, J=7.1 Hz).

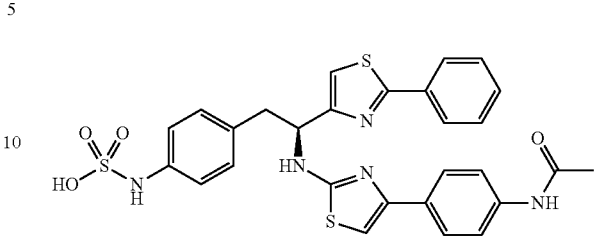

(S)-4-{2-[4-(4-acetamidophenyl)thiazol-2-ylamino]-2-(2-phenylthiazol-4-yl)ethyl}phenylsulfamic acid: ¹H NMR (CD₃OD): δ 8.11 (m, 2H), 7.82-7.80 (m, 2H), 7.71-7.61 (m, 6H), 7.40 (s, 1H), 7.23 (s, 4H), 5.32 (t, 1H, J=7.0 Hz), 3.51-3.35 (m, 2H), 2.28 (s, 3H).

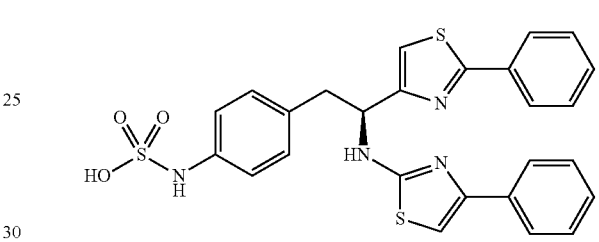

(S)-4-[2-(4-phenylthiazol-2-ylamino)-2-(2-phenylthiazol-4-yl)ethyl]phenylsulfamic acid: ¹H NMR (CD₃OD): δ 8.03-7.99 (m, 2H), 7.75-7.72 (d, 2H, J=8.4 Hz), 7.53-7.48 (m, 3H), 7.42 (m, 4H), 7.12 (s, 4H), 6.86 (s, 1H), 5.23 (t, 1H, J=7.2 Hz), 3.40-3.27 (m, 2H).

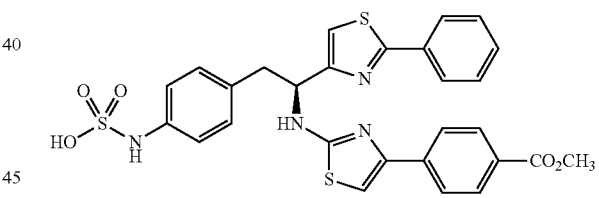

(S)-4-{2-[4-(4-(methoxycarbonyl)phenyl)thiazol-2-ylamino]-2-(2-phenylthiazol-4-yl)ethyl}phenylsulfamic acid: ¹H NMR (CD₃OD): δ 8.04-8.00 (m, 4H), 7.92-7.89 (d, 2H, J=9.0 Hz), 7.53-7.49 (m, 3H), 7.30 (s, 1H), 7.15 (s, 4H), 7.05 (s, 1H), 5.28 (t, 1H, J=6.9 Hz), 3.93 (s, 3H), 3.35-3.24 (m, 2H).

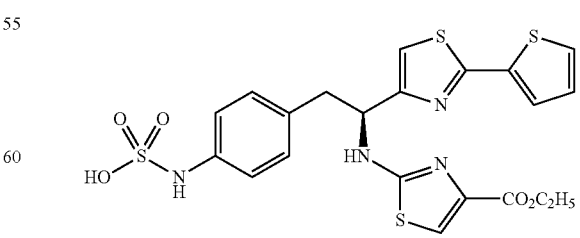

4-{(S)-2-[4-(Ethoxycarbonyl)thiazol-2-ylamino]-2-[2-(thiophen-2-yl)thiazol-4-yl]ethyl}phenylsulfamic acid: ¹H NMR (CD₃OD): δ 7.43-7.38 (m, 2H), 7.26 (s, 1H), 7.00-

6.94 (m, 3H), 6.89 (s, 4H), 5.02 (t, 1H, J=7.0 Hz), 4.16-4.09 (q, 2H, J=7.1 Hz), 3.14-2.94 (m, 2H), 1.17 (t, 3H, J=7.1 Hz).

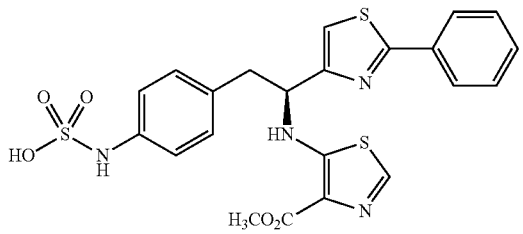 [SMILES: COC(=O)c1ncsc1N[C@@H](Cc1ccc(NS(=O)(=O)O)cc1)c1csc(-c2ccccc2)n1]

(S)-4-[2-(4-(Methoxycarbonyl)thiazol-5-ylamino)-2-(2-phenylthiazole-4-yl)ethyl]phenylsulfamic acid: $^1$H NMR (300 MHz, MeOH-d$_4$) δ 7.97-8.00 (m, 3H), 7.48-7.52 (m, 3H), 7.22 (s, 1H), 7.03-7.13 (m, 4H), 4.74 (t, J=6.6 Hz, 1H), 3.88 (s, 3H), 3.28-3.42 (m, 2H).

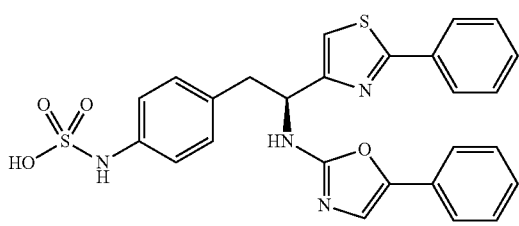 [SMILES: O=S(=O)(O)Nc1ccc(C[C@H](Nc2ncc(-c3ccccc3)o2)c2csc(-c3ccccc3)n2)cc1]

(S)-4-[2-(5-Phenyloxazol-2-ylamino)-2-(2-phenylthiazol-4-yl)ethyl]-phenylsulfamic acid: $^1$H NMR (300 MHz, MeOH-d$_4$) δ 7.94-7.96 (m, 2H), 7.45-7.49 (m, 5H), 7.32 (t, J=7.8 Hz, 2H), 7.12 (s, 1H), 7.19 (t, J=7.2 Hz, 1H), 7.12 (s, 4H), 7.05 (s, 1H), 5.15 (t, J=6.4 Hz, 1H), 3.34 (dd, J=14.1 and 8.4 Hz, 1H), 3.18 (dd, J=14.1 and 8.4 Hz, 1H).

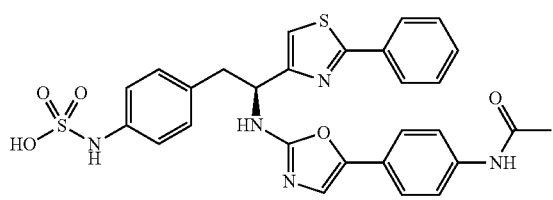 [SMILES: CC(=O)Nc1ccc(-c2cnc(N[C@@H](Cc3ccc(NS(=O)(=O)O)cc3)c3csc(-c4ccccc4)n3)o2)cc1]

(S)-4-{2-[5-(4-Acetamidophenyl)oxazol-2-ylamino]-2-(2-phenylthiazol-4-yl)ethyl}phenylsulfamic acid: $^1$H NMR (300 MHz, MeOH-d$_4$) δ 7.92-7.94 (m, 2H), 7.55-7.58 (m, 2H), 7.39-7.50 (m, 5H), 7.26 (s, 1H), 7.12 (s, 4H), 7.02 (s, 1H0), 5.14 (t, J=7.8 Hz, 1H), 3.13-3.38 (m, 2H), 2.11 (s, 3H).

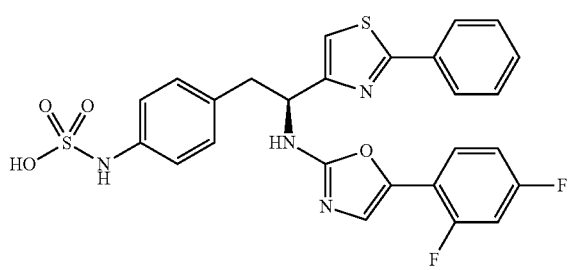 [SMILES: O=S(=O)(O)Nc1ccc(C[C@H](Nc2ncc(-c3ccc(F)cc3F)o2)c2csc(-c3ccccc3)n2)cc1]

4-((S)-2-(5-(2,4-Difluorophenyl)oxazole-2-ylamino)-2-(2-phenylthiazole-4-yl)ethyl)phenylsulfamic acid: $^1$H NMR (300 MHz, MeOH-d$_4$) δ 7.97-7.99 (m, 2H), 7.54-7.62 (m, 1H), 7.45-7.50 (m, 3H), 7.28 (s, 1H), 7.12 (s, 4H), 6.97-7.06 (m, 3H), 5.15-5.20 (m, 1H), 3.28-3.40 (m, 1H), 3.20 (dd, J=13.8 and 8.4 Hz, 1H).

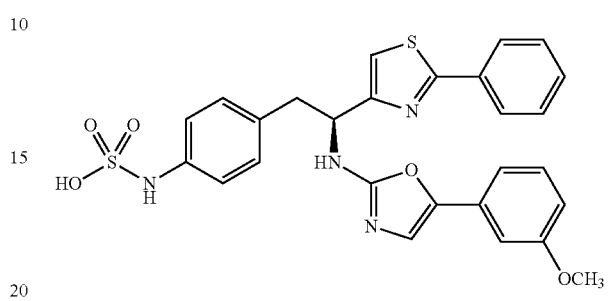

4-{(S)-2-[5-(3-Methoxyphenyl)oxazol-2-ylamino]-2-[(2-thiophen-2-yl)thiazole-4-yl]ethyl}phenylsulfamic acid: $^1$H NMR (300 MHz, MeOH-d$_4$) δ 7.55-7.60 (m, 2H), 7.26 (t, J=8.1 Hz, 1H), 7.21 (s, 1H), 7.04-7.15 (m, 8H), 6.77-6.81 (m, 1H), 5.10 (t, J=6.3 Hz, 1H), 3.81 (s, 3H), 3.29-3.36 (m, 1H), 3.15 (dd, J=14.1 and 8.4 Hz, 1H).

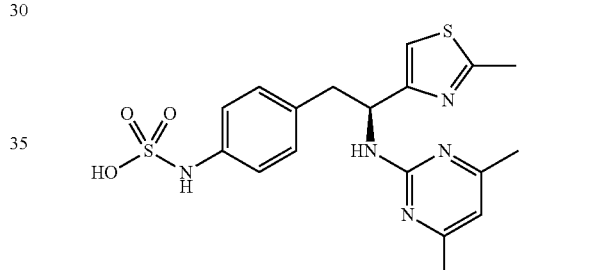

(S)-4-[2-(4,6-Dimethylpyrimidin-2-ylamino)-2-(2-methylthiazole-4-yl)ethyl]phenylsulfamic acid: $^1$H NMR (300 MHz, MeOH-d$_4$) δ 7.00-7.10 (m, 5H), 6.44 (s, 1H), 5.50 (t, J=7.2 Hz, 1H), 3.04-3.22 (m, 2H), 2.73 (s, 3H), 2.27 (s, 6H).

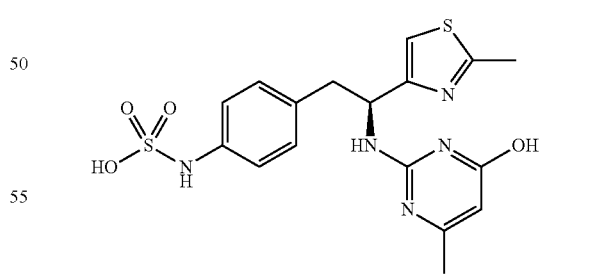

(S)-4-[2-(4-Hydroxy-6-methylpyrimidine-2-ylamino)-2-(2-methylthiazole-4-yl)ethyl]phenylsulfamic acid: $^1$H NMR (300 MHz, MeOH-d$_4$) δ 7.44 (d, J=8.4 Hz, 2H), 6.97-7.10 (m, 4H), 5.61 (s, 1H), 5.40-5.49 (m, 1H), 3.10-3.22 (m, 2H), 2.73 (s, 3H), 2.13 (s, 3H).

The first aspect of Category X of the present disclosure relates to compounds having the formula:

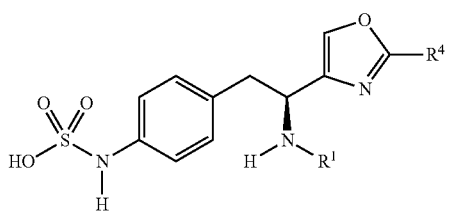

wherein R¹ is heteroaryl and R⁴ is further described below in Table XIX.

TABLE XIX

| No. | R⁴ | R¹ |
|---|---|---|
| S788 | phenyl | 4-(methoxycarbonyl)thiazol-5-yl |
| S789 | phenyl | 4-[(2-methoxy-2-oxoethyl)carbamoyl]thiazol-5-yl |
| S790 | phenyl | 5-[1-N-(2-methoxy-2-oxoethyl)-1-H-indol-3-yl]oxazol-2-yl |
| S791 | phenyl | 5-(2-methoxyphenyl)oxazol-2-yl |
| S792 | phenyl | 5-[(S)-1-(tert-butoxycarbonyl)-2-phenylethyl]oxazol-2-yl |
| S793 | phenyl | 5-[4-(methylcarboxy)phenyl]oxazol-2-yl |
| S794 | phenyl | 5-(3-methoxybenzyl)oxazol-2-yl |
| S795 | phenyl | 5-(4-phenyl)oxazol-2-yl |
| S796 | phenyl | 5-(2-methoxyphenyl)thiazol-2-yl |
| S797 | phenyl | 5-(3-methoxyphenyl)thiazol-2-yl |
| S798 | phenyl | 5-(4-fluorophenyl)thiazol-2-yl |
| S799 | phenyl | 5-(2,4-difluorophenyl)thiazol-2-yl |
| S800 | phenyl | 5-(3-methoxybenzyl)thiazol-2-yl |
| S801 | phenyl | 4-(3-methoxyphenyl)thiazol-2-yl |
| S802 | phenyl | 4-(4-fluorophenyl)thiazol-2-yl |
| S803 | thiophen-2-yl | 4-(methoxycarbonyl)thiazol-5-yl |
| S804 | thiophen-2-yl | 4-[(2-methoxy-2-oxoethyl)carbamoyl]thiazol-5-yl |
| S805 | thiophen-2-yl | 5-[1-N-(2-methoxy-2-oxoethyl)-1-H-indol-3-yl]oxazol-2-yl |
| S806 | thiophen-2-yl | 5-(2-methoxyphenyl)oxazol-2-yl |
| S807 | thiophen-2-yl | 5-[(S)-1-(tert-butoxycarbonyl)-2-phenylethyl]oxazol-2-yl |
| S808 | thiophen-2-yl | 5-[4-(methylcarboxy)phenyl]oxazol-2-yl |
| S809 | thiophen-2-yl | 5-(3-methoxybenzyl)oxazol-2-yl |
| S810 | thiophen-2-yl | 5-(4-phenyl)oxazol-2-yl |
| S811 | thiophen-2-yl | 5-(2-methoxyphenyl)thiazol-2-yl |
| S812 | thiophen-2-yl | 5-(3-methoxyphenyl)thiazol-2-yl |
| S813 | thiophen-2-yl | 5-(4-fluorophenyl)thiazol-2-yl |
| S814 | thiophen-2-yl | 5-(2,4-difluorophenyl)thiazol-2-yl |
| S815 | thiophen-2-yl | 5-(3-methoxybenzyl)thiazol-2-yl |
| S816 | thiophen-2-yl | 4-(3-methoxyphenyl)thiazol-2-yl |
| S817 | thiophen-2-yl | 4-(4-fluorophenyl)thiazol-2-yl |
| S818 | cyclopropyl | 4-(methoxycarbonyl)thiazol-5-yl |
| S819 | cyclopropyl | 4-[(2-methoxy-2-oxoethyl)carbamoyl]thiazol-5-yl |
| S820 | cyclopropyl | 5-[1-N-(2-methoxy-2-oxoethyl)-1-H-indol-3-yl]oxazol-2-yl |
| S821 | cyclopropyl | 5-(2-methoxyphenyl)oxazol-2-yl |
| S822 | cyclopropyl | 5-[(S)-1-(tert-butoxycarbonyl)-2-phenylethyl]oxazol-2-yl |
| S823 | cyclopropyl | 5-[4-(methylcarboxy)phenyl]oxazol-2-yl |
| S824 | cyclopropyl | 5-(3-methoxybenzyl)oxazol-2-yl |
| S825 | cyclopropyl | 5-(4-phenyl)oxazol-2-yl |
| S826 | cyclopropyl | 5-(2-methoxyphenyl)thiazol-2-yl |
| S827 | cyclopropyl | 5-(3-methoxyphenyl)thiazol-2-yl |
| S828 | cyclopropyl | 5-(4-fluorophenyl)thiazol-2-yl |
| S829 | cyclopropyl | 5-(2,4-difluorophenyl)thiazol-2-yl |
| S830 | cyclopropyl | 5-(3-methoxybenzyl)thiazol-2-yl |
| S831 | cyclopropyl | 4-(3-methoxyphenyl)thiazol-2-yl |
| S832 | cyclopropyl | 4-(4-fluorophenyl)thiazol-2-yl |

Compounds according to the first aspect of Category X can be prepared by the procedure outlined in Scheme XXII and described below in Example 23.

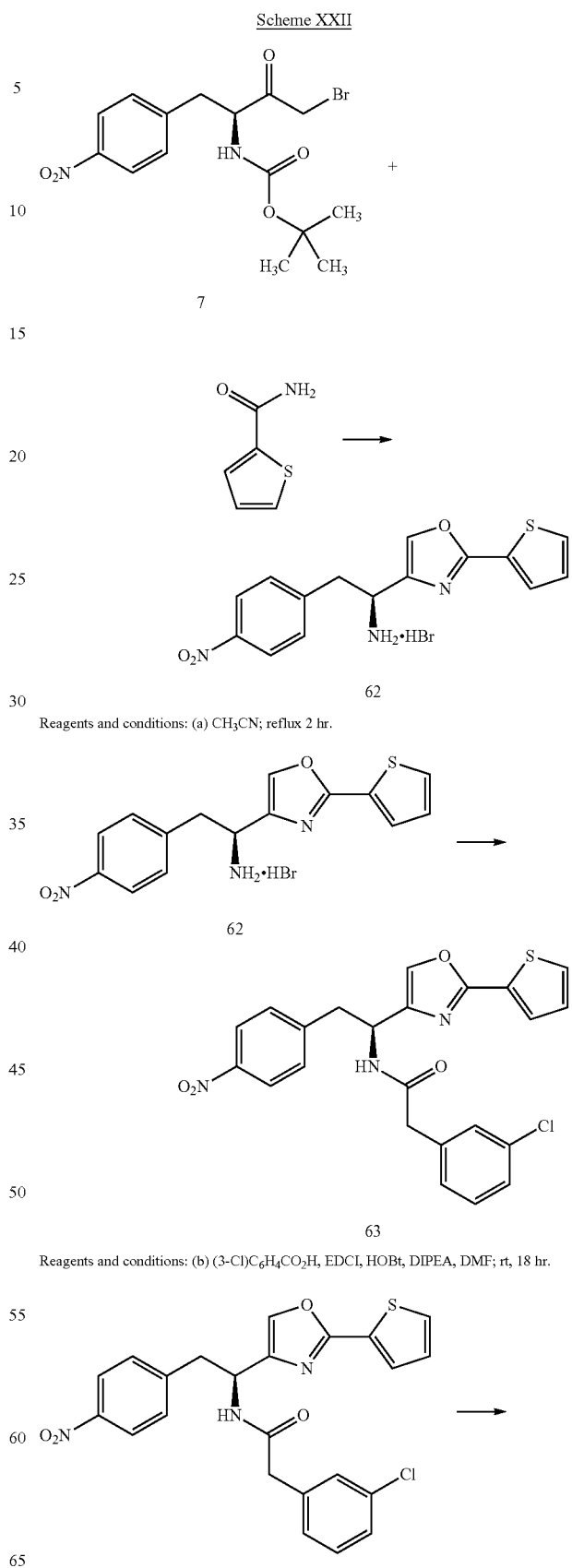

-continued

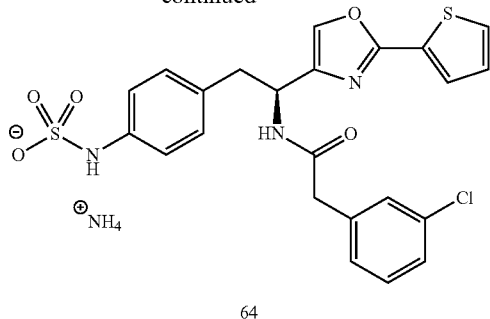

64

Reagents and conditions: (c) (i) H₂:Pd/C, MeOH; (ii) SO₃-pyridine, NH₄OH, rt, 18 hr.

EXAMPLE 23

4-((S)-2-(2-(3-Chlorophenyl)acetamido)-2-(2-(thiophen-2-yl)oxazol-4-yl)ethyl)phenylsulfamic acid (64)

Preparation of (S)-2-(4-nitrophenyl)-1-[(thiophen-2-yl)oxazol-4-yl]ethanamine hydrobromide salt (62): A mixture of (S)-tert-butyl 4-bromo-1-(4-nitrophenyl)-3-oxobutan-2-ylcarbamate, 7, (38.7 g, 100 mmol), and thiophen-2-carboxamide (14 g, 110 mmol) (available from Alfa Aesar) in CH₃CN (500 mL) is refluxed for 5 hours. The reaction mixture is cooled to room temperature and diethyl ether (200 mL) is added to the solution. The precipitate which forms is collected by filtration. The solid is dried under vacuum to afford the desired product which can be used for the next step without purification.

Preparation of 2-(3-chlorophenyl)-N—{(S)-2-(4-nitrophenyl)-1-[2-(thiophen-2-yl)oxazol-4-yl]ethyl}acetamide (63): To a solution of (S)-2-(4-nitrophenyl)-1-[(thiophen-2-yl)oxazol-4-yl]ethanamine HBr, 47, (3.15 g, 10 mmol) 3-chlorophenyl-acetic acid (1.70 g, 10 mmol) and 1-hydroxybenzotriazole (HOBt) (0.70 g, 5.0 mmol) in DMF (50 mL) at 0° C., is added 1-(3-dimethylaminopropyl)-3-ethylcarbodiimide (EDCI) (1.90 g, 10 mmol) followed by triethylamine (4.2 mL, 30 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford the desired product which is used without further purification.

Preparation of —((S)-2-(2-(3-chlorophenyl)acetamido)-2-(2-(thiophen-2-yl)oxazol-4-yl)ethyl)phenylsulfamic acid (64): 2-(3-chlorophenyl)-N—{(S)-2-(4-nitrophenyl)-1-[2-(thiophen-2-yl)oxazol-4-yl]ethyl}acetamide, 63, (3 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.157 g). The reaction is stirred at room temperature for 5 minutes after which a 7% solution of NH₄OH is added. The mixture is then concentrated and the resulting residue can be purified by reverse phase chromatography to afford the desired product as the ammonium salt.

The second aspect of Category X of the present disclosure relates to compounds having the formula:

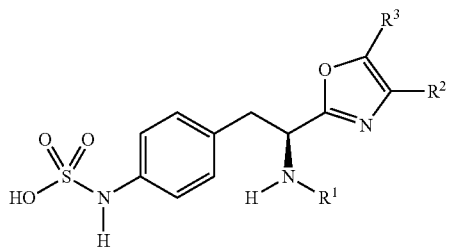

wherein $R^1$ is aryl and $R^2$ and $R^3$ are further described herein below in Table XX.

TABLE XX

| No. | $R^2$ | $R^3$ | $R^1$ |
|---|---|---|---|
| T833 | methyl | hydrogen | phenyl |
| T834 | methyl | hydrogen | benzyl |
| T835 | methyl | hydrogen | 2-fluorophenyl |
| T836 | methyl | hydrogen | 3-fluorophenyl |
| T837 | methyl | hydrogen | 4-fluorophenyl |
| T838 | methyl | hydrogen | 2-chlorophenyl |
| T839 | methyl | hydrogen | 3-chlorophenyl |
| T840 | methyl | hydrogen | 4-chlorophenyl |
| T841 | ethyl | hydrogen | phenyl |
| T842 | ethyl | hydrogen | benzyl |
| T843 | ethyl | hydrogen | 2-fluorophenyl |
| T844 | ethyl | hydrogen | 3-fluorophenyl |
| T845 | ethyl | hydrogen | 4-fluorophenyl |
| T846 | ethyl | hydrogen | 2-chlorophenyl |
| T847 | ethyl | hydrogen | 3-chlorophenyl |
| T848 | ethyl | hydrogen | 4-chlorophenyl |
| T849 | thien-2-yl | hydrogen | phenyl |
| T850 | thien-2-yl | hydrogen | benzyl |
| T851 | thien-2-yl | hydrogen | 2-fluorophenyl |
| T852 | thien-2-yl | hydrogen | 3-fluorophenyl |
| T853 | thien-2-yl | hydrogen | 4-fluorophenyl |
| T854 | thien-2-yl | hydrogen | 2-chlorophenyl |
| T855 | thien-2-yl | hydrogen | 3-chlorophenyl |
| T856 | thiene-2-yl | hydrogen | 4-chlorophenyl |

Compounds according to the second aspect of Category X can be prepared by the procedure outlined in Scheme XXIII and described below in Example 24.

Scheme XXIII

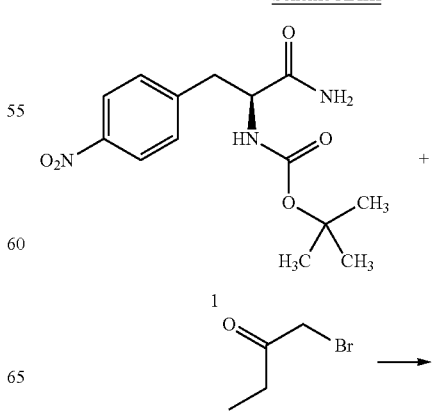

-continued

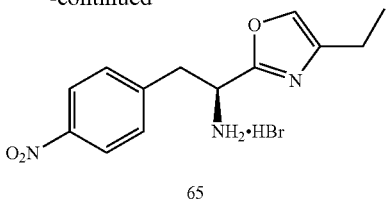

65

Reagents and conditions: (a) CH₃CN; reflux, 2 hr.

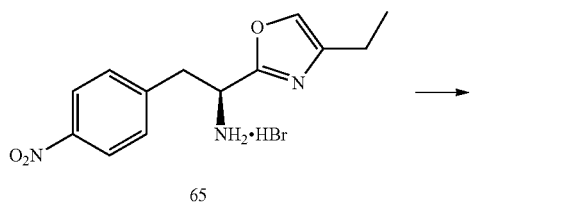

66

Reagents and conditions: (b) C₆H₅CH₂CO₂H, EDCI, HOBt, DIPEA, DMF; rt, 18 hr.

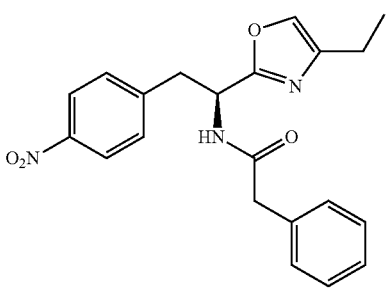

66

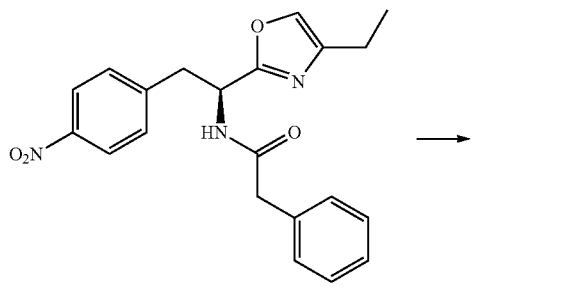

67

Reagents and conditions: (c) (i) H₂:Pd/C, MeOH; (ii) SO₃-pyridine, NH₄OH, rt, 18 hr.

EXAMPLE 24

{4-[2-(S)-(4-Ethyloxazol-2-yl)-2-phenylacetylaminoethyl]-phenyl}sulfamic acid (67)

Preparation of (S)-1-(4-ethyloxazol-2-yl)-2-(4-nitrophenyl)ethanamine (65): A mixture of [1-(S)-carbamoyl-2-(4-nitrophenyl)ethyl-carbamic acid tert-butyl ester, 1, (10 g, 32.3 mmol) and 1-bromo-2-butanone (90%, 4.1 mL, 36 mmol) in CH₃CN (500 mL) is refluxed for 18 hours. The reaction mixture is cooled to room temperature and diethyl ether is added to the solution and the precipitate which forms is removed by filtration and is used without further purification.

Preparation of N-[1-(4-ethyloxazol-2-yl)-2-(4-nitrophenyl)ethyl]-2-phenyl-acetamide (66): To a solution of (S)-1-(4-ethyloxazol-2-yl)-2-(4-nitrophenyl)ethanamine, 65, (2.9 g, 11 mmol), phenylacetic acid (1.90 g, 14 mmol) and 1-hydroxybenzotriazole (HOBt) (0.94 g, 7.0 mmol) in DMF (100 mL) at 0° C., is added 1-(3-dimethylaminopropyl)-3-ethylcarbodiimide (EDCI) (2.68 g, 14 mmol) followed by triethylamine (6.0 mL, 42 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford the desired product which is used without further purification.

Preparation of {4-[2-(S)-(4-ethyloxazol-2-yl)-2-phenylacetylaminoethyl]-phenyl}sulfamic acid (67): N-[1-(4-ethyloxazol-2-yl)-2-(4-nitrophenyl)ethyl]-2-phenyl-acetamide, 66, (0.260 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.177 g, 1.23). The reaction is stirred at room temperature for 5 minutes after which a 7% solution of NH₄OH (10 mL) is added. The mixture is then concentrated and the resulting residue is purified by reverse phase chromatography to afford the desired product as the ammonium salt.

Non-limiting examples of the HPTP-β IC$_{50}$ μM) activity for illustrative compounds are listed in Table XXI. HPTP-β inhibition can be tested by any method chosen by the formulator, for example, Amarasinge K. K. et al., "Design and Synthesis of Potent, Non-peptidic Inhibitors of HPTP-beta" *Bioorg Med Chem. Lett.* 2006 Aug. 15; 16(16):4252-6. Epub 2006 Jun. 12. Erratum in: *Bioorg Med Chem. Lett.* 2008 Aug. 15; 18(16):4745. Evdokimov, Artem G [corrected to Evdokimov, Artem G]: PMID: 16759857; and Klopfenstein S. R. et al. "1,2,3,4-Tetrahydroisoquinolinyl Sulfamic Acids as Phosphatase PTP1B Inhibitors" *Bioorg Med Chem. Lett.* 2006 Mar. 15; 16(6):1574-8, both of which are incorporated herein by reference in their entirety.

TABLE XXI
| No. | Compound | HPTP-β IC$_{50}$ μM |
|---|---|---|
| AA1 | 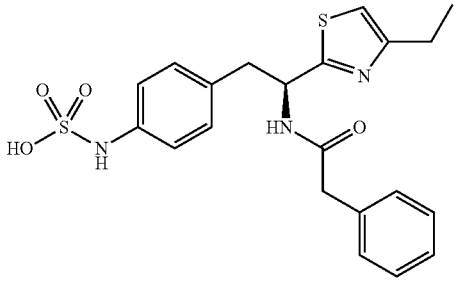<br>(S)-{4-[2-(4-Ethylthiazol-2-yl)-2-(phenylacetylamino)ethyl]-phenyl}sulfamic acid | 0.000157 |
| AA2 | 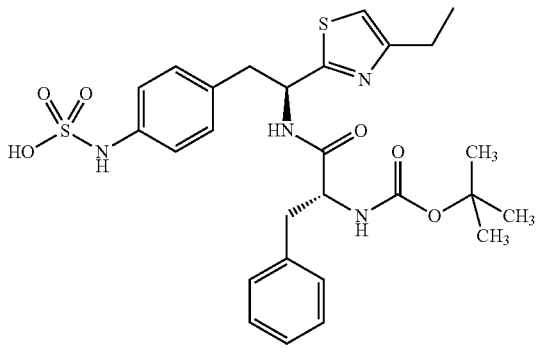<br>4-{(S)-2-[(R)-2-(tert-butoxycarbonylamino)-3-phenylpropanamido]-2-(4-ethylthiazol-2-yl)ethyl}phenylsulfamic acid | 0.004 |
| AA3 | 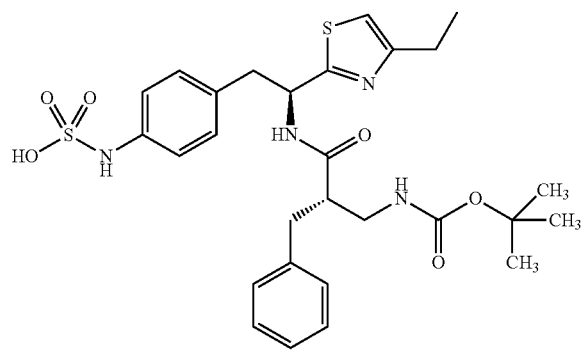<br>{1-[1-(5-Ethylthiazol-2-yl)-(S)-2-(4-sulfoaminophenyl)ethyl-carbamoyl]-(S)-2-phenylethyl}methyl carbamic acid tert-butyl ester | 0.031 |

TABLE XXI-continued
| No. | Compound | HPTP-β IC$_{50}$ μM |
|---|---|---|
| AA4 | 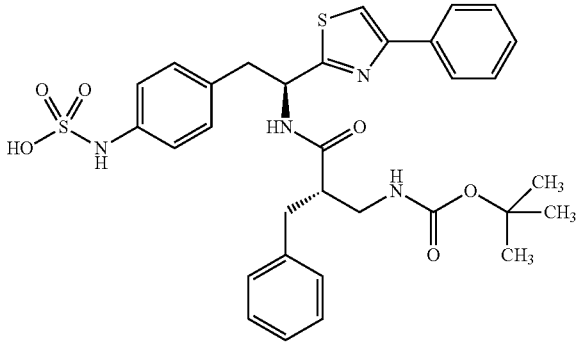{1-[1-(5-phenylthiazol-2-yl)-(S)-2-(4-sulfoaminophenyl)ethylcarbamoyl]-(S)-2-phenylethyl}methyl carbamic acid tert-butyl ester | <5 × 10$^{-8}$ |
| AA5 | 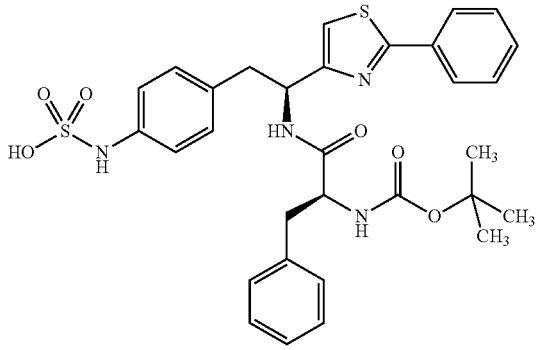4-{(S)-2-(S)-2-(tert-Butoxycarbonylamino)-3-phenylpropanamido-2-(2-phenylthiazol-4-yl)}phenylsulfamic acid | <5 × 10$^{-8}$ |
| AA6 | 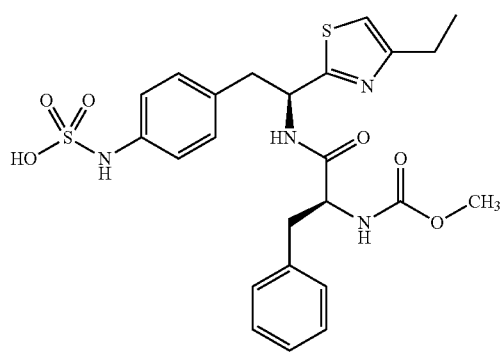4-{(S)-2-(4-Ethylthiazol-2-yl)-2-[(S)-2-(methoxycarbonylamino)-3-phenylpropanamido]ethyl}phenylsulfamic acid | 0.000162 |

TABLE XXI-continued
| No. | Compound | HPTP-β IC$_{50}$ μM |
|---|---|---|
| AA7 | 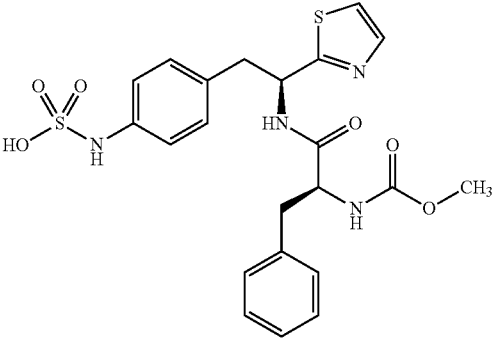<br>4-{(S)-2-[(S)-2-(Methoxycarbonylamino)-3-phenylpropanamido]-2-(thiazol-2-yl)ethyl}phenylsulfamic acid | 0.006 |
| AA8 | 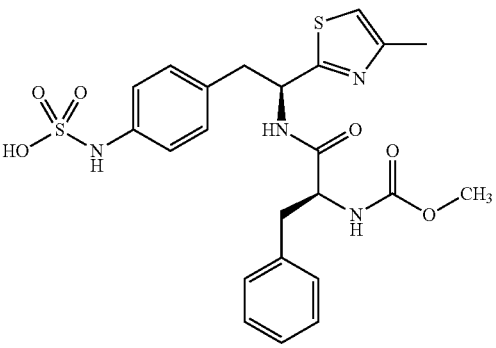<br>4-{(S)-2-[(S)-2-(Methoxycarbonylamino)-3-phenylpropanamido]-2-(4-methylthiazol-2-yl)ethyl}phenylsulfamic acid | 0.001 |
| AA9 | 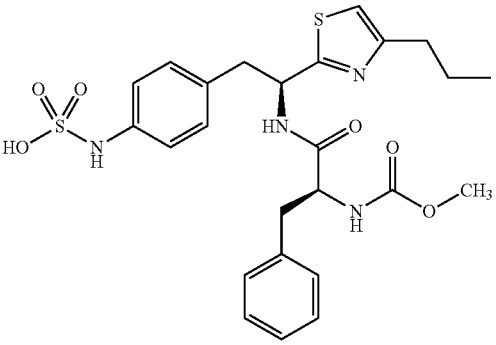<br>4-{(S)-2-[(S)-2-(Methoxycarbonylamino)-3-phenylpropanamido]-2-(4-propylthiazol-2-yl)ethyl}phenylsulfamic acid | 0.0001 |

TABLE XXI-continued

| No. | Compound | HPTP-β IC$_{50}$ μM |
|---|---|---|
| AA10 | 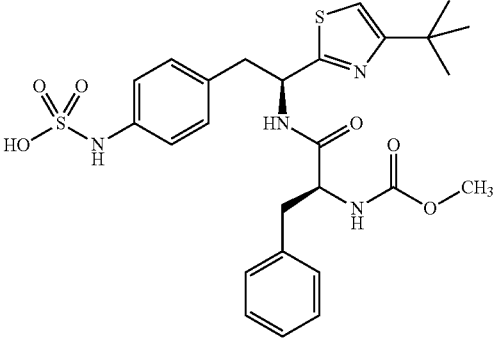<br>4-{(S)-2-(4-tert-Butylthiazol-2-yl)-2-[(S)-2-(methoxycarbonylamino)-3-phenylpropanamido]ethyl}phenylsulfamic acid | 0.0002 |
| AA11 | 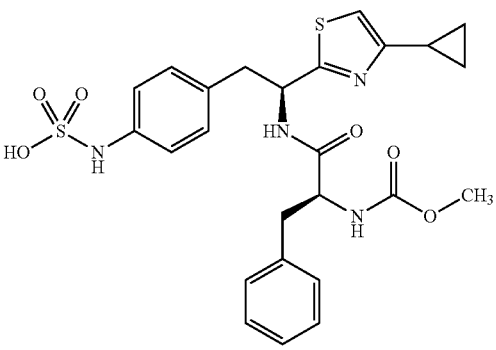<br>4-{(S)-2-(4-Cyclopropylthiazol-2-yl)-2-[(S)-2-(methoxycarbonylamino)-3-phenylpropanamido]ethyl}phenylsulfamic acid | 0.00001 |
| AA12 | 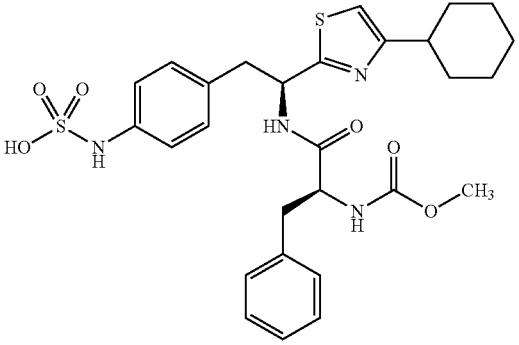<br>4-{(S)-2-(4-Cyclohexylthiazol-2-yl)-2-[(S)-2-(methoxycarbonylamino)-3-phenylpropanamido]ethyl}phenylsulfamic acid | $<5 \times 10^{-8}$ |

TABLE XXI-continued
| No. | Compound | HPTP-β IC$_{50}$ μM |
|---|---|---|
| AA13 | 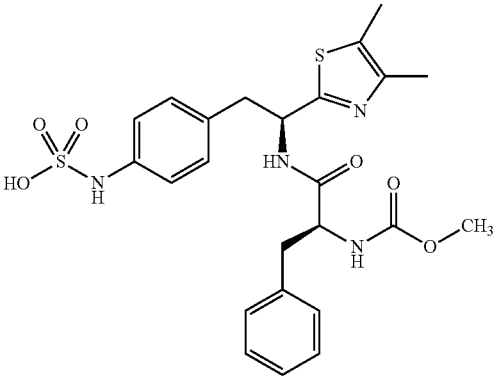<br>4-{(S)-2-(4,5-Dimethylthiazol-2-yl)-2-[(S)-2-(methoxycarbonylamino)-3-phenyl-propanamido]ethyl}phenylsulfamic acid | 0.001 |
| AA14 | 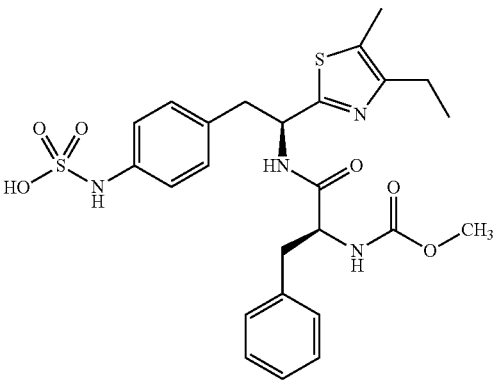<br>4-{(S)-2-(4-Ethyl-5-methylthiazol-2-yl)-2-[(S)-2-(methoxy-carbonylamino)-3-phenyl-propanamido]ethyl}phenylsulfamic acid | 0.0001 |
| AA15 | 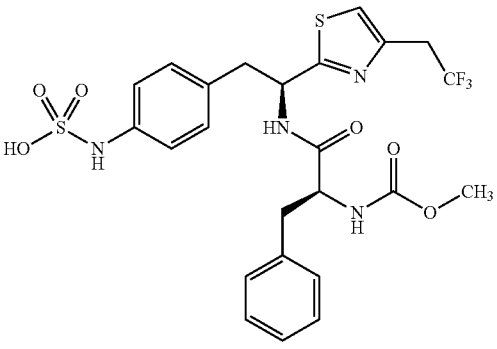<br>4-{(S)-2-[(S)-2-(Methoxycarbonylamino)-3-phenylpropanamido]-2-[4-(2,2,2-trifluoroethyl)thiazol-2-yl]ethyl}phenylsulfamic acid | 0.0003 |

TABLE XXI-continued

| No. | Compound | HPTP-β IC$_{50}$ μM |
|---|---|---|
| AA16 | 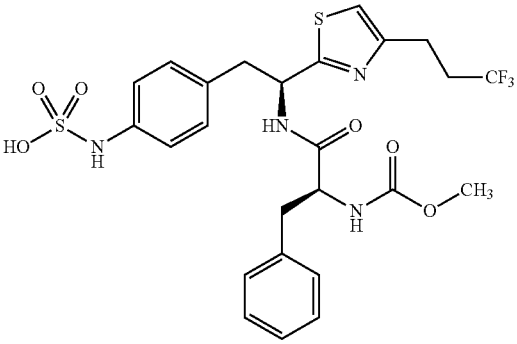<br>4-{(S)-2-[(S)-2-(Methoxycarbonylamino)-3-phenylpropanamido)-2-[4-(3,3,3-trifluoropropyl)thiazol-2-yl]ethyl}phenylsulfamic acid | 0.00008 |
| AA17 | 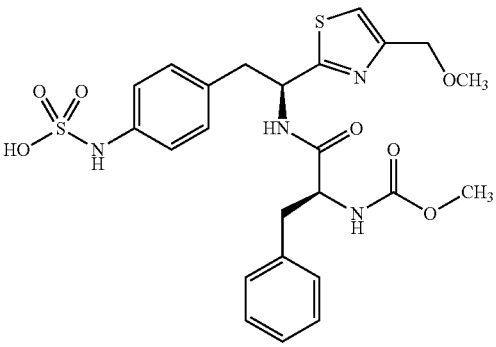<br>4-{(S)-2-[(S)-2-(Methoxycarbonylamino)-3-phenylpropanamido]-2-[4-(methoxymethyl)thiazol-2-yl]ethyl}phenylsulfamic acid | 0.001 |
| AA18 | 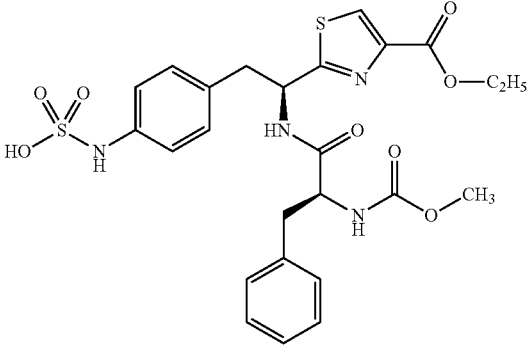<br>4-{(S)-2-(4-(Ethoxycarbonyl)thiazol-2-yl)-2-[(S)-2-(methoxy-carbonylamino)-3-phenylpropanamido]ethyl}phenylsulfamic acid | 0.0002 |

TABLE XXI-continued

| No. | Compound | HPTP-β IC$_{50}$ μM |
|---|---|---|
| AA19 | 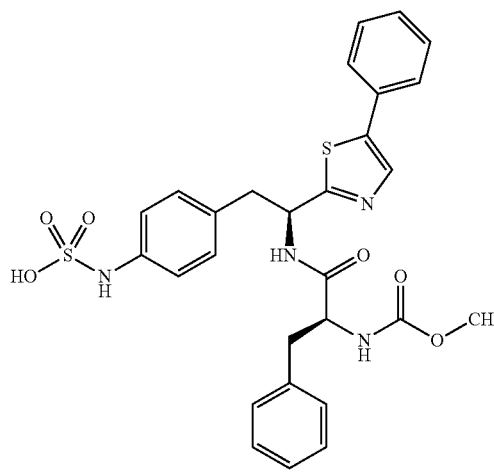 4-{(S)-2-[(S)-2-(Methoxycarbonylamino)-3-phenylpropanamido]-2-(5-phenylthiazol-2-yl)ethyl}phenylsulfamic acid | 0.0003 |
| AA20 | 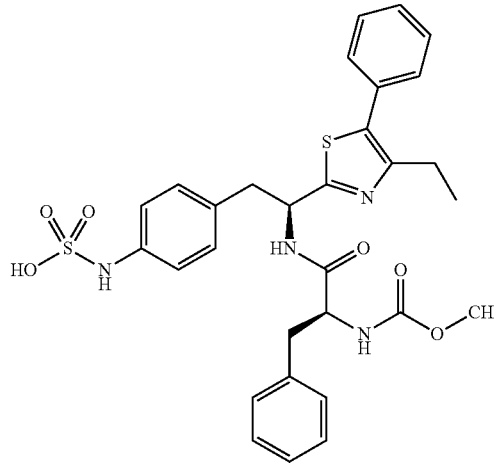 4-{(S)-2-(4-Ethyl-5-phenylthiazol-2-yl)-2-[(S)-2-(methoxy-carbonylamino)-3-phenyl-propanamido]ethyl}phenylsulfamic acid | $<5 \times 10^{-8}$ |
| AA21 | 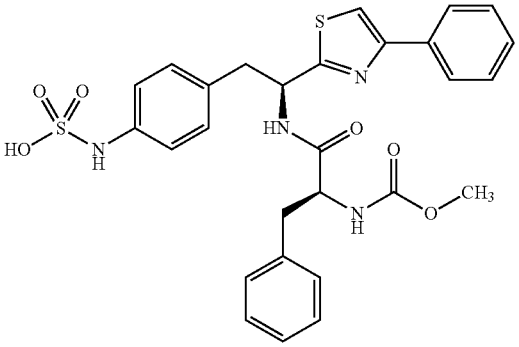 4-{(S)-2-[(S)-2-(Methoxycarbonylamino)-3-phenylpropanamido]-2-(4-phenylthiazol-2-yl)ethyl}phenylsulfamic acid | $<2 \times 10^{-6}$ |

TABLE XXI-continued

| No. | Compound | HPTP-β IC$_{50}$ μM |
|---|---|---|
| AA22 | 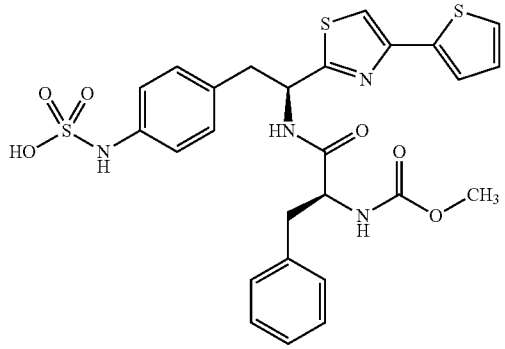<br>4-{(S)-2-[(S)-2-(Methoxycarbonylamino)-3-phenylpropanamido]-2-[4-(thiophen-2-yl)thiazol-2-yl]ethyl}phenylsulfamic acid | <5 × 10$^{-8}$ |
| AA23 | 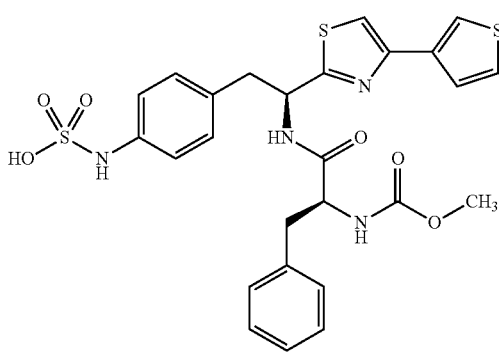<br>4-{(S)-2-[(S)-2-(Methoxycarbonylamino)-3-phenylpropanamido]-2-[4-(thiophen-3-yl)thiazol-2-yl]ethyl}phenylsulfamic acid | 0.00009 |
| AA24 | 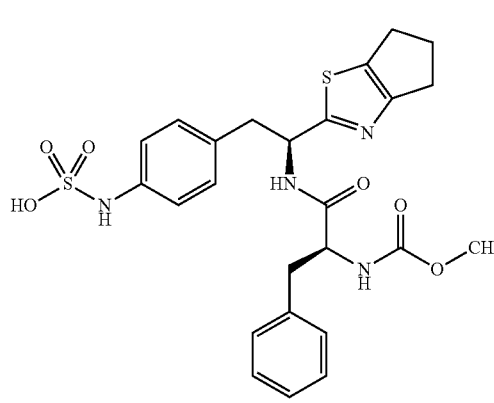<br>4-{(S)-2-(5,6-Dihydro-4H-cyclopenta[d]thiazol-2-yl)-2-[(S)-2-(methoxycarbonylamino)-3-phenylpropanamido]ethyl}phenylsulfamic acid | 0.001 |

TABLE XXI-continued

| No. | Compound | HPTP-β IC$_{50}$ μM |
|---|---|---|
| AA25 | 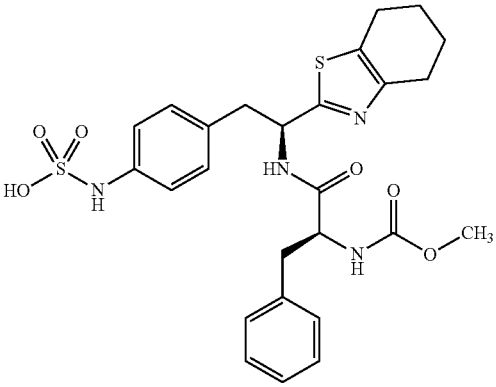<br>4-{(S)-2-[(S)-2-(Methoxycarbonylamino)-3-phenylpropanamido]-2-(4,5,6,7-tetrahydrobenzo[d]thiazol-2-yl)ethyl}phenylsulfamic acid | 0.0004 |
| AA26 | 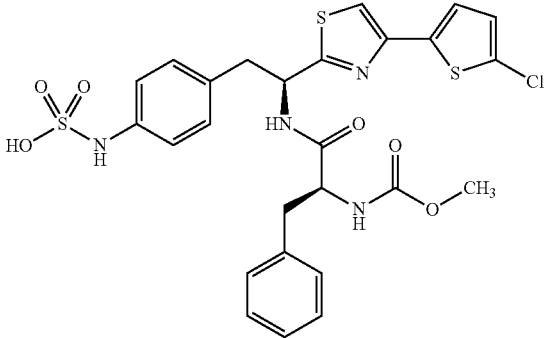<br>4-{(S)-2-[4-(5-Chlorothiophen-2-yl)thiazol-2-yl]-2-[(S)-2-(methoxycarbonylamino)-3-phenylpropanamido]ethyl}phenyl-sulfamic acid | <5 × 10$^{-8}$ |
| AA27 | 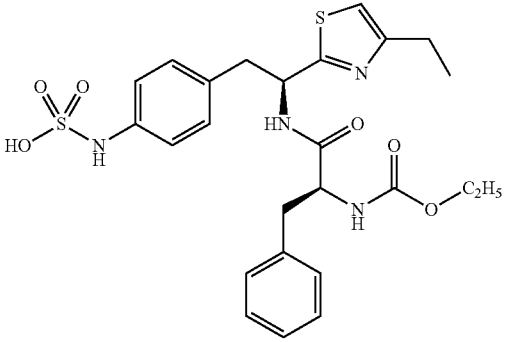<br>4-{(S)-2-[(S)-2-(Ethoxycarbonylamino)-3-phenylpropanamido]-2-(4-ethylthiazol-2-yl)ethyl}phenylsulfamic acid | 0.00014 |

TABLE XXI-continued
| No. | Compound | HPTP-β IC$_{50}$ μM |
|---|---|---|
| AA28 | 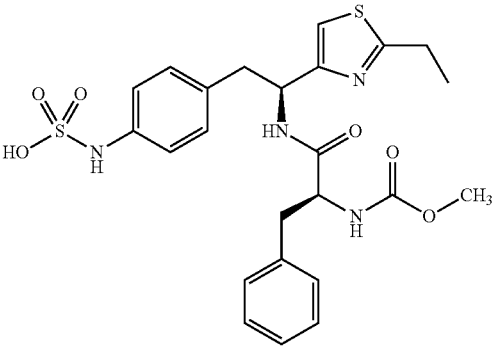4-{(S)-2-[(S)-2-(Methoxycarbonylamino)-3-phenylpropanamido]-2-(2-ethylthiazol-4-yl)ethyl}phenylsulfamic acid | 0.0001 |
| AA29 | 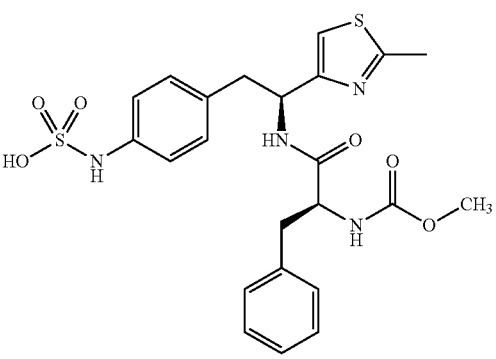4-{(S)-2-[(S)-2-(Methoxycarbonylamino)-3-phenylpropanamido]-2-(2-methylthiazol-4-yl)ethyl}phenylsulfamic acid | 0.001 |
| AA30 | 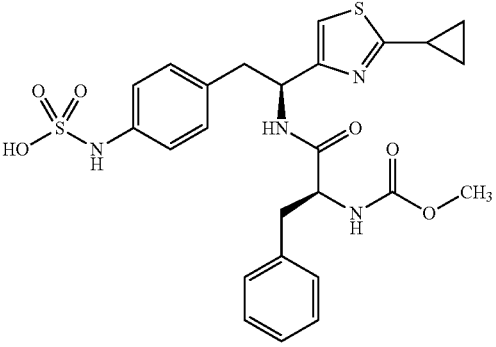4-{(S)-2-(2-Cyclopropylthiazol-4-yl)-2-[(S)-2-(methoxycarbonylamino)-3-phenylpropanamido]ethyl}phenylsulfamic acid | 0.0002 |

TABLE XXI-continued

| No. | Compound | HPTP-β IC$_{50}$ μM |
|---|---|---|
| AA31 | 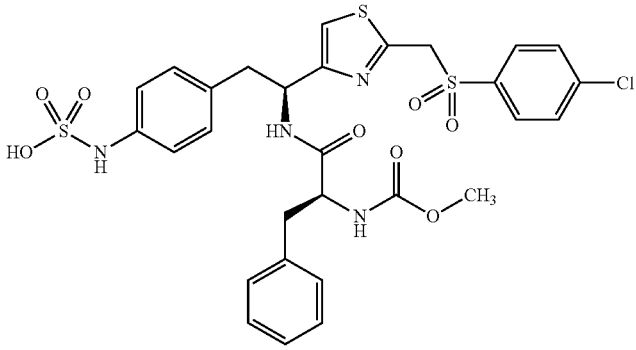  4-{(S)-2-{2-[(4-Chlorophenylsulfonyl)methyl]thiazol-4-yl}-2-[(S)-2-(methoxycarbonylamino)-3-phenylpropanamido]ethyl}phenylsulfamic acid | 0.00008 |
| AA32 | 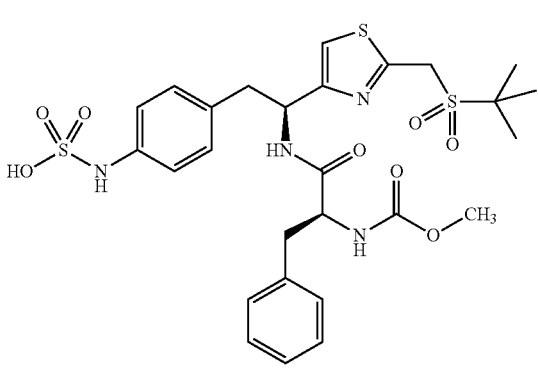  4-{(S)-2-[2-(tert-Butylsulfonylmethyl)thiazol-4-yl]-2-[(S)-2-(methoxycarbonylamino)-3-phenylpropanamido]ethyl}phenylsulfamic acid | 0.002 |
| AA33 | 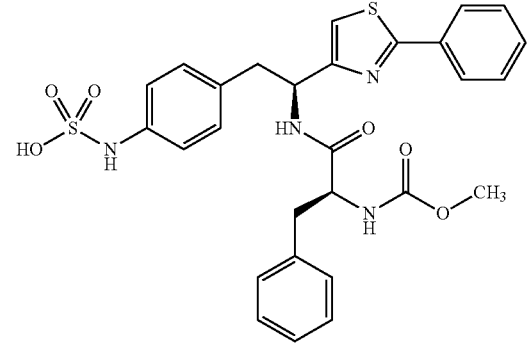  4-{(S)-2-[(S)-2-(Methoxycarbonylamino)-3-phenylpropionamido]-2-(2-phenylthiazole-4-yl)ethyl}phenylsulfamic acid | 7 × 10$^{-7}$ |

TABLE XXI-continued

| No. | Compound | HPTP-β IC$_{50}$ μM |
|---|---|---|
| AA34 | 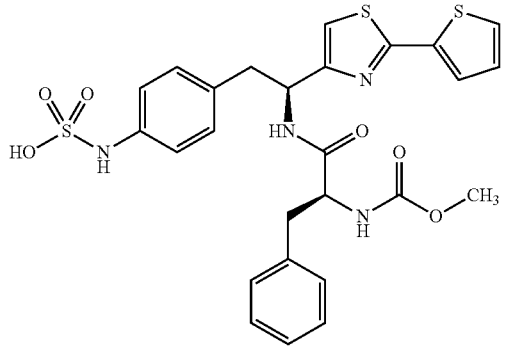 4-{(S)-2-[(S)-2-(Methoxycarbonylamino)-3-phenylpropanamido]-2-[2-(thiophen-2-yl)thiazol-4-yl]ethyl}phenylsulfamic acid | $5 \times 10^{-8}$ |
| AA35 | 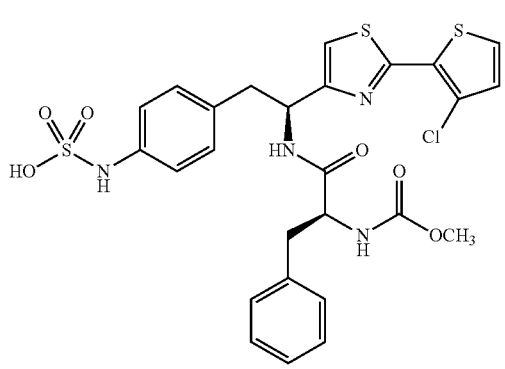 4-{(S)-2-[2-(3-Chlorothiophen-2-yl)thiazol-4-yl]-2-[(S)-2-(methoxycarbonylamino)-3-phenylpropanamido]ethyl}phenylsulfamic acid | $<5 \times 10^{-8}$ |
| AA36 | 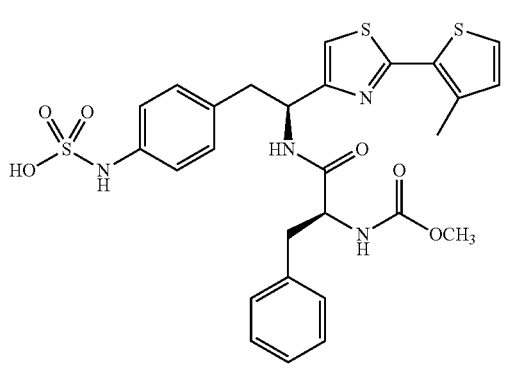 4-{(S)-2-[(S)-2-(Methoxycarbonylamino)-3-phenylpropanamido]-2-[2-(3-methylthiophen-2-yl)thiazol-4-yl]ethyl}phenylsulfamic acid | $<5 \times 10^{-8}$ |

TABLE XXI-continued
| No. | Compound | HPTP-β IC$_{50}$ μM |
|---|---|---|
| AA37 | 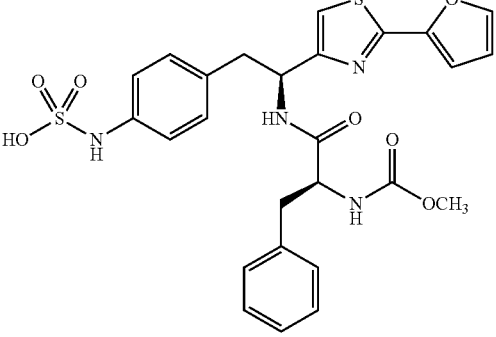<br>4-{[(S)-2-(2-(Furan-2-yl)thiazol-4-yl]-2-[(S)-2-(methoxy-carbonylamino)-3-phenylpropanamido]ethyl}phenylsulfamic acid | 0.0004 |
| AA38 | 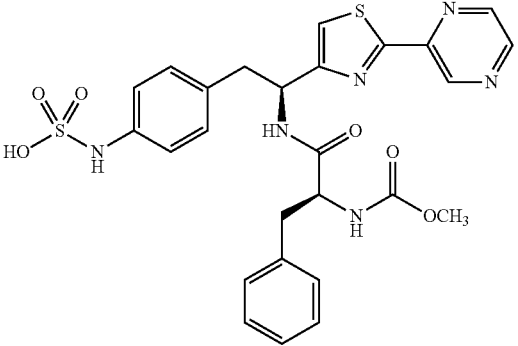<br>4-{(S)-2-[(S)-2-(Methoxycarbonylamino)-3-phenylpropanamido]-2-[2-(pyrazin-2-yl)thiazol-4-yl]ethyl}phenylsulfamic acid | 0.003 |
| AA39 | 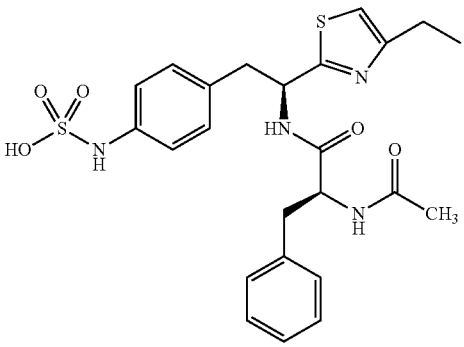<br>4-[(S)-2-((S)-2-Acetamido-3-phenylpropanamido)-2-(4-ethylthiazol-2-yl)ethyl]phenylsulfamic acid | 0.001 |

TABLE XXI-continued

| No. | Compound | HPTP-β IC$_{50}$ μM |
|---|---|---|
| AA40 | 4-[(S)-2-((S)-2-Acetamido-3-phenylpropanamido)-2-(4-tert-butylthiazol-2-yl)ethyl]phenylsulfamic acid | 0.0003 |
| AA41 | 4-{(S)-2-((S)-2-Acetamido-3-phenylpropanamido)-2-[4-(thiophen-3-yl)thiazol-2-yl]ethyl}phenylsulfamic acid | 0.00024 |
| AA42 | 4-{(S)-2-[(S)-2-(tert-Butoxycarbonylamino)-3-methylbutanamido]-2-(4-ethylthiazol-2-yl)ethyl}phenylsulfamic acid | 0.006 |
| AA43 | (S)-4-{2-[2-(tert-Butoxycarbonylamino)acetamido]-2-(4-ethylthiazol-2-yl)ethyl}phenylsulfamic acid | 0.028 |

TABLE XXI-continued

| No. | Compound | HPTP-β IC$_{50}$ μM |
|---|---|---|
| AA44 | 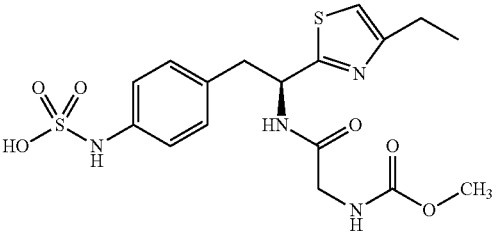<br>(S)-4-{2-(4-Ethylthiazol-2-yl)-2-[2-(methoxycarbonylamino)acetamido]ethyl}phenylsulfamic acid | 0.020 |
| AA45 | 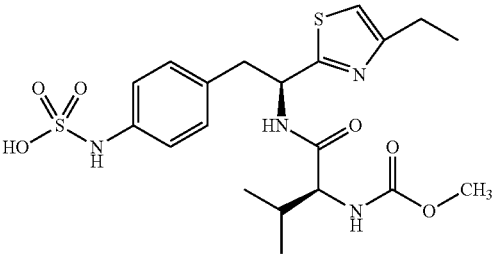<br>4-{(S)-2-(4-Ethylthiazol-2-yl)-2-[(S)-2-(methoxycarbonylamino)-3-methylbutanamido]-ethyl}phenylsulfamic acid | 0.003 |
| AA46 | 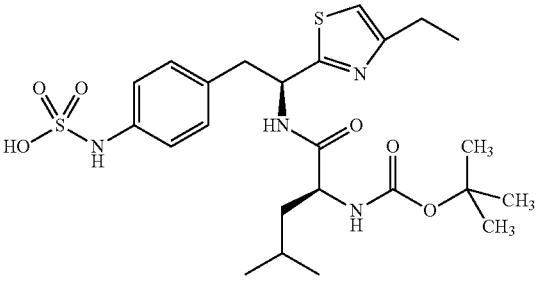<br>4-{(S)-2-[(S)-2-(tert-Butoxycarbonylamino)-4-methylpentanamido]-2-(4-ethylthiazol-2-yl)ethyl}phenylsulfamic acid | 0.001 |
| AA47 | 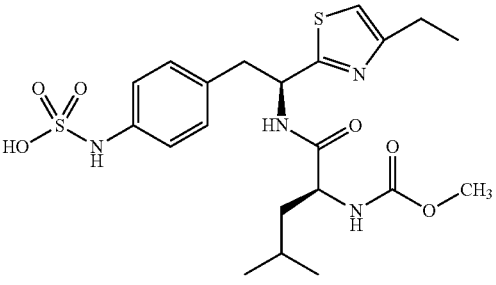<br>4-{(S)-2-(4-Ethylthiazol-2-yl)-2-[(S)-2-(methoxycarbonylamino)-4-methylpentanamido]ethyl}phenylsulfamic acid | 0.0003 |

TABLE XXI-continued

| No. | Compound | HPTP-β IC$_{50}$ μM |
|---|---|---|
| AA48 | 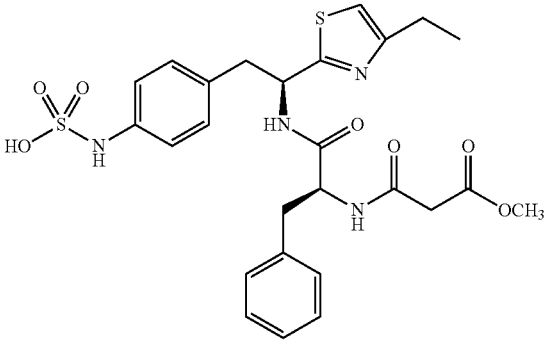<br>4-((S)-2-(4-Ethylthiazol-2-yl)-2-{(S)-2-[2-(methoxycarbonylamino)-acetamido]-3-phenylpropanamido}ethyl)phenylsulfamic acid | 0.0003 |
| AA49 | 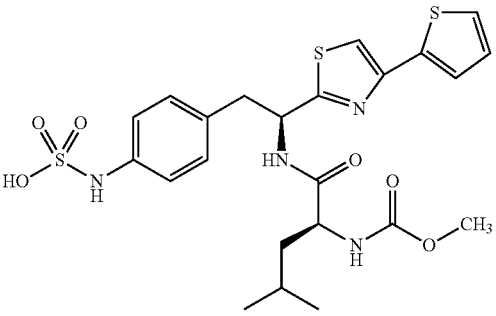<br>4-{(S)-2-[(S)-2-(Methoxycarbonylamino)-4-methylpentanamido]-2-[2-(thiophen-2-yl)thiazol-4-yl]ethyl}phenylsulfamic acid | <5 × 10$^{-8}$ |
| AA50 | 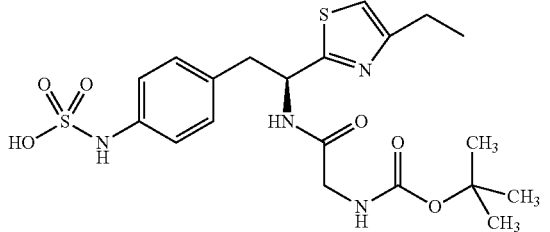<br>(S)-4-{2-[2-(tert-Butoxycarbonylamino)acetamido]-2-(4-ethylthiazol-2-yl)ethyl}-phenylsulfamic acid | 0.028 |
| AA51 | 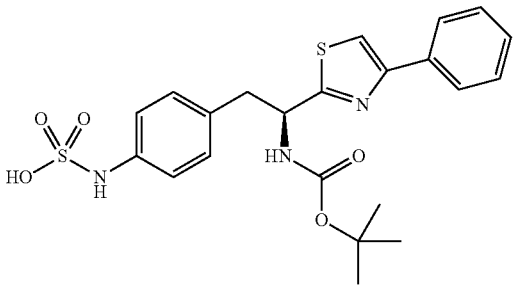<br>[1-(S)-(Phenylthiazol-2-yl)-2-(4-sulfoaminophenyl)ethyl]-carbamic acid tert-butyl ester | 0.049 |

TABLE XXI-continued

| No. | Compound | HPTP-β IC$_{50}$ μM |
|---|---|---|
| AA52 | (S)-4-(2-(4-Methylthiazol-2-yl)-2-pivalamidoethyl)phenyl-sulfamic acid | 0.112 |
| AA53 | (S)-4-(2-(4-Ethylthiazol-2-yl)-2-pivalamidoethyl)phenyl-sulfamic acid | 0.085 |
| AA54 | (S)-4-{2-[4-(hydroxymethyl)thiazol-2-yl]-2-pivalamidoethyl}phenyl-sulfamic acid | 0.266 |
| AA55 | (S)-4-{[2-(4-Ethoxycarbonyl)thiazol-2-yl]-2-pivalamidoethyl}phenylsulfamic acid | 0.584 |
| AA56 | (S)-4-(2-(4-Phenylthiazol-2-yl)-2-pivalamidoethyl)phenylsulfamic acid | 0.042 |

TABLE XXI-continued

| No. | Compound | HPTP-β IC$_{50}$ μM |
|---|---|---|
| AA57 | 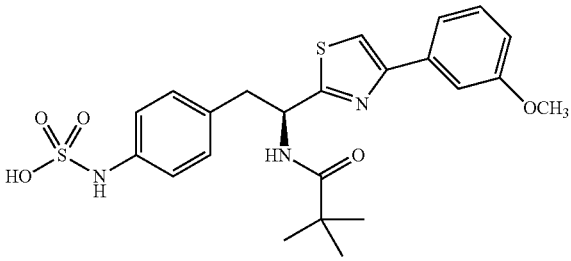 4-((S)-2-(4-(3-Methoxyphenyl)thiazol-2-yl)-2-pivalamidoethyl)phenylsulfamic acid | 0.110 |
| AA58 | 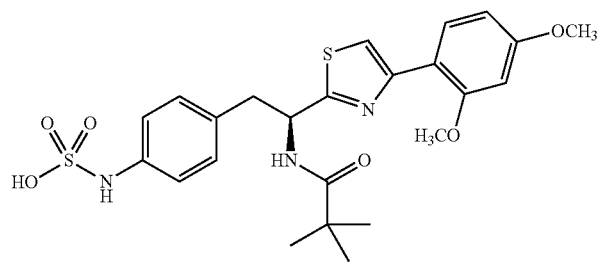 4-((S)-2-(4-(2,4-Dimethoxyphenyl)thiazol-2-yl)-2-pivalamidoethyl)phenyl-sulfamic acid | 0.086 |
| AA59 | 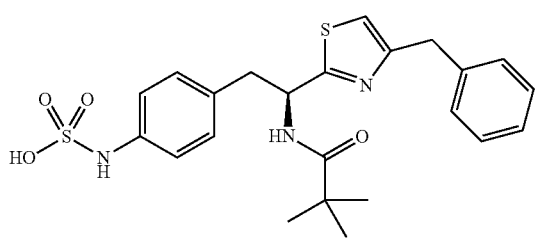 (S)-4-(2-(4-Benzylthiazol-2-yl)-2-pivalamidoethyl)phenylsulfamic acid | 0.113 |
| AA60 | 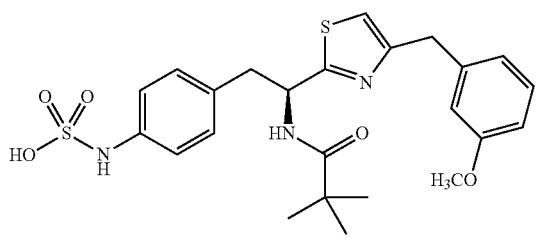 (S)-4-(2-(4-Methoxybenzyl)thiazol-2-yl)-2-pivalamidoethyl)phenylsulfamic acid | 0.132 |
| AA61 | 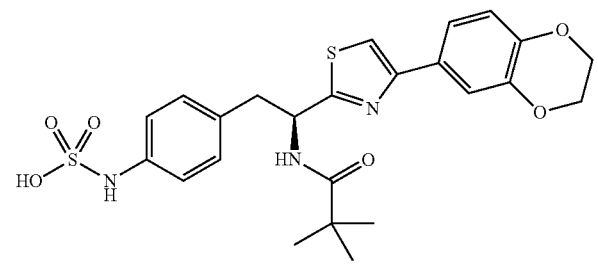 4-((S)-2-(4-(2,3-Dihydrobenzo[b][1,4]dioxin-6-yl)thiazol-2-yl)-2-pivalamidoethyl)phenylsulfamic acid | 0.138 |

TABLE XXI-continued
| No. | Compound | HPTP-β IC$_{50}$ μM |
|---|---|---|
| AA62 | 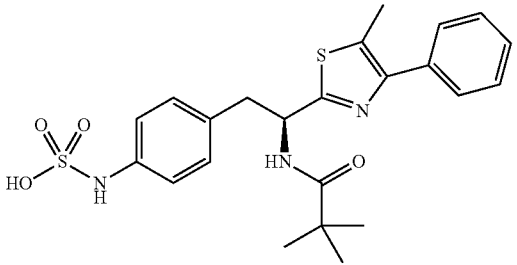<br>(S)-4-(2-(5-Methyl-4-phenylthiazol-2-yl)-2-pivalamidoethyl)phenylsulfamic acid | 0.098 |
| AA63 | 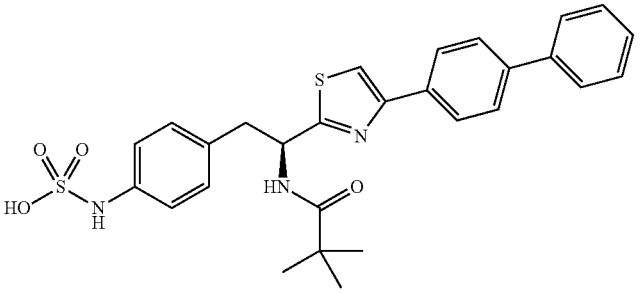<br>(S)-4-(2-(4-(Biphen-4-yl)thiazol-2-yl)-2-pivalamidoethyl)phenylsulfamic acid | 0.381 |
| AA64 | 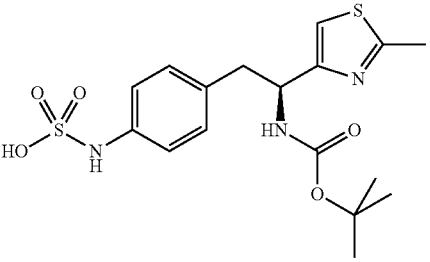<br>(S)-4-(2-tert-Butoxycarbonylamino)-2-(2-methylthiazol-4-yl)ethyl)phenylsulfamic acid | 0.033 |
| AA65 | 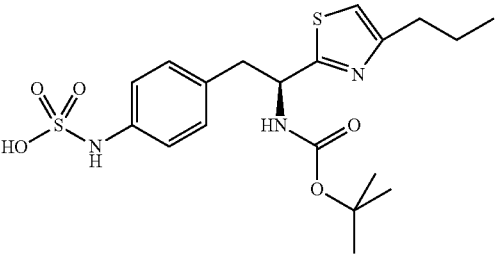<br>(S)-4-(2-(tert-Butoxycarbonylamino)-2-(4-propylthiazol-2-yl)ethyl)phenyl sulfamic acid | 0.04 |

TABLE XXI-continued

| No. | Compound | HPTP-β IC$_{50}$ μM |
|---|---|---|
| AA66 | 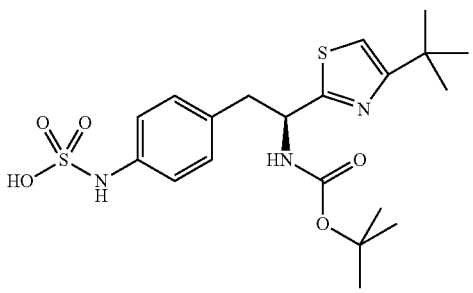<br>(S)-4-(2-(tert-Butoxycarbonylamino)-2-(4-tert-butylthiazol-2-yl)ethyl)phenyl sulfamic acid | 0.027 |
| AA67 | 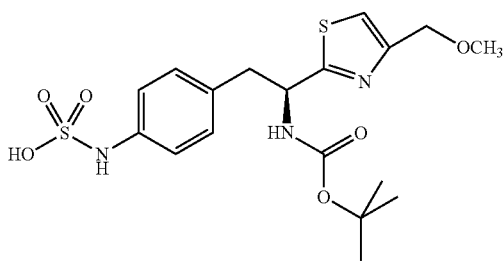<br>(S)-4-(2-(tert-Butoxycarbonylamino)-2-(4-(methoxymethyl)thiazol-2-yl)ethyl)-phenyl sulfamic acid | 0.18 |
| AA68 | 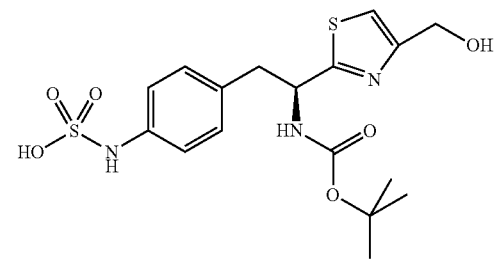<br>(S)-4-(2-(tert-Butoxycarbonylamino)-2-(4-(hydroxymethyl)thiazol-2-yl)ethyl)phenylsulfamic acid | 0.644 |
| AA69 | 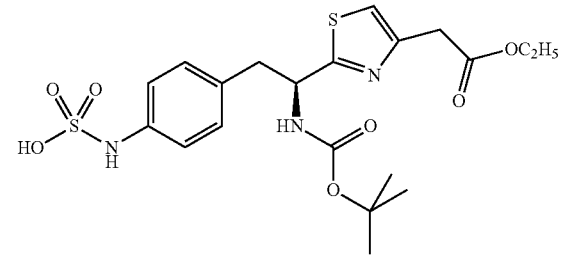<br>(S)-4-(2-tert-Butoxycarbonylamino)-2-(4-(2-ethoxy-2-oxoethyl)thiazol-2-yl)ethyl)phenylsulfamic acid | 0.167 |

TABLE XXI-continued

| No. | Compound | HPTP-β IC$_{50}$ μM |
|---|---|---|
| AA70 | 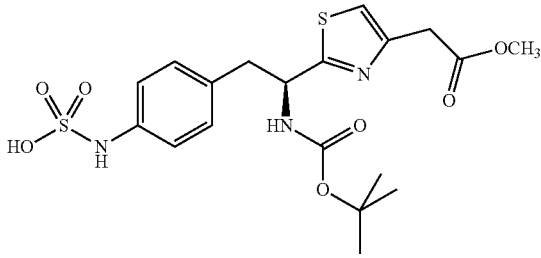<br>(S)-4-(2-(tert-Butoxycarbonyl)-2-(4-(2-(2-methoxy-2-oxoethyl amino)-2-oxoethyl)thiazole-2-yl)ethyl)phenylsulfamic acid | 0.132 |
| AA71 | 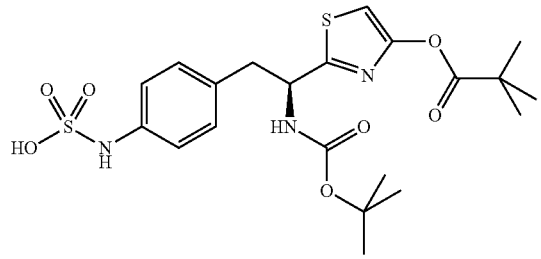<br>(S)-4-(2-(tert-Butoxycarbonylamino)-2-(2-pivalamidothiazol-4-yl)ethyl)phenylsulfamic acid | 0.555 |
| AA72 | 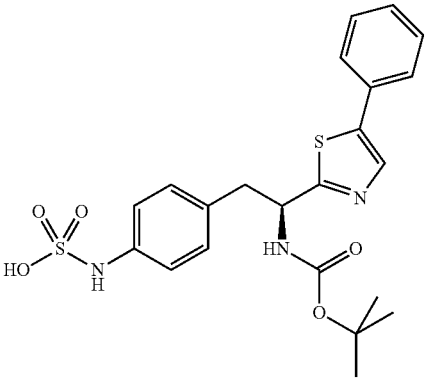<br>(S)-4-(2-(tert-Butoxycarbonylamino)-2-(5-phenylthiazol-2-yl)ethyl)-phenyl sulfamic acid | 0.308 |
| AA73 | 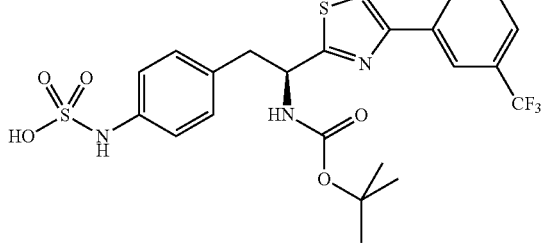<br>4-((S)-2-(tert-Butoxycarbonylamino)-2-(4-(3-(trifluoromethyl)phenyl)thiazol-2-yl)ethyl)-phenyl sulfamic acid | 0.253 |

TABLE XXI-continued
| No. | Compound | HPTP-β IC$_{50}$ μM |
|---|---|---|
| AA74 | 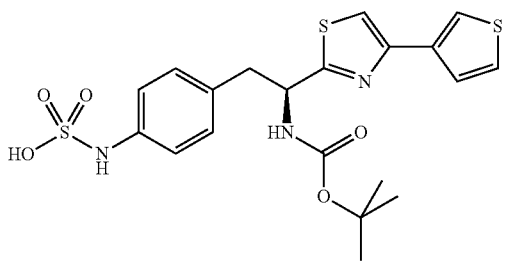<br>4-((S)-2-(tert-Butoxycarbonylamino)-2-(4-(thiophen-3-yl)thiazol-2-yl)ethyl)phenyl sulfamic acid | 0.045 |
| AA75 | 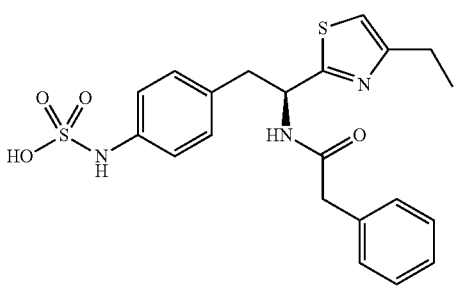<br>(S)-{4-[2-(4-Ethylthiazol-2-yl)-2-(phenylacetylamido)ethyl]-phenyl}sulfamic acid | 0.05 |
| AA76 | 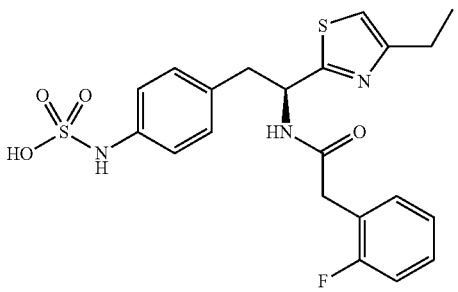<br>(S)-4-(2-(4-Ethylthiazol-2-yl)-2-(2-(2-fluorophenyl)acetamido)ethyl)phenyl-sulfamic acid | 0.012 |
| AA77 | 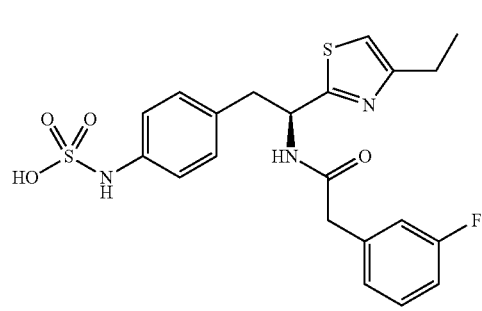<br>(S)-4-(2-(4-Ethylthiazol-2-yl)-2-(2-(3-fluorophenyl)acetamido)ethyl)phenyl-sulfamic acid | 0.0003 |

TABLE XXI-continued
| No. | Compound | HPTP-β IC$_{50}$ μM |
|---|---|---|
| AA78 | 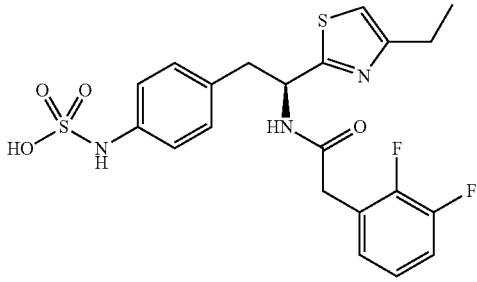<br>(S)-4-(2-(2-(2,3-Difluorophenyl)acetamido)-2-(4-ethylthiazol-2-yl)ethyl)phenyl-sulfamic acid | 0.028 |
| AA79 | 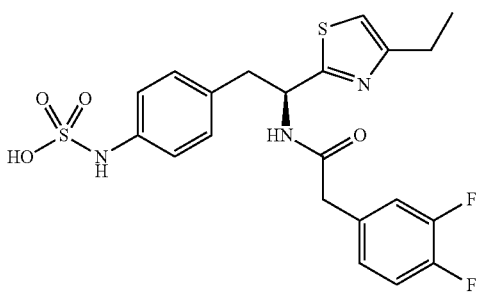<br>(S)-4-(2-(2-(3,4-Difluorophenyl)acetamido)-2-(4-ethylthiazol-2-yl)ethyl)phenyl-sulfamic acid | 0.075 |
| AA80 | 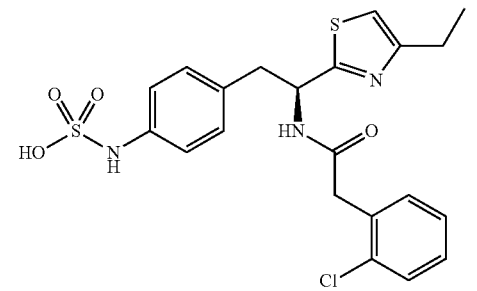<br>(S)-4-(2-(2-(2-Chlorophenyl)acetamido)-2-(4-ethylthiazol-2-yl)ethyl)phenyl-sulfamic acid | 0.056 |
| AA81 | 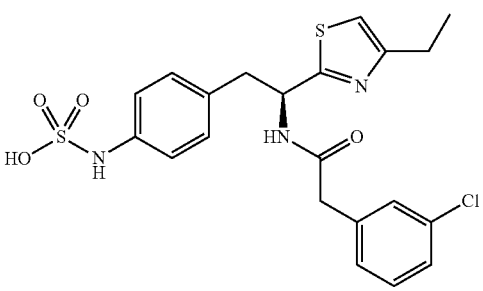<br>(S)-4-(2-(2-(3-Chlorophenyl)acetamido)-2-(4-ethylthiazol-2-yl)ethyl)phenyl-sulfamic acid | 0.033 |

TABLE XXI-continued
| No. | Compound | HPTP-β IC$_{50}$ μM |
|---|---|---|
| AA82 | 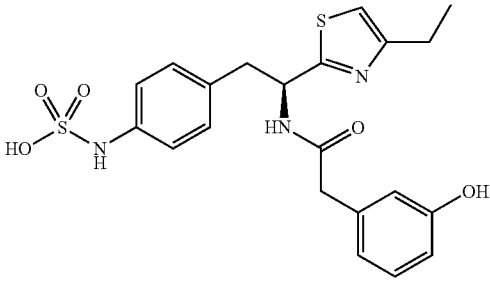<br>(S)-4-(2-(4-Ethylthiazol-2-yl)-2-(2-(3-hydroxyphenyl)acetamido)ethyl)phenyl-sulfamic acid | 0.04 |
| AA83 | 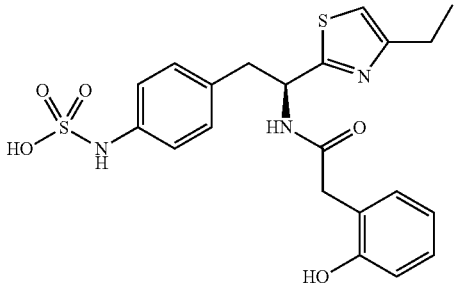<br>(S)-4-(2-(4-Ethylthiazol-2-yl)-2-(2-(2-methoxyphenyl)acetamido)ethyl)phenyl-sulfamic acid | 0.014 |
| AA84 | 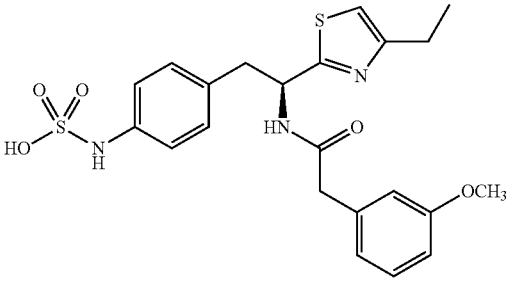<br>(S)-4-(2-(4-Ethylthiazol-2-yl)-2-(2-(3-methoxyphenyl)acetamido)ethyl)phenyl-sulfamic acid | 0.008 |
| AA85 | 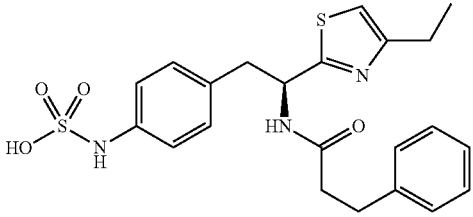<br>(S)-4-(2-(4-Ethylthiazol-2-yl)-2-(3-phenylpropanamido)ethyl)phenylsulfamic acid | 0.002 |

TABLE XXI-continued

| No. | Compound | HPTP-β IC$_{50}$ μM |
|---|---|---|
| AA86 | 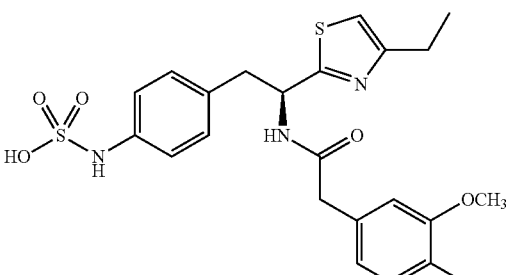<br>(S)-4-(2-(2-(3,4-Dimethoxyphenyl)acetamido)-2-(4-ethylthiazol-2-yl)ethyl)-phenylsulfamic acid | 0.028 |
| AA87 | 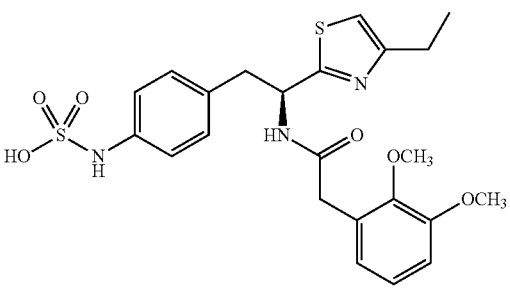<br>(S)-4-(2-(2-(2,3-Dimethoxyphenyl)acetamido)-2-(4-ethylthiazol-2-yl)ethyl)-phenylsulfamic acid | 0.037 |
| AA88 | 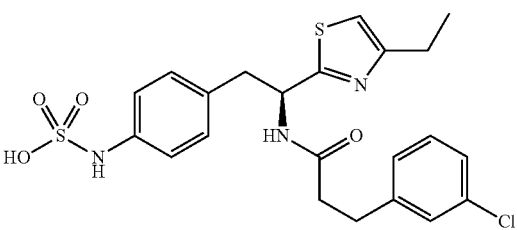<br>(S)-4-(2-(3-(3-Chlorophenyl)propanamido)-2-(4-ethylthiazol-2-yl)ethyl)phenyl-sulfamic acid | 0.0002 |
| AA89 | 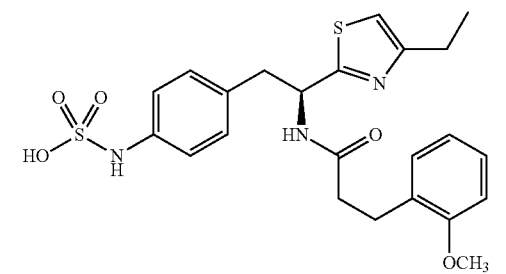<br>(S)-4-(2-(4-Ethylthiazol-2-yl)-2-(3-(2-methoxyphenyl)propanamido)ethyl)phenyl-sulfamic acid | 0.003 |

TABLE XXI-continued

| No. | Compound | HPTP-β IC$_{50}$ μM |
|---|---|---|
| AA90 | 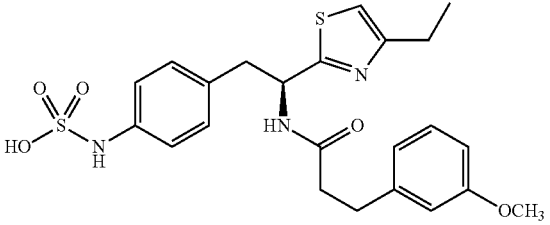<br>(S)-4-(2-(4-Ethylthiazol-2-yl)-2-(3-(3-methoxyphenyl)propanamido)ethyl)phenyl-sulfamic acid | 0.01 |
| AA91 | 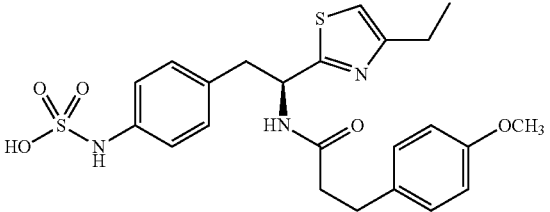<br>(S)-4-(2-(4-Ethylthiazol-2-yl)-2-(3-(4-methoxyphenyl)propanamido)ethyl)phenyl-sulfamic acid | 0.006 |
| AA92 | 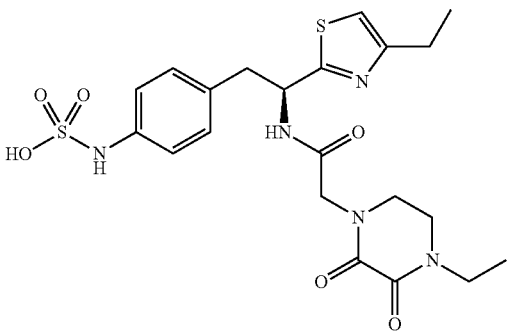<br>(S)-4-{2-[2-[(4-Ethyl-2,3-dioxopiperazin-1-yl)acetamide]-2-(4-ethylthiazol-2-yl)ethyl}phenylsulfamic acid | 0.002 |
| AA93 | 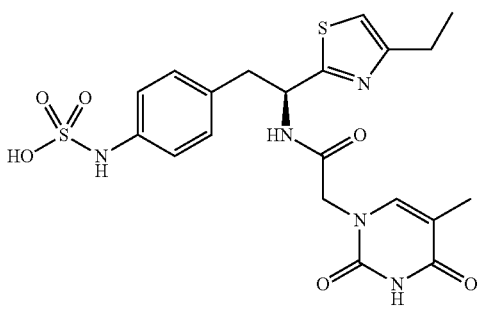<br>(S)-4-{2-(4-Ethylthiazol-2-yl)-2-[2-(5-methyl-2,4-dioxo-3,4-dihydropyrimidin-1(2H)-yl)acetamide]ethyl}phenylsulfamic acid | 0.002 |

TABLE XXI-continued

| No. | Compound | HPTP-β IC$_{50}$ μM |
|---|---|---|
| AA94 | 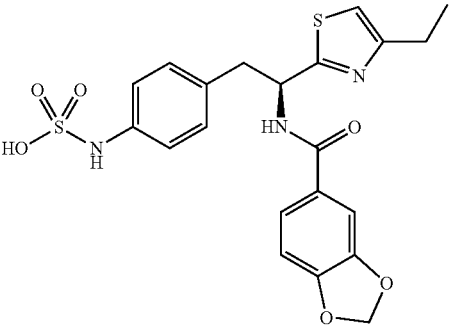<br>(S)-4-[2-(Benzo[d][1,3]dioxole-5-carboxamido)-2-(4-ethylthiazol-2-yl)ethyl]phenylsulfamic acid | 0.042 |
| AA95 | 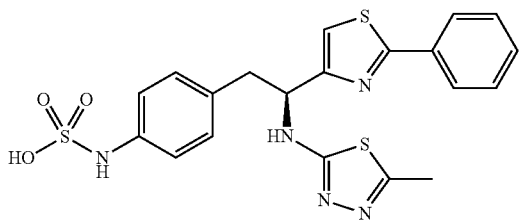<br>(S)-4-(2-(5-methyl-1,3,4-thiadiazol-2-ylamino)-2-(2-phenylthiazol-4-yl)ethyl)phenylsulfamic acid | 0.003 |
| AA96 | 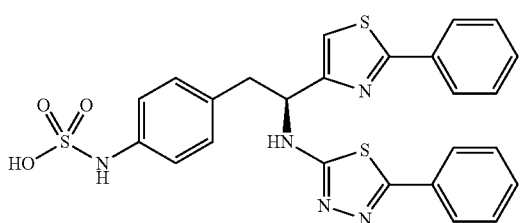<br>(S)-4-(2-(5-Phenyl-1,3,4-thiadiazol-2-ylamino)-2-(2-phenylthiazol-4-yl)ethyl)-phenylsulfamic acid | 0.046 |
| AA97 | 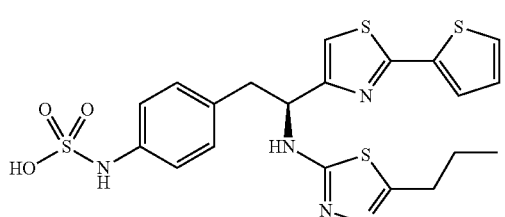<br>4-((S)-2-(5-Propyl-1,3,4-thiadiazol-2-ylamino)-2-(2-(thiophen-2-yl)thiazol-4-yl)ethyl)phenylsulfamic acid | 0.0002 |
| AA98 | 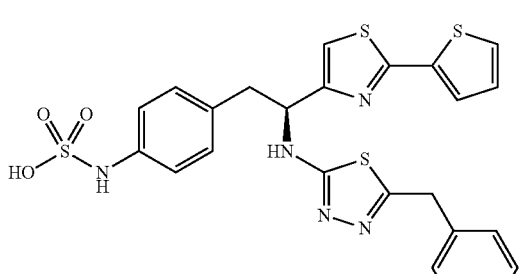<br>4-((S)-2-(5-Benzyl-1,3,4-thiadiazol-2-ylamino)-2-(2-(thiophen-2-yl)thiazol-4-yl)ethyl)phenylsulfamic acid | 0.0006 |

TABLE XXI-continued

| No. | Compound | HPTP-β IC$_{50}$ μM |
|---|---|---|
| AA99 | 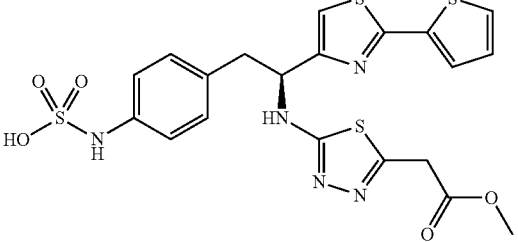  4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid | 0.002 |
| AA100 | 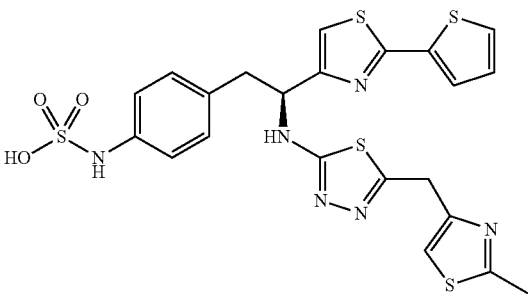  4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid | 9 × 10$^{-6}$ |

Non-limiting examples of compounds of the invention include:

(S)-4-[2-Benzamido-2-(4-ethylthiazol-2-yl)ethyl]phenylsulfamic acid;
(S)-4-{2-(4-Ethylthiazol-2-yl)-2-[2-(2-fluorophenyl)acetamido]ethyl}phenyl-sulfamic acid;
(S)-4-(2-(4-Ethylthiazol-2-yl)-2-(2-(3-fluorophenyl)acetamido)ethyl)phenylsulfamic acid;
(S)-4-(2-(2-(2,3-Difluorophenyl)acetamido)-2-(4-ethylthiazol-2-yl)ethyl)phenyl-sulfamic acid;
(S)-4-(2-(2-(3,4-Difluorophenyl)acetamido)-2-(4-ethylthiazol-2-yl)ethyl)phenyl-sulfamic acid;
(S)-4-(2-(2-(2-Chlorophenyl)acetamido)-2-(4-ethylthiazol-2-yl)ethyl)phenylsulfamic acid;
(S)-4-(2-(2-(3-Chlorophenyl)acetamido)-2-(4-ethylthiazol-2-yl)ethyl)phenyl-sulfamic acid;
(S)-4-(2-(4-Ethylthiazol-2-yl)-2-(2-(3-hydroxyphenyl)acetamido)phenyl-sulfamic acid;
(S)-4-(2-(4-Ethylthiazol-2-yl)-2-(2-(2-methoxyphenyl)acetamido)ethyl)phenyl-sulfamic acid;
(S)-4-(2-(4-Ethylthiazol-2-yl)-2-(2-(3-methoxyphenyl)acetamido)ethyl)phenyl-sulfamic acid;
(S)-4-(2-(4-Ethylthiazol-2-yl)-2-(3-phenylpropanamido)ethyl)phenylsulfamic acid;
(S)-4-(2-(2-(3,4-Dimethoxyphenyl)acetamido)-2-(4-ethylthiazol-2-yl)ethyl)-phenylsulfamic acid;
(S)-4-(2-(2-(2,3-Dimethoxyphenyl)acetamido)-2-(4-ethylthiazol-2-yl)ethyl)-phenylsulfamic acid;
(S)-4-(2-(3-(3-Chlorophenyl)propanamido)-2-(4-ethylthiazol-2-yl)ethyl)phenyl-sulfamic acid;
(S)-4-(2-(4-Ethylthiazol-2-yl)-2-(3-(2-methoxyphenyl)propanamido)ethyl)phenyl-sulfamic acid;
(S)-4-(2-(4-Ethylthiazol-2-yl)-2-(3-(3-methoxyphenyl)propanamido)ethyl)phenylsulfamic acid;
(S)-4-(2-(4-Ethylthiazol-2-yl)-2-(3-(4-methoxyphenyl)propanamido)ethyl)phenyl-sulfamic acid;
(S)-4-{2-[2-(4-Ethyl-2,3-dioxopiperazin-1-yl)acetamido]-2-(4-ethylthiazol-2-yl)ethyl}phenylsulfamic acid;
(S)-4-{2-(4-Ethylthiazol-2-yl)-2-[2-(5-methyl-2,4-dioxo-3,4-dihydropyrimidin-1(2H)-yl)acetamide]ethyl}phenylsulfamic acid;
(S)-4-[2-(Benzo[d][1,3]dioxole-5-carboxamido)-2-(4-ethylthiazol-2-yl)ethyl]-phenylsulfamic acid;
4-((S)-2-(2-(2-Chlorophenyl)acetamido)-2-(2-(thiophene2-yl)thiazol-4-yl)ethyl)-phenylsulfamic acid;
4-((S)-2-(2-(3-Methoxyphenyl)acetamido)-2-(2-(thiophene2-yl)thiazol-4-yl)ethyl)-phenylsulfamic acid;
4-{(S)-2-(3-Phenylpropanamido)-2-[2-(thiophene2-yl)thiazol-4-yl]ethyl}phenyl-sulfamic acid;
4-{(S)-2-(3-(3-Chlorophenyl)propanamido)-2-[2-(thiophene2-yl)thiazol-4-yl]ethyl}-phenylsulfamic acid;
4-{(S)-2-[2-(3-Fluorophenyl)acetamide]-2-[2-(thiophene2-yl)thiazol-4-yl]ethyl}-phenylsulfamic acid;
(S)-4-{2-[2-(2,5-Dimethylthiazol-4-yl)acetamide]-2-(4-ethylthiazol-2-yl]ethyl}-phenylsulfamic acid;
(S)-4-{2-[2-(2,4-Dimethylthiazol-5-yl)acetamide]-2-(4-methylthiazol-2-ylethyl}-phenylsulfamic acid;
(S)-4-{2-(4-Ethylthiazol-2-yl)-2-[3-(thiazol-2-yl)propanamido]ethyl}phenylsulfamic acid;
(S)-4-{2-(4-Ethylthiazol-2-yl)-2-[2-(4-ethylthiazol-2-yl)acetamide]ethyl}phenyl-sulfamic acid;
(S)-4-{2-[2-(3-Methyl-1,2,4-oxadiazol-5-yl)acetamide]-2-(2-phenylthiazol-4-yl)ethyl}phenylsulfamic acid;
4-{(S)-2-[2-(4-Ethyl-2,3-dioxopiperazin-1-yl)acetamide]-2-[2-(thiophen-2-yl)thiazol-4-yl]ethyl}phenylsulfamic acid;

(S)-4-(2-(2,3-Diphenylpropanamido)-2-(4-ethylthiazol-2-yl)ethyl)phenylsulfamic acid;
(S)-4-{2-(4-Ethylthiazol-2-yl)-2-[2-(2-methoxyphenyl)-3-phenylpropanamido]-ethyl}phenylsulfamic acid;
(S)-4-{2-(4-Ethylthiazol-2-yl)-2-[2-(3-fluorophenyl)-3-phenylpropanamido]-ethyl}phenylsulfamic acid;
(S)-4-{2-(4-Ethylthiazol-2-yl)-2-[2-(3-methoxyphenyl)-3-phenylpropanamido]-ethyl}phenylsulfamic acid;
4-{(S)-2-(4-Ethylthiazol-2-yl)-2-[2-(3-methyl)-1,2,4-oxadiazol-5-yl)-3-phenylpropanamido]ethyl}phenylsulfamic acid;
(S)-4-[2-(4-Ethylthiazol-2-yl)-2-(4-oxo-4-phenylbutanamido)-ethyl]phenylsulfamic acid;
(S)-4-(2-(4-Ethylthiazol-2-yl)-2-(5-methyl-4-oxohexanamido)ethyl)phenylsulfamic acid;
(S)-4-{2-[4-(3,4-Dihydro-2H-benzo[b][1,4]dioxepin-7-yl)-4-oxobutanamido]-2-(4-ethylthiazol-2-yl)ethyl}phenylsulfamic acid;
(S)-4-{2-[4-(2,3-Dimethoxyphenyl)-4-oxobutanamido]-2-(4-ethylthiazol-2-yl)ethyl}phenylsulfamic acid;
(S)-4-{2-(4-Ethylthiazol-2-yl)-2-[4-oxo-4-(pyridin-2-yl)butanamido]ethyl}phenyl-sulfamic acid;
(S)-4-{2-[4-(2,3-Dihydrobenzo[b][1,4]dioxin-6-yl)-4-oxobutanamido]-2-(4-ethylthiazol-2-yl)ethyl}phenylsulfamic acid;
(S)-4-[2-(4-tert-Butoxy-4-oxobutanamido)-2-(4-ethylthiazol-2-yl)ethyl]phenyl-sulfamic acid;
(S)-4-[2-(4-Ethoxy-4-oxobutanamido)-2-(4-ethylthiazol-2-yl)ethyl]phenylsulfamic acid;
(S)-4-(2-(3-Benzylureido)-2-(4-ethylthiazol-2-yl)ethyl)phenylsulfamic acid;
4-{[(S)-2-(2-Ethylthiazol-4-yl)-2-(3-(R)-1-methoxy-1-oxo-3-phenylpropan-2-yl)ureido]ethyl}phenylsulfamic acid;
4-{(S)-2-(3-Benzylureido)-2-[2-(thiophen-2-yl)thiazol-4-yl]ethyl}phenylsulfamic acid;
{4-(S)-[2-Phenylmethanesulfonylamino-2-(2-thiophen-2-ylthiazol-4-yl)ethyl]-phenylsulfamic acid;
4-{(S)-2-[(2-Methylthiazol-4-yl)methylsulfonamido]-2-[2-(thiophen-2-yl)thiazol-4-yl]ethyl}phenylsulfamic acid;
{4-(S)-[2-Phenylmethanesulfonylamino-2-(2-ethylthiazol-4-yl)ethyl]phenyl}-sulfamic acid;
{4-(S)-[2-(3-Methoxyphenyl)methanesulfonylamino-2-(2-ethylthiazol-4-yl)ethyl]phenyl}sulfamic acid;
(S)-4-{[1-(2-Ethylthiazol-4-yl)-2-(4-sulfoaminophenyl)ethylsulfamoyl]methyl}-benzoic acid methyl ester;
(S)-4-[2-(2-Ethylthiazol-4-yl)-2-(1-methyl-1H-imidazol-4-sulfonamido)ethyl]-phenylsulfamic acid;
4-{(S)-2-[2-(Thiophen-2-yl)thiazol-4-yl]-2-(2,2,2-trifluoroethylsulfonamido)-ethyl}phenylsulfamic acid;
{4-(S)-[2-(Phenylethanesulfonylamino)-2-(2thiophen-2-ylthiazol-4-yl)ethyl]-phenyl}sulfamic acid;
{4-(S)-[3-(Phenylpropanesulfonylamino)-2-(2thiophen-2-ylthiazol-4-yl)ethyl]-phenyl}sulfamic acid;
(S)-{4-[2-(4-Methyl-3,4-dihydro-2H-benzo[1,4]oxazine-7-sulfonylamino)-2-(2-thiophen-2-ylthiazol-4-yl)ethyl]phenyl}sulfamic acid;
4-{(S)-2-(4-Acetamidophenylsulfonamido)-2-[2-(thiophen-2-yl)thiazol-4-yl]ethyl}phenylsulfamic acid;
4-{(S)-2-(2-cyclopropylthiazol-4-yl)-2-[4-(3-methoxyphenyl)-thiazol-2-ylamino]ethyl}phenylsulfamic acid;
(S)-4-(2-(4-((2-Methoxy-2-oxoethyl)carbamoyl)thiazole-5-ylamino)-2-(2-ethylthiazole-4-yl)ethyl)phenylsulfamic acid;
4-((S)-2-(5-(1-N-(2-Methoxy-2-oxoethyl)-1-H-indol-3-yl)oxazole-2-ylamino)-2-(2-methylthiazol-4-yl)ethyl))phenylsulfamic acid;

4-((S)-2-(5-(2-Methoxyphenyl)oxazol-2-ylamino)-2-(2-methylthiazol-4-yl)ethyl)-phenylsulfamic acid;
4-((S)-2-(5-((S)-1-(tert-Butoxycarbonyl)-2-phenylethyl)oxazole-2-ylamino)-2-(2-methylthiazole-4-yl)ethyl)phenylsulfamic acid;
(S)-4-(2-(5-(4-Methoxycarbonyl)phenyl)oxazole-2-ylamino)2-(2-methylthiazole-4-yl)ethyl)phenylsulfamic acid;
(S)-4-(2-(5-(3-Methoxybenzyl)oxazole-2-ylamino)-2-(2-methylthiazole-4-yl)ethyl)-phenylsulfamic acid;
(S)-4-(2-(2-Methylthiazole-4-yl)-2-(5-phenyloxazole-2-ylamino)ethyl)phenyl-sulfamic acid;
4-((S)-2-(2-Cyclopropylthiazol-4-yl)-2-(4-(3-methoxyphenyl)thiazol-2-ylamino)-ethyl)phenylsulfamic acid;
(S)-4-(2-(2-cyclopropylthiazol-4-yl)-2-(4-(4-fluorophenyl)thiazol-2-ylamino)ethyl)-phenylsulfamic acid;
4-((S)-2-(2-cyclopropylthiazol-4-yl)-2-(4-(2-methoxyphenyl)thiazol-2-ylamino)-ethyl)phenylsulfamic acid;
4-((S)-2-(2-cyclopropylthiazol-4-yl)-2-(4-(2,4-difluorophenyl)thiazol-2-ylamino)-ethyl)phenylsulfamic acid;
(S)-4-(2-(4-(3-methoxybenzyl)thiazol-2-ylamino)-2-(2-cyclopropylthiazol-4-yl)ethyl)phenylsulfamic acid;
(S)-{5-[1-(2-Ethylthiazol-4-yl)-2-(4-sulfoaminophenyl)ethylamino]-2-methyl-2H-[1,2,4]triazole-3-yl}carbamic acid methyl ester;
4-((S)-2-(4-(2-Methoxyphenyl)thiazol-2-ylamino)-2-(2-(thiophen-2-yl)thiazol-4-yl)ethyl)phenylsulfamic acid;
4-{(S)-2-[5-(3-Methoxyphenyl)oxazole-2-ylamino]-2-(2-phenylthiazole-4-yl)ethyl}phenylsulfamic acid;
4-{(S)-2-[4-(2,4-Difluorophenyl)thiazol-2-ylamino]-2-[2-(thiophen-2-yl)thiazol-4-yl]ethyl}phenylsulfamic acid;
(S)-4-{2-[4-(Ethoxycarbonyl)thiazol-2-ylamino]-2-(2-phenylthiazol-4-yl)ethyl}-phenylsulfamic acid;
(S)-4-{2-[4-(2-Ethoxy-2-oxoethyl)thiazol-2-ylamino]-2-(2-phenylthiazol-4-yl)ethyl}phenylsulfamic acid;
(S)-4-{2-[4-(4-Acetamidophenyl)thiazol-2-ylamino]-2-(2-phenylthiazol-4-yl)ethyl}phenylsulfamic acid;
(S)-4-[2-(4-Phenylthiazol-2-ylamino)-2-(2-phenylthiazol-4-yl)ethyl]phenylsulfamic acid;
(S)-4-{2-[4-(4-(Methoxycarbonyl)phenyl)thiazol-2-ylamino]-2-(2-phenylthiazol-4-yl)ethyl}phenylsulfamic acid;
4-{(S)-2-[4-(Ethoxycarbonyl)thiazol-2-ylamino]-2-[2-(thiophen-2-yl)thiazol-4-yl]ethyl}phenylsulfamic acid;
(S)-4-[2-(4-(Methoxycarbonyl)thiazol-5-ylamino)-2-(2-phenylthiazole-4-yl)ethyl]-phenylsulfamic acid;
(S)-4-[2-(5-Phenyloxazole-2-ylamino)]-2-(2-phenylthiazole-4-yl)phenylsulfamic acid;
(S)-4-{2-[5-(4-Acetamidophenyl)oxazole-2-ylamino]-2-(2-phenylthiazole-4-yl)ethyl}phenylsufamic acid;
4-((S)-2-(5-(2,4-Difluorophenyl)oxazole-2-ylamino)-2-(2-phenylthiazole-4-yl)ethyl)phenylsulfamic acid;
4-{(S)-2-[5-(3-Methoxyphenyl)oxazol-2-ylamino]-2-[(2-thiophen-2-yl)thiazole-4-yl]ethyl}phenylsulfamic acid;
(S)-4-[2-(4,6-Dimethylpyrimidene-2-ylamino)-2-(2-methylthiazole-4-yl)ethyl]-phenylsulfamic acid;
(S)-4-[2-(4-Hydroxy-6-methylpyrimidine-2-ylamino)-2-(2-methylthiazole-4-yl)ethyl]phenylsulfamic acid; 4-{(S)-2-[(S)-2-(tert-Butoxycarbonylamino)-3-phenylpropanamido]-2-(4-ethylthiazol-2-yl)ethyl}phenylsulfamic acid;
4-{(S)-2-[(R)-2-(tert-Butoxycarbonylamino)-3-phenylpropanamido]-2-(4-ethylthiazol-2-yl)ethyl}phenylsulfamic acid;
{1-[1-(5-Ethylthiazol-2-yl)-(S)-2-(4-sulfoaminophenyl)ethylcarbamoyl]-(S)-2-phenylethyl}methyl carbamic acid tert-butyl ester;

{(S)-2-Phenyl-1-[1-(4-phenylthiazol-2-yl)-(S)-2-(4-sulfoaminophenyl)ethyl-carbamoyl]ethyl}carbamic acid tert-butyl ester;

4-{(S)-2-(S)-2-(tert-Butoxycarbonylamino)-3-phenylpropaneamido-2-(2-phenylthiazole-4-yl)}phenylsulfamic acid;

4-{(S)-2-(4-Ethylthiazol-2-yl)-2-[(S)-2-(methoxycarbonylamino)-3-phenyl-propanamido]ethyl}phenylsulfamic acid;

4-{(S)-2-[(S)-2-(Methoxycarbonylamino)-3-phenylpropanamido]-2-(thiazol-2-yl)ethyl}phenylsulfamic acid;

4-{(S)-2-[(S)-2-(Methoxycarbonylamino)-3-phenylpropanamido]-2-(4-methylthiazol-2-yl)ethyl}phenylsulfamic acid;

4-{(S)-2-[(S)-2-(Methoxycarbonylamino)-3-phenylpropanamido]-2-(4-propylthiazol-2-yl)ethyl}phenylsulfamic acid;

4-{(S)-2-(4-tert-Butylthiazol-2-yl)-2-[(S)-2-(methoxycarbonylamino)-3-phenylpropanamido]ethyl}phenylsulfamic acid;

4-{(S)-2-(4-Cyclopropylthiazol-2-yl)-2-[(S)-2-(methoxycarbonylamino)-3-phenylpropanamido]ethyl}phenylsulfamic acid;

4-{(S)-2-(4-Cyclohexylthiazol-2-yl)-2-[(S)-2-(methoxycarbonylamino)-3-phenyl-propanamido]ethyl}phenylsulfamic acid;

4-{(S)-2-(4,5-Dimethylthiazol-2-yl)-2-[(S)-2-(methoxycarbonylamino)-3-phenyl-propanamido]ethyl}phenylsulfamic acid;

4-{(S)-2-Phenyl-1-[1-(2-phenylthiazol-4-yl)-(S)-2-(4-sulfoaminophenyl)ethyl-carbamoyl]ethyl}carbamic acid tert-butyl ester;

4-{(S)-2-(4-Ethyl-5-methylthiazol-2-yl)-2-[(S)-2-(methoxycarbonylamino)-3-phenyl-propanamido]ethyl}phenylsulfamic acid;

4-{(S)-2-[(S)-2-(Methoxycarbonylamino)-3-phenylpropanamido]-2-[4-(2,2,2-trifluoroethyl)thiazol-2-yl]ethyl}phenylsulfamic acid;

4-{(S)-2-[(S)-2-(Methoxycarbonylamino)-3-phenylpropanamido]-2-[4-(3,3,3-trifluoropropyl)thiazol-2-yl]ethyl}phenylsulfamic acid;

4-{(S)-2-[4-(2,2-Difluorocyclopropyl)thiazol-2-yl]-2-[(S)-2-(methoxycarbonylamino)-3-phenylpropanamido]ethyl}phenylsulfamic acid;

4-{(S)-2-[(S)-2-(Methoxycarbonylamino)-3-phenylpropanamido]-2-[4-(methoxy-methyl)thiazol-2-yl]ethyl}phenylsulfamic acid;

4-{(S)-2-(4-(Ethoxycarbonylamino)thiazol-2-yl)-2-[(S)-2-(methoxycarbonylamino)-3-phenylpropanamido]ethyl}phenylsulfamic acid;

4-{(S)-2-[(S)-2-(Methoxycarbonylamino)-3-phenylpropanamido]-2-(5-phenylthiazol-2-yl))ethyl}phenylsulfamic acid;

4-{(S)-2-(4-tert-Butylthiazol-2-yl)-2-[(S)-2-(methoxycarbonylamino)-3-phenyl-propanamido]ethyl}phenylsulfamic acid;

4-{(S)-2-(4-Ethyl-5-phenylthiazol-2-yl)-2-[(S)-2-(methoxycarbonylamino)-3-phenyl-propanamido]ethyl}phenylsulfamic acid;

4-{(S)-2-[4-(3,4-Dimethylphenyl)thiazol-2-yl]-2-[(S)-2-(methoxycarbonylamino)-3-phenylpropanamido]ethyl}phenylsulfamic acid;

4-{(S)-2-[4-(4-Chlorophenyl)thiazol-2-yl]-2-[(S)-2-(methoxycarbonylamino)-3-phenylpropanamido]ethyl}phenylsulfamic acid;

4-{(S)-2-[(S)-2-(Methoxycarbonylamino)-3-phenylpropanamido]-2-(4-phenylthiazol-2-yl)ethyl}phenylsulfamic acid;

4-{(S)-2-[(S)-2-(Methoxycarbonylamino)-3-phenylpropanamido]-2-[4-(thiophen-2-yl)thiazol-2-yl]ethyl}phenylsulfamic acid;

4-{(S)-2-[(S)-2-(Methoxycarbonylamino)-3-phenylpropanamido]-2-[4-(thiophen-3-yl)thiazol-2-yl]ethyl}phenylsulfamic acid;

4-{(S)-2-(4-Ethylthiazol-2-yl)-2-[(S)-2-(methoxycarbinyl)-3-phenylpropionamido]ethyl}phenylsulfamic acid;

4-{(S)-2-(5,6-Dihydro-4H-cyclopenta[d]thiazol-2-yl)-2-[(S)-2-(methoxy-carbonyl)-3-phenylpropanamido]ethyl}phenylsulfamic acid;

4-{(S)-2-[(S)-2-(Methoxycarbonylamino)-3-phenylpropanamido]-2-(4,5,6,7-tetrahydrobenzo[d]thiazol-2-yl)ethyl}phenylsulfamic acid;

4-{(S)-2-[4-(5-Chlorothiophen-2-yl)thiazol-2-yl]-2-[(S)-2-(methoxycarbonylamino)-3-phenylpropanamido]ethyl}phenylsulfamic acid;

4-{(S)-2-[(S)-2-(Ethoxycarbonylamino)-3-phenylpropanamido]-2-(4-ethylthiazol-2-yl)ethyl}phenylsulfamic acid;

4-{(S)-2-[(S)-2-(Methoxycarbonylamino)-3-phenylpropanamido]-2-(2-ethylthiazol-4-yl)ethyl}phenylsulfamic acid;

4-{(S)-2-[(S)-2-(Methoxycarbonylamino)-3-phenylpropanamido]-2-(2-methylthiazol-4-yl)ethyl}phenylsulfamic acid;

4-{(S)-2-(2-Ethylthiazole-4-yl)-2-[(S)-2-(methoxycarbonylamino)-3-phenylpropan-amido]ethyl}phenylsulfamic acid;

4-{(S)-2-(2-Isopropylthiazol-4-yl)-2-[(S)-2-(methoxycarbonylamino)-3-phenyl-propan-amido]ethyl}phenylsulfamic acid;

4-{(S)-2-(2-Cyclopropylthiazol-4-yl)-2-[(S)-2-(methoxycarbonylamino)-3-phenylpropanamido]ethyl}phenylsulfamic acid;

4-{(S)-2-{2-[(4-Chlorophenylsulfonyl)methyl]thiazol-4-yl}-2-[(S)-2-(methoxy-carbonyl)-3-phenylpropanamido]ethyl}phenylsulfamic acid;

4-{(S)-2-[2-(tert-Butylsulfonylmethyl)thiazol-4-yl]-2-[(S)-2-(methoxycarbonylamino)-3-phenylpropanamido]ethyl}phenylsulfamic acid;

4-{(S)-2-[(S)-2-(Methoxycarbonylamino)-3-phenylpropionamido]-2-(2-phenylthiazole-4-yl)ethyl}phenylsulfamic acid;

4-{(S)-2-[(S)-2-(Methoxycarbonylamino)-3-phenylpropanamido]-2-[2-(thiophen-2-yl)thiazol-4-yl]ethyl}phenylsulfamic acid;

4-{(S)-2-[2-(3-Chlorothiophen-2-yl)thiazol-4-yl]-2-[(S)-2-(methoxycarbonylamino)-3-phenylpropanamido]ethyl}phenylsulfamic acid;

4-{(S)-2-[(S)-2-(Methoxycarbonylamino)-3-phenylpropanamido]-2-[2-(3-methylthiophen-2-yl)thiazol-4-yl]ethyl}phenylsulfamic acid;

4-{[(S)-2-(2-(Furan-2-yl)thiazol-4-yl]-2-[(S)-2-(methoxy-carbonylamino)-3-phenyl-propanamido]ethyl}phenylsulfamic acid;

4-{(S)-2-[(S)-2-(Methoxycarbonylamino)-3-phenylpropanamido]-2-[2-(2-methylthiazole-4-yl)thiazol-4yl]ethyl}phenylsulfamic acid;

4-{(S)-2-[(S)-2-(Methoxycarbonylamino)-3-phenylpropanamido]-2-(2-pyrazine-2-yl)thiazole-4-yl}phenylsulfamic acid;

4-{(S)-2-[(S)-2-(Methoxycarbonylamino)-3-phenylpropanamido]-2-[2-(6-methylpyridin-3-yl)thiazol-4-yl]ethyl}phenylsulfamic acid;

4-[(S)-2-((S)-2-Acetamido-3-phenylpropanamido)-2-(4-ethylthiazol-2-yl)ethyl]-phenylsulfamic acid;

4-[(S)-2-((S)-2-Acetamido-3-phenylpropanamido)-2-(4-tert-butylthiazol-2-yl)ethyl]-phenylsulfamic acid;
4-{(S)-2-((S)-2-Acetamido-3-phenylpropanamido)-2-[4-(thiophen-3-yl)thiazol-2-yl]ethyl)phenylsulfamic acid;
4-{(S)-2-[(S)-2-(tert-Butoxycarbonyl)-3-methylbutanamido]-2-(4-ethylthiazol-2-yl)ethyl}phenylsulfamic acid;
(S)-4-{2-[2-(tert-Butoxycarbonyl)acetamide]-2-(4-ethylthiazol-2-yl)ethyl}phenyl-sulfamic acid;
(S)-4-{2-(4-Ethylthiazol-2-yl)-2-[2-(methoxycarbonyl)acetamido]ethyl}phenyl-sulfamic acid;
4-{(S)-2-(4-Ethylthiazol-2-yl)-2-[(S)-2-(methoxycarbonyl)-3-methylbutanamido]-ethyl}phenylsulfamic acid;
4-{(S)-2-[(S)-2-(tert-Butoxycarbonyl)-4-methylpentanamido]-2-(4-ethylthiazol-2-yl)ethyl}phenylsulfamic acid;
4-{(S)-2-(4-Ethylthiazol-2-yl)-2-[(S)-2-(methoxycarbonyl)-4-methylpentanamido]ethyl}phenylsulfamic acid;
4-((S)-2-(4-Ethylthiazol-2-yl)-2-{(S)-2-[2-(methoxycarbonyl)acetamide]-3-phenylpropanamido}ethyl)phenylsulfamic acid;
4-{(S)-2-[(S)-2-(tert-Butoxycarbonyl)-4-methylpentanamido]-2-[2-(thiophen-2-yl)thiazol-4-yl] ethyl}phenylsulfamic acid;
4-{(S)-2-[(S)-2-(Methoxycarbonyl)-4-methylpentanamido]-2-[2-(thiophen-2-yl)thiazol-4-yl]ethyl}phenylsulfamic acid; and
(S)-4-{2-[2-(tert-Butoxycarbonyl)acetamide]-2-(4-ethylthiazol-2-yl)ethyl}-phenylsulfamic acid.

Pharmaceutically-Acceptable Salts.

The invention provides the use of pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

Antibodies.

Compounds of the invention can be co-formulated or co-administered with antibodies, for example, anti-VEGF agents. Non-limiting examples of such antibodies include ranibizumab, bevacizumab, and aflibercept.

An antibody can comprise a heavy chain and a light chain. In some embodiments, the heavy chain comprises SEQ ID NO:1:

GluValGlnLeuValGluSerGlyGlyGlyLeuValGlnProGlyGlySe rLeuArgLeuSerCysAlaAlaSerGlyTyrAspPheThrHisTyrGlyM etAsnTrpValArgGlnAlaProGlyLysGlyLeuGluTrpValGlyTrp

IleAsnThrTyrThrGlyGluProThrTyrAlaAlaAspPheLysArgAr gPheThrPheSerLeuAspThrSerLysSerThrAlaTyrLeuGlnMetA snSerLeuArgAlaGluAspThrAlaValTyrTyrCysAlaLysTyrPro

TyrTyrTyrGlyThrSerHisTrpTyrPheAspValTrpGlyGlnGlyTh rLeuValThrValSerSerAlaSerThrLysGlyProSerValPheProL euAlaProSerSerLysSerThrSerGlyGlyThrAlaAlaLeuGlyCys

LeuValLysAspTyrPheProGluProValThrValSerTrpAsnSerGl yAlaLeuThrSerGlyValHisThrPheProAlaValLeuGlnSerSerG lyLeuTyrSerLeuSerSerValValThrValProSerSerSerLeuGly

ThrGlnThrTyrIleCysAsnValAsnHisLysProSerAsnThrLysVa lAspLysLysValGluProLysSerCysAspLysThrHisLeu.

In some embodiments, the heavy chain is SEQ ID NO:1.

In some embodiments, the light chain comprises SEQ ID NO:2:

AspIleGlnLeuThrGlnSerProSerSerLeuSerAlaSerValGlyAs pArgValThrIleThrCysSerAlaSerGlnAspIleSerAsnTyrLeuA snTrpTyrGlnGlnLysProGlyLysAlaProLysValLeuIleTyrPhe

ThrSerSerLeuHisSerGlyValProSerArgPheSerGlySerGlySe rGlyThrAspPheThrLeuThrIleSerSerLeuGlnProGluAspPheA laThrTyrTyrCysGlnGlnTyrSerThrValProTrpThrPheGlyGln

GlyThrLysValGluIleLysArgThrValAlaAlaProSerValPheIl ePheProProSerAspGluGlnLeuLysSerGlyThrAlaSerValValC ysLeuLeuAsnAsnPheTyrProArgGluAlaLysValGlnTrpLysVal

AspAsnAlaLeuGlnSerGlyAsnSerGlnGluSerValThrGluGlnAs pSerLysAspSerThrTyrSerLeuSerSerThrLeuThrGlnSerSerG lyLeuTyrSerLeuSerSerValValThrValProSerSerSerLeuGly

ThrGlnThrTyrIleCysAsnValAsnHisLysProSerAsnThrLysVa lAspLysLysValGluProLysSerCysAspLysThrHisLeu.

In some embodiments, the lgith chain is SEQ ID NO:2.

An antibody used herein can comprise one or both of SEQ ID NOs: 1 and 2. An antibody used herein can consist of one or both of SEQ ID NOs: 1 and 2.

COMPOSITIONS

Disclosed are compositions and formulations for administration to a subject having one or more conditions, for example, one of the ocular diseases or ocular conditions as described herein. The compositions can comprise, for example:

a) a compound herein or a pharmaceutically acceptable salt thereof; and b) a solubilizing system.

The disclosed compositions can comprise from about 0.1 mg/mL to about 100 mg/mL of a compound herein.

Solubilizing Systems

The disclosed solubilizing systems can comprise one or more pharmaceutically acceptable agents, which alone or in combination solubilize a compound herein or a pharmaceutically acceptable salt thereof.

1. Alcohols

A non-limiting example of a solubilizing agent includes an organic solvent. Non-limiting examples of organic solvents includes: alcohols, for example, $C_1$-$C_4$ linear alkyl, $C_3$-$C_4$ branched alkyl, for example, ethanol, glycerin, 2-hydroxypropanol, propylene glycol, maltitol, sorbitol, xylitol and the like; substituted or unsubstituted $C_6$ or $C_{10}$ aryl; substituted or unsubstituted $C_7$ or $C_{14}$ alkylenearyl, for example, benzyl alcohol.

2. Cyclodextrins

A further non-limiting example of a solubilizing agent relates to cyclodextrins: β-cyclodextrin, β-cyclodextrin and β-cyclodextrin and derivatives thereof. Non-limiting examples of cyclodextrin derivatives includes methyl β-cyclodextrin, 2-hydroxypropyl-β-cyclodextrin, sulfobutyl ether-β-cyclodextrin sodium salt, and 2-hydroxypropyl-β-cyclodextrin. A cyclodextrin can possess a large cyclic structure with a channel passing through the center of the structure. The interior of the cyclodextrin can be hydrophobic, and interact favorably with hydrophobic molecules. The exterior of the cyclodextrin can be highly hydrophilic owing to the several hydroxyl groups exposed to bulk solvent. Capture of a hydrophobic molecule, such as a compound disclosed herein, in the channel of the cyclodextrin can result in formation of a complex stabilized by non-covalent hydrophobic interactions. The complex can be soluble in water, and carry the captures hydrophobic molecule into the bulk solvent.

3. Polyvinylpyrrolidione

Another non-limiting example of a solubilizing agent are the polyvinylpyrrolidones (PVP) having the formula:

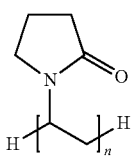

wherein the index n is from about 40 to about 200. PVP's can have an average molecular weight from about 5500 to about 28,000 g/mol. One non-limiting example is PVP-10, having an average molecular weight of approximately 10,000 g/mol.

4. Polyakyleneoxides

A further non-limiting example of solubilizing agents includes polyalkyleneoxides, and polymers of alcohols or polyols. Polymers can be mixed, or contain a single monomeric repeat subunit. For example, polyethylene glycols having an average molecular weight of from about 200 to about 20,000, for example, PEG 200, PEG 400, PEG 600, PEG 1000, PEG 1450, PEG 1500, PEG 4000, PEG 4600, and PEG 8000. In a further embodiment, the compositions comprise one or more polyethylene glycols chosen from PEG 400, PEG 1000, PEG 1450, PEG 4600 and PEG 8000.

Other polyalkyleneoxides are polypropylene glycols having the formula:

wherein the index x represents the average number of propyleneoxy units in the glycol polymer. As in the case of ethylene glycols, for propylene glycols the index x can be represented by a whole number or a fraction. For example, a polypropylene glycol having an average molecular weight of 8,000 g/mole (PEG 8000) can be equally represented by the formulae:

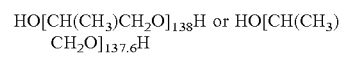

or the polypropylene glycol can be represented by the common, short hand notation: PEG 8000.

Another example of polypropylene glycols can have an average molecular weight from about 1200 g/mol to about 20,000 g/mol, i.e., a polypropylene glycol having an average molecular weight of about 8,000 g/mol, for example, PEG 8000.

Another solubilizing agent is Polysorbate 80 (Tween™ 80) which is an oleate ester of sorbitol and its anhydrides copolymerized with approximately 20 moles of ethylene oxide for each mole of sorbitol and sorbitol anhydrides. Polysorbate 80 is made up of sorbitan mono-9-octadecanoate poly(oxy-1,2-ethandiyl) derivatives.

Solubilizing agents also include poloxamers having the formula:

which are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol (PLURONICS™). These compound are commonly named with the word Poloxamer followed by a number to indicate the specific co-polymer, for example Poloxamer 407 having two PEG blocks of about 101 units ($y^1$ and $y^3$ each equal to 101) and a polypropylene block of about 56 units and poloxamer 185 [CAS No. 9003-11-6] wherein the indices $y^1$, $y^2$; and $y^3$ have the average values of 19, 30 and 10 respectively. Various poloxamers are available under the trade name LUTROL™, for example, LUTROL™ F-17. Pluronic F-68 is a commercially available poloxamer. Other non-limiting examples of suitable poloxamers for use are those such as poloxamer 188, Pluronic F-68, and the like.

5. Polyoxyethylene Glycol Alkyl Ethers

Still further solubilizing agents relate to polyoxyethylene glycol alkyl ethers having the formula:

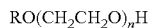

RO(CH$_2$CH$_2$O)$_n$H wherein R is a linear or branched alkyl group having from 6 to 20 carbon atoms and n is an integer of about 2 to about 20.

Examples of these compounds are ethoxylate alcohols such as the NEODOL™ ethoxylated alcohols. NEODOL™ 23-1 is a mixture of R units that are $C_{12}$ and $C_{13}$ in length with an average of 1 ethoxy unit. Non-limiting examples of ethoxylated alcohols include NEODOL™ 23-1, NEODOL™ 23-2, NEODOL™ 23-6.5, NEODOL™ 25-3, NEODOL™ 25-5, NEODOL™ 25-7, NEODOL™ 25-9, PLURONIC™ 12R3, and PLURONIC™ 25R2.

6. Polyoxypropylene Glycol Alkyl Ethers

Yet another example of a solubilizing agent includes polyoxypropylene glycol alkyl ethers having the formula:

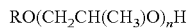

RO(CH$_2$CH(CH$_3$)O)$_n$H wherein R is a linear or branched alkyl group having from 6 to 20 carbon atoms and n is an integer of about 2 to about 20.

The formulator, however, can use any solubilizing agent or agents in combination to affect the solubility of a compound herein.

One aspect of the disclosure relates to compositions and formulations comprising the herein disclosed compounds or a pharmaceutically acceptable salt thereof. Compositions containing the disclosed inhibitors can comprise:
a) a compound herein or a pharmaceutically acceptable salt thereof; and
b) a solubilizing system.

Another aspect of the disclosed compositions relates to Tie-2 activators or HPTP-β inhibitors or a pharmaceutically acceptable salt thereof having the formula:

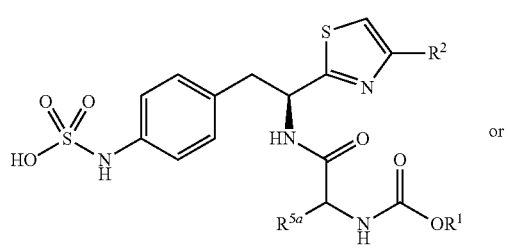

or

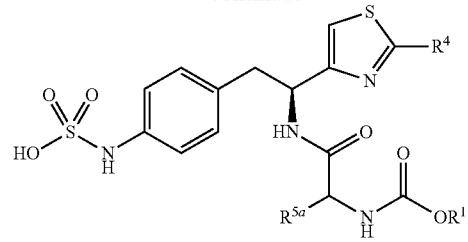

wherein $R^2$ and $R^4$ are chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted phenyl; or
iv) substituted or unsubstituted thiophenyl;
$R^1$ is $C_1$-$C_6$ linear, $C_3$-$C_6$ branched, or $C_3$-$C_6$ cyclic alkyl;
$R^{5a}$ is chosen from:
i) hydrogen;
ii) $C_1$-$C_6$ linear, $C_3$-$C_6$ branched, or $C_3$-$C_6$ cyclic alkyl; or
iii) benzyl; or
a pharmaceutically acceptable salt thereof.

A non-limiting embodiment of this aspect relates to HPTP-β inhibitors having the formula:

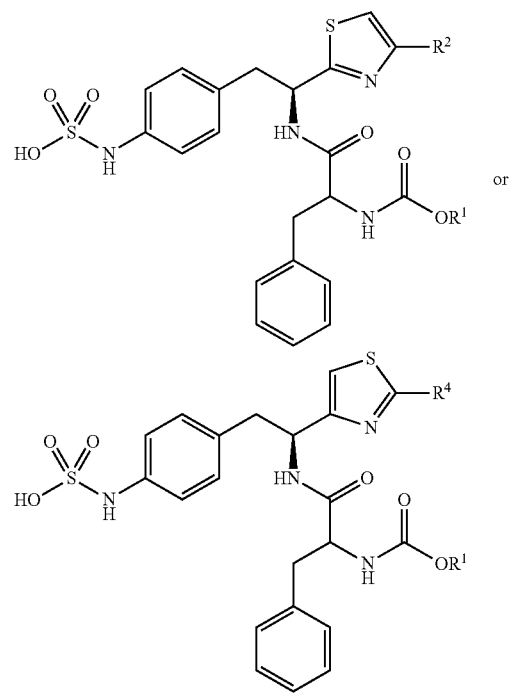

wherein $R^2$ and $R^4$ are chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted phenyl; or
iv) substituted or unsubstituted thiophenyl;
$R^1$ is $C_1$-$C_6$ linear, $C_3$-$C_6$ branched, or $C_3$-$C_6$ cyclic alkyl; or
a pharmaceutically acceptable salt.

An aspect of the disclosed compositions relates to HPTP-β inhibitors or a pharmaceutically acceptable salt thereof having the formula:

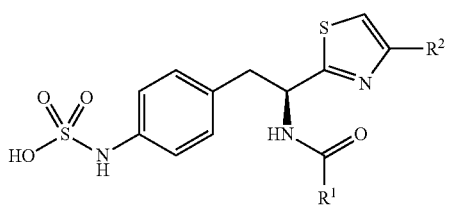

wherein $R^2$ is chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted thiophenyl;
$R^1$ is $C_1$-$C_3$ alkyl substituted by one or more optionally substituted phenyl; or
a pharmaceutically acceptable salt thereof.
In one iteration the substitutions for phenyl are chosen from fluoro, chloro and methoxy.

An aspect of the disclosed compositions relates to HPTP-β inhibitors or a pharmaceutically acceptable salt thereof having the formula:

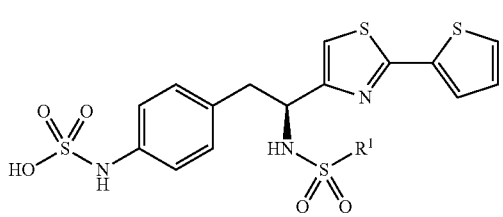

wherein R is chosen from, for example, benzyl, phenylethyl, (2-methylthiazol-4-yl)methyl, 4-methyl-3,4-dihydro-2H-benzo[b][1,4]oxazin-7-yl, (5-(4-chlorobenzamide)methyl)thiopen-2-yl, and (5-(methoxycarbonyl)methyl)-1,3,4-thiadiazol-2-yl.

Formulation Example 1

In one non-limiting example, compositions of compounds herein are prepared as follows. For example, about 100 mg of a sterile powder of, for example, 4-{(S)-2-[(S)-2-methoxycarbonylamino)-3-phenylpropanamido]-2-[2-(thiophen-2-yl)thiazol-4-yl]ethyl}phenylsulfamic acid is diluted in, for example, about 100 mL water to form a first composition. To the composition can be added, for example, 250 mg of hydroxypropyl beta cyclodextrin (HPβCD). Depending upon the formulation, the administrator of the compound can withdraw a sufficient amount such that the subject is injected subcutaneously with an amount that provides from about 5 mg to about 50 mg of the compound. The formulator, however, can prepare a composition having any concentration convenient or desirable. Non-limiting examples according to this embodiment include the following.

TABLE XXII

| Compound (mg) | HPβCD (mg) | Water (mL) |
|---|---|---|
| 50 | 250 | 25 |
| 50 | 250 | 50 |
| 50 | 250 | 75 |
| 50 | 250 | 100 |
| 100 | 250 | 25 |
| 100 | 250 | 50 |

TABLE XXII-continued

| Compound (mg) | HPβCD (mg) | Water (mL) |
|---|---|---|
| 100 | 250 | 75 |
| 100 | 250 | 100 |
| 50 | 250 | 200 |
| 50 | 250 | 300 |
| 50 | 250 | 400 |
| 50 | 250 | 500 |
| 100 | 250 | 200 |
| 100 | 250 | 300 |
| 100 | 250 | 400 |
| 100 | 250 | 500 |

Formulation Example 2

This formulation example relates to compositions comprising 4-{(S)-2-[(S)-2-(methoxycarbonylamino)-3-phenylpropanamido]-2-[2-(thiophen-2-yl)thiazol-4-yl]ethyl}-phenylsulfamic acid, having the formula:

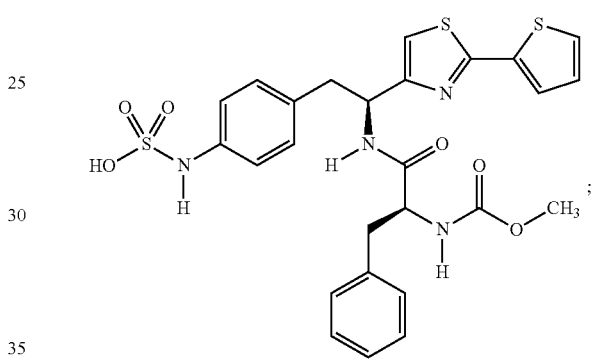

and
pharmaceutically acceptable salts thereof.
Formulation Example 2 comprises:
a) 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof;
b) a solubilizing system; and
c) a carrier system.

The compositions of Formulation Example 2 are formulated to deliver an amount of 4-{(S)-2-[(S)-2-methoxycarbonylamino)-3-phenylpropanamido]-2-[2-(thiophen-2-yl)thiazol-4-yl]ethyl}phenylsulfamic acid in the free acid form. For example, a composition which comprises 10 mg/mL of 4-{(S)-2-[(S)-2-methoxycarbonylamino)-3-phenylpropanamido]-2-[2-(thiophen-2-yl)thiazol-4-yl]ethyl}phenylsulfamic acid can have either 10 mg/mL of the free acid or an amount of a pharmaceutically acceptable salt in an amount sufficient to deliver 10 mg/mL of the free acid. As an example, a composition formulated to deliver 10 mg/mL of 4-{(S)-2-[(S)-2-methoxycarbonylamino)-3-phenylpropanamido]-2-[2-(thiophen-2-yl)thiazol-4-yl]ethyl}phenyl-sulfamic acid can comprise either 10 mg/mL of 4-{(S)-2-[(S)-2-methoxycarbonylamino)-3-phenylpropanamido]-2-[2-(thiophen-2-yl)thiazol-4-yl]ethyl}phenylsulfamic acid or alternatively 10.4 mg/mL of the sodium salt, (sodium (4-{(S)-2-[(S)-2-(methoxycarbonylamino)-3-phenyl-propanamido]-2-(2-(thiophen-2-yl)thiazol-4-yl)ethyl}phenyl)sulfamate). Therefore, a composition which delivers from about 0.1 mg/mL to about 60 mg/mL of (4-{(S)-2-[(S)-2-(methoxycarbonylamino)-3-phenylpropanamido]-2-(2-(thiophen-2-yl)thiazol-4-yl) ethyl}phenyl)sulfamic acid can comprise an amount of pharmaceutically acceptable salt thereof to deliver from about 0.1 mg/mL to about 60 mg/mL of the compound.

Therefore, when a composition according to Formulation I comprises an amount of 4-{(S)-2-[(S)-2-methoxycarbonylamino)-3-phenylpropanamido]-2-[2-(thiophen-2-yl)thiazol-4-yl]ethyl}phenylsulfamic acid per mL, it is understood that this amount is the amount of free acid that is delivered and if a salt form of the compound is used in the composition, the amount of the salt form can therefore reflect the difference in molecular weight between the free acid and the salt form. The following example demonstrates this equivalency.

A composition delivering 10 mg/mL of 4-{(S)-2-[(S)-2-methoxycarbonylamino)-3-phenylpropanamido]-2-[2-(thiophen-2-yl)thiazol-4-yl]ethyl}phenylsulfamic acid, comprises:

a) 10 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid; or about 10.4 mg/mL of sodium (4-{(S)-2-[(S)-2-(methoxycarbonylamino)-3-phenyl-propanamido]-2-(2-(thiophen-2-yl)thiazol-4-yl)ethyl}phenyl)sulfamate; or about 10.3 mg/mL of ammonium (4-{(S)-2-[(S)-2-(methoxycarbonylamino)-3-phenylpropanamido]-2-(2-(thiophen-2-yl)thiazol-4-yl)ethyl}phenyl)sulfamate, and the like;

b) an amount of a solubilizing system; and c) a carrier system.

The disclosed compositions according to Formulation Example 2 according to Formulation Example 2 comprise from about 0.1 mg/mL to about 60 mg/mL of 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof.

In one aspect the disclosed compositions according to Formulation Example 2 comprise from about 0.5 mg/mL to about 60 mg/mL of a compound herein or a pharmaceutically acceptable salt thereof. In one embodiment, the composition comprises from about 5 mg/mL to about 40 mg/mL of a compound herein or a pharmaceutically acceptable salt thereof. In another embodiment, the composition comprises from about 10 mg/mL to about 40 mg/mL of a compound herein or a pharmaceutically acceptable salt thereof. In a further embodiment, the composition comprises from about 10 mg/mL to about 30 mg/mL of a compound herein or a pharmaceutically acceptable salt thereof. In a still further embodiment, the composition comprises from about 0.5 mg/mL to about 20 mg/mL of a compound herein or a pharmaceutically acceptable salt thereof. In a further embodiment the composition comprises from about 1 mg/mL to about 20 mg/mL weight by volume of a compound herein or a pharmaceutically acceptable salt thereof. In a further embodiment, the composition comprises from about 15 mg/mL to about 30 mg/mL weight by volume of a compound herein or a pharmaceutically acceptable salt thereof. In another embodiment, the composition comprises from about 10 mg/mL to about 50 mg/mL weight by volume of a compound herein or a pharmaceutically acceptable salt thereof.

Particular embodiments of the disclosed compositions according to Formulation Example 2, can comprise, for example, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL 32 mg/mL, 33 mg/mL, 34 mg/mL, 35 mg/mL, 36 mg/mL, 37 mg/mL, 38 mg/mL, 39 mg/mL, 40 mg/mL, 41 mg/mL 42 mg/mL, 43 mg/mL, 44 mg/mL, 45 mg/mL, 46 mg/mL, 47 mg/mL, 48 mg/mL, 49 mg/mL, 50 mg/mL, 51 mg/mL 52 mg/mL, 53 mg/mL, 54 mg/mL, 55 mg/mL, 56 mg/mL, 57 mg/mL, 58 mg/mL, 59 mg/mL, and 60 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL about 52 mg/mL, about 53 mg/mL, about 54 mg/mL, about 55 mg/mL, about 56 mg/mL, about 57 mg/mL, about 58 mg/mL, about 59 mg/mL, and about 60 mg/mL of the compound herein.

A formulation that is disclosed herein can be made more soluble by the addition of an additive or agent. The improvement of solubility of the formulation can increase by about 5%, about 10%, about 15%, about 20%, about 25%, about 30%, about 35%, about 40%, about 45%, about 50%, about 55%, about 60%, about 65%, about 70%, about 75% about 80%, about 85%, about 90%, about 95%, about 100%, about 110%, about 120%, about 130%, about 140%, about 150%, about 160%, about 170%, about 180%, about 190%, about 200%, about 225%, about 250%, about 275%, about 300%, about 325%, about 350%, about 375%, about 400%, about 450%, or about 500%.

A formulation disclosed herein can be stable for about 1 day, about 2 days, about 3 days, about 4 days, about 5 days, about 6 days, about 7 days, about 8 days, about 9 days, about 10 days, about 2 weeks, about 4 weeks, about 6 weeks, about 8 weeks, about 10 weeks, about 12 weeks, about 3 months, about 4 months, about 5 months, about 6 months, about 7 months, about 8 months, about 9 months, about 10 months, about 11 months, or about one year. A formulation disclosed herein can be stable, for example, at about 0° C., about 5° C., about 10° C., about 15° C., about 20° C., about 25° C., about 30° C., about 35° C., about 40° C., about 45° C., about 50° C., about 60° C., about 70° C., or about 80° C.

Solubilizing Systems.

The disclosed compositions according to Formulation Example 2 can comprise, for example, from a ratio of about 1 part of a compound herein or a pharmaceutically acceptable salt thereof to 4 parts solubilizing system (1:4) to about 1 part of the compound or a pharmaceutically acceptable salt thereof to about 8 parts solubilizing system (1:8).

The disclosed solubilizing systems comprise 2-hydroxypropyl-beta-cyclodextrin (HPβ-CD). 2-Hydroxypropyl-β-cyclodextrin [CAS No. 128446-35-5] is commercially available as Cavitron™. 2-Hydroxypropyl-β-cyclodextrin, also described herein as hydroxypropyl-β-cyclodextrin, 2-hydroxypropyl-beta-cyclodextrin, hydroxypropyl-beta-cyclodextrin or HPβCD, can be represented by either of the following formulae:

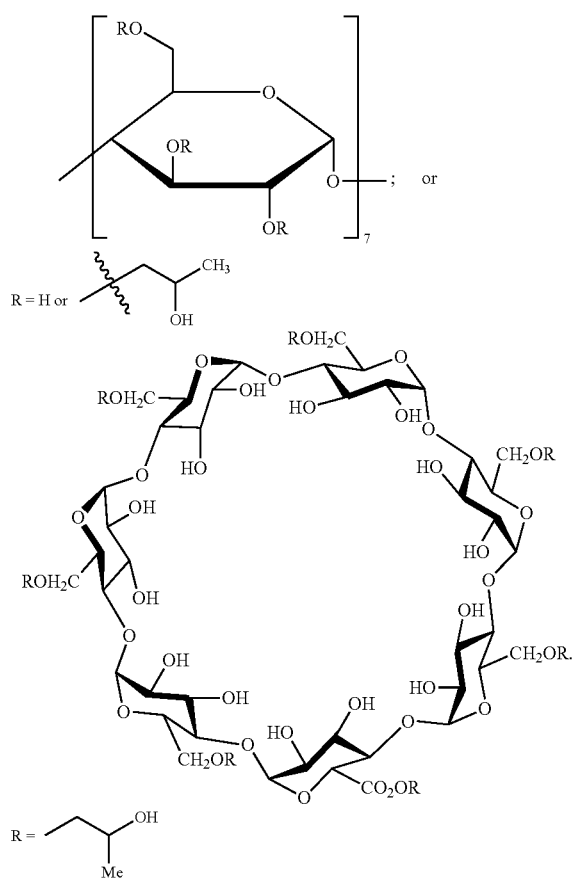

The average molecular weight of HPβCD as provided under the name Cavitron™, is approximately 1396 Da wherein the average degree of substitution is from about 0.5 to about 1.3 units of 2-hydroxypropyl per ring glucose unit. For calculation purposes it is convenient for the formulator to use 1400 Da as the molecular weight of HPβCD.

For example, a composition according to Formulation Example 2 comprising from about 0.1 mg/mL to about 60 mg/mL of the compound or a pharmaceutically acceptable salt thereof can comprise from about 0.25 mg/mL to about 500 mg/mL of HPβCD. Stated another way, a composition comprising about 10 mg/mL of a disclosed composition can comprise from 40 mg/mL (1:4) to about 80 mg/mL (1:8) of HPβCD. The formulator can adjust the ratios of compound to HPβCD based upon composition parameters, for example, choice and amount of a tonicity agent, pH, and the like.

The following are non-limiting examples of ratios of compound or a pharmaceutically acceptable salt and HPβCD: 1:4, 1:4.1, 1:4.2, 1:4.3, 1:4.4; 1:4.5, 1:4.6, 1:4.7, 1:4.8, 1:4.9, 1:5, 1:5.1, 1:5.2, 1:5.3, 1:5.4; 1:5.5, 1:5.6, 1:5.7, 1:5.8, 1:5.9, 1:6, 1:6.1, 1:6.2, 1:6.3, 1:6.4; 1:6.5, 1:6.6, 1:6.7, 1:6.8, 1:6.9, 1:7, 1:7.1, 1:7.2, 1:7.3, 1:7.4; 1:7.5, 1:7.6, 1:7.7, 1:7.8, 1:7.9, and 1:8, or alternatively, about 1:4, about 1:4. about 1, about 1:4.2, about 1:4.3, about 1:4.4; about 1:4.5, about 1:4.6, about 1:4.7, about 1:4.8, about 1:4.9, about 1:5, about 1:5. about 1, about 1:5.2, about 1:5.3, about 1:5.4; about 1:5.5, about 1:5.6, about 1:5.7, about 1:5.8, about 1:5.9, about 1:6, about 1:6.1, about 1:6.2, about 1:6.3, about 1:6.4; about 1:6.5, about 1:6.6, about 1:6.7, about 1:6.8, about 1:6.9, about 1:7, about 1:7.1, about 1:7.2, about 1:7.3, about 1:7.4; about 1:7.5, about 1:7.6, about 1:7.7, about 1:7.8, about 1:7.9, and about 1:8.

As such, the compositions can comprise an amount of HPβCD suitable for achieving the desired properties of the composition, i.e., concentration of a compound, such as 4-{(S)-2-[(S)-2-methoxy-carbonylamino)-3-phenylpropanamido]-2-[2-(thiophen-2-yl)thiazol-4-yl]ethyl}phenylsulfamic acid, the desired viscosity, and the desired osmolarity. The amount of HPβCD can vary depending upon the amount of the compound that the formulator desires to deliver in a single dose.

Carrier System

The disclosed compositions according to Formulation Example 2 comprise from about 1.35% to about 90% weight by volume of a carrier system. The amount of carrier system present is based upon several different factors or choices made by the formulator, for example, the final concentration of the compound and the amount of solubilizing agent.

The following is a non-limiting example of a composition comprising 15 mg/mL of 4-{(S)-2-[(S)-2-methoxycarbonylamino)-3-phenylpropanamido]-2-[2-(thiophen-2-yl)thiazol-4-yl]ethyl}phenylsulfamic acid:
  a) 15 mg of the 4-{(S)-2-[(S)-2-methoxycarbonylamino)-3-phenylpropanamido]-2-[2-(thiophen-2-yl)thiazol-4-yl]ethyl}phenylsulfamic acid;
  b) 93.75 mg of 2-hydroxypropyl-beta-cyclodextrin; and
  c) the balance a carrier system to a volume of 1 mL.

In one aspect, the carrier system comprises:
  i) one or more tonicity agents; and
  ii) water.

Non-limiting examples of tonicity agents include dextrose, mannitol and glycerin. The formulator can utilize more than one tonicity agent when formulating the disclosed compositions according to Formulation Example 2. The tonicity agent can comprise from about 0.5% to about 5% weight by volume of the final composition. In non-limiting examples, when preparing the final composition, the tonicity agent may be combined with 4-{(S)-2-[(S)-2-methoxycarbonylamino)-3-phenylpropanamido]-2-[2-(thiophen-2-yl)thiazol-4-yl]ethyl}phenylsulfamic acid before mixing with the carrier system. Alternately, when reconstituting the final composition the formulator can use commercially available solutions containing a tonicity agent, for example, 5% Dextrose Injection, USP.

The osmolarity of the disclosed compositions according to Formulation Example 2 can be within any range chosen by the formulator. In one aspect the osmolarity is from about 250 to about 350 mOsm/L. In one embodiment of this aspect of the disclosed osmolarity is from about 270 to about 310 mOsm/L.

The pH of the disclosed compositions according to Formulation Example 2 can be from about 6 to about 8. If the pH is outside the range desired by the formulator, the pH can be adjusted by using sufficient pharmaceutically-acceptable acids and bases.

One aspect of the disclosed compositions according to Formulation Example 2 relates to compositions comprising 4-{(S)-2-[(S)-2-methoxycarbonylamino)-3-phenylpropanamido]-2-[2-(thiophen-2-yl)thiazol-4-yl]ethyl}phenylsulfamic acid or pharmaceutically acceptable salts thereof.

One embodiment of this aspect of the disclosed compositions according to Formulation Example 2 comprises:
  a) from about 9.5 mg/mL to about 10.5 mg/mL of the 4-{(S)-2-[(S)-2-methoxycarbonylamino)-3-phenylpropanamido]-2-[2-(thiophen-2-yl)thiazol-4-yl]
ethyl}phenylsulfamic acid or a pharmaceutically acceptable salt thereof;
b) from about 59 mg/mL to about 65.5 mg/mL of 2-hydroxypropyl-β-cyclodextrin; and
c) a carrier system.

A non-limiting iteration of this embodiment of the disclosed compositions according to Formulation Example 2 comprises:
a) about 10 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) about 62.5 mg/mL of 2-hydroxypropyl-β-cyclodextrin; and
c) a carrier system.

One specific example of a composition according to this iteration comprises:
a) 10 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) 62.5 mg/mL of 2-hydroxypropyl-β-cyclodextrin; and
c) a carrier system containing:
i) 2% weight to volume of the composition dextrose; and
ii) water.
c) a carrier system containing:
i) dextrose; and
ii) water
wherein the dextrose is present in an amount such that the concentration of dextrose in the final composition is 2%.

Another embodiment of this aspect of the disclosed compositions according to Formulation Example 2 comprises:
a) from about 14 mg/mL to about 16 mg/mL of the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof;
b) from about 87.5 mg/mL to about 100 mg/mL of 2-hydroxypropyl-β-cyclodextrin; and
c) a carrier system.

A non-limiting iteration of this embodiment of the disclosed compositions according to Formulation Example 2 comprises:
a) about 15 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) about 93.75 mg/mL of 2-hydroxypropyl-β-cyclodextrin; and
c) a carrier system.

One specific example of a composition according to this iteration comprises:
a) 15 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) 93.75 mg/mL of 2-hydroxypropyl-β-cyclodextrin; and
c) a carrier system containing:
i) 2% weight to volume of the composition dextrose; and
ii) water.

A further embodiment of this aspect of the disclosed compositions according to Formulation Example 2 comprises:
a) from about 18.5 mg/mL to about 21.5 mg/mL of the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof;
b) from about 115.6 mg/mL to about 134.5 mg/mL of 2-hydroxypropyl-β-cyclodextrin; and
c) a carrier system.

A non-limiting iteration of this embodiment of the disclosed compositions according to Formulation Example 2 comprises:
a) about 20 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) about 125 mg/mL of 2-hydroxypropyl-β-cyclodextrin; and
c) a carrier system.

One specific example of a composition according to this iteration comprises:
a) 20 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) 125 mg/mL of 2-hydroxypropyl-β-cyclodextrin; and
c) a carrier system containing:
i) 2% weight to volume of the composition dextrose; and
ii) water.

A further embodiment of this aspect of the disclosed compositions according to Formulation Example 2 comprises:
a) from about 24 mg/mL to about 26 mg/mL of the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof;
b) from about 150 mg/mL to about 162.5 mg/mL of 2-hydroxypropyl-β-cyclodextrin; and
c) a carrier system.

A non-limiting iteration of this embodiment of the disclosed compositions according to Formulation Example 2 comprises:
a) about 25 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) about 156.25 mg/mL of 2-hydroxypropyl-β-cyclodextrin; and
c) a carrier system.

One specific example of a composition according to this iteration comprises:
a) 25 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) 156.25 mg/mL of 2-hydroxypropyl-β-cyclodextrin; and
c) a carrier system containing:
i) 2% weight to volume of the composition dextrose; and
ii) water.

A further embodiment of this aspect of the disclosed compositions according to Formulation Example 2 comprises:
a) from about 27.5 mg/mL to about 32 mg/mL of the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof;
b) from about 170 mg/mL to about 200 mg/mL of 2-hydroxypropyl-β-cyclodextrin; and
c) a carrier system.

A non-limiting iteration of this embodiment of the disclosed compositions according to Formulation Example 2 comprises:
   a) about 30 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
   b) about 187.5 mg/mL of 2-hydroxypropyl-β-cyclodextrin; and
   c) a carrier system.

One specific example of a composition according to this iteration comprises:
   a) 30 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
   b) 187.5 mg/mL of 2-hydroxypropyl-β-cyclodextrin; and
   c) a carrier system containing:
      i) 2% weight to volume of the composition dextrose; and
      ii) water.

Another embodiment of this aspect of the disclosed compositions according to Formulation Example 2 comprises:
   a) from about 34 mg/mL to about 36 mg/mL of the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof;
   b) from about 212.5 mg/mL to about 223.5 mg/mL of 2-hydroxypropyl-β-cyclodextrin; and
   c) a carrier system.

A non-limiting iteration of this embodiment of the disclosed compositions according to Formulation Example 2 comprises:
   a) about 35 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
   b) about 218.75 mg/mL of 2-hydroxypropyl-β-cyclodextrin; and
   c) a carrier system.

One specific example of a composition according to this iteration comprises:
   a) 35 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
   b) 218.75 mg/mL of 2-hydroxypropyl-β-cyclodextrin; and
   c) a carrier system containing:
      i) 2% weight to volume of the composition dextrose; and
      ii) water.

Another embodiment of this aspect of the disclosed compositions according to Formulation Example 2 comprises:
   a) from about 38 mg/mL to about 42 mg/mL of the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof;
   b) from about 237.5 mg/mL to about 262.5 mg/mL of 2-hydroxypropyl-β-cyclodextrin; and
   c) a carrier system.

A non-limiting iteration of this embodiment of the disclosed compositions according to Formulation Example 2 comprises:
   a) about 40 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
   b) about 250 mg/mL of 2-hydroxypropyl-β-cyclodextrin; and
   c) a carrier system.

One specific example of a composition according to this iteration comprises:
   a) 40 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
   b) 250 mg/mL of 2-hydroxypropyl-β-cyclodextrin; and
   c) a carrier system containing:
      i) 2% weight to volume of the composition dextrose; and
      ii) water.

EXAMPLE 25

To a 100 mL volumetric flask containing water (85 mL) was charged HPβCD (10 g) and dextrose (1.5 g). The solution was stirred for 1 hour at 20° C. then the volume made up to 100 mL with additional distilled water. The resulting solution comprised 10% HPβCD and 1.5% dextrose.

In a like manner, solutions comprising 15% HPβCD/1.5% dextrose and 17.5% HPβCD/1.5% dextrose were prepared. These stock solutions were used for the following experiments.

In a 25 mL volumetric flask is added the stock solution comprising 10% HPβCD/1.5% dextrose followed by the addition of sodium 4-{(S)-2-[(S)-2-(methoxy-carbonylamino)-3-phenylpropanamido]-2-[2-(thiophen-2-yl)thiazol-4-yl]ethyl}phenyl-sulfamate (550 mg). The total volume was made up to 25 mL by the addition of distilled water. The resulting solution had a nominal concentration of 4-{(S)-2-[(S)-2-methoxy-carbonylamino)-3-phenylpropanamido]-2-[2-(thiophen-2-yl)thiazol-4-yl]ethyl}phenyl-sulfamic acid of 20 mg/mL after applying a molecular weight correction factor.

Similarly, to a stock solution comprising 10% HPβCD/1.5% dextrose was added 4-{(S)-2-[(S)-2-(methoxy-carbonylamino)-3-phenylpropanamido]-2-[2-(thiophen-2-yl)thiazol-4-yl]ethyl}phenyl-sulfamate (687 mg). After dilution to 25 mL the resulting solution had a nominal concentration of 4-{(S)-2-[(S)-2-methoxy-carbonylamino)-3-phenylpropanamido]-2-[2-(thiophen-2-yl)thiazol-4-yl]ethyl}phenyl-sulfamic acid of 25 mg/mL after applying a molecular weight correction factor.

Compositions comprising 15% HPβCD/1.5% dextrose and 687 mg and 825 mg of 4-{(S)-2-[(S)-2-(methoxy-carbonylamino)-3-phenylpropanamido]-2-[2-(thiophen-2-yl)thiazol-4-yl]ethyl}phenyl-sulfamate were also prepared. Likewise, compositions comprising 17.5% HPβCD/1.5% dextrose and 825 mg and 962.5 mg of Compound A-Na were also prepared.

The following Table XXIII describes the test compositions each totaling 25 mL wherein 4-{(S)-2-[(S)-2-(methoxy-carbonylamino)-3-phenylpropanamido]-2-[2-(thiophen-2-yl)thiazol-4-yl]ethyl}phenyl-sulfamate is listed as Compound A-Na.

TABLE XXIII

| Stock Solution | 10% HPβCD/ 1.5% dex. | | 15% HPβCD/ 1.5% dex. | | 17.5% HPβCD/ 1.5% dex. | |
| --- | --- | --- | --- | --- | --- | --- |
| Comp A-Na (mg) | 550 | 687 | 687 | 825 | 825 | 962.5 |

TABLE XXIII-continued

| Stock Solution | 10% HPβCD/ 1.5% dex. | | 15% HPβCD/ 1.5% dex. | | 17.5% HPβCD/ 1.5% dex. | |
|---|---|---|---|---|---|---|
| Comp A mg/mL | 20 | 25 | 25 | 30 | 30 | 35 |

To 3 one-dram vials was transferred approximately 3 mL of each of the 6 solutions above. One vial of each was held at 4° C., 20° C. and 40° C. The vials were evaluated weekly for one month then monthly for three months.

After 3 months none of the vials appeared hazy or had any precipitate or flocculent. The above compositions where then further processed and submitted for in vivo testing.

Preparation of Compositions for Subcutaneous Deliver Via 0.75 mL Single Use Syringes

EXAMPLE 26

To 200 mL of Mille-Q water was added 2-hydroxypropyl-β-cyclodextrin (50 g) (Ashland/ISP Cavitron W7HP7) with stirring. Next, dextrose (96%) (1.3 g) (Sigma Aldrich) was added and the solution was stirred until all the solids were dissolved. Sodium (4-{(S)-2-[(S)-2-(methoxycarbonylamino)-3-phenylpropanamido]-2-(2-(2-thiophen-2-yl)thiazol-4-yl)ethyl}phenyl)-sulfamate (10.82 g) was added and the solution was stirred until the solids were dissolved. The resulting solution had a pH value of 7.26 and a density of 1.07 g/mL. Final solution filtered through Millipore™ MilliPak 20-0.22 micron PVDF filter. A calibrated peristaltic pump was used to dispense 0.75 mL of the final solution into HYpak 0.75 mL syringes having 27 g staked needles and Hypak FluoroTec stoppers.

EXAMPLE 27

To 200 mL of Milli-Q water was added 2-hydroxypropyl-β-cyclodextrin (43.75 g) (Ashland/ISP Cavitron W7HP7) with stirring. Next, Dextrose (96%) (2.61 g) (Sigma Aldrich) was added and the solution was stirred until all the solids were dissolved. Sodium (4-{(S)-2-[(S)-2-(methoxycarbonylamino)-3-phenylpropanamido]-2-(2-(2-thiophen-2-yl)thiazol-4-yl)ethyl}phenyl)-sulfamate (10.85 g) was added and the solution was stirred until the solids were dissolved. The resulting solution had a pH value of 7.32 which was adjusted to 7.04 with 1N HCl (0.5 mL). The final solution had a density of 1.064 g/mL. Final solution filtered through Millipore™ MilliPak 20-0.22 micron PVDF filter. A calibrated peristaltic pump was used to dispense 0.75 mL of the final solution into HYpak 0.75 mL syringes having 27 g staked needles and Hypak FluoroTec stoppers.

EXAMPLE 28

To 200 mL of Milli-Q water was added 2-hydroxypropyl-β-cyclodextrin (56.25 g) (Ashland/ISP Cavitron W7HP7) with stirring. Next, Dextrose (96%) (1.3 g) (Sigma Aldrich) was added and the solution was stirred until all the solids were dissolved. Sodium (4-{(S)-2-[(S)-2-(methoxycarbonylamino)-3-phenylpropanamido]-2-(2-(2-thiophen-2-yl)thiazol-4-yl)ethyl}phenyl)-sulfamate (10.86 g) was added and the solution was stirred until the solids were dissolved. The resulting solution had a pH value of 7.24 and a density of 1.074 g/mL. Final solution filtered through Millipore™ MilliPak 20-0.22 micron PVDF filter. A calibrated peristaltic pump was used to dispense 0.75 mL of the final solution into HYpak 0.75 mL syringes having 27 g staked needles and Hypak FluoroTec stoppers.

In the above examples, the formulator can alternatively heat the solution to about 40° C. to aid in solubilizing the components. In addition, the formulator can filter the solutions at any point in the process to remove any undissolved material.

The following is a non-limiting example of the process for preparing a pharmaceutical composition suitable for subcutaneous delivery of the disclosed compositions according to Formulation Example 2 comprising 4-{(S)-2-[(S)-2-methoxy-carbonylamino)-3-phenylpropanamido]-2-[2-(thiophen-2-yl)thiazol-4-yl]ethyl}phenyl-sulfamic acid or a pharmaceutically acceptable salt to humans.

Step-Wise Manufacturing Process: 20 Mg of 4-{(S)-2-[(S)-2-methoxycarbonylamino)-3-phenylpropanamido]-2-[2-(thiophen-2-yl)thiazol-4-yl]ethyl}phenylsulfamic acid Per mL Solution 1. Add approximately 16.0 kg of United States Pharmacopeia (USP) Sterile Water for Injection to an appropriately-sized glass vessel.
2. Add 2812.5 g of 2-hydroxylpropyl-beta-cyclodextrin (HPβCD) (USP) to the glass flask and mix for a minimum of 5 minutes or until dissolved.
3. Add 450 g of 4-{(S)-2-[(S)-2-methoxy-carbonylamino)-3-phenylpropanamido]-2-[2-(thiophen-2-yl)thiazol-4-yl]ethyl}phenyl-sulfamic acid (as the sodium salt factored for purity, volatiles and water) to the glass flask and mix for a minimum of 30 minutes or until all of the solids are dissolved.
4. Add 450 g of D-glucose (Dextrose) Anhydrous (USP) to the glass flask and mix for a minimum of 5 minutes or until all of the solids are dissolved.
5. Transfer the solution to a 36 L glass formulation vessel using a peristaltic pump.
6. QS the formulation to 22.7 kg by adding Sterile Water for Injection, USP and mix for a minimum of 30 minutes or until dissolved.
7. Adjust the pH to obtain a pH of 6.6-7.0.
8. Add sufficient quantities of Sterile Water for Injection, USP to the batch to obtain the final batch weight of 23.7 kg (22.5 L*1.052 g/mL-specific gravity) and mix for a minimum of 10 minutes or until all of the solids are dissolved.
9. Filter through two filters (Sartopore 2 XLG Midicap filters) connected in series into a similar 36 L glass fill vessel.
10. Fill into various syringes: i.e., 0.75 mL syringe (to deliver 15 mg of 4-{(S)-2-[(S)-2-methoxy-carbonylamino)-3-phenylpropanamido]-2-[2-(thiophen-2-yl)thiazol-4-yl]ethyl}phenyl-sulfamic acid), 1 mL syringe (20 mg of 4-{(S)-2-[(S)-2-methoxy-carbonylamino)-3-phenylpropanamido]-2-[2-(thiophen-2-yl)thiazol-4-yl]ethyl}phenyl-sulfamic acid), etc.

Dry Compositions

The disclosed compositions according to Formulation Example 2 can be re-constituted from a dry or solid composition. As such the dry or solid compositions comprise:
a) 4-{(S)-2-[(S)-2-methoxy-carbonylamino)-3-phenylpropanamido]-2-[2-(thiophen-2-yl)thiazol-4-yl]ethyl}phenyl-sulfamic acid or a pharmaceutically acceptable salt thereof; and
b) HPβCD.

The dry compositions are prepared such that upon re-constitution with a carrier system described herein, the resulting aqueous composition delivers from about 0.5 mg/mL to about 60 mg/mL of the 4-{(S)-2-[(S)-2-methoxy-carbonylamino)-3-phenylpropanamido]-2-[2-(thiophen-2-yl)thiazol-4-yl]ethyl}phenylsulfamic acid or a pharmaceutically acceptable salt thereof.

As in the aqueous compositions described herein, the ratio of the 4-{(S)-2-[(S)-2-methoxycarbonylamino)-3-phenyl-propanamido]-2-[2-(thiophen-2-yl)thiazol-4-yl]ethyl}phenylsulfamic acid to HPβCD is from about 1:4 to about 1:8. The amount of dry material in a container that can be reconstituted can vary depending upon the number of doses of dry material desired. For example, a single 15 mg/mL dose of the compound can be sealed or otherwise placed in a container that has an exact volume such that when the composition is re-constituted, an amount of composition that is reconstituted has 15 mg/mL of a compound.

In another embodiment, the dry compositions comprise:
a) 4-{(S)-2-[(S)-2-methoxy-carbonylamino)-3-phenyl-propanamido]-2-[2-(thiophen-2-yl)thiazol-4-yl]ethyl}phenyl-sulfamic acid or a pharmaceutically acceptable salt thereof;
b) HPβCD; and
c) a tonicity agent;

wherein the ratio of 4-{(S)-2-[(S)-2-(methoxycarbonylamino)-3-phenylpropanamido]-2-[2-(thiophen-2-yl)thiazol-4-yl]ethyl}phenylsulfamic acid to HPβCD is from about 1:4 to about 1:8 and the tonicity agent is present in an amount such that the re-constituted formula comprises from about 0.5% to about 5% weight to volume of the tonicity agent.

The use of further solubilizing agents was examined. In a first test of further solubilizing agents, polyvinylpyrrolidone (PVP) having the formula:

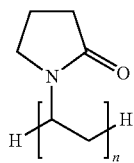

wherein the index n is from about 40 to about 200 was tested. PVP's have an average molecular weight from about 5500 to about 28,000 g/mol. One non limiting example is PVP-10 having an average molecular weight of approximately 10,000 g/mol available from Sigma-Aldrich.

The follow experiments were undertaken to determine the suitability of formulating a composition comprising PVP and HPβCD as a solubilizing system for sodium 4-{(S)-2-[(S)-2-(methoxycarbonylamino)-3-phenylpropanamido]-2-[2-(thiophen-2-yl)thiazol-4-yl]ethyl}phenylsulfamate. The following is a non-limiting example.

EXAMPLE 29

To a 25 mL volumetric flask containing 20 mL of distilled water is charged hydroxylpropyl-β-cyclodextrin (2.5 g) and polyvinylpyrrolidone, PVP-10, (0.125 g) and the solution stirred at room temperature for 0.5 hours. Additional water was added to bring the final volume to 25 mL. The following compositions were prepared according to this procedure.

TABLE XXIV

| Experiment No. | Concentration | HPβCD (g) | PVP-10 (g) |
|---|---|---|---|
| 1 | 10% HPβCD + 0.5% PVP | 2.5 | 0.125 |
| 2 | 10% HPβCD + 1.0% PVP | 2.5 | 0.25 |
| 3 | 10% HPβCD + 2.0% PVP | 2.5 | 0.5 |
| 4 | 15% HPβCD + 0.5% PVP | 3.75 | 0.125 |
| 5 | 15% HPβCD + 1.0% PVP | 3.75 | 0.25 |
| 6 | 15% HPβCD + 2.0% PVP | 3.75 | 0.5 |

To each solution was added sodium (4-{(S)-2-[(S)-2-(methoxycarbonylamino)-3-phenylpropanamido]-2-(2-(thiophen-2-yl)thiazol-4-yl)ethyl}-phenyl)sulfamate (1300 mg) was added to solutions 1, 2 and 3 and stirred for 6 hours at room temperature to provide a nominal concentration of 52 mg/mL. Similarly, the compound (1500 mg) was added to solutions 4 5, and 6 and stirred for 6 hours at room temperature to provide a nominal concentration of 60 mg/mL. Table XXV lists the solution obtained herein below.

TABLE XXV

| Experiment No. | Comp. A-Na mg/mL | HPβCD mg/mL | PVP-10 mg/mL |
|---|---|---|---|
| 7 | 52 | 100 | 5 |
| 8 | 52 | 100 | 10 |
| 9 | 52 | 100 | 20 |
| 10 | 60 | 150 | 5 |
| 11 | 60 | 150 | 10 |
| 12 | 60 | 150 | 20 |

Summary of Results

All compositions comprising polyvinylpyrrolidones were hazy upon 2 hours of standing or yielded a suspension. Experiments 10, 11 and 12 yielded a gel upon standing. Compositions formulated in the manner of Example 30 having only a PVP (no HPβCD) formed a hazy initial solution that setup as a gel and remained such upon standing for 3 days.

In one aspect of the disclosed compositions according to Formulation Example 2, the compositions do not comprise polyvinylpyrrolidone or a derivative thereof. Compositions which gel upon standing cannot be injected parentally, e.g., subcutaneously and, therefore, are incompatible with the disclosed compositions according to Formulation Example 2. This is because the temperature during shipment and storage of the compositions result in physical properties, i.e., formation of a gel that cannot be administered by the artisan.

In a further aspect of the disclosed compositions according to Formulation Example 26, the compositions do not comprise polyvinylpyrrolidone or a derivative thereof in combination with 2-hydroxypropyl-β-cyclodextrin.

The follow experiments were undertaken to determine the suitability of formulating a composition comprising a quaternary ammonium salt, PVP and HPβCD as a solubilizing system for sodium 4-{(S)-2-[(S)-2-methoxycarbonylamino)-3-phenylpropanamido]-2-[2-(thiophen-2-yl)thiazol-4-yl]ethyl}phenylsulfamate. The following is a non-limiting example.

Preparation of Stock Solution

Benzalkonium chloride (BAC; alkylbenzyldimethylammonium chloride, alkyl: $C_8$-$C_{18}$ available from Sigma-Aldrich) (36.3 mg) was added to water (200 mL) in a 250 mL volumetric flask. The mixture was stirred for 10 hours in a 35° C. water bath until the solution was clear. 2-Hydroxypropyl-β-cyclodextrin (27.5 g) was added and the volume made up to 250 mL with the addition of more water.

EXAMPLE 30

To a 25 mL volumetric flask is added the stock solution (22.8 mL followed by polyvinylpyrrolidone (Povidone 437190™ ex Sigma-Aldrich) (0.25 g) and sodium (4-{(S)-2-[(S)-2-(methoxycarbonylamino)-3-phenylpropanamido]-2-(2-(2-(thiophen-2-yl)thiazol-4-yl)ethyl}phenyl)-sulfamate (1.14 g). The volume was made up to 25 mL with the addition of more stock solution. The resulting suspension was stirred for 1 hour at 20° C. The solution was filtered through 0.65 micron then 0.45 micron filter paper and 5 mL of the filtrate was transferred to 3 separate vials. One vial was held at each of the following temperatures 4° C., 20° C. and 40° C.

EXAMPLE 31

To a 25 mL volumetric flask is added the stock solution (22.8 mL followed by polyvinylpyrrolidone (Povidone 437190™ ex Sigma-Aldrich) (0.375 g) and sodium (4-{(S)-2-[(S)-2-(methoxycarbonylamino)-3-phenylpropanamido]-2-(2-(2-(thiophen-2-yl)thiazol-4-yl)ethyl}phenyl)-sulfamate (1.14 g). The volume was made up to 25 mL with the addition of more stock solution. The resulting suspension was stirred for 1 hour at 20° C. The solution was filtered through 0.65 micron then 0.45 micron filter paper, however, the flow rate was extremely slow. 5 mL of the filtrate was transferred to 3 separate vials. One vial was held at each of the following temperatures 4° C., 20° C. and 40° C.

EXAMPLE 32

To a 25 mL volumetric flask is added the stock solution (22.8 mL followed by polyvinylpyrrolidone (Povidone 437190™ ex Sigma-Aldrich) (0.5 g) and sodium (4-{(S)-2-[(S)-2-(methoxycarbonylamino)-3-phenylpropanamido]-2-(2-(2-(thiophen-2-yl)thiazol-4-yl)ethyl}phenyl)-sulfamate (1.43 g). The volume was made up to 25 mL with the addition of more stock solution. The resulting suspension was stirred for 1 hour at 20° C. Attempt to filter solution through 0.65 micron then 0.45 micron filter paper and 5 mL of the filtrate was unsuccessful. Example 9 was abandoned.

Table XXVI below outlines the compositions of Examples 7-9: sodium 4-{(S)-2-[(S)-2-methoxy-carbonylamino)-3-phenylpropanamido]-2-[2-(thiophen-2-yl)thiazol-4-yl]ethyl}phenylsulfamate is referred to as Compd A-Na in the table.

TABLE XXVI

| Components | Ex. 11 (mg/mL) | Ex. 12 (mg/mL) | Ex. 13 (mg/mL) |
|---|---|---|---|
| Compd A-Na | 40 | 40 | 50 |
| PVP | 10 | 15 | 20 |
| BAC | 0.13 | 0.13 | 0.13 |
| HPβCD | 100 | 100 | 100 |

Summary of Results

Example 7: 4° C. sample gelled and remained so for 8 days.
20° C. a suspension was observed.
40° C. solution remained clear for 8 days.

Example 8: 4° C. sample gelled and remained so for 8 days.
20° C. the solution appeared hazy.
40° C. solution remained clear for 8 days.

In some embodiments of the disclosed compositions according to Formulation Example 2, the compositions do not comprise benzalkonium chloride or other quaternary ammonium salt. In some embodiments of the disclosed compositions according to Formulation Example 2, the compositions do comprise benzalkonium chloride or other quaternary ammonium salt.

In a further aspect of the disclosed compositions according to Formulation Example 2, in some embodiments, the compositions do comprise benzalkonium chloride or other quaternary ammonium salt in combination with 2-hydroxypropyl-β-cyclodextrin, and in some embodiments, the compositions do not comprise benzalkonium chloride or other quaternary ammonium salt in combination with 2-hydroxypropyl-β-cyclodextrin.

In a still further aspect of the disclosed compositions according to Formulation Example 2, in some embodiments, the compositions do comprise benzalkonium chloride or other quaternary ammonium salt in combination with polyvinylpyrrolidone or a derivative thereof, and in some embodiments, the compositions do not comprise benzalkonium chloride or other quaternary ammonium salt in combination with polyvinylpyrrolidone or a derivative thereof.

In a yet further aspect of the disclosed compositions according to Formulation Example 2, in the somebodiments, the compositions do comprise benzalkonium chloride or other quaternary ammonium salt in combination with polyvinylpyrrolidone or a derivative thereof and 2-hydroxypropyl-β-cyclodextrin, and in some embodiments, the compositions do not comprise benzalkonium chloride or other quaternary ammonium salt in combination with polyvinylpyrrolidone or a derivative thereof and 2-hydroxypropyl-β-cyclodextrin.

Some embodiments do, and some embodiments do not contain polyethylene glycol. Non-limiting examples of polyethylene glycols include those having an average molecular weight of from about 200 to about 20,000, for example, PEG 200, PEG 400, PEG 600, PEG 1000, PEG 1450, PEG 1500, PEG 4000, PEG 4600, and PEG 8000. In a further embodiment, the compositions comprise one or more polyethylene glycols chosen from PEG 400, PEG 1000, PEG 1450, PEG 4600 and PEG 8000. Non-limiting examples include any disclosed herein.

The disclosed compositions according to Formulation Example 2 optionally comprise from about 0.001% to about 0.5%, or from about 0.001% to about 1% weight by volume pharmaceutically acceptable preservatives. One non-limiting example of a suitable preservative is benzyl alcohol.

In some embodiments, the compositions according to Formula Example 1 consists essentially of 4-{(S)-2-[(S)-2-methoxy-carbonylamino)-3-phenylpropanamido]-2-[2-(thiophen-2-yl)thiazol-4-yl]ethyl}phenylsulfamic acid or a pharmaceutically acceptable salt thereof, a solubilizing system and a carrier system.

In some embodiments, the compositions according to Formula Example 1 consists of 4-{(S)-2-[(S)-2-methoxy-carbonylamino)-3-phenylpropanamido]-2-[2-(thiophen-2-yl)thiazol-4-yl]ethyl}phenylsulfamic acid or a pharmaceutically acceptable salt thereof, a solubilizing system and a carrier system.

In some embodiments, the compositions according to Formula Example 1 consists essentially of 4-{(S)-2-[(S)-2-methoxy-carbonylamino)-3-phenylpropanamido]-2-[2-

(thiophen-2-yl)thiazol-4-yl]ethyl}phenylsulfamic acid or a pharmaceutically acceptable salt thereof, a solubilizing system and a carrier system, wherein the solubilizing system consists of HPβCD.

In still other embodiments, the compositions according to Formula Example 1 consists essentially of 4-{(S)-2-[(S)-2-methoxycarbonylamino)-3-phenylpropanamido]-2-[2-(thiophen-2-yl)thiazol-4-yl]ethyl}phenyl-sulfamic acid or a pharmaceutically acceptable salt thereof, a solubilizing system and a carrier system wherein the carrier system consists of water and a tonicity agent.

In yet other embodiments, the compositions according to Formula Example 1 consists essentially of 4-{(S)-2-[(S)-2-methoxycarbonylamino)-3-phenylpropanamido]-2-[2-(thiophen-2-yl)thiazol-4-yl]ethyl}phenyl-sulfamic acid or a pharmaceutically acceptable salt thereof, a solubilizing system and a carrier system, wherein the solubilizing system consists of HPβCD and wherein the carrier system consists of water and a tonicity agent.

In still other embodiments, the compositions according to Formula Example 1 consists essentially of 4-{(S)-2-[(S)-2-methoxycarbonylamino)-3-phenylpropanamido]-2-[2-(thiophen-2-yl)thiazol-4-yl]ethyl}phenyl-sulfamic acid or a pharmaceutically acceptable salt thereof, HPβCD, a tonicity agent, water and optionally a preservative.

In a particular embodiment the compositions according to Formula Example 1 consists of 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof, HPβCD, a tonicity agent, water and optionally a preservative.

The disclosed compositions according to Formulation Example 2 can further comprise from about 0.01% to about 1% weight by volume pharmaceutically acceptable preservatives. One non-limiting example of a suitable preservative is benzyl alcohol, for example, 0.9% benzyl alcohol.

Excipients.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, rectal, aerosol, parenteral, ophthalmic, pulmonary, transdermal, vaginal, otic, nasal, and topical administration.

A pharmaceutical composition can be administered in a local or systemic manner, for example, via injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated readily by combining the active compounds with pharmaceutically-acceptable carriers or excipients. Such carriers can be used to formulate tablets, powders, pills, dragees, capsules, liquids, gels, syrups, elixirs, slurries, suspensions and the like, for oral ingestion by a subject.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can contain the active ingredients in admixture with filler such as lactose, binders such as starches, and/or lubricants such as talc or magnesium stearate and, stabilizers. In soft capsules, the active compounds can be dissolved or suspended in suitable liquids, such as fatty oils, liquid paraffin, or liquid polyethylene glycols. Stabilizers can be added. All formulations for oral administration are provided in dosages suitable for such administration.

For buccal or sublingual administration, the compositions can be tablets, lozenges, or gels.

Parental injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

Formulations suitable for transdermal administration of the active compounds can employ transdermal delivery devices and transdermal delivery patches, and can be lipophilic emulsions or buffered aqueous solutions, dissolved and/or dispersed in a polymer or an adhesive. Such patches can be constructed for continuous, pulsatile, or on demand delivery of pharmaceutical compounds. Transdermal delivery can be accomplished by means of iontophoretic patches. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin or the eye.

For administration by inhalation, the active compounds can be in a form as an aerosol, a mist, or a powder. Pharmaceutical compositions are conveniently delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compounds described herein can be manufactured, for example, by mixing, dissolving, granulating, dragee-making, levigating, emulsifying, encapsulating, entrapping, or compression processes.

The pharmaceutical compositions can include at least one pharmaceutically acceptable carrier, diluent, or excipient and compounds described herein as free-base or pharmaceutically-acceptable salt form. The methods and pharmaceutical compositions described herein include the use crystalline forms (also known as polymorphs), and active metabolites of these compounds having the same type of activity.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include feed, food, pellet, lozenge, liquid, elixir, aerosol, inhalant, spray, powder, tablet, pill, capsule, gel, geltab, nanosuspension, nano-particle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

Non-limiting examples of pharmaceutically-acceptable excipients suitable for use in the invention include granulating agents, binding agents, lubricating agents, disintegrating agents, sweetening agents, glidants, anti-adherents, antistatic agents, surfactants, anti-oxidants, gums, coating agents, coloring agents, flavouring agents, coating agents, plasticizers, preservatives, suspending agents, emulsifying agents, anti-microbial agents, plant cellulosic material and spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

The disclosed compositions can optionally comprise from about 0.001% to about 0.005% weight by volume pharmaceutically acceptable preservatives. One non-limiting example of a suitable preservative is benzyl alcohol.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

The disclosed methods include administration of a HPTP-β inhibitor or a pharmaceutically acceptable salt thereof in combination with a pharmaceutically acceptable carrier. The carrier can be selected to minimize any degradation of the active ingredient and to minimize any adverse side effects in the subject.

In another aspect, the 4 HPTP-β inhibitor or a pharmaceutically acceptable salt thereof can be used prophylactically, i.e., as a preventative agent after treatment with an anti-VEGF agent has stopped. The HPTP-β inhibitor or a pharmaceutically acceptable salt thereof herein can be conveniently formulated into pharmaceutical compositions composed of one or more pharmaceutically acceptable carriers. See e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compound described herein and which is incorporated by reference herein. Such pharmaceutical can be standard carriers for administration of compositions to humans and non-humans, including solutions such as sterile water, saline, and buffered solutions at physiological pH. Other compositions can be administered according to standard procedures used by those skilled in the art. For example, pharmaceutical compositions can also include one or more additional active ingredients such as antimicrobial agents, anti-inflammatory agents, anesthetics, and the like.

Non-limiting examples of pharmaceutically-acceptable carriers include, but are not limited to, saline, Ringer's solution and dextrose solution. The pH of the solution can be from about 5 to about 8, and can be from about 7 to about 7.5. Further carriers include sustained release preparations such as semipermeable matrices of solid hydrophobic polymers containing the HPTP-β inhibitor or a pharmaceutically-acceptable salt thereof, which matrices are in the form of shaped articles, e.g., films, liposomes, microparticles, or microcapsules.

The disclosed methods relate to administering the HPTP-β inhibitor or a pharmaceutically acceptable salt thereof as part of a pharmaceutical composition. Compositions suitable for topical administration can be used (see, for example, US Patent Application 2005/0059639 included herein by reference in its entirety). In various embodiments, compositions of the invention can comprise a liquid comprising an active agent in solution, in suspension, or both. Liquid compositions can include gels. In one embodiment, the liquid composition is aqueous. Alternatively, the composition can take form of an ointment. In another embodiment, the composition is an in situ gellable aqueous composition. In iteration, the composition is an in situ gellable aqueous solution. Such a composition can comprise a gelling agent in a concentration effective to promote gelling upon contact with the eye or lacrimal fluid in the exterior of the eye. Aqueous compositions of the invention have ophthalmically compatible pH and osmolality. The composition can comprise an ophthalmic depot formulation comprising an active agent for subconjunctival administration. The microparticles comprising active agent can be embedded in a biocompatible pharmaceutically acceptable polymer or a lipid encapsulating agent. The depot formulations may be adapted to release all or substantially all the active material over an extended period of time. The polymer or lipid matrix, if present, may be adapted to degrade sufficiently to be transported from the site of administration after release of all or substantially all the active agent. The depot formulation can be a liquid formulation, comprising a pharmaceutical acceptable polymer and a dissolved or dispersed active agent. Upon injection, the polymer forms a depot at the injections site, e.g. by gelifying or precipitating. The composition can comprise a solid article that can be inserted in a suitable location in the eye, such as between the eye and eyelid or in the conjuctival sac, where the article releases the active agent. Solid articles suitable for implantation in the eye in such fashion generally comprise polymers and can be bioerodible or non-bioerodible.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

An excipient can fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

The HPTP-β inhibitor or a pharmaceutically acceptable salt thereof can also be present in liquids, emulsions, or suspensions for delivery of active therapeutic agents in aerosol form to cavities of the body such as the nose, throat, or bronchial passages. The ratio of HPTP-β inhibitor or a pharmaceutically acceptable salt thereof to the other compounding agents in these preparations can vary as the dosage form requires.

Depending on the intended mode of administration, the pharmaceutical compositions administered as part of the disclosed methods can be in the form of solid, semi-solid or liquid dosage forms, such as, for example, tablets, suppositories, pills, capsules, powders, liquids, suspensions, lotions, creams, gels, or the like, for example, in unit dosage form suitable for single administration of a precise dosage. The compositions can, as noted above, an effective amount of the HPTP-β inhibitor or a pharmaceutically acceptable salt thereof in combination with a pharmaceutically acceptable carrier and, in addition, can include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. In one embodiment, a composition comprising the HPTP-β inhibitor or a pharmaceutically acceptable salt thereof in an amount of approximately 5 mg per 0.1 mL liquid is prepared. The liquid phase comprises sterile water and an appropriate amount of a saccharide or polysaccharide.

Methods of Administration and Treatment Methods.

Pharmaceutical compositions containing compounds described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition. Compounds can also be administered to lessen a likelihood of developing, contracting, or worsening a condition. Amounts effective for this use can vary based on the severity and course of the disease or condition, previous therapy, the subject's health status, weight, and response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills. The compounds can be packed together or separately, in a single package or in a plurality of packages. One or all of the therapeutic agents can be given in multiple doses. If not simultaneous, the timing between the multiple doses may vary to as much as about a month.

Compounds and compositions of the invention can be packaged as a kit. In some embodiments, a kit includes written instructions on the use of the compounds and compositions.

Compounds described herein can be administered before, during, or after the occurrence of a disease or condition, and the timing of administering the composition containing a compound can vary. For example, the compounds can be used as a prophylactic and can be administered continuously to subjects with a propensity to conditions or diseases in order to lessen a likelihood of the occurrence of the disease or condition. The compounds and compositions can be administered to a subject during or as soon as possible after the onset of the symptoms. The administration of the compounds can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A compound can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for parenteral injection can be presented in unit dosage form, for example, in ampoules, or in multi-dose containers with a preservative.

A compound described herein can be present in a composition in a range of from about 1 mg to about 2000 mg; from about 5 mg to about 1000 mg, from about 10 mg to about 25 mg to 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

Kits

The present disclosure further relates to kits containing compositions according to Formulation Example 2 for use by medical or other trained personnel, as well as for use by trained subjects for delivery of the disclosed compositions according to Formulation Example 2 to a subject. In general the disclosed kits comprise:

A) an aqueous composition as described herein containing from about 1 mg/mL to about 60 mg/mL of the 4-{(S)-2-[(S)-2-methoxycarbonylamino)-3-phenylpropanamido]-2-[2-(thiophen-2-yl)thiazol-4-yl] ethyl}phenylsulfamic acid; and B) a means for delivering the composition to a subject.

The compositions according to Formulation Example 2 can comprise the following concentrations of the 4-{(S)-2-[(S)-2-methoxycarbonylamino)-3-phenylpropanamido]-2-[2-(thiophen-2-yl)thiazol-4-yl]ethyl}phenylsulfamic acid: 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, 55 mg/mL, 56 mg/mL, 57 mg/mL, 58 mg/mL, 59 mg/mL, and 60 mg/mL.

The disclosed compositions according to Formulation Example 2 can be administered to a subject. Non-limiting examples of routes of administration include parenteral delivery, i.e., intravenous, subcutaneous, and intramuscular.

Delivery can be by, for example, syringes, needles, infusion pumps, injectors. Syringes and injectors can be, for example, single-dose, multi-dose, fixed-dose or variable-dose. Examples of injectors include, but are not limited to, pen injectors, auto-injectors, and electronic patch injector systems. One convenient means for delivering the disclosed compositions according to Formulation Example 2 is by single use disposable auto injectors. One non-limiting example is a single use injector configured like the single injector sold under the Tradename MOLLY™. Non-limiting examples of injectors are described in U.S. Pat. No. 7,442, 185; U.S. Pat. No. 8,038,649; U.S. Pat. No. 8,062,255; U.S. Pat. No. 8,075,517; U.S. Pat. No. 8,235,952; U.S. Pat. No. 8,277,412; U.S. Pat. No. 8,529,510; and U.S. Pat. No. 8,551,054.

The kits can comprise suitable components for the administration of a compound of the invention to a subject. In some embodiments a compound of the invention is present in the kit as a unit dosage form. For example, the kit may comprise a delivery device that is capable of holding a single dose volume of 0.75 mL is capable of delivering 15 mg/mL of compound when the concentration of the compound is 20 mg/mL. As such, the formulator can provide delivery devices having a higher concentration of compound and adjust the delivered volume to provide an amount of compound that is less than the amount in the entire solution. In another embodiment the kit comprises a delivery device that contains a sufficient amount of a composition to allow for administration of multiple doses from the delivery device.

In some embodiments, a kit of the invention comprises:
A) a composition for delivering a HPTP-β inhibitor or a pharmaceutically acceptable salt; and
B) a composition for delivering an anti-VEGF agent.

The kits can be modified to fit the dosing regimen prescribed for the subject being treated. The following is a non-limiting example of a kit for use with a patient receiving an intravenously delivered composition comprising the disclosed compounds and an intravireally administered anti-VEGF agent. This particular example provides dosing of the disclosed compounds twice daily for 3 months and for an injection of ranibizumab at week 12.

A. 3 packages, each package containing 4 vials. Each vial comprising a sufficient amount of a HPTP-β inhibitor or a pharmaceutically acceptable salt to provide 2 daily injections of 5 mg of the disclosed compounds for 7 days; and B. a vial of ranibizumab for injection at the end of week 12 which provides 0.5 mg of ranibizumab.

The artisan, however, can provide kits that comprise any combination of elements. In addition, when the disclosed HPTP-β inhibitors or a pharmaceutically acceptable salt provided orally, a single container with sufficient doses of the disclosed compounds can be supplied with the kit.

Also included with each kit labels providing instructions for use and disposal can be included, as well as instructions for use of the compositions to be delivered. The instructions can be modified from kit to kit to reflect the dosing regime prescribed. The instructions can describe any therapy, compounds, excipients, or method of administration described herein.

The following are additional non-limiting examples of compositions according to Formulation Example 2 that can comprise the disclosed kits.

One example is a kit comprising:
A) an aqueous composition containing:
   a) 10 mg/mL of 4-{(S)-2-[(S)-2-(methoxycarbonylamino)-3-phenylpropanamido]-2-[2-(thiophen-2-yl)thiazol-4-yl]ethyl}-phenylsulfamic acid;
   b) 62.5 mg/mL of 2-hydroxypropyl-β-cyclodextrin; and
   c) a carrier system, comprising:
      i) a tonicity agent; and
      ii) water
      wherein the tonicity agent is present in an amount such that the concentration in the final composition is from about 1% to about 5% weight to volume and the carrier system is present in an amount such that the concentration of the 4-{(S)-2-[(S)-2-methoxycarbonylamino)-3-phenylpropanamido]-2-[2-(thiophen-2-yl)thiazol-4-yl]ethyl}phenylsulfamic acid has a concentration of 10 mg/mL; and
B) a component for delivering the aqueous composition.

In one non-limiting example, the kit comprises:
A) 1 mL of an aqueous composition containing:
   a) 10 mg/mL of 4-{(S)-2-[(S)-2-(methoxycarbonylamino)-3-phenylpropanamido]-2-[2-(thiophen-2-yl)thiazol-4-yl]ethyl}-phenylsulfamic acid;
   b) 62.5 mg/mL of 2-hydroxypropyl-β-cyclodextrin; and
   c) the balance 2% weight to volume of aqueous dextrose; and
B) a component for delivering the aqueous composition; wherein the component for delivery is a single use syringe.

In another non-limiting example, the kit comprises:
A) 0.75 mL of an aqueous composition containing:
   a) 10 mg/mL of 4-{(S)-2-[(S)-2-(methoxycarbonylamino)-3-phenylpropanamido]-2-[2-(thiophen-2-yl)thiazol-4-yl]ethyl}-phenylsulfamic acid;
   b) 62.5 mg/mL of 2-hydroxypropyl-β-cyclodextrin; and
   c) the balance 2% weight to volume of aqueous dextrose; and
B) a component for delivering the aqueous composition; wherein the component for delivery is a single use syringe.

One example is a kit comprising:
A) an aqueous composition containing:
   a) 15 mg/mL of 4-{(S)-2-[(S)-2-(methoxycarbonylamino)-3-phenylpropanamido]-2-[2-(thiophen-2-yl)thiazol-4-yl]ethyl}-phenylsulfamic acid;
   b) 93.75 mg/mL of 2-hydroxypropyl-β-cyclodextrin; and
   c) a carrier system, comprising:
      i) a tonicity agent; and
      ii) water
      wherein the tonicity agent is present in an amount such that the concentration in the final compositions is from about 1% to about 10% weight to volume and the carrier system is present in an amount such that the concentration of the 4-{(S)-2-[(S)-2-methoxycarbonylamino)-3-phenylpropanamido]-2-[2-(thiophen-2-yl)thiazol-4-yl]ethyl}phenylsulfamic acid is 15 mg/mL; and
B) a component for delivering the aqueous composition.

In one non-limiting example, the kit comprises:
A) 1 mL of an aqueous composition containing:
   a) 15 mg/mL of 4-{(S)-2-[(S)-2-(methoxycarbonylamino)-3-phenylpropanamido]-2-[2-(thiophen-2-yl)thiazol-4-yl]ethyl}-phenylsulfamic acid;
   b) 93.75 mg/mL of 2-hydroxypropyl-β-cyclodextrin; and
   c) the balance 2% weight to volume of aqueous dextrose; and B) a component for delivering the aqueous composition; wherein the component for delivery is a single use syringe.

In another non-limiting example, the kit comprises:
A) 0.75 mL of an aqueous composition containing:
a) 15 mg/mL of 4-{(S)-2-[(S)-2-(methoxycarbonylamino)-3-phenylpropanamido]-2-[2-(thiophen-2-yl)thiazol-4-yl]ethyl}-phenylsulfamic acid;
b) 93.75 mg/mL of 2-hydroxypropyl-β-cyclodextrin; and
c) the balance 2% weight to volume of aqueous dextrose; and
B) a component for delivering the aqueous composition; wherein the component for delivery is a single use syringe.

In a further aspect the kits comprising a composition according to Formulation Example 2 is a kit, comprising:
A) an aqueous composition containing:
a) 20 mg/mL of 4-{(S)-2-[(S)-2-(methoxycarbonylamino)-3-phenylpropanamido]-2-[2-(thiophen-2-yl)thiazol-4-yl]ethyl}-phenylsulfamic acid;
b) 125 mg/mL of 2-hydroxypropyl-β-cyclodextrin; and
c) a carrier system, comprising:
i) a tonicity agent; and
ii) water
wherein the tonicity agent is present in an amount such that the concentration in the final composition is from about 1% to about 10% weight to volume; and
B) a component for delivering the aqueous composition.

In another aspect the kits comprising a composition according to Formulation Example 2 is a pharmaceutical kit, comprising:
A) a 0.75 mL single dose syringe, the syringe containing a composition, comprising:
a) 20 mg/mL of 4-{(S)-2-[(S)-2-(methoxycarbonylamino)-3-phenylpropanamido]-2-[2-(thiophen-2-yl)thiazol-4-yl]ethyl}-phenylsulfamic acid;
b) 125 mg/mL of 2-hydroxypropyl-β-cyclodextrin; and
c) a carrier system, comprising:
i) 2% weight to volume of dextrose of the composition; and
ii) water; and
B) instructions for use of the kit.

A further aspect of the compositions according to Formulation Example 2 relates to kits which comprise a solid composition for reconstitution. The amount of 4-{(S)-2-[(S)-2-(methoxycarbonylamino)-3-phenylpropanamido]-2-[2-(thiophen-2-yl)thiazol-4-yl]ethyl}-phenylsulfamic acid or a pharmaceutically acceptable salt thereof in the container of dry composition can be in any convenient amount. For example, a container comprising 20 mg of 4-{(S)-2-[(S)-2-(methoxycarbonylamino)-3-phenylpropanamido]-2-[2-(thiophen-2-yl)thiazol-4-yl]ethyl}-phenylsulfamic acid or a pharmaceutically acceptable salt thereof can have a demarcation line indicating a final volume of 1 mL. The user can then reconstitute the composition by adding sufficient carrier to create a composition comprising 20 mg/mL of the compound. The formulator also has options for use according to the instructions. For example, the instructions can direct the user to withdrawn a sufficient amount according to the prescribed dose. If the prescribed dose is 15 mg/mL the user can withdraw 0.75 mL's of the 20 mg/mL solution for delivery to the subject. Therefore, instructions for re-constitution can afford the user with the proper method of reconstitution, as well as the amount of re-constituted formula to be delivered to a subject.

The following is a non-limiting example of a kit containing a solid composition:
A) a solid or dry composition, comprising:
a) 4-{(S)-2-[(S)-2-(methoxycarbonylamino)-3-phenylpropanamido]-2-[2-(thiophen-2-yl)thiazol-4-yl]ethyl}-phenylsulfamic acid or a pharmaceutically acceptable salt thereof; and
b) HPβCD;
wherein the ratio of 4-{(S)-2-[(S)-2-(methoxycarbonylamino)-3-phenylpropanamido]-2-[2-(thiophen-2-yl)thiazol-4-yl]ethyl}-phenylsulfamic acid to HPβCD is from about 1:4 to about 1:8 and the tonicity agent is present in an amount such that the re-constituted formula comprises from about 0.5% to about 10% weight to volume of the tonicity agent In another iteration the dry compositions for reconstitution can comprise:
a) 4-{(S)-2-[(S)-2-(methoxycarbonylamino)-3-phenylpropanamido]-2-[2-(thiophen-2-yl)thiazol-4-yl]ethyl}-phenylsulfamic acid or a pharmaceutically acceptable salt thereof;
b) HPβCD; and
c) a tonicity agent;
wherein the ratio of 4-{(S)-2-[(S)-2-(methoxycarbonylamino)-3-phenylpropanamido]-2-[2-(thiophen-2-yl)thiazol-4-yl]ethyl}-phenylsulfamic acid to HPβCD is from about 1:4 to about 1:8 and the tonicity agent is present in an amount such that the re-constituted formula comprises from about 0.5% to about 10% weight to volume of the tonicity agent.

A set of instructions can be included in any of the herein described kits. The instructions can relate to the dosing amount, timing of dosing, and reconstitution of the composition when the kit contains a dry composition, methods of disposal of delivery means and unused composition, and the like.

4-{(S)-2-[(S)-2-(Methoxycarbonylamino)-3-phenylpropanamido]-2-[2-(thiophen-2-yl)thiazol-4-yl]ethyl}-phenylsulfamic acid can be prepared by the procedure outlined in Scheme XXIV and describe in Example 25 herein below.

Scheme XXIV

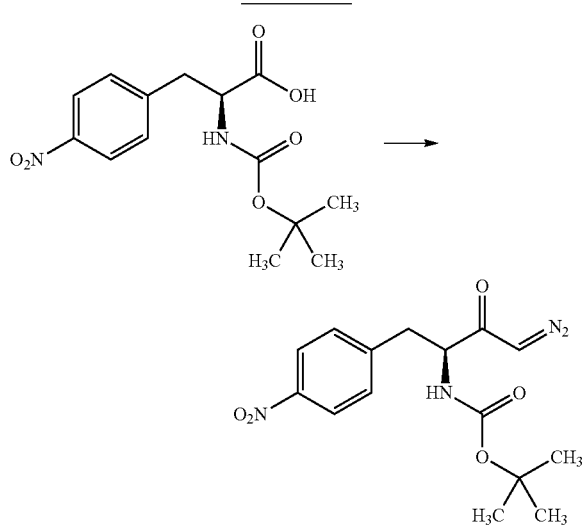

6

Reagents and conditions (a) (i) (iso-butyl)OCOCl, Et₃N, THF; 0° C., 20 min. (ii) CH₂N₂; room temp for 3 hours.

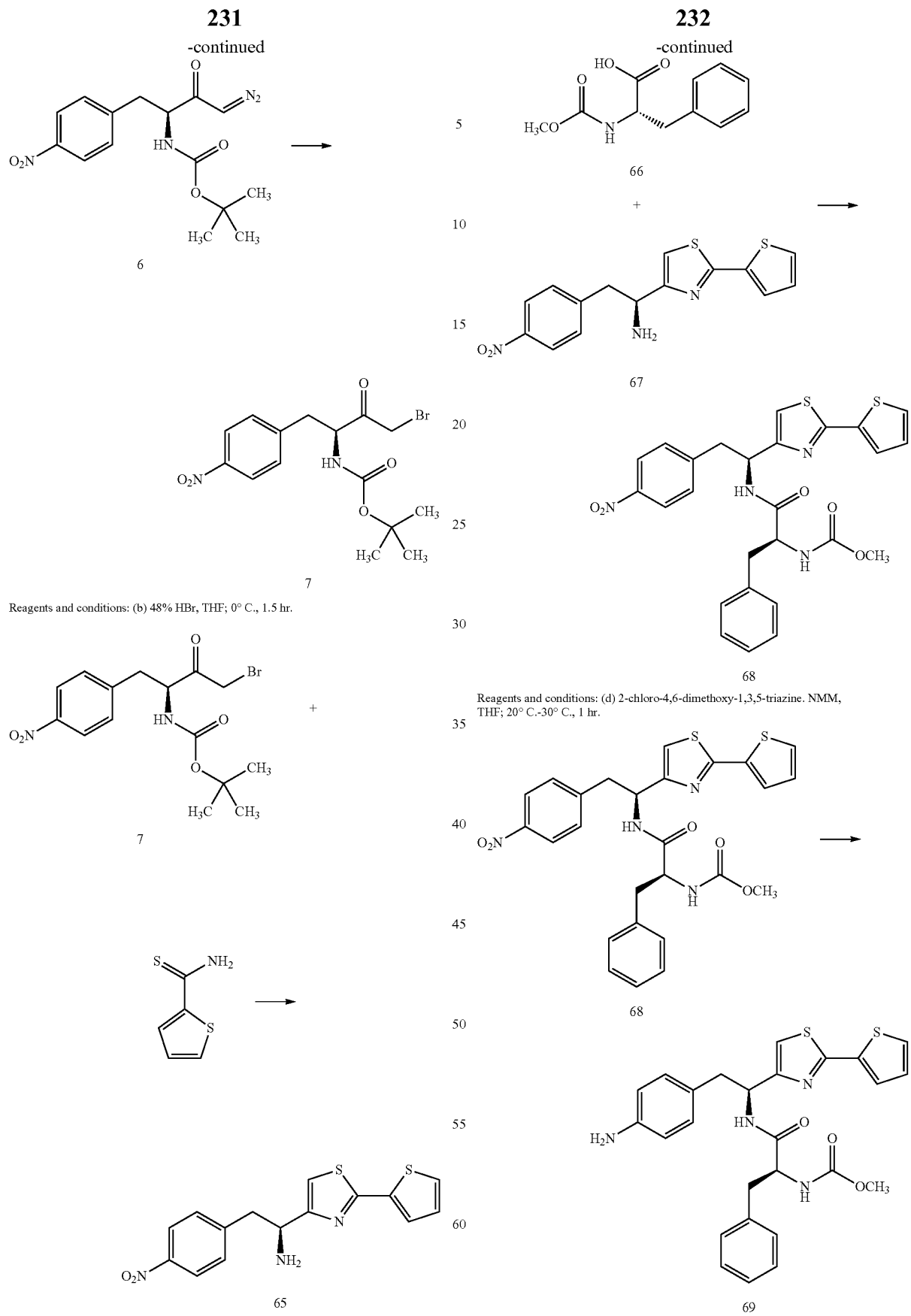

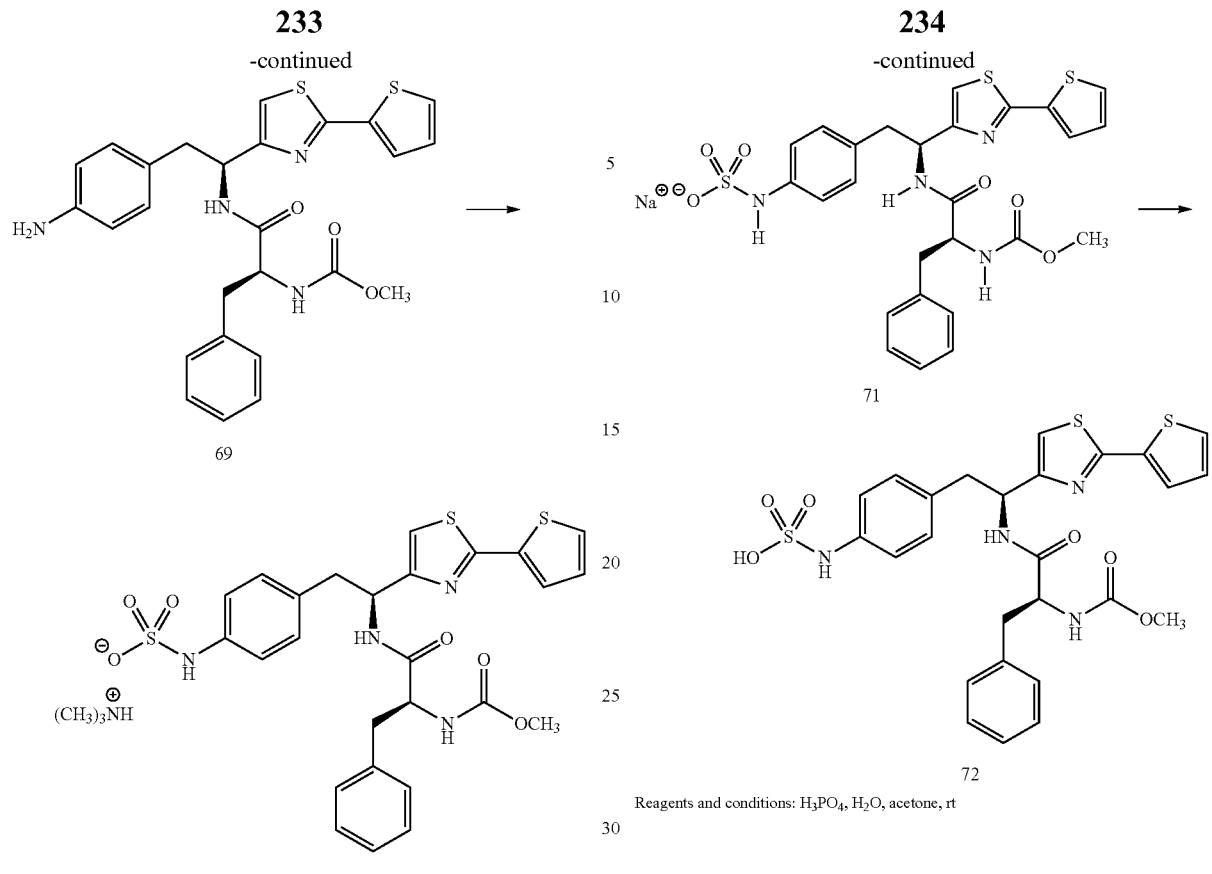

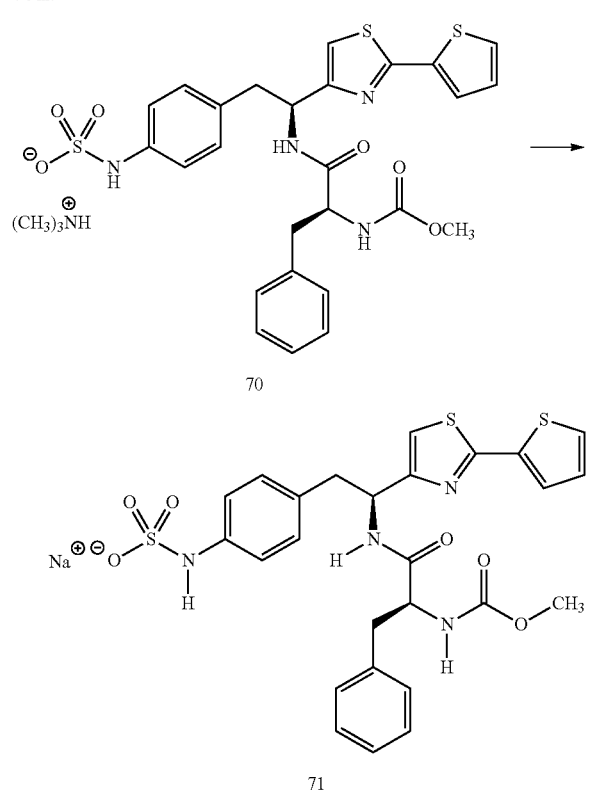

Reagents and conditions: (f) (CH₃)₃N:SO₃, TEA, THF; 35° C.-40° C., 4-8 hr.

Reagents and conditions: (g) NaOCH₃, MeOH; rt.

Reagents and conditions: H₃PO₄, H₂O, acetone, rt

EXAMPLE 33

4-{(S)-2-[(S)-2-Methoxycarbonylamino)-3-phenyl-propanamido]-2-[2-(thiophen-2-yl)thiazol-4-yl]ethyl}phenylsulfamic acid (72)

Preparation of (S)-[3-diazo-1-(4-nitrobenzyl)-2-oxo-propyl]-carbamic acid tert-butyl ester (6): To a 0° C. solution of 2-(S)-tert-butoxycarbonylamino-3-(4-nitrophenyl)-propionic acid, 1, (1.20 g, 4.0 mmol) in THF (20 mL) was added dropwise triethylamine (0.61 mL, 4.4 mmol) followed by iso-butyl chloroformate (0.57 mL, 4.4 mmol). The reaction mixture was stirred at 0° C. for 20 minutes and filtered. The filtrate was treated with an ether solution of diazomethane (~16 mmol) at 0° C. The reaction mixture was stirred at room temperature for 3 hours then concentrated in vacuo. The resulting residue was dissolved in EtOAc and washed successively with water and brine, dried (Na₂SO₄), filtered and concentrated. The residue was purified over silica (hexane/EtOAc 2:1) to afford 1.1 g (82% yield) of the desired product as a slightly yellow solid. ¹H NMR (300 MHz, CDCl₃) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of (S)-tert-butyl 4-bromo-1-(4-nitrophenyl)-3-oxobutan-2-ylcarbamate (7): To a 0° C. solution of (S)-[3-diazo-1-(4-nitrobenzyl)-2-oxo-propyl]-carbamic acid tert-butyl ester, 6, (0.350 g, 1.04 mmol) in THF (5 mL) is added dropwise 48% aq. HBr (0.14 mL, 1.25 mmol). The reaction mixture was stirred at 0° C. for 1.5 hours then the reaction was quenched at 0° C. with sat. Na₂CO₃. The mixture is extracted with EtOAc (3×25 mL) and the combined organic extracts are washed with brine, dried (Na₂SO₄), filtered and concentrated to obtain 0.400 g of the product which was used in the next step without further purification. ¹H NMR (300 MHz, CDCl₃) δ 8.20 (d, J=8.4 Hz, 2H), 7.39 (d, J=8.4 Hz, 2H), 5.06 (d, J=7.8 Hz, 1H), 4.80 (q, J=6.3 Hz, 2H), 4.04 (s, 2H), 1.42 (s, 9H).

Preparation of (S)-2-(4-Nitrophenyl)-1-(2-(thiophen-2-yl)thiazol-4-yl)ethanamine hydrobromide (65): Thiophene-2-carbothioamide in acetonitrile (4 vol. with respect to 7) was stirred at 15 to 25° C. for 30 to 60 minutes. To remove residual sulfur, the resulting mixture was filtered through Celite® and the reaction flask and filter cake are rinsed with acetonitrile (2×1 vol). The filtrate was then added to the reactor containing and (S)-tert-butyl 4-bromo-1-(4-nitrophenyl)-3-oxobutan-2-ylcarbamate, 7, (0.98 eq) under a nitrogen atmosphere. Additional ACN was added and the resulting bright yellow slurry was heated to 80° C. over 6 hours. The reaction mixture was refluxed for 6 to 16 hours. The reaction mixture was cooled to 65 to 70° C. over 1 hour and stirred for an additional 1 to 4 hours. The reaction mixture was then cooled to 50 to 60° C. over 1 hour. The reaction mixture was aged for an additional 1 to 2 hours at 50 to 60° C. The reaction mixture was then cooled to 20 to 25° C. over 1 hour. The reaction mixture was aged for an additional 4 to 16 hours at 20 to 25° C. The resulting slurry was filtered and the filter cake was washed with ACN. The wet cake was dried under vacuum at 40 to 45° C. to afford the desired product.

Preparation of methyl (S)-1-(S)-2-(4-nitrophenyl)-1-(2-(thiophen-2-yl)thiazol-4-yl)ethylamino-1-oxo-3-phenylpropan-2-ylcarbamate (68); A solution of (S)-2-[(methoxy-carbonyl)amino]-3-phenylpropanoic acid (66) (1.07 eq.) was added to a reactor containing (S)-2-(4-nitrophenyl)-1-(2-(thiophen-2-yl)thiazol-4-yl)ethanamine (67) (1.0 eq.) under a nitrogen atmosphere. 2-Chloro-4,6-dimethoxy-1,3,5-triazine (1.07 eq) was added to the stirred reaction mixture followed by tetrahydrofuran (THF) (ca. 13 vol. with respect to 67). The temperature was adjusted to 19 to 25° C. and N-methylmorpholine (NMM) (0.4 eq) was added at a rate such that the temperature was maintained between 20 and 30° C. The reaction mixture was stirred at 19 to 25° C. for 50 to 70 minutes. Additional NMM (0.4 eq) was added at a rate such that the temperature was maintained between 20 and 30° C. The resulting reaction mixture was stirred at 19 to 25° C. for 50 to 70 minutes. Additional NMM (0.2 eq) was added at a rate such that the temperature was maintained between 20 and 30° C. The resulting reaction mixture was stirred at 19 to 25° C. for 50 to 70 minutes. Additional NMM (1.2 eq) was added at a rate such that the temperature was maintained between 20 and 30° C. The resulting reaction mixture was stirred at 19 to 25° C. for 90 to 120 minutes. The reaction mixture was further stirred at 19 to 25° C. for 2 to 3 hours. A sample of reaction mixture was tested to determined chemical purity. The reaction mixture was then stirred at 19 to 25° C. for minimum 8 hours. The resulting slurry was filtered and the filter cake washed with THF (2×1 vol,). The wet cake was added back to the reactor and de-ionized water (40 vol.) was added. Tetrahydrofuran (20 vol.) was added to the stirred reaction mixture and stirring was continued for 4 to 16 hours at 19 to 25° C. The solids are collected by filtration. The filter cake was washed with a 2:1 (v/v) water/THF mixture. The wet cake was further dried under vacuum at room temperature or 40-50° C. for minimum 12 hours to afford the desired product.

Preparation of methyl ((S)-1-(((S)-2-(4-aminophenyl)-1-(2-(thiophen-2-yl)thiazol-4-yl)ethyl)amino)-1-oxo-3-phenylpropan-2-yl)carbamate (69): To a reactor purged with nitrogen was added methyl (S)-1-(S)-2-(4-nitrophenyl)-1-(2-(thiophen-2-yl)thiazol-4-yl)ethylamino-1-oxo-3-phenylpropan-2-ylcarbamate (68), the catalyst, Pd/C (10%) (0.2:1 ratio of catalyst to 68 by weight), and tetrahydrofuran (THF). The reactor was pressurized to 45 psi with nitrogen for minimum 5 minutes then depressurized to approximately 5 psi nitrogen. This procedure was repeated three times before reactor was finally pressurized to 30 to 36 psi with hydrogen. The resulting mixture was stirred for a minimum of 24 hours while maintaining the pressure at 30 to 36 psi with hydrogen. The reactor was then depressurized and purged with nitrogen for testing of reaction completion. The reaction mixture was filtered through a bed of Celite® filter aid to remove the catalyst and the filter cake was washed with THF. The combined filtrate and washes were concentrated under reduced pressure at 30 to 50° C. to approximately 3 volumes. The reaction mixture was cooled to 19 to 25° C. and methyl t-butyl ether (MTBE) (2.5 vol.) was added over 30 minutes. The resulting reaction mixture was stirred at 19 to 25° C. for 60 to 120 minutes during which time the product begins to precipitate. Additional MTBE (9.5 vol.) was added over a period of 60 to 90 minutes. The resulting slurry was aged at 19 to 25° C. for a period of 6 to 16 hours. The solids are collected by filtration and the filter cake was washed with MTBE. The wet cake was then dried under vacuum at room temperature or 40-50° C. to afford the desired product.

Preparation of trimethylammonium (4-((S)-2-((S)-2-((methoxycarbonyl)amino)-3-phenylpropanamido)-2-(2-(thiophen-2-yl)thiazol-4-yl)ethyl)phenyl)sulfamate (70): ((S)-1-(((S)-2-(4-aminophenyl)-1-(2-(thiophen-2-yl)thiazol-4-yl)ethyl)amino)-1-oxo-3-phenylpropan-2-yl)carbamate (69), trimethylamine sulfur trioxide complex (1.71 eq.) and tetrahydrofuran (THF) (7.1 vol.) were added to a reactor purged with nitrogen. The reaction mixture was stirred and triethylamine (0.106 eq.) was added at 19 to 25° C. The stirred reaction mixture was warmed to 35 to 40° C. and stirred for 4 to 8 hours. The reaction mixture was cooled to 19 to 25° C. and stirring was continued for 1 to 2 hours. The reaction mixture was filtered and the filter cake was washed with THF. The combined filtrate and washes are added to a stirred reactor containing methyl t-butyl ether (MTBE) (10 vol.) over a minimum of 2 hour period. On completion of the addition, the reaction mixture was stirred at 19 to 25° C. for 4 to 16 hours. The solids are collected by filtration and the wet cake was washed with MTBE. The wet cake was dried under vacuum at 20 to 25° C. for 2 hours to afford the desired product.

Preparation of sodium (4-{(S)-2-[(S)-2-(methoxycarbonylamino)-3-phenylpropan-amido]-2-(2-(thiophen-2-yl)thiazol-4-yl)ethyl}phenyl)sulfamate (71): trimethyl-ammonium (4-((S)-2-((S)-2-((methoxycarbonyl)amino)-3-phenylpropanamido)-2-(2-(thiophen-2-yl)thiazol-4-yl)ethyl)-phenyl)sulfamate (70) was added to a stirred reactor containing methanol (MeOH) (4.87 vol.) and sodium methoxide (25% solution in MeOH) (0.093 eq.). Sodium methoxide (25% solution in MeOH) (1.08 eq.) was added over 5 minutes while maintaining the temperature at 19 to 25° C. The resulting mixture was stirred at 19-25° C. for 30 to 60 minutes then 2 portions of sodium methoxide (25% solution in MeOH) (0.14 eq. and 0.07 eq.) are added over 30 minutes while maintaining the temperature at 19 to 25° C. The resulting mixture was stirred for 30 to 60 minutes while maintaining the temperature at 19 to 25° C. The reaction mixture was then filtered and the filter cake washed with methanol (MeOH). The filtrates and cake washes are concentrated under reduced pressure at 30 to 40° C. to approximately 8 volumes. The reaction mixture was cooled to 19 to 25° C. and methyl t-butyl ether (10 vol) was then added. The reaction mixture was then stirred for 15 to 20 minutes. The resulting solids are isolated by filtration and the filter cake was washed with MTBE. The wet cake was dried under vacuum at room temperature or 35-40° C. for a minimum of 2 hours to afford the desired product.

Preparation of 4-{(S)-2-[(S)-2-methoxycarbonylamino)-3-phenylpropanamido]-2-[2-(thiophen-2-yl)thiazol-4-yl]ethyl}phenylsulfamic acid (72): sodium (4-{(S)-2-[(S)-2-(methoxycarbonylamino)-3-phenylpropan-amido]-2-(2-(thiophen-2-yl)thiazol-4-yl)ethyl}phenyl)-sulfamate 71) (97.0 μm, 0.16 mol) was slowly added to distilled water (1.0 L) and acetone (200 mL) in a three-neck 5-L round bottom flask equipped with an overhead mechanical stirrer, a thermometer and an addition funnel at ambient temperature. To the resulting suspension 85% $H_3PO_4$ (20.33 g, 1.1 eq.) diluted with water (100 mL) was slowly added through the addition funnel over 15 minutes. No apparent temperature change was observed. A considerable amount of a free-flowing suspension formed in 10-15 minutes after the addition was complete. The suspension was stirred at ambient temperature for 2 hours and filtered. The solid cake was rinsed with 20% acetone in water (2×50 mL). The solid was removed and dried under vacuum to afford 88.05 g (93.8% yield) of the desired product as a light-yellow solid which HPLC analysis indicated had a purity of 99.26%. $^1$H ($CD_3OD$): δ 7.61-7.56 (m, 2H), 7.25-7.01 (m, 10H), 6.75 (s, 1H), 5.24-5.21 (q, 1H, J=7.2 Hz), 4.38 (t, 1H, J=7.2 Hz), 3.60 (s, 3H), 3.23-3.14 (m, 1H), 3.08-3.00 (m, 2H), 2.87-2.80 (m, 1H).

Formulation Example 3

This formulation example relates to compositions comprising 4-{(S)-2-[(S)-2-(methoxycarbonylamino)-3-phenylpropanamido]-2-(2-ethylthiazol-4-yl)ethyl}phenyl-sulfamic acid having the formula:

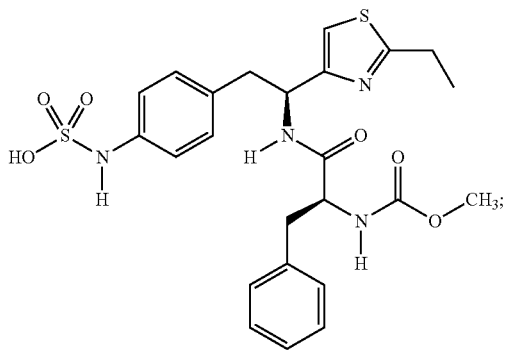

and
pharmaceutically acceptable salts thereof.
Formulation Example 3 comprises:
  a) 4-{(S)-2-[(S)-2-(methoxycarbonylamino)-3-phenyl-propanamido]-2-(2-ethylthiazol-4-yl)ethyl}phenylsulfamic acid or a pharmaceutically acceptable salt thereof;
  b) a solubilizing system; and
  c) a carrier system.

The compositions of Formulation Example 3 are formulated to deliver an amount of 4-{(S)-2-[(S)-2-(methoxycarbonylamino)-3-phenylpropanamido]-2-(2-ethylthiazol-4-yl)ethyl}phenylsulfamic acid in the free acid form. For example, a composition which comprises 10 mg/mL of 4-{(S)-2-[(S)-2-(methoxycarbonylamino)-3-phenylpropanamido]-2-(2-ethylthiazol-4-yl)ethyl}phenylsulfamic acid can have either 10 mg/mL of the free acid or an amount of a pharmaceutically acceptable salt in an amount sufficient to deliver 10 mg/mL of the free acid. As an example, a composition formulated to deliver 10 mg/mL of 4-{(S)-2-[(S)-2-(methoxycarbonylamino)-3-phenylpropanamido]-2-(2-ethylthiazol-4-yl)ethyl}phenylsulfamic acid can comprise either 10 mg/mL of 4-{(S)-2-[(S)-2-(methoxycarbonylamino)-3-phenylpropanamido]-2-(2-ethylthiazol-4-yl)ethyl}phenylsulfamic acid or alternatively 10.4 mg/mL of the sodium salt, (sodium 4-{(S)-2-[(S)-2-(methoxycarbonylamino)-3-phenylpropanamido]-2-(2-ethylthiazol-4-yl)ethyl}phenylsulfamate). Therefore, a composition which delivers from about 10 mg/mL to about 100 mg/mL of 4-{(S)-2-[(S)-2-(methoxycarbonylamino)-3-phenylpropanamido]-2-(2-ethylthiazol-4-yl)ethyl}phenylsulfamic acid can comprise an amount of pharmaceutically acceptable salt thereof to deliver from about 10 mg/mL to about 100 mg/mL of the compound Therefore, when a composition according to Formulation Example 3 comprises an amount of 4-{(S)-2-[(S)-2-(methoxycarbonylamino)-3-phenylpropanamido]-2-(2-ethylthiazol-4-yl)ethyl}phenylsulfamic acid per mL, it is understood that this amount is the amount of free acid that is delivered and if a salt form of the compound is used in the composition, the amount of the salt form can therefore reflect the difference in molecular weight between the free acid and the salt form. The following example demonstrates this equivalency.

A composition delivering 10 mg/mL of 4-{(S)-2-[(S)-2-(methoxycarbonylamino)-3-phenylpropanamido]-2-(2-ethylthiazol-4-yl)ethyl}phenylsulfamic acid, comprises:
  a) 10 mg/mL of 4-{(S)-2-[(S)-2-(methoxycarbonylamino)-3-phenylpropanamido]-2-(2-ethylthiazol-4-yl)ethyl}phenylsulfamic acid; or about 10.4 mg/mL of sodium 4-{(S)-2-[(S)-2-(methoxycarbonylamino)-3-phenylpropanamido]-2-(2-ethylthiazol-4-yl)ethyl}phenylsulfamate; or about 10.3 mg/mL, of ammonium 4-{(S)-2-[(S)-2-(methoxycarbonylamino)-3-phenylpropanamido]-2-(2-ethylthiazol-4-yl)ethyl}phenylsulfamate, and the like;
  b) an amount of 2-hydroxypropyl-β-cyclodextrin as defined herein; and
  c) a carrier system.

The disclosed compositions according to Formulation Example 3 according to Formulation Example 3 comprise from about 10 mg/mL to about 100 mg/mL of the 4-{(S)-2-[(S)-2-(methoxycarbonylamino)-3-phenylpropanamido]-2-(2-ethylthiazol-4-yl)ethyl}phenylsulfamic acid or a pharmaceutically acceptable salt thereof.

In one aspect the disclosed compositions according to Formulation Example 3 comprise from about 20 mg/mL to about 100 mg/mL of 4-{(S)-2-[(S)-2-(methoxycarbonylamino)-3-phenylpropanamido]-2-(2-ethylthiazol-4-yl)ethyl}phenylsulfamic acid or a pharmaceutically acceptable salt thereof. In one embodiment, the composition comprises from about 15 mg/mL to about 60 mg/mL of 4-{(S)-2-[(S)-2-(methoxycarbonylamino)-3-phenylpropanamido]-2-(2-ethylthiazol-4-yl)ethyl}phenylsulfamic acid or a pharmaceutically acceptable salt thereof. In another embodiment, the composition comprises from about 40 mg/mL to about 90 mg/mL of 4-{(S)-2-[(S)-2-(methoxycarbonylamino)-3-phenylpropanamido]-2-(2-ethylthiazol-4-yl)ethyl}-phenylsulfamic acid or a pharmaceutically acceptable salt thereof. In a further embodiment, the composition comprises from about 10 mg/mL to about 30 mg/mL of 4-{(S)-2-[(S)-2-(methoxy-carbonylamino)-3-phenylpropanamido]-2-(2-ethylthiazol-4-yl)ethyl}phenylsulfamic acid or a pharmaceutically acceptable salt thereof. In a still further embodiment, the composition comprises from about 40 mg/mL to about 80 mg/mL of 4-{(S)-2-[(S)-2-(methoxycarbonyl-lamino)-3-phenylpropanamido]-2-(2-ethylthiazol-4-yl)ethyl}phenylsulfamic acid or a pharmaceutically acceptable salt thereof. In a yet further embodiment the composition comprises from about 10 mg/mL to about 20 mg/mL weight by volume of 4-{(S)-2-[(S)-2-(methoxycarbonylamino)-3-phenylpropanamido]-2-(2-ethylthiazol-4-yl)ethyl}phenylsulfamic acid or a pharmaceutically acceptable salt thereof. In a still yet further embodiment, the composition comprises from about 60 mg/mL to about 90 mg/mL weight by volume of 4-{(S)-2-[(S)-2-(methoxycarbonylamino)-3-phenylpropanamido]-2-(2-ethylthiazol-4-yl)ethyl}phenyl-sulfamic acid or a pharmaceutically acceptable salt thereof. In still another embodiment, the composition comprises from about 50 mg/mL to about 100 mg/mL weight by volume of 4-{(S)-2-[(S)-2-(methoxycarbonylamino)-3-phenylpropanamido]-2-(2-ethylthiazol-4-yl)ethyl}phenyl-sulfamic acid or a pharmaceutically acceptable salt thereof.

Particular embodiments of the disclosed compositions according to Formulation Example 3, comprise 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL 32 mg/mL, 33 mg/mL, 34 mg/mL, 35 mg/mL, 36 mg/mL, 37 mg/mL, 38 mg/mL, 39 mg/mL, 40 mg/mL, 41 mg/mL 42 mg/mL, 43 mg/mL, 44 mg/mL, 45 mg/mL, 46 mg/mL, 47 mg/mL, 48 mg/mL, 49 mg/mL, 50 mg/mL, 51 mg/mL 52 mg/mL, 53 mg/mL, 54 mg/mL, 55 mg/mL, 56 mg/mL, 57 mg/mL, 58 mg/mL, 59 mg/mL, 60 mg/mL, 61 mg/mL 62 mg/mL, 63 mg/mL, 64 mg/mL, 65 mg/mL, 66 mg/mL, 67 mg/mL, 68 mg/mL, 69 mg/mL, 70 mg/mL, 71 mg/mL 72 mg/mL, 73 mg/mL, 74 mg/mL, 75 mg/mL, 76 mg/mL, 77 mg/mL, 78 mg/mL, 79 mg/mL, 80 mg/mL, 81 mg/mL 82 mg/mL, 83 mg/mL, 84 mg/mL, 85 mg/mL, 86 mg/mL, 87 mg/mL, 88 mg/mL, 89 mg/mL, 90 mg/mL, 91 mg/mL 92 mg/mL, 93 mg/mL, 94 mg/mL, 95 mg/mL, 96 mg/mL, 97 mg/mL, 98 mg/mL, 99 mg/mL, and 100 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL, about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL, about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL, about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL, about 92 mg/mL, about 93 mg/mL, about 94 mg/mL, about 95 mg/mL, about 96 mg/mL, about 97 mg/mL, about 98 mg/mL, about 99 mg/mL, and about 100 mg/mL of a compound disclosed herein, for example, 4-{(S)-2-[(S)-2-(methoxycarbonylamino)-3-phenylpropan-amido]-2-(2-ethylthiazol-4-yl)ethyl}phenylsulfamic acid.

Solubilizing Systems

In one embodiment, a formulation disclosed herein can comprise a ratio of about 20 parts of a compound herein or a pharmaceutically acceptable salt thereof to about 1 part solubilizing system (about 20:about 1), to about 1 part of the compound herein or a pharmaceutically acceptable salt thereof to about 20 parts solubilizing system (about 1:about 20). For example, a formulation containing about 100 mg of a compound herein or a pharmaceutically acceptable salt thereof can contain from about 5 mg to about 2000 mg of a solubilizing agent, such as a cyclodextrin. In another embodiment, the ratio can be based on number, or moles, or compound compared to number, or moles, of solubilizing system.

The disclosed solubilizing systems can comprise cyclodextrins: β-cyclodextrin, β-cyclodextrin and β-cyclodextrin and derivatives thereof. Non-limiting examples of cyclodextrin derivatives includes methyl-β-cyclodextrin, 2-hydroxypropyl-β-cyclodextrin, sulfobutyl ether-β-cyclodextrin sodium salt, and 2-hydroxypropyl-β-cyclodextrin.

The following are non-limiting examples of ratios of a compound herein and a solubilizing agent, such as a cyclodextrin. The following examples alternatively describe the ratio of a solubilizing agent, such as a cyclodextrin, and a compound herein. The ratio can be: about 20:about 1; about 19.9:about 1; about 19.8:about 1; about 19.7:about 1; about 19.6:about 1; about 19.5:about 1; about 19.4:about 1; about 19.3:about 1; about 19.2:about 1; about 19.1:about 1; about 19:about 1; about 18.9:about 1; about 18.8:about 1; about 18.7:about 1; about 18.6:about 1; about 18.5:about 1; about 18.4:about 1; about 18.3:about 1; about 18.2:about 1; about 18.1:about 1; about 18:about 1; about 17.9:about 1; about 17.8:about 1; about 17.7:about 1; about 17.6:about 1; about 17.5:about 1; about 17.4:about 1; about 17.3:about 1; about 17.2:about 1; about 17.1:about 1; about 17:about 1; about 16.9:about 1; about 16.8:about 1; about 16.7:about 1; about 16.6:about 1; about 16.5:about 1; about 16.4:about 1; about 16.3:about 1; about 16.2:about 1; about 16.1:about 1; about 16:about 1; about 15.9:about 1; about 15.8:about 1; about 15.7:about 1; about 15.6:about 1; about 15.5:about 1; about 15.4:about 1; about 15.3:about 1; about 15.2:about 1; about 15.1:about 1; about 15:about 1; about 14.9:about 1; about 14.8:about 1; about 14.7:about 1; about 14.6:about 1; about 14.5:about 1; about 14.4:about 1; about 14.3:about 1; about 14.2:about 1; about 14.1:about 1; about 14:about 1; about 13.9:about 1; about 13.8:about 1; about 13.7:about 1; about 13.6:about 1; about 13.5:about 1; about 13.4:about 1; about 13.3:about 1; about 13.2:about 1; about 13.1:about 1; about 13:about 1; about 12.9:about 1; about 12.8:about 1; about 12.7:about 1; about 12.6:about 1; about 12.5:about 1; about 12.4:about 1; about 12.3:about 1; about 12.2:about 1; about 12.1:about 1; about 12:about 1; about 11.9:about 1; about 11.8:about 1; about 11.7:about 1; about 11.6:about 1; about 11.5:about 1; about 11.4:about 1; about 11.3:about 1; about 11.2:about 1; about 11.1:about 1; about 11:about 1; about 10.9:about 1; about 10.8:about 1; about 10.7:about 1; about 10.6:about 1; about 10.5:about 1; about 10.4:about 1; about 10.3:about 1; about 10.2 about 1; about 10.1:about 1; about 10:about 1; about 9.9:about 1; about 9.8:about 1; about 9.7:about 1; about 9.6:about 1; about 9.5:about 1; about 9.4:about 1; about 9.3:about 1; about 9.2:about 1; about 9.1:about 1; about 9:about 1; about 8.9:about 1; about 8.8:about 1; about 8.7:about 1; about 8.6:about 1; about 8.5:about 1; about 8.4:about 1; about 8.3:about 1; about 8.2:about 1; about 8.1:about 1; about 8:about 1; about 7.9:about 1; about 7.8:about 1; about 7.7:about 1; about 7.6:about 1; about 7.5:about 1; about 7.4:about 1; about 7.3:about 1; about 7.2:about 1; about 7.1:about 1; about 7:about 1; about 6.9:about 1; about 6.8:about 1; about 6.7:about 1; about 6.6:about 1; about 6.5:about 1; about 6.4:about 1; about 6.3:about 1; about 6.2:about 1; about 6.1:about 1; about 6:about 1; about 5.9:about 1; about 5.8:about 1; about 5.7:about 1; about 5.6:about 1; about 5.5:about 1; about 5.4:about 1; about 5.3:about 1; about 5.2:about 1; about 5.1:about 1; about 5:about 1; about 4.9:about 1; about 4.8:about 1; about 4.7:about 1; about 4.6:about 1; about 4.5:about 1; about 4.4:about 1; about 4.3:about 1; about 4.2:about 1; about 4.1:about 1; about 4:about 1; about 3.9:about 1; about 3.8:about 1; about 3.7:about 1; about 3.6:about 1; about 3.5:about 1; about 3.4:about 1; about 3.3:about 1; about 3.2:about 1; about 3.1:about 1; about 3:about 1; about 2.9:about 1; about 2.8:about 1; about 2.7:about 1; about 2.6:about 1; about 2.5:about 1; about 2.4:about 1; about 2.3:about 1; about 2.2:about 1; about 2.1:about 1; about 2:about 1; about 1.9:about 1; about 1.8:about 1; about 1.7:about 1; about 1.6:about 1; about 1.5:about 1; about 1.4:about 1; about 1.3:about 1; about 1.2:about 1; about 1.1:about 1; or about 1:about 1.

As such, the compositions can comprise an amount of HPβCD suitable for achieving the desired properties of the composition, i.e., concentration of 4-{(S)-2-[(S)-2-(methoxycarbonyl-amino)-3-phenylpropanamido]-2-(2-ethylthiazol-4-yl)ethyl}phenylsulfamic acid, the desired viscosity, the desired osmolarity and the like. The amount of HPβCD can vary depending upon the amount of 4-{(S)-2-[(S)-2-(methoxycarbonylamino)-3-phenylpropanamido]-2-(2-ethylthiazol-4-yl)ethyl}phenylsulfamic acid the formulator desires to deliver in a single dose.

Carrier System

The disclosed compositions according to Formulation Example 3 comprise from about 1.5% to about 90% weight by volume of a carrier system. The amount of carrier system present is based upon several different factors or choices made by the formulator, for example, the final concentration of the compound and the amount of solubilizing agent.

The following is a non-limiting example of a composition comprising 60 mg/mL of 4-{(S)-2-[(S)-2-(methoxycarbonylamino)-3-phenylpropanamido]-2-(2-ethylthiazol-4-yl)ethyl}-phenylsulfamic acid:
  a) 60 mg of the 4-{(S)-2-[(S)-2-(methoxycarbonylamino)-3-phenylpropanamido]-2-(2-ethylthiazol-4-yl)ethyl}phenylsulfamic acid;
  b) 5 mg of 2-hydroxypropyl-beta-cyclodextrin; and
  c) the balance a carrier system to a volume of 1 mL.
In one aspect, the carrier system comprises:
  i) one or more tonicity agents; and
  ii) water.

Non-limiting examples of tonicity agents include dextrose, mannitol and glycerin. The formulator can utilize more than one tonicity agent when formulating the disclosed compositions according to Formulation Example 3. The tonicity agent can comprise from about 0.5% to about 5% weight by volume of the final composition. In non-limiting examples, when preparing the final composition, the tonicity agent may be combined with 4-{(S)-2-[(S)-2-(methoxycarbonyl-amino)-3-phenylpropanamido]-2-(2-ethylthiazol-4-yl)ethyl}phenylsulfamic acid before mixing with the carrier system. Alternately, when reconstituting the final composition the formulator can use commercially available solutions containing atonicity agent, for example, 5% Dextrose Injection, USP.

The osmolarity of the disclosed compositions according to Formulation Example 3 can be within any range chosen by the formulator. In one aspect the osmolarity is from about 250 to about 350 mOsm/L. In one embodiment of this aspect of the disclosed osmolarity is from about 270 to about 310 mOsm/L.

The pH of the disclosed compositions according to Formulation Example 3 can be from about 6 to about 8. If the pH is outside the range desired by the formulator, the pH can be adjusted by using sufficient pharmaceutically acceptable acids and bases.

One aspect of the disclosed compositions according to Formulation Example 3 relates to compositions comprising 4-{(S)-2-[(S)-2-(methoxycarbonylamino)-3-phenylpropanamido]-2-(2-ethylthiazol-4-yl)ethyl}phenylsulfamic acid or pharmaceutically acceptable salts thereof.

One embodiment of this aspect of the disclosed compositions according to Formulation Example 3 comprises:
  a) from about 42 mg/mL to about 48 mg/mL of the 4-{(S)-2-[(S)-2-(methoxycarbonylamino)-3-phenyl-propanamido]-2-(2-ethylthiazol-4-yl)ethyl}phenylsulfamic acid or a pharmaceutically acceptable salt thereof;
  b) from about 4.2 mg/mL to about 4.8 mg/mL of 2-hydroxypropyl-β-cyclodextrin; and
  c) a carrier system.

A non-limiting iteration of this embodiment of the disclosed compositions according to Formulation Example 3 comprises:
  a) about 45 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
  b) about 4.5 mg/mL of 2-hydroxypropyl-β-cyclodextrin; and
  c) a carrier system.

One specific example of a composition according to this iteration comprises:
  a) 45 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
  b) 45 mg/mL of 2-hydroxypropyl-β-cyclodextrin; and
  c) a carrier system containing:
    i) 2% weight to volume of the composition dextrose; and
    ii) water.

Another embodiment of this aspect of the disclosed compositions according to Formulation Example 3 comprises:
  a) from about 55 mg/mL to about 65 mg/mL of the 4-{(S)-2-[(S)-2-(methoxycarbonylamino)-3-phenyl-propanamido]-2-(2-ethylthiazol-4-yl)ethyl}phenylsulfamic acid or a pharmaceutically acceptable salt thereof;
  b) from about 110 mg/mL to about 6 mg/mL of 2-hydroxypropyl-β-cyclodextrin; and
  c) a carrier system.

A non-limiting iteration of this embodiment of the disclosed compositions according to Formulation Example 3 comprises:
  a) about 60 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;

b) about 600 mg/mL of 2-hydroxypropyl-β-cyclodextrin; and
c) a carrier system.

One specific example of a composition according to this iteration comprises:
a) 60 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) 60 mg/mL of 2-hydroxypropyl-β-cyclodextrin; and
c) a carrier system containing:
i) 2% weight to volume of the composition dextrose; and
ii) water.

A further embodiment of this aspect of the disclosed compositions according to Formulation Example 3 comprises:
a) from about 85 mg/mL to about 95 mg/mL of the 4-{(S)-2-[(S)-2-(methoxycarbonylamino)-3-phenylpropanamido]-2-(2-ethylthiazol-4-yl)ethyl}phenylsulfamic acid or a pharmaceutically acceptable salt thereof;
b) from about 20 mg/mL to about 30 mg/mL of 2-hydroxypropyl-β-cyclodextrin; and
c) a carrier system.

A non-limiting iteration of this embodiment of the disclosed compositions according to Formulation Example 3 comprises:
a) about 90 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) about 1000 mg/mL of 2-hydroxypropyl-β-cyclodextrin; and
c) a carrier system.

One specific example of a composition according to this iteration comprises:
a) 90 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) 500 mg/mL of 2-hydroxypropyl-β-cyclodextrin; and
c) a carrier system containing:
i) 2% weight to volume of the composition dextrose; and
ii) water.

Formulation Example 4

This formulation example relates to compositions comprising 4-{(S)-2-[(S)-2-(methoxycarbonylamino)-3-phenylpropanamido]-2-(4-ethylthiazol-2-yl)ethyl}phenylsulfamic acid having the formula:

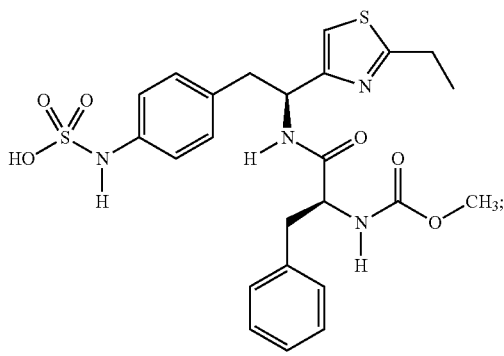 [SMILES: CCc1nc([C@H](Cc2ccc(NS(=O)(=O)O)cc2)NC(=O)[C@H](Cc2ccccc2)NC(=O)OC)cs1]

and
pharmaceutically acceptable salts thereof.

Formulation Example 4 comprises:
a) 4-{(S)-2-[(S)-2-(methoxycarbonylamino)-3-phenylpropanamido]-2-(4-ethylthiazol-2-yl)ethyl}phenylsulfamic acid or a pharmaceutically acceptable salt thereof;
b) a solubilizing system; and
c) a carrier system.

The compositions of Formulation Example 4 are formulated to deliver an amount of 4-{(S)-2-[(S)-2-(methoxycarbonylamino)-3-phenylpropanamido]-2-(4-ethylthiazol-2-yl)ethyl}-phenylsulfamic acid in the free acid form. For example, a composition which comprises 10 mg/mL of 4-{(S)-2-[(S)-2-(methoxycarbonylamino)-3-phenylpropanamido]-2-(4-ethylthiazol-2-yl)ethyl}phenylsulfamic acid can have either 10 mg/mL of the free acid or an amount of a pharmaceutically acceptable salt in an amount sufficient to deliver 10 mg/mL of the free acid. As an example, a composition formulated to deliver 10 mg/mL of 4-{(S)-2-[(S)-2-(methoxy-carbonylamino)-3-phenylpropanamido]-2-(4-ethylthiazol-2-yl)ethyl}phenylsulfamic acid can comprise either 10 mg/mL of 4-{(S)-2-[(S)-2-(methoxycarbonylamino)-3-phenylpropanamido]-2-(4-ethylthiazol-2-yl)ethyl}phenylsulfamic acid or alternatively 10.4 mg/mL of the sodium salt, (sodium 4-{(S)-2-[(S)-2-(methoxycarbonylamino)-3-phenylpropanamido]-2-(4-ethylthiazol-2-yl)ethyl}phenylsulfamate). Therefore, a composition which delivers from about 0.1 mg/mL to about 90 mg/mL of 4-{(S)-2-[(S)-2-(methoxycarbonylamino)-3-phenylpropanamido]-2-(4-ethylthiazol-2-yl)ethyl}phenylsulfamic acid can comprise an amount of pharmaceutically acceptable salt thereof to deliver from about 0.1 mg/mL to about 90 mg/mL of the compound Therefore, when a composition according to Formulation Example 4 comprises an amount of 4-{(S)-2-[(S)-2-(methoxycarbonylamino)-3-phenylpropanamido]-2-(4-ethylthiazol-2-yl)ethyl}phenylsulfamic acid per mL, it is understood that this amount is the amount of free acid that is delivered and if a salt form of the compound is used in the composition, the amount of the salt form can therefore reflect the difference in molecular weight between the free acid and the salt form. The following example demonstrates this equivalency.

A composition delivering 10 mg/mL of 4-{(S)-2-[(S)-2-(methoxycarbonylamino)-3-phenylpropanamido]-2-(4-ethylthiazol-2-yl)ethyl}phenylsulfamic acid, comprises:
a) 10 mg/mL of 4-{(S)-2-[(S)-2-(methoxycarbonylamino)-3-phenylpropanamido]-2-(4-ethylthiazol-2-yl)ethyl}phenylsulfamic acid; or about 10.4 mg/mL of sodium 4-{(S)-2-[(S)-2-(methoxycarbonylamino)-3-phenylpropanamido]-2-(4-ethylthiazol-2-yl)ethyl}phenylsulfamate; or about 10.3 mg/mL, of ammonium 4-{(S)-2-[(S)-2-(methoxycarbonylamino)-3-phenylpropanamido]-2-(4-ethylthiazol-2-yl)ethyl}phenylsulfamate, and the like;
b) an amount of 2-hydroxypropyl-β-cyclodextrin as defined herein; and
c) a carrier system.

The disclosed compositions according to Formulation Example 4 according to Formulation Example 4 comprise from about 10 mg/mL to about 90 mg/mL of the 4-{(S)-2-[(S)-2-(methoxycarbonylamino)-3-phenylpropanamido]-2-[4-ethylthiazol-2-yl]ethyl}phenyl-sulfamic acid or a pharmaceutically acceptable salt thereof.

In one aspect the disclosed compositions according to Formulation Example 4 comprise from about 20 mg/mL to about 100 mg/mL of 4-{(S)-2-[(S)-2-(methoxycarbonylamino)-3-phenylpropanamido]-2-[4-ethylthiazol-2-yl]ethyl}phenylsulfamic acid or a pharmaceutically acceptable salt thereof. In one embodiment, the composition comprises from about 15 mg/mL to about 60 mg/mL of 4-{(S)-2-[(S)-2-(methoxycarbonylamino)-3-phenylpropanamido]-2-[4-ethylthiazol-2-yl]ethyl}phenylsulfamic acid or a pharmaceutically acceptable salt thereof. In another embodiment, the composition comprises from about 40 mg/mL to about 90 mg/mL of 4-{(S)-2-[(S)-2-(methoxycarbonylamino)-3-phenylpropanamido]-2-(4-ethylthiazol-2-yl)ethyl}-phenylsulfamic acid or a pharmaceutically acceptable salt thereof. In a further embodiment, the composition comprises from about 10 mg/mL to about 30 mg/mL of 4-{(S)-2-[(S)-2-(methoxy-carbonylamino)-3-phenylpropanamido]-2-(4-ethylthiazol-2-yl)ethyl}phenylsulfamic acid or a pharmaceutically acceptable salt thereof. In a still further embodiment, the composition comprises from about 40 mg/mL to about 80 mg/mL of 4-{(S)-2-[(S)-2-(methoxycarbonyl-lamino)-3-phenylpropanamido]-2-(4-ethylthiazol-2-yl)ethyl}phenylsulfamic acid or a pharmaceutically acceptable salt thereof. In a yet further embodiment the composition comprises from about 10 mg/mL to about 20 mg/mL weight by volume of 4-{(S)-2-[(S)-2-(methoxycarbonylamino)-3-phenylpropanamido]-2-[4-ethylthiazol-2-yl]ethyl}phenylsulfamic acid or a pharmaceutically acceptable salt thereof. In a still yet further embodiment, the composition comprises from about 60 mg/mL to about 90 mg/mL weight by volume of 4-{(S)-2-[(S)-2-(methoxycarbonylamino)-3-phenylpropanamido]-2-(4-ethylthiazol-2-yl)ethyl}phenyl-sulfamic acid or a pharmaceutically acceptable salt thereof. In still another embodiment, the composition comprises from about 50 mg/mL to about 80 mg/mL weight by volume of 4-{(S)-2-[(S)-2-(methoxycarbonylamino)-3-phenylpropanamido]-2-(4-ethylthiazol-2-yl)ethyl}phenyl-sulfamic acid or a pharmaceutically acceptable salt thereof.

Particular embodiments of the disclosed compositions according to Formulation Example 4, comprise 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL 32 mg/mL, 33 mg/mL, 34 mg/mL, 35 mg/mL, 36 mg/mL, 37 mg/mL, 38 mg/mL, 39 mg/mL, 40 mg/mL, 41 mg/mL 42 mg/mL, 43 mg/mL, 44 mg/mL, 45 mg/mL, 46 mg/mL, 47 mg/mL, 48 mg/mL, 49 mg/mL, 50 mg/mL, 51 mg/mL 52 mg/mL, 53 mg/mL, 54 mg/mL, 55 mg/mL, 56 mg/mL, 57 mg/mL, 58 mg/mL, 59 mg/mL, 60 mg/mL, 61 mg/mL 62 mg/mL, 63 mg/mL, 64 mg/mL, 65 mg/mL, 66 mg/mL, 67 mg/mL, 68 mg/mL, 69 mg/mL, 70 mg/mL, 71 mg/mL 72 mg/mL, 73 mg/mL, 74 mg/mL, 75 mg/mL, 76 mg/mL, 77 mg/mL, 78 mg/mL, 79 mg/mL, 80 mg/mL, 81 mg/mL 82 mg/mL, 83 mg/mL, 84 mg/mL, 85 mg/mL, 86 mg/mL, 87 mg/mL, 88 mg/mL, 89 mg/mL, and 90 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL, about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL, about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL, about 82 mg/mL, about 83 mg/mL, about 84 mg/mL, about 85 mg/mL, about 86 mg/mL, about 87 mg/mL, about 88 mg/mL, about 89 mg/mL, and about 90 mg/mL of a compound herein, such as 4-{(S)-2-[(S)-2-(methoxycarbonylamino)-3-phenylpropanamido]-2-(4-ethylthiazol-2-yl)ethyl}phenylsulfamic acid.

Solubilizing Systems

In one embodiment, the disclosed compositions according to Formulation Example 4 can comprise from a ratio of about 20 parts of the compound herein or a pharmaceutically acceptable salt thereof to about 1 part solubilizing system (about 20:about 1) to about 1 part of the compound herein or a pharmaceutically acceptable salt thereof to about 20 parts solubilizing system (about 1:about 20). The disclosed solubilizing systems can comprise cyclodextrins, non-limiting examples of which include: β-cyclodextrin, β-cyclodextrin and β-cyclodextrin and derivatives thereof. Non-limiting examples of cyclodextrin derivatives includes methyl-β-cyclodextrin, 2-hydroxypropyl-β-cyclodextrin, sulfobutyl ether-β-cyclodextrin sodium salt, and 2-hydroxypropyl-β-cyclodextrin.

The formulator can adjust the ratios of the compound to HPβCD based upon composition parameters, for example, choice and amount of a tonicity agent and pH. Suitable ratios are described above. As such, the compositions can comprise an amount of solubilizing system suitable for achieving the desired properties of the composition, i.e., concentration of compound, the desired viscosity, and the desired osmolarity. The amount of HPβCD can vary depending upon the amount of compound that the formulator desires to deliver in a single dose.

Carrier System

The disclosed compositions according to Formulation Example 4 can comprise from about 1.5% to about 90% weight by volume of a carrier system. The amount of carrier system present is based upon several different factors or choices made by the formulator, for example, the final concentration of the compound and the amount of solubilizing agent.

The following is a non-limiting example of a composition comprising 60 mg/mL of 4-{(S)-2-[(S)-2-(methoxycarbonylamino)-3-phenylpropanamido]-2-(4-ethylthiazol-2-yl)ethyl}-phenylsulfamic acid:

a) 60 mg of the 4-{(S)-2-[(S)-2-(methoxycarbonylamino)-3-phenylpropanamido]-2-(4-ethylthiazol-2-yl)ethyl}phenylsulfamic acid;
b) 360 mg of 2-hydroxypropyl-beta-cyclodextrin; and
c) the balance a carrier system to a volume of 1 mL.

In one aspect, the carrier system comprises:
i) one or more tonicity agents; and
ii) water.

Non-limiting examples of tonicity agents include dextrose, mannitol and glycerin. The formulator can utilize more than one tonicity agent when formulating the disclosed compositions according to Formulation Example 4. The tonicity agent can comprise from about 0.5% to about 5% weight by volume of the final composition. In non-limiting examples, when preparing the final composition, the tonicity agent may be combined with 4-{(S)-2-[(S)-2-(methoxycarbonyl-amino)-3-phenylpropanamido]-2-(4-ethylthiazol-2-yl)ethyl}phenylsulfamic acid before mixing with the carrier system. Alternately, when reconstituting the final composition the formulator can use commercially available solutions containing a tonicity agent, for example, 5% Dextrose Injection.

The osmolarity of the disclosed compositions according to Formulation Example 4 can be within any range chosen by the formulator. In one aspect the osmolarity is from about 250 to about 350 mOsm/L. In one embodiment of this aspect of the disclosed osmolarity is from about 270 to about 310 mOsm/L.

The pH of the disclosed compositions according to Formulation Example 4 can be from about 6 to about 8. If the pH is outside the range desired by the formulator, the pH can be adjusted by using sufficient pharmaceutically acceptable acids and bases.

One aspect of the disclosed compositions according to Formulation Example 4 relates to compositions comprising 4-{(S)-2-[(S)-2-(methoxycarbonylamino)-3-phenylpropanamido]-2-(4-ethylthiazol-2-yl)ethyl}phenylsulfamic acid or pharmaceutically acceptable salts thereof.

One embodiment of this aspect of the disclosed compositions according to

Formulation Example 4 comprises:
a) from about 40 mg/mL to about 45 mg/mL of the 4-{(S)-2-[(S)-2-(methoxycarbonylamino)-3-phenyl-propanamido]-2-[4-ethylthiazol-2-yl]ethyl}phenylsulfamic acid or a pharmaceutically acceptable salt thereof;
b) from about 120 mg/mL to about 5.2 mg/mL of 2-hydroxypropyl-β-cyclodextrin; and
c) a carrier system.

A non-limiting iteration of this embodiment of the disclosed compositions according to Formulation Example 4 comprises:
a) about 40 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) about 240 mg/mL of 2-hydroxypropyl-β-cyclodextrin; and
c) a carrier system.

One specific example of a composition according to this iteration comprises:
a) 40 mg/mL of 4-{(S)-2-[(S)-2-(methoxycarbonylamino)-3-phenylpropanamido]-2-[2-(thiophen-2-yl)thiazol-4-yl]ethyl}phenylsulfamic acid;
b) 240 mg/mL of 2-hydroxypropyl-β-cyclodextrin; and
c) a carrier system containing:
  i) 2% weight to volume of the composition dextrose; and
  ii) water.

Another embodiment of this aspect of the disclosed compositions according to Formulation Example 4 comprises:
a) from about 55 mg/mL to about 65 mg/mL of the 4-{(S)-2-[(S)-2-(methoxycarbonylamino)-3-phenyl-propanamido]-2-[4-ethylthiazol-2-yl]ethyl}phenylsulfamic acid or a pharmaceutically acceptable salt thereof;
b) from about 5.5 mg/mL to about 650 mg/mL of 2-hydroxypropyl-β-cyclodextrin; and
c) a carrier system.

A non-limiting iteration of this embodiment of the disclosed compositions according to Formulation Example 4 comprises:
a) about 60 mg/mL of 4-{(S)-2-[(S)-2-(methoxycarbonylamino)-3-phenylpropanamido]-2-[4-ethylthiazol-2-yl]ethyl}phenylsulfamic acid;
b) about 30 mg/mL of 2-hydroxypropyl-β-cyclodextrin; and
c) a carrier system.

One specific example of a composition according to this iteration comprises:
a) 60 mg/mL of 4-{(S)-2-[(S)-2-(methoxycarbonylamino)-3-phenylpropanamido]-2-[4-ethylthiazol-2-yl]ethyl}phenylsulfamic acid;
b) 30 mg/mL of 2-hydroxypropyl-β-cyclodextrin; and
c) a carrier system containing:
  i) 2% weight to volume of the composition dextrose; and
  ii) water.

A further embodiment of this aspect of the disclosed compositions according to Formulation Example 4 comprises:
a) from about 70 mg/mL to about 77 mg/mL of the 4-{(S)-2-[(S)-2-(methoxycarbonylamino)-3-phenyl-propanamido]-2-[4-ethylthiazol-2-yl]ethyl}phenylsulfamic acid or a pharmaceutically acceptable salt thereof;
b) from about 20 mg/mL to about 1000 mg/mL of 2-hydroxypropyl-β-cyclodextrin; and
c) a carrier system.

A non-limiting iteration of this embodiment of the disclosed compositions according to Formulation Example 4 comprises:
a) about 74 mg/mL of 4-{(S)-2-[(S)-2-(methoxycarbonylamino)-3-phenylpropanamido]-2-[4-ethylthiazol-2-yl]ethyl}phenylsulfamic acid;
b) about 225 mg/mL of 2-hydroxypropyl-β-cyclodextrin; and
c) a carrier system.

One specific example of a composition according to this iteration comprises:
a) 74 mg/mL of 4-{(S)-2-[(S)-2-(methoxycarbonylamino)-3-phenylpropanamido]-2-[4-ethylthiazol-2-yl]ethyl}phenylsulfamic acid;
b) 225 mg/mL of 2-hydroxypropyl-β-cyclodextrin; and
c) a carrier system containing:
  i) 2% weight to volume of the composition dextrose; and
  ii) water.

4-{(S)-2-(4-Ethylthiazol-2-yl)-2-[(S)-2-(methoxycarbonylamino)-3-phenylpropanamido]-ethyl}phenylsulfamic acid can be prepared by the procedure outlined in Scheme XXV and described in Example 34 herein below.

Scheme XXV
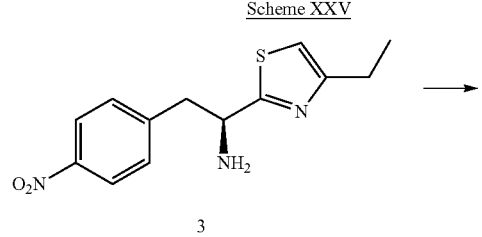
3
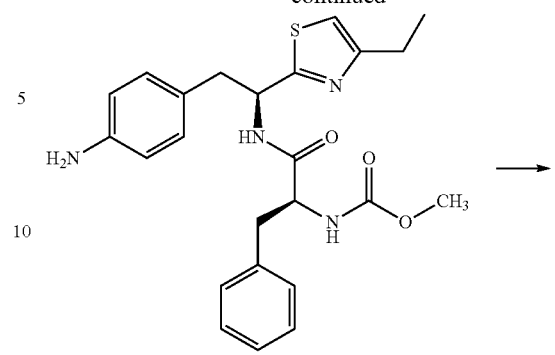
74
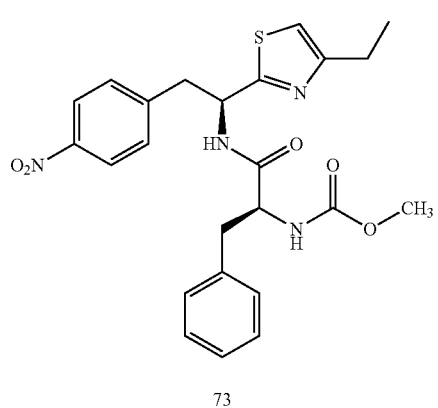
73
Reagents and conditions: (a) Moc—Phe, EDCI, HOBt, DIPEA, DMF; rt, 18 hr.
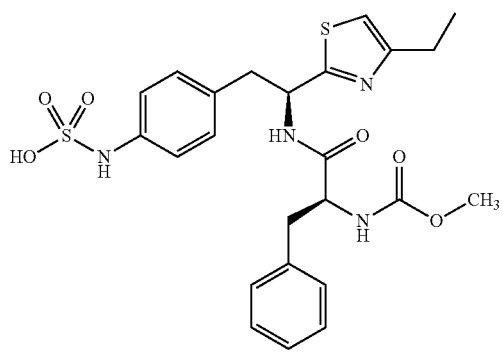
75
Reagents and conditions: (c) (CH₃)₃NSO₃, NMM; THF.
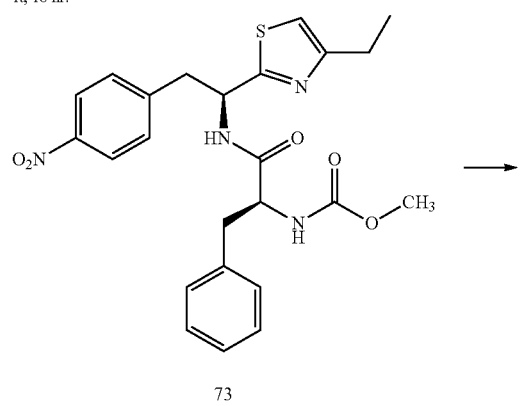
73
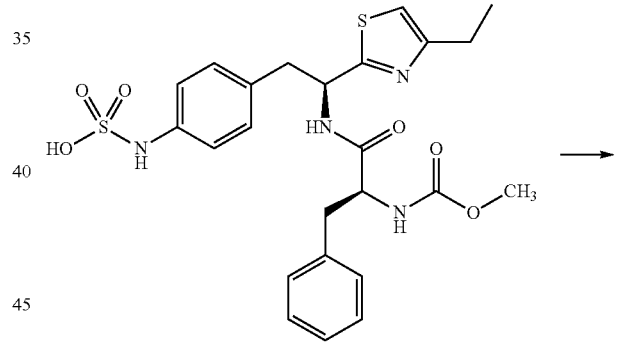
75
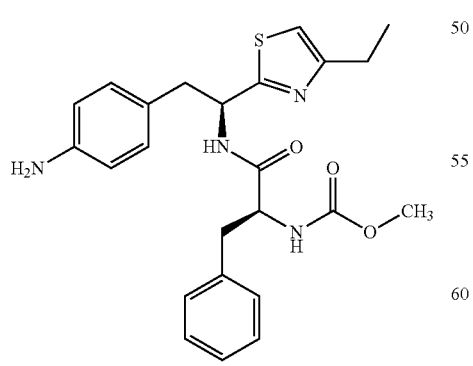
74
Reagents and conditions: (b) FeCl₃; NH₂NH₂—H₂O, EtOH.
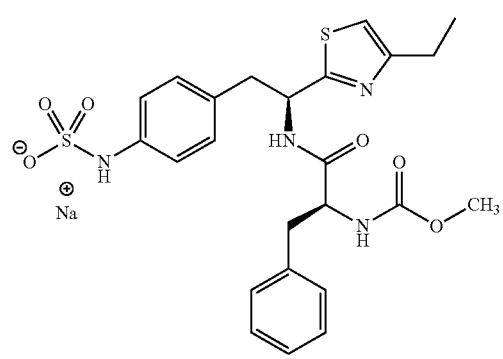
76
Reagents and conditions: (d) NaOH.

EXAMPLE 34

4-{(S)-2-(4-Ethylthiazol-2-yl)-2-[(S)-2-(methoxycarbonylamino)-3-phenylpropanamido]ethyl}phenylsulfamic acid (75)

Preparation of Methyl (S)-1-(S)-1-(4-ethylthiazol-2-yl)-2-(4-nitrophenyl)ethylamino)-1-oxo-3-phenylpropan-2-yl-carbamate (73): To a solution of 1-(S)-(4-ethylthiazol-2-yl)-2-(4-nitrophenyl)ethyl amine (3) (307 g, 82%, 1.1 mol), (S)-(2-methoxycarbonylamino)-3-phenylpropionic acid (333 g, 89%, 1.33 mol, 1.2 eq) and 1-hydroxybenzotriazole (HOBt) (180 g, 1.33 mol, 1.2 eq) in DMF (5 L) at 0° C., was added 1-(3-dimethylaminopropyl-3-ethylcarbodiimide (EDCI) (255 g, 1.33 mol, 1.2 eq) followed by diisopropylamine (285 g, 2.2 mol, 2 eq). The mixture was stirred at 0° C. for 30 minutes then at room temperature overnight. The reaction mixture was diluted with water (20 L) and extracted with EtOAc (30 L×3). The combined organic phase was washed with 1 N aqueous HCl, 5% aqueous NaHCO$_3$, brine and dried over Na$_2$SO$_4$. The solvent was removed in vacuo and the crude product was washed with a small amount of EtOAc to afford 245 g of the desired product with 94% HPLC purity. Yield: 56%. LC/MS (M+1): 483; $^1$H NMR (300 MHz, CD$_3$OD): δ 8.14-8.11 (d, 2H, J=8.4 Hz), 7.50-7.47 (d, 2H, J=8.4 Hz), 7.20-7.17 (m, 5H), 7.03 (s, 1H), 5.52-5.47 (m, 1H), 4.35-4.30 (t, 1H, J=7.8 Hz), 3.67-3.54 (m, 4H), 3.25-3.17 (m, 1H), 3.02-2.95 (m, 1H), 2.81-2.74 (m, 3H), 1.31-1.26 (t, 3H, J=7.5 Hz).

Preparation of Methyl (S)-1-(S)-2-(4-aminophenyl)-1-(4-ethylthiazol-2-yl)ethylamino)-1-oxo-3-phenylpropan-2-yl-carbamate (74): Methyl (S)-1-((S)-1-(4-ethylthiazol-2-yl)-2-(4-nitrophenyl)ethylamino)-1-oxo-3-phenylpropan-2-ylcarbamate (73) (220 g, 0.45 mol) was dissolved in 4.5 L of ethanol. FeCl$_3$ (15.0 g, 0.09 mol, 0.2 equiv.) and activated carbon (96.8 g) were added to the above solution. The resulting mixture was then refluxed while hydrated hydrazine (440 mL, 7.04 mol) was added dropwise during 1 h. The mixture was refluxed for another 2 h and then cooled down to rt. The activated carbon was filtered. Filtrate was concentrated under reduced pressure, diluted with 1 L water and extracted with ethyl acetate, washed with brine, dried over Na$_2$SO$_4$. The combined organic layer was concentrated and washed with ethyl ether to afford 10 as off-white solid (163 g, yield: 78.6%). LC/MS (M+1): 453; $^1$H NMR (300 MHz, CD$_3$OD) δ: 7.21-6.98 (m, 10H), 5.40-5.38 (t, 1H, J=7.5 Hz), 4.38-4.33 (t, 1H, J=7.5 Hz), 3.70 (s, 3H), 3.24-3.22 (m, 1H), 3.11-3.01 (m, 2H), 2.81-2.72 (m, 3H), 1.32-1.26 (t, 3H, J=7.5 Hz). HPLC: 96.5%.

Preparation of 4-((S)-2-(4-ethylthiazol-2-yl)-2-(S)-2-(methoxycarbonylamino)-3-phenylpropanamido)ethyl)phenylsulfamic acid (75): Methyl (S)-1-((S)-2-(4-aminophenyl)-1-(4-ethylthiazol-2-yl)ethylamino)-1-oxo-3-phenylpropan-2-ylcarbamate (74) (123 g, 0.272 mol) and N-methylmorpholine (50 g, 0.495 mol) were dissolved in 1.1 L of THF. Me$_3$NSO$_3$ complex (58 g, 0.417 mol) was added in one portion. The resulting mixture was warmed up to 50° C. for 3 hours and then concentrated under reduced pressure. The residue was purified by silica gel column chromatography (DCM/MeOH=20/1 to DCM/MeOH=10/1) to give the desired product 11 (150 g, yield: 104%), which contained a small amount of Me$_3$N and MeOSO$_3$H. LC/MS (M−1): 531; $^1$H NMR (300 MHz, CD$_3$OD) δ: 7.21-6.99 (m, 10H), 5.39-5.34 (t, 1H, J=6.0 Hz), 4.39-4.34 (t, 1H, J=8.1 Hz), 3.61 (s, 3H), 3.25-3.23 (m, 1H), 3.10-3.00 (m, 2H), 2.81-2.74 (m, 3H), 1.31-1.26 (t, 3H, J=7.2 Hz); HPLC: 98.1%.

Preparation of sodium 4-{(S)-2-(4-Ethylthiazol-2-yl)-2-[(S)-2-(methoxycarbonyl-amino)-3-phenyl-propanamido]ethyl}phenylsulfamate (76): To a solution of 4-((S)-2-(4-ethylthiazol-2-yl)-2-((S)-2-(methoxycarbonylamino)-3-phenylpropanamido)ethyl)-phenylsulfamic acid (75) (150 g, 0.272 mmol) in methanol (1.2 L) was added 50% NaOH (11.3 g, 0.272 mol, 1.0 equiv.) at room temperature. The resulting mixture was stirred at rt for 30 min and then concentrated under reduced pressure to give the crude product, which contained a small amount of Me$_3$N and MeOSO$_3$Na. To a stirred slurry of the crude product (75 g) in H$_2$O (150 mL) was added aq. NaOH (2 g, 0.05 mol; in 50 mL H$_2$O) in dropwise at room temperature. The slurry was continued to stir for 20 min, filtered and washed with water (10 mL) and ethyl ether (50 mL). Then the filter cake was dried under reduced pressure at 50° C. to give 62 g (83%) of the desired compound. LC/MS (M−1): 531; H-NMR (300 MHz, CD$_3$OD) δ: 7.21-6.98 (m, 10H), 5.40-5.36 (t, 1H, J=6.9 Hz), 4.38-4.34 (t, 1H, J=7.5 Hz), 3.61 (s, 3H), 3.24-3.23 (m, 1H), 3.11-3.01 (m, 2H), 2.81-2.74 (m, 3H), 1.31-1.26 (t, 3H, J=7.5 Hz); HPLC: 98.5%.

Methods

Disclosed are methods for the treatment of diseases or conditions of the eye, especially diabetic macular edema, age-related macular degeneration (wet form), choroidal neovascularization, diabetic retinopathy, ocular ischemia, uveitis, retinal vein occlusion (central or branch), ocular trauma, surgery induced edema, surgery induced neovascularization, cystoid macular edema, ocular ischemia, uveitis, and the like. These diseases or conditions are characterized by changes in the ocular vasculature whether progressive or non-progressive, whether a result of an acute disease or condition, or a chronic disease or condition. These diseases can be characterized by an increased level of plasma Vascular Endothelial Growth Factor.

In some embodiments, the disclosed methods relate to the administration of the HPTP-β inhibitor or a pharmaceutically acceptable salt thereof, as well as compositions comprising the HPTP-β inhibitor or a pharmaceutically acceptable salt thereof.

In some embodiments, the methods of the disclosure are drawn towards co-administration of a HPTP-β inhibitor or a pharmaceutically acceptable salt thereof which stabilizes the vasculature against leakage and one or more anti-VEGF agents.

In some embodiments, the methods of the disclosure are drawn towards co-administration of a HPTP-β inhibitor or a pharmaceutically acceptable salt thereof which stabilizes the vasculature against neovascularization and one or more anti-VEGF agents.

In some embodiments, the inhibitor stabilizes the vasculature against leakage and neovascularization.

In one embodiment of the disclosed methods, a human subject with at least one visually impaired eye is treated with from about 0.1 mg to about 100 mg of the HPTP-β inhibitor or a pharmaceutically acceptable salt thereof via subcutaneous or intravitreal injection. Improvement of clinical symptoms can be monitored by one or more methods known to the art, for example, indirect ophthalmoscopy, fundus photography, fluorescein angiopathy, electroretinography, external eye examination, slit lamp biomicroscopy, applanation tonometry, pachymetry, optical coherence tomography and autorefaction. As described herein, the dosing can occur at any frequency determined by the administrator. After cessation of the anti-VEGF agent treatment, subsequent doses can be administered weekly or monthly, e.g., with a frequency of 2-8 weeks or 1-12 months apart depending upon the response.

One aspect of the disclosed methods relates to diseases that are a direct or indirect result of diabetes, inter alia, diabetic macular edema and diabetic retinopathy. The ocular vasculature of the diabetic becomes unstable over time leading to conditions such as non-proliferative retinopathy, macular edema, and proliferative retinopathy. As fluid leaks into the center of the macula, the part of the eye where sharp, straight-ahead vision occurs, the buildup of fluid and the associated protein begin to deposit on or under the macula. This results in swelling that causes the subject's central vision to gradually become distorted. This condition is referred to as "macular edema." Another condition that may occur is non-proliferative retinopathy in which vascular changes, such as microaneurysms, outside the macular region of the eye may be observed.

These conditions may or may not progress to diabetic proliferative retinopathy which is characterized by increased neovascularization. These new blood vessels are fragile and are susceptible to bleeding. The result is scaring of the retina, as well as occlusion or total blockage of the light pathway through the eye due to the over formation of new blood vessels. Typically subjects having diabetic macular edema are suffering from the non-proliferative stage of diabetic retinopathy; however, it is not uncommon for subjects to only begin manifesting macular edema at the onset of the proliferative stage.

Diabetic retinopathy is the most common cause of vision loss in working-aged Americans (Klein R et al., "The Wisconsin Epidemiologic Study of Diabetic Retinopathy. II. Prevalence and risk of diabetic retinopathy when age at diagnosis is less than 30 years," Arch. Ophthalmol. 1984, 102:520-526). Severe vision loss occurs due to tractional retinal detachments that complicate retinal neovascularization (NV), but the most common cause of moderate vision loss is diabetic macular edema (DME). The pathogenesis of diabetic macular edema is not completely understood, but hypoxia is a contributing factor (Nguyen Q D et al., "Supplemental inspired oxygen improves diabetic macular edema; a pilot study," Invest. Ophthalmol. Vis. Sci. 2003, 45:617-624). Vascular endothelial growth factor (Vegf) is a hypoxia-regulated gene and VEGF levels are increased in hypoxic or ischemic retina. Injection of VEGF into mouse eyes causes breakdown of the inner blood-retinal barrier (See, Derevjanik N L et al. Quantitative assessment of the integrity of the blood-retinal barrier in mice, Invest. Ophthalmol. Vis. Sci. 2002, 43:2462-2467) and sustained release of VEGF in the eyes of monkeys causes macular edema (Ozaki H et al., "Intravitreal sustained release of VEGF causes retinal neovascularization in rabbits and breakdown of the blood-retinal barrier in rabbits and primates," Exp Eye Res 1997, 64:505-517). This combination of observations in patients and animal models led to the hypothesis that VEGF plays an important role in the pathogenesis of diabetic macular edema. This hypothesis has been confirmed by several clinical trials that have shown that VEGF antagonists reduce foveal thickening and improve vision in patients with diabetic macular edema (Nguyen Q D et al., "Vascular endothelial growth factor is a critical stimulus for diabetic macular edema," Am. J. Ophthalmol. 2006, 142:961-969; and Nguyen Q D et al. "Primary End Point (Six Months) Results of the Ranibizumab for Edema of the mAcula in Diabetes (READ-2) Study," Ophthalmology 2009, 116:2175-2181).

The effects of VEGF on vascular endothelial cells are modulated by Tie2 receptors, which are selectively expressed on vascular endothelial cells and are required for embryonic vascular development (Dumont D J et al., "Dominant-negative and targeted null mutations in the endothelial receptor tyrosine kinase, tek, reveal a critical role in vasculogenesis of the embryo," Genes Dev. 1994, 8:1897-1909). Angiopoietin 1 (Ang1) binds Tie2 with high affinity and initiates phosphorylation and downstream signaling (Davis S et al., "Isolation of angiopoietin-1, a ligand for the TIE2 receptor, by secretion-trap expression cloning," Cell 1996, 87:1161-1169). Mice deficient in Ang1 die around E12.5 with vascular defects similar to, but less severe than those seen in Tie2-deficient mice. Angiopoietin 2 (Ang2) binds Tie2 with high affinity, but does not stimulate phosphorylation in cultured endothelial cells. It acts as a competitive inhibitor of Ang1 and transgenic mice overexpressing Ang2 have a phenotype similar to Ang1-deficient mice. Several lines of evidence indicate that Ang2 is a developmentally- and hypoxia-regulated permissive factor for VEGF-induced neovascularization in the retina (Hackett S F et al., "Angiopoietin 2 expression in the retina: upregulation during physiologic and pathologic neovascularization," J. Cell. Physiol. 2000, 184:275-284). Double transgenic Tet/opsin/ang2 and Tet/opsin/ang1 mice with inducible expression of Ang2 or Ang1, respectively, have also helped to elucidate the role of Tie2 in the retina (Nambu H et al., "Angiopoietin 1 inhibits ocular neovascularization and breakdown of the blood-retinal barrier," Gene Ther. 2004, 11:865-873). In mice with ischemic retinopathy, increased expression of Ang2 when VEGF is high (P12-17) increases retinal neovascularization, but increased expression at P20 when VEGF levels have come down, hastens regression of retinal neovascularization and findings were similar in other models of ocular neovascularization. In contrast, increased expression of Ang1 suppressed neovascularization and reduced vascular leakage in several models. Therefore, Ang2 reduces stabilizing signals from the matrix making endothelial cells dependent upon VEGF and other soluble stimulators; when VEGF is high, neovascularization is stimulated and when VEGF is low, neovascularization regresses. In contrast, Ang1 increases stabilizing signals from the matrix and makes the vasculature unresponsive to soluble stimulators like VEGF.

Angiopoietin 2 binds Tie2, but does not stimulate phosphorylation and therefore acts as an antagonist under most circumstances. In the eye, angiopoietin 2 is upregulated at sites of neovascularization and acts as a permissive factor for VEGF. Increased expression of VEGF in the retina does not stimulate sprouting of neovascularization from the superficial or intermediate capillary beds of the retina or the choriocapillaris, but does stimulate sprouting from the deep capillary bed where there is constitutive expression of angiopoietin 2 (Hackett S F et al., "Angiopoietin-2 plays an important role in retinal angiogenesis," J. Cell. Physiol. 2002, 192:182-187). Co-expression of VEGF and angiopoietin 2 at the surface of the retina causes sprouting of neovascularization from the superficial retinal capillaries (Oshima Y et al., "Angiopoietin-2 enhances retinal vessel sensitivity to vascular endothelial growth factor," J. Cell. Physiol. 2004, 199:412-417). In double transgenic mice with inducible expression of angiopoietin 2 in the retina, expression of angiopoietin 2 when VEGF levels were high markedly enhanced neovascularization and expression of angiopoietin 2 when VEGF levels were low caused regression of neovascularization. In double transgenic mice with inducible expression of angiopoietin 1, the induced expression of angiopoietin 1 in the retina strongly suppressed VEGF-induced vascular leakage or neovascularization (Nambu H et al., "Angiopoietin 1 inhibits ocular neovascularization and breakdown of the blood-retinal barrier," *Gene Ther.* 2004, 11:865-873). In fact, in mice with high expression of VEGF in the retina which develop severe NV and retinal detachment, angiopoietin 1 is able to prevent the VEGF-induced detachments.

Regulation of Tie2 also occurs through an endothelial-specific phosphatase, vascular endothelial protein tyrosine phophatase (VE-PTP) in mice (Fachinger G et al., "Functional interaction of vascular endothelial-protein-tyrosine phosphatase with the angiopoietin receptor Tie-2," *Oncogene* 1999, 18:5948-5943) and its human orthologue human protein tyrosine phosphatase-β (HPTP-β) (Krueger N X et al., "Structural diversity and evolution of human receptor-like protein tyrosine phosphatases," *EMBO J.* 1990, 9:3241-3252). Mice, deficient in VE-PTP die at E10 with severe defects in vascular remodeling and maturation of developing vasculature. Silencing of HPTP-β in cultured human endothelial cells, enhances Ang1-induced phosphorylation of Tie2 and survival-promoting activity while hypoxia increases expression of HPTP-β and reduces Ang1-induced phosphorylation of Tie2 (Yacyshyn O K et al., "Thyrosine phosphatase beta regulates angiopoietin-Tie2 signaling in human endothelial cells," *Angiogenesis* 2009, 12:25-33).

Macular degeneration is a condition characterized by a gradual loss or impairment of eyesight due to cell and tissue degeneration of the yellow macular region in the center of the retina. Macular degeneration is often characterized as one of two types, non-exudative (dry form) or exudative (wet form). Although both types are bilateral and progressive, each type may reflect different pathological processes. The wet form of age-related macular degeneration (AMD) is the most common form of choroidal neovascularization and a leading cause of blindness in the elderly. AMD affects millions of Americans over the age of 60, and is the leading cause of new blindness among the elderly.

Choroidal neovascular membrane (CNVM) is a problem that is related to a wide variety of retinal diseases, but is most commonly linked to age-related macular degeneration. With CNVM, abnormal blood vessels stemming from the choroid (the blood vessel-rich tissue layer just beneath the retina) grow up through the retinal layers. These new vessels are very fragile and break easily, causing blood and fluid to pool within the layers of the retina.

Diabetes (diabetes mellitus) is a metabolic disease caused by the inability of the pancreas to produce insulin or to use the insulin that is produced. The most common types of diabetes are type 1 diabetes (often referred to as Juvenile Onset Diabetes Mellitus) and type 2 diabetes (often referred to as Adult Onset Diabetes Mellitus). Type 1 diabetes results from the body's failure to produce insulin due to loss of insulin producing cells, and presently requires the person to inject insulin. Type 2 diabetes generally results from insulin resistance, a condition in which cells fail to use insulin properly.

Diabetes can be correlated to a large number of other conditions, including conditions or diseases of the eye including diabetic retinopathy (DR) and diabetic macular edema (DME) which are leading causes of vision loss and blindness in most developed countries. The increasing number of individuals with diabetes worldwide suggests that DR and DME continues to be major contributors to vision loss and associated functional impairment for years to come.

Diabetic retinopathy is a complication of diabetes that results from damage to the blood vessels of the light-sensitive tissue at the back of the eye (retina). At first, diabetic retinopathy may cause no symptoms or only mild vision problems. Eventually, however, diabetic retinopathy can result in blindness. Diabetic retinopathy can develop in anyone who has type 1 diabetes or type 2 diabetes.

At its earliest stage, non-proliferative retinopathy, microaneurysms occur in the retina's tiny blood vessels. As the disease progresses, more of these blood vessels become damaged or blocked and these areas of the retina send signals into the regional tissue to grow new blood vessels for nourishment. This stage is called proliferative retinopathy. The new blood vessels grow along the retina and along the surface of the clear, vitreous gel that fills the inside of the eye. By themselves, these blood vessels do not cause symptoms or vision loss. However, they have thin, fragile walls and without timely treatment, these new blood vessels can leak blood (whole blood or some constituents thereof) which can result in severe vision loss and even blindness. Also, fluid can leak into the center of the macula, the part of the eye where sharp, straight-ahead vision occurs. The fluid and the associated protein begin to deposit on or under the macula swell the patient's central vision becomes distorted. This condition is called macular edema. It can occur at any stage of diabetic retinopathy, although it is more likely to occur as the disease progresses. About half of the people with proliferative retinopathy also have macular edema.

Uveitis is a condition in which the uvea becomes inflamed. The eye is shaped much like a tennis ball, hollow on the inside with three different layers of tissue surrounding a central cavity. The outermost is the sclera (white coat of the eye) and the innermost is the retina. The middle layer between the sclera and the retina is called the uvea. The uvea contains many of the blood vessels that nourish the eye. Complications of uveitis include glaucoma, cataracts or new blood vessel formation (neovascularization).

Ocular trauma is any sort of physical or chemical injury to the eye. Ocular trauma can affect anyone and major symptoms include redness or pain in the affected eye. Neither symptom may occur if tiny projectiles are the cause of the trauma.

Surgery-induced edema is the development of swelling in the eye tissues following surgery on the retina or other part of the eye. Cystoid macular edema (CME) is an example of this phenomenon. CME can occur not only in people who have had cataract surgery, but also those with diabetes, retinitis pigmentosa, AMD, or conditions that cause chronic inflammation in the eye. The major symptoms of CME are blurred or decreased central vision.

Ocular ischemic syndrome (OIS) encompasses the signs and symptoms that result from chronic vascular insufficiency. It is caused by ocular hypoperfusion due to occlusion or stenosis of the common or internal carotid arteries. OIS generally affects those between the ages of 50-80 and they may also have systemic diseases such as hypertension or diabetes. The major symptoms of OIS are orbital pain, vision loss, changes of the visual field, asymmetric cataract, and sluggish reaction to light, among a variety of other symptoms.

Retinal vein occlusion (RVO) is the most common retinal vascular disease after diabetic retinopathy. Depending on the area of retinal venous drainage effectively occluded, it is broadly classified as either central retinal vein occlusion (CRVO), hemispheric retinal vein occlusion (HRVO), or branch retinal vein occlusion (BRVO). It has been observed that each of these has two subtypes. Presentation of RVO in general is with variable painless visual loss with any combination of fundal findings consisting of retinal vascular tortuosity, retinal hemorrhages (blot and flame shaped), cotton wool spots, optic disc swelling and macular edema. In a CRVO, retinal hemorrhages can be found in all four quadrants of the fundus, whilst these are restricted to either the superior or inferior fundal hemisphere in a HRVO. In a BRVO, hemorrhages are largely localized to the area drained by the occluded branch retinal vein. Vision loss occurs secondary to macular edema or ischemia.

Angiogenesis, the process of creating new blood vessels from pre-existing vessels, is essential to a wide range of physiological and pathological events including embryological development, menstruation, wound healing, and tumor growth. Most, if not all, tumors require angiogenesis to grow and proliferate. VEGF has been shown to a major factor in angiogenesis where it can increase vessel permeability and capillary number. Due to the essential function of angiogenesis in tumor development, much effort has been put forth to develop therapies that target regulators of angiogenesis, including VEGF.

Vascular endothelial growth factor (VEGF) is a protein that is primarily found in endothelial cells and has functions in vasculogenesis, angiogenesis, and permeabilization of blood vessels. The expression of VEGF is induced by hypoxia, activated oncogenes, and cytokines. It has been found that VEGF activation not only leads to angiogenesis in normal human cells and tissues, but also angiogenesis in tumors, allowing for tumor progression and growth. Inhibition of VEGF inhibits tumor growth leading to tumor regression. A variety of retinopathies are associated with increased levels of VEGF; ischemia in the eye leads to an induction of VEGF production due to lack of oxygen. This increase in VEGF can cause hyperproliferation of blood vessels in the retina, eventually leading to blindness. The disclosed HPTP-β inhibitors act to stabilize ocular vasculature and, in some embodiments, a compound of the invention serves to counter act the stimulation caused by VEGF and other inflammatory agents that can be present in the diseased retina. In some embodiments, administration of HPTP-β inhibitors to a subject can be used to maintain the level of disease reversal after administration of anti-VEGF drugs to the subject have been withdrawn.

Diabetic retinopathy, if left untreated, can lead ultimately to blindness. Indeed, diabetic retinopathy is the leading cause of blindness in working-age populations.

Therefore, the disclosed methods relate to preventing, treating, controlling, abating, and/or otherwise minimizing ocular neovascularization in a subject having diabetes or a subject diagnosed with diabetes. In addition, subjects having or subjects diagnosed with diabetes can be alerted to or can be made aware of the risks of developing diabetes-related blindness, therefore the present methods can be used to prevent or delay the onset of non-proliferative retinopathy in subjects known to be at risk. Likewise, the present methods can be used for treating subjects having or being diagnosed with non-proliferative diabetic retinopathy to prevent progression of the condition.

The disclosed methods relate to preventing or controlling ocular neovascularization or treating a disease or condition that is related to the onset of ocular neovascularization by administering to a subject the 4-{(S)-2-[(S)-2-methoxycarbonylamino)-3-phenylpropanamido]-2-[2-(thiophen-2-yl) thiazol-4-yl]ethyl}phenylsulfamic acid s and one or more anti-VEGF agents as disclosed herein.

Unlike previous ocular treatments which comprise administration of an anti-VEGF agent, inter alia, ranibizumab (Lucentis™), bevacizumab (Avastin™) and aflibercept (Eylea™), wherein these vascular leak inhibitors are injected directly into the eye itself, the HPTP-β inhibitor or a pharmaceutically acceptable salt thereof can be administered systemically or into the eye. The HPTP-β inhibitor or a pharmaceutically acceptable salt thereof can be used to increase or enhance the effect of anti-VEGF agents, thereby improving the rate and magnitude of the response and reducing the number of treatments.

In one aspect, the HPTP-β inhibitor or a pharmaceutically acceptable salt thereof are administered in combination with one or more pharmaceutical compounds or compositions useful for treating ocular diseases. In one embodiment, the present disclosure relates to a method for treating an ocular disease, comprising administering:

a) a HPTP-β inhibitor or a pharmaceutically acceptable salt thereof; and b) ranibizumab.

In one aspect of the disclosure the methods comprise administering:

a) a HPTP-β inhibitor or a pharmaceutically acceptable salt thereof as disclosed herein; and b) ranibizumab.

In another aspect the methods comprise administering:

a) a HPTP-β inhibitor having the formula:

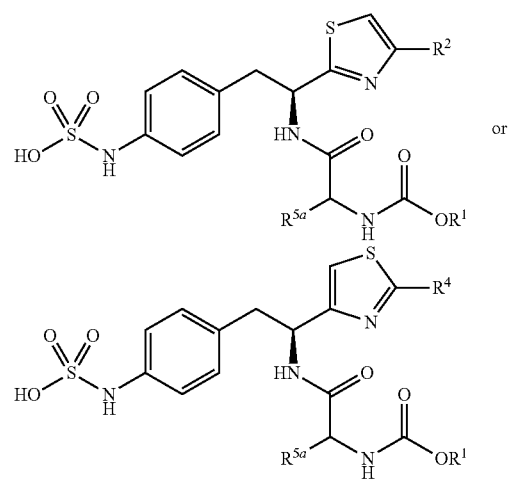

or wherein $R^2$ and $R^4$ are chosen from:

i) hydrogen;

ii) substituted or unsubstituted $C_1$-$C_6$ linear, $C_3$-$C_6$ branched, or $C_3$-$C_6$ cyclic alkyl;

iii) substituted or unsubstituted phenyl; or iv) substituted or unsubstituted thiophenyl;

$R^1$ is $C_1$-$C_6$ linear, $C_3$-$C_6$ branched, or $C_3$-$C_6$ cyclic alkyl;

$R^{5a}$ is chosen from:

i) hydrogen;

ii) $C_1$-$C_6$ linear, $C_3$-$C_6$ branched, or $C_3$-$C_6$ cyclic alkyl; or iii) benzyl; or a pharmaceutically acceptable salt thereof; and b) ranibizumab.

A non-limiting embodiment of this aspect relates to methods comprising administering:
a) a HPTP-β inhibitor having the formula:

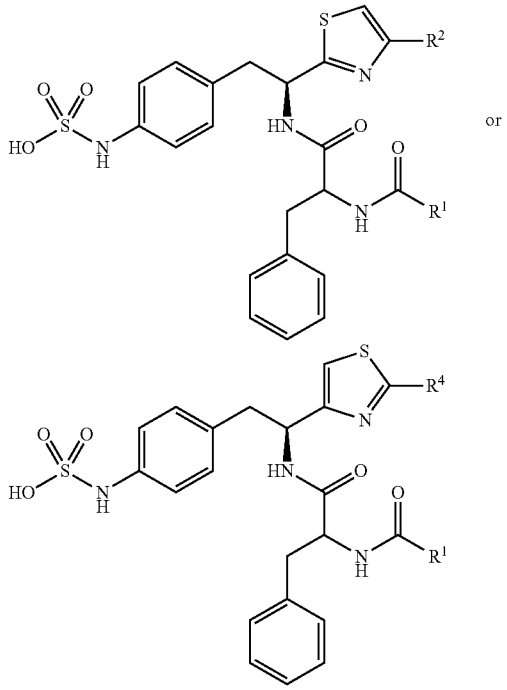

or wherein $R^2$ and $R^4$ are chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted phenyl; or
iv) substituted or unsubstituted thiophenyl;
$R^1$ is $C_1$-$C_6$ linear, $C_3$-$C_6$ branched, or $C_3$-$C_6$ cyclic alkyl; or
a pharmaceutically acceptable salt; and
b) ranibizumab.

The compounds can be administered in any order convenient to the user or to the subject receiving treatment. In one non-limiting example of the disclosed methods, a compound herein or a pharmaceutically acceptable salt thereof is administered first followed by administration of ranibizumab. In another iteration of this embodiment ranibizumab is administered first followed by administration of the compound herein or a pharmaceutically acceptable salt thereof. The time period between dosing/administration of the first component of treatment can be any time period convenient to the formulator or subject receiving treatment. For example, the compound herein or a pharmaceutically acceptable salt thereof can be administered minutes, hours, days or weeks prior to the administration of ranibizumab or more than one dosage of the compound herein or a pharmaceutically acceptable salt thereof can be given to establish a therapeutic amount in the subject being treated.

In another iteration, a compound herein or a pharmaceutically acceptable salt thereof and ranibizumab can be given in alternating administrations. For example, the compound herein or a pharmaceutically acceptable salt thereof can be administered then after a time desired by the administrator ranibizumab is administered.

In a further iteration, the compound herein or a pharmaceutically acceptable salt thereof are administered daily in one or more doses and the ramibizumab is administered according to a separate schedule. For example, in addition to daily dosing of the compound herein, ranibizumab can be administered once a month, once every 2 months, once every 3 months, once every 4 months, once every 6 months, etc.

In another non-limiting example of the disclosed methods, a compound herein or a pharmaceutically acceptable salt thereof is administered first followed by administration of ranibizumab. In another iteration of this embodiment, ranibizumab is administered first followed by administration of the compound herein or a pharmaceutically acceptable salt thereof. The time period between dosing/administration of the first component of treatment can be any time period convenient to the formulator or subject receiving treatment. For example, the compound herein or a pharmaceutically acceptable salt thereof can be administered minutes, hours, days or weeks prior to the administration of ranibizumab or more than one dosage of the compound herein or a pharmaceutically acceptable salt thereof can be given to establish a therapeutic amount in the subject being treated.

In another iteration, the compound herein or a pharmaceutically acceptable salt thereof and ranibizumab can be given in alternating administrations. For example, the compound herein or a pharmaceutically acceptable salt thereof can be administered then after a time desired by the administrator ranibizumab is administered.

In a further iteration, the compound herein or a pharmaceutically acceptable salt thereof are administered daily in one or more doses and the ramibizumab is administered according to a separate schedule. For example, in addition to daily dosing of the compound herein, ranibizumab can be administered once a month, once every 2 months, once every 3 months, once every 4 months, once every 6 months, etc.

In a further non-limiting example of the disclosed methods, a compound herein or a pharmaceutically acceptable salt thereof is administered first followed by administration of ranibizumab. In another iteration of this embodiment ranibizumab is administered first followed by administration of the compound herein or a pharmaceutically acceptable salt thereof. The time period between dosing/administration of the first component of treatment can be any time period convenient to the formulator or subject receiving treatment. For example, the compound herein or a pharmaceutically acceptable salt thereof can be administered minutes, hours, days or weeks prior to the administration of ranibizumab or more than one dosage of the compound herein or a pharmaceutically acceptable salt thereof can be given to establish a therapeutic amount in the subject being treated.

In another iteration, the compound herein or a pharmaceutically acceptable salt thereof and ranibizumab can be given in alternating administrations. For example, the compound herein or a pharmaceutically acceptable salt thereof can be administered then after a time desired by the administrator ranibizumab is administered.

In a further iteration, the compound herein or a pharmaceutically acceptable salt thereof are administered daily in one or more doses and the ramibizumab is administered according to a separate schedule. For example, in addition to daily dosing of the compound herein, ranibizumab can be administered once a month, once every 2 months, once every 3 months, once every 4 months, once every 6 months, etc.

The dosage for ranibizumab can be in any amount necessary. In one embodiment, ranibizumab is administered in an amount from about 0.05 mg to about 1.5 mg. In a further embodiment, ranibizumab is administered in an amount from about 0.1 mg to about 1.5 mg. In another embodiment, ranibizumab is administered in an amount from about 0.05 mg to about 1 mg. In a still further embodiment, ranibizumab is administered in an amount from about 0.1 mg to about 1 mg. In one non-limiting example, ranibizumab is administered in an amount of approximately 0.5 mg. The amount of an antibody, such as ranibizumab, administered per treatment can be in any amount, for example, about 0.05 mg, about 0.06 mg, about 0.07 mg, about 0.08 mg, about 0.09 mg, about 0.1 mg, about 0.11 mg, about 0.12 mg, about 0.13 mg, about 0.14 mg, about 0.15 mg, about 0.16 mg, about 0.17, mg, about 0.18 mg, about 0.19 mg, about 0.2 mg, about 0.21 mg, about 0.22 mg, about 0.23 mg, about 0.24 mg, about 0.25 mg, about 0.26 mg, about 0.27, mg, about 0.28 mg, about 0.29 mg, about 0.3 mg, about 0.31 mg, about 0.32 mg, about 0.33 mg, about 0.34 mg, about 0.35 mg, about 0.36 mg, about 0.37, mg, about 0.38 mg, about 0.39 mg, about 0.4 mg, about 0.41 mg, about 0.42 mg, about 0.43 mg, about 0.44 mg, about 0.45 mg, about 0.46 mg, about 0.47, mg, about 0.48 mg, about 0.49 mg, about 0.5 mg, about 0.51 mg, about 0.52 mg, about 0.53 mg, about 0.54 mg, about 0.55 mg, about 0.56 mg, about 0.57, mg, about 0.58 mg, about 0.59 mg, about 0.6 mg, about 0.61 mg, about 0.62 mg, about 0.63 mg, about 0.64 mg, about 0.65 mg, about 0.66 mg, about 0.67, mg, about 0.68 mg, about 0.69 mg, about 0.7 mg, about 0.71 mg, about 0.72 mg, about 0.73 mg, about 0.74 mg, about 0.75 mg, about 0.76 mg, about 0.77, mg, about 0.78 mg, about 0.79 mg, about 0.8 mg, about 0.81 mg, about 0.82 mg, about 0.83 mg, about 0.84 mg, about 0.85 mg, about 0.86 mg, about 0.87, mg, about 0.88 mg, about 0.89 mg, about 0.9 mg, about 0.91 mg, about 0.92 mg, about 0.93 mg, about 0.94 mg, about 0.95 mg, about 0.96 mg, about 0.97, mg, about 0.98 mg, about 0.99 mg, about 1 mg, about 1.5 mg, about 2 mg, about 2.5 mg, about 3 mg, about 3.5 mg, about 4 mg, about 4.5 mg, about 5 mg, about 6 mg, about 7 mg, about 8 mg, about 9 mg, or about 10 mg.

If the antibody is not administered simultaneously with the other compound herein, then the time between administration of the compound and the antibody can range, for example, from about 1 minute, about 2 minutes, about 3 minutes, about 4 minutes, about 5 minutes, about 10 minutes, about 15 minutes, about 20 minutes, about 25 minutes, about 30 minutes, about 40 minutes, about 50 minutes, about 60 minutes, about 2 hours, about 3 hours, about 4 hours, about 5 hours, about 10 hours, about 20 hours, about 1 day, about 2 days, about 3 days, about 4 days, about 5 days, about 6 days, about 1 week, about 2 weeks, about 3 weeks, to about 4 weeks.

In another embodiment, the present disclosure relates to a method for treating an ocular disease, comprising administering:

a) a HPTP-β inhibitor or a pharmaceutically acceptable salt thereof; and
b) bevacizumab.

In one aspect of the disclosure the methods comprise administering:

a) a HPTP-β inhibitor or a pharmaceutically acceptable salt thereof as disclosed herein; and
b) bevacizumab.

In another aspect the methods comprise administering:
a) a HPTP-β inhibitor having the formula:

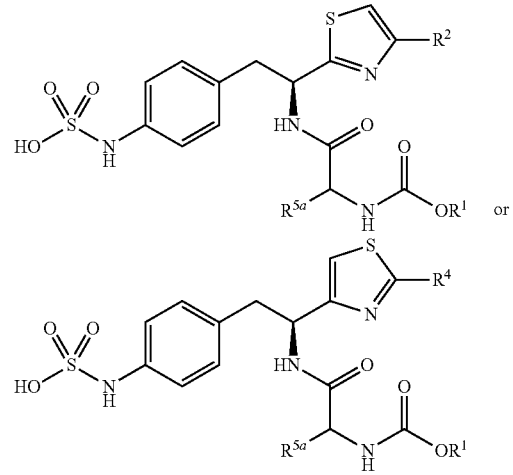

wherein $R^2$ and $R^4$ are chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted phenyl; or
iv) substituted or unsubstituted thiophenyl;
$R^1$ is $C_1$-$C_6$ linear, $C_3$-$C_6$ branched, or $C_3$-$C_6$ cyclic alkyl;
$R^{58}$ is chosen from:
i) hydrogen;
ii) $C_1$-$C_6$ linear, $C_3$-$C_6$ branched, or $C_3$-$C_6$ cyclic alkyl; or
iii) benzyl; or
a pharmaceutically acceptable salt thereof; and
b) bevacizumab.

A non-limiting embodiment of this aspect relates to methods comprising administering:
a) a HPTP-β inhibitor having the formula:

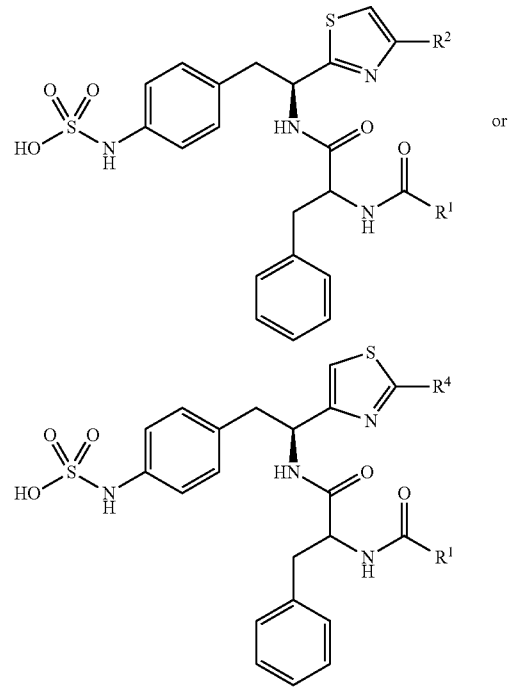

wherein $R^2$ and $R^4$ are chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted phenyl; or
iv) substituted or unsubstituted thiophenyl;

$R^1$ is $C_1$-$C_6$ linear, $C_3$-$C_6$ branched, or $C_3$-$C_6$ cyclic alkyl; or a pharmaceutically acceptable salt; and
b) bevacizumab.

The compounds can be administered in any order convenient to the user or to the subject receiving treatment. In one non-limiting example of the disclosed methods 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof is administered first followed by administration of bevacizumab. In another iteration of this embodiment bevacizumab is administered first followed by administration of the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof. The time period between dosing/administration of the first component of treatment can be any time period convenient to the formulator or subject receiving treatment. For example, the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof can be administered minutes, hours, days or weeks prior to the administration of bevacizumab or more than one dosage of the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof can be given to establish a therapeutic amount in the subject being treated.

In another iteration, the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof and bevacizumab can be given in alternating administrations. For example, the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof can be administered then after a time desired by the administrator bevacizumab is administered.

In a further iteration, the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof are administered daily in one or more doses and the ramibizumab is administered according to a separate schedule. For example, in addition to daily dosing of the 4-{(S)-2-[(S)-2-methoxycarbonylamino)-3-phenylpropanamido]-2-[2-(thiophen-2-yl)thiazol-4-yl]ethyl}phenylsulfamic acid s, bevacizumab can be administered once a month, once every 2 months, once every 3 months, once every 4 months, once every 6 months, etc.

In another non-limiting example of the disclosed methods 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof is administered first followed by administration of bevacizumab. In another iteration of this embodiment bevacizumab is administered first followed by administration of the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof. The time period between dosing/administration of the first component of treatment can be any time period convenient to the formulator or subject receiving treatment. For example, the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof can be administered minutes, hours, days or weeks prior to the administration of bevacizumab or more than one dosage of the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof can be given to establish a therapeutic amount in the subject being treated.

In another iteration, the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof and bevacizumab can be given in alternating administrations. For example, the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof can be administered then after a time desired by the administrator bevacizumab is administered.

In a further iteration, the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof in one or more doses and the ramibizumab is administered according to a separate schedule. For example, in addition to daily dosing of the 4-{(S)-2-[(S)-2-methoxycarbonylamino)-3-phenylpropanamido]-2-(2-ethylthiazol-4-yl)ethyl}phenylsulfamic acid s, bevacizumab can be administered once a month, once every 2 months, once every 3 months, once every 4 months, once every 6 months, etc.

In a further non-limiting example of the disclosed methods 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof is administered first followed by administration of bevacizumab. In another iteration of this embodiment bevacizumab is administered first followed by administration of the 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof. The time period between dosing/administration of the first component of treatment can be any time period convenient to the formulator or subject receiving treatment. For example, the 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof can be administered minutes, hours, days or weeks prior to the administration of bevacizumab or more than one dosage of the 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof can be given to establish a therapeutic amount in the subject being treated.

In another iteration, the 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof and bevacizumab can be given in alternating administrations. For example, the 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof can be administered then after a time desired by the administrator bevacizumab is administered.

In a further iteration, the 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof are administered daily in one or more doses and the ramibizumab is administered according to a separate schedule. For example, in addition to daily dosing of 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof, bevacizumab can be administered once a month, once every 2 months, once every 3 months, once every 4 months, once every 6 months, etc.

The dosage for bevacizumab can be in any amount necessary. In one embodiment, bevacizumab is administered in an amount from about 0.1 mg to about 5 mg. In a further embodiment, bevacizumab is administered in an amount from about 0.1 mg to about 3 mg. In another embodiment, bevacizumab is administered in an amount from about 0.5 mg to about 3 mg. In a still further embodiment, bevacizumab is administered in an amount from about 0.5 mg to about 2 mg. In one non-limiting example, bevacizumab is administered in an amount of 1.2 mg. The amount of bevacizumab administered per treatment can be in any amount, for example, about 0.5 mg, about 0.51 mg, about 0.52 mg, about 0.53 mg, about 0.54 mg, about 0.55 mg, about 0.56 mg, about 0.57, mg, about 0.58 mg, about 0.59 mg, about 0.6 mg, about 0.61 mg, about 0.62 mg, about 0.63 mg, about 0.64 mg, about 0.65 mg, about 0.66 mg, about 0.67, mg, about 0.68 mg, about 0.69 mg, about 0.7 mg, about 0.71 mg, about 0.72 mg, about 0.73 mg, about 0.74 mg, about 0.75 mg, about 0.76 mg, about 0.77, mg, about 0.78 mg, about 0.79 mg, about 0.8 mg, about 0.81 mg, about 0.82 mg, about 0.83 mg, about 0.84 mg, about 0.85 mg, about 0.86 mg, about 0.87, mg, about 0.88 mg, about 0.89 mg, about 0.9 mg, about 0.91 mg, about 0.92 mg, about 0.93 mg, about 0.94 mg, about 0.95 mg, about 0.96 mg, about 0.97, mg, about 0.98 mg, about 0.99 mg, about 1 mg, about 1.01 mg, about 1.02 mg, about 1.03 mg, about 1.04 mg, about 1.05 mg, about 1.06 mg, about 1.07, mg, about 1.08 mg, about 1.09 mg, 1.1 mg, about 1.11 mg, about 1.12 mg, about 1.13 mg, about 1.14 mg, about 1.15 mg, about 1.16 mg, about 1.17, mg, about 1.18 mg, about 1.19 mg, about 1.2 mg, about 1.21 mg, about 1.22 mg, about 1.23 mg, about 1.24 mg, about 1.25 mg, about 1.26 mg, about 1.27, mg, about 1.28 mg, about 1.29 mg, about 1.3 mg, about 1.31 mg, about 1.32 mg, about 1.33 mg, about 1.34 mg, about 1.35 mg, about 1.36 mg, about 1.37, mg, about 1.38 mg, about 1.39 mg, about 1.4 mg, about 1.41 mg, about 1.42 mg, about 1.43 mg, about 1.44 mg, about 1.45 mg, about 1.46 mg, about 1.47, mg, about 1.48 mg, about 1.49 mg, about 1.5 mg, about 1.51 mg, about 1.52 mg, about 1.53 mg, about 1.54 mg, about 1.55 mg, about 1.56 mg, about 1.57, mg, about 1.58 mg, about 1.59 mg, or about 1.6 mg.

In another embodiment, the present disclosure relates to a method for treating an ocular disease, comprising administering:
  a) a HPTP-β inhibitor or a pharmaceutically acceptable salt thereof; and
  b) aflibercept.

In one aspect of the disclosure the methods comprise administering:
  a) a HPTP-β inhibitor or a pharmaceutically acceptable salt thereof as disclosed herein; and
  b) aflibercept.

In another aspect the methods comprise administering:
a) a HPTP-β inhibitor having the formula:

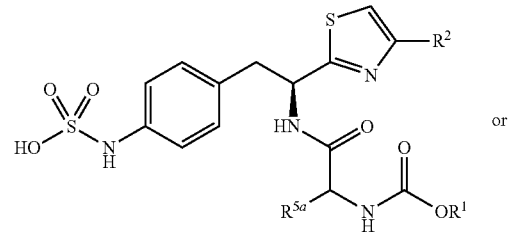

or

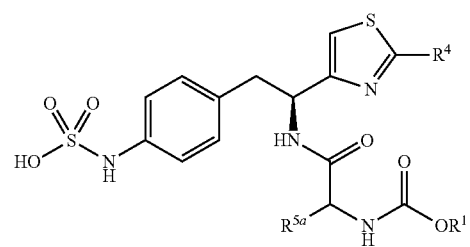

wherein $R^2$ and $R^4$ are chosen from:
  i) hydrogen;
  ii) substituted or unsubstituted $C_1$-$C_6$ linear, $C_3$-$C_6$ branched, or $C_3$-$C_6$ cyclic alkyl;
  iii) substituted or unsubstituted phenyl; or
  iv) substituted or unsubstituted thiophenyl;
$R^1$ is $C_1$-$C_6$ linear, $C_3$-$C_6$ branched, or $C_3$-$C_6$ cyclic alkyl;
$R^{5a}$ is chosen from:
  i) hydrogen;
  ii) $C_1$-$C_6$ linear, $C_3$-$C_6$ branched, or $C_3$-$C_6$ cyclic alkyl; or
  iii) benzyl; or
a pharmaceutically acceptable salt thereof; and
b) aflibercept.

A non-limiting embodiment of this aspect relates to methods comprising administering:
a) a HPTP-β inhibitor having the formula:

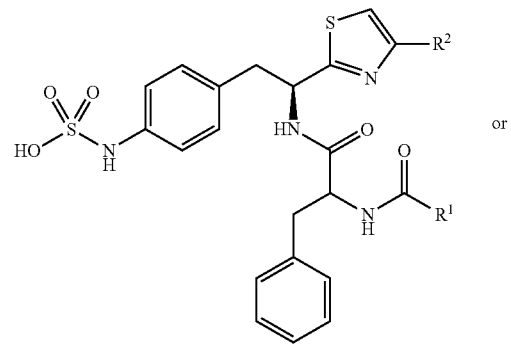

-continued wherein $R^2$ and $R^4$ are chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted phenyl; or
iv) substituted or unsubstituted thiophenyl;
$R^1$ is $C_1$-$C_6$ linear, $C_3$-$C_6$ branched, or $C_3$-$C_6$ cyclic alkyl; or
a pharmaceutically acceptable salt; and
b) aflibercept.

The compounds can be administered in any order convenient to the user or to the subject receiving treatment. In one non-limiting example of the disclosed methods 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof is administered first followed by administration of aflibercept. In another iteration of this embodiment aflibercept is administered first followed by administration of the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof. The time period between dosing/administration of the first component of treatment can be any time period convenient to the formulator or subject receiving treatment. For example, the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof can be administered minutes, hours, days or weeks prior to the administration of aflibercept or more than one dosage of the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof can be given to establish a therapeutic amount in the subject being treated.

In another iteration, the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof and aflibercept can be given in alternating administrations. For example, the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof can be administered then after a time desired by the administrator aflibercept is administered.

In a further iteration, the 4-{(S)-2-[(S)-2-methoxycarbonylamino)-3-phenylpropanamido]-2-[2-(thiophen-2-yl)thiazol-4-yl]ethyl}phenylsulfamic acid or a pharmaceutically acceptable salt thereof are administered daily in one or more doses and the ramibizumab is administered according to a separate schedule. For example, in addition to daily dosing of the 4-{(S)-2-[(S)-2-methoxycarbonylamino)-3-phenylpropanamido]-2-[2-(thiophen-2-yl)thiazol-4-yl]ethyl}phenylsulfamic acid s, aflibercept can be administered once a month, once every 2 months, once every 3 months, once every 4 months, once every 6 months, etc.

In another non-limiting example of the disclosed methods 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof is administered first followed by administration of aflibercept. In another iteration of this embodiment aflibercept is administered first followed by administration of the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof. The time period between dosing/administration of the first component of treatment can be any time period convenient to the formulator or subject receiving treatment. For example, the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof can be administered minutes, hours, days or weeks prior to the administration of aflibercept or more than one dosage of the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof can be given to establish a therapeutic amount in the subject being treated.

In another iteration, the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof and aflibercept can be given in alternating administrations. For example, the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof can be administered then after a time desired by the administrator aflibercept is administered.

In a further iteration, the 4-{(S)-2-[(S)-2-methoxycarbonylamino)-3-phenylpropanamido]-2-(2-ethylthiazol-4-yl)ethyl}phenylsulfamic acid or a pharmaceutically acceptable salt thereof are administered daily in one or more doses and the ramibizumab is administered according to a separate schedule. For example, in addition to daily dosing of the 4-{(S)-2-[(S)-2-methoxycarbonylamino)-3-phenylpropanamido]-2-(2-ethylthiazol-4-yl)ethyl}phenylsulfamic acid s, aflibercept can be administered once a month, once every 2 months, once every 3 months, once every 4 months, once every 6 months, etc.

In a further non-limiting example of the disclosed methods 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof is administered first followed by administration of aflibercept. In another iteration of this embodiment aflibercept is administered first followed by administration of the 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof. The time period between dosing/administration of the first component of treatment can be any time period convenient to the formulator or subject receiving treatment. For example, the 4-j{(S)-2-[(S)-2-methoxycarbonylamino)-3-phenylpropanamido]-2-(4-ethylthiazol-2-yl)ethyl}phenylsulfamic acid or a pharmaceutically acceptable salt thereof can be administered minutes, hours, days or weeks prior to the administration of aflibercept or more than one dosage of the 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof can be given to establish a therapeutic amount in the subject being treated.

In another iteration, the 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof and aflibercept can be given in alternating administrations. For example, the 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof can be administered then after a time desired by the administrator aflibercept is administered.

In a further iteration, the 4-{(S)-2-[(S)-2-methoxycarbonylamino)-3-phenylpropanamido]-2-(4-ethylthiazol-2-yl)ethyl}phenylsulfamic acid or a pharmaceutically acceptable salt thereof are administered daily in one or more doses and the ramibizumab is administered according to a separate schedule. For example, in addition to daily dosing of the 4-{(S)-2-[(S)-2-methoxycarbonylamino)-3-phenylpropanamido]-2-(4-ethylthiazol-2-yl)ethyl}phenylsulfamic acid s, aflibercept can be administered once a month, once every 2 months, once every 3 months, once every 4 months, once every 6 months, etc.

The dosage for aflibercept can be in any amount necessary. In one embodiment, aflibercept is administered in an amount from about 0.05 mg to about 5 mg. In a further embodiment, aflibercept is administered in an amount from about 0.1 mg to about 3 mg. In another embodiment, aflibercept is administered in an amount from about 0.5 mg to about 2.5 mg. In a still further embodiment, aflibercept is administered in an amount from about 0.5 mg to about 2 mg. The amount of aflibercept administered per treatment can be in any amount, for example, about 0.5 mg, about 0.51 mg, about 0.52 mg, about 0.53 mg, about 0.54 mg, about 0.55 mg, about 0.56 mg, about 0.57, mg, about 0.58 mg, about 0.59 mg, about 0.6 mg, about 0.61 mg, about 0.62 mg, about 0.63 mg, about 0.64 mg, about 0.65 mg, about 0.66 mg, about 0.67, mg, about 0.68 mg, about 0.69 mg, about 0.7 mg, about 0.71 mg, about 0.72 mg, about 0.73 mg, about 0.74 mg, about 0.75 mg, about 0.76 mg, about 0.77, mg, about 0.78 mg, about 0.79 mg, about 0.8 mg, about 0.81 mg, about 0.82 mg, about 0.83 mg, about 0.84 mg, about 0.85 mg, about 0.86 mg, about 0.87, mg, about 0.88 mg, about 0.89 mg, about 0.9 mg, about 0.91 mg, about 0.92 mg, about 0.93 mg, about 0.94 mg, about 0.95 mg, about 0.96 mg, about 0.97, mg, about 0.98 mg, about 0.99 mg, about 1 mg, about 1.01 mg, about 1.02 mg, about 1.03 mg, about 1.04 mg, about 1.05 mg, about 1.06 mg, about 1.07, mg, about 1.08 mg, about 1.09 mg, 1.1 mg, about 1.11 mg, about 1.12 mg, about 1.13 mg, about 1.14 mg, about 1.15 mg, about 1.16 mg, about 1.17, mg, about 1.18 mg, about 1.19 mg, about 1.2 mg, about 1.21 mg, about 1.22 mg, about 1.23 mg, about 1.24 mg, about 1.25 mg, about 1.26 mg, about 1.27, mg, about 1.28 mg, about 1.29 mg, about 1.3 mg, about 1.31 mg, about 1.32 mg, about 1.33 mg, about 1.34 mg, about 1.35 mg, about 1.36 mg, about 1.37, mg, about 1.38 mg, about 1.39 mg, about 1.4 mg, about 1.41 mg, about 1.42 mg, about 1.43 mg, about 1.44 mg, about 1.45 mg, about 1.46 mg, about 1.47, mg, about 1.48 mg, about 1.49 mg, about 1.5 mg, about 1.51 mg, about 1.52 mg, about 1.53 mg, about 1.54 mg, about 1.55 mg, about 1.56 mg, about 1.57, mg, about 1.58 mg, about 1.59 mg, about 1.6 mg, about 1.61 mg, about 1.62 mg, about 1.63 mg, about 1.64 mg, about 1.65 mg, about 1.66 mg, about 1.67, mg, about 1.68 mg, about 1.69 mg, about 1.7 mg, about 1.71 mg, about 1.72 mg, about 1.73 mg, about 1.74 mg, about 1.75 mg, about 1.76 mg, about 1.77, mg, about 1.78 mg, about 1.79 mg, about 1.8 mg, about 1.81 mg, about 1.82 mg, about 1.83 mg, about 1.84 mg, about 1.85 mg, about 1.86 mg, about 1.87, mg, about 1.88 mg, about 1.89 mg, about 1.9 mg, about 1.91 mg, about 1.92 mg, about 1.93 mg, about 1.94 mg, about 1.95 mg, about 1.96 mg, about 1.97, mg, about 1.98 mg, about 1.99 mg, or about 2 mg.

The HPTP-β inhibitors or a pharmaceutically acceptable salt thereof can be administered in any amount necessary or convenient. For example, the compound can be administered in an amount from about 0.1 mg to about 100 mg per dose as described herein above in the disclosure relating to the compositions.

The HPTP-β inhibitors or a pharmaceutically acceptable salt thereof can be administered at any interval desired. For example, the compound can be administered once a week, 2 times a week, 3 times a week, 4 times a week, 6 times a week, 6 times a week, 7 times a week, 8 times a week, 9 times a week or 10 times a week. The interval between daily dosing can be any hourly interval, for example, every hour, every 2 hours, every 3 hours, every 4 hours, every 5 hours, every 6 hours, every 7 hours, every 8 hours, every 9 hours, every 10 hours, every 11 hours, and every 12 hours. The administration of the compound can have irregular dosing schedules to accommodate either the person administering the compound or the subject receiving the compound. As such, the compound can be administered once a day, twice a day, three times a day, and the like.

In addition, the amount administered can be of the same amount in each dose or the dosage can vary. For example, a first amount dosed in the morning and a second amount administered in the evening. The dosage for administration can be varied depending upon the schedule of the anti-VEGF administration.

The HPTP-β inhibitors or a pharmaceutically acceptable salt thereof can be administered in combination with any anti-VEGF agent in any combination, for example, at the beginning of the treatment, at any time during the treatment or at any time after treatment with the anti-VEGF agent has concluded. In addition, the dosage of the HPTP-β inhibitors or a pharmaceutically acceptable salt thereof can be adjusted during treatment. Also, the amount of anti-VEGF agent can be adjusted during treatment.

Further non-limiting examples of anti-VEGF agents includes dexamethasone, fluocinolone and triamcinolone. In addition, the disclosed methods can include implants which deliver an anti-VEGF agent. For example, HPTP-β inhibitors or a pharmaceutically acceptable salt thereof can be co-administered either before, during or after an implant is provided to a subject suffering from a disease or condition described herein. For example, Ozurdex™ is an intraviteal implant which provides a supply of dexamethasone to a subject, Retisert™ and Iluvien™ are intraviteal implants which provides a supply of fluocinolone.

In one aspect, anti-VEGF treatments if typically given monthly, can have the frequency of treatment extended, for example, to once every 3 months, once every 6 months or yearly wherein the HPTP-β inhibitor or a pharmaceutically acceptable salt thereof is administered at any frequency between treatments.

Also disclosed herein are methods for decreasing the Central Foveal Thickness (CFT) in a patient having a disease or condition as disclosed herein. The method comprises administering to an eye:
 a) a HPTP-β inhibitor or a pharmaceutically acceptable salt thereof; and
 b) one or more anti-VEGF agents;
wherein the administration of the HPTP-β inhibitor or a pharmaceutically acceptable salt thereof and the anti-VEGF agent can be conducted in any manner desired by the administrator, for example, as further described herein.

A further aspect relates to a method comprising administering to the eye:
a) a disclosed HPTP-β inhibitor or a pharmaceutically acceptable salt thereof; and
b) one or more anti-VEGF agents;
wherein the administration of the HPTP-β inhibitor or a pharmaceutically acceptable salt thereof and the anti-VEGF agent can be conducted in any manner desired by the administrator, for example, as further described herein.

In one aspect the decrease in Central Foveal Thickness is from about 50 μm to about 1000 μm. In one embodiment, the decrease in Central Foveal Thickness is from about 50 μm to about 750 μm. In another embodiment, the decrease in Central Foveal Thickness is from about 200 μm to about 1000 μm. In a further embodiment, the decrease in Central Foveal Thickness is from about 150 μm to about 500 μm. In a still further embodiment, the decrease in Central Foveal Thickness is from about 50 μm to about 500 μm. In a yet another embodiment, the decrease in Central Foveal Thickness is from about 250 μm to about 650 μm. In a yet still further embodiment, the decrease in Central Foveal Thickness is from about 200 μm to about 500 μm. In another still further embodiment, the decrease in Central Foveal Thickness is from about 400 μm to about 700 μm.

Further disclosed herein are methods for increasing the visual acuity of a subject having a disease or condition as disclosed herein.

Visual Acuity

Visual acuity (VA) is acuteness or clearness of vision, which is dependent on the sharpness of the retinal focus within the eye and the sensitivity of the interpretative faculty of the brain. Visual acuity is a measure of the spatial resolution of the visual processing system. VA is tested by requiring the person whose vision is being tested to identify characters typically numbers or letters on a chart from a set distance. Chart characters are represented as black symbols against a white background. The distance between the person's eyes and the testing chart is set at a sufficient distance to approximate infinity in the way the lens attempts to focus. Twenty feet, or six meters, is essentially infinity from an optical perspective. In the present disclosure, an improvement in visual acuity was assessed by an increase in the number of letters read from the chart.

Visual Acuity Testing.

One non-limiting test for measuring Visual Acuity is the use of the ESV-3000 ETDRS testing device (see, U.S. Pat. No. 5,078,486) self-calibrated test lighting. The ESV-3000 device incorporates highly advanced LED light source technology. The auto-calibration circuitry constantly monitors the LED light source and calibrates the test luminance to 85 cd/m2 or 3 cd/m2.

Although designed for clinical trials where large-format ETDRS testing (up to 20/200) is performed at 4 meters, the device can be used in a non-research setting, i.e., hospital or clinic where ocular disease monitoring is conducted. To properly evaluate ETDRS, the test should be conducted under standardized lighting conditions, for, example, photopic test level of 85 cd/m2. This light level has been recommended by the National Academy of Sciences and by the American National Standards Institute for ETDRS and contrast sensitivity vision testing. Scoring of visual acuity can be accomplished in any manner chosen by the monitor. After providing a baseline evaluation, the increase or decrease in the number of letters that can be identified by the test subject provides a measure of sight increase or decrease during treatment.

In one aspect, disclosed herein is a method for increasing visual acuity in a subject having a disease or condition of the eye as disclosed herein. This method comprises administering to a patient having a disease or condition of the eye:
a) a HPTP-β inhibitor or a pharmaceutically acceptable salt thereof; and
b) one or more anti-VEGF agents;

A further embodiment of this aspect relates to a method for increasing visual acuity in a subject, comprising administering to a patient having a disease or condition of the eye:
a) a disclosed HPTP-β inhibitor or a pharmaceutically acceptable salt thereof; and
b) one or more anti-VEGF agents;
wherein the administration of the HPTP-β inhibitor or a pharmaceutically acceptable salt thereof and the anti-VEGF agent can be conducted in any manner desired by the administrator, for example, as further described herein.

In some embodiments, the disclosure provides a method for increasing visual acuity, the method comprising administering to a subject in need thereof a compound disclosed herein.

In one embodiment, the method provides a method for increasing the number of letters recognizable by a treated eye form about 1 to about 30 letters. In another embodiment, the number of letters recognizable is increased from about 5 to about 25 letters. In a further embodiment, the number of letters recognizable is increased from about 5 to about 20 letters. In another further embodiment, the number of letters recognizable is increased from about 5 to about 15 letters. In a still further embodiment, the number of letters recognizable is increased from about 5 to about 10 letters. In a yet another embodiment, the number of letters recognizable is increased from about 10 to about 25 letters. In a yet still further embodiment, the number of letters recognizable is increased from about 15 to about 25 letters. In yet still another embodiment, the number of letters recognizable is increased from about 20 to about 25 letters. The increase in visual acuity can be about 1 letter, about 5 letters, about 10 letters, about 15 letters, about 20 letters, or about 25 letters.

EXAMPLE 35

Baseline Study for Determining the Effectiveness of the Disclosed Methods for Treating Ocular Diseases Described herein below is a study of four human subjects with visual acuity loss due to diabetic macular edema (central retinal thickness [CRT] of more than 325 microns and best corrected visual acuity less than 70 letters) that were treated with subcutaneous injections of 5 mg of the 4-{(S)-2-[(S)-2-methoxycarbonyl-amino)-3-phenylpropanamido]-2-[2-(thiophen-2-yl)thiazol-4-yl] ethyl}phenylsulfamic acid twice a day for 28 days. Improvement of visual acuity in these subjects was observed for a period of two months (days 28 through 84). At any time during the course of the study, investigators could administer additional therapy consisting of intravitreal injection of an anti-VEGF agent, for example, ranibizumab, bevacizumab and/or aflibercept, if considered by the investigator to be medically necessary. Retinal thickness as measured by ocular coherence tomography and best corrected visual acuity as measured by a standard vision test (ETDRS) were assessed at regular intervals during the 28 day active treatment phase and through the 2 month post-treatment observation phase, (Screening, Day 1 [baseline], Day 7, Day 14, Day 21, Day 28, Day 42, Day 56 and Day 84). The main efficacy outcomes for the study were change in CRT and visual acuity over time with treatment.

FIG. 1 depicts the results of two phase three studies to determine the effect of intravitreal injections of ranibizumab in patients with diabetic macular edema. In this study patients received intravitreal injections with either 0.3 mg (♦) or 0.5 mg (■) ranibizumab monthly, whereas the control group (▲) received placebo. As depicted in FIG. 1 the reduction in Central Foveal Thickness (CFT) for both the 0.3 mg and 0.5 mg cohorts were essentially identical. As shown in FIG. 1, the two groups receiving ranibizumab had a reduction in Central Foveal Thickness of approximately 120 to 160 µm from day 7 to 1 month after the first injection of ranibizumab.

Figure 2:
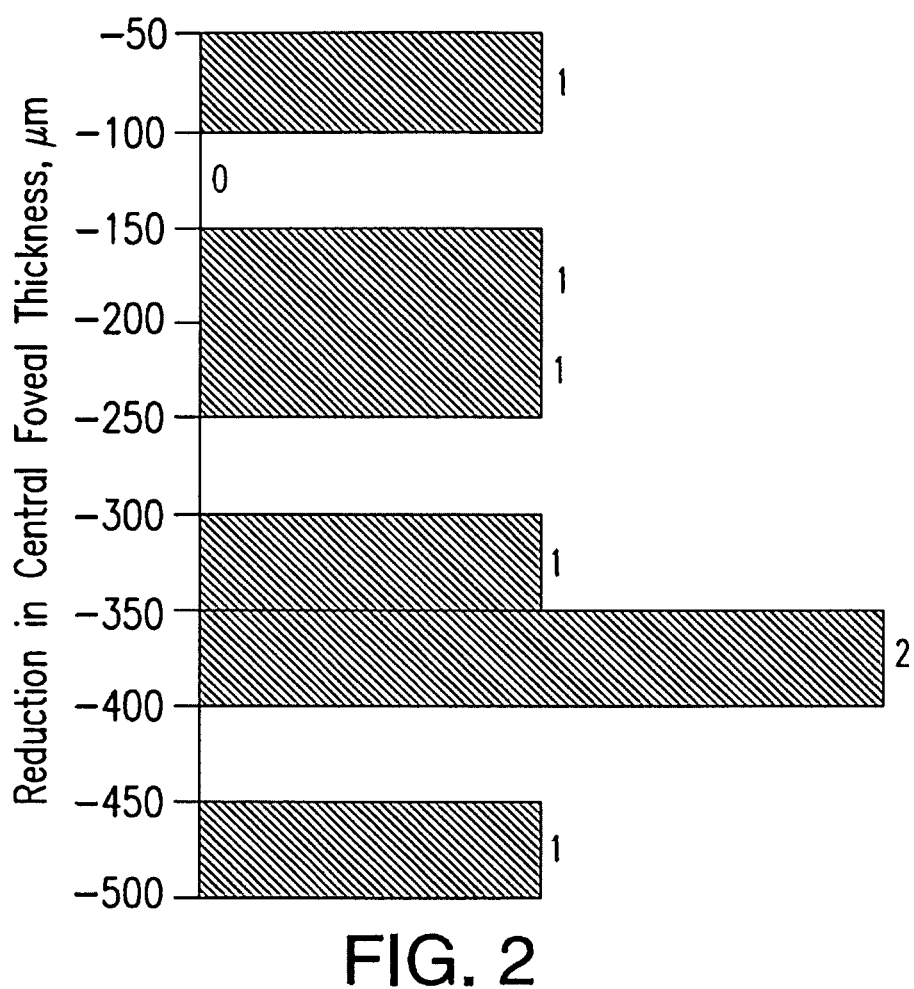
FIG. 2 depicts the results of a study wherein 4 patients received 5 mg of the 4-{(S)-2-[(S)-2-methoxycarbonylamino)-3-phenylpropanamido]-2-[2-(thiophen-2-yl)thiazol-4-yl]ethyl}phenylsulfamic acid subcutaneously twice daily for 28 days and subsequently were treated in one or both eyes (7 eyes total) with either ranibizumab (0.3 or 0.5 mg) or aflibercept (2 mg) by intravitreal injection at the discretion of the study investigator.

FIG. 2 depicts the results of a study wherein 4 patients received 5 mg of the 4-{(S)-2-[(S)-2-methoxycarbonylamino)-3-phenylpropanamido]-2-[2-(thiophen-2-yl)thiazol-4-yl]ethyl}phenylsulfamic acid subcutaneously twice daily for 28 days and subsequently were treated in one or both eyes (7 eyes total) with either ranibizumab (0.3 or 0.5 mg) or aflibercept (2 mg) by intravitreal injection at the discretion of the study investigator. FIG. 2 is read in this manner: 1 patient eye had a Central Foveal Reduction of between 50-100 µm, 1 patient eye had a Central Foveal Reduction of between 150-200 µm, 1 patient eye had a Central Foveal Reduction of between 200-250 µm, 1 patient eye had a Central Foveal Reduction of between 300-350 µm, 2 patient eyes had a Central Foveal Reduction of between 350-400 µm, and 1 patient eye had a Central Foveal Reduction of between 450-500 µm at 14-28 days post ranibizumab or aflibercept. The mean change in Central Foveal Thickness was −289 µm, approximately double the reduction seen after ranibizumab injection in the study in FIG. 1.

Figure 3:
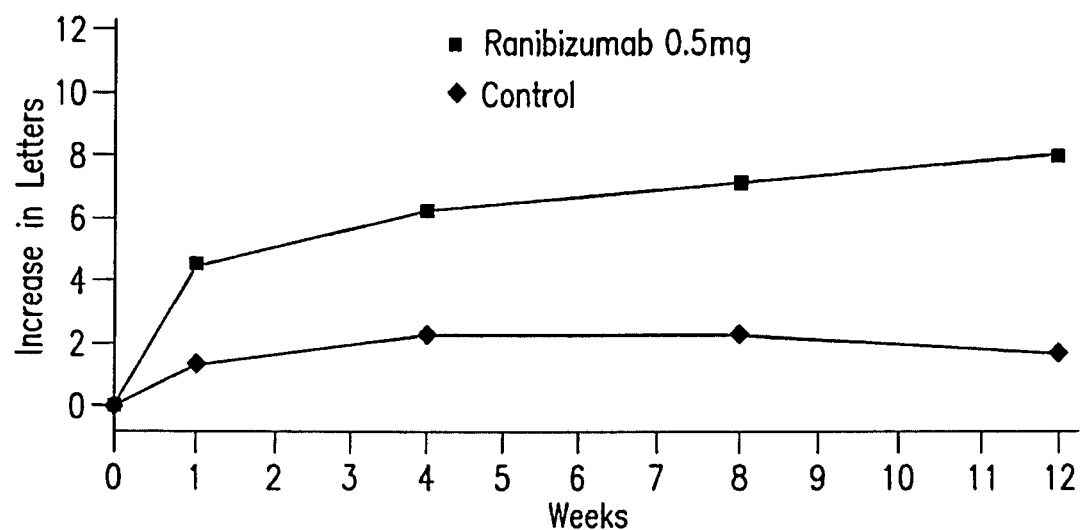
FIG. 3 depicts the results of phase three studies to determine the effect of intravitreal injections of ranibizumab in patients with diabetic macular edema.

FIG. 3 depicts the results of two phase three studies performed to determine the effect of intravitreal injections of ranibizumab in patients with diabetic macular edema. Results of these studies were used to determining the effectiveness of the disclosed methods for treating ocular diseases. The control group is represented by (♦). Patients receiving 0.5 mg of ranibizumab monthly via ocular injection are represented by (■). As shown in FIG. 3, the group receiving ranibizumab had an increase in visual acuity of between approximately 4 to 6 letters from day 7 to 1 month after the first injection of ranibizumab.

Figure 4:
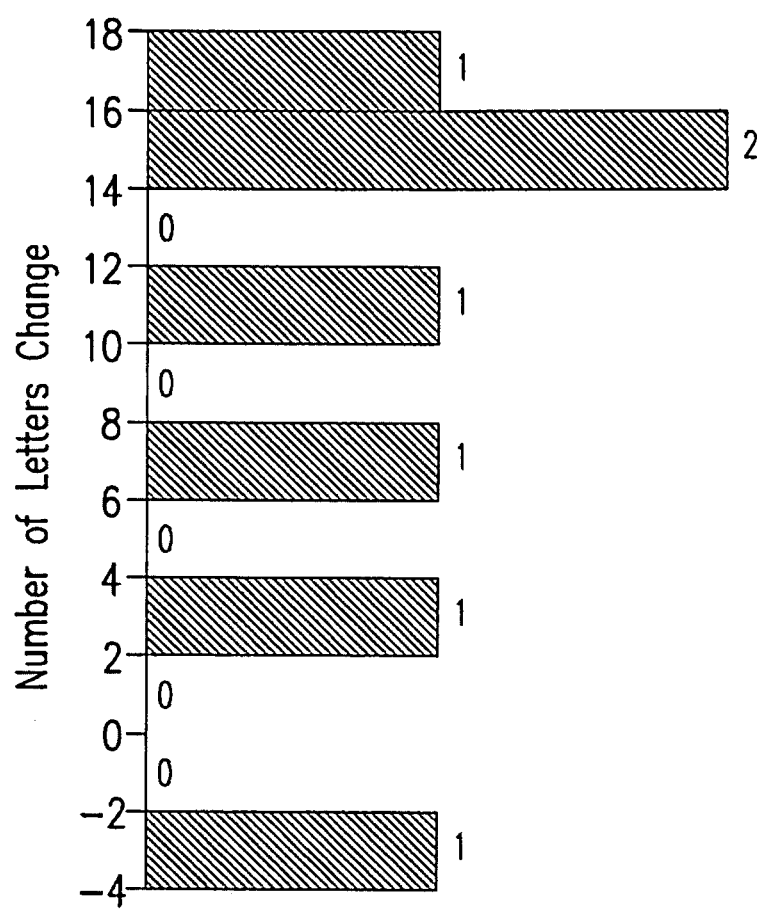
FIG. 4 depicts the increased visual acuity of a study wherein 4 patients received 5 mg of the 4-{(S)-2-[(S)-2-methoxycarbonylamino)-3-phenylpropanamido]-2-[2-(thiophen-2-yl)thiazol-4-yl]ethyl}phenylsulfamic acid subcutaneously twice daily for 28 days and subsequently were treated with either ranibizumab (0.3 or 0.5 mg) or aflibercept (2 mg) by intravitreal injection.

FIG. 4 depicts the increased visual acuity of a study wherein 4 patients received 5 mg of the 4-{(S)-2-[(S)-2-methoxycarbonylamino)-3-phenylpropanamido]-2-[2-(thiophen-2-yl)thiazol-4-yl]ethyl}phenylsulfamic acid subcutaneously twice daily for 28 days and subsequently were treated with either ranibizumab (0.3 or 0.5 mg) or aflibercept (2 mg) by intravitreal injection at the discretion of the study investigator. FIG. 4 is read in this manner: 1 patient eye had an increase of from 16 to 18 letters improvement, 2 patient eyes had an increase of from 14 to 16 letters improvement, 1 patient eye had an increase of from 10 to 12 letters improvement, 1 patient eye had an increase of from 6 to 8 letters improvement, 1 patient eye had an increase of from 2 to 4 letters improvement, and 1 patient eye had a decrease of from 2 to 4 letters at 14-28 days post ranibizumab or aflibercept. The mean change in Visual Acuity was 9 letters, approximately 3 to 5 letters more improvement than seen in the benchmark study of ranibizumab alone depicted in FIG. 3.

Figure 5:
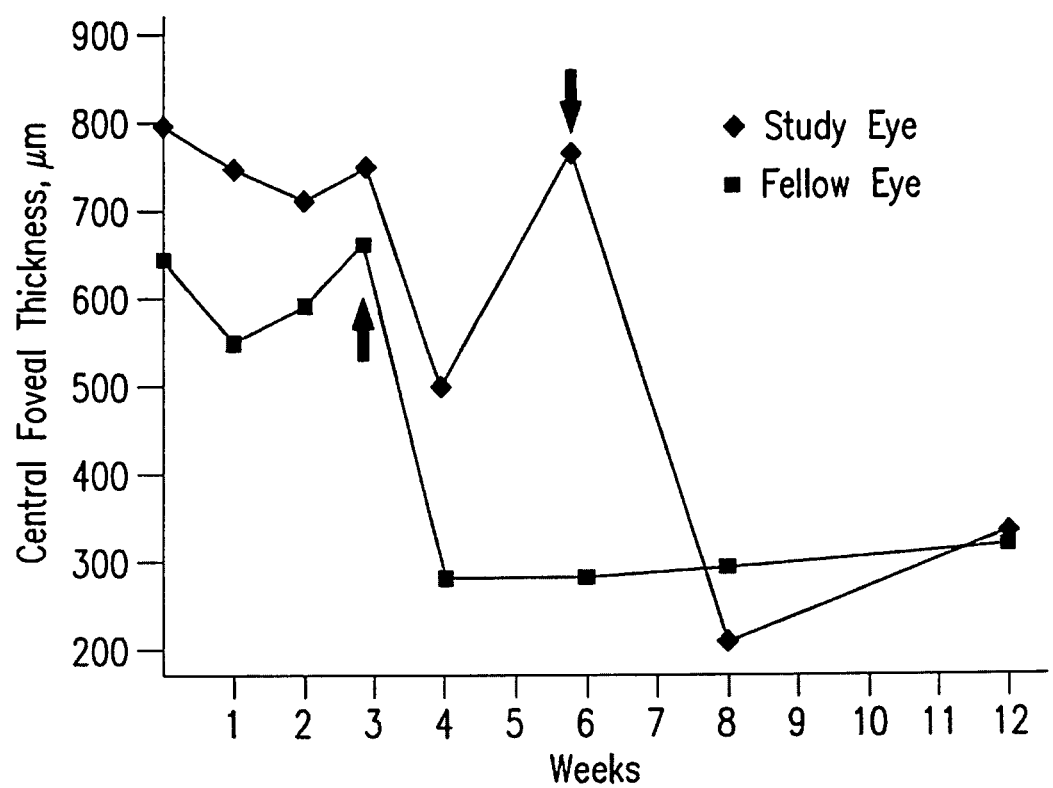
FIG. 5 graphs changes in central foveal thickness over time in an eye treated with a drug/antibody combination.

FIG. 5 represents the results of a single patient. The eye having the greater Central Foveal Thickness was chosen as the Study Eye. The patient from day one was given 5 mg of the 4-{(S)-2-[(S)-2-methoxycarbonylamino)-3-phenylpropanamido]-2-[2-(thiophen-2-yl)thiazol-4-yl]ethyl}phenylsulfamic acid subcutaneously twice daily. At week 3 (21 days, indicated by arrow) the fellow eye was treated with 0.5 mg of ranibizumab by injection. At week 6 (42 days, indicated by arrow) the treated eye was treated with 0.5 mg of ranibizumab. As seen in FIG. 5, the Central Foveal Thickness of the fellow eye fell significantly (350 µm) by week 4 (28 days). As a result, there was a pronounced reduction in CFT in the study eye from day 21 to day 28 (approximately 250 □m). As seen in FIG. 5, by the next monitoring point, week 6, the effects of the systemically received ranibizumab were no longer present and the CFT returned to approximately 775 µm. At week 6, the study eye was treated with an intravitreal injection of 0.5 mg of ranibizumab. As depicted in FIG. 5, by week 8, there was an overall reduction in CFT of approximately 500 µm, wherein the CFT of the subject eye was approximately 225 µm. Compared to the study depicted in FIG. 1 wherein the average change in CFT at one month after ranibizumab injection was approximately 160 mm, the combination disclosed method provided substantially greater reductions at 2-4 weeks following ranibizumab injection.

Figure 6:
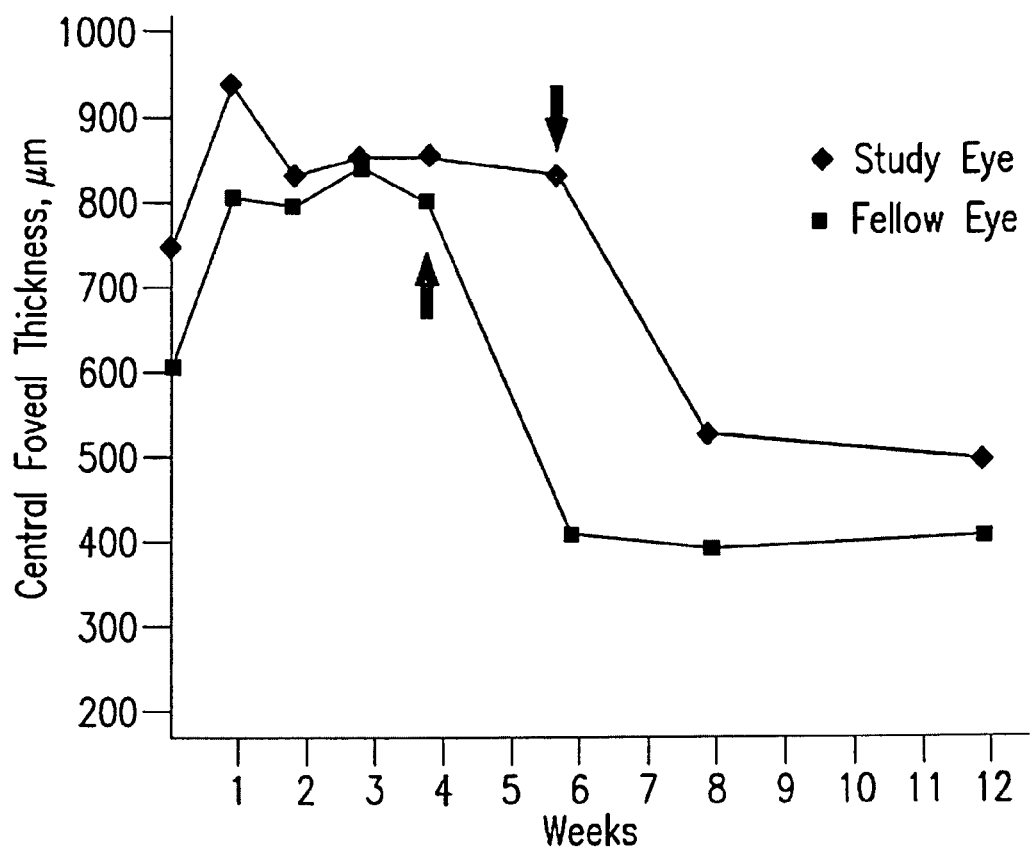
FIG. 6 graphs changes in central foveal thickness over time in an eye treated with a drug/antibody combination.

FIG. 6 represents the results of a single patient. The eye having the greater Central Foveal Thickness was chosen as the Study Eye. The patient from day one was given 5 mg of the 4-{(S)-2-[(S)-2-methoxycarbonylamino)-3-phenylpropanamido]-2-[2-(thiophen-2-yl)thiazol-4-yl]ethyl}phenylsulfamic acid subcutaneously twice daily. At week 4 (28 days, indicated by arrow) the fellow eye was rescued with 2 mg of aflibercept. After rescue, the Fellow eye had a CFT reduction of approximately 400 µm. At week 6 (42 days, indicated by arrow) the study eye was rescued with 2 mg of aflibercept. After rescue, the Study eye had a CFT reduction of approximately 300 µm. Unlike the results depicted for the ranibizumab protocol, there was no evidence of systemically delivered aflibercept to the Fellow Eye. From onset of the study, there was a reduction of CFT in the study eye and non-treated eye of approximately 300 µm and 280 µm respectively.

Figure 7:
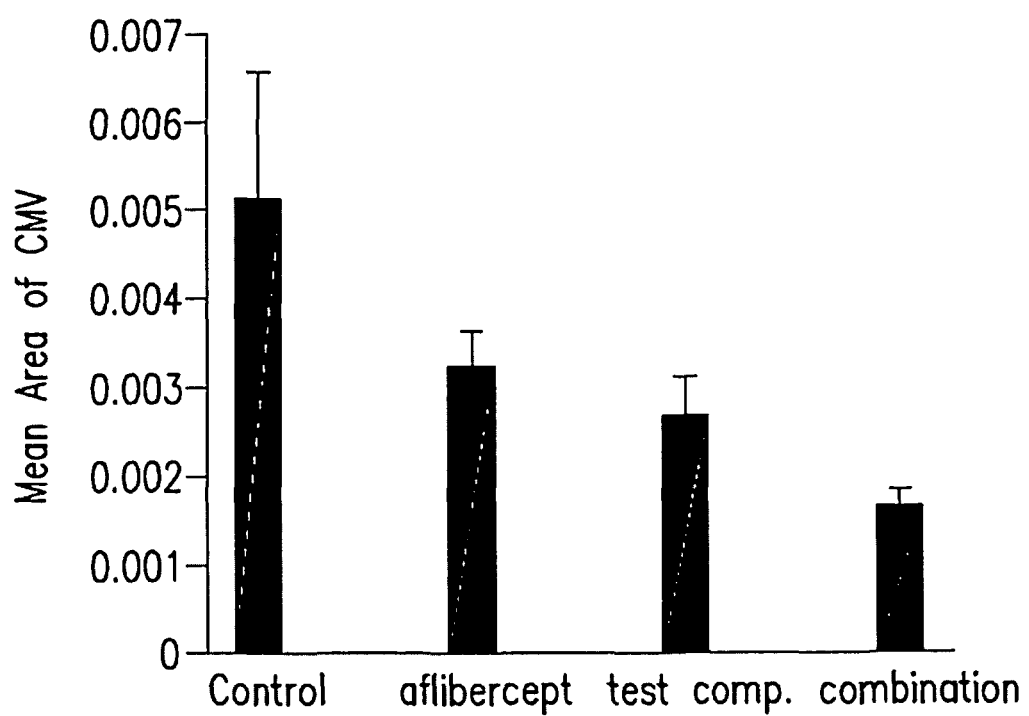
FIG. 7 is a graphic representation of in vivo experiments performed in 6 week old C57BL/6 mice.

FIG. 7 graphically represents the results of a choroidal neovascularization murine test involving an active control, aflibercept (Eylea™), the 4-{(S)-2-[(S)-2-methoxycarbonylamino)-3-phenylpropanamido]-2-[2-(thiophen-2-yl)thiazol-4-yl]ethyl}phenylsulfamic acid and a combination of aflibercept and the 4-{(S)-2-[(S)-2-methoxycarbonylamino)-3-phenylpropanamido]-2-[2-(thiophen-2-yl)thiazol-4-yl]ethyl}phenylsulfamic acid. Rupture of Burch's membrane in three locations of the eye was induced by standard laser methods (see, Tobe T et al., "Targeted Disruption of the FGF2 Gene Does Not Prevent Choroidal Neovascularization in a Murine Model," Am. J. Pathology, Vol. 153, No. 5, (1998)). Control animals were given intraocular injections of phosphate buffered saline (PBS), animals treated with aflibercept received one intraocular 40 µg of the drug on the day of laser treatment. The mice were then treated with either the 4-{(S)-2-[(S)-2-methoxycarbonylamino)-3-phenylpropanamido]-2-[2-(thiophen-2-yl)thiazol-4-yl]ethyl}phenylsulfamic acid at 20 mg/kg by subcutaneous injections twice daily or PBS injections twice daily. This yielded four groups of mice; a negative control group treated with intraocular and subcutaneous PBS, a monotherapy group treated with intraocular aflibercept and subcutaneous PBS, a monotherapy group treated with intraocular PBS and subcutaneous injections of the 4-{(S)-2-[(S)-2- methoxycarbonylamino)-3-phenylpropanamido]-2-[2-(thiophen-2-yl)thiazol-4-yl]ethyl}phenylsulfamic acid and a combination therapy group receiving one intraocular injection of 40 μg of the drug on the day of laser treatment and 20 mg/kg subcutaneous injections twice daily.

Figure 8A:
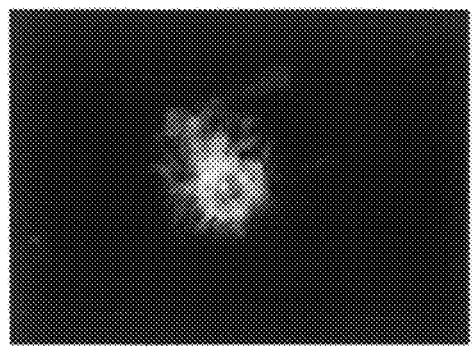
FIG. 8A illustrates the extent of choroidal neovascularization evident in a control sample stained with FITC-labeled *Griffonia simplicifolia* (GSA) of the experiment of FIG. 7.
Figure 8B:
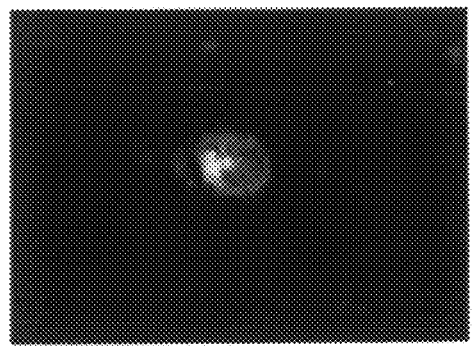
FIG. 8B represents the extent of neovascularization in the choroidal tissue of animals treated with aflibercept, stained with FITC-labeled *Griffonia simplicifolia* (GSA).
Figure 8C:
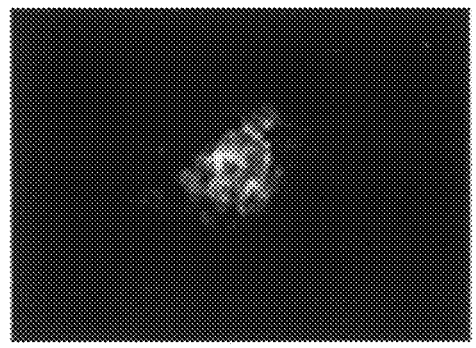
FIG. 8C represents the extent of neovascularization in tissue treated with a Tie-2 signaling enhancer, tissue stained with FITC-labeled *Griffonia simplicifolia* (GSA).
Figure 8D:
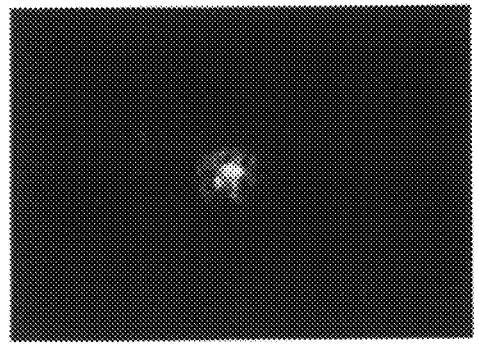
FIG. 8D represents the extent of neovascularization present in tissue receiving a combined therapy of aflibercept and the 4-{(S)-2-[(S)-2-methoxycarbonylamino)-3-phenylpropanamido]-2-[2-(thiophen-2-yl)thiazol-4-yl]ethyl}phenylsulfamic acid, stained with FITC-labeled *Griffonia simplicifolia* (GSA).

FIG. 8A-D depicts the flat mounts of excised choroidal tissue stained with FITC-labeled *Griffonia simplicifolia* (GSA). The extent of choroidal neovascular is evident in the control sample FIG. 8A. FIG. 8B represents the extent of neovascularization in the choroidal tissue of animals treated with aflibercept, FIG. 8C represents animals treated with the disclosed Tie-2 signaling enhancer and FIG. 8D represents the extent of neovascularization present in animals having a combined therapy of aflibercept and the 4-{(S)-2-[(S)-2-methoxycarbonylamino)-3-phenylpropanamido]-2-[2-(thiophen-2-yl)thiazol-4-yl]ethyl}phenylsulfamic acid.

EXAMPLE 36

Solubility of Compounds of the Disclosure

The room temperature aqueous solubility (mg/mL) of the a compound (4-{(S)-2-[(S)-2-methoxycarbonylamino)-3-phenylpropanamido]-2-[2-(thiophen-2-yl)thiazol-4-yl]ethyl}phenylsulfamic acid) in water, HPβCD, Poloxamer 407, and sulfobutylether-β-cyclodextrin, is provided in TABLE XXVII. Solubility in saline for the test compound is reduced presumably due to the common ion effect. All the solubilizing agents tested provided good improvements in aqueous solubility of the test compound.

TABLE XXVII

|  | Solubility |
| --- | --- |
| % HPβCD | |
| 0 | 27 |
| 10 | 45 |
| 20 | 57 |
| 30 | 72 |
| % SBE-β-CD | |
| 15 | 44 |
| % Poloxamer 407 | |
| 20 | 44 |

The solubility (mg/mL) of the test compound in mixtures of HPβCD and PEG400 is illustrated in TABLE XXVIII. Use of either HPβCD or PEG400 individually provided an increase in solubility. However, addition of PEG400 to a mixture of the test compound and HPβCD caused an erosion of solubility, with solubility being inversely proportional to the amount of PEG400.

TABLE XXVIII

| % HPβCD | % PEG400 | Solubility |
| --- | --- | --- |
| 0 | 15 | 30 |
| 0 | 30 | 68 |
| 15 | 0 | 59 |
| 15 | 5 | 57 |
| 15 | 10 | 34 |
| 15 | 15 | 6 |

TABLE XXIX contains aqueous solution formulations of the test compound above with the denoted solvents that have been prepared and shown to be chemically stable through 1 month at 50° C., and physically stable at 5° C., at ambient temperature, and at 50° C. The formulations are more stable at pH values above pH 4. The target pH range for the formulations is pH 7+/−0.5 pH units.

TABLE XXIX

| Formulation | Concentration of test compound |
| --- | --- |
| 10% HPβCD | 15 mg/mL |
| 25% HPβCD | 50 mg/mL |
| 30% HPβCD | 50 mg/mL |
| 15% HPβCD/0.25% saline | 40 mg/mL[a] |
| 4.5% mannitol | 5 mg/mL[b] |

[a]Evaluated for short-term physical stability at 5° C. and ambient temperature.
[b]Physically and chemically stable through one week at room temperature and one week at 50° C.

TABLE XXX shows the solubility (mg/mL) of two compounds with varying concentrations of HPβCD. TABLE XXX shows that 25% HPβCD almost doubles the solubility of the test compounds when compared to their solubility in pure water.

TABLE XXX

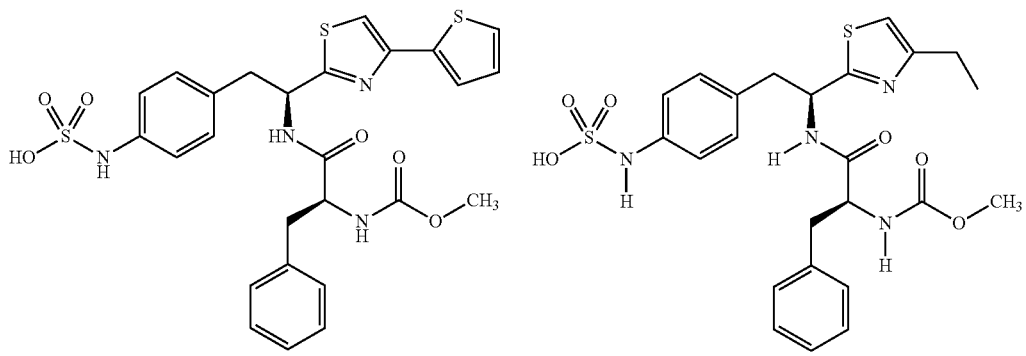

| % HPβCD | Solubility | | Solubility |
| --- | --- | --- | --- |
| 0 | 38 | | 45 |
| 5 | 42 | | 60 |
| 15 | 60 | | NT |
| 25 | 74 | | 89 |

Pharmacokinetic and Pharmacodynamic Measurements

EXAMPLE 37

Plasma Concentration in Human Test Subjects

Figure 9:
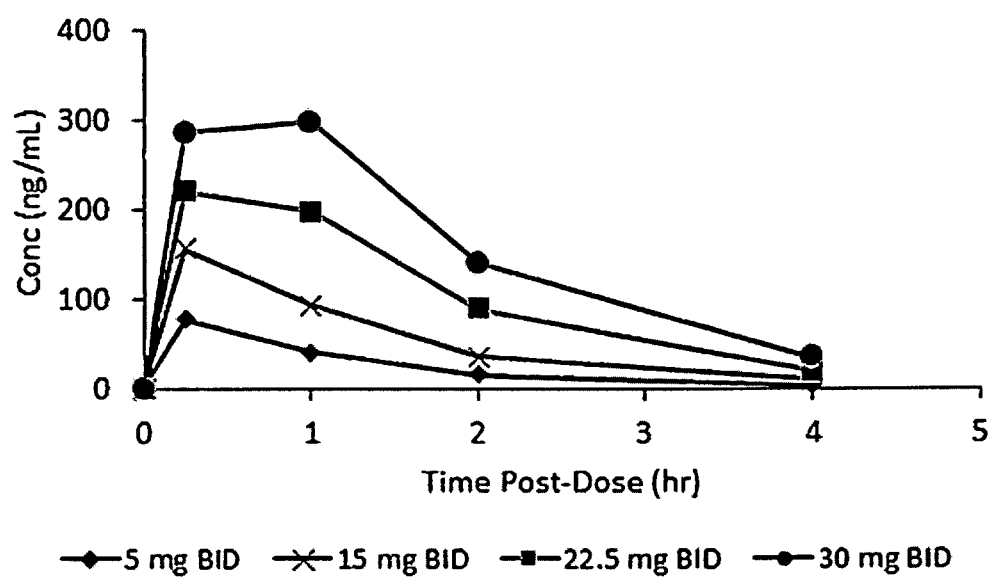
FIG. 9 shows the plasma concentration of 4-{(S)-2-[(S)-2-(methoxycarbonylamino)-3-phenylpropanamido]-2-[2-(thiophen-2-yl)thiazol-4-yl]ethyl}phenylsulfamic acid, pre-dose (0), 15 minutes, 1 hour, 2 hours, 3 hours and 4 hours after administration after the first dose on day 14.

FIG. 9 depicts the mean plasma concentration over time after a single dose of a 5 mg, a 15 mg, a 22.5 mg, or a 30 mg of a test compound on day 14, respectively, in a multiple ascending dose study in patients with diabetic macular edema. The concentration time curves are consistent with rapid absorption and elimination of test compound with rapid Tmax (range 0.2 to 1.0 hours) and short elimination half-life (range 0.6 to 1.5 hours). The overall exposures were approximately dose proportional with Cmax ranging from approximately 40-430 ng/ml and AUC ranging from approximately 70-920 ng·hr/ml at 5-30 mg dose.

EXAMPLE 38

Phase 1B/2A Clinical Trial

A phase 1B/2A open-label, Multiple-ascending dose cohort study to assess the pharmacokinetics and pharmacodynamics effect of 28-day repeat subcutaneous dose of 4-{(S)-2-[(S)-2-(methoxycarbonylamino)-3-phenylpropanamido]-2-[2-(thiophen-2-yl)thiazol-4-yl]ethyl}phenylsulfamic acid (drug) in subjects with diffuse diabetic macular edema (DME).

The aim of this study was to evaluate tolerability, safety, efficacy and pharmacokinetics and pharmacodynamics in patients with DME involving the center of the fovea with central subfield mean thickness ≥325 µm measured by spectral domain-optical coherence tomography (SD-OCT).

Twenty-four patients were administered ascending doses of test compound twice daily (BID) for 28 days in 4 separate cohorts at 5, 15, 22.5 or 30 mg BID, respectively.

Drug was supplied as a lyophilized powder in a vial for reconstitution. Each vial contained 100 mg drug and 250 mg HPβCD. Vials were reconstituted with sterile 5% dextrose for cohort 1 (5 mg BID) and with sterile diluent containing 5% HPβCD/1% dextrose for cohorts 2, 3, and 4 (15 mg, 22.5 mg and 30 mg BID).

For cohorts 1 (5 mg BID) and 2 (15 mg BID) the volume administered for each dose was 0.5 ml (10 and 30 mg/ml, respectively) and for cohorts 3 and 4 the volume was 0.75 ml (30 and 40 mg/ml, respectively).

Blood samples for pharmacokinetic profiling were taken pre-dose (0), 15 minutes, 1 hour, 2 hours, 3 hours and 4 hours after administration of the first dose on day 14.

Plasma drug concentration was determined with a validated LC/MS-MS method. The pharmacokinetic (PK) parameters were determined using a standard non-compartmental method, and Cmax, $AUC_{last}$ (with last being from time 0 to the last quantifiable point), AUCinf, were analyzed statistically using log-transformed data. The dose proportionality 90% confidence intervals were calculated from the mean.

The PK/PD parameter data and statistical analyses are provided in Tables XXXI to XXXV (Day 14). FIG. 9 shows the drug plasma concentration over time for Day 14.

Day 14 PK/PD Parameters

TABLE XXXI

| | 5 mg BID (N = 6) | 15 mg BID (N = 6) | 22.5 mg BID (N = 5) | 30 mg BID (N = 7) |
|---|---|---|---|---|
| | Day 14 | | | |
| $C_{max}$ (ng/mL) | | | | |
| N | 6 | 6 | 4 | 6 |
| Mean (SD) | 77.75 | 156.57 | 237.40 | 320.48 |
| | (24.103) | (51.767) | (122.075) | (68.471) |
| Median | 73.44 | 138.05 | 203.20 | 320.85 |
| Min-Max | 44.7-108.1 | 102.5-226.3 | 142.7-400.5 | 220.9-426.1 |
| % CV | 31.0 | 33.1 | 51.4 | 21.4 |
| Geometric Mean | 74.48 | 149.86 | 215.72 | 314.24 |
| Geometric % CV | 33.6 | 32.9 | 53.3 | 22.2 |
| Power Model of Dose Proportionality | | | | |
| Slope | 0.815 | | | |
| Standard Error | 0.1009 | | | |
| 90% CI | (0.602, 0.950) | | | |

TABLE XXXII

| | 5 mg BID (N = 6) | 15 mg BID (N = 6) | 22.5 mg BID (N = 5) | 30 mg BID (N = 7) |
|---|---|---|---|---|
| $t_{max}$ (hr) | | | | |
| N | 6 | 6 | 4 | 6 |
| Mean (SD) | 0.31 (0.134) | 0.27 (0.039) | 0.45 (0.370) | 0.63 (0.391) |
| Median | 0.26 | 0.25 | 0.27 | 0.64 |
| Min-Max | 0.3-0.6 | 0.2-0.3 | 0.3-1.0 | 0.2-1.0 |
| % CV | 42.9 | 14.3 | 82.9 | 62.3 |

TABLE XXXIII

| | 5 mg BID (N = 6) | 15 mg BID (N = 6) | 22.5 mg BID (N = 5) | 30 mg BID (N = 7) |
|---|---|---|---|---|
| | Day 14 | | | |
| $AUC_{last}$ (ng · hr/mL) | | | | |
| N | 6 | 6 | 4 | 6 |
| Mean (SD) | 101.56 | 239.08 | 437.51 | 669.37 |
| | (26.956) | (71.302) | (235.327) | (130.226) |
| Median | 97.03 | 213.32 | 328.84 | 700.90 |
| Min-Max | 67.9-142.6 | 170.4-353.3 | 302.7-789.6 | 444.1-796.1 |
| % CV | 26.5 | 29.8 | 53.8 | 19.5 |
| Geometric Mean | 98.63 | 230.97 | 400.80 | 657.33 |
| Geometric % CV | 27.0 | 28.8 | 47.9 | 21.9 |
| Power Model of Dose Proportionality | | | | |
| Slope | 1.021 | | | |
| Standard Error | 0.0966 | | | |
| 90% CI | (0.854, 1.187) | | | |

TABLE XXXIV

|  | 5 mg BID (N = 6) | 15 mg BID (N = 6) | 22.5 mg BID (N = 5) | 30 mg BID (N = 7) |
| --- | --- | --- | --- | --- |
| Day 14 | | | | |
| $AUC_{inf}$ (ng·hr/mL) | | | | |
| N | 6 | 6 | 3 | 3 |
| Mean (SD) | 106.46 (30.665) | 255.08 (78.518) | 498.12 (273.956) | 828.62 (95.996) |
| Median | 100.55 | 232.89 | 358.19 | 834.70 |
| Min-Max | 70.1-155.1 | 176.8-387.4 | 322.4-813.8 | 729.7-921.4 |
| % CV | 28.8 | 30.8 | 55.0 | 11.6 |
| Geometric Mean | 102.92 | 245.89 | 454.63 | 824.87 |
| Geometric % CV | 29.0 | 29.8 | 54.1 | 11.7 |
| Power Model of Dose Proportionality | | | | |
| Slope | 1.056 | | | |
| Standard Error | 0.1174 | | | |
| 90% CI | (0.851, 1.261) | | | |

TABLE XXXV

|  | 5 mg BID (N = 6) | 15 mg BID (N = 6) | 22.5 mg BID (N = 5) | 30 mg BID (N = 7) |
| --- | --- | --- | --- | --- |
| Day 14 | | | | |
| $t_{1/2}$ (hr) | | | | |
| N | 6 | 6 | 3 | 3 |
| Mean (SD) | 0.85 (0.186) | 0.96 (0.282) | 0.84 (0.093) | 1.07 (0.338) |
| Median | 0.83 | 0.89 | 0.87 | 0.93 |
| Min-Max | 0.6-1.1 | 0.6-1.4 | 0.7-0.9 | 0.8-1.5 |
| % CV | 21.9 | 29.5 | 11.0 | 31.4 |

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 80 ng/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $AUC_{last}$ of the HPTP-β inhibitor is within 70% to 130% of an $AUC_{last}$ of 100 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $AUC_{last}$ of the HPTP-β inhibitor is within 70% to 130% of an $AUC_{inf}$ of 100 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $t_{1/2}$ of the HPTP-β inhibitor is within 70% to 130% of at $t_{1/2}$ of 1 hour, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 80 ng/ml, after administration of a single dose of the HPTP-β inhibitor to a human; and wherein the mean $AUC_{last}$ of the HPTP-β inhibitor is within 70% to 130% of an $AUC_{last}$ of 100 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 80 ng/ml, after administration of a single dose of the HPTP-β inhibitor to a human; and wherein the mean $AUC_{last}$ of the HPTP-β inhibitor is within 70% to 130% of an $AUC_{inf}$ of 100 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 80 ng/ml, after administration of a single dose of the HPTP-β inhibitor to a human; and wherein the mean $t_{1/2}$ of the HPTP-β inhibitor is within 70% to 130% of a $t_{1/2}$ of 1 hour, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 150 ng/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $AUC_{last}$ of the HPTP-β inhibitor is within 70% to 130% of an $AUC_{last}$ of 217 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $AUC_{last}$ of the HPTP-β inhibitor is within 70% to 130% of an $AUC_{inf}$ of 255 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 150 ng/ml, after administration of a single dose of the HPTP-β inhibitor to a human; and wherein the mean $AUC_{last}$ of the HPTP-β inhibitor is within 70% to 130% of an $AUC_{last}$ of 217 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 150 ng/ml, after administration of a single dose of the HPTP-β inhibitor to a human; and wherein the mean $AUC_{last}$ of the HPTP-β inhibitor is within 70% to 130% of an $AUC_{inf}$ of 255 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 150 ng/ml, after administration of a single dose of the HPTP-β inhibitor to a human; and wherein the mean $t_{1/2}$ of the HPTP-β inhibitor is within 70% to 130% of at $t_{1/2}$ of 1 hour, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 240 ng/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $AUC_{last}$ of the HPTP-β inhibitor is within 70% to 130% of an $AUC_{last}$ of 440 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $AUC_{last}$ of the HPTP-β inhibitor is within 70% to 130% of an $AUC_{inf}$ of 500 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 240 ng/ml, after administration of a single dose of the HPTP-β inhibitor to a human; and wherein the mean $AUC_{last}$ of the HPTP-β inhibitor is within 70% to 130% of an $AUC_{last}$ of 440 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 240 ng/ml, after administration of a single dose of the HPTP-β inhibitor to a human; and wherein the mean $AUC_{last}$ of the HPTP-β inhibitor is within 70% to 130% of an $AUC_{inf}$ of 500 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 240 ng/ml, after administration of a single dose of the HPTP-β inhibitor to a human; and wherein the mean $t_{1/2}$ of the HPTP-β inhibitor is within 70% to 130% of at $t_{1/2}$ of 1 hour, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 300 ng/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $AUC_{last}$ of the HPTP-β inhibitor is within 70% to 130% of an $AUC_{last}$ of 640 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $AUC_{last}$ of the HPTP-β inhibitor is within 70% to 130% of an $AUC_{inf}$ of 830 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 300 ng/ml, after administration of a single dose of the HPTP-β inhibitor to a human; and wherein the mean $AUC_{last}$ of the HPTP-β inhibitor is within 70% to 130% of an $AUC_{last}$ of 640 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 300 ng/ml, after administration of a single dose of the HPTP-β inhibitor to a human; and wherein the mean $AUC_{last}$ of the HPTP-β inhibitor is within 70% to 130% of an $AUC_{inf}$ of 830 ng·hr/ml, after administration of a single dose of the HPTP-β inhibitor to a human.

In some embodiments, the invention provides a pharmaceutical composition in unit dose form for subcutaneously delivery of a composition comprising an HPTP-β inhibitor and 2-hydroxypropyl-β-cyclodextrin wherein the mean $C_{max}$ of the HPTP-β inhibitor is within 70% to 130% of a $C_{max}$ of 300 ng/ml, after administration of a single dose of the HPTP-β inhibitor to a human; and wherein the mean $t_{1/2}$ of the HPTP-β inhibitor is within 70% to 130% of at $t_{1/2}$ of 1 hour, after administration of a single dose of the HPTP-β inhibitor to a human.

In some embodiments, the HPTP-β inhibitor is 4-{(S)-2-[(S)-2-(methoxycarbonylamino)-3-phenylpropanamido]-2-[2-(thiophen-2-yl)thiazol-4-yl]ethyl}phenylsulfamic acid.

In some embodiments, the HPTP-β inhibitor is (4-{(S)-2-[(S)-2-(methoxycarbonylamino)-3-phenylpropanamido]-2-[4-ethylthiazol-2-yl]ethyl}phenyl)sulfamic acid.

In some embodiments, the HPTP-β inhibitor is 4-{(S)-2-[(S)-2-(methoxycarbonylamino)-3-phenylpropanamido]-2-(2-ethylthiazol-4-yl)ethyl}phenylsulfamic acid.

In some embodiments, the HPTP-β inhibitor is (4-((S)-2-((S)-2-((methoxycarbonyl)amino)-3-phenylpropanamido)-2-(4-(thiophen-2-yl)thiazol-2-yl)ethyl)phenyl)sulfamic acid.

A dose can be modulated to achieve a desired pharmacokinetic or pharmacodynamics profile, such as a desired or effective blood profile, as described herein.

Pharmacokinetic and pharmacodynamic data can be obtained by various experimental techniques. Appropriate pharmacokinetic and pharmacodynamic profile components describing a particular composition can vary due to variations in drug metabolism in human subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined, for example, by calculating the average of all subject's measurements for each parameter measured. A dose can be modulated to achieve a desired pharmacokinetic or pharmacodynamics profile, such as a desired or effective blood profile, as described herein.

The pharmacodynamic parameters can be any parameters suitable for describing compositions of the invention. For example, the pharmacodynamic profile can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

The pharmacokinetic parameters can be any parameters suitable for describing a compound. The $C_{max}$ can be, for example, not less than about 1 ng/mL; not less than about 5 ng/mL; not less than about 10 ng/mL; not less than about 15 ng/mL; not less than about 20 ng/mL; not less than about 25 ng/mL; not less than about 50 ng/mL; not less than about 75 ng/mL; not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; or any other $C_{max}$ appropriate for describing a pharmacokinetic profile of a compound described herein. The $C_{max}$ can be, for example, about 1 ng/mL to about 5,000 ng/mL; about 1 ng/mL to about 4,500 ng/mL; about 1 ng/mL to about 4,000 ng/mL; about 1 ng/mL to about 3,500 ng/mL; about 1 ng/mL to about 3,000 ng/mL; about 1 ng/mL to about 2,500 ng/mL; about 1 ng/mL to about 2,000 ng/mL; about 1 ng/mL to about 1,500 ng/mL; about 1 ng/mL to about 1,000 ng/mL; about 1 ng/mL to about 900 ng/mL; about 1 ng/mL to about 800 ng/mL; about 1 ng/mL to about 700 ng/mL; about 1 ng/mL to about 600 ng/mL; about 1 ng/mL to about 500 ng/mL; about 1 ng/mL to about 450 ng/mL; about 1 ng/mL to about 400 ng/mL; about 1 ng/mL to about 350 ng/mL; about 1 ng/mL to about 300 ng/mL; about 1 ng/mL to about 250 ng/mL; about 1 ng/mL to about 200 ng/mL; about 1 ng/mL to about 150 ng/mL; about 1 ng/mL to about 125 ng/mL; about 1 ng/mL to about 100 ng/mL; about 1 ng/mL to about 90 ng/mL; about 1 ng/mL to about 80 ng/mL; about 1 ng/mL to about 70 ng/mL; about 1 ng/mL to about 60 ng/mL; about 1 ng/mL to about 50 ng/mL; about 1 ng/mL to about 40 ng/mL; about 1 ng/mL to about 30 ng/mL; about 1 ng/mL to about 20 ng/mL; about 1 ng/mL to about 10 ng/mL; about 1 ng/mL to about 5 ng/mL; about 10 ng/mL to about 4,000 ng/mL; about 10 ng/mL to about 3,000 ng/mL; about 10 ng/mL to about 2,000 ng/mL; about 10 ng/mL to about 1,500 ng/mL; about 10 ng/mL to about 1,000 ng/mL; about 10 ng/mL to about 900 ng/mL; about 10 ng/mL to about 800 ng/mL; about 10 ng/mL to about 700 ng/mL; about 10 ng/mL to about 600 ng/mL; about 10 ng/mL to about 500 ng/mL; about 10 ng/mL to about 400 ng/mL; about 10 ng/mL to about 300 ng/mL; about 10 ng/mL to about 200 ng/mL; about 10 ng/mL to about 100 ng/mL; about 10 ng/mL to about 50 ng/mL; about 25 ng/mL to about 500 ng/mL; about 25 ng/mL to about 100 ng/mL; about 50 ng/mL to about 500 ng/mL; about 50 ng/mL to about 100 ng/mL; about 100 ng/mL to about 500 ng/mL; about 100 ng/mL to about 400 ng/mL; about 100 ng/mL to about 300 ng/mL; or about 100 ng/mL to about 200 ng/mL.

The $T_{max}$ of a compound described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other $T_{max}$ appropriate for describing a pharmacokinetic profile of a compound described herein. The $T_{max}$ can be, for example, about 0.1 hours to about 24 hours; about 0.1 hours to about 0.5 hours; about 0.5 hours to about 1 hour; about 1 hour to about 1.5 hours; about 1.5 hours to about 2 hour; about 2 hours to about 2.5 hours; about 2.5 hours to about 3 hours; about 3 hours to about 3.5 hours; about 3.5 hours to about 4 hours; about 4 hours to about 4.5 hours; about 4.5 hours to about 5 hours; about 5 hours to about 5.5 hours; about 5.5 hours to about 6 hours; about 6 hours to about 6.5 hours; about 6.5 hours to about 7 hours; about 7 hours to about 7.5 hours; about 7.5 hours to about 8 hours; about 8 hours to about 8.5 hours; about 8.5 hours to about 9 hours; about 9 hours to about 9.5 hours; about 9.5 hours to about 10 hours; about 10 hours to about 10.5 hours; about 10.5 hours to about 11 hours; about 11 hours to about 11.5 hours; about 11.5 hours to about 12 hours; about 12 hours to about 12.5 hours; about 12.5 hours to about 13 hours; about 13 hours to about 13.5 hours; about 13.5 hours to about 14 hours; about 14 hours to about 14.5 hours; about 14.5 hours to about 15 hours; about 15 hours to about 15.5 hours; about 15.5 hours to about 16 hours; about 16 hours to about 16.5 hours; about 16.5 hours to about 17 hours; about 17 hours to about 17.5 hours; about 17.5 hours to about 18 hours; about 18 hours to about 18.5 hours; about 18.5 hours to about 19 hours; about 19 hours to about 19.5 hours; about 19.5 hours to about 20 hours; about 20 hours to about 20.5 hours; about 20.5 hours to about 21 hours; about 21 hours to about 21.5 hours; about 21.5 hours to about 22 hours; about 22 hours to about 22.5 hours; about 22.5 hours to about 23 hours; about 23 hours to about 23.5 hours; or about 23.5 hours to about 24 hours.

The $AUC_{(0-inf)}$ or $AUC_{(last)}$ of a compound described herein can be, for example, not less than about 1 ng·hr/mL, not less than about 5 ng·hr/mL, not less than about 10 ng·hr/mL, not less than about 20 ng·hr/mL, not less than about 30 ng·hr/mL, not less than about 40 ng·hr/mL, not less than about 50 ng·hr/mL, not less than about 100 ng·hr/mL, not less than about 150 ng·hr/mL, not less than about 200 ng·hr/mL, not less than about 250 ng·hr/mL, not less than about 300 ng·hr/mL, not less than about 350 ng·hr/mL, not less than about 400 ng·hr/mL, not less than about 450 ng·hr/mL, not less than about 500 ng·hr/mL, not less than about 600 ng·hr/mL, not less than about 700 ng·hr/mL, not less than about 800 ng·hr/mL, not less than about 900 ng·hr/mL, not less than about 1000 ng·hr/mL, not less than about 1250 ng·hr/mL, not less than about 1500 ng·hr/mL, not less than about 1750 ng·hr/mL, not less than about 2000 ng·hr/mL, not less than about 2500 ng·hr/mL, not less than about 3000 ng·hr/mL, not less than about 3500 ng·hr/mL, not less than about 4000 ng·hr/mL, not less than about 5000 ng·hr/mL, not less than about 6000 ng·hr/mL, not less than about 7000 ng·hr/mL, not less than about 8000 ng·hr/mL, not less than about 9000 ng·hr/mL, not less than about 10,000 ng·hr/mL, or any other $AUC_{(0-inf)}$ appropriate for describing a pharmacokinetic profile of a compound described herein. The $AUC_{(0-inf)}$ of a compound can be, for example, about 1 ng·hr/mL to about 10,000 ng·hr/mL; about 1 ng·hr/mL to about 10 ng·hr/mL; about 10 ng·hr/mL to about 25 ng·hr/mL; about 25 ng·hr/mL to about 50 ng·hr/mL; about 50 ng·hr/mL to about 100 ng·hr/mL; about 100 ng·hr/mL to about 200 ng·hr/mL; about 200 ng·hr/mL to about 300 ng·hr/mL; about 300 ng·hr/mL to about 400 ng·hr/mL; about 400 ng·hr/mL to about 500 ng·hr/mL; about 500 ng·hr/mL to about 600 ng·hr/mL; about 600 ng·hr/mL to about 700 ng·hr/mL; about 700 ng·hr/mL to about 800 ng·hr/mL; about 800 ng·hr/mL to about 900 ng·hr/mL; about 900 ng·hr/mL to about 1,000 ng·hr/mL; about 1,000 ng·hr/mL to about 1,250 ng·hr/mL; about 1,250 ng·hr/mL to about 1,500 ng·hr/mL; about 1,500 ng·hr/mL to about 1,750 ng·hr/mL; about 1,750 ng·hr/mL to about 2,000 ng·hr/mL; about 2,000 ng·hr/mL to about 2,500 ng·hr/mL; about 2,500 ng·hr/mL to about 3,000 ng·hr/mL; about 3,000 ng·hr/mL to about 3,500 ng·hr/mL; about 3,500 ng·hr/mL to about 4,000 ng·hr/mL; about 4,000 ng·hr/mL to about 4,500 ng·hr/mL; about 4,500 ng·hr/mL to about 5,000 ng·hr/mL; about 5,000 ng·hr/mL to about 5,500 ng·hr/mL; about 5,500 ng·hr/mL to about 6,000 ng·hr/mL; about 6,000 ng·hr/mL to about 6,500 ng·hr/mL; about 6,500 ng·hr/mL to about 7,000 ng·hr/mL; about 7,000 ng·hr/mL to about 7,500 ng·hr/mL; about 7,500 ng·hr/mL to about 8,000 ng·hr/mL; about 8,000 ng·hr/mL to about 8,500 ng·hr/mL; about 8,500 ng·hr/mL to about 9,000 ng·hr/mL; about 9,000 ng·hr/mL to about 9,500 ng·hr/mL; or about 9,500 ng·hr/mL to about 10,000 ng·hr/mL.

The plasma concentration of a compound described herein can be, for example, not less than about 1 ng/mL, not less than about 5 ng/mL, not less than about 10 ng/mL, not less than about 15 ng/mL, not less than about 20 ng/mL, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, not less than about 600 ng/mL, not less than about 700 ng/mL, not less than about 800 ng/mL, not less than about 900 ng/mL, not less than about 1000 ng/mL, not less than about 1200 ng/mL, or any other plasma concentration of a compound described herein. The plasma concentration can be, for example, about 1 ng/mL to about 2,000 ng/mL; about 1 ng/mL to about 5 ng/mL; about 5 ng/mL to about 10 ng/mL; about 10 ng/mL to about 25 ng/mL; about 25 ng/mL to about 50 ng/mL; about 50 ng/mL to about 75 ng/mL; about 75 ng/mL to about 100 ng/mL; about 100 ng/mL to about 150 ng/mL; about 150 ng/mL to about 200 ng/mL; about 200 ng/mL to about 250 ng/mL; about 250 ng/mL to about 300 ng/mL; about 300 ng/mL to about 350 ng/mL; about 350 ng/mL to about 400 ng/mL; about 400 ng/mL to about 450 ng/mL; about 450 ng/mL to about 500 ng/mL; about 500 ng/mL to about 600 ng/mL; about 600 ng/mL to about 700 ng/mL; about 700 ng/mL to about 800 ng/mL; about 800 ng/mL to about 900 ng/mL; about 900 ng/mL to about 1,000 ng/mL; about 1,000 ng/mL to about 1,100 ng/mL; about 1,100 ng/mL to about 1,200 ng/mL; about 1,200 ng/mL to about 1,300 ng/mL; about 1,300 ng/mL to about 1,400 ng/mL; about 1,400 ng/mL to about 1,500 ng/mL; about 1,500 ng/mL to about 1,600 ng/mL; about 1,600 ng/mL to about 1,700 ng/mL; about 1,700 ng/mL to about 1,800 ng/mL; about 1,800 ng/mL to about 1,900 ng/mL; or about 1,900 ng/mL to about 2,000 ng/mL.

The pharmacodynamic parameters can be any parameters suitable for describing compositions of the disclosure. For example, the pharmacodynamic profile can exhibit decreases in viability phenotype for the tumor cells or tumor size reduction in tumor cell lines or xenograft studies, for example, about 24 hours, about 48 hours, about 72 hours, or 1 week.

Non-limiting examples of pharmacodynamic and pharmacokinetic parameters that can be calculated for a compound that is administered with the methods of the invention include: a) the amount of drug administered, which can be represented as a dose D; b) the dosing interval, which can be represented as $\tau$; c) the apparent volume in which a drug is distributed, which can be represented as a volume of distribution $V_d$, where $V_d = D/C_0$; d) the amount of drug in a given volume of plasma, which can be represented as concentration $C_0$ or $C_{ss}$, where $C_0$ or $C_{ss} = D/Vd$ and can be represented as a mean plasma concentration over a plurality of samples; e) the half-life of a drug $t_{1/2}$, where $t_{1/2} = \ln(2)/k_e$; f) the rate at which a drug is removed from the body $k_e$, where $k_e = \ln(2)/t_{1/2} = CL/V_d$; g) the rate of infusion required to balance the equation $K_{in}$, where $K_{in} = C_{ss} \cdot CL$; h) the integral of the concentration-time curve after administration of a single dose, which can be represented as $AUC_{0-\infty}$, wherein $\int_0^\infty C\,dt$, or in steady-state, which can be represented as $AUC_{\tau,ss}$, wherein $\int_t^{t+\tau} C\,dt$; i) the volume of plasma cleared of the drug per unit time, which can be represented as CL (clearance), wherein $CL = V_d \cdot k_e = D/AUC$; j) the systemically available fraction of a drug, which can be represented as f, where $$f = \frac{AUCpo \cdot Div}{AUCiv \cdot Dpo}; k)$$

the peak plasma concentration of a drug after administration $C_{max}$; 1) the time taken by a drug to reach $C_{max}$, $t_{max}$; m) the lowest concentration that a drug reaches before the next dose is administered $C_{min}$; and n) the peak trough fluctuation within one dosing interval at steady state, which can be represented as $$\% PTF = 100 \cdot \frac{(Cmax, ss - Cmin, ss)}{Cav, ss} \text{ where } C_{av,ss} = \frac{AUC\tau, ss}{\tau}.$$

EMBODIMENTS

The following are illustrative embodiments.

Embodiment A1

A method of treating a condition in a subject in need thereof, the method comprising administering to the subject a therapeutically-effective amount of a compound that activates Tie-2, or a pharmaceutically-acceptable salt thereof, and an agent that increases solubility of the compound that activates Tie-2, or the pharmaceutically-acceptable salt thereof as compared to solubility in absence of the agent.

Embodiment A2

The method of embodiment A1, wherein the compound that activates Tie-2 or the pharmaceutically-acceptable salt thereof binds HPTP-beta.

Embodiment A3

The method of embodiment A1, wherein the compound that activates Tie-2 or the pharmaceutically-acceptable salt thereof inhibits HPTP-beta.

Embodiment A4

The method of embodiment A1, wherein the compound that activates Tie-2 or the pharmaceutically-acceptable salt thereof is a phosphate mimetic.

Embodiment A5

The method of embodiment A1, wherein the compound that activates Tie-2 comprises an amino acid backbone.

Embodiment A6

The method of embodiment A1, wherein the compound that activates Tie-2 comprises a sulfamic acid.

Embodiment A7

The method of embodiment A1, wherein the agent that improves the aqueous solubility of the compound that activates Tie-2 or the pharmaceutically-acceptable salt thereof comprises a polymer.

Embodiment A8

The method of embodiment A1, wherein the agent that improves the aqueous solubility of the compound that activates Tie-2 or the pharmaceutically-acceptable salt thereof comprises a poly-ethylene glycol moiety.

Embodiment A9

The method of embodiment A1, wherein the agent that improves the aqueous solubility of the compound that activates Tie-2 or the pharmaceutically-acceptable salt thereof comprises a cyclodextrin moiety.

Embodiment A10

The method of embodiment A1, wherein the agent that improves the aqueous solubility of the compound that activates Tie-2 or the pharmaceutically-acceptable salt thereof comprises a 2-hydroxypropyl-β-cyclodextrin moiety.

Embodiment A11

The method of embodiment A1, wherein the agent that improves the aqueous solubility of the compound that activates Tie-2 or the pharmaceutically-acceptable salt thereof comprises a sulfobutylether-β-cyclodextrin moiety.

Embodiment A12

The method of embodiment A1, wherein the compound that activates Tie-2, or the pharmaceutically-acceptable salt thereof, and the agent that improves the aqueous solubility of the compound that activates Tie-2 or the pharmaceutically-acceptable salt thereof are held in a complex by non-covalent interactions.

Embodiment A13

The method of embodiment A1, wherein the agent that improves the aqueous solubility of the compound that activates Tie-2 or the pharmaceutically-acceptable salt thereof comprises a surfactant moiety.

Embodiment A14

The method of embodiment A1, wherein the agent that increases solubility of the compound that activates Tie-2 or the pharmaceutically-acceptable salt thereof increases aqueous solubility by at least 10% at each of 5° C., ambient temperature, and 50° C.

Embodiment A15

The method of embodiment A1, wherein the agent that increases solubility of the compound that activates Tie-2 or the pharmaceutically-acceptable salt thereof increases aqueous solubility by at least 25%.

Embodiment A16

The method of embodiment A1, wherein the agent that increases solubility of the compound that activates Tie-2 or the pharmaceutically-acceptable salt thereof increases aqueous solubility by at least 50%.

Embodiment A17

The method of embodiment A1, wherein the therapeutically-effective amount is from about 0.1 mg to about 100 mg.

Embodiment A18

The method of embodiment A1, wherein the therapeutically-effective amount is from about 0.5 mg to about 30 mg.

Embodiment A19

The method of embodiment A1, wherein the compound that activates Tie-2, or the pharmaceutically-acceptable salt thereof, and the agent that improves the aqueous solubility of the compound that activates Tie-2 or the pharmaceutically-acceptable salt thereof are coadministered in a unit dosage form.

Embodiment A20

The method of embodiment A19, wherein the unit dosage form is administered subcutaneously.

Embodiment A21

The method of embodiment A19, wherein the unit dosage form is administered to an eye.

Embodiment A22

The method of embodiment A1, wherein the condition is an ocular condition.

Embodiment A23

The method of embodiment A1, wherein the condition is diabetic macular edema.

Embodiment A24

The method of embodiment A1, wherein the condition is diabetic retinopathy.

Embodiment A25

The method of embodiment A1, wherein the condition is macular degeneration.

Embodiment A26

The method of embodiment A1, wherein the condition is vascular leak.

Embodiment A27

The method of embodiment A1, wherein the condition is a cancer.

Embodiment A28

The method of embodiment A1, wherein the subject is a human.

Embodiment A29

The method of embodiment A1, wherein the subject's visual acuity improves by at least 5 letters.

Embodiment A30

The method of embodiment A1, wherein the compound that activates Tie-2 is a compound of the formula:

$$\text{Aryl}^1 \diagdown X \diagdown \underset{Y}{\diagup} \diagup \text{Aryl}^2$$

wherein aryl$^1$ is an aryl group which is substituted or unsubstituted, aryl$^2$ is an aryl group which is substituted or unsubstituted, X is alkylene, alkenylene, alkynylene, an ether linkage, an amine linkage, an amide linkage, an ester linkage, a thioether linkage, a carbamate linkage, a carbonate linkage, a urethane linkage, a sulfone linkage, any of which is substituted or unsubstituted, or a chemical bond, and Y is H, aryl, heteroaryl, NH(aryl), NH(heteroaryl), NHSO$_2$R$^g$, or NHCOR$^g$, any of which is substituted or unsubstituted, or <structure> wherein L$^2$ is alkylene, alkenylene, or alkynylene, any of which is substituted or unsubstituted, or together with the nitrogen atom to which L is bound forms an amide linkage, a carbamate linkage, a urethane linkage, or a sulfonamide linkage, or a chemical bond, or together with any of R$^a$, R$^b$, R$^c$, and R$^d$ forms a ring that is substituted or unsubstituted. R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^b$, R$^c$, and R$^d$ forms a ring that is substituted or unsubstituted. R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^a$, R$^c$, and R$^d$ forms a ring that is substituted or unsubstituted. R$^c$ is H or alkyl which is substituted or unsubstituted, or together with any of L$^2$, R$^a$, R$^b$, and R$^d$ forms a ring that is substituted or unsubstituted. R$^d$ is H or alkyl which is substituted or unsubstituted, or together with any of L$^2$, R$^a$, R$^b$, and R$^c$ forms a ring that is substituted or unsubstituted, and R$^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

Embodiment A31

The method of embodiment A30, wherein aryl$^1$ is substituted or unsubstituted phenyl, aryl$^2$ is substituted or unsubstituted heteroaryl, and X is alkylene.

Embodiment A32

The method of embodiment A31, wherein aryl$^1$ is substituted phenyl, aryl$^2$ is substituted heteroaryl, and X is methylene.

Embodiment A33

The method of embodiment A32, wherein the compound that activates Tie-2 is a compound of the formula:

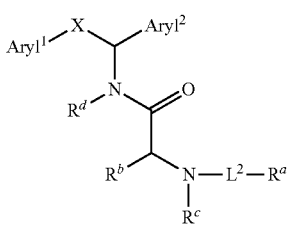

wherein aryl¹ is para-substituted phenyl, aryl² is substituted heteroaryl, X is methylene. L² is alkylene, alkenylene, or alkynylene, any of which is substituted or unsubstituted, or together with the nitrogen atom to which L is bound forms an amide linkage, a carbamate linkage, a urethane linkage, or a sulfonamide linkage, or a chemical bond. $R^a$ is H, alkyl, alkenyl, alkynyl, aryl, arylalkyl, heterocyclyl, heterocyclylalkyl, heteroaryl, or heteroarylalkyl, any of which is substituted or unsubstituted. $R^b$ is H, alkyl, alkenyl, alkynyl, aryl, arylalkyl, heterocyclyl, heterocyclylalkyl, heteroaryl, or heteroarylalkyl, any of which is substituted or unsubstituted. $R^c$ is H or alkyl which is substituted or unsubstituted, and $R^d$ is H or alkyl which is substituted or unsubstituted.

Embodiment A34

The method of embodiment A33, wherein aryl¹ is para-substituted phenyl, aryl² is a substituted thiazole moiety. X is methylene, L² together with the nitrogen atom to which L is bound forms a carbamate linkage, $R^a$ is alkyl, which is substituted or unsubstituted, $R^b$ is arylalkyl, which is substituted or unsubstituted, $R^c$ is H, and $R^d$ is H.

Embodiment A35

The method of embodiment A34, wherein Aryl² is:

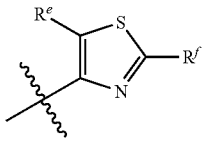

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a urethane group, a thioether group, a thioester group, a thioacid group, aryl, arylalkyl, heterocyclyl, heterocyclylalkyl, heteroaryl, or heteroarylalkyl, any of which is substituted or unsubstituted, and $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a urethane group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment A36

The method of embodiment A35, wherein $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted, and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment A37

The method of embodiment A35, wherein $R^e$ is H, OH, F, Cl, Br, I, alkyl, or an alkoxy group, any of which is substituted or unsubstituted and $R^f$ is alkyl, aryl, heterocyclyl, or heteroaryl, any of which is substituted or unsubstituted.

Embodiment A38

The method of embodiment A35, wherein aryl¹ is 4-phenylsulfamic acid, $R^a$ is alkyl, which is substituted or unsubstituted, $R^b$ is arylalkyl, which is substituted or unsubstituted, $R^e$ is H; and $R^f$ is heteroaryl.

Embodiment A39

The method of embodiment A30, wherein the compound is:

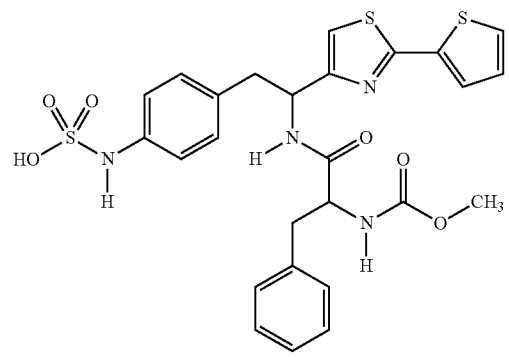

Embodiment A40

The method of embodiment A30, wherein the compound is:

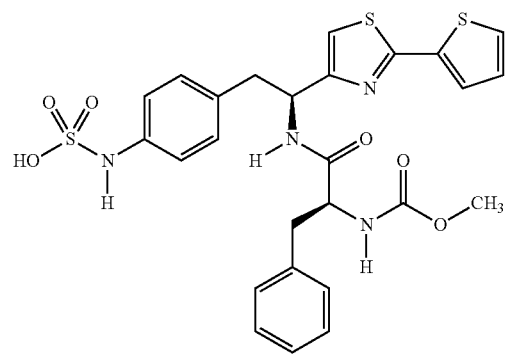

Embodiment A41

The method of embodiment A35, wherein aryl¹ is 4-phenylsulfamic acid, $R^a$ is alkyl, which is substituted or unsubstituted, $R^b$ is arylalkyl, which is substituted or unsubstituted, $R^e$ is H; and $R^f$ is alkyl.

Embodiment A42

The method of embodiment A30, wherein the compound is:

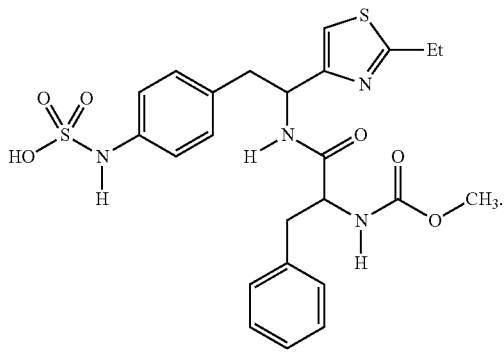 [SMILES: CCc1nc(C(Cc2ccc(NS(=O)(=O)O)cc2)NC(=O)C(Cc2ccccc2)NC(=O)OC)cs1]

Embodiment A43

The method of embodiment A32, wherein the compound is:

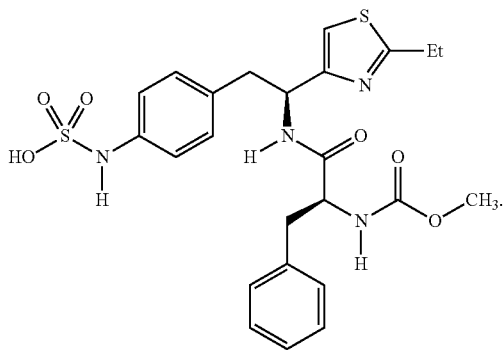 [SMILES: CCc1nc([C@H](Cc2ccc(NS(=O)(=O)O)cc2)NC(=O)[C@H](Cc2ccccc2)NC(=O)OC)cs1]

Embodiment A44

The method of embodiment A34, wherein Aryl² is:

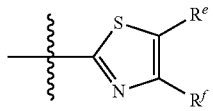

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a urethane group, a thioether group, a thioester group, a thioacid group, aryl, arylalkyl, heterocyclyl, heterocyclylalkyl, heteroaryl, or heteroarylalkyl, any of which is substituted or unsubstituted, $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a urethane group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment A45

The method of embodiment A44, wherein $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment A46

The method of embodiment A44, wherein $R^e$ is H, OH, F, Cl, Br, I, alkyl, or an alkoxy group, any of which is substituted or unsubstituted and $R^f$ is alkyl, aryl, heterocyclyl, or heteroaryl, any of which is substituted or unsubstituted.

Embodiment A47

The method of embodiment A44, wherein aryl¹ is 4-phenylsulfamic acid, $R^a$ is alkyl, which is substituted or unsubstituted, $R^b$ is arylalkyl, which is substituted or unsubstituted, $R^e$ is H; and $R^f$ is heteroaryl.

Embodiment A48

The method of embodiment A30, wherein the compound is:

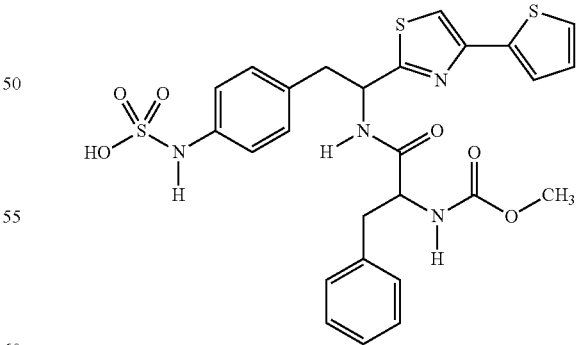

Embodiment A49

The method of embodiment A30, wherein the compound is:

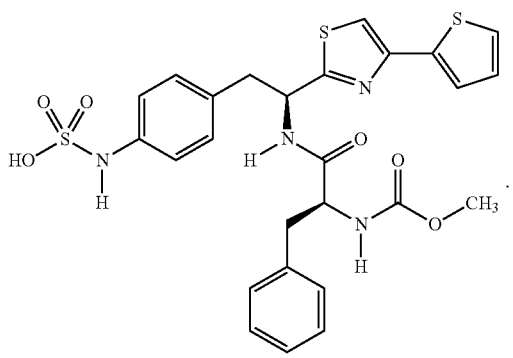

Embodiment A50

The method of embodiment A40, wherein the agent that improves the aqueous solubility of the compound that activates Tie-2 or the pharmaceutically-acceptable salt thereof comprises a 2-hydroxypropyl-β-cyclodextrin moiety.

Embodiment A51

The method of embodiment A50, wherein the condition is diabetic macular edema.

Embodiment A52

The method of embodiment A51, wherein a plasma concentration in the subject of the compound that activates Tie-2 or the pharmaceutically-acceptable salt thereof is no greater than 500 ng/mL at about 0.25 hours after the administration.

Embodiment A53

The method of embodiment A51, wherein a plasma concentration in the subject of the compound that activates Tie-2 or the pharmaceutically-acceptable salt thereof is about 50 ng/mL to about 350 ng/mL at about 0.25 hours after the administration; about 30 ng/mL to about 350 ng/mL at about 1 hour after the administration; about 10 ng/mL to about 200 ng/mL at about 2 hours after the administration; and about 0 ng/mL to about 50 ng/mL at about 4 hours after the administration.

Embodiment A54

The method of embodiment A51, wherein a plasma concentration in the subject of the compound that activates Tie-2 or the pharmaceutically-acceptable salt thereof is for administration of a dose of about 5 mg, about 50 ng/mL to about 100 ng/mL at about 0.25 hours after the administration; about 30 ng/mL to about 80 ng/mL at about 1 hour after the administration; about 10 ng/mL to about 50 ng/mL at about 2 hours after the administration; and about 0 ng/mL to about 30 ng/mL at about 4 hours after the administration; for administration of a dose of about 15 mg, about 120 ng/mL to about 180 ng/mL at about 0.25 hours after the administration; about 70 ng/mL to about 130 ng/mL at about 1 hour after the administration; about 20 ng/mL to about 70 ng/mL at about 2 hours after the administration; and about 0 ng/mL to about 40 ng/mL at about 4 hours after the administration; for administration of a dose of about 22.5 mg, about 190 ng/mL to about 250 ng/mL at about 0.25 hours after the administration; about 170 ng/mL to about 240 ng/mL at about 1 hour after the administration; about 70 ng/mL to about 120 ng/mL at about 2 hours after the administration; and about 10 ng/mL to about 60 ng/mL at about 4 hours after the administration; and for administration of a dose of about 30 mg, about 250 ng/mL to about 330 ng/mL at about 0.25 hours after the administration; about 270 ng/mL to about 330 ng/mL at about 1 hour after the administration; about 130 ng/mL to about 180 ng/mL at about 2 hours after the administration; and about 25 ng/mL to about 75 ng/mL at about 4 hours after the administration.

Embodiment B1

A method of treating a condition in a subject in need thereof, the method comprising administering to the subject a therapeutically-effective amount of a compound that activates Tie-2, or a pharmaceutically-acceptable salt thereof, wherein the administration provides a plasma concentration in the subject of the compound that activates Tie-2 or the pharmaceutically-acceptable salt thereof of about 25 ng/mL to about 500 ng/mL.

Embodiment B2

The method of embodiment B1, wherein the plasma concentration in the subject of the compound that activates Tie-2 or the pharmaceutically-acceptable salt thereof is no greater than 350 ng/mL at about 0.25 hours after the administration.

Embodiment B3

The method of embodiment B2, wherein the plasma concentration in the subject of the compound that activates Tie-2 or the pharmaceutically-acceptable salt thereof is greater than 50 ng/mL.

Embodiment B4

The method of embodiment B1, wherein the plasma concentration in the subject of the compound that activates Tie-2 or the pharmaceutically-acceptable salt thereof is about 50 ng/mL to about 350 ng/mL at about 0.25 hours after the administration; about 30 ng/mL to about 350 ng/mL at about 1 hour after the administration; about 10 ng/mL to about 200 ng/mL at about 2 hours after the administration; and about 0 ng/mL to about 50 ng/mL at about 4 hours after the administration.

Embodiment B5

The method of embodiment B1, wherein the plasma concentration in the subject of the compound that activates Tie-2 or the pharmaceutically-acceptable salt thereof is for administration of a dose of about 5 mg, about 50 ng/mL to about 100 ng/mL at about 0.25 hours after the administration; about 30 ng/mL to about 80 ng/mL at about 1 hour after the administration; about 10 ng/mL to about 50 ng/mL at about 2 hours after the administration; and about 0 ng/mL to about 30 ng/mL at about 4 hours after the administration; for administration of a dose of about 15 mg, about 120 ng/mL to about 180 ng/mL at about 0.25 hours after the administration; about 70 ng/mL to about 130 ng/mL at about 1 hour after the administration; about 20 ng/mL to about 70 ng/mL at about 2 hours after the administration; and about 0 ng/mL to about 40 ng/mL at about 4 hours after the administration; for administration of a dose of about 22.5 mg, about 190 ng/mL to about 250 ng/mL at about 0.25 hours after the administration; about 170 ng/mL to about 240 ng/mL at about 1 hour after the administration; about 70 ng/mL to about 120 ng/mL at about 2 hours after the administration; and about 10 ng/mL to about 60 ng/mL at about 4 hours after the administration; and for administration of a dose of about 30 mg, about 250 ng/mL to about 330 ng/mL at about 0.25 hours after the administration; about 270 ng/mL to about 330 ng/mL at about 1 hour after the administration; about 130 ng/mL to about 180 ng/mL at about 2 hours after the administration; and about 25 ng/mL to about 75 ng/mL at about 4 hours after the administration.

Embodiment B6

The method of embodiment B1, wherein the compound that activates Tie-2, or the pharmaceutically-acceptable salt thereof, is administered in a unit dosage form, wherein the unit dosage form further comprises a pharmaceutically-acceptable excipient.

Embodiment B7

The method of embodiment B6, wherein the pharmaceutically-acceptable excipient comprises a poly-ethylene glycol moiety.

Embodiment B8

The method of embodiment B6, wherein the pharmaceutically-acceptable excipient comprises a cyclodextrin moiety.

Embodiment B9

The method of embodiment B6, wherein the pharmaceutically-acceptable excipient comprises a 2-hydroxypropyl-β-cyclodextrin moiety.

Embodiment B10

The method of embodiment B6, wherein the pharmaceutically-acceptable excipient comprises a sulfobutylether-β-cyclodextrin moiety.

Embodiment B11

The method of embodiment B6, wherein the compound that activates Tie-2, or the pharmaceutically-acceptable salt thereof, and the pharmaceutically-acceptable excipient are held in a complex by non-covalent interactions.

Embodiment B12

The method of embodiment B6, wherein the pharmaceutically-acceptable excipient comprises a surfactant moiety.

Embodiment B13

The method of embodiment B1, wherein the therapeutically-effective amount is from about 0.1 mg to about 100 mg.

Embodiment B14

The method of embodiment B1, wherein the therapeutically-effective amount is from about 0.5 mg to about 30 mg.

Embodiment B15

The method of embodiment B1, wherein the administration is subcutaneous.

Embodiment B16

The method of embodiment B1, wherein the administration is to an eye.

Embodiment B17

The method of embodiment B1, wherein the condition is an ocular condition.

Embodiment B18

The method of embodiment B1, wherein the condition is diabetic macular edema.

Embodiment B19

The method of embodiment B1, wherein the condition is diabetic retinopathy.

Embodiment B20

The method of embodiment B1, wherein the condition is macular degeneration.

Embodiment B21

The method of embodiment B1, wherein the condition is vascular leak.

Embodiment B22

The method of embodiment B1, wherein the condition is a cancer.

Embodiment B23

The method of embodiment B1, wherein the subject is a human.

Embodiment B24

The method of embodiment B1, wherein the compound that activates Tie-2 or the pharmaceutically-acceptable salt thereof binds HPTP-beta.

Embodiment B25

The method of embodiment B1, wherein the compound that activates Tie-2 or the pharmaceutically-acceptable salt thereof inhibits HPTP-beta.

Embodiment B26

The method of embodiment B1, wherein the compound that activates Tie-2 or the pharmaceutically-acceptable salt thereof is a phosphate mimetic.

Embodiment B27

The method of embodiment B1, wherein the compound that activates Tie-2 comprises an amino acid backbone.

Embodiment B28

The method of embodiment B1, wherein the compound that activates Tie-2 comprises a sulfamic acid.

Embodiment B29

The method of embodiment B1, wherein the subject's visual acuity improves by at least 5 letters.

Embodiment B30

The method of embodiment B9, wherein the compound that activates Tie-2 is:

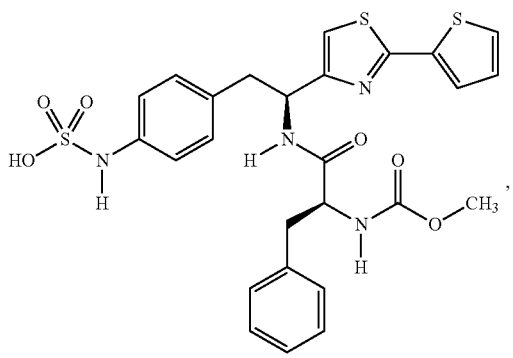 [SMILES: COC(=O)N[C@@H](Cc1ccccc1)C(=O)N[C@@H](Cc1ccc(NS(=O)(=O)O)cc1)c1csc(-c2cccs2)n1]

or a pharmaceutically-acceptable salt or zwitterion thereof.

Embodiment B31

The method of embodiment B30, wherein a plasma concentration in the subject of the compound that activates Tie-2 or the pharmaceutically-acceptable salt thereof is no greater than 350 ng/mL at about 0.25 hours after the administration.

Embodiment B32

The method of embodiment B30, wherein the plasma concentration in the subject of the compound that activates Tie-2 or the pharmaceutically-acceptable salt thereof is about 50 ng/mL to about 350 ng/mL at about 0.25 hours after the administration; about 30 ng/mL to about 350 ng/mL at about 1 hour after the administration; about 10 ng/mL to about 200 ng/mL at about 2 hours after the administration; and about 0 ng/mL to about 50 ng/mL at about 4 hours after the administration.

Embodiment B33

The method of embodiment B30, wherein the plasma concentration in the subject of the compound that activates Tie-2 or the pharmaceutically-acceptable salt thereof is for administration of a dose of about 5 mg, about 50 ng/mL to about 100 ng/mL at about 0.25 hours after the administration; about 30 ng/mL to about 80 ng/mL at about 1 hour after the administration; about 10 ng/mL to about 50 ng/mL at about 2 hours after the administration; and about 0 ng/mL to about 30 ng/mL at about 4 hours after the administration; for administration of a dose of about 15 mg, about 120 ng/mL to about 180 ng/mL at about 0.25 hours after the administration; about 70 ng/mL to about 130 ng/mL at about 1 hour after the administration; about 20 ng/mL to about 70 ng/mL at about 2 hours after the administration; and about 0 ng/mL to about 40 ng/mL at about 4 hours after the administration; for administration of a dose of about 22.5 mg, about 190 ng/mL to about 250 ng/mL at about 0.25 hours after the administration; about 170 ng/mL to about 240 ng/mL at about 1 hour after the administration; about 70 ng/mL to about 120 ng/mL at about 2 hours after the administration; and about 10 ng/mL to about 60 ng/mL at about 4 hours after the administration; and for administration of a dose of about 30 mg, about 250 ng/mL to about 330 ng/mL at about 0.25 hours after the administration; about 270 ng/mL to about 330 ng/mL at about 1 hour after the administration; about 130 ng/mL to about 180 ng/mL at about 2 hours after the administration; and about 25 ng/mL to about 75 ng/mL at about 4 hours after the administration.

Embodiment B34

The method of any above embodiment wherein the compound that activates Tie-2 is any compound described herein.

Embodiment C1

A pharmaceutical composition comprising a compound that activates Tie-2, or a pharmaceutically-acceptable salt thereof and an agent that increases solubility of the compound that activates Tie-2, or the pharmaceutically-acceptable salt thereof compared to solubility in absence of the agent.

Embodiment C2

The pharmaceutical composition of embodiment C1, wherein the agent that increases solubility of the compound that activates Tie-2 or the pharmaceutically-acceptable salt thereof comprises a polymer.

Embodiment C3

The pharmaceutical composition of embodiment C1, wherein the agent that increases solubility of the compound that activates Tie-2 or the pharmaceutically-acceptable salt thereof comprises a poly-ethylene glycol moiety.

Embodiment C4

The pharmaceutical composition of embodiment C1, wherein the agent that increases solubility of the compound that activates Tie-2 or the pharmaceutically-acceptable salt thereof comprises a cyclodextrin moiety.

Embodiment C5

The pharmaceutical composition of embodiment C1, wherein the agent that increases solubility of the compound that activates Tie-2 or the pharmaceutically-acceptable salt thereof comprises a 2-hydroxypropyl-β-cyclodextrin moiety.

Embodiment C6

The pharmaceutical composition of embodiment C1, wherein the agent that increases solubility of the compound that activates Tie-2 or the pharmaceutically-acceptable salt thereof comprises a sulfobutylether-β-cyclodextrin moiety.

Embodiment C7

The pharmaceutical composition of embodiment C1, wherein the agent that increases solubility of the compound that activates Tie-2 or the pharmaceutically-acceptable salt thereof comprises a surfactant moiety.

Embodiment C8

The pharmaceutical composition of embodiment C1, wherein the agent that increases solubility of the compound that activates Tie-2 or the pharmaceutically-acceptable salt thereof increases aqueous solubility by at least 10% at each of 5° C., ambient temperature, and 50° C.

Embodiment C9

The pharmaceutical composition of embodiment C1, wherein the agent that increases solubility of the compound that activates Tie-2 or the pharmaceutically-acceptable salt thereof improves solubility by at least 25%.

Embodiment C10

The pharmaceutical composition of embodiment C1, wherein the agent that increases solubility of the compound that activates Tie-2 or the pharmaceutically-acceptable salt thereof improves solubility by at least 50%.

Embodiment C11

The pharmaceutical composition of embodiment C1, wherein the agent that increases solubility of the compound that activates Tie-2 or the pharmaceutically-acceptable salt thereof is a cyclodextrin, and the pharmaceutical composition has a solubility of the compound that activates Tie-2, or the pharmaceutically-acceptable salt thereof, that is greater than that of an alternative formulation, wherein the alternative formulation comprises the compound that activates Tie-2, or the pharmaceutically-acceptable salt thereof; the cyclodextrin; and a polyethylene glycol moiety.

Embodiment C12

The pharmaceutical composition of embodiment C1, wherein the compound that activates Tie-2, or the pharmaceutically-acceptable salt thereof, is present in an amount from about 0.1 mg to about 100 mg.

Embodiment C13

The pharmaceutical composition of embodiment C1, wherein the compound that activates Tie-2, or the pharmaceutically-acceptable salt thereof, is present in an amount from about 0.5 mg to about 30 mg.

Embodiment C14

The pharmaceutical composition of embodiment C1, wherein the pharmaceutical composition is stable at about 5° C. for at least 30 days.

Embodiment C15

The pharmaceutical composition of embodiment C1, wherein the pharmaceutical composition is stable at about 50° C. for at least 30 days.

Embodiment C16

The pharmaceutical composition of embodiment C1, wherein the compound that activates Tie-2, or the pharmaceutically-acceptable salt thereof, and the agent that increases solubility of the compound that activates Tie-2 or the pharmaceutically-acceptable salt thereof are in a unit dosage form.

Embodiment C17

The pharmaceutical composition of embodiment C16, wherein the unit dosage for further comprises a pharmaceutically-acceptable carrier.

Embodiment C18

The pharmaceutical composition of embodiment C16, wherein the unit dosage form is formulated for subcutaneous administration.

Embodiment C19

The pharmaceutical composition of embodiment C16, wherein the unit dosage form is formulated for administration to an eye.

Embodiment C20

The pharmaceutical composition of embodiment C1, wherein the compound that activates Tie-2 or the pharmaceutically-acceptable salt thereof binds HPTP-beta.

Embodiment C21

The pharmaceutical composition of embodiment C1, wherein the compound that activates Tie-2 or the pharmaceutically-acceptable salt thereof inhibits HPTP-beta.

Embodiment C22

The pharmaceutical composition of embodiment C1, wherein the compound that activates Tie-2 or the pharmaceutically-acceptable salt thereof is a phosphate mimetic.

Embodiment C23

The pharmaceutical composition of embodiment C1, wherein the compound that activates Tie-2 comprises an amino acid backbone.

Embodiment C24

The pharmaceutical composition of embodiment C1, wherein the compound that activates Tie-2 comprises a sulfamic acid.

Embodiment C25

The pharmaceutical composition of any above embodiment wherein the compound that activates Tie-2 is any compound described herein.

Embodiment D1

A pharmaceutical composition comprising a Tie-2 activator or a pharmaceutically-acceptable salt thereof, and an antibody.

Embodiment D2

The pharmaceutical composition of embodiment D1, wherein the Tie-2 activator or the pharmaceutically-acceptable salt thereof binds HPTP-beta.

Embodiment D3

The pharmaceutical composition of embodiment D1, wherein the Tie-2 activator or the pharmaceutically-acceptable salt thereof inhibits HPTP-beta.

Embodiment D4

The pharmaceutical composition of embodiment D1, wherein the Tie-2 activator or the pharmaceutically-acceptable salt thereof is a phosphate mimetic.

Embodiment D5

The pharmaceutical composition of embodiment D1, wherein the Tie-2 activator comprises an amino acid backbone.

Embodiment D6

The pharmaceutical composition of embodiment D1, wherein the Tie-2 activator comprises a sulfamic acid.

Embodiment D7

The pharmaceutical composition of embodiment D1, wherein the antibody binds HPTP-beta.

Embodiment D8

The pharmaceutical composition of embodiment D1, wherein the antibody is an anti-VEGF agent.

Embodiment D9

The pharmaceutical composition of embodiment D1, wherein the antibody is ranibizumab.

Embodiment D10

The pharmaceutical composition of embodiment D1, wherein the antibody is bevacizumab.

Embodiment D11

The pharmaceutical composition of embodiment D1, wherein the antibody is aflibercept.

Embodiment D12

The pharmaceutical composition of embodiment D1, wherein the antibody comprises SEQ ID NO: 1.

Embodiment D13

The pharmaceutical composition of embodiment D1, wherein the antibody comprises SEQ ID NO: 2.

Embodiment D14

The pharmaceutical composition of embodiment D1, wherein the antibody comprises SEQ ID NO: 1 and SEQ ID NO: 2.

Embodiment D15

The pharmaceutical composition of embodiment D1, wherein the Tie-2 activator or the pharmaceutically-acceptable salt thereof and the antibody are in a unit dosage form, wherein the unit dosage form further comprises a pharmaceutically-acceptable excipient.

Embodiment D16

The pharmaceutical composition of embodiment D15, wherein the pharmaceutically-acceptable excipient comprises a poly-ethylene glycol moiety.

Embodiment D17

The pharmaceutical composition of embodiment D15, wherein the pharmaceutically-acceptable excipient comprises a cyclodextrin moiety.

Embodiment D18

The pharmaceutical composition of embodiment D15, wherein the pharmaceutically-acceptable excipient comprises a 2-hydroxypropyl-β-cyclodextrin moiety.

Embodiment D19

The pharmaceutical composition of embodiment D15, wherein the pharmaceutically-acceptable excipient comprises a sulfobutylether-β-cyclodextrin moiety.

Embodiment D20

The pharmaceutical composition of embodiment D15, wherein the Tie-2 activator, or the pharmaceutically-acceptable salt thereof, and the pharmaceutically-acceptable excipient are held in a complex by non-covalent interactions.

Embodiment D21

The pharmaceutical composition of embodiment D15, wherein the pharmaceutically-acceptable excipient comprises a surfactant moiety.

Embodiment D22

The pharmaceutical composition of embodiment D15, wherein the unit dosage form is formulated for subcutaneous administration.

Embodiment D23

The pharmaceutical composition of embodiment D15, wherein the unit dosage form is formulated for administration to an eye.

Embodiment D24

The pharmaceutical composition of embodiment D1, wherein the Tie-2 activator is present in an amount from about 0.1 mg to about 100 mg.

Embodiment D25

The pharmaceutical composition of embodiment D1, wherein the Tie-2 activator is present in an amount from about 0.5 mg to about 30 mg.

Embodiment D26

The pharmaceutical composition of embodiment D1, wherein the antibody is present in an amount from about 0.01 mg to about 5 mg.

Embodiment D27

The pharmaceutical composition of embodiment D1, wherein the antibody is present in an amount from about 0.1 mg to about 5 mg.

Embodiment D28

The pharmaceutical composition of any above embodiment wherein the compound that activates Tie-2 is any compound described herein.

Embodiment D1

A kit comprising a Tie-2 activator or a pharmaceutically-acceptable salt thereof, an antibody, and written instructions on use of the kit in treatment of a condition.

Embodiment D2

The kit of embodiment D1, wherein the condition is an ocular condition.

Embodiment D3

The kit of embodiment D1, wherein the condition is an ocular condition.

Embodiment D4

The kit of embodiment D1, wherein the condition is diabetic macular edema.

Embodiment D5

The kit of embodiment D1, wherein the condition is diabetic retinopathy.

Embodiment D6

The kit of embodiment D1, wherein the condition is macular degeneration.

Embodiment D7

The kit of embodiment D1, wherein the condition is vascular leak.

Embodiment D8

The kit of embodiment D1, wherein the condition is a cancer.

Embodiment D9

The kit of embodiment D1, wherein the instructions describe administration by subcutaneous injection.

Embodiment D10

The kit of embodiment D1, wherein the instructions describe administration to an eye.

Embodiment D11

The kit of any above embodiment wherein the Tie-2 activator is any compound described herein.

Embodiment E1

A method of treating a condition, the method comprising administering to a subject in need thereof a therapeutically-effective amount of a Tie-2 activator or a pharmaceutically-acceptable salt thereof and a therapeutically-effective amount of an antibody.

Embodiment E2

The method of embodiment E1, wherein the Tie-2 activator or the pharmaceutically-acceptable salt thereof binds HPTP-beta.

Embodiment E3

The method of embodiment E1, wherein the Tie-2 activator or the pharmaceutically-acceptable salt thereof inhibits HPTP-beta.

Embodiment E4

The method of embodiment E1, wherein the Tie-2 activator or the pharmaceutically-acceptable salt thereof is a phosphate mimetic.

Embodiment E5

The method of embodiment E1, wherein the Tie-2 activator comprises an amino acid backbone.

Embodiment E6

The method of embodiment E1, wherein the Tie-2 activator comprises a sulfamic acid.

Embodiment E7

The method of embodiment E1, wherein the antibody binds HPTP-beta.

Embodiment E8

The method of embodiment E1, wherein the antibody is an anti-VEGF agent.

Embodiment E9

The method of embodiment E1, wherein the antibody is ranibizumab.

Embodiment E10

The method of embodiment E1, wherein the antibody is bevacizumab.

Embodiment E11

The method of embodiment E1, wherein the antibody is aflibercept.

Embodiment E12

The method of embodiment E1, wherein the antibody comprises SEQ ID NO: 1.

Embodiment E13

The method of embodiment E1, wherein the antibody comprises SEQ ID NO: 2.

Embodiment E14

The method of embodiment E1, wherein the antibody comprises SEQ ID NO: 1 and SEQ ID NO: 2.

Embodiment E15

The method of embodiment E1, wherein the Tie-2 activator or the pharmaceutically-acceptable salt thereof and the antibody are in a unit dosage form, wherein the unit dosage form further comprises a pharmaceutically-acceptable excipient.

Embodiment E16

The method of embodiment E15, wherein the pharmaceutically-acceptable excipient comprises a poly-ethylene glycol moiety.

Embodiment E17

The method of embodiment E15, wherein the pharmaceutically-acceptable excipient comprises a cyclodextrin moiety.

Embodiment E18

The method of embodiment E15, wherein the pharmaceutically-acceptable excipient comprises a 2-hydroxypropyl-β-cyclodextrin moiety.

Embodiment E19

The method of embodiment E15, wherein the pharmaceutically-acceptable excipient comprises a sulfobutylether-β-cyclodextrin moiety.

Embodiment E20

The method of embodiment E15, wherein the Tie-2 activator, or the pharmaceutically-acceptable salt thereof, and the pharmaceutically-acceptable excipient are held in a complex by non-covalent interactions.

Embodiment E21

The method of embodiment E15, wherein the pharmaceutically-acceptable excipient comprises a surfactant moiety.

Embodiment E22

The method of embodiment E1, wherein the therapeutically-effective amount of the Tie-2 activator or the pharmaceutically-acceptable salt thereof is from about 0.1 mg to about 100 mg.

Embodiment E23

The method of embodiment E1, wherein the therapeutically-effective amount of the Tie-2 activator or the pharmaceutically-acceptable salt thereof is from about 0.5 mg to about 30 mg.

Embodiment E24

The method of embodiment E1, wherein the therapeutically-effective amount of the antibody is from about 0.01 mg to about 5 mg.

Embodiment E25

The method of embodiment E1, wherein the therapeutically-effective amount of the antibody is from about 0.1 mg to about 5 mg.

Embodiment E26

The method of embodiment E1, wherein the administration of the Tie-2 activator or the pharmaceutically-acceptable salt thereof is subcutaneous administration.

Embodiment E27

The method of embodiment E1, wherein the administration of the antibody is subcutaneous administration.

Embodiment E28

The method of embodiment E1, wherein the administration of the Tie-2 activator or the pharmaceutically-acceptable salt thereof is to an eye.

Embodiment E29

The method of embodiment E1, wherein the administration of the antibody is to an eye.

Embodiment E30

The method of embodiment E1, wherein the Tie-2 activator or the pharmaceutically-acceptable salt thereof and the antibody are administered simultaneously.

Embodiment E31

The method of embodiment E1, wherein the Tie-2 activator or the pharmaceutically-acceptable salt thereof and the antibody are administered sequentially.

Embodiment E32

The method of embodiment E31, wherein the sequential administration is administration of the Tie-2 activator or the pharmaceutically-acceptable salt thereof and the antibody on the same day.

Embodiment E33

The method of embodiment E31, wherein the sequential administration is administration of the Tie-2 activator or the pharmaceutically-acceptable salt thereof and the antibody within one month.

Embodiment E34

The method of embodiment E1, wherein the condition is an ocular condition.

Embodiment E35

The method of embodiment E1, wherein the condition is diabetic macular edema.

Embodiment E36

The method of embodiment E1, wherein the condition is diabetic retinopathy.

Embodiment E37

The method of embodiment E1, wherein the condition is macular degeneration.

Embodiment E38

The method of embodiment E1, wherein the condition is vascular leak.

Embodiment E39

The method of embodiment E1, wherein the condition is a cancer.

Embodiment E40

The method of embodiment E1, wherein the subject is a human.

Embodiment E41

The method of embodiment E1, wherein the subject's visual acuity improves by at least 5 letters.

Embodiment E42

The method of any above embodiment wherein the Tie-2 activator is any compound described herein.

Embodiment F1

A complex comprising a Tie-2 activator, or a pharmaceutically-acceptable salt thereof, and a molecule comprising a channel, wherein the compound that activates Tie-2, or the pharmaceutically-acceptable salt thereof is held in the channel of the molecule by non-covalent interactions.

Embodiment F2

The complex of embodiment F1, wherein the Tie-2 activator or the pharmaceutically-acceptable salt thereof binds HPTP-beta.

Embodiment F3

The complex of embodiment F1, wherein the Tie-2 activator or the pharmaceutically-acceptable salt thereof inhibits HPTP-beta.

Embodiment F4

The complex of embodiment F1, wherein the Tie-2 activator or the pharmaceutically-acceptable salt thereof is a phosphate mimetic.

Embodiment F5

The complex of embodiment F1, wherein the Tie-2 activator comprises an amino acid backbone.

Embodiment F6

The complex of embodiment F1, wherein the Tie-2 activator comprises a sulfamic acid.

Embodiment F7

The complex of embodiment F1, wherein the molecule comprising the channel comprises a cyclodextrin moiety.

Embodiment F8

The complex of embodiment F1, wherein the molecule comprising the channel comprises a 2-hydroxypropyl-β-cyclodextrin moiety.

Embodiment F9

The complex of embodiment F1, wherein the molecule comprising the channel comprises a sulfobutylether-β-cyclodextrin moiety.

Embodiment F10

The complex of embodiment F1, wherein the complex is more soluble in water than is the Tie-2 activator in the absence of the molecule comprising the channel.

Embodiment F11

The complex of any above embodiment wherein the Tie-2 activator is any compound described herein.

Embodiment G1

A method of treating a condition, the method comprising administering to a subject in need thereof a therapeutically-effective amount of complex comprising a Tie-2 activator, or a pharmaceutically-acceptable salt thereof and a molecule comprising a channel, wherein the Tie-2 activator or the pharmaceutically-acceptable salt thereof is held in the channel of the molecule by non-covalent interactions.

Embodiment G2

The method of embodiment G1, wherein the Tie-2 activator or the pharmaceutically-acceptable salt thereof binds HPTP-beta.

Embodiment G3

The method of embodiment G1, wherein the Tie-2 activator or the pharmaceutically-acceptable salt thereof inhibits HPTP-beta.

Embodiment G4

The method of embodiment G1, wherein the Tie-2 activator or the pharmaceutically-acceptable salt thereof is a phosphate mimetic.

Embodiment G5

The method of embodiment G1, wherein the Tie-2 activator comprises an amino acid backbone.

Embodiment G6

The method of embodiment G1, wherein the Tie-2 activator comprises a sulfamic acid.

Embodiment G7

The method of embodiment G1, wherein the molecule comprising the channel comprises a cyclodextrin moiety.

Embodiment G8

The method of embodiment G1, wherein the molecule comprising the channel comprises a 2-hydroxypropyl-β-cyclodextrin moiety.

Embodiment G9

The method of embodiment G1, wherein the molecule comprising the channel comprises a sulfobutylether-β-cyclodextrin moiety.

Embodiment G10

The method of embodiment G1, wherein the complex is more soluble in water than is the Tie-2 activator in the absence of the molecule comprising the channel.

Embodiment G11

The method of embodiment G1, wherein the administration of the complex is subcutaneous administration.

Embodiment G12

The method of embodiment G1, wherein the administration of the complex is to an eye.

Embodiment G13

The method of embodiment G1, wherein the complex is in a unit dosage form.

Embodiment G14

The method of embodiment G1, wherein the therapeutically-effective amount of the complex is from about 0.1 mg to about 300 mg.

Embodiment G15

The method of embodiment G1, wherein the therapeutically-effective amount of the Tie-2 activator or the pharmaceutically-acceptable salt thereof is from about 0.5 mg to about 100 mg.

Embodiment G16

The method of embodiment G1, wherein the condition is an ocular condition.

Embodiment G17

The method of embodiment G1, wherein the condition is diabetic macular edema.

Embodiment G18

The method of embodiment G1, wherein the condition is diabetic retinopathy.

Embodiment G19

The method of embodiment G1, wherein the condition is macular degeneration.

Embodiment G20

The method of embodiment G1, wherein the condition is vascular leak.

Embodiment G21

The method of embodiment G1, wherein the condition is a cancer.

Embodiment G22

The method of embodiment G1, further comprising administering to the subject a therapeutically-effective amount of an additional therapeutic agent.

Embodiment G23

The method of embodiment G22, wherein the additional therapeutic agent is an antibody.

Embodiment G24

The method of embodiment G22, wherein the additional therapeutic agent binds HPTP-beta.

Embodiment G25

The method of embodiment G22, wherein the additional therapeutic agent is an anti-VEGF agent.

Embodiment G26

The method of embodiment G22, wherein the additional therapeutic agent is ranibizumab.

Embodiment G27

The method of embodiment G22, wherein the additional therapeutic agent is bevacizumab.

Embodiment G28

The method of embodiment G22, wherein the additional therapeutic agent is aflibercept.

Embodiment G29

The method of embodiment G22, wherein the additional therapeutic agent comprises SEQ ID NO: 1.

Embodiment G30

The method of embodiment G22, wherein the additional therapeutic agent comprises SEQ ID NO: 2.

Embodiment G31

The method of embodiment G22, wherein the additional therapeutic agent comprises SEQ ID NO: 1 and SEQ ID NO: 2.

Embodiment G32

The method of embodiment G22, wherein the therapeutically-effective amount of the additional therapeutic agent is from about 0.01 mg to about 5 mg.

Embodiment G33

The method of embodiment G22, wherein the therapeutically-effective amount of the additional therapeutic agent is from about 0.1 mg to about 5 mg.

Embodiment G34

The method of embodiment G22, wherein the administration of the additional therapeutic agent is subcutaneous administration.

Embodiment G35

The method of embodiment G22, wherein the administration of the additional therapeutic agent is to an eye.

Embodiment G36

The method of embodiment G22, wherein the complex and the additional therapeutic agent are administered simultaneously.

Embodiment G37

The method of embodiment G22, wherein the complex and the additional therapeutic agent are administered sequentially.

Embodiment G38

The method of embodiment G37, wherein the sequential administration is administration of the Tie-2 activator or the pharmaceutically-acceptable salt thereof and the antibody on the same day.

Embodiment G39

The method of embodiment G37, wherein the sequential administration is administration of the Tie-2 activator or the pharmaceutically-acceptable salt thereof and the antibody within one month.

Embodiment G40

The method of embodiment G1, wherein the subject is a human.

Embodiment G41

The method of embodiment G1, wherein the subject's visual acuity improves by at least 5 letters.

Embodiment G42

The method of any above embodiment wherein the Tie-2 activator is any compound described herein.

---

What is claimed is:

1. A method of treating an ocular condition in a subject in need thereof, the method comprising administering to the subject a therapeutically-effective amount of a compound that activates Tie-2, wherein the compound is of the formula:

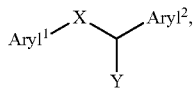

wherein:

Aryl$^1$ is an aryl group which is substituted or unsubstituted; Aryl$^2$ is an aryl group which is substituted or unsubstituted; X is alkylene, alkenylene, alkynylene, an ether linkage, an amine linkage, an amide linkage, an ester linkage, a thioether linkage, a carbamate linkage, a carbonate linkage, a sulfone linkage, any of which is substituted or unsubstituted, or a chemical bond; and Y is H, aryl, heteroaryl, NH(aryl), NH(heteroaryl), NHSO$_2$R$^g$, or NHCOR$^g$, any of which is substituted or unsubstituted, or

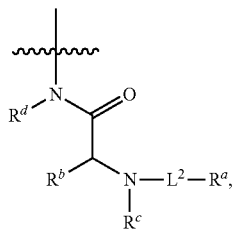

wherein:

L$^2$ is alkylene, alkenylene, or alkynylene, any of which is substituted or unsubstituted, or together with the nitrogen atom to which L$^2$ is bound forms an amide linkage, a carbamate linkage, or a sulfonamide linkage, or a chemical bond, or together with any of R$^a$, R$^b$, R$^c$, and R$^d$ forms a ring that is substituted or unsubstituted;

R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^b$, R$^c$, and R$^d$ forms a ring that is substituted or unsubstituted;

R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^a$, R$^c$, and R$^d$ forms a ring that is substituted or unsubstituted;

R$^c$ is H or alkyl which is substituted or unsubstituted, or together with any of L$^2$, R$^a$, R$^b$, and R$^d$ forms a ring that is substituted or unsubstituted;

R$^d$ is H or alkyl which is substituted or unsubstituted, or together with any of L$^2$, R$^a$, R$^b$, and R$^c$ forms a ring that is substituted or unsubstituted; and R$^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof, and an agent that increases aqueous solubility of the compound that activates Tie-2, or the pharmaceutically-acceptable salt, tautomer, or zwitterion thereof as compared to solubility of the compound that activates Tie-2 or the pharmaceutically-acceptable salt, tautomer, or zwitterion thereof in absence of the agent, wherein the agent that increases solubility of the compound that activates Tie-2 or the pharmaceutically-acceptable salt, tautomer, or zwitterion thereof increases aqueous solubility of the compound that activates Tie-2 or the pharmaceutically-acceptable salt, tautomer, or zwitterion thereof by at least 10% at each of 5° C., ambient temperature, and 50° C., wherein the agent is a cyclodextrin.

2. The method of claim 1, wherein the agent that improves the aqueous solubility of the compound that activates Tie-2 or the pharmaceutically-acceptable salt, tautomer, or zwitterion thereof comprises a 2-hydroxypropyl-β-cyclodextrin moiety.

3. The method of claim 1, wherein the agent that improves the aqueous solubility of the compound that activates Tie-2 or the pharmaceutically-acceptable salt, tautomer, or zwitterion thereof comprises a sulfobutylether-β-cyclodextrin moiety.

4. The method of claim 1, wherein the agent that improves the aqueous solubility of the compound that activates Tie-2 or the pharmaceutically-acceptable salt, tautomer, or zwitterion thereof comprises a surfactant moiety.

5. The method of claim 1, wherein the agent that increases solubility of the compound that activates Tie-2 or the pharmaceutically-acceptable salt, tautomer, or zwitterion thereof increases aqueous solubility by at least 25%.

6. The method of claim 1, wherein the agent that increases solubility of the compound that activates Tie-2 or the pharmaceutically-acceptable salt, tautomer, or zwitterion thereof increases aqueous solubility by at least 50%.

7. The method of claim 1, wherein the therapeutically-effective amount is from about 0.1 mg to about 100 mg.

8. The method of claim 1, wherein the therapeutically-effective amount is from about 0.5 mg to about 30 mg.

9. The method of claim 1, wherein the compound that activates Tie-2, or the pharmaceutically-acceptable salt, tautomer, or zwitterion thereof, and the agent that improves aqueous solubility of the compound that activates Tie-2 or the pharmaceutically-acceptable salt thereof are coadministered in a unit dosage form.

10. The method of claim 9, wherein the unit dosage form is administered subcutaneously.

11. The method of claim 9, wherein the unit dosage form is administered to an eye.

12. The method of claim 1, wherein the ocular condition is diabetic macular edema.

13. The method of claim 1, wherein the ocular condition is diabetic retinopathy.

14. The method of claim 1, wherein the ocular condition is macular degeneration.

15. The method of claim 1, wherein the ocular condition is vascular leak in an eye of the subject.

16. The method of claim 1, wherein the subject is a human.

17. The method of claim 1, wherein:
Aryl$^1$ is substituted or unsubstituted phenyl;
Aryl$^2$ is substituted or unsubstituted heteroaryl; and
X is alkylene.

18. The method of claim 17, wherein:
Aryl$^1$ is substituted phenyl;
Aryl$^2$ is substituted heteroaryl; and
X is methylene.

19. The method of claim 18, wherein the compound that activates Tie-2 is a compound of the formula:

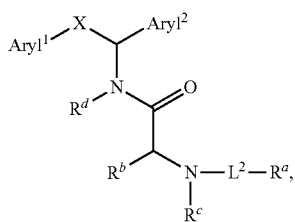

wherein
Aryl$^1$ is para-substituted phenyl;
Aryl$^2$ is substituted heteroaryl;
X is methylene;
L$^2$ is alkylene, alkenylene, or alkynylene, any of which is substituted or unsubstituted, or together with the nitrogen atom to which L$^2$ is bound forms an amide linkage, a carbamate linkage, or a sulfonamide linkage, or a chemical bond;
R$^a$ is H, alkyl, alkenyl, alkynyl, aryl, arylalkyl, heterocyclyl, heterocyclylalkyl, heteroaryl, or heteroarylalkyl, any of which is substituted or unsubstituted;
R$^b$ is H, alkyl, alkenyl, alkynyl, aryl, arylalkyl, heterocyclyl, heterocyclylalkyl, heteroaryl, or heteroarylalkyl, any of which is substituted or unsubstituted;
R$^c$ is H or alkyl which is substituted or unsubstituted; and
R$^d$ is H or alkyl which is substituted or unsubstituted.

20. The method of claim 19, wherein:
Aryl$^1$ is para-substituted phenyl;
Aryl$^2$ is a substituted thiazole moiety;
X is methylene;
L$^2$ together with the nitrogen atom to which L$^2$ is bound forms a carbamate linkage;
R$^a$ is alkyl, which is substituted or unsubstituted;
R$^b$ is arylalkyl, which is substituted or unsubstituted;
R$^c$ is H; and
R$^d$ is H.

21. The method of claim 20, wherein Aryl$^2$ is:

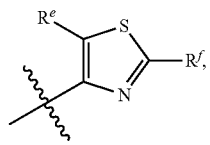

wherein:
R$^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and R$^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

22. The method of claim 21, wherein:
R$^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and
R$^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

23. The method of claim 21, wherein:
R$^e$ is H, OH, F, Cl, Br, I, alkyl, or an alkoxy group, any of which is substituted or unsubstituted; and
R$^f$ is alkyl, aryl, heterocyclyl, or heteroaryl, any of which is substituted or unsubstituted.

24. The method of claim 21, wherein:
Aryl$^1$ is 4-phenylsulfamic acid;
R$^a$ is alkyl, which is substituted or unsubstituted;
R$^b$ is arylalkyl, which is substituted or unsubstituted;
R$^e$ is H; and
R$^f$ is heteroaryl.

25. The method of claim 1, wherein the compound is:

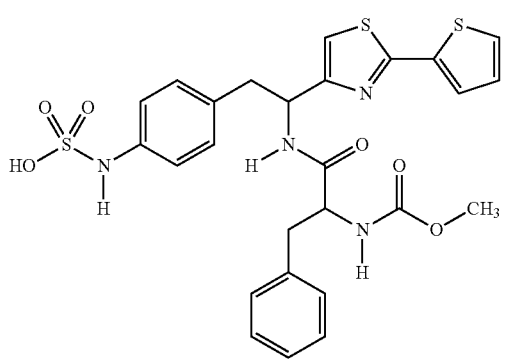

26. The method of claim 1, wherein the compound is:

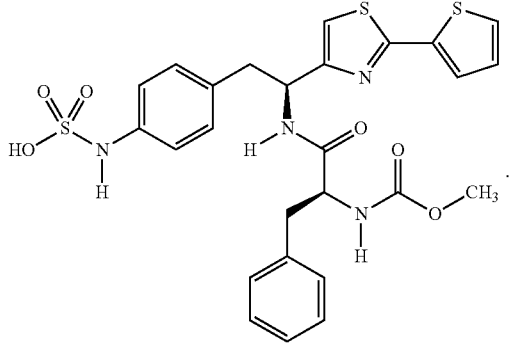 [SMILES: COC(=O)N[C@@H](Cc1ccccc1)C(=O)N[C@@H](Cc1ccc(NS(=O)(=O)O)cc1)c1csc(-c2cccs2)n1]

27. The method of claim 21, wherein:
Aryl$^1$ is 4-phenylsulfamic acid;
R$^a$ is alkyl, which is substituted or unsubstituted;
R$^b$ is arylalkyl, which is substituted or unsubstituted;
R$^e$ is H; and
R$^f$ is alkyl.

28. The method of claim 1, wherein the compound is:

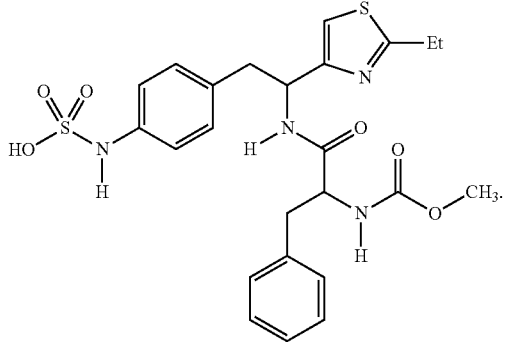 [SMILES: CCc1nc(C(Cc2ccc(NS(=O)(=O)O)cc2)NC(=O)C(Cc2ccccc2)NC(=O)OC)cs1]

29. The method of claim 18, wherein the compound is:

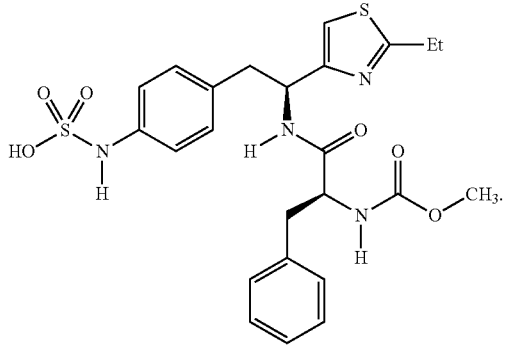 [SMILES: CCc1nc([C@H](Cc2ccc(NS(=O)(=O)O)cc2)NC(=O)[C@H](Cc2ccccc2)NC(=O)OC)cs1]

30. The method of claim 20, wherein Aryl$^2$ is:

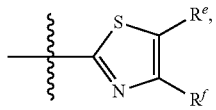

wherein:

R$^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and R$^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

31. The method of claim 30, wherein:

R$^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and R$^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

32. The method of claim 30, wherein:

R$^e$ is H, OH, F, Cl, Br, I, alkyl, or an alkoxy group, any of which is substituted or unsubstituted; and R$^f$ is alkyl, aryl, heterocyclyl, or heteroaryl, any of which is substituted or unsubstituted.

33. The method of claim 30, wherein:

Aryl$^1$ is 4-phenylsulfamic acid;

R$^a$ is alkyl, which is substituted or unsubstituted;

R$^b$ is arylalkyl, which is substituted or unsubstituted;

R$^e$ is H; and

R$^f$ is heteroaryl.

34. The method of claim 1, wherein the compound is:

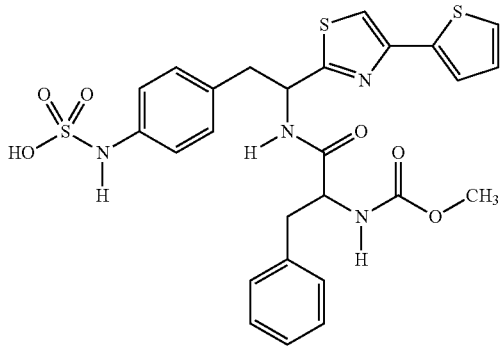

35. The method of claim 1, wherein the compound is:

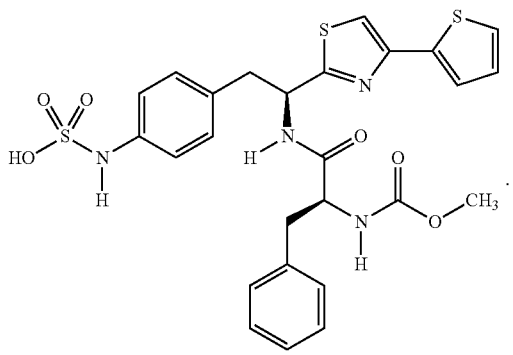 [SMILES: COC(=O)N[C@@H](Cc1ccccc1)C(=O)N[C@@H](Cc1ccc(NS(=O)(=O)O)cc1)c1nc(-c2cccs2)cs1]

36. The method of claim 26, wherein the agent that improves the aqueous solubility of the compound that activates Tie-2 or the pharmaceutically-acceptable salt, tautomer, or zwitterion thereof comprises a 2-hydroxypropyl-β-cyclodextrin moiety.

37. The method of claim 36, wherein the condition is diabetic macular edema.

38. The method of claim 37, wherein a plasma concentration in the subject of the compound that activates Tie-2 or the pharmaceutically-acceptable salt, tautomer, or zwitterion thereof is no greater than 500 ng/mL at about 0.25 hours after the administration.

39. The method of claim 37, wherein a plasma concentration in the subject of the compound that activates Tie-2 or the pharmaceutically-acceptable salt, tautomer, or zwitterion thereof is about 50 ng/mL to about 350 ng/mL at about 0.25 hours after the administration; about 30 ng/mL to about 350 ng/mL at about 1 hour after the administration; about 10 ng/mL to about 200 ng/mL at about 2 hours after the administration; and about 0 ng/mL to about 50 ng/mL at about 4 hours after the administration.

40. The method of claim 37, wherein a plasma concentration in the subject of the compound that activates Tie-2 or the pharmaceutically-acceptable salt, tautomer, or zwitterion thereof is:
a) for administration of a dose of about 5 mg, about 50 ng/mL to about 100 ng/mL at about 0.25 hours after the administration; about 30 ng/mL to about 80 ng/mL at about 1 hour after the administration; about 10 ng/mL to about 50 ng/mL at about 2 hours after the administration; and about 0 ng/mL to about 30 ng/mL at about 4 hours after the administration;
b) for administration of a dose of about 15 mg, about 120 ng/mL to about 180 ng/mL at about 0.25 hours after the administration; about 70 ng/mL to about 130 ng/mL at about 1 hour after the administration; about 20 ng/mL to about 70 ng/mL at about 2 hours after the administration; and about 0 ng/mL to about 40 ng/mL at about 4 hours after the administration;
c) for administration of a dose of about 22.5 mg, about 190 ng/mL to about 250 ng/mL at about 0.25 hours after the administration; about 170 ng/mL to about 240 ng/mL at about 1 hour after the administration; about 70 ng/mL to about 120 ng/mL at about 2 hours after the administration; and about 10 ng/mL to about 60 ng/mL at about 4 hours after the administration; and
d) for administration of a dose of about 30 mg, about 250 ng/mL to about 330 ng/mL at about 0.25 hours after the administration; about 270 ng/mL to about 330 ng/mL at about 1 hour after the administration; about 130 ng/mL to about 180 ng/mL at about 2 hours after the administration; and about 25 ng/mL to about 75 ng/mL at about 4 hours after the administration.

41. The method of claim 1, wherein the administration is topical.

42. The method of claim 1, wherein the administration is topical to an eye of the subject.

43. The method of claim 9, wherein the unit dosage form is administered topically.

44. The method of claim 9, wherein the unit dosage form is administered topically to an eye of the subject.

45. The method of claim 9, wherein the unit dosage form is formulated as a drop.

46. The method of claim 9, wherein the unit dosage form is formulated as a drop, wherein the drop is administered to an eye of the subject.

47. The method of claim 9, wherein the unit dosage form is administered topically to an eye of the subject, wherein the therapeutically-effective amount of the compound that activates Tie-2, or the pharmaceutically-acceptable salt, tautomer, or zwitterion thereof is from about 15 mg to about 30 mg.

48. The method of claim 47, wherein the unit dosage form is formulated as a drop.

49. The method of claim 48, wherein the compound is:

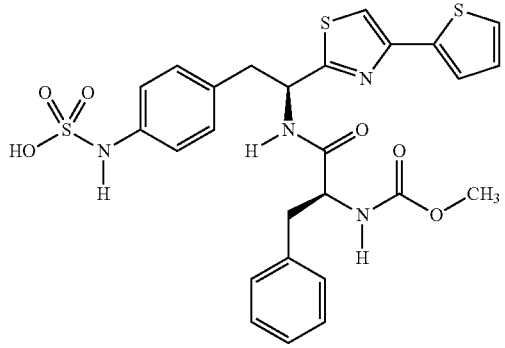

50. The method of claim 49, wherein the cyclodextrin is 2-hydroxypropyl-β-cyclodextrin.

51. The method of claim 50, wherein the therapeutically-effective amount is about 30 mg.

52. The method of claim 50, wherein the therapeutically-effective amount is about 15 mg.

53. The method of claim 48, wherein the compound is:

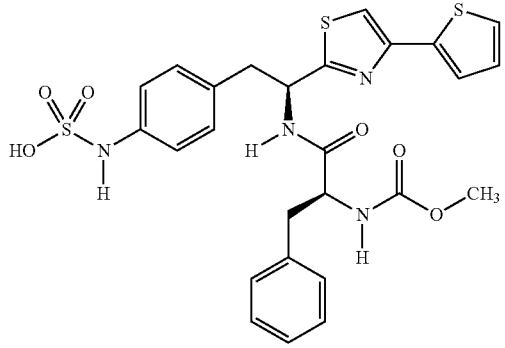

54. The method of claim 53, wherein the cyclodextrin is 2-hydroxypropyl-β-cyclodextrin.

55. The method of claim 54, wherein the therapeutically-effective amount is about 30 mg.

56. The method of claim 54, wherein the therapeutically-effective amount is about 15 mg.

57. The method of claim 48, wherein the compound is:

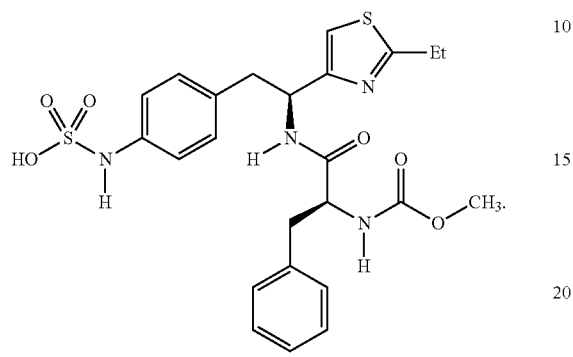

58. The method of claim 57, wherein the cyclodextrin is 2-hydroxypropyl-β-cyclodextrin.

59. The method of claim 58, wherein the therapeutically-effective amount is about 30 mg.

60. The method of claim 58, wherein the therapeutically-effective amount is about 15 mg.

* * * * *

SEQUENCE LISTING

```
<160> NUMBER OF SEQ ID NOS: 2

<210> SEQ ID NO 1
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60
```

```
Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Leu
225                 230

<210> SEQ ID NO 2
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Leu Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
                 20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Gln Ser Ser Gly Leu Tyr Ser Leu Ser Ser Val Val
```

-continued

```
              180                 185                 190
Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Leu
225                 230
```